US009952216B2

(12) United States Patent
Visel et al.

(10) Patent No.: US 9,952,216 B2
(45) Date of Patent: Apr. 24, 2018

(54) BRAIN-SPECIFIC ENHANCERS FOR CELL-BASED THERAPY

(71) Applicants: Axel Visel, El Cerrito, CA (US); John L. R. Rubenstein, San Francisco, CA (US); Ying-Jiun (Jasmine) Chen, South San Francisco, CA (US); Len A. Pennacchio, Sebastopol, CA (US); Daniel Vogt, Burlingame, CA (US); Cory Nicholas, San Francisco, CA (US); Arnold Kriegstein, Mill Valley, CA (US)

(72) Inventors: Axel Visel, El Cerrito, CA (US); John L. R. Rubenstein, San Francisco, CA (US); Ying-Jiun (Jasmine) Chen, South San Francisco, CA (US); Len A. Pennacchio, Sebastopol, CA (US); Daniel Vogt, Burlingame, CA (US); Cory Nicholas, San Francisco, CA (US); Arnold Kriegstein, Mill Valley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/512,306

(22) Filed: Oct. 10, 2014

(65) Prior Publication Data

US 2015/0044187 A1 Feb. 12, 2015

Related U.S. Application Data

(63) Continuation of application No. PCT/US2013/036030, filed on Apr. 10, 2013.

(60) Provisional application No. 61/622,467, filed on Apr. 10, 2012, provisional application No. 61/676,606, filed on Jul. 27, 2012.

(51) Int. Cl.

| | |
|---|---|
| ***C12N 15/85*** | (2006.01) |
| ***G01N 33/569*** | (2006.01) |
| ***G01N 33/50*** | (2006.01) |
| ***A61K 35/545*** | (2015.01) |
| ***C12N 15/86*** | (2006.01) |
| *A61K 48/00* | (2006.01) |

(52) U.S. Cl.

CPC ..... *G01N 33/56966* (2013.01); *A61K 35/545* (2013.01); *C12N 15/85* (2013.01); *C12N 15/86* (2013.01); *G01N 33/5014* (2013.01); *A61K 48/00* (2013.01); *C12N 2830/008* (2013.01)

(58) Field of Classification Search

None

See application file for complete search history.

(56) References Cited

U.S. PATENT DOCUMENTS 5,436,128 A * 7/1995 Harpold ............ G01N 33/6872 435/365

OTHER PUBLICATIONS

Ferguson et al. The human synaptotagmin IV gene defines an evolutionary break point between syntenic mouse and human chromosome regions but retains ligand inducibility and tissue specificity. The Journal of Biological Chemistry, vol. 275, No. 47, pp. 36920-36926, 2000.*

Skottman et al. Gene expression signatures of seven individual human embryonic stem cell lines. Stem Cells, vol. 23, pp. 1343-1356, 2005.*

De Vita et al. Flow cytometric and cytogenetic analyses in human spontaneous abortions. Human Genetics, vol. 91, pp. 409-415, Jun. 1993.*

GenBank Accession No. AC044873.13, publicly available Oct. 2002, printed as pp. 1/40-40/40.*

* cited by examiner

*Primary Examiner* — Jennifer Dunston

(74) *Attorney, Agent, or Firm* — Kilpatrick Townsend & Stockton LLP

(57) ABSTRACT

Herein are described a set of novel specific human enhancers for specific forebrain cell types used to study and select for human neural progenitor cells. This approach enables the ability to generate interneurons from human ES, iPS and iN cells, making them available for human transplantation and for molecular/cellular analyzes. These approaches are also directly applicable to generating other neuronal cell types, such as cortical and striatal projection neurons, which have implications for many human diseases.

10 Claims, 32 Drawing Sheets

FIG. 1

A

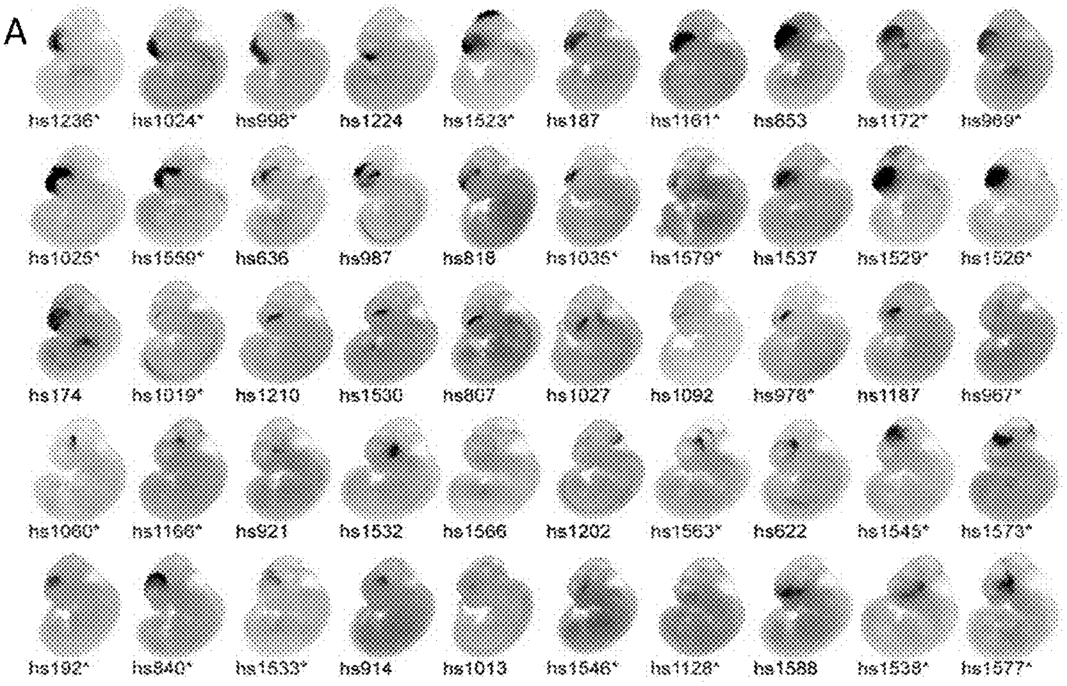

Figure 2:
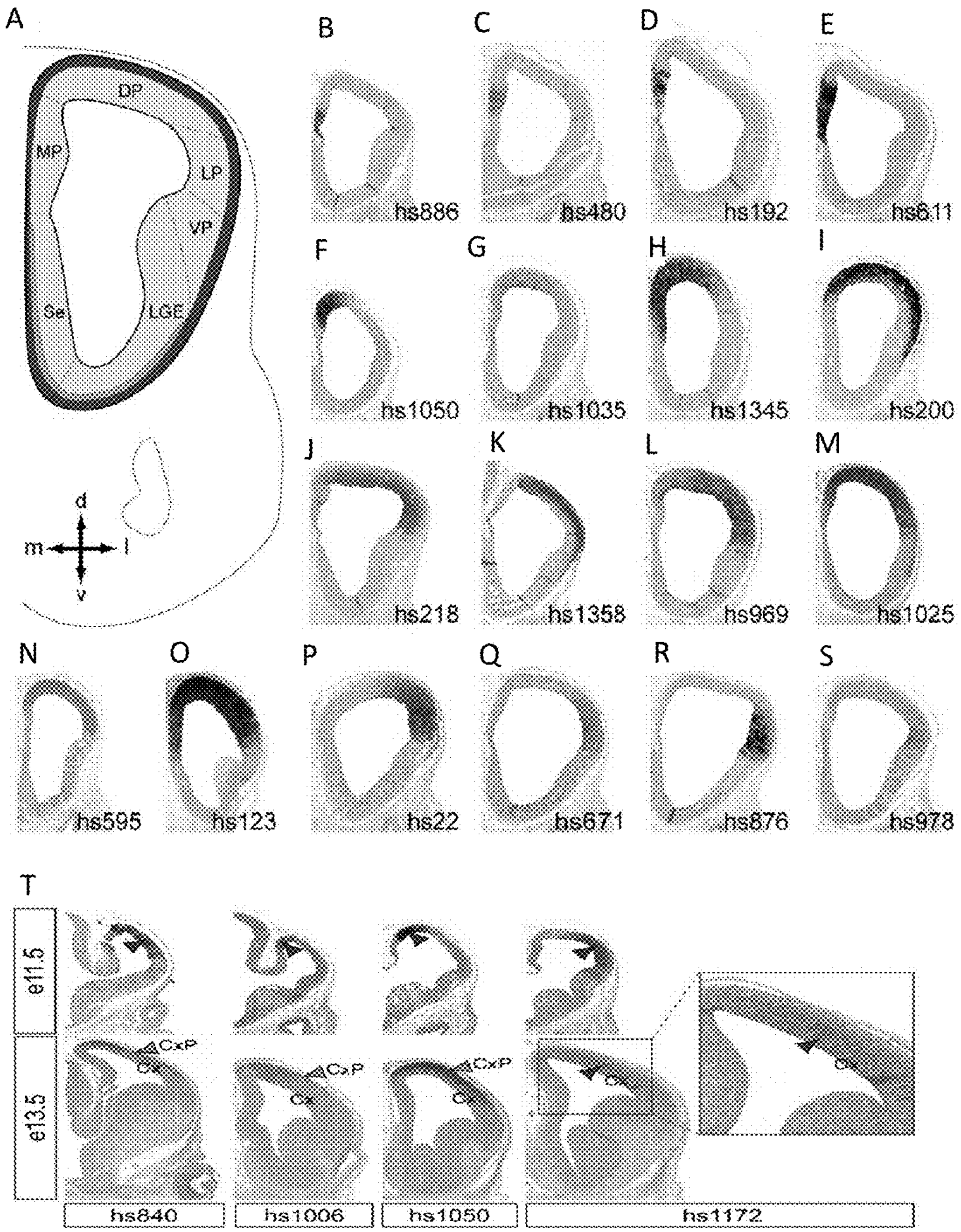

* enhancers near genes implicated in telencephalon development or function:

B

| enhancer element(s) | gene symbol | gene name |
|---|---|---|
| hs987, hs998 | *ASCL1* | achaete scute complex homolog 1 |
| hs1025 | *EMX1* | empty spiracles homeobox 1 |
| hs1236 | *EMX2* | empty spiracles homeobox 2 |
| hs840 | *EPHA5* | Eph receptor A5 |
| hs1523 | *FOXG1* | forkhead box G1 |
| hs1563 | *HES1* | hairy and enhancer of split 1 |
| hs1533 | *ID4* | inhibitor of DNA binding 4 |
| hs1545 | *LEF1* | lymphoid enhancer binding factor 1 |
| hs1161 | *LMO4* | LIM domain only 4 |
| hs1024, hs1060, hs1172, hs1577 | *NR2F1* | nuclear receptor subfamily 2, group F |
| hs1579 | *OTX2* | orthodenticle homeobox 2 |
| hs1546 | *POU3F1* | POU domain, class 3, transcription factor 6}OCT |
| hs978, hs1035, hs1128 | *POU3F2* | POU class 3 homeobox 2 |
| hs969, hs1526, hs1529 | *POU3F3* | POU class 3 homeobox 3 |
| hs192 | *SOX2* | SRYbox containing gene 2 |
| hs1019 | *SP4* | transacting transcription factor 4 |
| hs1166, hs1538 | *NKX21* | NK2 homeobox 1 (TITF1) |
| hs1559 | *WNT7B* | winglessrelated MMTV integration site 7B |
| hs1573 | *ZIC1* | zinc finger protein of the cerebellum 1 |

MP, medial pallium; DP, dorsal pallium; LP, lateral pallium; VP, ventral pallium; LGE, lateral ganglionic eminence; Se, septum Pallium Pallium and subpallium Subpallium Telencephalon

BRAIN-SPECIFIC ENHANCERS FOR CELL-BASED THERAPY

CROSS-REFERENCE TO RELATED APPLICATIONS

This application is a continuation application of International Patent Application No. PCT/US13/36030, filed on Apr. 10, 2013, which claims benefit of U.S. Provisional Patent Application Ser. No. 61/622,467, filed on Apr. 10, 2012, and to U.S. Provisional Patent Application Ser. No. 61/676,606, filed on Jul. 27, 2012, all of which are hereby incorporated in their entirety for all purposes.

STATEMENT OF GOVERNMENTAL SUPPORT

This work was supported Grant Nos. HG003988 awarded by the National Human Genome Research Institute, Grant Nos. MH081880 and MH049428 awarded by the NIH-NIMH, Grant Nos. NS062859A and NS071785 awarded by the NIH-NINDS, by Grant Nos. RB2-01602 and RC1-00346-1 awarded by the California Institute for Regenerative Medicine, and by Contract DE-AC02-05CH11231 awarded by the Department of Energy. The government has certain rights in the invention.

REFERENCE TO AN ELECTRONIC SEQUENCE LISTING

This application incorporates by reference the electronically filed Sequence Listing, filed as a *.txt file entitled, "077429-014900US_Substitute_SequenceListing.txt", created Jan. 5, 2017 with a file size of 312,884 bytes.

BACKGROUND OF THE INVENTION

Field of the Invention

The present invention relates to enhancer sequences and their derivative structures, and compositions and methods for generating embryonic stem (ES) cells, induced pluripotent stem (iPS) cells and induced neural (iN) cells and cell-based therapies, especially therapies for use in mental and brain diseases and disorders.

Related Art

Cortical interneuron dysfunction contributes to the risk of developing autism, epilepsy, bipolar disorder, schizophrenia, and dementia (Powell et al., 2003; Cossart et al., 2005; Andrews-Zwilling et al., 2010; Marin, 2012; Stanley et al., 2012). Cortical interneurons are born in the progenitor zones of the medial ganglionic eminence (MGE), the caudal ganglionic eminence (CGE) and preoptic area (POA), and migrate tangentially into the cortex (Anderson et al., 1997a; Wonders and Anderson, 2006; Gelman et al., 2011). Several transcription factors, such as Dlx1&2, Nkx2-1 and Lhx6, regulate interneuron development. For instance, Dlx1&2 are required for interneuron migration to the cortex (Anderson et al., 1997a; Anderson et al., 1997b; Cobos et al., 2005; Polley et al., 2006; Cobos et al., 2007; Petryniak et al., 2007). $Dlx1^{-/-}$ mice are viable, but, due to late-onset interneuron loss, develop cortical dysrhythmias and epilepsy (Cobos et al., 2005). Nkx2-1 specifies MGE identity; in Nkx2-1 null mice the MGE is transformed towards LGE/CGE identity and lack MGE-derived interneurons, in part because they fail to express Lhx6 (Sussel et al., 1999; Butt et al., 2008; Du et al., 2008). In turn, Lhx6 is required for differentiation of $Parvalbumin^{+}$ and $Somatostatin^{+}$ interneurons (Liodis et al., 2007; Zhao et al., 2008).

Heterochronic transplantation of rodent embryonic MGE cells into neonatal cortex or adult hippocampus results in their efficient dispersion and integration within host circuits (Wichterle et al., 1999; Alvarez-Dolado et al., 2006; Waldau et al., 2010; Zipancic et al., 2010). Furthermore, studies have demonstrated a therapeutic proof of concept that transplantation of normal MGE cells into rodent models of neuropsychiatric or neurological disorders can suppress seizures, ameliorate phencyclidine-induced cognitive deficits and partially rescue Parkinsonian symptoms (Baraban et al., 2009; Daadi et al., 2009; Martinez-Cerdeno et al., 2010; Waldau et al., 2010; Zipancic et al., 2010; De la Cruz et al., 2011; Tanaka et al., 2011).

While fetal MGE is a potential source for human transplantation, generating MGE cells from stem cells is advantageous due to limited availability and ethical issues surrounding the use of fetal tissue. Thus, several groups have embarked on generating MGE cells from embryonic stem (ES) cells (Watanabe et al., 2005; Eiraku et al., 2008; Danjo et al., 2011).

There are now viable experimental approaches to elucidate the genetic and molecular mechanisms that underlie severe brain disorders through the generation of stem cells, called iPS cells, from the skin of patients. Scientists are now challenged to develop methods to program iPS cells to become the specific types of brain cells that are most relevant to each specific brain disease. For instance, there is evidence that defects in cortical interneurons contribute to epilepsy, autism and schizophrenia.

We have recently demonstrated that transplantation of immature interneurons from an embryonic structure called the medial ganglionic eminence (MGE) into the cortex of epileptic mice (Kv1.1 mutants) suppresses their seizures (Baraban et al, 2009). Thus, transplantation of interneuron precursors into humans who have treatment-resistant epilepsy could be an important therapeutic approach. However, those experiments are not yet feasible as current methods are insufficient to generate and purify human MGE progenitors.

Mouse and human ES cells lines have been generated that express GFP under the control of loci that mark MGE cells. A mouse ES cell line (named: J14) expressing GFP from an Lhx6 BAC transgene can differentiate into Lhx6-$GFP^{+}$ mature cortical interneurons after transplantation (Maroof et al., 2010). Human NKX2-$1^{GFP/w}$ ES cells express GFP from the endogenous NKX2-1 locus; NKX2-$1^{GFP/w}$ cells were differentiated into NKX2-1-$GFP^{+}$ basal forebrain progenitors that further differentiated into $GABA^{+}$ and $TH^{+}$ neurons, and $PDGFR\alpha^{+}$ oligodendrocytes (Goulburn et al., 2011).

Others have described stem cells and identification or purification methods such as, Reubinoff, et al. U.S. Pat. No. 7,947,498, Embryonic stem cells and neural progenitor cells derived therefrom; Reubinoff, et al. U.S. Pat. No. 7,604,992, Generation of neural stem cells from undifferentiated human embryonic stem cells; and Slukvin, I et al., US Patent Publication No. 20110117135, Method of Forming Dendritic Cells from Embryonic Stem Cells, all of which are hereby incorporated by reference. However, there are significant hurdles to identify/purify specific cells states from differentiating human ES/iPS cells. For instance, current methods of MGE induction are inefficient, especially in hES cells, with <1% of the cells expressing the appropriate markers. Thus, there is a current need for robust methods to generate and purify human MGE progenitor cells.

SUMMARY OF THE INVENTION

Herein we describe a strategy for the use of human brain region-specific enhancers to select for interneuron precursors produced from human ES cells. In particular, we have: a) used ChiP-seq, comparative genomics and transgenic mouse data to identify a set of human transcriptional enhancers (SEQ ID NOS:1-145) that are shown to be brain region-specific enhancers for the selection process (See FIG. 1); b) devised a molecular cloning strategy to construct vectors for driving selectable markers (See FIG. 14); c) devised protocols for detecting reporter gene activity driven by such constructs in brain regions and in differentiating stem cells; d) devised a strategy to use these constructs for the differentiation of mouse and human ES cells into progenitor cells of that resemble the MGE and other brain regions; e) devised a strategy to use these constructs for the induction of neural cells from non-pluriopotent cells; and f) devised the use of FACS cell sorting to purify the cells to enable cell transplantation for phenotype analysis (including the identification of cell surface molecules, that will enable other purification approaches).

Thus, the present invention provides for an isolated polynucleotide comprising a sequence selected from one of SEQ ID NOS:1 to 145. The isolated polynucleotide further comprising an inducible promoter and reporter gene. In some embodiments, the isolated polynucleotide further comprising a stem cell-associated gene. In other embodiments, a vector comprising the isolated polynucleotide comprising an enhancer selected from SEQ ID NOS:1-145. In one embodiment, the enhancer selected from SEQ ID NOS: 83, 84, 99-104, 106-108, 110-118, 120-128, and 144-145. In another embodiment, an expression cassette incorporating the vector is also provided.

The present invention further describes a set of enhancers for driving expression in and labeling specific subregions of the mouse or human forebrain, the set consisting of SEQ ID NOS:1-145.

In some embodiments, stem cells, induced pluripotent stem cells, and reprogrammed cells can be generated and isolated using the present set of enhancers. In other embodiments, the cells generated through reprogramming or induced pluripotency can then be used for screening analytes or drugs for therapeutic effects. In other embodiments, the cells generated through reprogramming or induced pluripotency used for transplantation in an organism or subject.

A method for detecting cell differentiation comprising: (1) providing a vector having a promoter, reporter gene and an enhancer selected from SEQ ID NOS:1-145; (2) transfecting a stem cell with the vector; (3) directing differentiation of the stem cell to the desired cell type and expression; (4) detecting cells of the desired cell type by detecting reporter gene expression.

A method for detecting and isolating cells having a specific cell type comprising (1) providing a vector having a promoter, reporter gene and an enhancer selected from SEQ ID NOS:1-145; (2) transfecting a stem cell with the vector; (3) directing differentiation of the stem cell to the desired cell type and expression; (4) detecting cells of the desired cell type by detecting reporter gene expression and (5) isolating the cells of the desired cell type.

A method for generating stem cells comprising the steps of: (1) providing a vector comprising a promoter, a reporter gene, and an enhancer selected from SEQ ID NOS:1-145; (2) transfecting a stem cell with the vector; (3) directing differentiation of the stem cell to the desired cell type and expression; (5) inducing reporter gene expression; (6) detecting cells of the desired cell type by detecting reporter gene expression and (7) isolating the cells of the desired cell type.

A method for screening or assaying drugs for therapeutic effect on neural cells, comprising (1) providing a vector having a promoter, reporter gene and an enhancer selected from SEQ ID NOS:1-145; (2) transfecting a stem cell or programmable cell with the vector; (3) directing differentiation of the cell to the desired cell type and expression; (4) detecting cells of the desired cell type by detecting reporter gene expression; (5) isolating the cells of the desired cell type; (6) contacting said cells with a drug to screen or assay for desired therapeutic effect; and (7) detecting response of said cells to said drug to determine the therapeutic effect of said drug on said cell.

A method for driving expression in specific forebrain substructure regions, comprising (1) providing a vector having a promoter, reporter gene and an enhancer selected from SEQ ID NOS:1-145; (2) transfecting a stem cell with the vector; (3) directing differentiation of the stem cell to the desired cell type and expression; (4) detecting cells of the desired cell type by detecting reporter gene expression; (5) isolating cells the cells of the desired cell type; and (6) transplanting said cells into a subject to drive expression in specific forebrain substructure regions.

A method for detecting induction and differentiation in induced pluripotent cells comprising: (1) providing a vector comprising a promoter, a reporter gene, stem cell-associated genes, and an enhancer selected from SEQ ID NOS:1-145; (2) transfecting a non-pluripotent cell with the vector; (3) inducing pluripotency in the non-pluripotent cell; (4) directing differentiation of the induced pluripotent cell to the desired cell type and expression; (5) inducing reporter A method for generating induced pluripotent stem cells comprising the steps of: (1) providing a vector comprising a promoter, a reporter gene, stem cell-associated genes, and an enhancer selected from SEQ ID NOS:1-145; (2) transfecting a non-pluripotent cell with the vector; (3) inducing pluripotency in the non-pluripotent cell; (4) directing differentiation of the induced pluripotent cell to the desired cell type and expression; (5) inducing reporter gene expression; (6) detecting cells of the desired cell type by detecting reporter gene expression and (7) isolating the cells of the desired cell type.

A method for screening or assaying drugs for therapeutic effect on neural cells, comprising (1) providing a vector having a promoter, reporter gene and an enhancer selected from SEQ ID NOS:1-145; (2) transfecting a non-pluripotent cell with the vector; (3) inducing pluripotency in the non-pluripotent cell; (4) directing differentiation of the cell to the desired cell type and expression; (5) inducing reporter gene expression; (6) detecting cells of the desired cell type by detecting reporter gene expression; (7) isolating the cells of the desired cell type; (8) contacting said cells with a drug to screen or assay for desired therapeutic effect; and (9) detecting response of said cells to said drug to determine the therapeutic effect of said drug on said cell.

A method for driving expression in specific forebrain substructure regions, comprising (1) providing a vector having a promoter, reporter gene and an enhancer selected from SEQ ID NOS:1-145; (2) transfecting a non-pluripotent cell with the vector; (3) inducing pluripotency in the non-pluripotent cell; (4) directing differentiation of the cell to the desired cell type and expression; (5) inducing reporter gene expression; (6) detecting cells of the desired cell type by detecting reporter gene expression; (7) isolating the cells of the desired cell type; and (8) transplanting said cells into a subject to drive expression in specific forebrain substructure regions.

A method for driving expression in specific forebrain substructure regions, comprising (1) providing a vector having a promoter, reporter gene and an enhancer selected from SEQ ID NOS:1-145; (2) transfecting a non-pluripotent cell with the vector; (3) reprogramming of the non-pluriopotent cell to the desired cell type and expression; (4) detecting cells of the desired cell type by detecting reporter gene expression; (5) isolating cells the cells of the desired cell type; and (6) transplanting said cells into a subject to drive expression in specific forebrain substructure regions.

A method for isolating neural cells comprising the steps of: (1) providing a vector comprising a promoter, a reporter gene, neural cell-associated genes for reprogramming, and an enhancer selected from SEQ ID NOS:1-145; (2) transfecting a non-pluripotent cell with the vector; (3) reprogramming said cell to a specific cell type; (4) inducing reporter gene expression; (5) detecting cells of the desired cell type by detecting reporter gene expression and (6) isolating the cells of the desired cell type.

A method for detecting reprogrammed neural cells comprising: (1) providing a vector comprising a promoter, a reporter gene, neural cell-associated genes for reprogramming, and an enhancer selected from SEQ ID NOS:1-145; (2) transfecting a non-pluripotent cell with the vector; (3) reprogramming said cell to a specific cell type; (4) inducing reporter gene expression; (5) detecting cells of the desired cell type by detecting reporter gene expression.

A method for screening drugs for therapeutic effect comprising: (a) providing a vector comprising a promoter, a reporter gene, neural cell-associated genes for reprogramming, and an enhancer selected from SEQ ID NOS:1-145; (2) transfecting a non-pluripotent cell with the vector; (3) reprogramming said cell to a specific cell type; (4) inducing reporter gene expression; (5) detecting cells of the desired cell type by detecting reporter gene expression; (6) isolating the cells of the desired cell type; (7) contacting said cells of the desired cell type with a drug to be screened for therapeutic effect; and (8) detecting any change in the cells of the desired cell type after contact with said drug.

A method for driving expression in specific forebrain substructure regions, comprising (1) providing a vector having a promoter, reporter gene, neural cell-associated genes for reprogramming and an enhancer selected from SEQ ID NOS:1-145; (2) transfecting a non-pluripotent cell with the vector; (3) reprogramming said cell to a specific cell type; (4) detecting cells of the desired cell type by detecting reporter gene expression; (5) isolating the cells of the desired cell type; and (6) transplanting said cells into a subject to drive expression in specific forebrain substructure regions.

BRIEF DESCRIPTION OF THE FIGURES AND TABLES

FIG. 1: Subset of forebrain enhancers identified by conservation or p300 binding at whole-mount resolution. a) A selection of 50 reproducible forebrain enhancers at e11.5 identified in this study. In each case, only one of several (minimum: 3) embryos with the same pattern is shown. Additional embryos obtained with each enhancer construct can be viewed at the http internet address enhancer.lbl.gov. Enhancer elements are sorted by broad similarities of patterns as evident at whole-mount resolution. b) Examples of genes implicated in forebrain development that were screened for enhancers in the present study and for which enhancers are shown in a). A full list of all 329 constructs tested in this study, including annotations of enhancer activity patterns and information about neighboring genes are provided in Table 5.

FIG. 2: Subset of forebrain enhancers with activity in different subregions of the developing pallium. a) Overview of annotated structures in the approximate coronal sectioning plane shown in b)-s). b)-s) Selected enhancers that reproducibly label subregions of the developing pallium. Enhancers are arranged by their spatial specificities, sorted from medial through dorsal and lateral to ventral pallium. Detailed annotations of all patterns, as well as additional enhancers that drive expression in these subregions are provided in Table 2. Full serial sets of sections for each enhancer can be viewed at the enhancer.lbl.gov website, using the enhancer IDs indicated in the figure panels. MP, medial pallium; DP, dorsal pallium; LP, lateral pallium; VP, ventral pallium; LGE, lateral ganglionic eminence; Se, septum. t) Comparison of enhancer activities between e11.5 and e13.5. Arrowheads indicate activity in neuronal precursor/differentiation zones, and additional arrowheads indicate immature neurons in the cortical plate.

Figure 3:
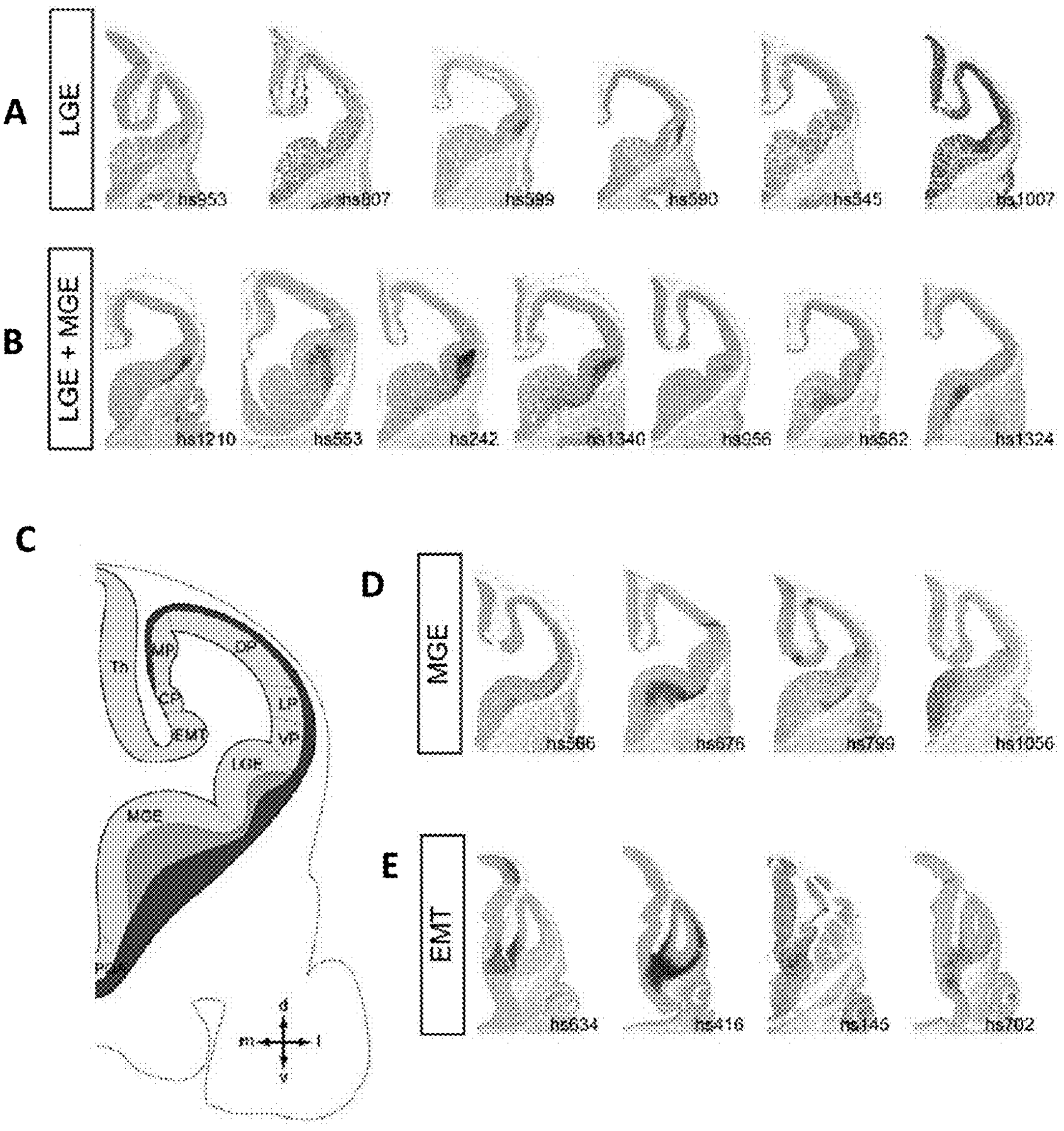

FIG. 3: Subset of forebrain enhancers with activity in different subregions of the subpallium and eminentia thalami. a), b), d), e) Selected enhancers that target LacZ expression a) predominantly or exclusively to subregions of the LGE, b) both the LGE and MGE, d) predominantly the MGE and e) the EMT. c) Schematic overview of structures in the approximate sectioning plane shown in a), b), d) and e). Depending on the rostrocaudal extent of staining for some enhancers more rostral or caudal planes than indicated in c) were chosen to illustrate salient features of the respective patterns. The majority of subpallial enhancers drove expression to the marginal zone, but we also observed enhancers that were active in the ventricular zone (e.g., panel d, hs1056). Th, thalamus; EMT, eminentia thalami; CP, choroid plexus; MP, medial pallium; DP, dorsal pallium; LP, lateral pallium; VP, ventral pallium; LGE, lateral ganglionic eminence; MGE, medial ganglionic eminence; POA, preoptic area.

Figure 4:
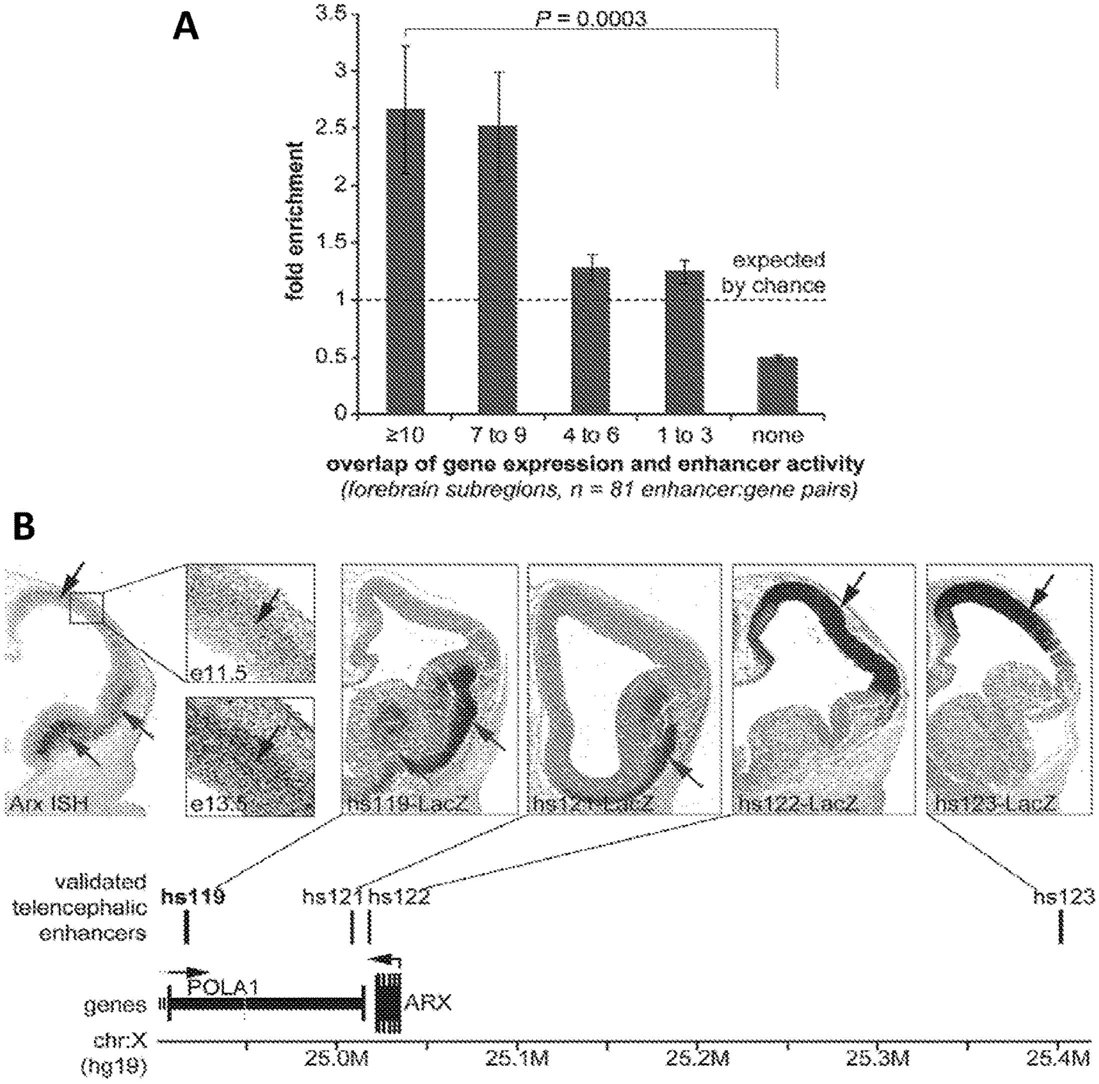
Figure 4:
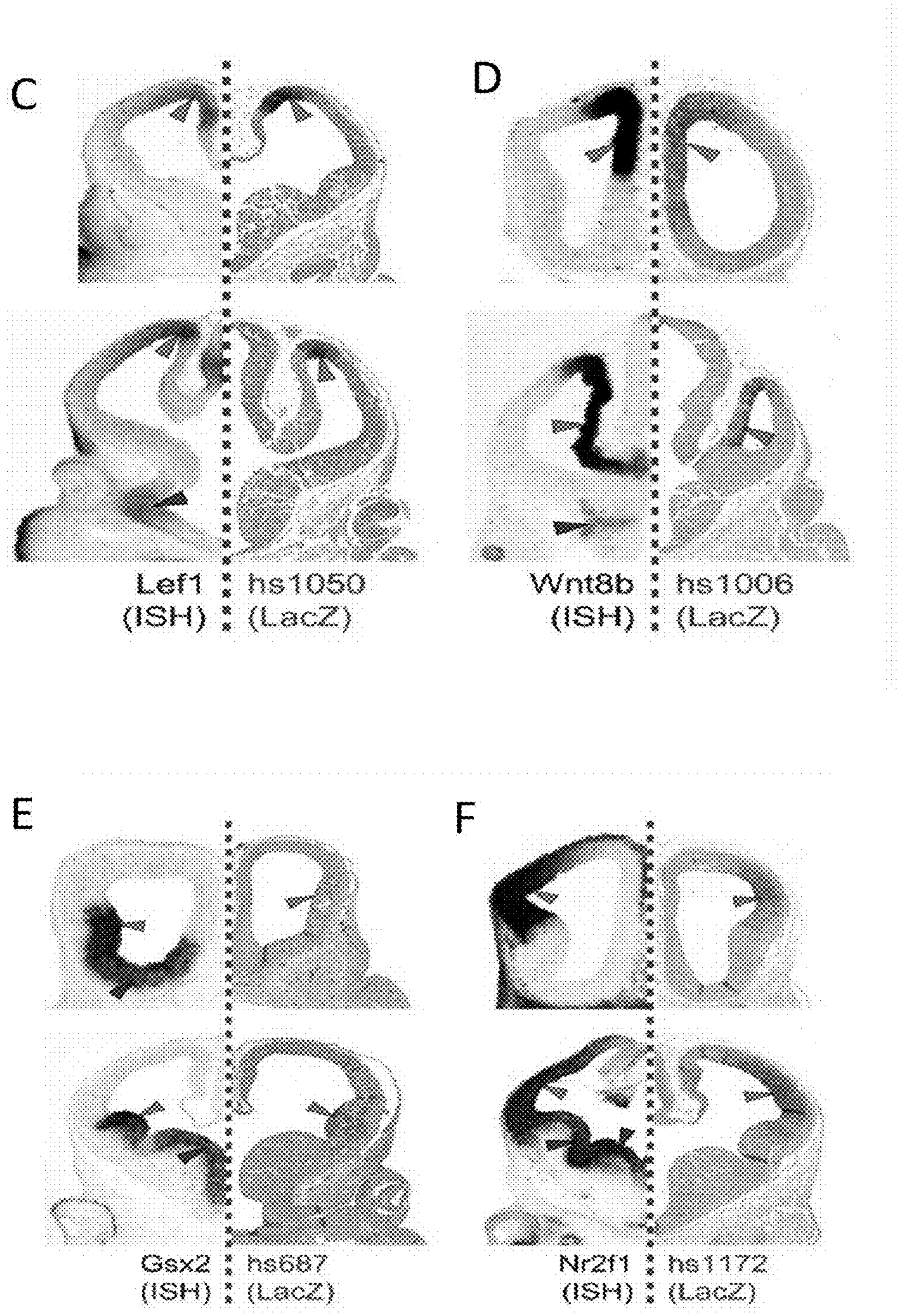

FIG. 4: Correlation of spatial enhancer activity patterns with mRNA expression patterns of nearby genes. a) To assess overall correlations, the annotated activity patterns of telencephalic enhancers were compared to mRNA expression patterns of nearby genes. Compared to randomly assigned enhancer:gene pairs, there is a highly significant enrichment of cases in which concordant enhancer activity and gene expression is observed in one or multiple telencephalic subregions (P=0.0003, Mann-Whitney test). b) Example of individual enhancers recapitulating aspects of the gene expression pattern. The Arx gene is expressed both in subpallial (arrows) and pallial (additional arrows) regions, with increasing expression in pallial regions from e11.5 to e13.5 (insets). The activity patterns of four enhancers in the extended Arx locus are shown, two of which drive subpallial (hs119, hs121) and two of which drive pallial expression (hs122, hs123), revealing that developmental Arx regulation is more complex than initially suggested (23). RNA in situ hybridization images: Allen Developing Mouse Brain Atlas (Website for developingmouse.brain-map.org), reproduced with permission from Allen Institute for Brain Science. c-f) Additional examples of overlap in enhancer activity with expression of nearby genes in rostral (top) and more caudal (bottom) areas of the telencephalon at e11.5. In all four cases, there was spatial overlap in activity (arrowheads), as well as gene expression in additional regions that did not show enhancer activity (additional arrowheads).

Figure 5A:
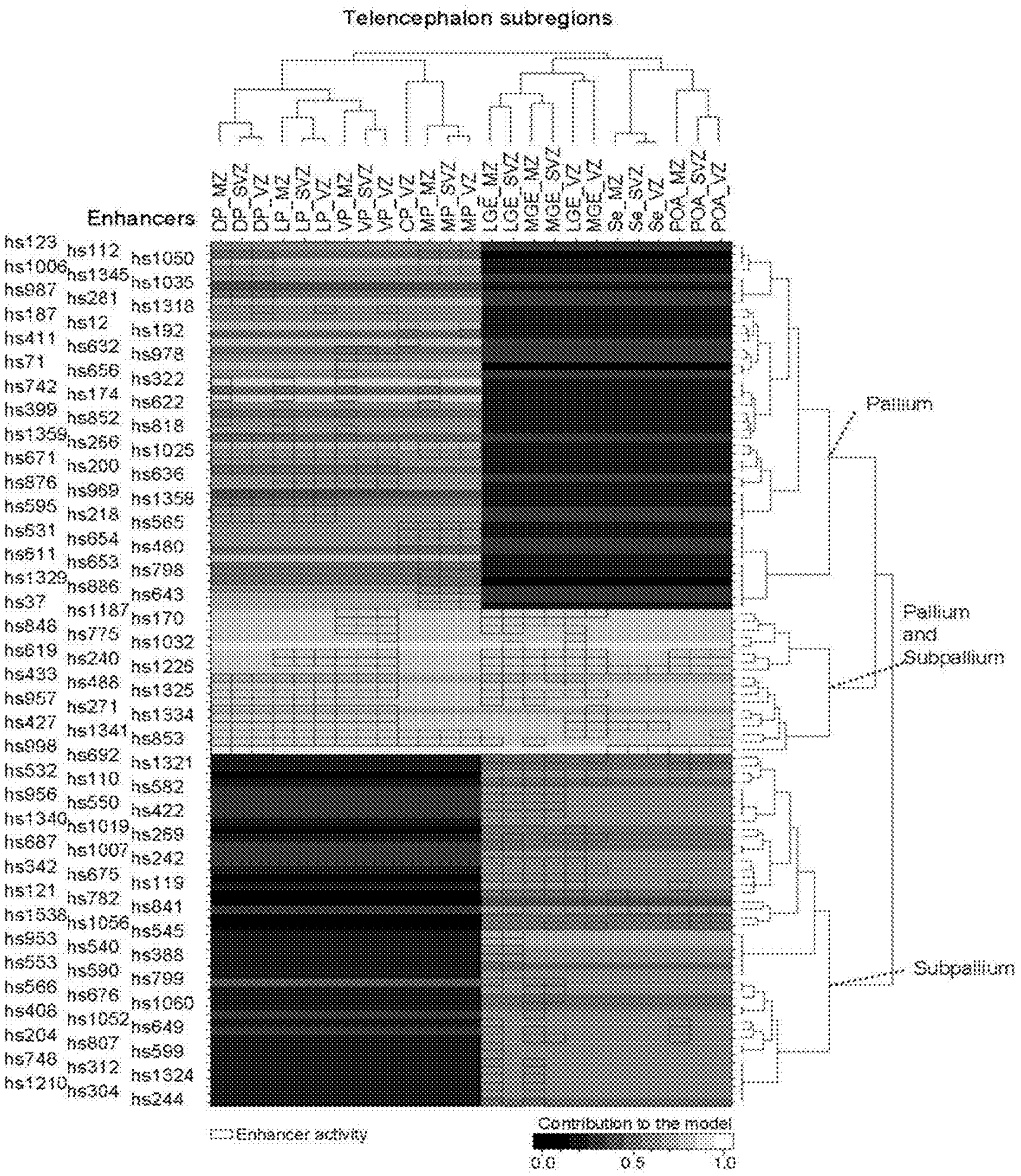
Figure 5B:
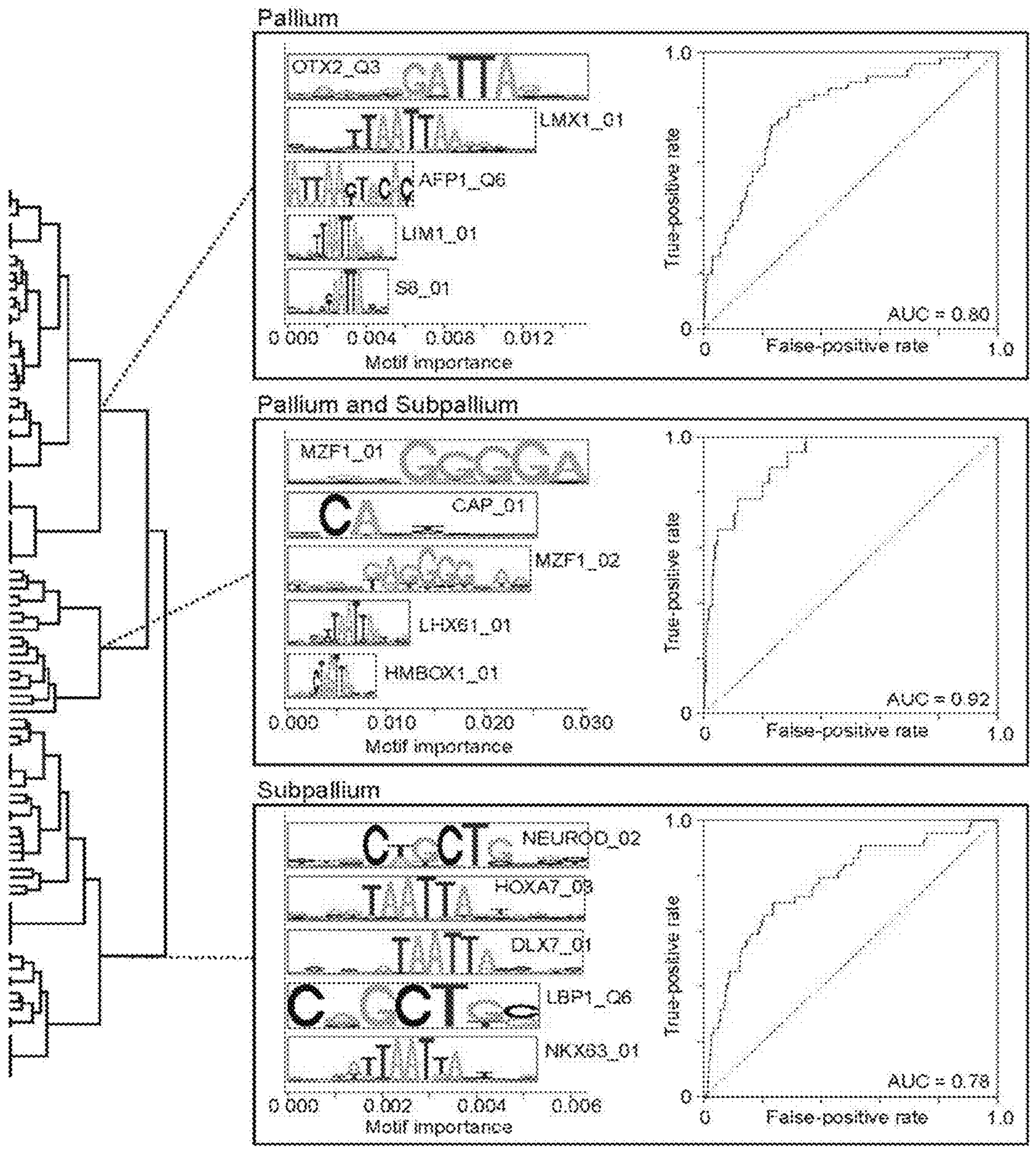
Figure 5C:
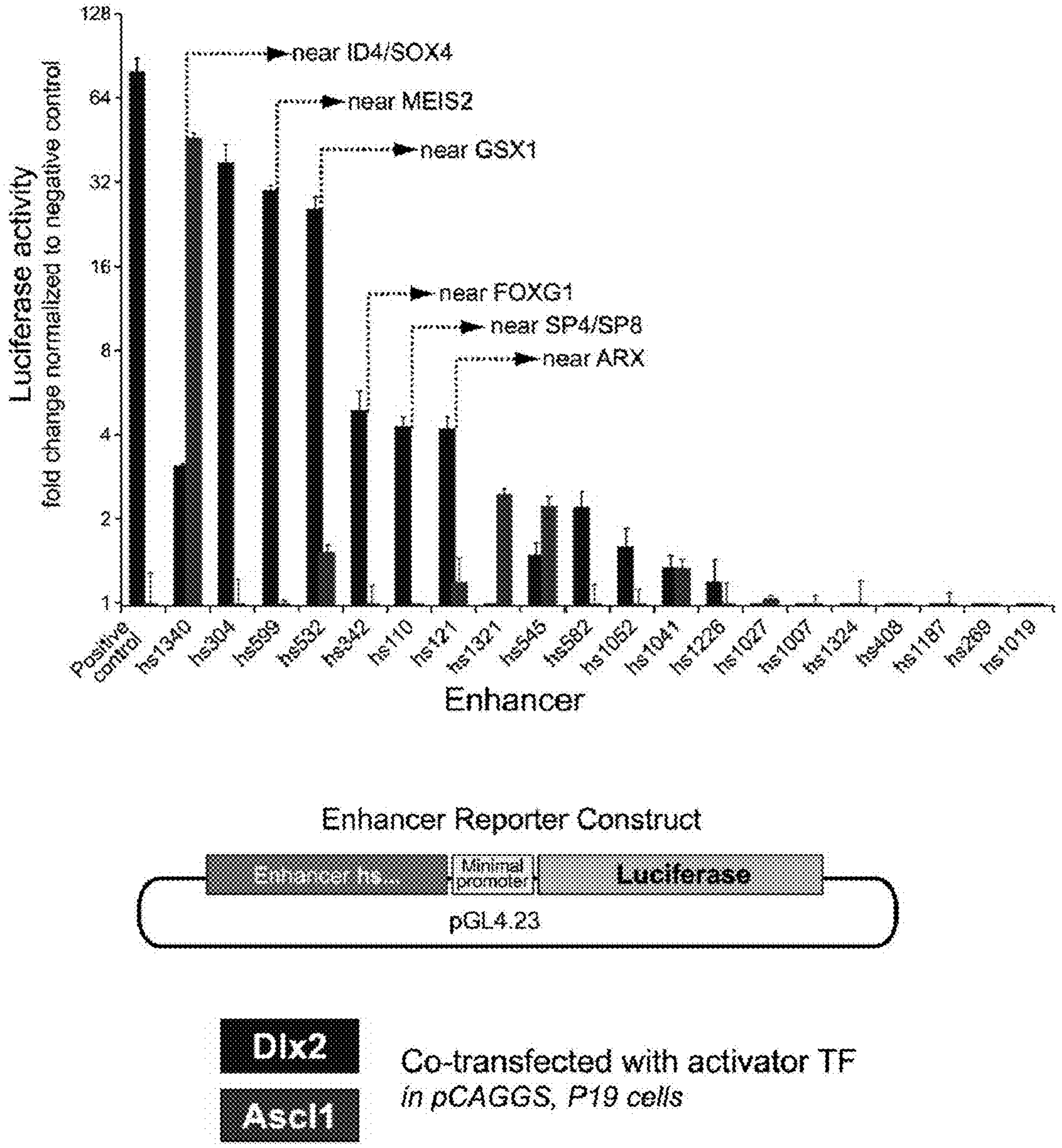
Figure 7:
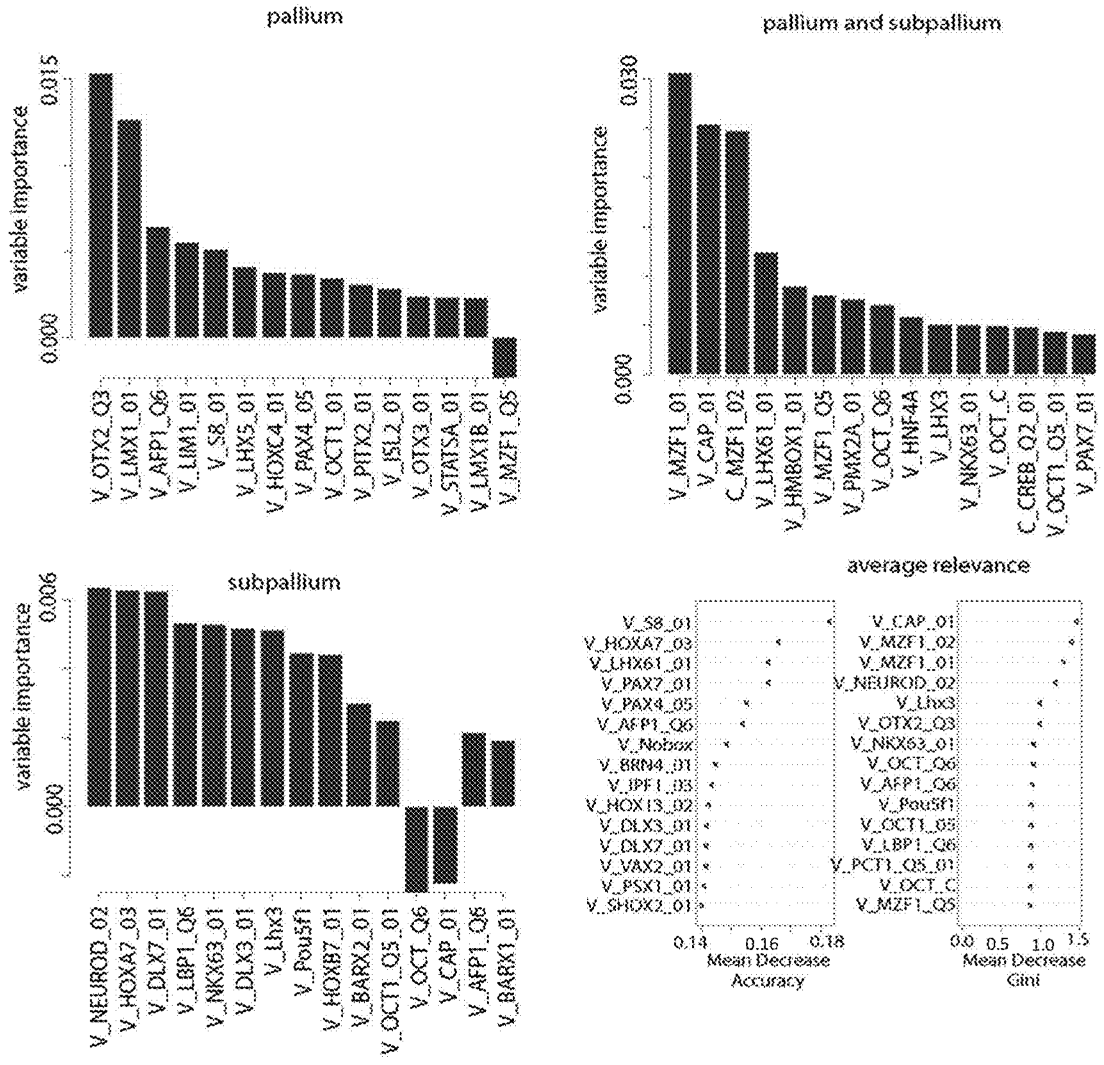

FIGS. 5A-C: Sequence classifier derived from high-resolution activity annotations. FIG. 5A) Squares indicate enhancers (rows) active in different telencephalic subregions (columns). Unsupervised clustering (Jaccard's coefficient, average linkage) of telencephalic subregions by similarity of enhancer activity profiles (top dendrogram) largely follows known developmental, functional and topological relations of telencephalic subregions. Clustering (Euclidean distances, Ward's method) of enhancers by similarity of observed activity in telencephalic subregions suggests functional subgroups (right dendrogram). Shades of gray indicate the proportion of decision trees assigning each enhancer to the pallium or subpallium class (for pallium and subpallium enhancers) or to the compound pallium/subpallium class (for compound enhancers). FIG. 5B) The Random Forest (RF) classifier distinguishes enhancers that are active in pallium only (top), in both pallium and subpallium (center), and in subpallium only (bottom). Left: Top 5 sequence motifs characterizing each class of enhancers and their relative contribution to the classification. Additional motifs are shown in FIG. 7. Right: Receiver-operating characteristic (ROC) curves of predictive performances. The area under the curve (AUC) measures the ability of the classifier to limit incorrect predictions while maintaining accuracy in true predictions. For example, the "pallium and subpallium" classifier correctly identifies ~70% of enhancers in this cluster at a false positive rate of 10%. FIG. 5C) Luciferase cotransfection assays of 20 subpallial enhancers with either the transcription factors Dlx2 or Ascl1 in P19 cells. Error bars represent SD. See also FIGS. 7-10, and, Tables 2, 6, 7, 8 and 9.

Figure 6:
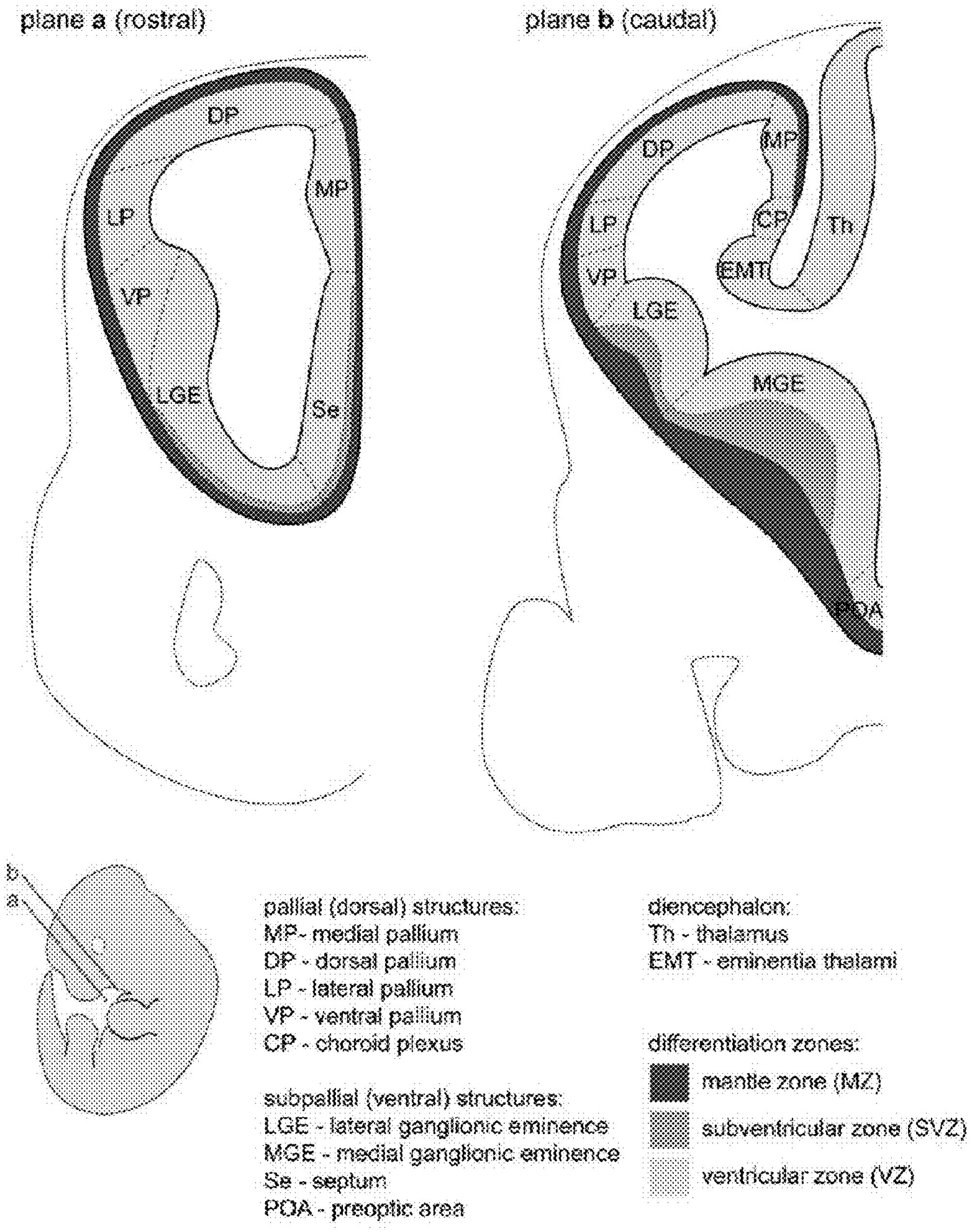

FIG. 6: Neuroanatomical regions and boundaries used for annotation of enhancer activities and gene expression patterns in the e11.5 telencephalon and adjacent brain regions.

FIG. 7: Most relevant binding site occurrence for the prediction of three different classes of forebrain enhancers (pallium, subpallium, and pallium and subpallium enhancers), ranked in decreasing order of importance with respect to the mean decrease in prediction accuracy. The panel on the bottom right shows the overall top ranking binding sites and their mean decrease in accuracy and GINI measure in discriminating forebrain enhancers and control genomic regions.

Figure 8:
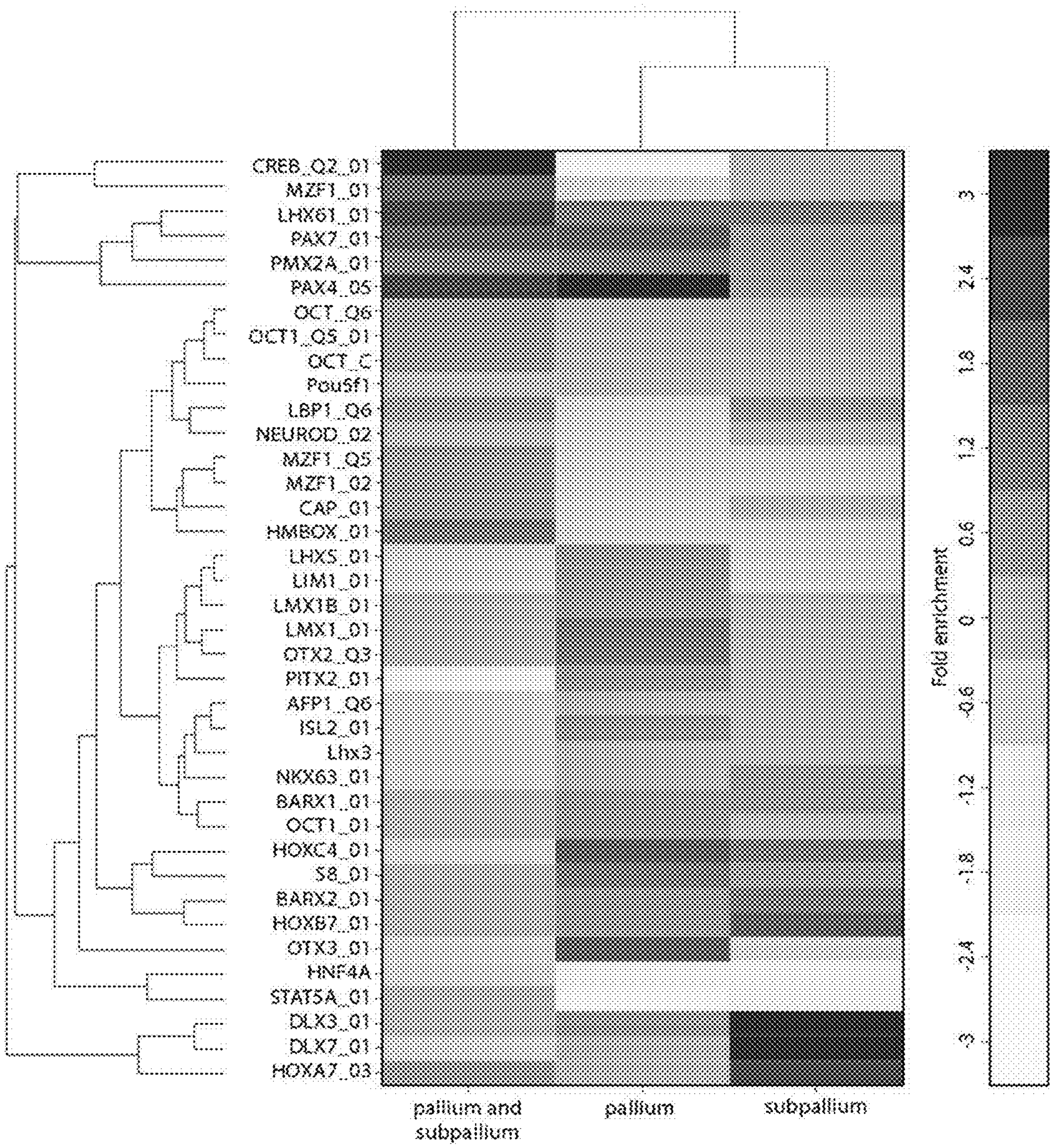

FIG. 8: Distribution of most important TF binding sites. The heat map shows the over-/under-representation of the most important TRANSFAC and JASPAR TF binding sites as identified by the RF classifier among enhancers active in three different telencephalon subregions, relative to the genomic background. Negative values indicate under-representation and positive values over-representation. Rows (binding sites) and columns (subregions) are hierarchically clustered and ordered by similarity to each other, using Euclidean distance measure with average linkage in the case of rows, and the Spearman correlation with average linkage in the case of columns.

Figure 9A:
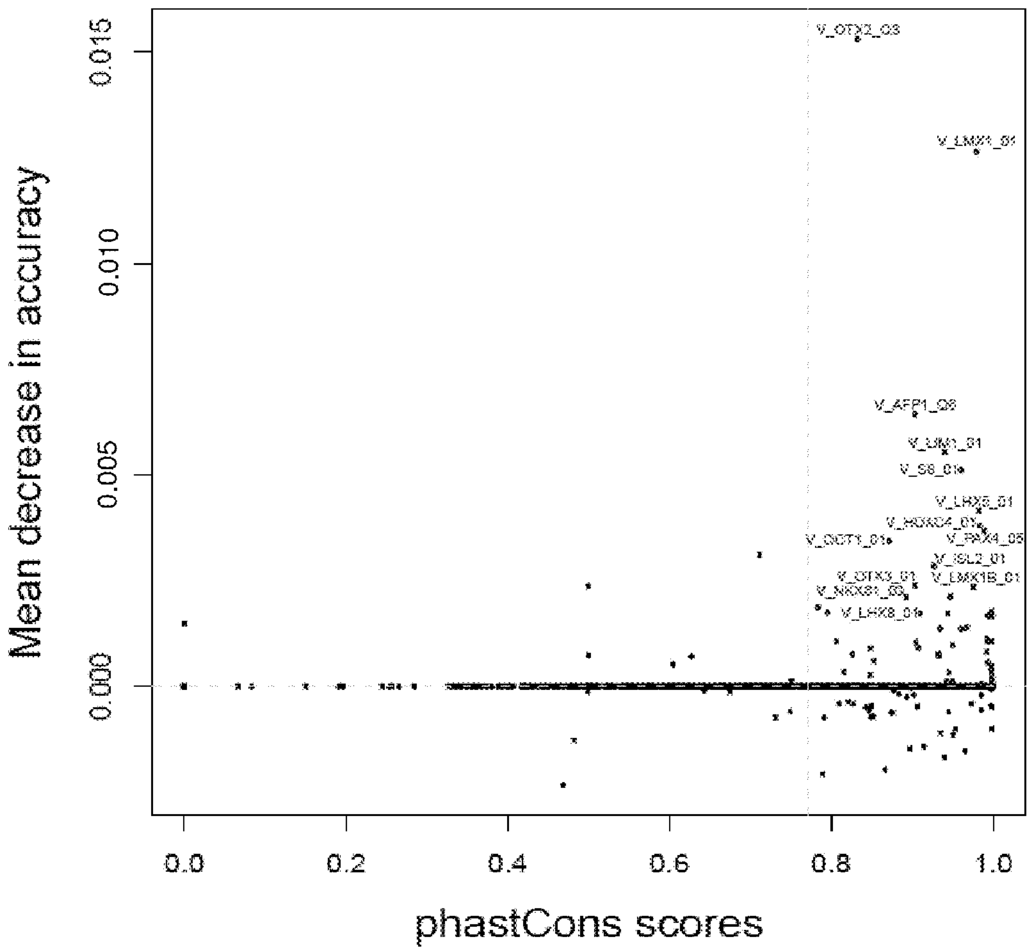
Figure 9B:
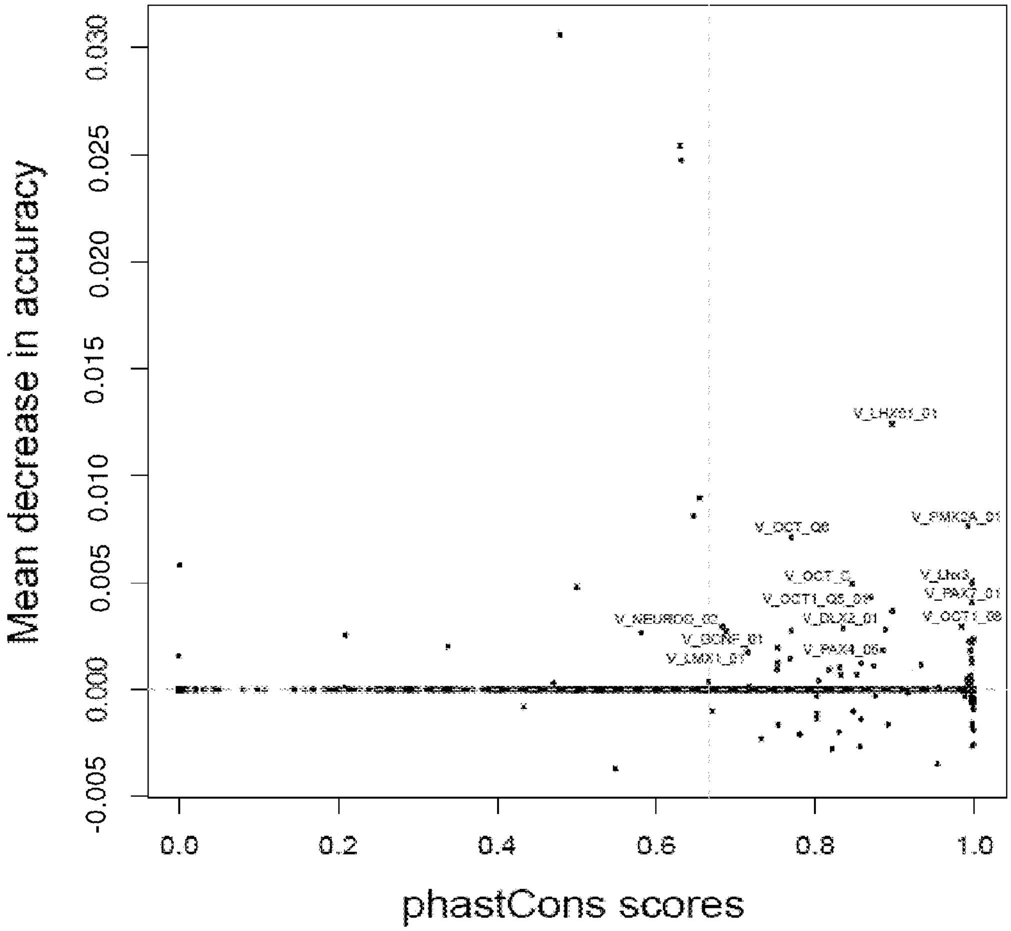
Figure 9C:
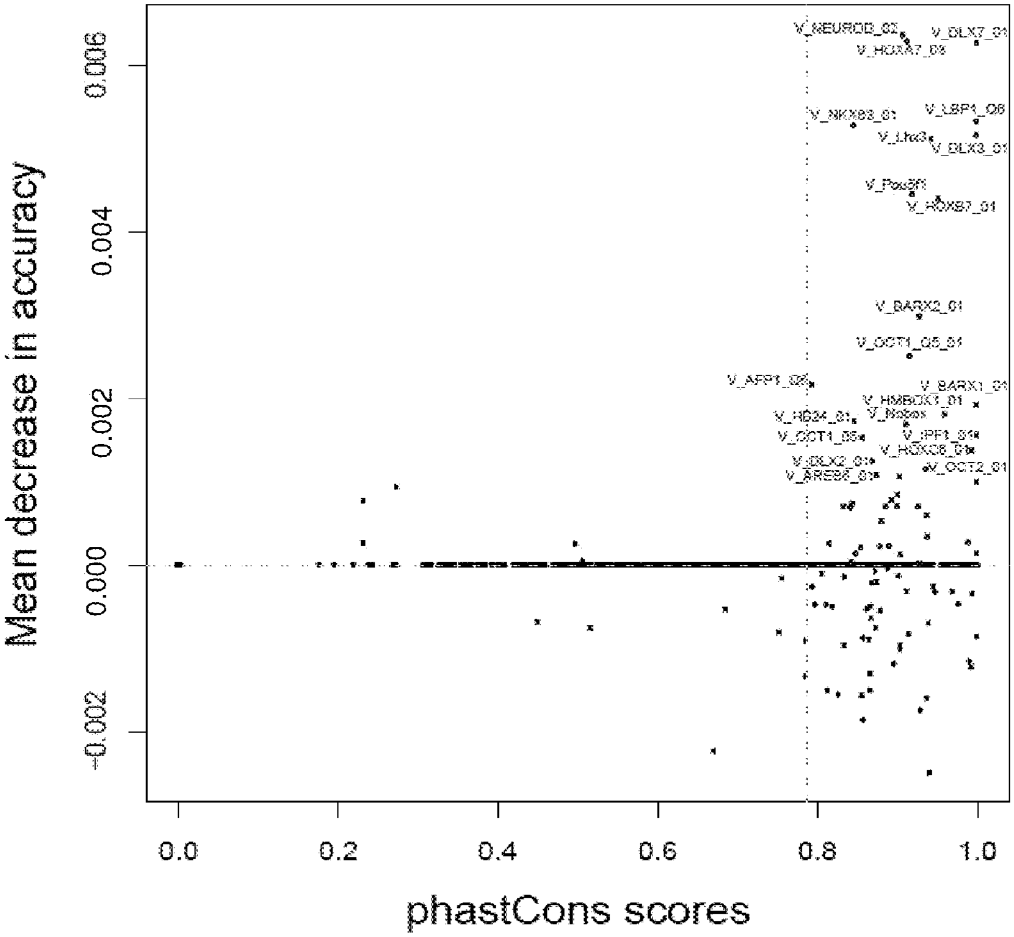
Figure 9D:
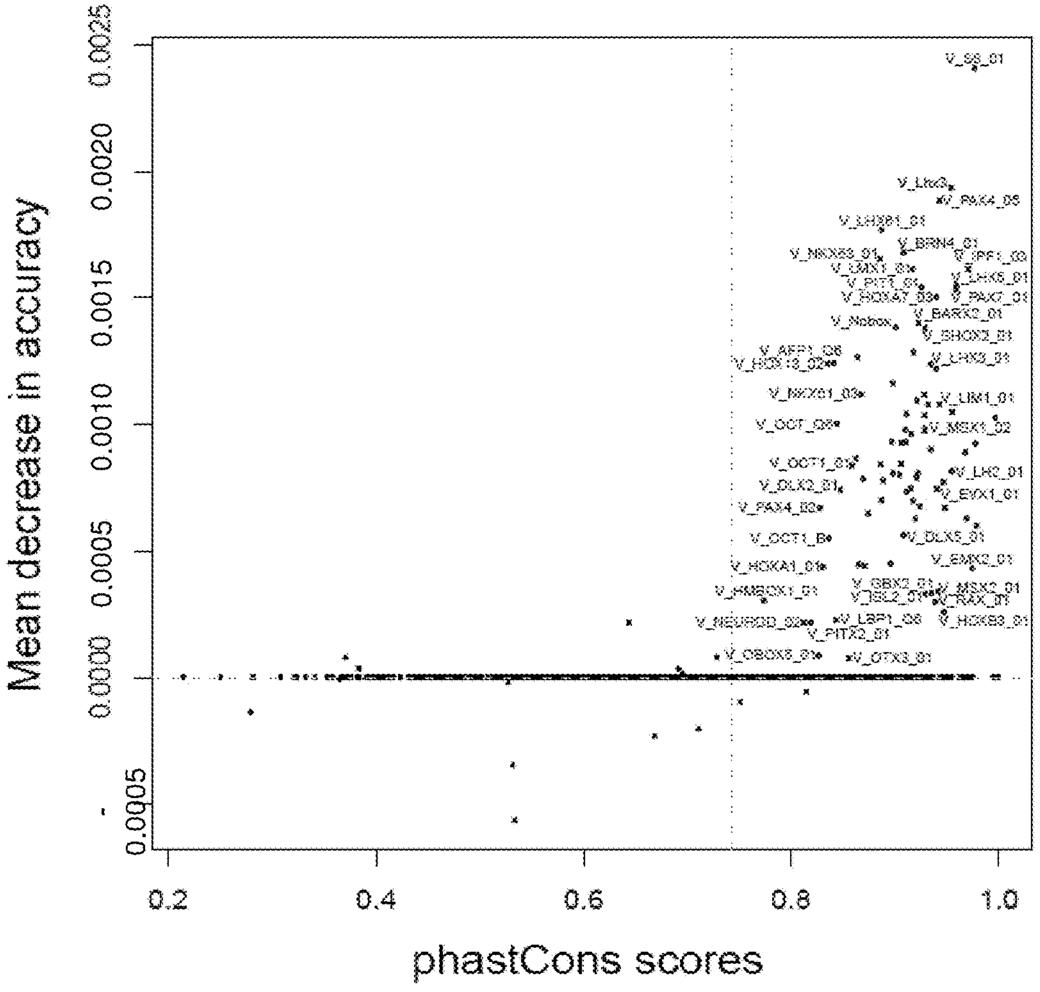

FIGS. 9A-9D: Conservation of putative TF binding sites identified as important by the RF classifier. Each point represents a particular binding site in the TRANSFAC and JASPAR motif databases. The y-axis shows the means decrease in accuracy of the RF classifier when the frequencies of the corresponding TF binding site are randomly permuted across the enhancer sequences. The x-axis indicates the average phastCons scores for putative TF binding sites in the predicted forebrain enhancers. Medians are denoted by gray dotted lines. TF binding sites for which both importance and conservation values are greater than the respective medians are depicted, names of selected TF binding sites are indicated. FIG. 9A shows data relating to the pallium only. FIG. 9B shows data relating to pallium and subpallium. FIG. 9C shows data relating to the subpallium only FIG. 9D shows the average across the classifier when trying to separate sequences active in any part of the pallium and/or subpallium from random controls.

Figure 10:
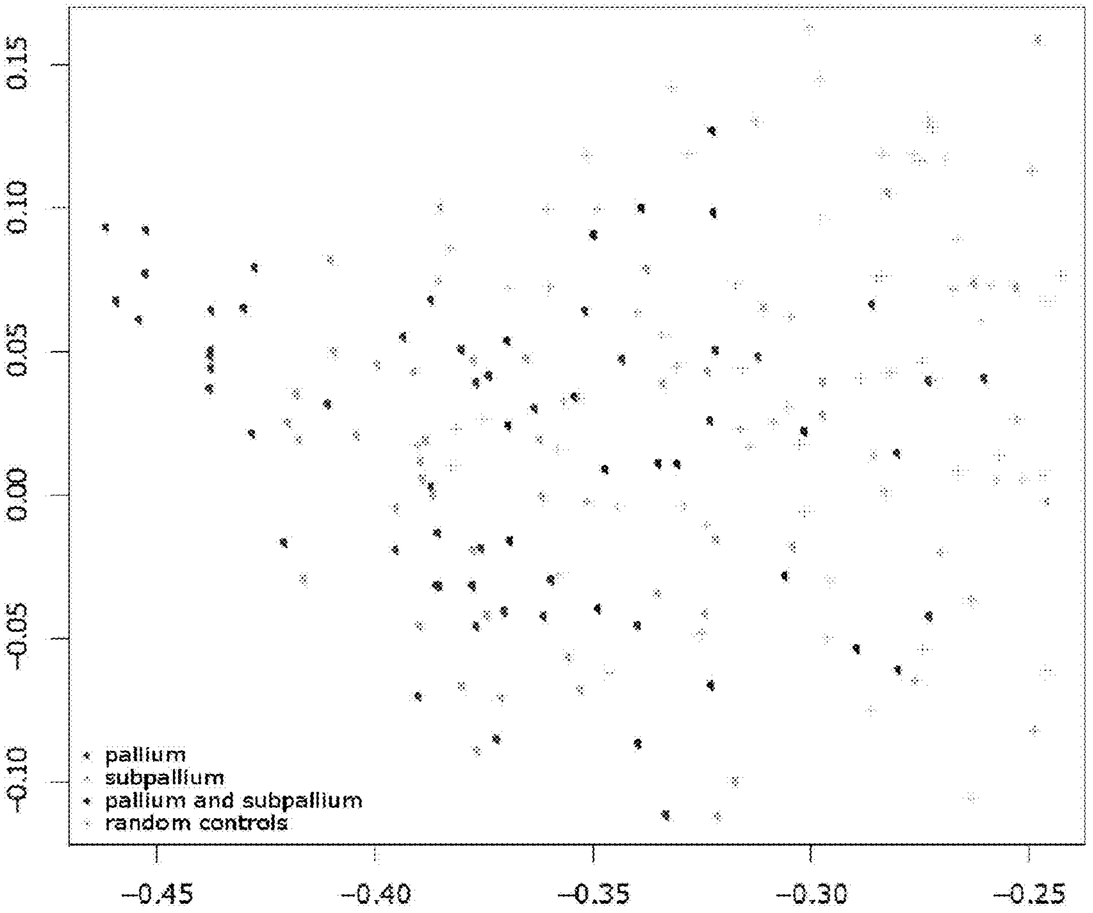

FIG. 10: Multidimensional scaling plot displaying the level of similarity between enhancer sequences active in three forebrain subregions (plot axes represent arbitrary units and are therefore dimensionless).

Figure 11:
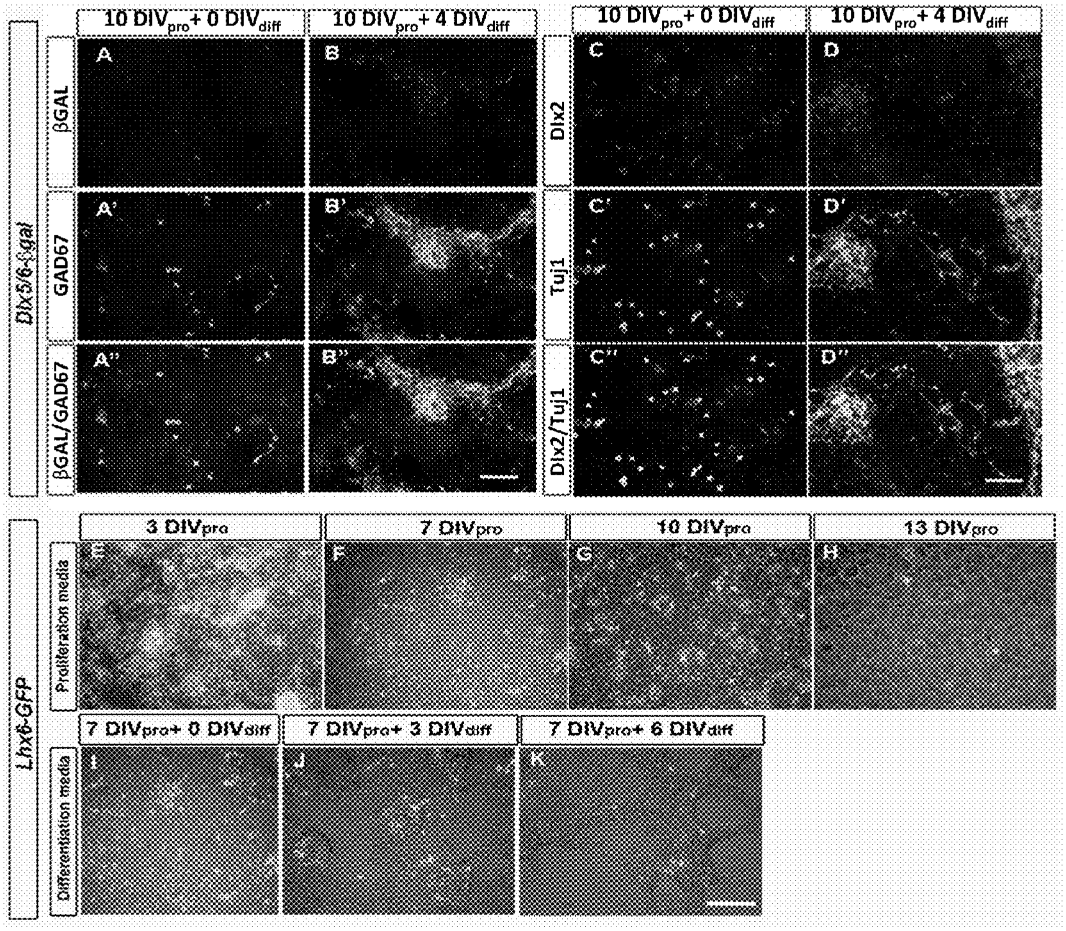

FIG. 11. Primary MGE cells in vitro differentiate into Dlx2$^+$ GABAergic neurons, but lose Lhx6 expression. A-D", E13.5 MGE (ventricular and subventricular zone of the MGE) from Dlx5/6-LacZ$^+$ embryos was removed from the telencephalon, dissociated and cultured in vitro using the media as described (Walton et al., 2006). Ten days after growing in the proliferation media (10 DIV$_{pro}$), the cells were differentiated using differentiation media (DIV$_{diff}$). The state of differentiation was compared during proliferation (A-A" and C-C") or after 4 days of differentiation (B-B" and D-D") by immunostaining with antibodies to β-Galactosidase (β-Gal), GAD1 (GAD67), Dlx2 and Class III β-Tubulin (Tuj1). Scale bar, 100 μm. E-K, Lhx6-GFP expression in cells derived from E12.5 MGE (ventricular and subventricular zone of the MGE). The Lhx6-GFP$^+$ MGEs were dissociated and cultured in vitro Top row: MGE cells grown in proliferation media for 3 (E), 7 (F), 10 (G) and 13 (H) days. Bottom row: MGE cells cultured in proliferation media for seven days and then in differentiation media for 0 (I), 3 (J), and 6 (K) days. Images are overlay of DIC images and green fluorescent images. Scale bar, 150 μm.

Figure 12:
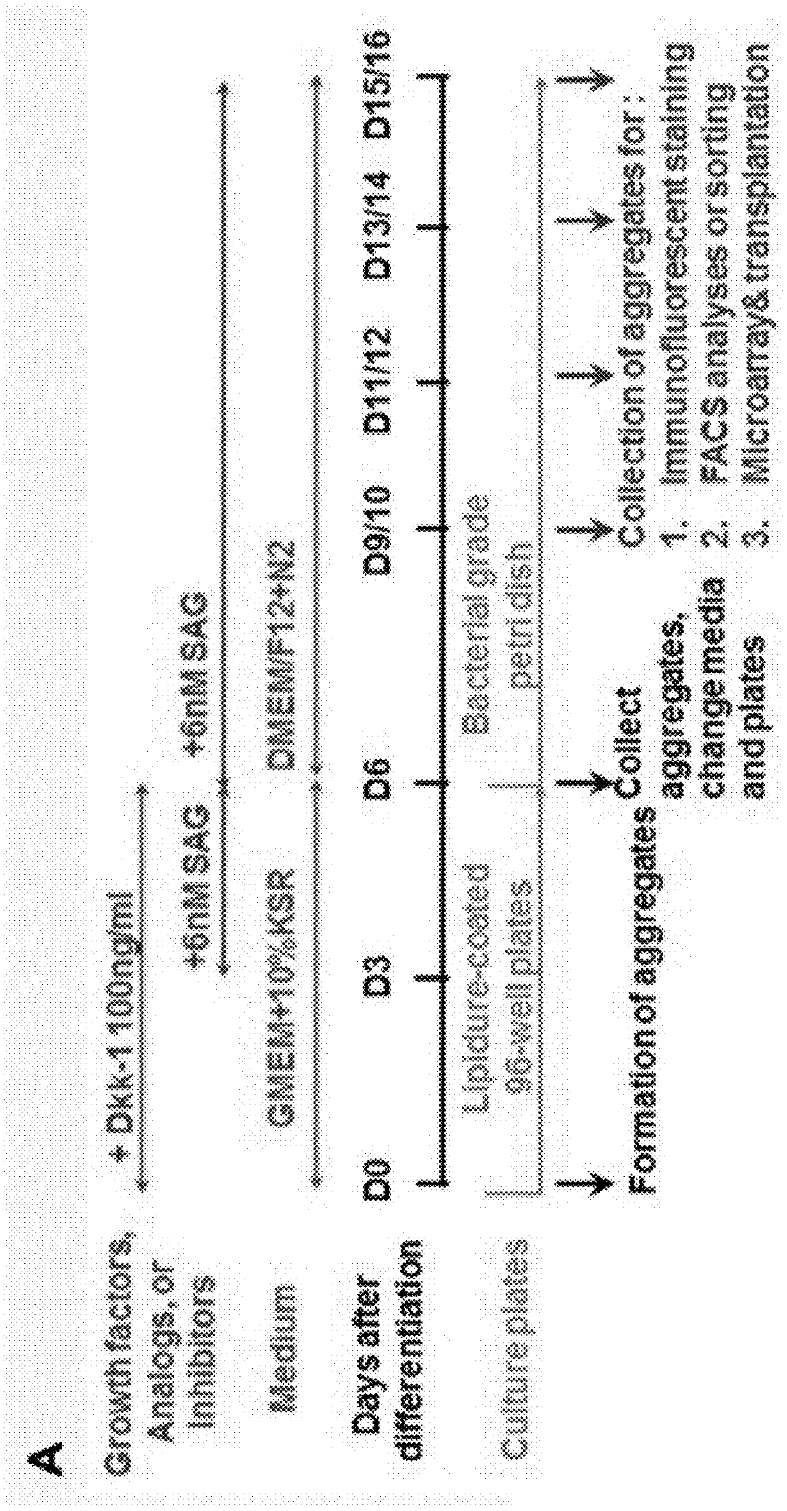
Figure 12:
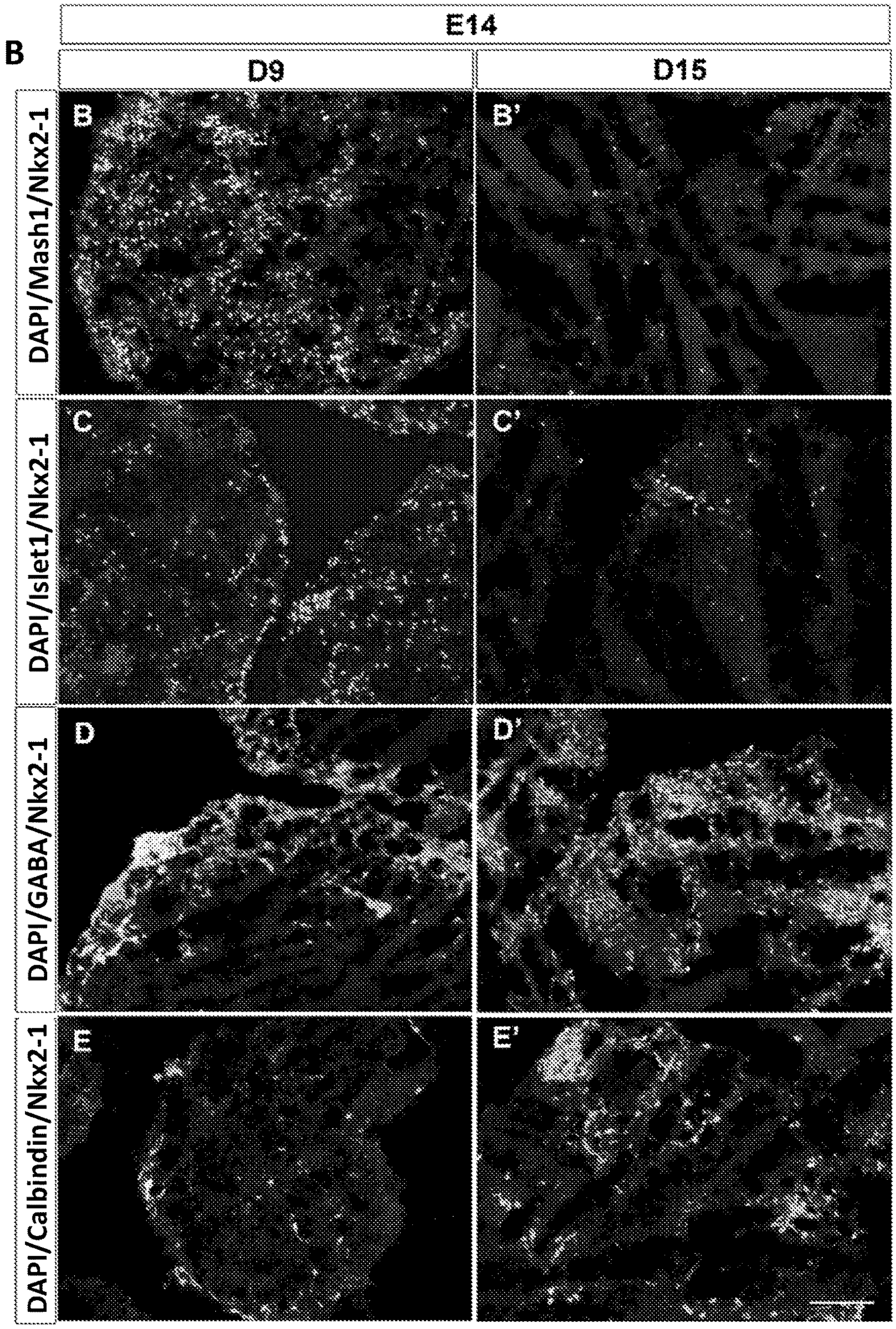

FIG. 12. MGE differentiation protocol from mouse ES cells and characterization of differentiated E14 cells. A, Schema outlining the MGE differentiation protocol. The black horizontal line: time line of days after initiation of differentiation. Days when a treatment was introduced are indicated (see Materials and Methods for details). From day 0 (D0) to day 6 (D6), cells were cultured with GMEM and 10% KSR in a lipidure-coated 96-well plate). Dkk-1 (100 ng/ml) was added on D0 and SAG (6 nM) was added on D3. On D6, cell aggregates were collected and transferred to a bacterial grade sterile petri dish in DMEM/F-12 supplemented with N2. Additional SAG (6 nM) was added to the medium on D6. Starting on D9 (and the following days), aggregates were collected either for immunofluorescent staining, FACS analysis, or FACS purification followed by gene expression microarray analysis, or transplantation. B-E', Expression of Nkx2-1 with other markers: Mash1 (B, B'), Islet1 (C, C'), GABA (D, D'), and Calbindin (E, E'), in E14 cell line on D9 and D15 after differentiation. DAPI nucleus staining was shown in all panels. There are more Mash1$^+$ cells than Nloc2-1$^+$ cells (and some of them express both proteins) on D9. On D15, both protein expressions are reduced with more Nkx2-1$^+$ cells than Mash1$^+$ cells. Scale bar: 100 μm.

Figure 13:
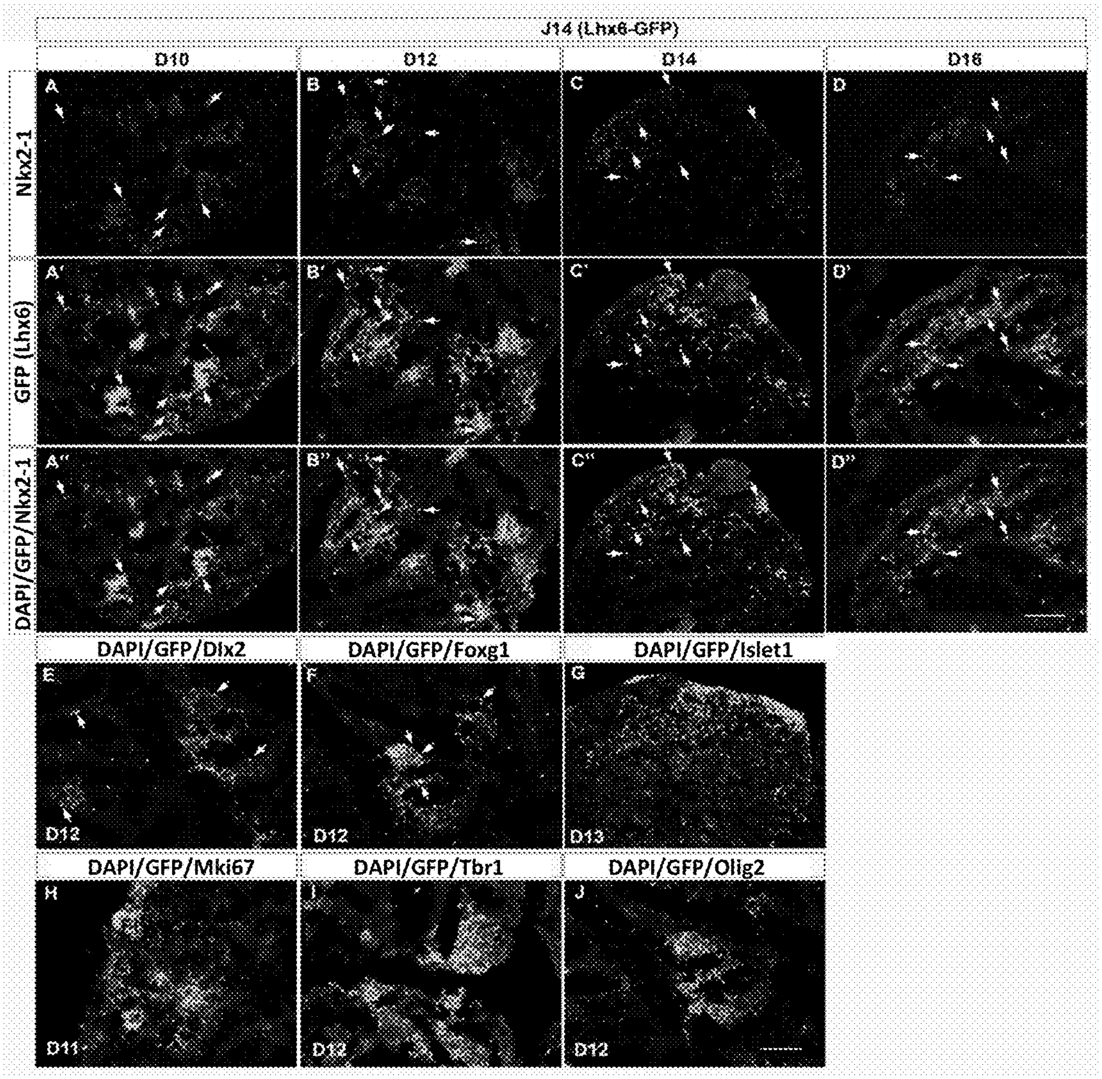

FIG. 13. Characterization of MGE-like differentiated J14 (Lhx6-GFP) cells. A-D", Nkx2-1 expression is shown; Lhx6-GFP expression is shown; DAPI stains the nucleus blue. A-A": D10; B-B": D12; C-C": D14; D-D": D16. White arrows indicate cells co-expressing Nkx2-1 and Lhx6-GFP. E, Dlx2 and Lhx6-GFP expression on D12. White arrows indicate co-localization of Dlx2 and Lhx6-GFP. F, Foxg1 and Lhx6-GFP expression on D12. White arrows indicate co-localization of Foxg1 and Lhx6-GFP. G, Islet1 and Lhx6-GFP expression on D12. H, There were only a few Mki67$^+$ cells that expressed Lhx6-GFP on D11. I, No Tbr1$^+$ cells were detected on D12. J, Olig2$^+$ cells and Lhx6-GFP$^+$ cells were mutually exclusive on D12. Scale bar for all panels: 100 μm.

Figure 14:
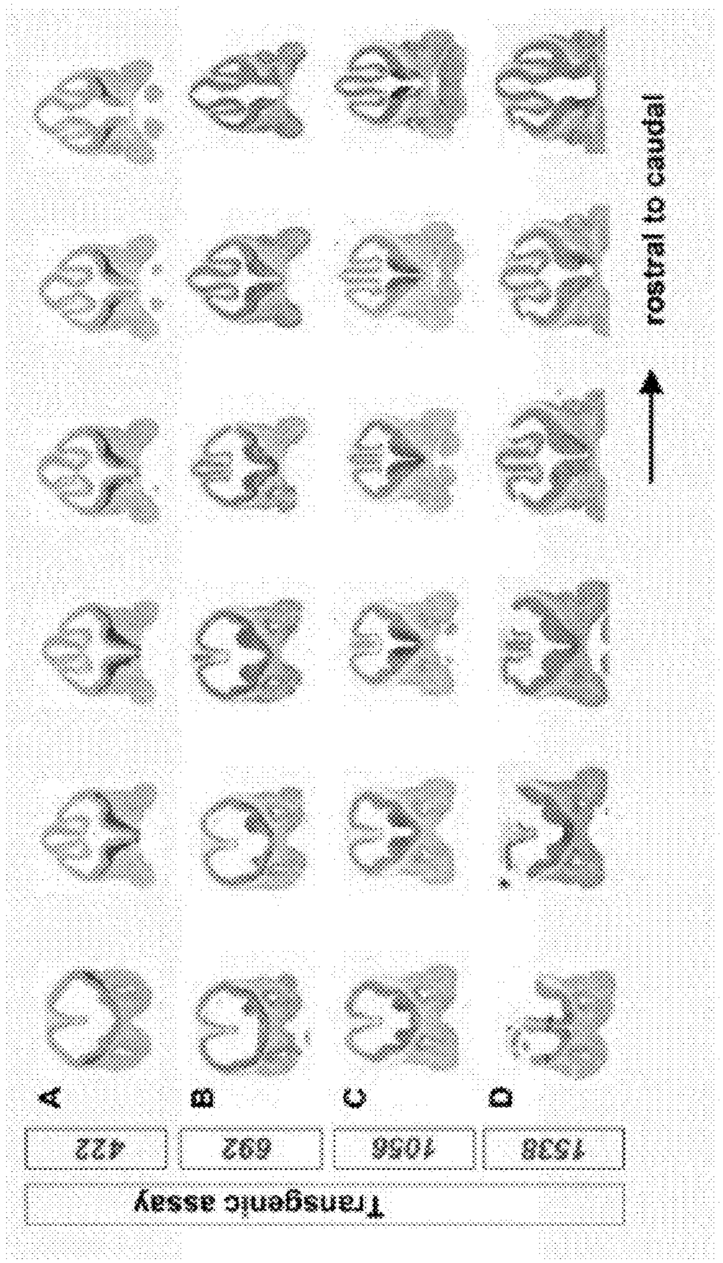
Figure 14E:
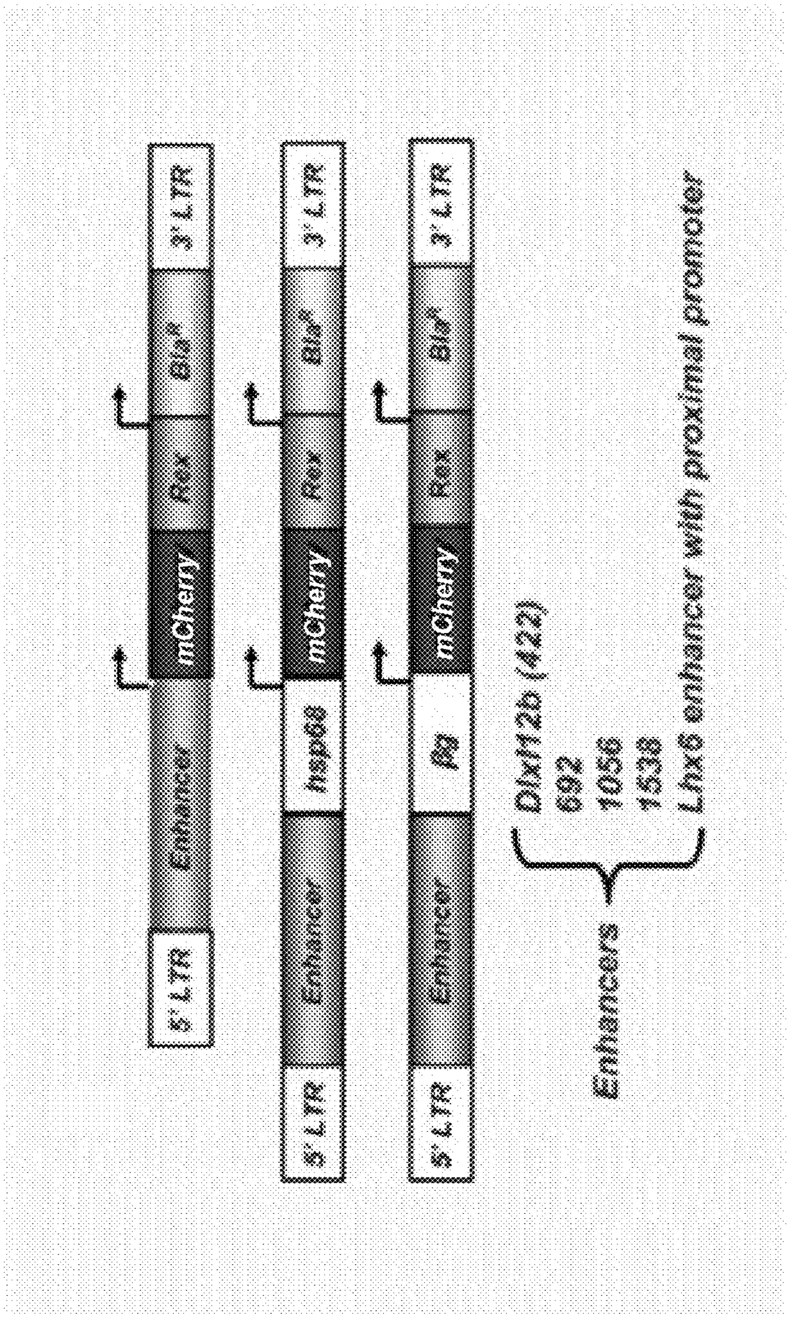
Figure 14:
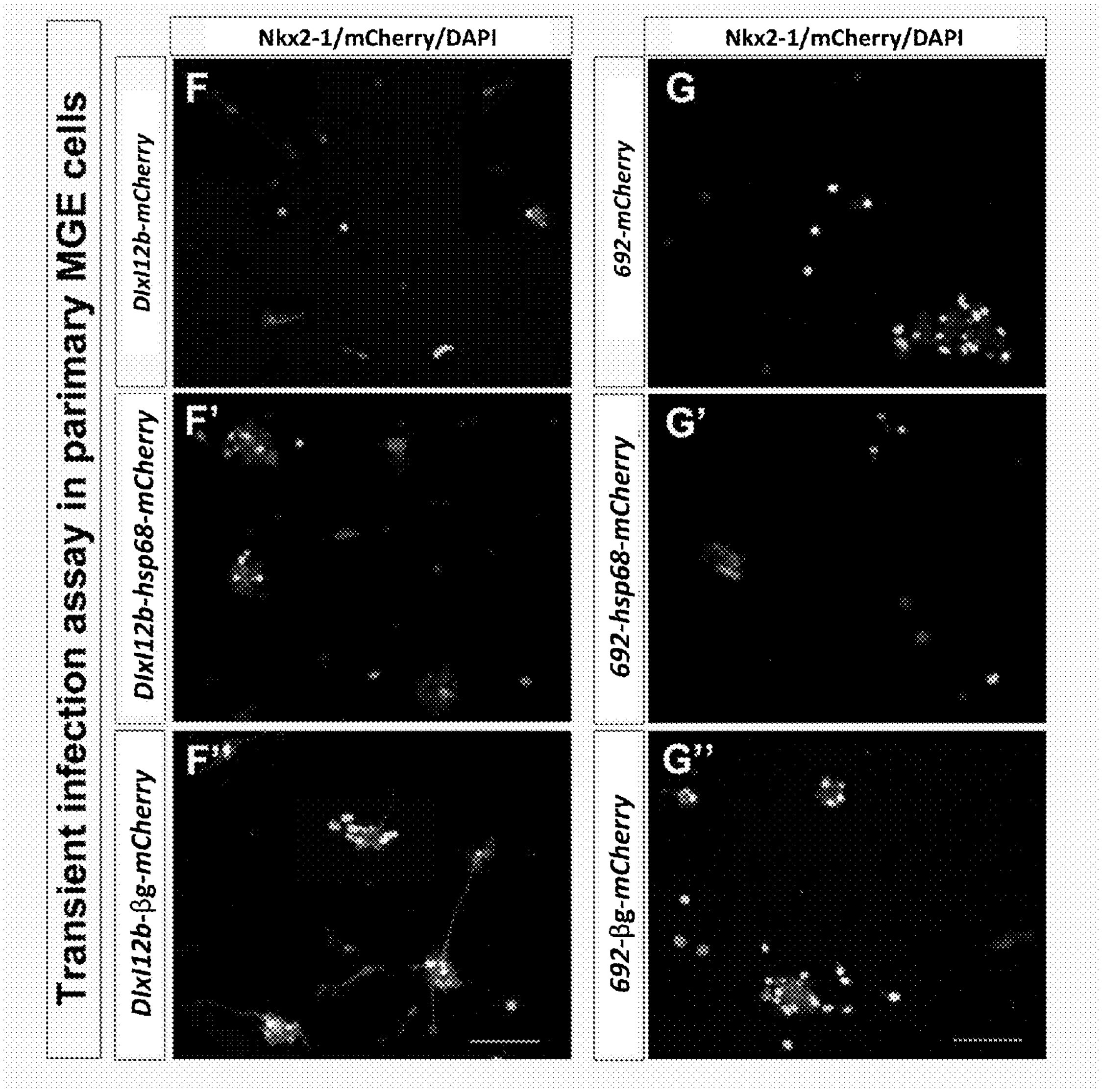

FIG. 14. Expression of MGE enhancers, and lentiviral constructs used to transduce them into primary MGE cells and ES cells. A-D, MGE enhancers driving β-galactosidase expression (X-Gal staining) of E11.5 telencephalic sections from transient transgenic mice. Coronal sections are shown from rostral to caudal (left to right). Each transgene is composed of one enhancer element 422 (A), 692 (B), 1056 (C), or 1538 (D), followed by an hsp68 minimal promoter that drives expression of LacZ (β-Galactosidase). E, Lentiviral constructs harboring each enhancer reporter cassette for making stable mouse embryonic stem cell clones. Each construct is flanked by a lentiviral 5'LTR and a 3'LTR, and contains two separated gene expression cassettes: the first is the enhancer/promotor driving a mCherry reporter gene; the second is Rex-1 promoter driving the Blasticidin resistant gene (BlaR) (Kita-Matsuo et al., 2009). The enhancers tested in this study were: mouse DlxI12b enhancer (a shorter version of enhancer 422), three novel human enhancers (692, 1056, and 1538), and a mouse Lhx6 proximal enhancer/promoter DNA element (Du et al., 2008). F-G", Enhancer activity in MGE primary cultures. E13.5 MGE cells were infected with lentiviruses indicated (F: DlxI12b-mCherry; F': DlxI12b-hsp-mCherry; F": DlxI12b-βg-mCherry; G: 692-mCherry, G': 692-hsp-mCherry; G":692-βg-mCherry), followed by three days of culture prior to Nkx2-1 and mCherry immunostaining; DAPI nuclear stain in blue. Pictures are composites from several different fields. Scale bar, 50 μm FIG. 15. Characterization of DlxI12b-βglobin-mCherry in E14 & J14 ES cells differentiated toward an MGE-like identity. Marker expression analysis was done with immunofluorescence of sections from aggregates of differentiated ES cells. (A-C) mCherry expression driven by the DlxI12b-βglobin enhancer/promoter; Lhx6-GFP expression in panels A-A" (D11 aggregates), B-B" (D13), C-C" (D15). D, DlxI12b-βg-mCherry and Nkx2-1 expression on D13 of differentiation. E, DlxI12b-βg-mCherry and Dlx2 expression on D13. (F) DlxI12b-βg-mCherry and Foxg1 expression on D11. G, DlxI12b-βg-mCherry and Islet1 expression on D13. H, DlxI12b-βg-mCherry and Olig2 expression on day 12. I, Most of the DlxI12b-βg-mCherry$^+$ cells also express Calbindin. Scale bar, 100 μm. White arrows indicates markers co-labeling.

Figure 16:
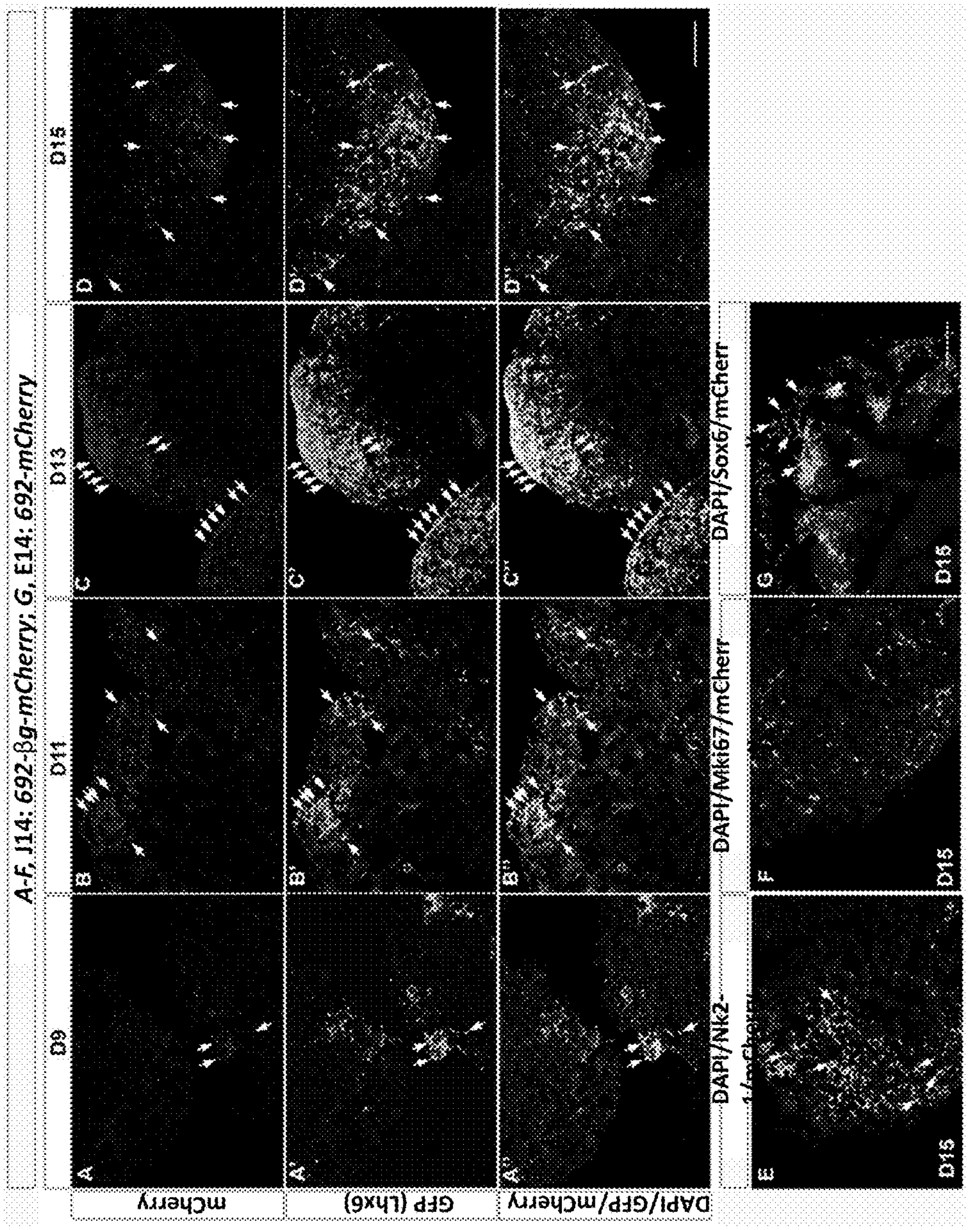

FIG. 16. Enhancer 692-βg-mCherry was active in 70% of Lhx6 GFP$^+$ cells. A-D", mCherry expression driven by 692-βg and Lhx6-GFP expression in panels A-A" (D9 aggregates), B-B" (D11), C-C" (D13), and D-D" (D15). On D13 and D15, about 70% of the 692-mCherry$^+$ cells were labeled with Lhx6-GFP (white arrows). E, 692-βg-mCherry and Nkx2-1 expression on D15. F, 692-βg-mCherry$^+$ cells are postmitotic, as they don't express Mki67 on D15 (and other earlier time points). G, E14 cells line carrying 692-mCherry was examined with Sox6 expression. All of the 692-mCherry$^+$ cells express Sox6. White arrows indicate markers co-labeling. Scale bar, 100 μm.

Figure 17:
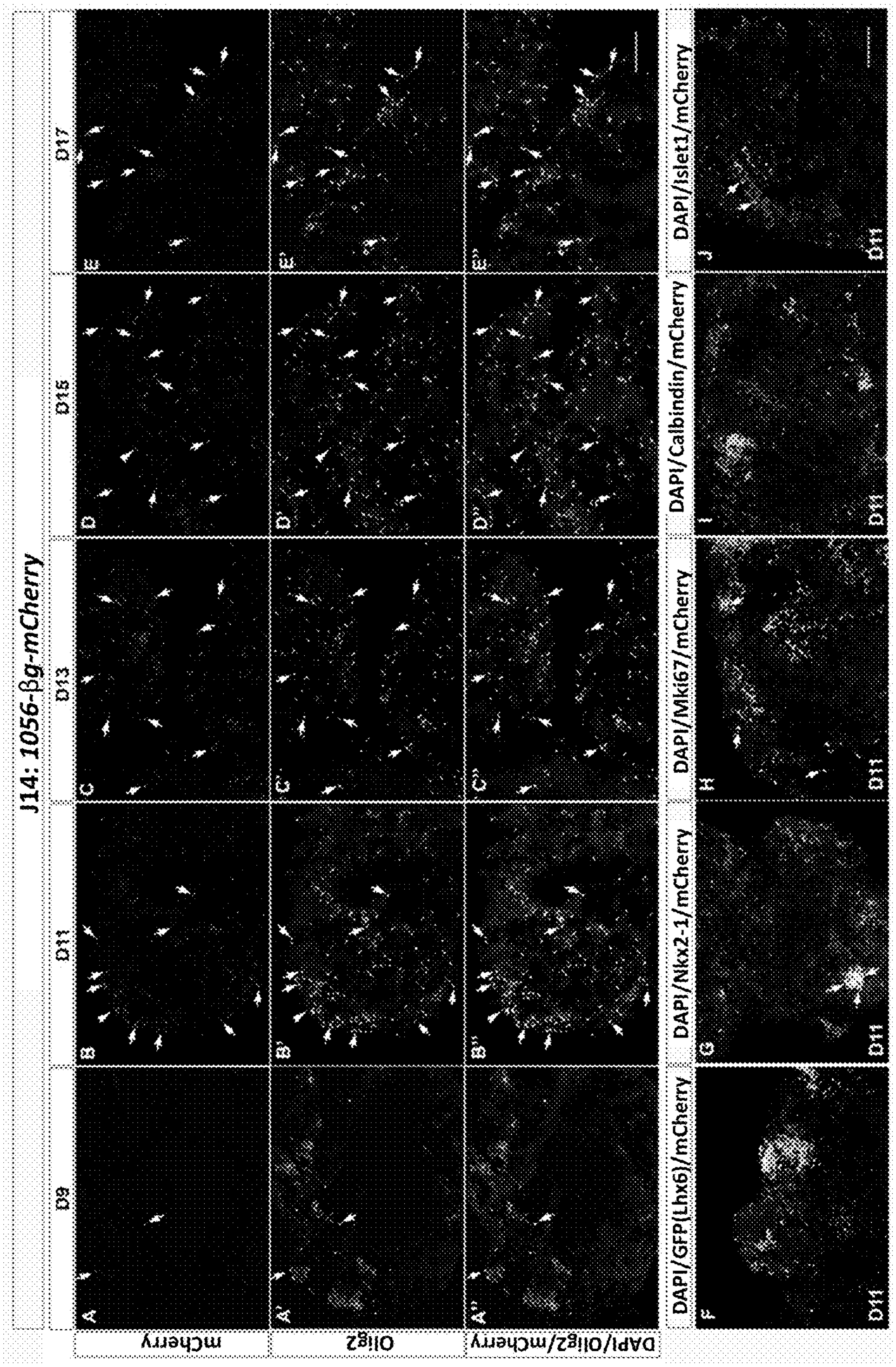

FIG. 17. Characterization of 1056-βg-mCherry in J14 ES cells differentiated toward an MGE-like identity with immunofluorescent staining. Enhancer 1056-βg-mCherry$^+$ cells are Olig2$^+$ and don't express markers of MGE-derived neurons. A-E", mCherry expression driven by the 1056-βg and Olig2 expression are shown in panels A-A" (D9 aggregates), B-B" (D11), C-C" (D13), D-D" (D15) and E-E" (D17). At all the time point examined, almost all of the 1056-βg-mCherry$^+$ cells express Olig2 (white arrows). Only a few 1056-βg-mCherry$^+$ cells are Olig2$^-$ (white arrowheads). F, 1056-βg-mCherry and Lhx6-GFP expression on D11. G, 1056-βg-mCherry and Nkx2-1 expression on D11. Some of the Nkx2-1$^+$ cells are also 1056-βg-mCherry$^+$. H, A few 1056-βg-mCherry$^+$ cells are still mitotically active, as indicated by Mki67$^+$ staining on D11. I, 1056-βg-mCherry and Calbindin expression on D11. J, 1056-βg-mCherry and Islet1 expression on D11. White arrows indicates co-labeling of respective markers shown. Scale bar for all panels, 100 μm.

Figure 18:
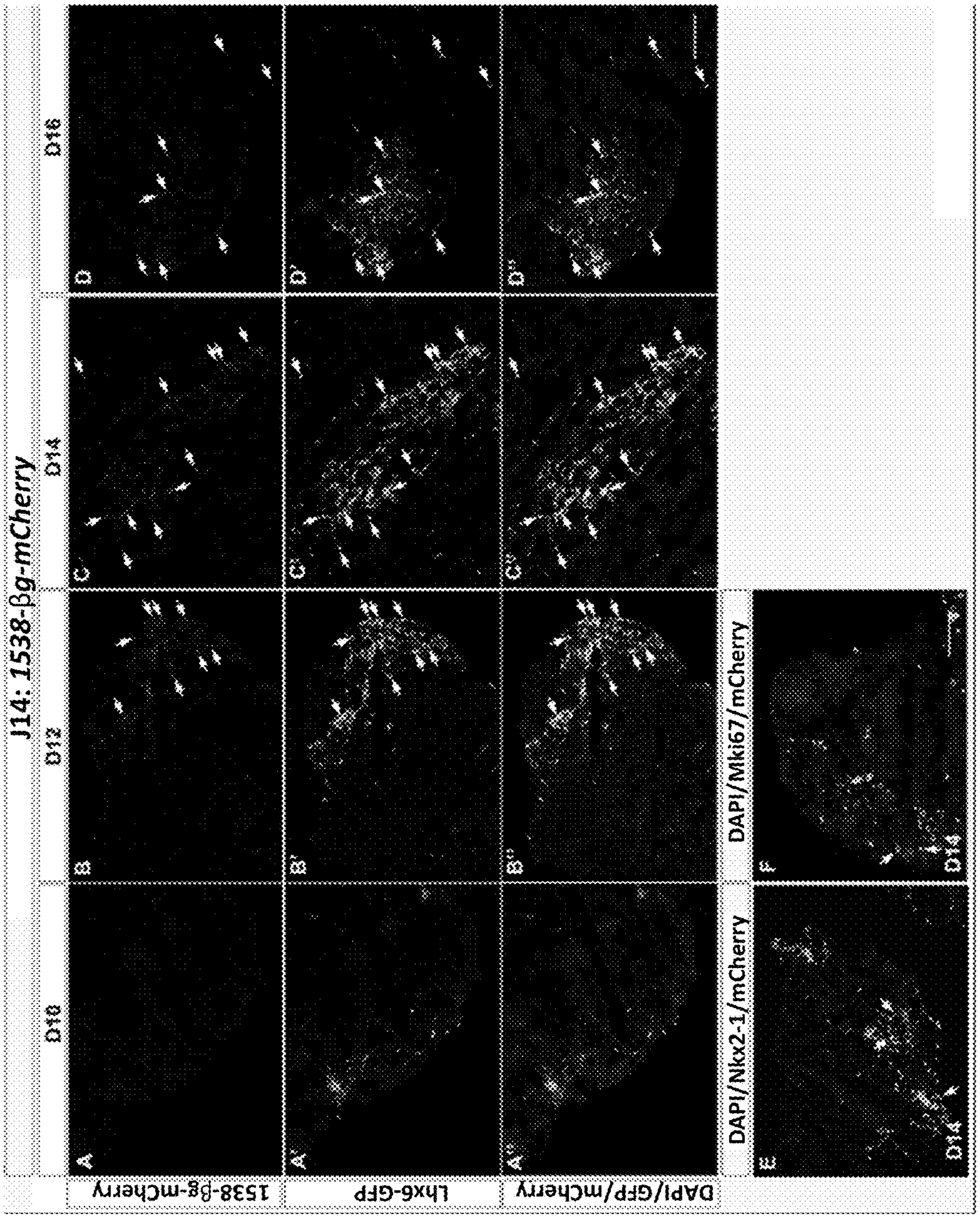

FIG. 18. Enhancer 1538-βg-mCherry$^+$ labeled 40% of Lhx6-GFP$^+$ cells. A-D", mCherry expression driven by 1538-βg and Lhx6-GFP expression in panels A-A" (D10 aggregates), B-B" (D12), C-C" (D14), and D-D" (D16). On D14, 40% of Lhx6-GFP$^+$ cells are 1538-mCherry$^+$ and more than 90% of the 1538-βg-mCherry$^+$ cells were also labeled with Lhx6-GFP (white arrows). E, 1538-βg-mCherry and Nkx2-1 expression on D14. F, 1538-βg-mCherry$^+$ cells are postmitotic, as they do not express Mki67 on D14 (and other earlier time points). Scale bar, 100 μm.

Figure 19:
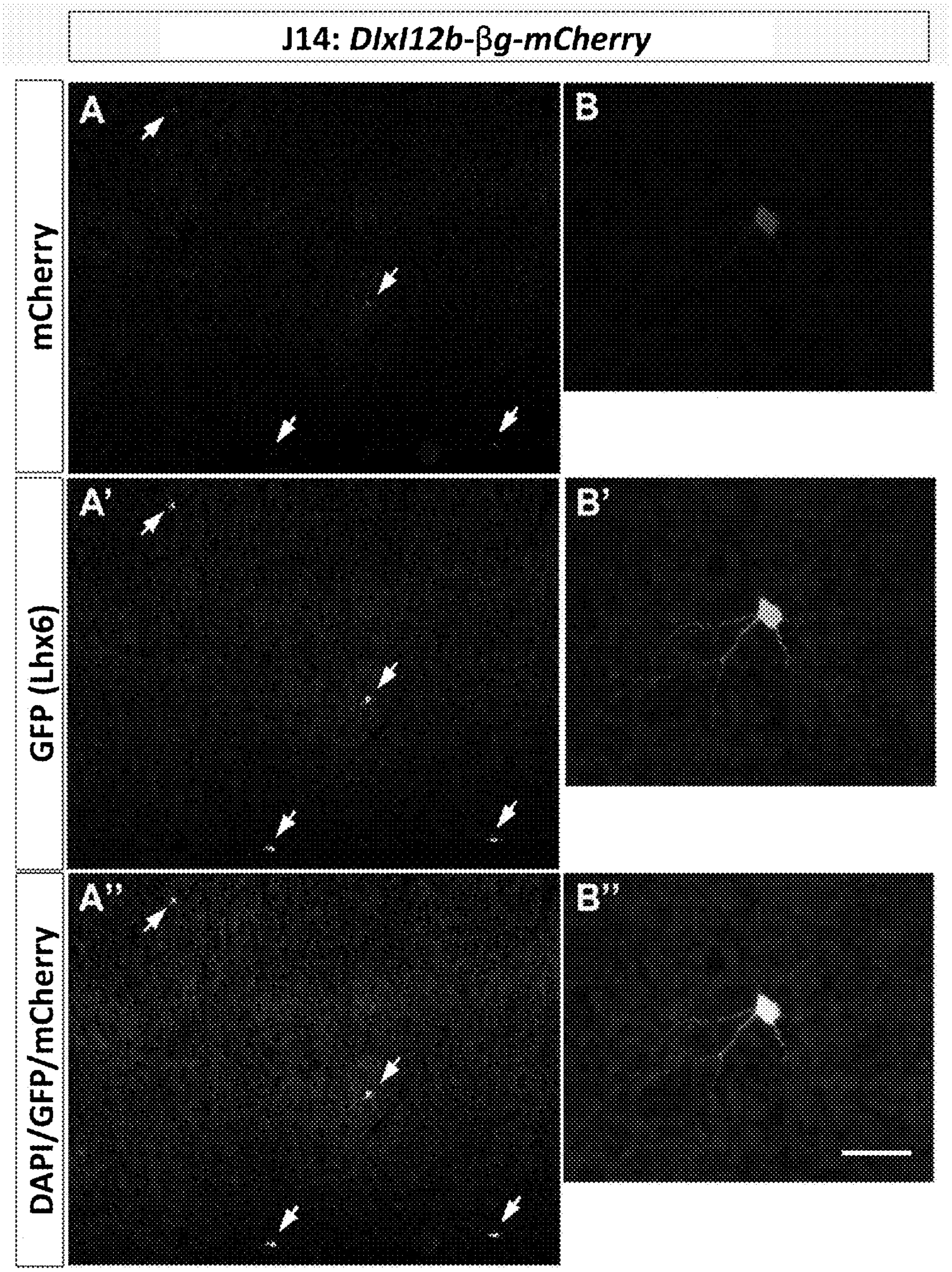

FIG. 19. All of the DlxI12b-βg-mCherry$^+$ cells express Lhx6-GFP thirty-three days after transplantation into the neocortex (white arrows in A-A"). About 28% of Lhx6-GFP$^+$ cells are also DlxI12b-mCherry$^+$. One of the double positive cells (DlxI12b-βg-mCherry$^+$, Lhx6-GFP$^+$) is shown in B-B". Scale bar for A-A": 200 μm; for B-B": 50 μm.

Figure 20:
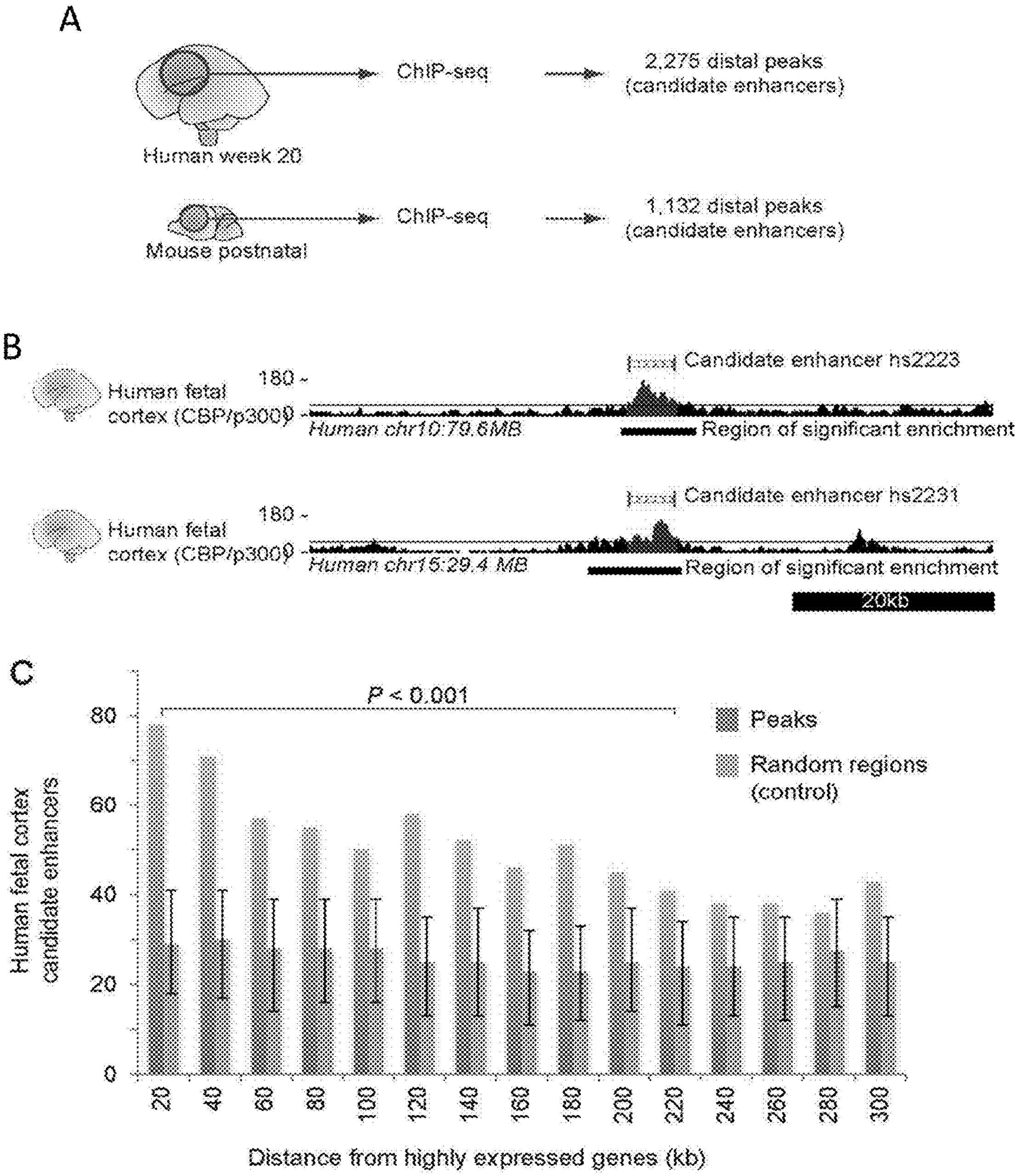
Figure 20:
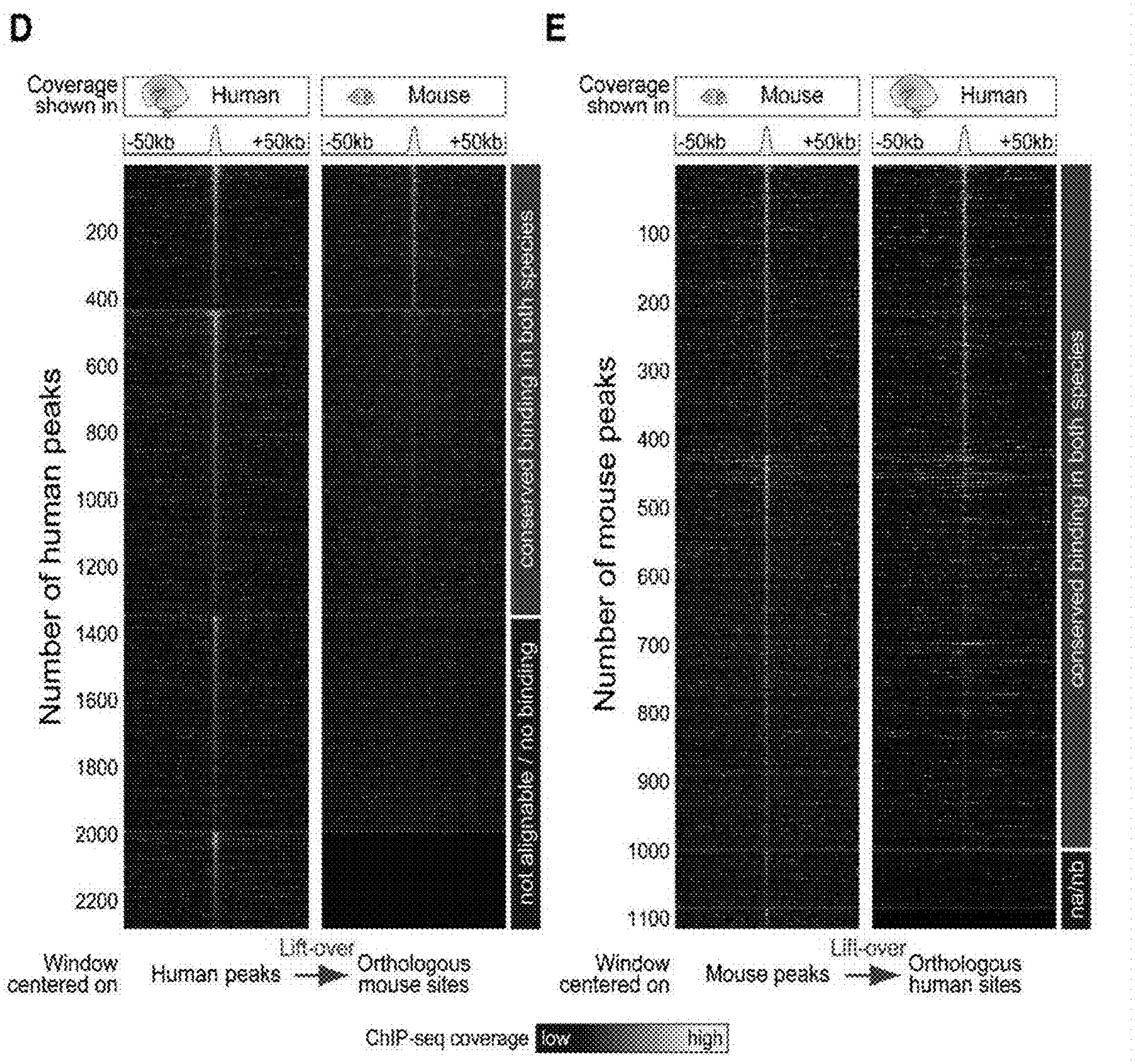
Figure 20:
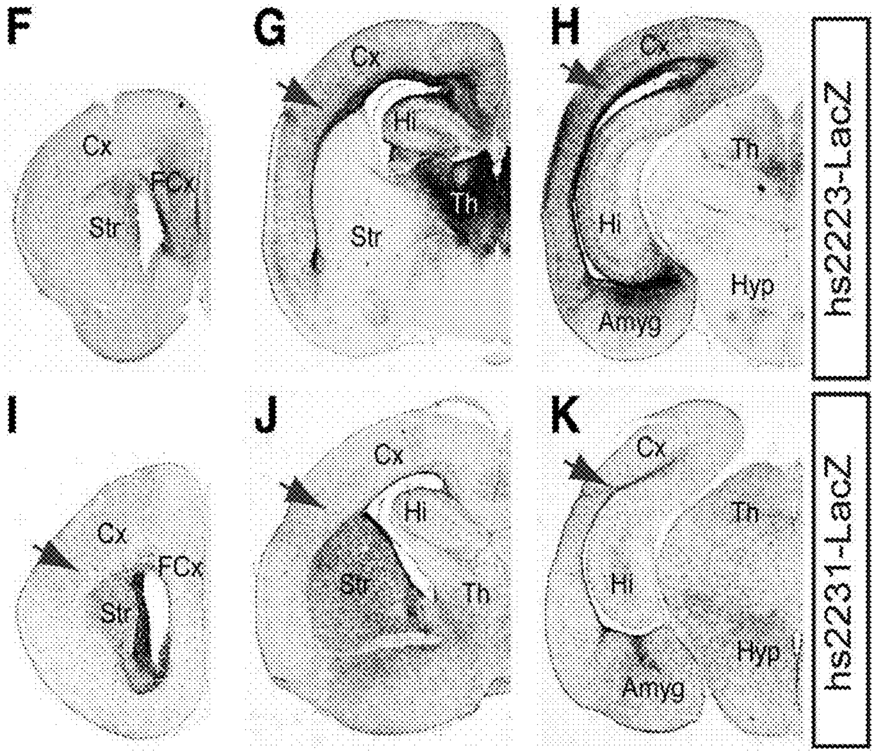

FIG. 20. Genome-wide Experimental Comparison of Enhancers Active during Human and Mouse Cortex Development (A) ChIP-seq analysis was performed on human gestational week 20 and mouse postnatal day 0 cortex tissue using an antibody directed against the enhancer-associated p300/CBP proteins. (B) Two representative peaks (candidate enhancers) identified from the human fetal data set. (C) Predicted human fetal cortex enhancers are significantly enriched in the larger vicinity (up to 220 kb away) of genes highly expressed in the human fetal cortex. Error bars represent the 90% confidence interval on the basis of 1,000 iterations of randomized distribution (see experimental procedures in the Examples below). (D) The majority of candidate enhancers identified from human fetal cortex show evidence of p300/CBP binding at orthologous sites in the mouse genome (top two sectors of heat map). However, a substantial proportion of human peaks either shows no evidence of p300/CBP binding at orthologous sites in the mouse genome (third sector) or falls into regions of the human genome that have no known orthologous sequence in the mouse (fourth sector). (E) A substantially larger proportion of mouse P0 cortex candidate enhancers was found to be bound by p300/CBP at orthologous sites in the human genome. (F-K) Transgenic activity analysis of two candidate enhancers (B) in transgenic mice at postnatal day 1. Each pattern was reproducible in a minimum of three $F_0$ animals; three sectioning planes from one representative brain per enhancer are shown. Arrows indicate expression in the cortex.

Figure 21:
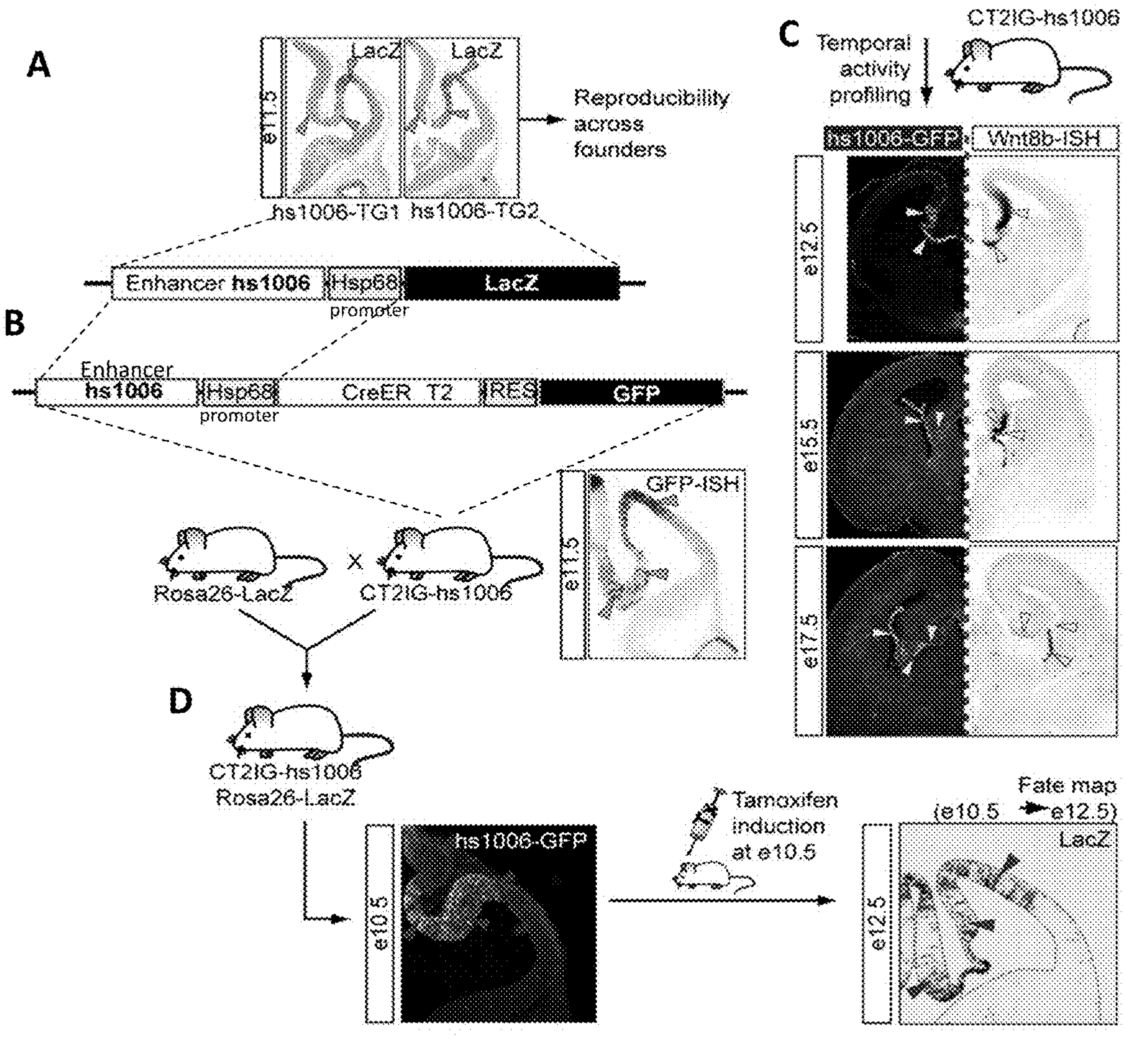

FIG. 21. Using Telencephalon Enhancers as Tissue-Specific Reagents (A) Approach used for the generation of the large-scale high-resolution atlas at e11.5. (B) Enhancers can be used as drivers of other reporter and effector genes, such as GFP or tamoxifen-inducible Cre recombinase. GFP reporter expression at e11.5 recapitulates the annotated LacZ expression pattern (arrowheads). Schematic components of constructs in (A) and (B) are not shown to scale. (C) Stable transgenic lines facilitate temporal profiling of enhancer activity and comparisons with corresponding gene expression patterns. (D) Tamoxifen induction at e10.5, followed by LacZ staining at a later time point (shown: e12.5) can be used for developmental fate mapping of neuronal cell populations.

Table 1 shows the SEQ ID NO., the enhancer element human sequence (hs) ID, and the chromosome location and coordinates, and the location start, end and length for each of the 145 enhancers, SEQ ID NOS:1-145.

Table 2A shows the identified human and mouse forebrain subregions where the enhancers SEQ ID NOS:1-145 are shown to have activity and drive expression. Sequence coordinates and neuroanatomical activity annotations of 145 enhancers analyzed at histological resolution. See FIG. 6 for abbreviations and boundaries of telencephalon subregions. Table 2B provides further comments for each of the subregions where the enhancers are shown to have activity.

Table 3. Genomic intervals near 79 genes with known roles in forebrain development, screened for enhancers in the present study.

Table 4. Genomic coordinates of 231 candidate enhancer sequences near genes with known roles in forebrain development (see Table 3) identified by extreme human-mouse-rat conservation (17) and/or extreme constraint in vertebrates (20) that were tested in vivo in the present study.

Table 5. Overview of all 329 sequences tested for enhancer activity in transgenic mice at e11.5 in the present study.

Table 6. Gene expression patterns of 113 transcription factors in the embryonic forebrain. See FIG. 6 for abbreviations and boundaries of telencephalon subregions.

Table 7. Top enriched annotations of putative target genes near 4,430 ChIP-seq predicted forebrain enhancers.

Table 8. Top 100 motifs associated with each of the three main classes of enhancers.

Table 9. Confusion matrix for the RF classifier. The matrix shows how many enhancers active in pallium only, pallium and subpallium, and subpallium, as well as randomly selected (genomic background) sequences (rows) are classified in one of these possible four classes (columns). The numbers denote total numbers of classified sequences Table 10. Select marker genes expression from differentiated ES cells (ES Lhx6-$GFP^+$ and ES Lhx6-$GFP^-$) and E12.5 MGE cells (MGE Lhx6-$GFP^+$) and the comparisons (fold change) of ES Lhx6-$GFP^+$ vs. ES Lhx6-$GFP^-$, MGE Lhx6-$GFP^+$ vs. ES Lhx6-$GFP^-$, and MGE Lhx6-$GFP^+$ vs. ES Lhx6-$GFP^+$. Column 1 lists marker genes for specific cell types and regions. Note that many of these are not specific for those cells states, but are recognized as useful markers. The expression levels in the columns 2-4 represent the averaged normalized log 2 intensity for each gene. The numbers in columns 5-7 (the fold change) are ratios of the average signal intensity (unlogged) of the two groups in comparison. Light gray highlighted genes are enriched in ES Lhx6-$GFP^-$ cells whereas dark gray highlighted genes are enriched in both MGE Lhx6-$GFP^+$ and ES Lhx6-$GFP^+$ cells. For most of the genes, the expression in the ES Lhx6-$GFP^+$ cells and MGE Lhx6-$GFP^+$ cells show similar expression trends, in comparison to ES Lhx6-$GFP^-$ cells. However, there are a few genes (shown in black) that do not follow this trend.

Table 11. Enhancer activities at different time points after differentiation. Percentage of $mCherry^+$ (mCh), $GFP^+$ (GFP) and $mCherry^+$/$GFP^+$ (mCh/GFP) cells from each enhancer carrying clones at D9, D11, D13, and D16 of differentiation. DlxI12b: J14 with DlxI12b-βg-mCherry; 692: J14 with 692-mCherry; 1056: J14 with 1056-βg-mCherry; 1538: J14 with 1538-βg-mCherry.

DETAILED DESCRIPTION OF THE EMBODIMENTS

MGE-derived interneuron progenitors have tremendous potential for regenerative medicine (Baraban et al., 2009; Sebe and Baraban, 2011; Tanaka et al., 2011). Towards this end, we explored two approaches using mouse cells to generate and purify these MGE interneuron progenitors: 1) culturing dissociated primary MGE cells; and 2) introducing “MGE-specific” enhancer-reporter constructs into mouse ES cells, and using a modification of published methods to generate MGE-type cells.

In one embodiment, compositions and methods are described to generate specific types of neural cells from stem cells or reprogrammed cells. In some embodiments, the approach is general, and should be applicable to any type of brain cells. It involves the use of a novel set of gene regulatory elements that we have recently identified that are specifically expressed in progenitors of specific brain cells. We explored new approaches to identify and select for specific interneuron precursors generated from human ES, iPS and iN cells. These approaches will take advantage of recent discoveries about the distinct origins, lineages and molecular properties of different interneuron subtypes and will use a novel set of human enhancers expressed in the MGE. Furthermore, these studies will elucidate basic information on the molecular steps for making various types of neurons generated by the human MGE.

In one embodiment, a method for generating neurons active in various structures/cell types as follows: (a) computational identification of a candidate enhancer sequence; (b) transgenic testing in mice, including photography of whole embryos and generic descriptions of patterns such as “active in forebrain”; (c) sectioning of such transgenic embryos and photography of serial sets of sections; (d) neuroanatomical annotation (interpretation) of these sets of sections to describe embryonic enhancer activity patterns; (e) through the further interpretation of these descriptions of embryonic enhancer activity patterns, define which enhancers are likely to be active in a certain cell type and can thus be used as a method for neuronal differentiation or reprogramming protocols. In one embodiment, the method was used to identify enhancer sequences SEQ ID NOS:1-145.

In one embodiment, compositions and methods are used for the generation of a specific type of cells derived from the embryonic forebrain-cortical and hippocampal GABAergic (inhibitory) interneurons. Cortical and hippocampal GABAergic (inhibitory) interneurons have fundamental roles in controlling cortical excitatory/inhibitory balance and thereby regulate cognitive processes and prevent hyperexcitability states, such as epilepsy. In addition, there is strong evidence for interneuron defects in other disorders, such as schizophrenia (Gonzalez-Burgos and Lewis, 2008), and suggestive evidence in autism (Rubenstein and Merzenich, 2003). There are several reasons why it is important to generate these interneurons in vitro from stem cells. First, using iPS or iN cell technology, one could generate these cells from patients with various forms of epilepsy, schizophrenia and autism, and determine whether abnormal interneuron function could contribute to these disorders because of cellular and/or electrophysiological defects. Second, roughly 30% of epileptic patients continue to have disabling seizures despite maximum pharmacotherapy; many require surgical resection of the epileptic focus, and therefore could benefit from a cell-based therapy.

The use of the human enhancers SEQ ID NOS: 1-145 provides key insights into the transcriptional mechanisms that regulate interneuron specification and differentiation. We used novel human enhancers that were found to drive expression in progenitor domains that generate interneurons, and antibodies that recognize endogenous human cell surface markers, as selection agents to identify and purify interneuron precursors. We identified specific human enhancers and have shown in the attached Tables that the enhancers drive expression to particular regions of the human forebrain. The specific human enhancers are identified as SEQ ID NOS: 1-145. Certain enhancers have not yet been described elsewhere including SEQ ID NOS: 83, 84, 99-104, 106-108, 110-118, 120-128, and 144-145.

Thus, in one embodiment, herein are described novel and specific human enhancers which drive expression and/or differentiation of specific forebrain cell types. Referring now to FIG. 2, the forebrain enhancers SEQ ID NOS: 1-145 are shown to have activity in different subregions of the developing mouse pallium (cortex) and thus in some embodiments, the enhancers may be used to drive expression in the identified region where the enhancer is shown to have activity in Table 2. In the Examples, it was shown that the enhancers reproducibly label subregions of the developing pallium and drive expression in these subregions as provided in Table 2. Full serial sets of sections for some of the enhancers can be viewed at the enhancer.lbl.gov website, using the enhancer IDs indicated in the Figure and Table panels. Referring now to Table 2, each subregion of the forebrain is identified by an X where the enhancer was shown to demonstrate activity and drive expression. The majority of subpallial enhancers drove expression in the subventricular zone and the marginal zone, but we also observed enhancers that were active in the ventricular zone (e.g., panel d, hs1056 (SEQ ID NO.:120)). Throughout and as in Table 2 and FIG. 2, the following abbreviations are used: MP, medial pallium; DP, dorsal pallium; LP, lateral pallium; VP, ventral pallium; LGE, lateral ganglionic eminence; Se, septum; Th, thalamus; EMT, eminentia thalami; CP, choroid plexus; MGE, medial ganglionic eminence; and POA, preoptic area.

In some embodiments, the enhancers and their derivative structures may be used as a molecular reagent or reporter construct to drive expression in selectable regions as identified in Table 2. For example, in one embodiment, enhancer hs422 (SEQ ID NO:42) may be used to drive expression to the subregions LGE SV, LGE MZ, MGE VZ and MGE MZ. Hs422 (SEQ ID NO:42) which is flanked by genes DLX1 and DLX2, comprising the sequence of:

```
aggggggtcttcctaggttcaatttcccctaggagatgtgactttgctagt

gcgaagatttctgtccggcatctgactcaggtcccccagacggcagctag

ggcccaatgcctcaagctacaggcaaaatctgtttggtcaagcggattgt

aatactttgagatattagcttatactaatttaataatctcttgctaacag

ttcaaatagagaaattattagttttagctcaacgaaaacggtctttagtt

aggctttattataattataagcggttgtactttttaaaaatgttaatctc

aatataggcctaattaatgctgccttgttactgacaagtagttcatcaaa

tatctgattcaaagattttcataatgagtatattaattaaactatgaata

atctaaaggtggttatatttaaacaatacctcattataatgattaaatac

tgatttcgaatattatgtcttaacaattgtcacttagaaaacacaacctt

tccttatgtatgagtctgtaatggcaaaatgcaattttgggattttttc
```

-continued

```
ccttgttcaaaaaatgtgaaactcattttaaaacacttctgaaataggtt

acacacagcttaatgattatcaaaatgactcttttctgcaaaaaaagacc

ccaaagtgcgcgtacagctgcaaacccaagagggtcagcatcatttcact

gtattctcttcttgattacaagccgggcccatcaaacacaacataattac

agtaatttcaggtttatttattctaatgcagtttccccatctctctggta

attatgagcaatttttcgcccagggaatctttttgcattaacaaaagag

ataacgcactgaaagccaaatttgctgtgcattgagaaaaggaaaaaaa

aaatcaaataggtgcgagctgccatctctgcaattctctggtaccggagc

cggcaaattgcttgcaggtgtatggagcaagcttgtcaatggccaggcct

ccaaattagcaaatgcacagcagcaaagtaatgaagacagacttagcaaa

attgccaaacaacagatatccctttaatatcttctctcacccacactagc

tctaaaaaggggtaggggtagggagagaagcaacagtccccagccccctc

ctcactggtcttggctttcaggag
```

Enhancer hs422 Primers are (+)AGGGGGTCTTCCTAGGTTCA (SEQ ID NO:146) and (+)CTCCTGAAAGCCAAGACCAG (SEQ ID NO:147).

In another embodiment, enhancer hs692 (SEQ ID NO:78) located at (hg19) chr11:15587042-15588314 and residing near the gene SOX6, may be used to drive expression to the subregions LGE MZ, MGE VZ, MGE SVZ, MGE MZ, POA VZ, POA SVZ, POA MZ, comprising the sequence of:

```
ACATCTCAGTGGCTCATAAGATTCTACTGACCAGAGCTCTGCAGAGCCCA

GGGTGCAGGCTGGGAAGGAGAAAGCAAAGGGGACCTCACAAGTCAGAGTC

ATTGGTTTCATTTCCCAATATCCAAATGCCTCTGTCCAATAAGACCTATA

ACCAATTTCCCAGAGAAGGCCCCCGAAGAGGCTGAGCTTGATGGAGTTGG

GTAGTGGGCTTTTTTTTTTTTTTTTTTTTTTGGCTTTTTTTTGGACTAAA

AGCAATTTCCATTTTATGCCTTTTGTCTCTTCATCCAAGCAAATGCCGGT

GGGATCTGGCAACCTGAGTTCAATAGCCAGTCCTTTTGGTCTTTCAAAGG

CTATGAATGTAATAAGAGCACTCAACCCTTCTGAAGATATGCAAATCCGT

GCATTTAAAAGATTTACATTCATCCTTCACAGGCCCTGAAATATAAATAT

GAAATACCCAGAACCTTGTCACTTCAGTAATAATTAAGCTGATGGCCTAT

TATGTTCGATTGCAAATCAATATAGTATCTTTTGGTGCCACTTGAGTTCT

TGAGGGTTGGCGCGGGGCCAGCTCCAGTTATACAATTGAATTGCTGCAGC

TGCCTGGGAAACTTCGCTGCCGTTCCCATTCAGGAAGAATAGGCGGGTAA

CAATGGTGACCAGCCTCCCTACAGTAATTGTGTACGAGGACACATTTCCA

ATGGGGTTTTTGTTCAGCAGGTGCTGTTATTTTAGTTTAATTTGAATTCT

GAAATATGGAGGAGAGAAGGAGACCAATCTTAACAGCATCTAACCTACAG

CTGTTCGAAAGAGGCCAGCAAACAGCATATGTTGCTTAGATGGAAATCAT

AATTGCTCATTCTCCCTGGGATGTTGGCCCACCAACGTGGAGCCTCTGAA

ATTAGCTGGCATTTTTCTGGCATTTTCCTCAGTGGTGAGGCCTCTGCAGA

GCTCAGGAGGAACTATTCTAGAGTGGCTCGCTCCCTGGGAGGCTTTGGTG

GTGGCGGCTGCTGCGTCTCCTTTTTCTTCTCCTTCCCTCTTTCTCCTTCA
```

-continued

TGGTAGGCTGAGGTGAATTCCAAACACTACACAAAACACATCCAGGGTTG

GCCTCCTCATTGGAGGCTGCCATGGGGCGCACAAGGAAACAGGCAGTGGC

GAGGTCTGGTGGAGCCCCAGGGCCAGACTCTCTCTGAGAGCAGCGACCAA

CACCCCTGGGTCAGGGTCAGGGCAAGAGGAAAACTCAGATAGTAAGGAGA

ATAGCATCAACACAGACACCCTG

In another embodiment, enhancer hs1056 (SEQ ID NO:120) is located at (hg19) chr18:76481723-76483257, near the gene SAL LIKE 3 (SALL3), may be used to drive expression to the MGE VA, MGE SVZ, POA VZ and POA SVZ subregions, comprising the sequence of:

TCCCTCACAGAACTCAGGACTAAACCGGGGGCTAGGAGGCCTCACATCTC

GGCCCACTCCGCGGCAGCCCCGCGCCAGCCAGGAAGACGTTATCCGTCCA

TCGCCGGAGACTGTTCGTGTATTAGCAATTCACTGTCAAACGCTCAAGAG

TTTGCCAAAGCATAATAGATGCTTTACATTTTATGCATAACTAGTTCTGA

GACCAGGGCTATAAAAGTTTTCTATTAACATGTAAGCACTAAGACAAGTT

TTTTTTCACTTGATAAATATACATAACTCCTTGACAATGAGGCCCTTGTG

TTGCTAATGGGGCCCTTAATGGAGAGTTATATTTCCAGGATTATATCTTT

ATTCAGTTGCAAATGATTTTTGGGGGGAGTTTTAATGCTCTGCTCCGTCT

ATGAATAATAGTATCGTTTGAATGCAGCGGACACCTGGTGCCGGAGGACA

GTGGGGCTCTGCAGTGACCTGGCGACGCTGCCAAGTTCGCATTTTCCCAG

CCTTTCCTACCCGCTCCATTCAGCATCTAATTTCATTCTCCCTCAGCAGA

ATGCTAGACACTTGTAACTTTATTCTCCCTCCGCAAAAACTTGCTCTCTT

GTAAGGAAAAAATCCTGGAAGAAAAAAATTTCTCTTATCAATCTCTTCTT

ATATAGAGTCTAGTAATTTGAAGGCTGGCTAAAGTTTCAGGAAAAACCTT

CCAATTAAATACTGTAAAAAGATAAAATAACAGTGGCCTTGCTGCTGCCC

AATAGCTTTATTGAAGCGCTCTTTTGTTGATTTATTGTACGTTAGCCACC

GAGCCGTGCAAAGAACATTACGTTTCAGAAAGAGCTATTCGTATGCGGCC

TGCATCCACTCCAAAAACAATCAGGCCTGTATTGCGTTTTGCAAATTTAT

ACCAGGATGTTGGTTTAGAGTGTTTCCCTGAAAAGTTTTTCAAGTAAGTG

TCTGCTTTCATGGGCGAGAGTGATTGAGGCACACAAACAAACCTTTGTTT

CAAAACTCACAGATGTATGGCCGGGCTGAGCTTTGTTTTCCCCTTTAAGA

AGTATTCTCAGATTTGTGTTTGGAGCACAACACAGGATTGTACAAAAAAA

AAAAAATCAGCTTGAGGATGAATGTCTCGTATAATCTGAGGCTTTTCCAG

ATTTTCCCAGGGTTAATTTTTCTACCCTGAACTTTGCGTGTTGGGTAGGT

TAGGGTTTTTTTTTTTTTCTTTAATTTATTTATTTGTTTGTTCGTTTGTT

TTTGTTTTTAAATTCAGGCATGCCATGAAAAAGAATCCTGCCTACTTCAG

CTTTGAATGTGGCTTCAGGAAACTTCATTTCAAAGCTATTAGGGAGTTTG

CAAGCTCCATAAATATACTTTTGTTCAAGTTGCAATCTGCCCTTCTCTCT

CGCGGGCGCCCGAGCATCGTGCTGGGACATCCGGCAGCCCCAGGCTGCGC

GACGTGGAGCCAAGAGGACAGCCACCTGGGTCGGGGCTGAAGGAAATCCT

AAGTGACAAAATATTTAGACTTCAAGGCAGGCATC

In another embodiment, enhancer hs1538 (SEQ ID NO:144) is located at (hg19) chr14 36911162 36914360, near the forebrain gene TITF1, and directly neighboring the genes DPPA3 and SFTA3, and may be used to drive expression to the POA VZ, POA SVZ, and POA MZ subregions, comprising the sequence of:

GCTGCCTCAAACAAGAATGAAACCATTTTTCTCAAACTGGTAGAAAAACC

TTATTTCAATTATTTTTTCTAGTCCTATACTTCCAGAGGATGGGAAACTG

TTCTTAAAAGTGCAATGGACTGACAGAAAGCAGATCCGCGGTTGCCTCCA

GGGCTGGGGGAGGGGATTGACTGCAAAGGGGCGCACGGGAATTTACTGGG

GTGACAGAAAGATTCCACATCACAATTAAGGTGGTGGTTACATGATTGTA

TACATTTGCCAAAATTTACTACATTTACAATTAAAATGAGTGGATTGTAT

TATACATTGCTCAATAAAACTATTTTTAAATAGCTTTAGTAATAAGTGAA

CTAGTGCTTTTTTTTTGGTGATCATTTGCAAGAATACTCCAAATTCAATA

AGAACCAGGATTCTCTTTTCAAAAGTCCAAAAACTAGTAACAAGTGCTGT

GTTAGATTTGAAGAGCTGGAAGGACTTTACATACTTAAATTCCATTTTAA

TCTAGTTGAAACTCCCATAGAAAGAAGAAAAAAATACATTTTTAAAGTAC

AGATTTTTATTCAATAATTCTTTAGTTCTTTTCTCTTTTAACTTCCCTGG

GGGGAGCAGGGAACTCTCATTCTGGTACCGATATTTGGATTAAAACAAAT

ATCCACCCATTCATTAAAAGTTTCTCTCATATAAAGGAATTCATTTTTTT

TCTTGATTGGTGCTAGACTCACAGACAGACAGAAATAAGCTGCCATTCTT

CCATTTGATAGCCAGACGCTGCCAGTTGTAGCCAGGGTAGTCATGCTGTT

AAATTAGGTCTAATGAAGGAGTAATTGCTTTAGATATAGTGAACCATTTC

AAAGAAAACAAGGATTCTAATTGATTTGCAATTTGTTTGGCACATTGCAT

TGTCTGCGGCTATTGATTAGTCTTCTGGATTTCACACTGCATGTGTTTCC

CTTTATTAAGGGAATAACAGGTTACTGATTACTTTCTTTCTGGGTTTAAT

GTAGCGGTTAATGTCTACTTTGTTCTTGTGTCATGTCACAGGCGAGGAAG

GAATAATAGGCAAGTGGGTGGCCCTTTGCTAAGCAACTTCCCTGCTGCTC

TGAGCTGTGTGCTCTGAGACAGGCTGAAAAGCAGATCAAGAGAAAGGGTT

AGAATAGCAGGACTCACAAGTTAAGGCCTGAGTCAGGCTAGACCCAGCTC

AAAACTTGGCTTTCCCCTCCCAGTCAAAGCATAGCATGGGACAAAGCAGC

TGGTGGTAGATTTGTTCTTGTATCATTCGATTATTTGTAGACAGGATATG

AATCTATGCCCATTGTTTTGCTTAATAGGTATGCATGCTAAATGGATGCA

GAAAAAGAATATTTGAGGGTGAGGTCTTTTGGTTCATTTAACCCTTTGGA

AAGTGACATTTTGTTGGCACCTGGGAAGCACTTGTTGCTGAGGTGTCGAT

ATGATCATCAAAATGGCTCTTATGTTTATACCAACTGCAGGGGAGGGAGA

AAAAGTTCTCAGGGTTGCAGTCATTTCATTGCCCTCAAAGCACAGCAGGA

ATTATTAGCTTACCCTGGCGTGCCCCTTTGTTTTCCTAGGGCTTTGCTCC

TCCAGCAGATACTCATTTAAGGCGAATCCACTGCTTTCTGAAATGTGTTT

TGCAATGGTGCACAGAACAGGCACTCACTTAGCGGATCTAATCCTTTCAT

GGCTCAGCTTGTTAATGTAGCAAACTGCTGAAAATGGGAAATGGATTCTT

TAATGAGAACAGTCCCTTCATGGCTTTATTCTCCCAGTCCAACCCCCAGG

CATTCATTCAAGTCCCCCCACGCCCGACCTCCCACGCCAGGATCAGGCAC

CCCCACTTCCCACCCAGCAAGCAGCCCATTTTCCAGCACGAAGTCCCCCA

-continued

```
TCTCTAGGCCCCTTGCTTCCCCACGACCTTCCCAGAGCCCTTGGAAGCTC
ACAAATAACAAAGGGGTGTAGGCAGTAAAAGATTCCCTTTCTCTGCTTCA
GTTACCTCCTTCCTAAGCCTGAGCCCGTCTTTTCCTGTGCTTCAAATCTG
ACATGGTTATAGAGTGGAGCCTTTTCCTGATAAATTGCAAAGTAGCTAAC
ACCCAGGGATTACATCTAAATTTATCAAATAAACACACTTTTGATATAAA
CATACTACCCAAGGTATTATAGATTTAATATCTTTCTTTAACATAGCTTT
TGTACTATACAGGTTGAATATCCTTGGGACTAGACATGTTTTGGATATTT
TTGGATTTTGGACTATTTGCATATACATAATGAGGTCTCTTGGGATGAGA
CTCAGGTCTCAACATTAAATTTATTTACGTTTCATATACACCTTATAGAC
ATAGCCTGAAGGTAATTTTAGACAATACGATACTAATTTTGTGCATAGAA
CAATGTTTGTGTTAAGTGCTATTAAGACTTTTTTTAAAGTGTTAAGACTT
TTCCACTGTGGCGTCATGTGAGTACTCAAAAAGTTTTAAATTTTGGAGCA
TTTTGGGTTTTGGATTTTCAGATTAAGGATGCTCAACCTGAATTGGATTT
TATAATGATGCTGATTGCCAAGGGTTTCAAAATGGAGCCAATCAGTGAAA
GTTAACTTGGACTCTGGTCTTTATTATTTTTCTTTTACGATTTTTACTCC
TGTGGGTCTTCCTGAAGCTTTGGTACTTCTCTAGAAATCCACTCCAAAGA
AAAAAAATCAGGCCTGGCACAGTGGTTCACATCTGTAATTCCAGCACTTT
GGGAGGCCAAGGTGAGAGGATCACCTGAGGTCAGGAGTTCAAAACCAGCC
TGGCCAACATGGCAAAATCCCATCTCTACTAAAAATACAAAAATTAGCTG
GGCGTAGTGGTGCACACCTGTAATCCGAGCTTACCCGAGAGGCTGAGGCA
GGAGAATCACTTGAACCCGGGAGGTGAAGGTTGCATTGAGCCGACCGAGA
TCGCCCCACTGCACTCCAGCCTGGGCGACAGAGGGAGACTGTCTCAAAAA
AAAAAAAAAAAAAAAGTACTCGAAGCAGGTAAAGTTTAGGTTAAGAAGAT
ATTCAAGATTACTTGGAAGTCATGACAGGGCAGCCTGGAGTTTGAAGTGT
ACATTTAAAAGAGAAAATGAGGATAGTTATGCCCATTTTGCCTTAGAGAT
AGGAAAGTAAATTATGTGTACATGAGCCCAGGTCTTTCCCTCATCCAA
```

In one embodiment, the presently described neural enhancer sequences described in SEQ ID NOS: 1 to 145, in conjunction with Table 2, are contemplated for use in any of the applications herein described. In some embodiments, an isolated nucleic acid molecule encoding a human enhancer (SEQ ID NOS:1-145), wherein said nucleotide sequence is optimized for activity in the host organism.

In another embodiment, the nucleic acid molecule comprising a human enhancer sequence that promotes the identification, isolation and/or differentiation of human interneurons or ES-derived cells. The human enhancer sequence may be selected from any of the enhancer sequences of SEQ ID NOS:1-145. Thus, in one embodiment, an expression cassette comprising a nucleic acid molecule comprising a human interneuron enhancer sequence selected from SEQ ID NOS:1-145.

The expression vector usable in the present methods with the enhancer nucleotide sequences of SEQ ID NOS:1-145 of the present invention include pUC vectors (for example pUC118, pUC119), pBR vectors (for example pBR322), pBI vectors (for example pBI112, pBI221), pGA vectors (pGA492, pGAH), pNC (manufactured by Nissan Chemical Industries, Ltd.). In addition, virus vectors can also used including but not limited to lentiviral, adenoviral, retroviral or sendai viral vectors. The terminator gene to be ligated may include a 35S terminator gene and Nos terminator gene.

The expression system usable in a method with the enhancer sequences of SEQ ID NOS:1-145 include any system utilizing RNA or DNA sequences. It can be used to transform transiently or stably in the selected host (bacteria, fungus, plant and animal cells). It includes any plasmid vectors, such as pUC, pBR, pBI, pGA, pNC derived vectors (for example pUC118, pBR322, pBI221 and pGAH). It also includes any viral DNA or RNA fragments derived from virus such as phage and retro-virus derived (TRBO, pEYK, LSNLsrc). Genes presented in the invention can be expressed by direct translation in case of RNA viral expression system, transcribed after in vivo recombination, downstream of promoter recognized by the host expression system (such as pLac, pVGB, pBAD, pPMA1, pGa14, pHXT7, pMet26, pCaMV-35S, pCMV, pSV40, pEM-7, pNos, pUBQ10, pDET3, or pRBCS.) or downstream of a promoter present in the expression system (vector or linear DNA). Promoters can be from synthetic, viral, prokaryote and eukaryote origins.

The neural enhancer sequences can be first cloned from cDNA, genomic DNA libraries or isolated using amplification techniques with oligonucleotide primers or synthesized. For example, sequences of candidate genes are typically isolated from nucleic acid (genomic or cDNA) libraries by hybridizing with a nucleic acid probe, the sequence of which can be derived from publicly available genomic sequence or the primers provided herein as SEQ ID NOS: 146-. In another embodiment, RNA and genomic DNA can be isolated from any mammal including: primates such as humans, monkeys, and chimpanzees; rodents, including mice and rats. Methods for making and screening cDNA libraries and genomic DNA libraries are well known (see, e.g., Gubler & Hoffman, Gene 25:263-269 (1983); Sambrook et al., supra; Ausubel et al., supra; Benton & Davis, *Science* 196:180-182 (1977); and Grunstein et al., *PNAS USA,* 72:3961-3965 (1975)).

Nucleic acids encoding the present neural enhancer sequences of SEQ ID NOS:1-145 can also be isolated from expression libraries using antibodies as probes. Such polyclonal or monoclonal antibodies can be raised using, for example, the polypeptides comprising the sequences such as the neural enhancer sequence set forth in SEQ ID NO:1, and subsequences thereof, using methods known in the art (see, e.g., Harlow and Lane, Antibodies: A Laboratory Manual (1988)).

Substantially identical nucleic acids encoding sequences of the candidate genes can be isolated using nucleic acid probes and oligonucleotides under stringent hybridization conditions, by screening libraries.

Alternatively, expression libraries can be used to clone these sequences, by detecting expressed homologues immunologically with antisera or purified antibodies made against the core domain of nucleic acids encoding sequences of the candidate genes which also recognize and selectively bind to the homologue.

In some embodiments, a vector comprising a promoter operably linked to a heterologous enhancer nucleotide sequence of the invention, i.e., any nucleotide sequence in SEQ ID NOS:1-145, that is a neural enhancer or DNA regulatory element are further provided. In another embodiment, the expression cassette comprising the vector containing an enhancer sequence selected from SEQ ID NOS:1-145.

The expression cassettes of the invention find use in generating transgenic embryonic stem cells. The expression cassette may include 5' and 3' regulatory sequences operably linked to an enhancer nucleotide sequence of the invention. “Operably linked” is intended to mean a functional linkage between two or more elements. For example, an operable linkage between a polynucleotide of interest and a regulatory sequence (i.e., a promoter) is functionally linked that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be co-transfected into the organism. Alternatively, the additional gene(s) can be provided on multiple expression cassettes. Such an expression cassette is provided with a plurality of restriction sites and/or recombination sites for insertion of the neural enhancer sequence. The expression cassette may additionally contain selectable marker genes or a reporter gene to be under the transcriptional regulation of the regulatory regions.

The expression cassette will include in the 5'-3' direction of transcription, a transcriptional initiation region (i.e., a promoter), translational initiation region, a polynucleotide of the invention, a translational termination region and, optionally, a transcriptional termination region functional in the host organism. The regulatory regions (i.e., promoters, transcriptional regulatory regions, and translational termination regions) and/or the polynucleotide of the invention may be native/analogous to the host cell or to each other. Alternatively, the regulatory regions and/or the polynucleotide of the invention may be heterologous to the host cell or to each other. As used herein, “heterologous” in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

Where appropriate, the polynucleotides may be optimized for increased expression in the transformed organism. For example, the polynucleotides can be synthesized using preferred codons for improved expression.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassette can also comprise a selectable marker gene for the selection of transformed or differentiated cells. Selectable marker genes are utilized for the selection of transformed or differentiated cells or tissues. Marker genes include genes encoding antibiotic resistance, such as those encoding neomycin phosphotransferase II (NEO) and hygromycin phosphotransferase (HPT). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54), and m-Cherry (Shaner et al., Nature Biotechnology 22: 1567-72). The above list of selectable marker genes is not meant to be limiting. Any selectable marker gene can be used in the present invention.

To drive increased levels expression of a cloned gene or nucleic acid sequence in a specific subregion, one can subclone the gene or nucleic acid sequence along with an appropriate enhancer sequence selected from SEQ ID NOS: 1-145 into an expression vector that is subsequently transfected into a suitable host cell. The enhancer sequence is selected based upon the subregion where it has been identified as driving expression and shown in Table 2. In some embodiments, the expression vector also contains other (strong) promoters or an additional enhancer from SEQ ID NOS: 1-145 to direct transcription, a transcription/translation terminator, and for a nucleic acid encoding a protein, a ribosome binding site for translational initiation. The enhancer and promoter are operably linked to the nucleic acid sequence. Suitable bacterial promoters are well known in the art and described, e.g., in Sambrook et al. and Ausubel et al. The elements that are typically included in expression vectors also include a replicon that functions in a suitable host cell such as *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable.

In one embodiment, an expression cassette comprising the nucleotide sequence operably linked to a promoter that drives expression of a selective agent, signal peptide or label in the host organism, and the expression cassette further comprising an operably linked polynucleotide encoding a selective agent, signal peptide or reporter.

In one embodiment, a neural enhancer nucleotide sequence selected from SEQ ID NOS: 1-145 and a gene encoding a selective agent, signal peptide or label are cloned into an appropriate plasmid under an inducible promoter. This plasmid can then be used to transform human stem cells or progenitor cells to become a differentiated neuronal cell. In one embodiment, this system may maintain the expression of the inserted gene silent unless an inducer molecule (e.g., IPTG) is added to the medium.

In another embodiment, a cell comprising in its genome at least one transiently incorporated expression cassette, said expression cassette comprising a heterologous enhancer nucleotide sequence, operably linked to a promoter that can drive expression in the cell.

In another embodiment, a cell comprising in its genome at least one stably incorporated expression cassette, said expression cassette comprising a heterologous enhancer nucleotide sequence, operably linked to a promoter that can drive expression in the cell.

When referring to a cell, it is meant to include any number of cell types including but not limited to stem cells, progenitor cells, and in specific embodiments, neural progenitor cells such as MGE cells, or non-pluripotent cells such as fibroblasts which may be induced to become pluripotent or reprogrammed to a desired cell type.

In another embodiment, a method for enhancing embryonic stem cell differentiation in a cell, said method comprising introducing into a cell at least one expression cassette, said expression cassette comprising a neural enhancer nucleotide sequence selected from SEQ ID NO:1 to 145, operably linked to a promoter that drives expression in the cell. In one embodiment, an expression cassette comprising a neural enhancer nucleotide sequence and operably linked to a promoter that drives expression in progenitor cells. In another embodiment, transformed embryonic stem cells comprising at least one expression cassette.

In another embodiment, the progenitor cells are allowed to grow and differentiate and the enhancer activates or initiates expression of a marker or a reporter (e.g., green fluorescent protein, mCherry, etc.) after induction of cell differentiation. Thus the marker expression signals that the precursor cells have differentiated and have reached the proper cell state.

In another embodiment, an expression vector comprising a nucleic acid sequence for a cluster of neural enhancer sequences, selected from any of the polynucleotide sequences in SEQ ID NOS:1-145, which drive expression in a specific subregion. In some embodiments, expression in an organism is augmented by addition of an inducible molecule.

In some embodiments, it will be beneficial to provide more than one copy of the enhancer nucleotide sequence to the progenitor cell to induce differentiation.

In one embodiment, an induced pluripotent stem cell, such as those from a human patient, is transformed and undergoes cell differentiation by the enhancer nucleotide sequence of the present invention. Such differentiation can be confirmed by the expression of a selective agent, marker or label which is controlled by a suitable promoter capable of functioning in the stem cell, or with the enhancer nucleotide sequence of the present invention integrated in a suitable vector. The transformed and differentiated stem cell of the present invention, now a differentiated progenitor cell, can then be purified and used to generate specific cell and tissue types according to the present invention.

In another embodiment, a method for enriching and isolating differentiated stem cells, said method comprising introducing into a stem cell at least one expression cassette, said expression cassette comprising a neural enhancer nucleotide sequence and operably linked to a promoter that drives expression in the stem cell. In one embodiment, an expression cassette comprising a neural enhancer nucleotide sequence operably linked to a promoter that drives expression when cells have differentiated and reach proper cell state. In another embodiment, transformed cells comprising at least two copies of the expression cassette.

The expression vector usable in the present methods with the enhancer nucleotide sequence of the present invention include pUC vectors (for example pUC118, pUC119), pBR vectors (for example pBR322), pBI vectors (for example pBI112, pBI221), pGA vectors (pGA492, pGAH), pNC (manufactured by Nissan Chemical Industries, Ltd.). In addition, virus vectors can also used including but not limited to lentiviral, adenoviral, retroviral or sendai viral vectors. The terminator gene to be ligated may include a 35S terminator gene and Nos terminator gene.

The expression system usable in a method with the enhancer sequences of SEQ ID NOS:1-145 include any system utilizing RNA or DNA sequences. It can be used to transform transiently or stably in the selected host (bacteria, fungus, plant and animal cells). It includes any plasmid vectors, such as pUC, pBR, pBI, pGA, pNC derived vectors (for example pUC118, pBR322, pBI221 and pGAH). It also includes any viral DNA or RNA fragments derived from virus such as phage and retro-virus derived (TRBO, pEYK, LSNLsrc). Genes presented in the invention can be expressed by direct translation in case of RNA viral expression system, transcribed after in vivo recombination, downstream of promoter recognized by the host expression system (such as pLac, pVGB, pBAD, pPMA1, pGal4, pHXT7, pMet26, pCaMV-35S, pCMV, pSV40, pEM-7, pNos, pUBQ10, pDET3, or pRBCS.) or downstream of a promoter present in the expression system (vector or linear DNA). Promoters can be from synthetic, viral, prokaryote and eukaryote origins.

The neural enhancer sequences can be first cloned from cDNA, genomic DNA libraries or isolated using amplification techniques with oligonucleotide primers or synthesized. For example, sequences of candidate genes are typically isolated from nucleic acid (genomic or cDNA) libraries by hybridizing with a nucleic acid probe, the sequence of which can be derived from publicly available genomic sequence or the primers provided herein as SEQ ID NOS: 146-. In another embodiment, RNA and genomic DNA can be isolated from any mammal including: primates such as humans, monkeys, and chimpanzees; rodents, including mice and rats. Methods for making and screening cDNA libraries and genomic DNA libraries are well known (see, e.g., Gubler & Hoffman, Gene 25:263-269 (1983); Sambrook et al., supra; Ausubel et al., supra; Benton & Davis, *Science* 196:180-182 (1977); and Grunstein et al., *PNAS USA,* 72:3961-3965 (1975)).

Nucleic acids encoding the present neural enhancer sequences can also be isolated from expression libraries using antibodies as probes. Such polyclonal or monoclonal antibodies can be raised using, for example, the polypeptides comprising the sequences such as the neural enhancer sequence set forth in SEQ ID NO:1, and subsequences thereof, using methods known in the art (see, e.g., Harlow and Lane, Antibodies: A Laboratory Manual (1988)).

Substantially identical nucleic acids encoding sequences of the candidate genes can be isolated using nucleic acid probes and oligonucleotides under stringent hybridization conditions, by screening libraries.

Alternatively, expression libraries can be used to clone these sequences, by detecting expressed homologues immunologically with antisera or purified antibodies made against the core domain of nucleic acids encoding sequences of the candidate genes which also recognize and selectively bind to the homologue.

To drive increased levels expression of a cloned gene or nucleic acid sequence in a specific subregion, one can subclone the gene or nucleic acid sequence along with an appropriate enhancer sequence selected from SEQ ID NOS: 1-145 into an expression vector that is subsequently transfected into a suitable host cell. The enhancer sequence is selected based upon the subregion where it has been identified as driving expression and shown in Table 2. In some embodiments, the expression vector also contains other (strong) promoters or an additional enhancer from SEQ ID NOS: 1-145 to direct transcription, a transcription/translation terminator, and for a nucleic acid encoding a protein, a ribosome binding site for translational initiation. The enhancer and promoter are operably linked to the nucleic acid sequence. Suitable bacterial promoters are well known in the art and described, e.g., in Sambrook et al. and Ausubel et al. The elements that are typically included in expression vectors also include a replicon that functions in a suitable host cell such as *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable.

To increase the expression levels of a gene of interest in a specific subregion, one can subclone an appropriate enhancer sequence selected from SEQ ID NOS: 1-145 into a vector that contains the gene of interest. The vector is subsequently transfected into a suitable host cell in an organism. Based upon the subregion where it has been identified as driving expression (as shown in Table 2), the enhancer sequence is selected to direct expression of the gene of interest in the specific subregion of the forebrain of the organism. Genes of interest can be genes for example such as, GDNF glial derived growth factor to increase expression in the striatum to prevent cell death as in Parkinson's death.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to the recombinant neural enhancer sequences to provide convenient methods of isolation, e.g., His tags. In some case, enzymatic cleavage sequences (e.g., Met-(His) g-Ile-Glu-GLy-Arg which form the Factor Xa cleavage site) are added to the recombinant 14-3-3sigma inhibitor peptides. Bacterial expression systems for expressing the selectable markers or reporter genes are available in, e.g., *E. coli, Bacillus* sp., and *Salmonella* (Palva et al., Gene 22:229-235 (1983); Mosbach et al., Nature 302:543-545 (1983). Kits for such expression systems are commercially available. Eukaryotic expression systems for mammalian cells, yeast, and insect cells are well known in the art and are also commercially available.

Standard transfection methods can be used to promote differentiation of stem cells into neural progenitor cells, which can then purified using standard techniques (see, e.g., Colley et al., J. Biol. Chem. 264:17619-17622 (1989); Guide to Protein Purification, in Methods in Enzymology, vol. 182 (Deutscher, ed., 1990)). Transformation of cells is performed according to standard techniques (see, e.g., Morrison, J. Bact. 132:349-351 (1977); Clark-Curtiss & Curtiss, Methods in Enzymology 101:347-362 (Wu et al., eds, 1983). For example, any of the well known procedures for introducing foreign nucleotide sequences into host cells may be used. These include the use of calcium phosphate transfection, lipofectamine, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one enhancer nucleotide sequence into the stem cell capable of differentiating into a neural progenitor cell.

After the expression vector is introduced into the cells, the transfected cells are cultured under conditions favoring differentiation of stem cells into neural progenitor cells. Examples of conditions and methods for inducing cell differentiation are described in Reubinoff et al. U.S. Pat. No. 7,947,498, Embryonic stem cells and neural progenitor cells derived therefrom, Reubinoff et al. U.S. Pat. No. 7,604,992, Generation of neural stem cells from undifferentiated human embryonic stem cells, and Slukvin, I et al., US Patent Publication No. 20110117135, Method of Forming Dendritic Cells from Embryonic Stem Cells, all of which are hereby incorporated by reference in their entireties.

In another embodiment, a method for generating cell types using the enhancers SEQ ID NOS: 1-145 further comprising using growth factor inhibitors to generate cortical interneuron progenitors from ES cells. For example, in Eiraku et al., Cell Stem Cell 2008, 3:519-532; Danjo et al. J Neurosci 2011 31:1919-1933, hereby incorporated by reference, mouse ES cells were dissociated and 5000 cells/well were plated in 96-well lipidure-coated plates to facilitate embryoid body formation. Addition of two growth factor inhibitors, the anti-Wnt reagent Dickkopf-1 (Dkk1) and the anti-Nodal reagent Lefty-A (or SB431542), during the early time points of differentiation efficiently produced $Foxg1^+$ telencephalic neural stem cells. To convert neural stem cells into ventral telencephalic cells (MGE/LGE/POA-type neuron progenitors), Shh (or SAG, a Shh agonist) was added on day 3 and day 6 after differentiation.

In another embodiment, mouse ES cells are dissociated and grown as embryoid body (EB) as described in Maroof et al., J Neurosci 2010, 30(13):4667-4675), hereby incorporated by reference. Cells that become floating EB are grown in a 1:1 mixture of KSR and N2 media supplemented with noggin (250 ng/ml). On differentiation day 5 (dd5), embryoid bodies (EBs) are mechanically dissociated using Accutase (Invitrogen) and plated onto polyornithine-, laminin-, and fibronectin-coated plates using high density droplets (~10,000 cells/μl) in N2 medium with bFGF (10 ng/ml, day 5-8), IGF1 (20 ng/ml, day 5-8), and SHH (50 ng/ml, Shh-N-C25II, R&D Systems).

Such an approach exemplifies the ability to generate interneuron precursors from mouse ES cells. Using the methods and enhancers SEQ ID NOS:1-145, it is further possible to generate interneuron precursors from human ES and iPS cells, making them available for human transplantation and for molecular/cellular analyses. These approaches are also directly applicable to generating other neuronal cell types, such as cortical and striatal projection neurons, which have implications for many human diseases.

There are several reasons why it is important to generate these interneurons in vitro from stem cells. There are now viable experimental approaches to elucidate the genetic and molecular mechanisms that underlie these neuropsychiatric disorders through the generation of induced pluripotent stem cells, called iPS cells, from the skin of patients. Scientists are now challenged to develop methods to program iPS cells to become the specific types of brain cells that are most relevant to each specific brain disease. Therefore, the present constructs and examples incorporating the enhancers SEQ ID NOS:1-145 can be used to drive the production of specific subtypes of these cells from human stem cells. SEQ ID NOS:1-145 enable one to make these types of neurons from iPS cells to study human disease, and potentially to the production of these neurons for transplantation into patients whose interneurons are deficient in regulating their brain function.

Using iPS cell technology, one could generate these cells from patients with various forms of epilepsy, schizophrenia and autism, and determine whether abnormal interneuron function could contribute to these disorders because of cellular and/or electrophysiological defects. Furthermore, the approach herein described is general and readily applicable to the generation of other brain cells. Roughly 30% of epileptic patients continue to have disabling seizures despite maximum pharmacotherapy; many require surgical resection of the epileptic focus, and therefore could benefit from a cell-based therapy.

Thus, in some embodiments, enhancers SEQ ID NOS:1-145 can be used for generating several types of neurons, interneurons or other neural cell types, by driving expression and directing neuronal stem cell differentiation. For examples, SEQ ID NO: 73(hs671) can be used to generate cortical projection neurons by directing differentiation of DP, LP and VP progenitors. SEQ ID NOS: 63, 67 and 69 (hs631, hs643, and hs653 respectively) can be used to generate hippocampal projection neurons by directing differentiation of MP progenitors. SEQ ID NOS: 21(hs242) and 35 (hs342) can be used to generate striatal neurons by directing differentiation of LGE/CGE progenitors. SEQ ID NO: 35 (hs342) can be used to generate pallial neurons by directing differentiation of MGE progenitors. SEQ ID NOS: 35 (hs342) can be used to generate cortical interneurons by directing differentiation of MGE and LGE/CGE progenitors.

In one embodiment, a sample containing non-pluripotent cells (e.g., fibroblasts) can be obtained from a patient suffering from a neural disease or disorder and transfected with stem cell-associated genes to induce pluripotency. Induced pluripotent stem cells (iPS cells) can be generated by transfection of the fibroblasts with a vector containing known stem cell-associated genes from gene families such as KLF, OCT3/4 (POU5F1), MYC and SOX genes, and at least one enhancer of SEQ ID NOS:1-145 and an inducible promoter. The enhancer is selected based upon the preferred subregion of expression as identified in Table 2.

In another embodiment, a sample containing non-pluripotent cells (e.g., fibroblasts) can be obtained from a human, for example, from a patient suffering from a neural disease or disorder, and transfected with a gene or combination of genes to directly induce a neural fate. Induced neural cells (iN cells) can be generated by transfection of the fibroblasts with a vector containing genes known to be important in neural development (for example, ASCL1, BRN2, MYT1L), and at least one enhancer of SEQ ID NOS:1-145 and an inducible promoter. The enhancer is selected based upon the preferred subregion of expression as identified in Table 2. Alternatively, an enhancer can be introduced into the iN cells after the neural induction step.

Methods describing appropriate genes and vectors and fibroblast induction are described in Desponts, Shi; Desponts, Caroline; Do, Jeong Tae; Hahm, Heung Sik; Schöler, Hans R.; Ding, Sheng (2008). "Induction of pluripotent stem cells from mouse embryonic fibroblasts by Oct4 and Klf4 with small-molecule compounds". *Cell Stem Cell* 3 (5): 568-74; Zhou, Wi; Freed, Curt R. (2009). "Adenoviral gene delivery can reprogram human fibroblasts to induced pluripotent stem cells". *Stem Cells* 27 (11): 2667-74.; and Yamanaka, et. al (2006). Induction of pluripotent stem cells from mouse embryonic and adult fibroblast cultures by defined factors. *Cell* 126(4):663-676; Boland, M Y; Hazen, Jennifer L.; Nazor, Kristopher L.; Rodriguez, Alberto R.; Gifford, Wesley; Martin, Greg; Kupriyanov, Sergey; Baldwin, Kristin K. (2009). "Adult mice generated from induced pluripotent stem cells". *Nature* 461 (7260): 91-4; Vierbuchen T, Ostermeier A, Pang Z P, Kokubu Y, Südhof T C, Wernig M., "Direct conversion of fibroblasts to functional neurons by defined factors," *Nature.* 2010 Feb. 25; 463 (7284):1035-41. Epub 2010 Jan. 27; Pang Z P, Yang N, Vierbuchen T, Ostermeier A, Fuentes D R, Yang T Q, *Citri* A, Sebastiano V, Marro S, Südhof T C, Wernig M., "Induction of human neuronal cells by defined transcription factors," *Nature.* 2011 May 26; 476(7359):220-3; Lujan E, Chanda S, Ahlenius H, Südhof T C, Wernig M, "Direct conversion of mouse fibroblasts to self-renewing, tripotent neural precursor cells," *Proc Natl Acad Sci USA.* 2012 Feb. 14; 109(7):2527-32. Epub 2012 Jan. 30, all of which are hereby incorporated by reference for all purposes.

Upon successful transfection and subsequent induction to iPS cells, the iPS cells can be identified and isolated using a reporter gene. In some embodiments, the vector contains a reporter gene as described above. In other embodiments, enhancers SEQ ID NOS:1-145 can be used to label several types of neural progenitor cells, neurons, interneurons or other neural cell types, by directing reporter expression. For examples, SEQ ID NO: 73(hs671) can be used to label cortical projection neurons by directing reporter expression of DP, LP and VP progenitor cells. SEQ ID NOS: 63, 67 and 69 (hs631, hs643, and hs653 respectively) can be used to label hippocampal projection neurons by directing reporter expression of MP progenitor cells. SEQ ID NOS: 21(hs242) and 35 (hs342) can be used to label striatal neurons by directing reporter expression of LGE/CGE progenitor cells. SEQ ID NO: 78 (hs692) can be used to label pallial interneurons by directing reporter expression of MGE progenitors. SEQ ID NOS: 35 (hs342) can be used to label cortical interneurons by directing reporter expression of MGE and LGE/CGE progenitors.

Isolation and purification of specific cell types can be carried out using known cellular isolation and purification techniques including but not limited to fluorescence-activated cell sorting (FACS), flow cytometry, or other optical, electrical or droplet based isolation or purification.

In other embodiments, it is contemplated that SEQ ID NOS:1-145 may be used in conjunction with other types of enhancers (e.g. ventral midbrain for dopamine neurons).

The use of molecular markers of specific cell states can be used for studying or detecting cell differentiation. In one embodiment, the enhancer driven selectable marker is used to identify and or purify a cell type. Expression of fluorescent proteins provide a means of identification of a particular cell state, and thus allow for selection and/or purification of those cells identified by the expressed protein. For example, dual reporter/selection lentiviruses can be made containing one or more of the enhancers of SEQ ID NOS:1-145 and an Hsp68 promoter or beta-globin minimal promoter to select and purify for specific cell types.

Thus, a method for detecting and isolating cell types comprising (1) providing a lentivirus having a promoter, reporter gene and an enhancer selected from SEQ ID NOS: 1-145; (2) transfecting a stem cell with the lentivirus; (3) directing differentiation of the stem cell to the desired cell type and expression; (4) detecting reporter gene expression and (5) isolating cells using reporter gene.

In another embodiment, the enhancers SEQ ID NOS: 1-145 are used to generate specific types of cells (e.g. neurons, glia, etc.) from specific genotypic backgrounds (i.e. healthy individuals, or those with genetic predisposition to a particular disease [derived from iPS cells or other stem cells, or fibroblasts or other programmable cells]). Cells generated using the enhancers by such a method can then be used for screening or assaying drugs having a therapeutic effect. For examples, neurons from healthy individuals (cortical, striatal, motor neurons) could be used to test for neurotoxicity of a compound.), or cortical neurons from patient who has a neurodegenerative disease (e.g., ALS, Alzheimers, Huntington's, Parkinson's, frontotemporal dementia) could be tested for compounds that prolong the survival of the cells, or neurons from patient with a neurological disease that alters neuronal function (e.g., epilepsy caused by an electrophysiological, signaling, synaptic defect) could be tested for compounds that improve that aspect of neuronal function.

Example 1

The experiments described herein aim to understand basic mechanisms that underlie the development of cortical interneurons. This Example and Example 2 are also described by Axel Visel, et al., in "A High-Resolution Enhancer Atlas of the Developing Telencephalon," *Cell*, Volume 152, Issue 4, 14 Feb. 2013, Pages 895-908, and all the supplemental information, hereby incorporated by reference in their entirety. We are discovering regulatory elements (called enhancers) in the human genome that control gene expression in developing interneurons. In Example 1, we will study when and where these enhancers are expressed during mouse brain development. We will concentrate on identifying enhancers that control gene expression during development of specific types of cortical interneurons, although we hope to use this approach for additional cell types. We have identified and characterized where and when these enhancers are active. In Example 2 we will use the enhancers as tools in human stem cells to produce specific types of cortical interneurons in the test tube. The enhancers will be used to express proteins in the stem cells that will enable us purify only those cells that have specific properties (e.g. properties of cortical interneurons). We also plan to explore whether the human brain produces cortical interneurons in the same way as the mouse brain; this information is essential to identify molecular markers on the developing interneurons that could be used for further characterization and purification of the interneurons that we care generating in Example 2. While the examples focus on cortical interneuron subtypes, our work has general implications for the other types of brain cells our labs study, such as cortical and striatal neurons. In sum, the basic science mechanisms that we will discover will provide novel insights into how to generate specific types of neurons that can be used to study and treat brain diseases.

The telencephalon is the largest part of the mammalian forebrain with critical roles in cognition, behavior and neuropsychiatric disorders. A set of genes that control telencephalon development has been identified, but the regulatory sequences orchestrating their spatiotemporal expression are largely unknown. Here we describe an integrated genomic analysis and a comprehensive digital atlas of developmental telencephalon enhancer in vivo activities. Using non-coding sequence conservation and chromatin immunoprecipitation-sequencing (ChIP-seq) with the enhancer-associated p300 protein from embryonic mouse forebrain tissue, we identified over 4,600 forebrain candidate enhancer sequences. Focusing on genomic regions surrounding 79 genes with known roles in telencephalon development, 329 enhancer candidate sequences were characterized in transgenic reporter assays in day 11.5 mouse embryos. To explore forebrain enhancer activity patterns at high resolution, we generated serial brain sections for 145 forebrain enhancers. Annotation to a standardized neuroanatomical model revealed functionally related groups of enhancers that drive expression to distinct domains of the telencephalon and contain different sets of subregion-associated sequence motifs. Taken together, our comprehensive analysis of the regulatory architecture of mammalian telencephalon development identified thousands of high-confidence telencephalic enhancer candidates for genetic studies of neurodevelopmental disorders and provides a primary resource for investigating gene regulatory mechanisms of telencephalon development.

The telencephalon is the seat of consciousness, higher cognition, language, motor control and other pivotal human brain functions (Wilson, S W, Rubenstein J L, Induction and dorsoventral patterning of the telencephalon. *Neuron* 28, 641 (2000)). Impaired telencephalic development and function is associated with major neuropsychiatric disorders including schizophrenia and autism (Lewis D A, Sweet R A, Schizophrenia from a neural circuitry perspective: advancing toward rational pharmacological therapies. *J Clin Invest* 119, 706 (2009); Walsh, C A, Morrow E M, Rubenstein J L, Autism and brain development. *Cell* 135, 396 (2008)). Genetic and developmental studies in mice have identified many of the genes required for embryonic specification, morphological development and functional differentiation of the telencephalon (Hebert, J M, Fishell G, The genetics of early telencephalon patterning: some assembly required. *Nat Rev Neurosci* 9, 678 (2008); Hoch, R V, Rubenstein J L, Pleasure S, Genes and signaling events that establish regional patterning of the mammalian forebrain. *Semin Cell Dev Biol* 20, 378 (2009)). Significant progress has also been made towards defining spatially resolved gene expression patterns in the developing and adult mouse brain on a genomic scale (Gong, et al., A gene expression atlas of the central nervous system based on bacterial artificial chromosomes. *Nature* 425, 917 (2003); Visel, A, Thaller C, Eichele G, GenePaint.org: an atlas of gene expression patterns in the mouse embryo. *Nucleic Acids Res* 32, D552 (2004); Gray, P A, Fu H, Luo P, Zhao Q, Yu J et al., Mouse brain organization revealed through direct genome-scale TF expression analysis. *Science* 306, 2255 (2004); Lein, E S, Hawrylycz M J, Ao N, Ayres M, Bensinger A et al., Genome-wide atlas of gene expression in the adult mouse brain. *Nature* 445, 168 (2007). These studies show that many genes involved in brain development are transcriptionally regulated in dynamic and precisely controlled spatiotemporal patterns. Many aspects of such complex expression patterns are controlled by distant-acting transcriptional enhancers (Visel A, Rubin E M, Pennacchio L A, Genomic views of distant-acting enhancers. *Nature* 461, 199 (2009)). However, the precise genomic location and in vivo activity patterns of enhancers active during brain development have been difficult to determine, since these sequences can be located at large distances from the genes they regulate. Moreover, their sequence code is not sufficiently understood to distinguish them reliably from non-functional genomic sequences by computational methods. Extreme non-coding sequence conservation coupled to transgenic reporter assays revealed first sizeable sets of in vivo brain enhancers, but the majority of enhancers discovered through such studies were active in embryonic structures other than the forebrain (Nobrega M A, Ovcharenko I, Afzal V, Rubin E M, Scanning human gene deserts for long-range enhancers. *Science* 302, 413 (2003); Pennacchio, et al., *Nature* 444, 499 (2006); Visel, et al., *Nat Genet* 40, 158 (2008)). As a complementary approach, ChIP-seq with the enhancer-associated transcriptional co-activator protein p300 directly from ex vivo tissues enables the accurate genome-wide prediction of both the location and tissue-specific activity of in vivo enhancers (Visel A, Rubin E M, Pennacchio L A, Genomic views of distant-acting enhancers. *Nature* 461, 199 (2009)). Initial datasets obtained through this method, while limited in scope, demonstrated the general efficiency of this strategy (Visel, et al., *Nature* 461, 199 (2009)). In the present study, we have combined conservation- and ChIP-seq-based enhancer prediction with large-scale mouse transgenics and detailed histological analysis of enhancer activity patterns to explore on a genomic scale the enhancer architecture active during forebrain development.

To obtain a genome-wide set of forebrain enhancer candidate sequences, we collected forebrain tissue from approximately 200 mouse embryos (embryonic day [e]11.5) and performed tissue-ChIP-seq using an antibody for the enhancer-associated protein p300 (Visel A, Blow M J, Li Z, Zhang T, Akiyama J A et al., ChIP-seq accurately predicts tissue-specific activity of enhancers. *Nature* 457, 854 (2009)). Genome-wide enrichment analysis of these data led to the identification of 4,425 non-coding regions genome-wide that are distal from transcription start sites and significantly enriched in p300 binding in the e11.5 forebrain (See Table 1, complete data not shown). These sequences were thus predicted to be distant-acting forebrain enhancers. As a complementary approach to identify additional forebrain enhancers that act through p300-independent mechanisms, we also used extreme sequence conservation in conjunction with genomic location. Screening the genomic vicinity of 79 genes with a known role in forebrain development or function (Table 3) for the presence of sequences under extreme evolutionary constraint (Visel, et al, *Nat Genet* 40, 158 (2008)) revealed a total of 231 additional candidate forebrain enhancer sequences (Table 4). These two datasets combined comprise a total of 4,656 noncoding sequence elements that are expected to be enriched in forebrain enhancers.

To validate sequences identified through either approach and define their respective in vivo activities in more detail, we selected 329 candidate elements for experimental testing. Nearly all of these selected elements were located near genes with a known function in the forebrain. The selected candidate enhancer sequences were amplified from human genomic DNA, cloned into an enhancer reporter vector (Hsp68-LacZ), and used to generate transgenic mice by pronuclear injection. Transgenic embryos were stained for LacZ activity at e11.5 and annotated using established reproducibility criteria (Pennacchio, et al., In vivo enhancer analysis of human conserved non-coding sequences. *Nature* 444, 499 (2006)). Only elements that drove expression to the same general subregion of the forebrain in at least three embryos resulting from independent transgenic integration events were considered reproducible forebrain enhancers. In total, 105 of 329 (32%) candidate sequences tested were reproducible forebrain enhancers at e11.5. Enhancer candidate sequences that overlapped p300 ChIP-seq peaks were more enriched in verifiable in vivo forebrain enhancers than extremely conserved sequences that showed no evidence of p300 binding (58% compared to 23%). Selected examples of reproducible forebrain enhancers whose in vivo activity was confirmed in transgenic mice are shown in FIG. 1. Sequence coordinates and annotations of all reporter expression patterns including reproducible staining in anatomical structures other than the forebrain are summarized in Table 5 and are accessible online through the Vista Enhancer Browser (Visel A, Minovitsky S, Dubchak I, Pennacchio L A, VISTA Enhancer Browser—a database of tissue-specific human enhancers. *Nucleic Acids Res* 35, D88 (2007)). The collection of reproducible forebrain enhancers identified through these experiments provides in vivo-derived functional annotations for a large number of noncoding sequences that are likely to play a role in regulating gene expression during forebrain development.

Close examination of whole-mount annotated data suggests that a variety of distinct subdomains of the forebrain are reproducibly targeted by the identified enhancer elements. To define the spatial specificities of telencephalon enhancers active at e11.5 in detail, we selected a total of 145 enhancers for in-depth analysis (Table 2). These sequences were selected from the 105 forebrain enhancers discovered in the present study and from complementary sets of forebrain enhancers identified at whole-mount resolution in previous enhancer screens (Pennacchio, et al., In vivo enhancer analysis of human conserved non-coding sequences. *Nature* 444, 499 (2006); Visel A, Blow M J, Li Z, Zhang T, Akiyama J A et al., ChIP-seq accurately predicts tissue-specific activity of enhancers. *Nature* 457, 854 (2009); Visel A, Rubin E M, Pennacchio L A, Genomic views of distant-acting enhancers. *Nature* 461, 199 (2009); Visel A, Prabhakar S, Akiyama J A, Shoukry M, Lewis K D et al., Ultraconservation identifies a small subset of extremely constrained developmental enhancers. *Nat Genet* 40, 158 (2008). For each enhancer, a full set of contiguous coronal paraffin sections (average: 200 sections) was obtained. Full-resolution digital images of all 33,000 sections are available through the Vista Enhancer Browser (Visel A, et al. *Nucleic Acids Res* 35, D88 (2007)). Selected sections of patterns driven by different enhancers in the subregions of the pallium and subpallium are shown in FIGS. 2 and 3, illustrating the diversity of spatial specificities observed. Analysis of expression boundaries for individual enhancers confirmed that the reproducibility of patterns observed in whole-mount embryos was generally recapitulated at the histological level. Taken together, these data provide a large collection of enhancers with well-defined in vivo activities. All enhancers characterized through these efforts are freely available from the authors as reagents to drive expression of reporter or biologically active genes reproducibly to specific forebrain subregions of interest.

Referring now to FIG. 3, in order to facilitate computational analysis of this forebrain enhancer histology atlas, we devised a standardized neuroanatomical annotation scheme for this stage of telencephalon development (FIG. 6). This scheme considers morphological, developmental and molecular aspects of development {Puelles et al., Pallial and subpallial derivatives in the embryonic chick and mouse telencephalon, traced by the expression of the genes Dlx-2, Emx-1, Nkx-2.1, Pax-6, and Tbr-1. *J Comp Neurol* 424, 409 (2000), #335} to subdivide the e11.5 telencephalon and adjacent diencephalic regions into 11 major domains, of which 5 are pallial (dorsal) and 4 are subpallial (ventral) components of the actual telencephalon (FIGS. 2*a* and 2*c*). These domains can be further subdivided into ventricular, subventricular (where present at e11.5) and mantle zone. All telencephalon enhancer activity patterns examined in this study were annotated using this standardized annotation scheme, in some cases complemented by additional descriptions of aspects of patterns that further subdivide the standardized domains or are restricted to subsets of cells (Table 2). The standardized annotations assigned to each enhancer through this systematic annotation effort enable systematic comparisons and computational analysis of enhancer activity patterns, as well as a comparison to gene expression patterns of relevant transcription factors at this stage of development.

To systematically test whether enhancer activity patterns recapitulate the expression patterns of nearby genes, we performed correlation analysis based on our standardized annotation scheme. We annotated the mRNA expression patterns of 113 genes with known or suggested roles in forebrain development (predominantly transcription factors)

based on expression information available in public databases and/or the literature, using the same annotation scheme as for enhancer activity patterns (Table 6). We then compared these gene expression patterns to the activity patterns of enhancers located in the genomic vicinity (up to 1 Mb away) of the genes. Among 81 enhancers that were assigned to nearby genes with annotated forebrain expression patterns, we observed that in 67 cases (83%) at least one of the forebrain subregions in which the enhancer was active also showed evidence of mRNA expression. Overall, we found a highly significant correlation between the activity patterns of enhancers and telencephalic expression patterns of nearby annotated genes (P=0.0003, Mann-Whitney test, FIG. 4). These results support that the telencephalon enhancers identified and annotated in this study contribute to the spatial RNA expression patterns of nearby genes.

TABLE 7

Top enriched annotations of putative target genes near 4,430 ChIP-seq predicted forebrain enhancers.

| Rank* | Mouse Phenotypes | Binom Raw P-Value | Binom Fold Enrichment |
|---|---|---|---|
| Top enriched annotations near predicted mouse e11.5 forebrain enhancers | | | |
| 1 | abnormal forebrain development | 7.8E-44 | 2.5 |
| 2 | abnormal brain white matter morphology | 1.5E-43 | 2.4 |
| 3 | abnormal nervous system tract | 3.4E-42 | 2.4 |
| 4 | abnormal brain commissure morphology | 6.6E-42 | 2.5 |
| 5 | abnormal brain ventricle/choroid plexus morphology | 2.5E-39 | 2.2 |
| 6 | abnormal dorsal telencephalic commissure morphology | 2.8E-39 | 2.8 |
| 7 | abnormal corpus callosum morphology | 3.6E-39 | 2.8 |
| 8 | abnormal telencephalon development | 1.2E-33 | 2.7 |
| 9 | abnormal brain ventricle morphology | 4.6E-32 | 2.2 |
| 10 | abnormal neural tube closure | 1.8E-30 | 2.0 |
| Top enriched annotations near predicted human fetal cortex enhancers | | | |
| 1 | abnormal brain ventricle/choroid plexus morphology | 3.8E-19 | 2.1 |
| 2 | abnormal telencephalon development | 1.9E-18 | 2.6 |
| 3 | abnormal forebrain development | 3.0E-18 | 2.2 |
| 5 | abnormal neuronal precursor proliferatio | 7.1E-15 | 3.0 |

| | GO Terms (Biological Process) | Binom Raw P-Value | Binom Fold Enrichment |
|---|---|---|---|
| 1 | negative regulation of transcription from RNA polymerase II promoter | 1.7E-35 | 2.0 |
| 2 | forebrain development | 1.6E-33 | 2.1 |
| 3 | cell fate commitment | 3.8E-28 | 2.1 |
| 4 | central nervous system neuron differentiation | 4.4E-25 | 2.3 |
| 5 | oligodendrocyte differentiation | 2.0E-22 | 3.6 |
| 6 | Wnt receptor signaling pathway | 2.1E-19 | 2.1 |
| 7 | negative regulation of neuron differentiation | 3.0E-19 | 2.8 |
| 8 | pallium development | 3.9E-18 | 2.5 |
| 9 | cell fate specification | 1.7E-17 | 2.7 |
| 10 | telencephalon development | 1.1E-16 | 2.0 |

Table 7 top panel shows unsupervised enrichment analysis (McLean C Y, Bristor D, Hiller M, Clarke S L, Schaar B T et al., GREAT improves functional interpretation of cis-regulatory regions. *Nat Biotechnol* 28, 495 (2010), Cummings M P, Segal M R, Few amino acid positions in rpoB are associated with most of the rifampin resistance in *Mycobacterium tuberculosis. BMC Bioinformatics* 5, 137 (2004)) of annotated genes in the proximity of p300/CBP distal peaks. The test set of 4,430 genomic regions picked 3,955 genes (22%) of all 18,038 genes. The 10 most significantly enriched terms from the Mouse Phenotypes ontology are shown. Highly significant enrichment of predicted forebrain enhancers near genes with relevant phenotypes is observed (bold terms). * Only terms exceeding 2-fold binomial enrichment were considered and ranked by binomial p-values.

Nine of the ten most significantly enriched terms from the Mouse Phenotypes ontology are relevant to forebrain development. The only non-relevant phenotype was rank 10, “abnormal neural tube closure” (not shown). Bottom: For genes in the proximity of p300/CBP candidate enhancers identified from human fetal cortex, four of the five most significantly enriched terms are relevant to forebrain development. The only non-relevant phenotype was rank 4, “absent Purkinje cell layer” (not shown), which was associated with predicted cortical enhancers located near genes that play roles both in cerebral cortex and cerebellum development, including CCND1, CCND2, CDK5R1, LHX1, LHX5. In each species, only terms exceeding 2-fold binomial enrichment were considered and ranked by P-value (binomial raw P-values).

Table 7 bottom panel shows the top enriched GO Term annotations of putative target genes near 4,425 ChIP-seq predicted forebrain enhancers. Analysis was performed as shown in Table 1. The 10 most significantly enriched terms from the GO Biological Process ontologys are shown. Enrichment of predicted forebrain enhancers near genes with relevant functions is observed (bold terms). * Only terms exceeding 2-fold binomial enrichment were considered and ranked by binomial p-values.

In addition to the high-resolution comparisons of enhancer and gene activity patterns, we also assessed whether the genome-wide set of 4,425 forebrain enhancer candidate sequences identified by ChIP-seq from forebrain tissues is overall significantly associated with genes with known functions in the telencephalon. Using unbiased genome-wide enrichment analysis (24), we observed highly significant enrichment of forebrain candidate enhancers near genes with relevant biological functions and mouse phenotypes (Table 7). These observations support on a genomic scale that the large set of forebrain candidate enhancers predicted by ChIP-seq in this study is enriched near genes that are involved in telencephalon development.

Sequence Analysis of Subregion-Specific Enhancers.

A large set of telencephalon enhancers, analyzed at high spatial resolution and annotated to a standardized scheme, offers the possibility to examine sequence features that are associated with in vivo activity in different telencephalic subregions. To explore this regulatory code, we used the Random Forests (RF) method, a tree-based classification approach that is particularly effective for this purpose (See for example, Breiman L, Random Forests. *Machine Learning* 45, 5 (2001); Bureau A, Dupuis J, Falls K, Lunetta K L, Hayward B et al., Identifying SNPs predictive of phenotype using random forests. *Genet Epidemiol* 28, 171 (2005); Cummings M P, Segal M R, Few amino acid positions in rpoB are associated with most of the rifampin resistance in *Mycobacterium tuberculosis. BMC Bioinformatics* 5, 137 (2004); Lunetta K L, Hayward L B, Segal J, Van Eerdewegh P, Screening large-scale association study data: exploiting interactions using random forests. *BMC Genet* 5, 32 (2004)). Based on the broad expression characteristics of the annotated enhancers within the telencephalon, we trained a RF classifier to discriminate between enhancers active in 1. pallium only, 2. pallium and subpallium (compound pattern), or 3. subpallium only, and a background set of random genomic sequences with matching length and GC content (see FIG. 5 and Methods). Classification is based on the presence or absence of combinations of sequence motifs matching known transcription factor binding sites (Matys V, Kel-Margoulis O V, Fricke E, Liebich I, Land S et al., TRANSFAC and its module TRANSCompel: transcriptional gene regulation in eukaryotes. *Nucleic Acids Res* 34, D108 (2006), Bryne J C, Valen E, Tang M H, Marstrand T, Winther O et al., JASPAR, the open access database of transcription factor-binding profiles: new content and tools in the 2008 update. *Nucleic Acids Res* 36, D102 (2008)). The five most relevant motifs distinguishing the three classes of enhancers and their respective importance are shown in FIG. 5*b* (for additional motifs, see FIG. 3 and Table 8). We did not observe any single motif that was sufficient to accurately discriminate between the different classes of enhancers, suggesting that only the combinatorial binding of multiple transcription factors determines the observed spatial regulatory activity. The majority of the most discriminatory motifs (at least 60% of the top 15 motifs characterizing enhancers active in each of the telencephalic subregions considered) correspond to predicted binding sites for homeodomain-containing transcription factors, consistent with the known critical role of these proteins in telencephalon development (Hebert J M, Fishell G, The genetics of early telencephalon patterning: some assembly required. *Nat Rev Neurosci* 9, 678 (2008)). FIG. 8 summarizes the enrichment of the 15 most relevant motifs for enhancer activity in the three different telencephalic subregions considered. Despite possible ambiguities associated with computational transcription factor binding site predictions, the RF classifier accurately predicts approximately 80% of the sequences (see Methods, Table 9). The classifier is notably good at distinguishing enhancers active in pallium only, pallium and subpallium, and subpallium only from background genomic sequences, with accuracies ranging from 0.78 to 0.92, as measured by the area under the receiver operating characteristic curve (FIG. 5*b*). Furthermore, the classifier can separate enhancers controlling expression in the subpallium from those active in the pallium with reasonable accuracy (Table 9).

In addition, sequence motifs with high quantitative importance for discriminating between different classes of telencephalon enhancers are overall more conserved in evolution compared to non-important motifs, further supporting their functional relevance (FIG. 9). These results show that different sets of transcription factor binding sites are associated with enhancers active in different subregions of the developing telencephalon and highlight the value of high-resolution annotation of enhancer activity patterns for computational studies of their regulatory code.

Beyond such functional genomic studies, the enhancers identified and characterized as SEQ ID NOS:1-145 provide a comprehensive set of molecular reagents that can be used to target gene expression to defined subregions of the developing brain, or to defined cell states when differentiating stem cells in vitro. This will enable tissue-specific homologous recombination and deletion strategies or expression of reporter and selectable genes.

Human Brain ChIP-Seq.

Our large-scale transgenic testing and high-resolution analysis of telencephalon enhancers focused on sequences that are highly conserved in evolution, with the goal being to characterize the most conserved core regulatory architecture of mammalian telencephalon development. However, epigenomic methods also enable the systematic discovery of poorly conserved and lineage-specific enhancers (Schmidt et al., Five-vertebrate ChIP-seq reveals the evolutionary dynamics of transcription factor binding, *Science,* 328 (2010), pp. 1036-1040). To explore possible differences between human and mouse telencephalon enhancers in greater detail, we determined the genome-wide occupancy of the enhancer-associated proteins p300/CBP in human fetal (gestational week 20) cortex (FIGS. 20A and 20B). ChIP-seq analysis identified 2,275 peaks (candidate enhancers) genome wide that were located at least 2.5 kb from the nearest transcript start site. Comparison with transcriptome data from human fetal cortex tissue revealed a 2.7-fold enrichment in candidate enhancers within 2.5-20 kb of the transcript start sites of genes highly expressed in fetal human cortex ($p<1\times10^{-14}$, binomial distribution), with significant enrichment up to 220 kb away from promoters ($p<0.001$, binomial distribution, FIG. 20C). In contrast, no enrichment of p300/CBP binding sites was observed near genes highly expressed in other tissues. Similar to candidate enhancers predicted from mouse e11.5 forebrain, unsupervised statistical enrichment analysis of functional gene annotations (McLean et al., 2010) showed significant association with genes implicated in nervous-system-related phenotypes (Table 7). Although many extremely conserved noncoding sequences in the human genome are enhancers active in the developing nervous system (Pennacchio et al., 2006), we observed that one-third (36.5%) of ChIP-seq-predicted human brain candidate enhancers are under weak (phastCons<350) or no detectable evolutionary constraint, suggesting that subsets of human brain enhancers may not be functionally conserved in mice.

At gestational week 20, the human cortex is considerably further developed than the mouse pallium at e11.5 and instead corresponds broadly to early postnatal stages in mouse (Clancy et al., Extrapolating brain development from experimental species to humans *Neurotoxicology,* 28 (2007), pp. 931-937). To enable a direct experimental comparison between the two species, we performed p300/CBP ChIP-seq on mouse postnatal (P0) cortex tissue. Using identical methods to those used for human tissue, we identified 1,132 candidate enhancers (distal ChIP-seq peaks). The majority (58%) of human-derived peaks showed significant or suggestive (subsignificant) enrichment in ChIP-seq reads at the orthologous site in the mouse genome (FIG. 20D). The remaining 42% either showed no enrichment in the orthologous mouse region or were not alignable to the mouse genome. Though the lower sequencing coverage in the mouse data set may lead to an underestimation of mouse—compared to human-specific peaks (compare FIGS. 20D and 20E), the presence of 307 peaks in nonalignable regions of the human genome (FIG. 20D) supports that a nonnegligible proportion of human brain enhancers emerged in evolution after the divergence of primates and rodents from their last common ancestor.

Similar to the large collection of telencephalon enhancers identified and characterized at e11.5, ChIP-seq peaks derived from human fetal cortex are expected to include enhancers with a variety of in vivo activity patterns. To illustrate this, we examined the in vivo activities of candidate enhancers from human fetal cortex in postnatal transgenic mice. Two examples of such enhancers driving reproducible expression in a minimum of three independent transgenic animals are shown in FIGS. 20F-20K. Consistent with the ChIP-seq prediction, both enhancers were active in the cortex (arrows) as well as in additional but distinct and reproducible regions of the telencephalon.

To illustrate the value of the genome-wide sets of human and mouse candidate enhancers for the interpretation of human genetic data sets, we compared the genomic position of these sequences with different catalogs of regions in the human genome implicated in neurodevelopmental, neurological, or neuropsychiatric diseases. We intersected the genome-wide sets of candidate enhancers identified in the three different ChIP-seq experiments with (1) lead single-nucleotide polymorphisms (SNPs) from genome-wide association studies of relevant traits (Hindorff et al., Potential etiologic and functional implications of genome-wide association loci for human diseases and traits, Proc. Natl. Acad. Sci. USA, 106 (2009), pp. 9362-9367), (2) catalogs of syndromic microdeletions and microduplications (Firth et al., DECIPHER: Database of Chromosomal Imbalance and Phenotype in Humans Using Ensembl Resources, *Am. J. Hum. Genet.,* 84 (2009), pp. 524-533), and (3) a set of autism-associated rare copy-number variants (Marshall et al., Structural variation of chromosomes in autism spectrum disorder, *Am. J. Hum. Genet.,* 82 (2008), pp. 477-488; Szatmari et al., Mapping autism risk loci using genetic linkage and chromosomal rearrangements, *Nat. Genet.,* 39 (2007), pp. 319-328). Fourteen lead SNPs from genome-wide association studies, including SNPs associated with attention deficit hyperactivity disorder, bipolar disease, and schizophrenia, were found to be located within predicted forebrain enhancers. Moreover, 381 enhancers mapped within recurrent microdeletions or microduplications associated with neurological phenotypes, and 421 enhancers overlapped copy-number variants present in autism cases, but not healthy controls. Though further experimental studies will be required to examine possible causal roles of variants affecting enhancer sequences, the genome-wide sets of candidate enhancers identified from human and mouse brain tissue through this study provide a starting point to explore the role of telencephalon enhancers in human diseases.

Telencephalon Enhancers as Molecular Reagents.

The enhancers described in our high-resolution atlas can be used as molecular reagents to drive in vivo expression of reporter or effector genes to specific telencephalic subregions of interest, owing to the reproducibility of their activity patterns (FIG. 21A). To illustrate some of the resulting applications, we coupled enhancer hs1006, associated with the WNT8B gene, to a minimal Hsp68 promoter, followed by a tamoxifen-inducible Cre recombinase (CreER$^{T2}$), an internal ribosomal entry site, and a green fluorescent protein (GFP) reporter (FIG. 21B). In stable transgenic mouse lines generated with this construct, termed CT2IG-hs1006, GFP expression at e11.5 was indistinguishable from LacZ reporter expression (FIGS. 21A and 21B). GFP expression in these stable lines facilitates a temporally resolved mapping of enhancer activity. A comparison of GFP activity at e12.5, e15.5, and e17.5 with Wnt8b RNA expression reveals that enhancer activity spatially coincides with Wnt8b gene expression, indicating that this enhancer controls region-specific expression of the gene over an extended period of prenatal telencephalon development.

Because expression of the compound effector/reporter transcript in CT2IG-hs1006 mice faithfully resembled Wnt8b expression across multiple stages of development, the chemically inducible CreER$^{T2}$ recombinase can be used for spatially and temporally highly restricted genomic recombineering applications such as neuronal fate mapping studies. To demonstrate this, we crossed CT2IG-hs1006 mice with Rosa26-LacZ mice (FIG. 21B) (Indra et al., Temporally-controlled site-specific mutagenesis in the basal layer of the epidermis: comparison of the recombinase activity of the tamoxifen-inducible Cre-ER(T) and Cre-ER (T2) recombinases, *Nucleic Acids Res.,* 27 (1999), pp. 4324-4327). Tamoxifen induction of CreER$^{T2}$ in pregnant compound CT2IG-hs1006:Rosa26-LacZ mice at e10.5 leads to recombination only in the small proportion of pallial cells in which the enhancer is active at this time point. LacZ staining at later stages revealed the spatial fate of cells in which the enhancer was active at e10.5. For example, hs1006-driven e10.5→e12.5 fate mapping marked pallial cell populations with a distribution that is clearly distinct from hs1006 activity at this time point (compare e12.5 patterns in FIGS. 21C and 21D). These data highlight the utility of these enhancers to precisely drive gene expression in the developing brain and their value as a rich resource for a diversity of uses.

This work provides a comprehensive resource for basic studies of telencephalon enhancers. Our targeted screen identified the genomic location of thousands of candidate enhancers putatively active in the embryonic forebrain. The mapping and annotation of the activity patterns of nearly 150 human telencephalon enhancers at histological resolution in transgenic mice provide insight into the regulatory architecture of individual genes that are required for forebrain development and will facilitate studies of molecular genetic pathways by identifying the genomic regions to which upstream transcription factors bind.

Our analysis revealed several cases of enhancers that drive similar patterns and are associated with the same gene (e.g., FIG. 4B) in a manner reminiscent of the "shadow enhancers" observed in invertebrate models (Frankel et al., Phenotypic robustness conferred by apparently redundant transcriptional enhancers, *Nature,* 466 (2010), pp. 490-493; Hong et al., Shadow enhancers as a source of evolutionary novelty, *Science,* 321 (2008), p. 1314). The data provided through this work will support the identification of minor spatial activity differences between such enhancers, as well as the functional exploration of their apparent redundancies. It is also remarkable that a large proportion of enhancers examined in this study drove patterns that were at least partially different from all other enhancers examined, highlighting the complexity of the developing forebrain, as well as the regulatory sequence code orchestrating its development.

The motif-based classifiers derived from enhancers active in different subregions of the telencephalon demonstrate the value of systematically annotated enhancer activity data sets for computational studies aimed at deciphering the correlation between the transcription factor binding sites present in an enhancer and its precise spatial activity pattern. Beyond such functional genomic studies, the enhancers identified and characterized in this work provide a comprehensive set of molecular reagents that can be used to target gene expression to defined subregions of the developing brain or to defined cell states when differentiating stem cells in vitro. This will enable tissue-specific homologous recombination and deletion strategies or expression of reporter and selectable genes, as illustrated in FIG. 21.

Finally, results from this study are expected to enable and facilitate the functional genomic exploration of the role of enhancers in human brain disorders. There is accumulating evidence that non-coding sequence variants, as well as copy number variation in coding and non-coding portions of the genome have important impacts on a wide spectrum of disorders including bipolar, schizophrenia, autism, intellectual disability and epilepsy (See Visel A, Rubin E M, Pennacchio L A, Genomic views of distant-acting enhancers. *Nature* 461, 199 (2009); Durbin R M, Abecasis G R, Altshuler D L, Auton A, Brooks L D et al., A map of human genome variation from population-scale sequencing. *Nature*

467, 1061 (2010), Sebat J, Lakshmi B, Malhotra D, Troge J, Lese-Martin C et al., Strong association of de novo copy number mutations with autism. *Science* 316, 445 (2007); International Schizophrenia Consortium, Rare chromosomal deletions and duplications increase risk of schizophrenia. *Nature* 455, 237 (2008); Malhotra D, McCarthy S, Michaelson J J, Vacic V, Burdick K E et al., High frequencies of de novo CNVs in bipolar disorder and schizophrenia. *Neuron* 72, 951 (2011); Cooper G M, Coe B P, Girirajan S, Rosenfeld J A, Vu T H et al., A copy number variation morbidity map of developmental delay. *Nat Genet* 43, 838 (2011); Walsh T, McClellan J M, McCarthy S E, Addington A M, Pierce S B et al., Rare structural variants disrupt multiple genes in neurodevelopmental pathways in schizophrenia. *Science* 320, 539 (2008); Vacic V, McCarthy S, Malhotra D, Murray F, Chou H H et al., Duplications of the neuropeptide receptor gene VIPR2 confer significant risk for schizophrenia. *Nature* 471, 499 (2011)). However, owing to the incomplete genomic annotation of tissue-specific in vivo enhancers, the functional interpretation of non-coding sequence or copy number variants remains a major challenge; hence few potentially causative connections linking neurological traits to molecular variation in enhancers have been identified (e.g., Poitras L, Yu M, Lesage-Pelletier C, Macdonald R B, Gagne J P et al., An SNP in an ultraconserved regulatory element affects Dlx5/Dlx6 regulation in the forebrain. *Development* 137, 3089 (2010)). Many of the genes near the telencephalon enhancers we identified and characterized herein have been directly implicated in neurological or neuropsychiatric disorders (e.g., 39-45). Thus, the systematic mapping and high-resolution analysis of telencephalon enhancers through this work is expected to be extremely useful in providing functional genomic insights to guide studies that will mechanistically relate individual non-coding sequence and copy number variants to brain disorders.

Materials and Methods

Chromatin immunoprecipitation followed by sequencing (ChIP-seq). ChIP-seq with a p300 antibody (rabbit polyclonal anti-p300 (C-20), Santa Cruz Biotechnology) on forebrain tissue isolated from e11.5 CD-1 strain mouse embryos was performed according to previously described procedures (Visel A, Blow M J, Li Z, Zhang T, Akiyama J A et al., ChIP-seq accurately predicts tissue-specific activity of enhancers. *Nature* 457, 854 (2009)). To improve analysis depth, reads resulting from massive-parallel sequencing were enriched with reads from a previously described forebrain p300 ChIP-seq dataset (generated using the same antibody) and analyzed alongside forebrain input DNA reads (Visel A, et al., *Nature* 457, 854 (2009)). All reads were mapped to the mouse genome (mm9) using the Burrows-Wheeler Alignment (BWA) tool (Li H, Durbin R, Fast and accurate short read alignment with Burrows-Wheeler transform. *Bioinformatics* 25, 1754 (2009)). Repetitively mapped reads (mapping to multiple sites) and likely PCR artifacts (multiple reads mapping with identical start sites) were removed, resulting in U.S. Pat. Nos. 5,450,531 and 4,454,682 reads from forebrain p300 ChIP and forebrain input DNA samples respectively. P300-enriched regions were identified using CCAT (Xu H, Handoko L, Wei X, Ye C, Sheng J et al., A signal-noise model for significance analysis of ChIP-seq with negative control. *Bioinformatics* 26, 1199 (2010)), using default parameters for 'histone' ChIP-Seq, except for minscore=2. Enriched regions were filtered to remove those with: i) a mapping site located in an unassembled genomic fragment, ii) an FDR<0.2, iii) a CCAT enrichment score of <6.5, iv) a sample/control read depth ratio of <2, v) overlap with another CCAT peak with a higher-score region, and vi) length>7 kb. Finally, peaks within 5 kb of the nearest transcript start site were excluded as likely promoters, resulting in 4,425 p300-marked candidate forebrain enhancers (entire table not shown).

Transgenic mouse assays. Enhancer candidate regions (see Table 1 for sequence coordinates) were amplified by PCR (see enhancer.lbl.gov website for primer sequences) from human genomic DNA and cloned into an Hsp68-promoter-LacZ reporter vector using Gateway (Invitrogen) cloning as previously described (Pennacchio L A, Ahituv N, Moses A M, Prabhakar S, Nobrega M A et al., In vivo enhancer analysis of human conserved non-coding sequences. *Nature* 444, 499 (2006), Kothary R, Clapoff S, Brown A, Campbell R, Peterson A et al., A transgene containing lacZ inserted into the dystonia locus is expressed in neural tube. *Nature* 335, 435 (1988)). Transgenic mouse embryos were generated by pronuclear injection. $F_0$ embryos were collected at E11.5 and stained for LacZ activity as previously described in Pennacchio L A, Ahituv N, Moses A M, Prabhakar S, Nobrega M A et al., In vivo enhancer analysis of human conserved non-coding sequences. *Nature* 444, 499 (2006) and hereby incorporated by reference. Only patterns that were observed in at least three different embryos resulting from independent transgenic integration events of the same construct were considered reproducible. In the case of reproducible forebrain activity, subregional activity patterns (to the extent recognizable at whole-mount resolution) were taken into account; elements that drove LacZ activity to different regions of the forebrain in different transgenic embryos (as assessed by whole-mount staining) were not annotated reproducible forebrain enhancers and not considered for further analysis by sectioning.

Sectioning. LacZ-stained embryos were embedded in paraffin, sectioned in coronal orientation and counter-stained with eosin using standard protocols. Serial sets of sections were digitally photographed and uploaded to the Vista Enhancer Browser (http internet address enhancer.lbl.gov). Annotation of detailed telencephalic activity patterns was performed using a standardized neuroanatomical annotation scheme (FIG. 6) and recorded in tabulated format for computational downstream analysis (Table 6).

Dlx2 and Ascl1 were selected for luciferase reporter assays due to their well-established roles in subpallial development and because they are representatives of two major groups of transcription factors found among the top motifs of the subpallium classifier (see Experimental Procedures described herein). P19 cells were grown by previously described methods (Farah et al., Generation of neurons by transient expression of neural bHLH proteins in mammalian cells, *Development,* 127 (2000), pp. 693-702).

Images of whole-mount-stained embryos and full sets of e11.5 coronal brain sections are available through the Vista Enhancer Browser (enhancer.lbl.gov website). All enhancer reporter vectors described in this study are freely available. In addition, archived surplus transgenic embryos for many constructs can be made available upon request for complementary studies. The genome-wide set of ChIP-seq peaks derived from mouse e11.5 forebrain is provided in Table S1A in Visel et al., *Cell*, Volume 152, Issue 4, 14 Feb. 2013, *Pages* 895-908, hereby incorporated by reference. Raw data and additional ChIP-seq data sets from postnatal mouse and fetal human cortex are available from GEO under accession number GSE42881, also hereby incorporated by reference.

Random Forest Classifiers.

Enhancer datasets. We separated the experimentally assayed forebrain enhancers into non-overlapping classes of pallium (46), subpallium (44), and pallium and subpallium (18) enhancers, according to the reporter gene expression patterns driven by the enhancers. In addition, for each enhancer, we sampled 10 random sequences from the human genome, with matching length, GC- and repeat-content (background set).

Enhancer similarity. A random forest (RF) is a collection of decision trees. Therefore, the proximity between two enhancer sequences can be measured as the frequency with which they are assigned to the same forebrain subregion. The proximity matrix constructed in such way can be visualized using multidimensional scaling (MDS, FIG. 10)

Enhancer Representation. Enhancers were transformed into 1064-dimensional feature vectors, where each feature corresponds to a binding site in the TRANSFAC (Matys V, Kel-Margoulis O V, Fricke E, Liebich I, Land S et al., TRANSFAC and its module TRANSCompel: transcriptional gene regulation in eukaryotes. *Nucleic Acids Res* 34, D108 (2006)) or JASPAR (Bryne J C, Valen E, Tang M H, Marstrand T, Winther O et al., JASPAR, the open access database of transcription factor-binding profiles: new content and tools in the 2008 update. *Nucleic Acids Res* 36, D102 (2008)) databases. Significant occurrences of binding sites in the sequences were determined with MAST (Bailey T L, Gribskov M, Methods and statistics for combining motif match scores. *J Comput Biol* 5, 211 (1998)). Each feature represents the number of occurrences of a given binding site per base pair of sequence.

Preliminary feature selection. We used the F-score as preliminary screening to remove redundant and irrelevant features:

$$Fscore = \frac{(\overline{x}_i^{(+)} - \overline{x}_i)^2 + (\overline{x}_i^{(-)} - \overline{x}_i)^2}{\frac{1}{n^{(+)}-1}\sum_{k=i}^{n^+}(x_{k,i}^{(+)} - \overline{x}_i^{(+)})^2 + \frac{1}{n^{(-)}-1}\sum_{k=i}^{n^-}(x_{k,i}^{(-)} - \overline{x}_i^{(-)})^2}$$

where $\overline{x}_i$, $\overline{x}_i^{(+)}$, and $\overline{x}_i^{(-)}$ are the average of the ith binding site of the complete forebrain and control datasets, respectively; $n^{(+)}n^{(+)}$ is the number of forebrain enhancers and $n^{(-)}$ is the number of controls; $\overline{x}_{k,i}^{(+)}x_{k,i}^{(+)}$ is the ith binding site of the kth forebrain enhancer, and $\overline{x}_{k,i}^{(-)}x_{k,i}^{(-)}$ is the ith binding site of the kth control instance. Only the top 100 features ranked by the F-score were employed in the subsequent analysis.

Random forest classifier. A random forest (RF) trains a set of decision trees on subsets of features. Each tree in the forest assigns a class to each of the enhancers. The final classification of a given enhancer is decided by a simple majority vote. In the construction of the decision tree, a subset of n out of the total N features are randomly selected at each split, and the feature with maximum information gain out of the n is used to split the node. We constructed a RF with 500 decision trees, and randomly selected 10 out of the total 100 features to split the nodes. We used the RF implementation from the 'randomForest' R package (Liaw A, Wiener M, Classification and Regression by randomForest. *R News* 2, 18 (2002)). A visualization of the RF model to distinguish among 1. pallium only, 2. both pallium and subpallium, and 3. subpallium only enhancers, as well as random genomic sequences with matching length and GC content is shown in FIG. 5. For simplicity, we have omitted the proportion of trees in the RF that assign the enhancers to class 2, except for those enhancers that show activity in both pallium and subpallium.

During the construction of a RF, the out-of-bag (OOB) data, approximately one-third of the enhancers, are then used to estimate the prediction accuracy. Small classification errors would indicate classes of enhancers with strong tissue-specific signatures (Narlikar L, Sakabe N J, Blanski A A, Arimura F E, Westlund J M et al., Genome-wide discovery of human heart enhancers. *Genome Res* 20, 381 (2010)). The OOB estimate of the error rate for this model is 23.65%. The model performs reasonably well for each individual class (. Table 9).

The false positive rate (FPR) computed for enhancers active in pallium only, pallium and subpallium, and subpallium only with respect to random controls are 0.09, 0.03, and 0.08, respectively.

Extraction of relevant motifs. To assess the importance of a motif, we first randomly interchanged its frequencies of occurrence among all test sequences, then computed the prediction accuracy, and finally compared this value with the accuracy obtained for the original, unaltered sequences.

A critically important characteristic of RFs for this analysis is their ability to quantify which variables, in this case motifs, contribute most to the prediction accuracy and thus identify presumably biologically relevant motifs and their corresponding transcription factors. In the initial formulation, it was proposed to quantify the importance of a variable by verifying internal OOB prediction estimates using only selected variables (Breiman L, Random Forests. *Machine Learning* 45, 5 (2001)). To evaluate the importance of a given variable we first disrupt the association between the variable and the classifier response by randomly reshuffling the values of the variable across all forebrain enhancer sequences and then predict the response and measure the difference in the prediction accuracy before and after reshuffling the values of the variable. If the original variable was associated with the response, the prediction accuracy (i.e. the number of observations classified correctly) will decrease substantially.

We obtained a ranking of variable importance for each forebrain enhancer class. The 15 binding sites with highest impact in the prediction accuracy of the respective classifiers are shown in FIG. 7. Of note, some of the sequence motifs are predicted to be binding sites for transcription factors not expressed in the respective structure. For instance, Otx1 but not Otx2 is expressed in the pallium (Table 6). These apparent discrepancies likely result from the large numbers of related transcription factors with virtually indistinguishable binding sites, such as Otx1 and Otx2 (52). Therefore, many of the identified motif occurrences may represent in vivo binding sites for different, closely related transcription factors.

Conservation of relevant motifs. We hypothesized that if the predictive binding sites reflect actual transcription factor binding sites, they would tend to be preferentially located within these evolutionarily conserved localized regions. To test this systematically, we examined the correlation between the average 17-way phastCons conservation score (Siepel A, Bejerano G, Pedersen J S, Hinrichs A S, Hou M et al., Evolutionarily conserved elements in vertebrate, insect, worm, and yeast genomes. *Genome Res* 15, 1034 (2005)) of each binding site and the binding site importance, as determined by the RF algorithm. The average conservation score of each binding site was computed over all forebrain enhancer sequences containing at least one instance of the binding site. Also, for each forebrain enhancer sequence, only the binding site instance with the highest conservation score was considered for the average.

Indeed, for all classes of forebrain enhancers we observed that important binding sites identified by the RF algorithm (with a mean decrease in accuracy greater than the median value over all binding sites) are significantly more conserved than non-important binding sites (FIG. 5; P-values 2.0×$10^{-13}$, 2.5×$10^{-9}$, 1.1×$10^{-6}$, and 2.2×$10^{-16}$, for pallium, subpallium, pallium and subpallium, and the complete forebrain dataset, respectively, Wilcoxon Rank-Sum Test).

Relevant motifs and tissue-specificity. To determine and compare the density of putative binding sites among the different classes of forebrain enhancers we computed the over- or under-representation of binding sites as compared with randomly sampled genomic background (FIG. 8). Only binding sites among the 30 most relevant for each of the three enhancer classes considered were selected, with a total of 70. Our analysis showed that 38 (54%) of the most relevant binding sites were overrepresented in all forebrain enhancer classes. We used the Z-score to visualize the results as a heat map where rows are binding sites in TRANSFAC and JASPAR and columns correspond to pallium, subpallium, and pallium/subpallium enhancers. Binding sites were subjected to hierarchical clustering using the Euclidean distance measure with average linkage; enhancer classes were clustered using the Spearman correlation and average linkage.

Predicted distribution of pallium and subpallium enhancers. To investigate the distribution of pallium and subpallium enhancers in our telencephalon enhancer dataset, we applied the trained RF classifier with very strict cut-off parameters (FDR=5%) to 4,425 p300 ChIP-seq based telencephalon enhancer predictions. Over 1,855 enhancers were assigned to one of the 3 telencephalon classes at this level of stringency. From this set, 80% were predicted to be active in both pallium and subpallium, 9% active in pallium only, and 11% specific to subpallium.

TABLE 9

Confusion matrix for the RF classifier.

| | | classified as | | | |
|---|---|---|---|---|---|
| | | pallium | pallium and subpallium | sub-pallium | genomic background |
| true class | pallium | 19 | 4 | 14 | 9 |
| | pallium and sub-pallium | 1 | 12 | 0 | 5 |
| | subpallium | 10 | 4 | 14 | 16 |
| | genomic background | 98 | 31 | 89 | 862 |

The matrix shows how many enhancers active in pallium only, pallium and subpallium, and subpallium, as well as randomly selected (genomic background) sequences (rows) are classified in one of these possible four classes (columns). The numbers denote total numbers of classified sequences.

Example 2: Generating Neuron Progenitors Using MGE Enhancers

The medial ganglionic eminence (MGE) is an embryonic structure that generates the majority of cortical interneurons. MGE transplantation into the postnatal CNS modifies circuit function and improves deficits in mouse models of epilepsy, Parkinson's disease and psychosis. Herein, we describe approaches to generate mouse MGE progenitor cells from primary dissociated MGE cells as well as from embryonic stem (ES) cells. Using a modified embryoid body method for mouse ES cells, we provided gene expression evidence that ES-derived Lhx6$^{+}$ cells closely resemble immature interneurons generated from authentic MGE-derived Lhx6$^{+}$ cells. We also demonstrate the utility of enhancer elements [422 (DlxI12b), Lhx6, 692, 1056, and 1538] as tools to mark MGE-like cells in ES differentiation experiments. We found that enhancers DlxI12b, 692, and 1538 are active in MGE-like cortical interneuron progenitors while enhancer 1056 is active only in oligodendrocyte (Olig2$^{+}$) progenitors. These data demonstrate unique techniques to follow and purify GABAergic cortical interneurons and oligodendrocytes for use in stem cell-based therapeutic assays and treatments.

MGE enhancer constructs and cultures were made as described herein.

MGE Primary Culture.

E12.5 or E13.5 MGE from transgenic mouse brains were dissected and dissociated into single cells with 0.05% Trypsin with 10 μg/ml DNase I at 37° C. for 15 min. Defined proliferating media (Walton et al., 2006) included DMEM/F-12 glutamax (Invitrogen) with 5% FBS (Hyclone Defined Serum), 1× N2 (Invitrogen), 1× Pen/Strep (Cell Culture Facility at UCSF), 35 μg/ml bovine pituitary gland extract (Invitrogen), 20 ng/ml human bFGF (Peprotech) and 20 ng/ml human EGF (Peprotech). For differentiation media, serum, pituitary gland extracts and both growth factors were removed. For the serum free media, RHB-basal media (Stem Cell Sciences) was supplemented with 1× N2 (Millipore), 10 ng/ml EGF, 100 ng/ml FGF-8 (Peprotech), 5 ng/ml WNT-3a (R&D System) and 250 ng/ml Sonic hedgehog N-terminus (Shh-N) (R&D System). Cells could only be grown on laminin-treated culture plates with the serum free media. With all 4 growth factors combined, MGE cells continued to proliferate in vitro for up to 10 passages that last 7 weeks.

ES Cells Maintenance and Differentiation.

Mouse Foxg1::venus (Eiraku et al., 2008) and E14 ES cells maintenance medium was GMEM medium supplemented with 10% Knock Out Serum Replacement (KSR) (Invitrogen), 1% FBS (Hyclone, Define Serum), 1 mM sodium pyruvate, 0.1 mM MEM nonessential amino acids (NEAA), 0.1 mM 2-ME (2-mercaptoethanol, freshly prepared each time). For J14 cells (Maroof et al., 2010), maintenance medium was Knockout DMEM (Invitrogen) supplemented with 15% FBS, 2 mM glutamate, 0.1 mM NEAA, 1× Pen/Strep, 0.1 mM 2-ME. In all ES cells, 2000 U/ml Leukaemic Inhibitory Factor (LIF, Millipore) was added freshly every other day. For feeder cells (SNL and SNLB, see below) media: DMEM with 10% FBS with glutamate and 1× Pen/Strep. For all ES cell differentiation media: GMEM medium supplemented with 10% KSR, 1 mM sodium pyruvate, 0.1 mM NEAA, 0.1 mM 2-ME. It is important to note that different lots of KSR produced different percentage of Lhx6-GFP$^{+}$ cells (and Foxg1::venus$^{+}$ cells) and therefore required testing for differentiation media. For SFEBq culture (modified from the study by Danjo et al. 2010), ESCs were dissociated to single cells in 0.25% trypsin-EDTA and quickly re-aggregated in the differentiation medium containing 100 ng/ml Dkk-1 (5000 cells/100μl/well) using 96-well low cell adhesion plates (Lipidure-coat plate A-U96 from NOF America). On day 3 of differentiation (D3), 20 ul of differentiation media containing SAG (Alexis Biochemicals) was added into each well so that the final concentration for SAG is 6 nM. On D6, ES cell aggregates (embryoid body (EB) aggregates) were transferred to a 10 cm bacterial-grade dish with DMEM/F12 supplemented with N2 and 6 nM SAG.

Immunohistochemistry.

ES EB aggregates at various time points of differentiation were collected and fixed with 4% paraformaldehyde, then cryoprotected with 15% sucrose overnight before embedding in OCT media. Each aggregate was sectioned into 30×10 μm sections for immunofluorescent analyses. For antibody staining, glass slides with sections were washed with PBS three times and permeabilized with 0.3% Triton X-100 before blocking with 2% skim milk (Difco). Primary antibodies were guinea pig anti-β-Gal (1:500, kindly provided by Thomas Finger, University of Colorado) (Yee et al., 2003), chicken anti-GFP (1:500, Ayes Labs), rabbit anti-Ds-Red (mCherry) (1:500, Clontech), rat anti-Ds-Red (1:500, ChromoTeK), mouse anti-Nkx2-1 (1:200, Leica microsystems), rabbit anti-Nkx2-1 (1:200, Santa Cruz Biotechnology, Inc.), guinea pig anti-Dlx2 (1:2000, kindly provided by Kazuaki Yoshikawa, Osaka University, Osaka, Japan) ((Kuwajima et al., 2006), rabbit anti-Foxg1 (1:2000 (Watanabe et al., 2005)), mouse anti-Islet1 (1:250, IOWA Hybridoma Bank), mouse anti-human Ki67 (1:200, BD Pharmingen), rabbit anti-Tbr1 (1:1000, Millipore), rabbit anti-Olig2 (1:500, Millipore), mouse anti-Mash1 (1:500, BD Pharmingen), rabbit anti-GABA (1:1000, Sigma), rabbit anti-Calbindin (1:2000, Swant), rabbit anti-Math (1:1000, Bethyl Laboratories), rabbit anti-PV (1:2000, Swant), rat anti-Sst (1:250, Millipore), goat anti-Sst (1:200, Santa Cruz Biotechnology, Inc.), rabbit anti-NPY (1:250, ImmunoStar), mouse anti-β-III-Tubulin (TUBIII) (1:1000, TUJ1, Covance), Alexa 488 and Alexa 594 secondary antibodies (1:500, Invitrogen) were used accordingly to the primary antibody species. Sections were counterstained with 4', 6-diamidino-2-phenylindole (DAPI, 5 ng/ml, Invitrogen).

Image Analyses.

For co-localization of various markers with Lhx6-GFP$^+$, DlxI12b-βg-mCherry$^+$ and 692-mCherry$^+$ (692-βg-mCherry$^+$) cells we wrote a macro for cell counting of each channel (red and green channels) and of the co-localized channel in image J. The threshold was set 81-255 for green channel, and 69-255 for red channel; then it run “convert to mask” “watershed” “analyze particle size=15-200 circularity=0.20-1.00” for each channel and for the co-localized channel (created by “colocalization”, “channel1=red; channel2=green, ratio=50, threshold channel 1=50, threshold channel 2=50, display=255, co-localized”).

For co-localization of 692-mCherry$^+$, 692-βg-mCherry$^+$ cells with Lhx6-GFP$^+$, we manually counted cells from images taken from immunofluorescent staining (the data was comparable to that done by image J analyses but included more in depth analyses). GFP$^+$ and mCherry$^+$ cells were counted according to its expression level as bright cells or dim cells (there were 3-10 times more of dim mCherry$^+$ cells than bright mCherry$^+$ cells, whereas there were usually 2-3 times more of bright GFP+ cells than dim GFP+ cells). The percentage of co-localization in the result sections considered all cells. From one of the clones from each construct (J6M1 and J6βM31) we also calculated the percentage of co-localization among bright GFP$^+$ and mCherry$^+$ cells. In summary, 92.94%±9.85% of 692-mCherry$^+$ cells are Lhx6-GFP$^+$; 88.09%±4.7% of 692-βg-mCherry$^+$ cells are Lhx6-GFP$^+$; among Lhx6-GFP$^+$ cells, 35.44%±9.22% are 692-mCherry$^+$ and 31.05%±3.59% are 692-βg-mCherry$^+$.

For co-localization of 1538-βg-mCherry$^+$ cells with Lhx6-GFP$^+$, we also manually counted cells from 6 images taken from immunofluorescent staining on D14.

Transplantation.

On D12 of differentiation, ES EB aggregates from 20 96-wells plates were collected (1920 aggregates) and dissociated with the enzyme solution of the Neural Tissue Dissociation Kit (Sumitomo Bakelite, MB-X9901) (Danjo et al., 2011). Rock inhibitor Y-27632 (10 nM) was added in all the solutions to prevent cell death. Cells were stained with Sytox Blue (Invitrogen, to eliminate dead cells) in 1% BSA/HBSS 30 minutes before sorting to distinguish dead vs. live cells. Lhx6-GFP$^+$ cells were sorted with BD FACSAria II using 100 μm nozzle and collected in 10% FBS/DMEM/F-12. Fifty to one hundred thousand sorted Lhx6-GFP$^+$ cells were delivered into P0-P2 neonatal mouse cortices (anesthetized on ice for 3 min). Depth of injection: ~1 mm from the surface of skull, three transplantation sites each hemisphere. The pups were revived by on a 37° C. warm plate before being returned to the litter. Transplanted mice (4 days, 1 or 2 months after transplantation) were perfused transcardially with 4% paraformaldehyde, and 50 μm-thick brain sections were obtained for immunostaining.

RNA Microarray Analyses.

RNA was isolated from fluorescent activated cell sorting (FACS) purified ES-Lhx6-GFP$^+$ (two batches, 466K and 220K cells), ES-Lhx6-GFP$^-$ (158K cells), and MGE-Lhx6-GFP$^+$ (551K) cells using RNeasy Micro kit (QIAGEN) according manufacturer's instructions. The procedure of EB aggregates dissociation, FACS purification and collection of cells were the same as described above for cell transplantation. For E12.5 MGE, cells were dissociated as described in MGE primary culture. Purified total RNA was submitted to the Genomic Core at UCSF (arrays.ucsf.edu website), for quality assessment using a Pico Chip on an Agilent 2100 Bioanalyzer (Agilent Technologies). Total RNA was amplified using the Sigma whole transcriptome amplification kits following the manufacturer's protocol (Sigma) and Cy3-CTP labeled with NimbleGen one-color labeling kits (Roche-NimbleGen Inc). Equal amounts of Cy3 labeled target were hybridized to Agilent whole mouse genome 8×60K Ink-jet arrays. The data was extracted with Feature Extraction v10.1 software.

Genome Coordinates of Enhancers.

Enhancer 422 is located between Dlx1 and Dlx2 genes (human: chr2:172,955,879-172,957,052; corresponding to mouse: chr2:71,373,435-71,374,614), and encompasses the Dlx1 and Dlx2 intragenic enhancer, DlxI12b, (mouse: chr2:71,374,047-71,374,552) (Ghanem et al., 2007; Potter et al., 2009). Enhancer 692 is located on human chromosome 11 (chr11:15,587,041-15,588,314) near Sox6. Enhancer 1056 is on human chromosome 18 (human coordinates: chr18:76,481,720-76,483,257) near Sall3. Enhancer 1538 is on human chromosome 14 (ch14: 36,911,211-36,914,360) near Nkx2-1. The 2.1 kb mouse Lhx6 enhancer with proximal promoter was described by Du et al., NKX2.1 specifies cortical interneuron fate by activating Lhx6, *Development* 135:1559-1567, 2008.

Transgenic Mouse Enhancer Assay.

Enhancer candidates were amplified by PCR from human genomic DNA (Clontech) and cloned into the Hsp68 promoter-β-galactosidase reporter vector as previously described (Blow et al., ChIP-Seq identification of weakly conserved heart enhancers. Nat Genet 42:806-810, 2010). Transgenic mouse embryos were generated by pronuclear injection and F0 embryos were collected at E11.5 and stained for β-galactosidase activity with 5-bromo-4-chloro-3-indolyl β-D-galactopyranoside (X-Gal). Only patterns that were observed in at least three different embryos resulting from independent transgenic integration events of the same construct were considered reproducible. For detailed section analyses, embryos collected at E11.5 were fixed in 4% paraformaldehyde and stained with X-Gal overnight. X-Gal-stained embryos were then embedded in paraffin using standard methods. Coronal sections of the head were cut using standard methods, counterstained with Eosin for visualization of LacZ-negative embryonic structures and photographed.

Lentiviral Vector Generation.

The DlxI12b DNA fragment was PCR amplified from the DlxI12b-βglobin-Cre vector (Potter et al., 2009) with introduced 5' BamHI and 3' AgeI sites in the primers: (forward: 5'-CTCTGGATCCACACAGCTTAATGATTATC-3'(SEQ ID NO:148), reverse: 5'-GAGAACCGGTGCAGGAATTCATCGATGATA-3'(SEQ ID NO:149)). The 692, 1056 and 1538 DNA fragments were PCR amplified from human genomic DNA (Roche) with introduced 5' BamHI and 3' AgeI sites in the primers: (692 forward: 5'-ACAAGGATCCCACATCTCAGTGGCTCAT-3'(SEQ ID NO:150), reverse: 5'-TCTAACCGGTCAGGGTGTCTGTGTTGATG-3'(SEQ ID NO:151)), (1056 forward: 5'-GACAGGATCCGTCCCTCACAGAACTCAG-3'(SEQ ID NO:152), reverse: 5'-GACAACCGGTGATGCCTGCCTTGAAGTC-3'(SEQ ID NO:153)), (1538 forward: 5'-TCTAGGATCCTGCTGCCTCAAACAAGAATG-3'(SEQ ID NO:154), reverse: 5'-AGTTACCGGTTTGGATGAGGGAAAGACCTG-3'(SEQ ID NO:155)). Digested DNA fragments of enhancers were cloned into the BamHI and AgeI sites of the pLenti-mcs-mCherry_Rex1-Blasticidin$^r$ vector (Kita-Matsuo et al., 2009). The β-globin minimal promoter (template: DlxI12b-β-globin-Cre) and the hsp68 minimal promoter (Kothary et al., 1988) were PCR amplified with the following primers: (β-globin forward: 5'-CTATACCGGTAGCCCGGGCTGGGCATAA-3'(SEQ ID NO:156), reverse: 5'-GAGAACCGGTCGCCGCGCTCTGCTTCTGG-3'(SEQ ID NO:157)), (hsp68 forward: 5'-GAGAACCGGTGCATCGGCGCGCCGACC-3'(SEQ ID NO:158), reverse: 5'-ATATTCCGGAGGCGCCGCGCTCTGCTTC-3'(SEQ ID NO:159)). The minimal promoters were inserted into the AgeI site that preceded the mCherry gene. The Dlx-I12b-β-globin fragment was PCR amplified directly from (Potter et al., 2009), using the Dlx-I12b forward and β-globin reverse primers described above. All PCR fragments and lentiviral constructs were verified by restriction enzyme digests and DNA sequencing.

Lentivirus Production.

HEK293T cells grown in DMEM with 10% FBS were transfected using Fugene 6 transfection reagent (Roche) with four plasmids to generate lentivirus particles. Plasmids used for a 10 cm tissue culture plate of HEK293T cells (at about 50-70% confluence): 6.4 ug of Lentiviral vector DNA, with 1.2 ug each of 3 helper plasmids (pVSV-g, pRSVr and pMDLg-pRRE). Media was completely replaced 4 hours after transfection, and cells were grown for four days before harvesting. On day four of culture, all the media was collected and filtered through a 0.45 low protein binding membrane to remove cells and large debris. Filtered media was either aliquoted then stored at −80° C. (unconcentrated), or pooled and ultracentrifuged at 100,000×g for 2.5 hours at 4° C. The concentrated viral pellet was resuspended overnight in sterile PBS (adding 50 ul of PBS to the pellet for each 10 cm plate used), then stored at −80° C.

Transient Lentiviral Infection.

E13.5 MGE from wild type mouse brains were dissected and dissociated into single cells as described above. For differentiated ES cells, D11 aggregates were collected and dissociated with 0.05% Trypsin with 10 μg/ml DNase I for 20 min. Twenty thousand primary or ES cells were incubated with each of the lentiviruses for one hour in a 1.5 ml microcentrifuge tube at 37° C. water bath, and then cells were seeded in poly-L-lysine/laminin coated 16-well slide chambers overnight in the DMEM media (10% FBS) with the viruses. The next day, viral-containing media was removed and new media added. For MGE primary cells, the defined proliferation media was added; for differentiated ES cells, DMEM/F-12 with N2 supplement was added. Three days after infection, cells were washed and fixed with 4% paraformaldehyde before immunostaining.

Generation of Lentivirus-Transduced ES Cell Clones.

To generate ES cell clones containing lentiviral constructs, proliferating cells (E14 or J14) were dissociated and 400,000 cells were incubated with concentrated virus in a 1.5-ml microcentrifuge tube at 37° C. for 1 hour (mixing every 15 minutes). Then the virus/cells were transferred to ES maintenance media with LIF overnight (for E14, cells were seeded in gelatin coated plates alone; for J14, cells were seeded onto mitomycin C-treated SNLB feeder cells (see below)). The next day, the supernatant/virus was removed and fresh media with LIF was supplied for another day before adding Blasticidin (20 ug/ml for E14 cells and 4 ug/ml for J14) for 1 week of selection (changing media daily or every other day depending on cell density). Individual colonies emerged ~1 week after virus infection and were picked up by blunt 10 μl tips, then trypsinized into one well of a 96-well plates. Each clone was expanded and frozen down for further analyses. To establish blasticidin-resistant feeder cells, SNLB, an STO cell line (SNL76/7, a kind gift from Louis Reichardt, University of California, San Francisco, Calif.) that expresses Neomycin resistance gene and LIF gene, was transfected with pcDNA6/V5-His ABC plasmid (Invitrogen, empty vector with Blasticidin resistance gene driven by EM7). Mixed colonies of blasticidin resistance SNLB cells were expanded for frozen aliquots, or treated with mitomycin C for J14 enhancer cell line selection and maintenance.

Using Embryonic Tissue to Generate Cortical Interneuron Precursors.

We initially attempted to expand MGE progenitors directly from dissociated embryonic mouse MGE tissue. Because previous studies had been successful in expanding neural stem cells in serum-free or serum-containing media with the addition of epidermal growth factor (EGF) and basic fibroblast growth factor (bFGF, or FGF-2) (Conti et al., Niche-independent symmetrical self-renewal of a mammalian tissue stem cell. *PLoS biology* 3:e2832005; Walton et al., Microglia instruct subventricular zone neurogenesis. *Glia* 54:815-825, 2006), we tested several different protocols for MGE cells. We used MGE cells dissociated from E12.5/E13.5 transgenic embryos that expressed β-Galactosidase (β-Gal) or GFP in postmitotic MGE neurons, including immature cortical interneurons, under the control of a zebrafish Dlx5/6 enhancer or a mouse Lhx6-GFP BAC transgene (Stuhmer et al., Expression from a Dlx gene enhancer marks adult mouse cortical GABAergic neurons. *Cereb Cortex* 12:75-85, 2002; Gong et al., A gene expression atlas of the central nervous system based on bacterial artificial chromosomes. *Nature* 425:917-925, 2003; Cobos et al., Cellular patterns of transcription factor expression in developing cortical interneurons. Cereb Cortex 16 Suppl 1:i82-88, 2006).

We first used the serum containing media (proliferation media) (Walton et al., Microglia instruct subventricular zone neurogenesis. Glia 54:815-825, 2006) to culture dissociated MGE ventricular zone (VZ) and subventricular zone (SVZ) cells from Dlx5/6-βgal mice. In the serum containing media MGE cells continued to proliferate in vitro for ~3 weeks (5 passages). Removing growth factors and serum from the media (differentiation media) promotes neural differentiation (Walton et al., Microglia instruct subventricular zone neurogenesis. Glia 54:815-825, 2006), and in our hands resulted in a significant increase of β-Gar, GAD67$^+$, Dlx2$^+$ and Tuj1$^+$ cells in MGE culture after 4 days of differentiation (FIG. 1A-D"). Both GAD67 and Dlx2 expression mark forebrain GABAergic cells; similarly, β-Gal expression, driven by Dlx5/6 enhancer, is expressed by basal ganglionic GABAergic progenitors and neurons. Tuj1 is a pan-neuronal marker. Therefore, this protocol can generate forebrain GABAergic neurons. To test whether these cells maintain MGE identity we followed the expression of Lhx6.

Using MGE cells from Lhx6-GFP transgenic mice, we found that Lhx6-$GFP^+$ cells were present for 3-7 days in vitro, and formed clusters or aggregates (30-50% of the cells are Lhx6-$GFP^+$) in the adherent culture in the proliferation media (FIG. 11E-F). Prolonged culture (more than 10 days in vitro), or passage of cells (even with just one or two passages) resulted in a marked decrease in Lhx6-$GFP^+$ cells (FIG. 11G-H). Despite the increase of GABAergic neurons generated in the differentiation protocol, we found that numbers of Lhx6-$GFP^+$ cells went down (FIG. 11I-K), suggesting that this protocol was not effective at producing stable pools of MGE-type cortical interneurons.

Next, we attempted to maintain MGE identity using growth factors implicated in basal ganglia development (EGF, FGF-8, WNT-3a and Sonic hedgehog, individually and in combination) in a serum free media. However, this approach also failed to maintain Nkx2-1 and Lhx6-GFP expression, even after 1 passage (data not shown). Thus, we were unable to expand or maintain the identity of embryonic MGE cells in vitro, and concentrated on using ES cells to generate MGE-like neurons.

Using embryonic stem cells to generate cortical interneuron precursors. Embryonic stem (ES) cells, grown feeder-free or on feeder cells, can be expanded and differentiated into forebrain progenitors and neurons. The serum-free, floating culture of embryoid body-like aggregates ('SFEW') method is an efficient approach for converting ES cells into neural stem cells (Watanabe et al., 2005). In particular, addition of two growth factor inhibitors, the anti-Wnt reagent Dickkopf-1 (Dlck-1) and the anti-Nodal reagent Lefty-A (or SB431542), during the early time points of differentiation efficiently made Foxgr telencephalic neural stem cells (Watanabe et al., 2005; Eiraku et al., 2008). An improved SFEBq method using low cell-adhesion U-shape 96-well plates facilitates the aggregation of mouse ES cells after dissociation, generating aggregates of uniform size during differentiation and with higher efficiency of producing Foxg1$^+$ cells (Eiraku et al., 2008). To convert neural stem cells into ventral telencephalic cells, Shh (or SAG, an Shh agonist) was added on days 3 and 6 (D3 and D6) after differentiation (Danjo et al., 2011).

We used the SFEBq method (FIG. 12A) to generate MGE progenitor-like cells with three mouse ES cell lines: Foxg1::venus (Danjo et al., 2011), E14 (the parental cell line for Foxg1::venus) and J14 (Lhx6-GFP transgenic line) (Maroof et al., 2010). We optimized concentrations of Dkk-1, Shh, SAG, and other growth factors for MGE-like cell production based on Nkx2-1, Lhx6-GFP, and/or Foxg1 expression (data not shown). We found that a modification of Danjo et al., 2011 was the best procedure (adding 100 ng/ml Dkk-1 on D0 and 6 nM SAG on D3 and D6 of differentiation; FIG. 12A), and that SAG was more efficient and reproducible than recombinant Shh-N at generating Nkx2-1$^+$ cells (data not shown); the efficiency of our current protocol for induction of Lhx6-GFP expression at D15 was ~2-fold greater than that using the protocol of Danjo et al., 2011. Furthermore, Nkx2-1$^+$ induction was most efficient from the E14 cell line among the three cell lines tested (FIG. 12B-F' and data not shown).

At D9, the E14 cells expressed markers of MGE and POA VZ and SVZ progenitors (Nkx2-1, Mash1, and Islet 1; FIGS. 2B&C); by D15, there was a reduction of Nkx2-1 expression, and almost no Mash1 and Islet1 expression (FIG. 12B'&C'), suggesting a reduction in MGE and POA-type progenitors. On the other hand, between D9-D15, there was an increase in cells expressing GABA and Calbindin, markers of MGE and POA-type neurons (FIG. 12D-E"). To obtain better evidence for MGE neuronal differentiation we needed more specific markers for this cell type, and therefore turned to the J14 ES cell line.

MGE progenitor cells give rise to Lhx6$^+$ cortical interneurons, striatal interneurons, and globus pallidus neurons (Marin et al., 2000; Anderson et al., 2001; Flandin et al., 2010). To examine if Lhx6 expressed in our MGE differentiation protocol, we studied GFP expression in J14 cells (Lhx6-GFP transgenic line). Using the SFEBq method, we found that Lhx6-$GFP^+$ cells began to emerge on D9-10, when there was robust induction of Nkx2-1 expression (FIG. 13A-A"). The number of Lhx6-$GFP^+$ cells peaked on D12-13 (FIG. 13B') with a slight decline on D15-16 (FIG. 13D'). By contrast, the number of Nkx2-1$^+$ cells peaked on D9-D10 and gradually decreased from D12 to D16 (FIG. 13A-D). We measured the fraction of Nkx2-1$^+$ cells that expressed Lhx6-GFP with immunofluorescence analysis. On D10, about 50% of Nkx2-1$^+$ cells were Lhx6-$GFP^+$ (mean±SEM: 48.9±3.8%, n=3), whereas 70% of Lhx6-$GFP^+$ cells were Nkx2-1$^+$ (72.1±15.0%). On D12, 75% of Nkx2-1$^+$ cells were Lhx6-$GFP^+$ (75.3±12.9%), and 63% of Lhx6-$GFP^+$ cells were Nkx2-1$^+$ (62.9±6.0%, n=3). By D14 and D16, the percentage of Nkx2-1 and Lhx6-GFP co-expression decreased; only 43.3±1.9% and 42.8±5.2% of Nkx2-1$^+$ cells were Lhx6-$GFP^+$, and 34.7±1.8% and 47.3±13.8% of Lhx6-$GFP^+$ cells were Nkx2-1$^+$ on D14 and D16 respectively (n=3). Therefore, using an optimized SFEBq method, J14 and E14 ES cells can be differentiated into MGE-like Nkx2-1$^+$ progenitors and Lhx6-$GFP^+$ neurons. To further define the molecular properties of the Lhx6-$GFP^+$ cells, we used gene expression array analysis.

Comparing RNA Expression Profiles Between Lhx6-GFP+ Cells and Lhx6-$GFP^-$ Cells Generated from Mouse J14 ES Cells.

We used RNA expression array analysis to investigate molecular properties of Lhx6-$GFP^+$ cells generated from J14 cells at D12 of the MGE differentiation protocol. Lhx6-$GFP^+$ cells and Lhx6-$GFP^-$ cells (both from D12 EB aggregates) were isolated by fluorescent activated cell sorting (FACS) and were subjected to RNA expression microarray analyses (Table 7). Compared to Lhx6-$GFP^-$ cells (ES Lhx6-$GFP^-$), the Lhx6-$GFP^+$ cells (ES Lhx6-$GFP^+$) had lower expression of neural progenitor markers such as the HES genes (HESS in Table 1 and data not shown), suggesting that the Lhx6-$GFP^-$ cells were in a more proliferative state. Proliferation marker Mki67 (an antigen recognized by monoclonal antibody Ki67) was lower in expression in Lhx6-$GFP^+$ cells (data not shown). Subpallial-specific genes Dlx1, Dlx2, Dlx5, Dlx6, GAD1 (GAD67) and GAD2 (GAD65) were present in higher levels in the Lhx6-$GFP^+$ cells, consistent with its ventral telencephalic identity (Table 1 and data not shown). There were also higher levels of (mRNA) Nkx2-1, Lhx6, Lhx8 and Sox6 expression (Table 1), consistent with MGE identity. Markers of migrating immature interneurons such as ErbB4, MafB, NPAS1, Sst (Somatostatin) (Table 7), NPY (Neuropeptide Y) and Calb1 (Calbindin) (data not shown) were also expressed at higher levels in the Lhx6-$GFP^+$ cells. By contrast, genes expressed in oligodendrocytes, such as Olig2 and Sox10, were expressed higher in the Lhx6-GFP$^-$ cells (Table 7 and data not shown). There was also higher expression of pallial markers (Pax6, Tbr1 and Neurod1) and LGE (striatal) markers (Ebf1 and FoxP1) in the Lhx6-GFP$^-$ cells (Table 1 and data not shown).

We also examined hypothalamic and retinal marker expression in our microarray analyses. Rax expression is higher in the ES-Lhx6-GFP$^+$ cells than in the ES-Lhx6-GFP$^-$ cells (Table 7), suggesting that some of these cells may have either hypothalamic or retinal properties as Rax (Rx) is essential for early retinal and hypothalamic development (Mathers et al., 1997; Wataya et al., 2008; Medina-Martinez et al., 2009). On the other hand, Nkx2-2 expression is lower in the ES Lhx6GFP$^+$ cells compared to the ES Lhx6-GFP$^-$ cells (Table 10). Nkx2-2 is a marker of the hypothalamus and not the early retina (Shimamura et al., 1995; Kurrasch et al., 2007), although at mature stages it is expressed in retinal glia (Fischer et al., 2010). Finally, Otp expression is near background levels in all three samples (Table 10); Otp is a marker of the paraventricular nucleus analage (Bardet et al., 2008; Wataya et al., 2008). As Lhx6 is expressed in a small domain of the caudoventral hypothalamus (Allen Brain Atlas), it is possible that some of the ES Lhx6-GFP$^+$ cells have differentiated towards a hypothalamic fate.

To confirm these data, we analyzed protein expression with immunostaining on aggregates collected 9-16 days after differentiation (D9-D16). Consistent with our microarray data, ~50% of the Lhx6-GFP$^+$ cells co-expressed Dlx2 and ~75% of the Lhx6-GFP$^+$ cells co-expressed Foxg1 at D12 (FIGS. 13E&F), few Lhx6-GFP$^+$ cells expressed Islet1 (FIG. 13G), and none co-expressed Mki67, Tbr1, and Olig2 (FIG. 13H-J) on D11-D13 (and at other time points; data not shown). Thus the RNA expression array and immunostaining result provided strong evidence that Lhx6-GFP$^+$ cells from J14 ES cells had properties of MGE-derived neurons. To further solidify this conclusion, we directly compared RNA expression of Lhx6-GFP$^+$ J14 cells and Lhx6-GFP$^+$ MGE cells.

Comparing RNA Expression Profiles Between Lhx6-GFP$^+$ MGE Cells and ES-Derived Lhx6-GFP$^+$ Cells.

To investigate how closely ES cells-derived Lhx6-GFP$^+$ cells resembled authentic Lhx6$^+$ MGE cells, we compared their gene expression profiles. We used FACS to purify GFP$^+$ cells from the E12.5 MGE of Lhx6-GFP transgenic mice, and from J14 differentiated ES cells at D12 (see above). RNA was isolated from the cells and analyzed by gene expression array. We focused on the expression levels of genes with known regulatory functions and/or expression within the forebrain. We compared expression between the MGE Lhx6-GFP$^+$ (MGE-GFP$^+$) and J14 Lhx6-GFP$^+$-(ES-GFP$^+$) cells, and between MGE-GFP$^+$ cells and J14 Lhx6-GFP$^-$ (ES-GFP$^-$) cells (Table 10 and data not shown). There was a remarkable similarity in the properties of the MGE-GFP$^+$ and ES-GFP$^+$ cells (genes shown in green indicated those genes that were expressed higher in both MGE-GFP$^+$ and ES-GFP$^+$ than in ES-GFP$^-$). MGE-GFP$^+$ and ES-GFP$^+$ cells had relatively high expression (>10 arbitrary units) of MGE progenitor markers (Dlx1, Lhx6, Lhx8, Nbx2-1 and Sox6) and markers of immature MGE-derived pallial interneurons (ErbB4, GAD1, Lhx6, MafB, Sox6, and Sst). High levels of Coup-TF1 (NR2F1) suggest that the cells have properties of the dorsal MGE and/or the caudal MGE and CGE.

While MGE-GFP$^+$ and ES-GFP$^+$ cells shared properties of the MGE and immature cortical interneurons, only the MGE-GFP$^+$ showed robust expression of globus pallidus markers (Table 1 and data not shown), including Etv1 (ER81), Gbx2, Kctd12, Lhx8 and Zic1 (Flandin et al., 2010) (McKinsey, G., and Rubenstein, J L., unpublished observations). Furthermore, markers of the ventricular zone (Hess), oligodendrocytes (Olig2 and Sox10), pallium (i.e. cortex; Pax6 and Neurod1), LGE/striatum (Ebf1) and hypothalamus (Nkx2-2) were expressed lower in both MGE-GFP$^+$ and ES-GFP$^+$ cells than in ES-GFP$^-$ (shown highlighted in light gray in Table 10 and data not shown). Therefore, in vitro D12 differentiated J14-GFP$^+$ expressed RNAs that are similar to those expressed in immature MGE-derived interneurons, and not MGE-derived projection neurons (i.e. globus pallidus) or other MGE-derived cells such as oligodendrocytes. Next we studied the properties of these cells in vivo.

Lhx6-GFP$^+$ cells derived from mouse J14 ES cells became cortical interneurons after transplantation into mouse neonatal cortices. Our analyses indicated that our differentiation protocol generates MGE-type cells from J14 ES cells. Previous analyses of these cells showed that they can become cortical interneurons using a cell transplantation assay (Maroof et al., 2010). We confirmed this using our MGE-differentiation protocol of D12 Lhx6-GFP$^+$ sorted cells. Four days after transplantation, about 20% of these Lhx6-GFP$^+$ cells expressed markers of migrating cortical interneurons including GABA, Calbindin and MafB (data not shown). Thirty to sixty-nine days after transplantation, the Lhx6-GFP$^+$ cells had a very low survival rate (~1%), similar to a previous report (Maroof et al., 2010). Among Lhx6-GFP$^+$ cells, 22% (mean±SEM: 22.38±5.01%, n=4) of them also expressed Parvalbumin; 58% (57.96±11.50%, n=3) of them expressed Somatostatin; and 16% (15.51±6.57%, n=4) of them co-expressed Neuropeptide Y (data not shown), results that are very similar to Maroof et al., 2010. Therefore, the Lhx6-GFP$^+$ cells derived from J14 ES cells have properties of MGE cells based on gene expression data (previous sections) and have properties of cortical interneurons based on transplantation analysis (this section). In the next section we describe the use of J14 ES cells to study the activity of enhancers that are expressed in vivo in the MGE.

Generation of MGE-Like Cells In Vitro.

We were not successful in expanding MGE-type neurons in vitro from dissociated primary MGE cells (FIG. 11). While MGE cells became Dlx2$^+$ GABAergic neurons, they lost Lhx6-GFP expression. Thus, studies are needed to identify the signaling system(s) that maintain Lhx6 expression in dissociated primary MGE cell cultures.

In contrast to primary MGE cultures, protocols for differentiating ES cells into MGE-like progenitors and neurons have been devised, including the SFEBq method (Watanabe et al., 2005; Maroof et al., 2010; Danjo et al., 2011; Goulburn et al., 2011). We used a modified SFEBq protocol to generate MGE-like progenitors and immature MGE-like interneurons from mouse ES cells. Our modified SFEBq MGE differentiation protocol improved the efficiency (about 2-fold increase) of inducing Lhx6-GFP$^+$ cells compared to that of Danjo et al., 2011 (data not shown). We hypothesize that this improvement was because we did not dissociate the aggregates on D9 of differentiation, followed by FACS purification and reaggregation.

Our differentiation protocol generated progenitors and neurons with MGE-like molecular properties. At D12 clusters of cells within the aggregates expressed markers of immature MGE-derived neurons (Nkx2-1$^+$/Lhx6$^+$) (FIG. 13B"). However, many cells did not show expression of MGE markers, though they did not appear to be pallial cells as they lacked detectable Tbr1 and Pax6 expression (FIG.

13I and Table 10). Some Nkx2-1⁻/Lhx6⁻ regions may contain LGE/striatal cells as there was some Islet1 and CTIP2 expression (FIG. 3G and data not shown), although neither marker was LGE-specific. Olig2⁺ cells contributed to some of the Nkx2-1⁻/Lhx6-GFP⁻ cells (FIG. 13J), and probably correspond to immature oligodendrocytes. We are uncertain about the identity of the majority of the Nkx2-1⁻/Lhx6-GFP⁻ cells. Therefore, the MGE-differentiation protocol, while relatively specific for MGE specification, is not highly efficient.

The Nkx2-1⁺ MGE-like domains within the ES aggregates appeared around D8-9, similar to previous studies (Watanabe et al., 2005; Danjo et al., 2011). More than 50% of these Nkx2-1⁺ cells were proliferating at D9 based on Mki67 expression (data not shown). From D10 to D12, there was an increase of Nkx2-1⁺/Lhx6⁺ cells (FIG. 13A-B"); this expansion of the "MGE" clusters from D9-D13-suggested that Nkx2-1⁺ cells continued to divide. Later, the aggregates expressed makers of immature MGE-derived neurons (Lhx6, GABA and Calbindin; FIG. 12E-F' & 3D'). Furthermore, transplantation of FAC-sorted Lhx6-GFP⁺ cells generated neurons that expressed markers of MGE-derived interneurons (data not shown) as reported by Maroof et al., 2010.

Comprehensive gene expression analysis showed that the global RNA profile of ES-derived Lhx6-GFP⁺ cells (at D12 of differentiation) was quite similar to authentic E13.5 mouse Lhx6⁺ MGE cells. Furthermore, the RNA microarray profiles of both types of Lhx6-GFP⁺ sorted cells were similar to immature MGE-derived interneurons, and lacked prominent expression of markers of MGE-derived projection neurons (i.e. globus pallidus) or other MGE-derived cells such as oligodendrocytes.

Since the ES-derived Lhx6-GFP⁺ cells expressed Nkx2-1 and Lhx8 RNAs (Table 1), they probably correspond to cells that can differentiate into several lineages of MGE-derived neurons, including pallial and striatal interneurons and the globus pallidus neurons (Fragkouli et al., LIM homeodomain transcription factor-dependent specification of bipotential MGE progenitors into cholinergic and GABAergic striatal interneurons. *Development* 136:3841-3851, 2009; Flandin et al., The progenitor zone of the ventral medial ganglionic eminence requires Nkx2-1 to generate most of the globus pallidus but few neocortical interneurons. *J Neurosci* 30:2812-2823, 2010; Flandin et al., Lhx6 and Lhx8 coordinately induce neuronal expression of Shh that controls the generation of interneuron progenitors. *Neuron* 70:939-950, 2011). However, the gene expression array data showed lower expression of markers of globus pallidus neurons (e.g. ER81; Table 10; data not shown); therefore, we postulate that the ES-derived Lhx6-GFP⁺ cells are most similar to bi-potential immature interneurons. Furthermore, we suggest that these cells do not differentiate into subpallial cholinergic neurons because they have low expression of Islet1 and Gbx2 (Elshatory and Gan, The LIM-Homeobox gene Islet-1 is required for the development of restricted Forebrain cholinergic neurons. *Journal of Neuroscience* 28:3291-3297, 2008; Fragkouli et al., LIM homeodomain transcription factor-dependent specification of bipotential MGE progenitors into cholinergic and GABAergic striatal interneurons. *Development* 136:3841-3851, 2009; Chen et al., The mouse homeobox gene Gbx2 is required for the development of cholinergic interneurons in the striatum. *The Journal of neuroscience: the official journal of the Society for Neuroscience* 30:14824-14834, 2010) based on immunofluorescent (FIG. 3G) and gene expression array data (data not shown).

Finally, we found higher expression of MGE-derived cortical interneuron markers MafB and cMaf (McKinsey and Rubenstein, unpublished) in the Lhx6-GFP⁺ ES cells, providing evidence that this cell population has a bias towards pallial vs. striatal GABAergic interneurons.

We showed that ES-derived Lhx6-GFP⁺ cells transplantation into neonatal mouse produced cortical interneurons (data not shown). We did not test striatal transplantation, although we would expect that it would result in striatal interneurons, as found for MGE transplantation (Martinez-Cerdeno et al., Embryonic MGE precursor cells grafted into adult rat striatum integrate and ameliorate motor symptoms in 6-OHDA-lesioned rats. Cell Stem Cell 6:238-250, 2010). Future studies are needed to establish methods to promote pallial interneuron differentiation from these bi-potential progenitors. For instance, we have evidence that Zfhx1b transcription factor participates in the switch between pallial and striatal interneuron identity (McKinsey, G., and Rubenstein, J L., unpublished observations). Zfhx1b expression is expressed 3-fold higher in MGE-derived Lhx6-GFP⁺ cells than the ES-derived Lhx6-GFP⁺ cells (Table 1); perhaps increased Zfhx1b function would repress Nkx2-1 and Lhx8, and potentiate the differentiation of pallial interneurons.

Example 3: Enhancers Used to Enrich MGE-Derived Cells

Multiple small mouse enhancer elements that drive expression in mouse MGE cells have been identified. These include Dlx1 & Dlx2 (Dlx1/2) intergenic enhancer, Dlx5 & Dlx6 (Dlx5/6) intergenic enhancer, and Lhx6 promoter/enhancers (Zerucha et al., A highly conserved enhancer in the Dlx5/Dlx6 intergenic region is the site of cross-regulatory interactions between Dlx genes in the embryonic forebrain. *J Neurosci* 20:709-721, 2000; Ghanem et al., Distinct cis-regulatory elements from the Dlx1/Dlx2 locus mark different progenitor cell populations in the ganglionic eminences and different subtypes of adult cortical interneurons. *J Neurosci* 27:5012-5022, 2007; Du et al., NKX2.1 specifies cortical interneuron fate by activating Lhx6. Development 135:1559-1567, 2008; Potter et al., Generation of Cre-transgenic mice using Dlx1/Dlx2 enhancers and their characterization in GABAergic interneurons. *Mol Cell Neurosci* 40:167-186, 2009). In addition, we have been characterizing novel human telencephalic enhancers, some of which drive expression in MGE cells (Visel, et al., unpublished data) (enhancer.lbl.gov website). Although none of the enhancers is entirely specific for MGE cells, they may be extremely useful in stem cell studies. Thus, we have explored their utility in identifying cell types using the MGE differentiation protocol of mouse E14 and J14 ES cells. We compared the enhancer activities with markers of MGE cell identity, including expression of Lhx6-GFP.

Here we focused on five enhancers (FIG. 14D, see Table 1 and 2 for genome coordinates). Enhancer 422 is located between human Dlx1 and Dlx2; it includes in its sequences the Dlx1/2 intragenic enhancer DlxI12b that drives expression in forebrain GABAergic neurons, including those derived from the MGE (Ghanem et al., 2007). Similar to the reported mouse enhancer DlxI12b activity (Potter et al., 2009), human enhancer 422 (driving β-Gal expression) was active in MGE subventricular zone (SVZ) and mantle zones (MZ), as well as in the LGE/striatum region of E11.5 transgenic mouse brains (FIG. 4A). Enhancer 692 is located on human chromosome 11 in the region (~500 Kb away) of Sox6, a gene that is expressed in the MGE and its derived neurons. Enhancer 692 drove the β-Gal expression in VZ, SVZ, and MZ of MGE, as well as in migrating neurons of E11.5 transgenic embryonic brains (FIG. 14B). Enhancer 1056 was active only in the ventral part of the E11.5 MGE VZ and SVZ region (FIG. 14C). The nearest gene from enhancer 1056 is Sal-like 3 (Sall3), at about 250 Kb away. Enhancer 1538 was active in the VZ, SVZ and MZ of the ventral E11.5 MGE (FIG. 14D) and resides in the vicinity of the Nkx2-1 gene (~70 Kb away). Lhx6 enhancer with proximal promoter (Lhx6 E/P) sits just 5' to the Lhx6 translational start site and presumably contains an Lhx6 promoter (Du et al., 2008). The Lhx6 E/P is active in regions where endogenous Nkx2-1 is expressed; it responds to exogenous Nkx2-1 induction in brain slices and its activities were lost in Nkx2-1-null brain slices (Du et al., 2008).

To determine if these enhancers could be used in labeling mouse ES cells differentiated toward an MGE fate, we utilized a lentiviral vector, α-MHC-mCherry_Rex-Blasticidin$^r$, that previously was used to detect and isolate specific populations of differentiated ES cells (Kita-Matsuo et al., 2009). As mouse DlxI12b enhancer is smaller than human enhancer 422 (see Materials and Methods), and its activities were well documented, we used DlxI12b instead of 422 for the lentiviral constructs. We constructed three versions of the lentiviral vector for each enhancer, with different minimal promoters or none at all (FIG. 4E).

We first tested the lentiviruses (of three different vectors for DlxI12b & 692) in dissociated primary MGE cells from E13.5 mouse brains to evaluate enhancer activities. As shown in FIG. 4F-G", enhancer DlxI12b and enhancer 692 drove mCherry expression in these cells in the absence of an introduced minimal promoter (FIGS. 4F&G; DlxI12b-mCherry and 692-mCherry). In the presence of the heat shock promoter 68 minimal promoter (hsp68), both DlxI12b and 692 produced mCherry$^+$ cell clusters; however, these cells had no DAPI nuclear stains, suggesting that they were dead (FIGS. 14F'&G'). The addition of a β-globin minimal promoter (βg) resulted in stronger mCherry expression driven by DlxI12b, and increased the number of mCherry$^+$ cells compared to DlxI12b-mCherry (FIGS. 14F&G"). By contrast, no obvious effect was observed from the addition of the β-globin promoter to the enhancer 692 construct (692-βg-mCherry, FIG. 4G"). We also tested enhancer-less hsp68-mCherry and βg-mCherry lentiviral constructs in dissociated primary MGE cells. We found that hsp68 promoter alone drove mCherry expression, whereas β-globin promoter did not. Thus, the β-globin promoter appeared to be more suitable for our experiments.

In addition, we tested these lentiviruses by transient infection of MGE-like differentiated mouse ES cells (infected on D11, and harvested on D14) with the three different versions of lentiviral constructs for DlxI12b and 692; we found similar results as in dissociated primary MGE cells (data not shown).

Enhancer 1056 with or without a β-globin promoter produced similar amounts of mCherry+ cells in dissociated primary MGE cells (data not shown). On the contrary, enhancer 1538 without a minimal promoter did not drive mCherry expression in dissociated primary MGE cells (data not shown).

Enhancer DlxI12b Drives mCherry Expression in ~30% of Lhx6-GFP$^+$ Mouse ES-Derived MGE-Like Cells.

To explore DlxI12b enhancer activities in MGE-like, differentiated mouse ES cells, we generated stable mouse ES clones from both the E14 and J14 (Lhx6-GFP) cell lines with the DlxI12b-βg-mCherry_Rex-Blasticidin$^r$ lentiviral vector (the Foxg1::venus cell line is blasticidin-resistant and cannot be used for this purpose). We analyzed mCherry expression from two independent stable clones from each cell line (EI12bBM7, EI12bBM8; JI12bBM11, JI12bBM12). All four clones produced similar numbers of mCherry$^+$ cells in MGE-like differentiated ES cells (using our optimal MGE differentiation protocol). We then analyzed the expression of mCherry along the time course of ES cells differentiation. We started to detected a few DlxI12b-βg-mCherry$^+$ cellson D9 (data not shown) and then the numbers of mCherry$^+$ cells increased substantially on D11 and D13; by D15 there was little increase (FIG. 5A-C). Double staining of mCherry with Lhx6-GFP revealed frequent mCherry/GFP co-expression on D11, D13 and D15 (FIG. 15A"-C"). FACS analyses provided quantification of mCherry/GFP co-expression and individual protein expression (Table 11). The percentage of DlxI12b-βg-mCherry$^+$ cells was low on D9. On D11, about 70-80% of the DlxI12b-βg-mCherry$^+$ cells co-expressed Lhx6-GFP. On D13 and D15, 33-50% and 24-50% of the DlxI12b-βg-mCherry$^+$ cells co-expressed Lhx6-GFP (Table 11).

Figure 15:
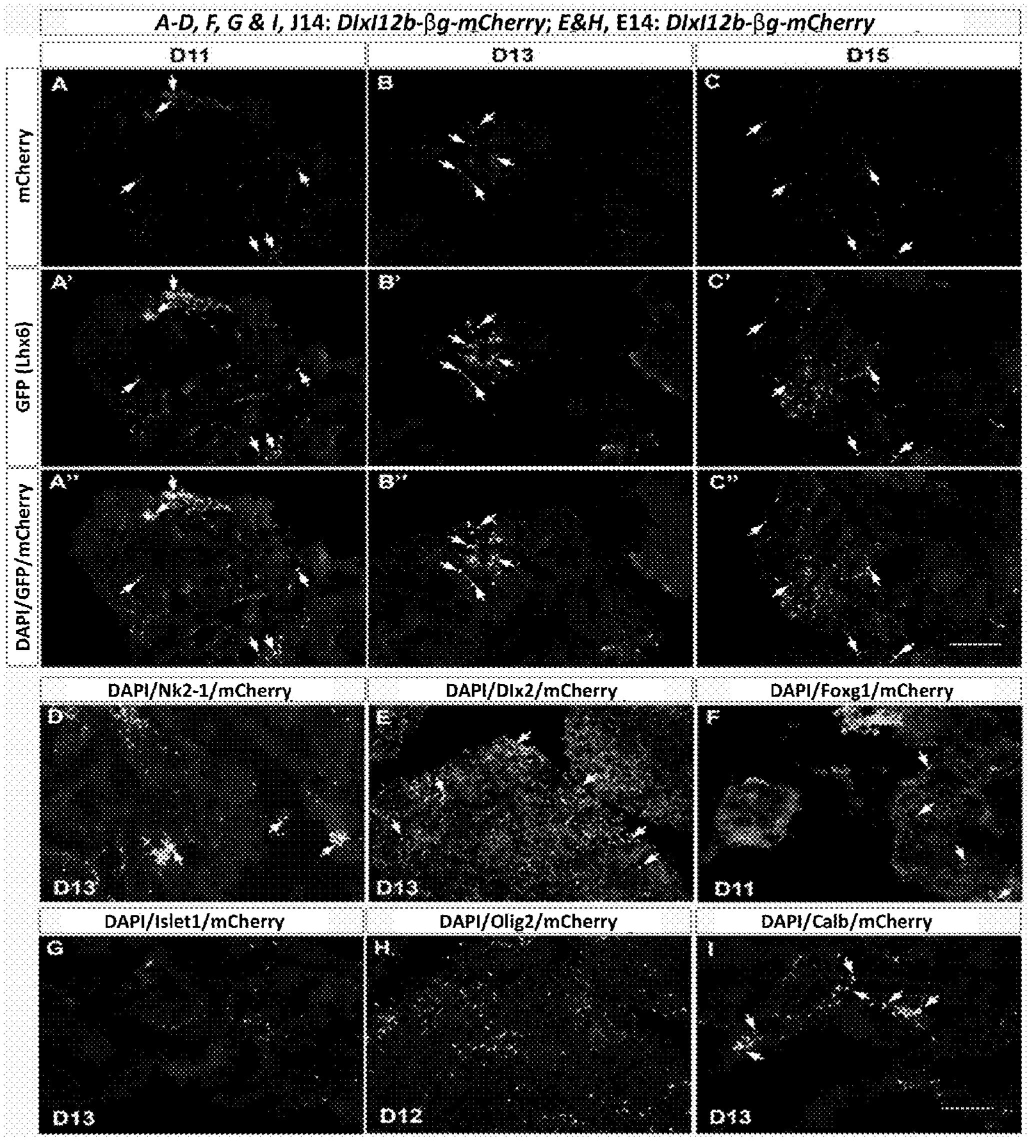

Examining DlxI12b-βg-mCherry expression with markers of telencephalic cell types showed that 49% of the mCherry$^+$ cells co-expressed Nkx2-1 on D13, and 55% of the Nkx2-1$^+$ cells co-expressed mCherry (FIG. 15D and data not shown). The vast majority of DlxI12b-βg-mCherry$^+$ cells co-expressed Dlx2, and Calbindin on D11, D13, and D15 (FIGS. 15 E&I and data not shown). Some of the DlxI12b-βg-mCherry$^+$ cells also express Foxg1, although to a smaller extent (FIG. 15F), perhaps because DlxI12b-βg-mCherry expression increased after D9, whereas Foxg1 expression decreased after D9. None of the DlxI12b-βg-mCherry$^+$ cells expressed Islet1 or Olig2 (FIGS. 5G&H and data not shown), providing evidence that DlxI12b enhancer was active in the MGE-derived cortical interneuron progenitors, rather than LGE (Islet1 is expressed in LGE neurons), or oligodendrocytes (Olig2 is an early marker of oligodendrocytes).

Enhancer 692 Drives mCherry Expression in >70% of Lhx6-GFP$^+$ Mouse ES-Derived MGE-Like Cells.

To analyze enhancer 692 activity we attempted to generate stable ES clones from all three lentiviral vectors (692-mCherry_Rex-Blasticidin$^r$, 692-hsp68-mCherry_Rex-Blasticidin$^r$, and 692-βg-mCherry_Rex-Blasticidin$^r$). With the 692-mCherry_Rex-Blasticidin$^r$ lentivirus, 8 out of the 13 E14 clones (from two different screens) and 6 out of the 7 J14 clones analyzed expressed mCherry$^+$ cells. With the 692-hsp68-mCherry_Rex-Blasticidin$^r$ lentivirus, none of the 6 E14 clones and none of the only 2 J14 clones analyzed expressed mCherry$^+$ cells. With the 692-βg-mCherry_Rex-Blasticidin$^r$ lentivirus, 1 out of the 3 E14 clones and 4 out of 8 J14 clones (from two different screens) expressed mCherry$^+$ cells. The lack of mCherry$^+$ cells from 692-hsp68-mCherry clones may reflect the hsp68-dependent toxicity we identified in transiently infected MGE cells (FIG. 14F'&G'). Thus, we focused on the 692-mCherry and 692-βg-mCherry clones.

We began by studying the time course of mCherry expression. Both 692-mCherry and 692-βg-mCherry expression began in a few cells at D9 in all of the clones examined (FIG. 6A and data not shown). By D11, a few more 692-βg-mCherry$^+$ and 692-mCherry$^+$ cells appeared (FIG. 16B). By D13, D15, and D17 there were increasing numbers of 692-mCherry$^+$ and 692-βg-mCherry$^+$ cells (FIGS. 16C&D, and data not shown).

The emergence of 692-mCherry$^+$ and 692-βg-mCherry$^+$ cells was positively correlated with the increase of Lhx6-GFP$^+$ cells. Indeed more than 50% of the Lhx6-GFP$^+$ cells co-localized with the 692-mCherry$^+$ and 692-βg-mCherry$^+$ cells at all the time points examined. This was particularly obvious when the fraction of mCherry cells reached its highest on D15 and D17 (FIG. 16C-D" and data not shown). Image analyses on three J14 692-mCherry clones (J6M1, J6M2, and J6M7) on D17 and three J14 692-βg-mCherry clones (J6βM31, J6βM32, J6βM33) on D15 indicated that 692-mCherry and 692-βg-mCherry were present in similar numbers of cells and the percentages of co-localization between Lhx6-GFP and mCherry were comparable (43.28%±6.13% of 692-mCherry$^+$ cells were Lhx6-GFP$^+$; 51.04%±8.48% of 692-βg-mCherry$^+$ cells were Lhx6-GFP$^+$; among Lhx6-GFP$^+$ cells, 72.87%±5.22% were 692-mCherry$^+$ and 70.08%±4.02% were 692-βg-mChcrry$^+$).

About 30-50% of 692-mCherry$^+$ and 692-βg-mCherry$^+$ cells co-expressed Nkx2-1 on D15 and D17; among Nkx2-1$^+$ cells, 63% are 692-mCherry$^+$ or 692-βg-mCherry$^+$ (white arrows in FIG. 16E). On the other hand, we did not detect co-expression of mCherry with Mki67 (FIG. 16F and data not shown), suggesting that 692 enhancer was active only in postmitotic cells. Essentially all 692-mCherry$^+$ cells were Sox6$^+$, an MGE marker (FIG. 16G). This is interesting considering that enhancer 692 resides near the Sox6 gene.

Unfortunately, mCherry expression from enhancer 692 was not robust enough to be seen by mCherry's intrinsic fluorescence (Table 11 and data not shown); all of our analyses required immunofluoresence. Thus, we could not use FACS to isolate 692-mCherry$^+$ or 692-βg-mCherry$^+$ cells.

Enhancer 1056 Drives mCherry Expression in Olig2$^+$ Cells and not Lhx6-GFP$^+$ Cells.

Next we made J14 ES cell clones with 1056-βg-mCherry_Rex-Blasticidin$^r$. From the 4 colonies that we picked and analyzed, just 1 of them expressed mCherry. To our surprise, 1056-βg-mCherry expression did not co-localize with Lhx6-GFP expression (FIG. 17F and data not shown). Nor did 1056-βg-mCherry$^+$ cells express Calbindin or GABA at all the time points examined, despite the fact that there were substantial numbers of mCherry$^+$ cells (FIG. 17I and data not shown). Rarely Nkx2-1 was co-expressed with mCherry, mainly where Nkx2-1$^+$ cells formed clusters (FIG. 17G). Likewise, very few of 1056-βg-mCherry$^+$ cells co-expressed Islet1$^+$ (FIG. 17J).

The MGE generates GABAergic neurons and oligodendrocytes (Kessaris et al., 2006; Petryniak et al., 2007). Thus, we tested whether 1056-βg-mCherry$^+$ cells were oligodendrocytes, by studying Olig2 expression. As shown in FIG. 17A-E", essentially all of the 1056-βg-mCherry$^+$ expressed Olig2, although there were generally fewer 1056-βg-mCherry$^+$ than Olig2$^+$ cells. In addition, we found more 1056-βg-mCherry/Mki67 double positive cells on D15 and D17, than on D9 and D11 (FIG. 17H and data not shown) though there were decreased numbers of both 1056-βg-mCherry$^+$ and Mki67$^+$ cells on D15 and D17. This suggested some of the 1056 enhancer-labeled cells continued to divide at late time points of differentiation.

Enhancer 1538 Drives mCherry Expression in >40% of Lhx6-GFP$^+$ Mouse ES-Derived MGE-Like Cells.

To test enhancer 1538 activity, we generated J14 stable ES lines with 1538-βg-mCherry_Rex-Blasticidin$^r$. We analyzed 5 clones; 2 of the clones had mCherry expression starting at D12 (FIGS. 8A&B). There were almost no mCherry$^+$ cells on D10 (FIG. 18A). On D12-D14, many 1538-βg-mCherry$^+$ cells appeared (FIGS. 18B&C). Though 1538 enhancer resides in close proximity to Nkx2-1 gene locus, its activity in the differentiating ES cells did not fully correlate with that of Nkx2-1 expression (FIG. 18E). In addition, enhancer 1538 activity was not detected in mitotically active (MKi67$^+$) cells (FIG. 18F and data not shown). However, its expression did highly correlated to that of Lhx6-GFP (FIG. 18B"-D"). We analyzed the Lhx6-GFP$^+$ and mCherry$^+$ cells on D14: 40% (41.18%±4.32%) of Lhx6-GFP$^+$ cells were mCherry$^+$; 90% (92.26%±3.78%) of mCherry$^+$ cells were Lhx6-GFP$^+$. Enhancer 1538 activity was not strong enough that we did not detect any mCherry$^+$ cell by FACS (Table 11); thus our analyses required mCherry immunofluorescence.

There was No mCherry Expression with Lhx6 Enhancer/Promoter Constructs.

In addition, we also generated a lentiviral vector with a putative Lhx6 promoter/enhancer DNA fragment (Lhx6 E/P-mCherry_Rex-blasticidin$^r$) hoping that it could substitute Lhx6-GFP BAC's activities. Unfortunately despite the fact that it was active in dissociated MGE cells (data not shown), we did not see any mCherry$^+$ cells from MGE-like differentiated ES cells in any of the 7 stable J14 ES clones with this construct.

The DlxI12b Enhancer Continued to be Active in the Adult Cortex.

While our work focused on the activity of the enhancers in MGE-like differentiated ES cells in vitro, we did briefly explore whether the DlxI12b and 692 enhancers maintained their expression in vivo following transplantation into neonatal mouse cortex. We used FACS to purify GFP$^+$ cells from MGE differentiated (D12) J14 ES cells that also carried either enhancer DlxI12b [line: DlxI12b-βg-mCherry (JI12bβM11)] or 692: [line: 692-mCherry (J6M1)]. As described above, in vitro (on D12) 30% of these Lhx6-GFP+ cells are DlxI12b-βg-mCherry$^+$ (for JI12bβM11), and 70% of the Lhx6-GFP+ cells are 692-mCherry$^+$ (for J6M1).

Analyses of seven transplants from JI12bβM11 [4 animals from 69 days after transplant (DAT), and 3 animals from 33 DAT] found 28.33±2.81% (mean±SEM, n=7) of Lhx6-GFP$^+$ cells were DlxI12b-βg-mChetTy$^+$ (FIG. 9A-B"), showing that the DlxI12b enhancer continued to be active in the adult cortex. On the other hand, we had difficulty finding 692-mCherry$^+$/Lhx6-GFP$^+$ cells in 4 transplants from J6M1 (33 DAT) suggesting either that enhancer 692 is not active, or is very weak, in mature neurons (data not shown). Thus, enhancer DlxI12b, but not 692, is effective for labeling ES cell-derived MGE-derived mature neurons in the adult cortex.

Example 4: Use of "MGE Enhancers" to Monitor MGE Cell Differentiation

The use of molecular markers of specific cell states is a powerful tool for studying cell differentiation. In particular, expression of fluorescent proteins, from specific endogenous gene loci, or from transgenes (e.g. bacterial artificial chromosomes, BACs), is an effective method to identify cell states, and purify those cells. Currently, two cell lines have been generated that are useful for MGE differentiation: 1) mouse J14 ES cells that express GFP from an Lhx6 BAC (Maroof et al., 2010); 2) human ES cells that express GFP from the endogenous Nkx2-1 locus (Goulburn et al., 2011). An alternative approach, as demonstrated here, is to drive reporter expression using cell/tissue-specific promoters and/or small enhancer elements (Kita-Matsuo et al., 2009). The latter approach has several potential advantages: 1) the small size of the enhancers, often less than 1 kb, makes them ideal for insertion into viral vectors; 2) the small enhancers often have a more restricted range of tissue and cell type expression; 3) the approach is ideal for marking multiple cell lines, which would be extremely difficult using BAC transgenic or knock-in strategies; 4) knock-in strategies often alter the function of the endogenous gene which can alter the developmental potential of the cells.

In Example 1, we have identified a large number of enhancer-like elements in the human genome that drive expression in specific subdivisions of the embryonic mouse telencephalon (Visel et al., submitted; see enhancer.lbl.gov website). Some of these enhancers drive expression in the E11.5 MGE. Here we explored the function of three of these (novel enhancers 692, 1056, and 1538), in addition to the DlxI12b and Lhx6 promoter/enhancers (Ghanem et al., Distinct cis-regulatory elements from the Dlx1/Dlx2 locus mark different progenitor cell populations in the ganglionic eminences and different subtypes of adult cortical interneurons. J Neurosci 27:5012-5022, 2007; Du et al., NKX2.1 specifies cortical interneuron fate by activating Lhx6. Development 135:1559-1567, 2008; Potter et al., Generation of Cre-transgenic mice using Dlx1/Dlx2 enhancers and their characterization in GABAergic interneurons. Mol Cell Neurosci 40:167-186, 2009). We introduced each of these five enhancers into the E14 and J14 (Lhx6-GFP) lines of mouse ES cells (Maroof et al., Prospective isolation of cortical interneuron precursors from mouse embryonic stem cells. J Neurosci 30:4667-4675, 2010) using the vector described by Kita-Matsuo et al., Lentiviral vectors and protocols for creation of stable hESC lines for fluorescent tracking and drug resistance selection of cardiomyocytes. PLoS One 4:e5046 (2009), subjected them to the MGE differentiation protocol, and analyzed mCherry expression in differentiated ES cells. Four of the enhancers drove mCherry expression in MGE-like cells; only the Lhx6 enhancer did not work. Enhancer 1056 drove expression in $OLIG2^+$/Lhx6-$GFP^-$ cells (FIG. 17). This is consistent with the observation that the MGE generates oligodendrocytes (Kessaris et al., Competing waves of oligodendrocytes in the forebrain and postnatal elimination of an embryonic lineage. Nature neuroscience 9:173-179, 2006; Petryniak et al., Dlx1 and Dlx2 control neuronal versus oligodendroglial cell fate acquisition in the developing forebrain. Neuron 55:417-433, 2007). We predict that enhancer 1056 will be useful for driving expression in oligodendrocyte progenitors.

Enhancers DlxI12b, 692, and 1538 drove mCherry expression in MGE-like neurons (Nkx2-$1^+$/Lhx6-$GFP^+$), but not $Olig2^+$ cells (FIGS. 15, 16 & 18). Given that $Lhx6^+$ cells derived from J14 cells have properties of immature pallial interneurons, based on gene expression array analysis (Table 1) and in transplantation assays (FIG. 19; data not shown; (Maroof et al., Prospective isolation of cortical interneuron precursors from mouse embryonic stem cells. J Neurosci 30:4667-4675, 2010)), we propose that DlxI12b, 692, and 1538 drive expression in cells with properties of MGE-derived interneurons.

DlxI12b enhancer was active in both immature and mature pallial interneurons sixty days after transplantation into the neocortex, whereas enhancer 692 appeared to be active only in immature MGE cells. In the future, one could follow the fate of $692^+$ cells at postnatal ages by transducing a constitutive GFP reporter into the cells prior to transplantation. Furthermore, it will be of interest to follow the fate of enhancer 1056 marked cells (1056-βg-$mCherry^+$ cells) following cortical transplantation to determine whether they develop into mature oligodendrocytes, or whether they die, as proposed for some MGE-derived oligodendrocytes (Kessaris et al., Competing waves of oligodendrocytes in the forebrain and postnatal elimination of an embryonic lineage. Nature neuroscience 9:173-179, 2006).

The survival rate of FACS sorted cells after transplantation into the cortex was extremely low, about 1% (similar to Maroof et al., J Neurosci 30:4667-4675, 2010). We suspect that some of the low viability may be due to the cell sorting process. In the future it will be beneficial to pursue other possible methods of isolating cells, such as using magnetic bead-conjugated antibodies, or finding enhancers that drive expression in dividing cells. Currently, aside from enhancer 1056, which is expressed in mitotically active ($Mki67^+$) $Olig2^+$ cells, none of the "MGE neuronal enhancers" show robust expression in mitotically active cells. In vivo, some of the enhancers (692, 1056, and 1538) are active in the VZ (FIGS. 4B&C, and data not shown), whereas only 1056 shows activity in mitotically active ES cells (FIG. 17H). We do not know why 692 and 1538 activity is not detected in the ES-derived dividing MGE-like progenitors cells. It will be helpful to identify an "MGE enhancer" that drives expression in dividing cells, to enable selection with a drug-resistance gene. This would greatly facilitate generating large numbers of homogeneous MGE interneuron progenitors for further study and, ultimately, for transplantation in diseased states.

Our approach of using highly specific small enhancers may have general utilities for generating diverse types of CNS cells. For instance, we have identified enhancers for the LGE and pallium, including its regional subdivisions (Visel et al., submitted; see enhancer.lbl.gov website) that can be used for selecting these types of progenitors and their derivatives. Introducing these enhancer constructs into ES and iPS cells may facilitate identification and isolation of many different neural cell lineages for basic and translational studies.

Example 5: Use of "MGE Enhancers" to Purify MGE Cells

Several methods can be used to purify enhancer-labeled MGE-derived cells. 1. FACSorting. This is as described above and in Chen et al., submitted paper. Briefly, enhancer-drived fluorescent proteins (such as GFP or mCherry) can be detected in a fluorescent activated cell sorting (FACS) machine. Cells that are of the right cell state in which an enhancer is active will express the fluorescent proteins and be purified by FACS. 2. Magnetic beads purification. There are many surface protein antibodies that are conjugated with magnetic beads. Using a surface protein that is not expressed in neural cells, we can drive its expression in the differentiated embryonic stem cells with an enhancer selected from SEQ ID NOS:1-145. Cells that are of the right cell state can then be purified through incubation with antibody-beads, and by magnetic field. Cells that are not bound with antibody-beads (because it does not express the enhancer-surface protein) will be washed away. 3. Immunopanning. This is similar to magnetic beads purification. But instead of using magnetic field, antibodies for surface proteins are fixed on a plate. Cells that are of the right cell state (and therefore express the enhancer-surface protein) will bind and remain inside the plate, whereas cells that are not of the right state will be washed away.

Example 6: Use of "MGE Enhancers" in Non-Pluripotent Cells for Cell Transplantation and Drug Screening Non-pluripotent somatic cells would be obtained from a patient (for example during a skin biopsy or blood test procedure) not affected or affected by a disorder or disease.

Somatic cells would then be cultured and transfected with an MGE Enhancer(s) and promoter driving a fluorescent protein, and with reprogramming genes. In one embodiment, somatic cells would first be reprogrammed to pluripotency with genes such as OCT4, KLF4, SOX2, NANOG, CMYC and then differentiated toward an MGE neural cell fate.

In a second embodiment, somatic cells would be cultured and transfected with neural-determinate genes, such as ASCL1, BRN2, MYT1L, NEUROD1/2, in order to directly induce an MGE neural cell fate. An MGE Enhancer(s) and promoter driving a fluorescent protein would be transfected before and/or after the reprogramming step. Induced MGE cells would then be identified by virtue of their fluorescence, and could also be isolated by fluorescence-activated cell sorting and resuspended in solution.

Somatic cells reprogrammed into MGE cells with MGE enhancers can then be used for transplantation into the nervous system to treat patients with epilepsy, Parkinson's disease, schizophrenia, neuropathic pain, spinal cord injury, autism, Alzheimer's disease, and/or Huntington's disease. Cells could be isolated based on their MGE enhancer activity, and the MGE cell suspension would be injected into the nervous system.

Reprogrammed MGE cells generated using the enhancers could also be used for screening or assaying drugs for a therapeutic effect. For examples, neurons from healthy individuals (e.g., cortical, striatal, motor neurons) could be used to test for neurotoxicity of a compound.), or cortical neurons from patient who has a neurodegenerative disease (e.g., ALS, Alzheimers, Huntington's, Parkinson's, frontotemporal dementia) could be tested for compounds that prolong the survival of the cells, or neurons from patient with a neurological disease that alters neuronal function (e.g., epilepsy caused by an electrophysiological, signaling, synaptic defect) could be tested for compounds that improve that aspect of neuronal function.

The above examples are provided to illustrate the invention but not to limit its scope. Other variants of the invention will be readily apparent to one of ordinary skill in the art and are encompassed by the appended claims. All patents and publications referenced herein are hereby incorporated by reference in their entireties for all purposes.

TABLE 1

| Data retrieved from sequence database | | | | | | | |
|---|---|---|---|---|---|---|---|
| | human coordinates (hg19) | | | | | | |
| Element ID<br>Element ID | chromosome | start | end | length | SEQ ID<br>NO: | number | coordinates (hg19) |
| hs12 | chr16 | 78510608 | 78511944 | 1336 | 1 | 12 | chr16:78510609-78511944 |
| hs22 | chr16 | 72254566 | 72255825 | 1259 | 2 | 22 | chr16:72254567-72255825 |
| hs37 | chr16 | 54650598 | 54651882 | 1284 | 3 | 37 | chr16:54650599-54651882 |
| hs71 | chr16 | 51671181 | 51672039 | 858 | 4 | 71 | chr16:51671182-51672039 |
| hs110 | chr7 | 21003280 | 21004750 | 1470 | 5 | 110 | chr7:21003281-21004750 |
| hs11 | chr7 | 42191728 | 42193638 | 1910 | 6 | 111 | chr7:42191729-42193638 |
| hs112 | chr9 | 973435 | 975288 | 1853 | 7 | 112 | chr9:973436-975288 |
| hs119 | chrX | 24915382 | 24918272 | 2890 | 8 | 119 | chrX:24915383-24918272 |
| hs121 | chrX | 25007879 | 25009581 | 1702 | 9 | 121 | chrX:25007880-25009581 |
| hs122 | chrX | 25017067 | 25018756 | 1689 | 10 | 122 | chrX:25017068-25018756 |
| hs123 | chrX | 25400224 | 25402334 | 2110 | 11 | 123 | chrX:25400225-25402334 |
| hs145 | chrX | 25018871 | 25020532 | 1661 | 12 | 145 | chrX:25018872-25020532 |
| hs170 | chr2 | 164450144 | 164451758 | 1614 | 13 | 170 | chr2:164450145-164451758 |
| hs174 | chr1 | 87821621 | 87823082 | 1461 | 14 | 174 | chr1:87821622-87823082 |
| hs187 | chr3 | 71290418 | 71292584 | 2166 | 15 | 187 | chr3:71290419-71292584 |
| hs192 | chr3 | 180773639 | 180775802 | 2163 | 16 | 192 | chr3:180773640-180775802 |
| hs200 | chr1 | 51165195 | 51166786 | 1591 | 17 | 200 | chr1:51165196-51166786 |
| hs204 | chr1 | 213597964 | 213599524 | 1560 | 18 | 204 | chr1:213597965-213599524 |
| hs218 | chr7 | 114056847 | 114058647 | 1800 | 19 | 218 | chr7:114056848-114058647 |
| hs240 | chr9 | 83727123 | 83728378 | 1255 | 20 | 240 | chr9:83727124-83728378 |
| hs242 | chr2 | 174114371 | 174115933 | 1562 | 21 | 242 | chr2:174114372-174115933 |
| hs244 | chr2 | 174988737 | 174990363 | 1626 | 22 | 244 | chr2:174988738-174990363 |
| hs262 | chr5 | 76940836 | 76941396 | 560 | 23 | 262 | chr5:76940837-76941396 |
| hs266 | chr5 | 87168414 | 87169433 | 1019 | 24 | 266 | chr5:87168415-87169433 |
| hs267 | chr5 | 87239942 | 87241645 | 1703 | 25 | 267 | chr5:87239943-87241645 |
| hs268 | chr5 | 87692154 | 87693265 | 1111 | 26 | 268 | chr5:87692155-87693265 |
| hs269 | chr5 | 90928612 | 90929226 | 614 | 27 | 269 | chr5:90928613-90929226 |
| hs271 | chr5 | 93226985 | 93228322 | 1337 | 28 | 271 | chr5:93226986-93228322 |
| hs281 | chr6 | 41523224 | 41523677 | 453 | 29 | 281 | chr6:41523225-41523677 |
| hs293 | chr7 | 1265154 | 1266318 | 1164 | 30 | 293 | chr7:1265155-1266318 |
| hs304 | chr9 | 8095553 | 8096166 | 613 | 31 | 304 | chr9:8095554-8096166 |
| hs312 | chr9 | 81471747 | 81473114 | 1367 | 32 | 312 | chr9:81471748-81473114 |
| hs313 | chr9 | 81870622 | 81872224 | 1602 | 33 | 313 | chr9:81870623-81872224 |
| hs322 | chr1 | 87821793 | 87822910 | 1117 | 34 | 322 | chr1:87821794-87822910 |
| hs342 | chr14 | 29860529 | 29862348 | 1819 | 35 | 342 | chr14:29860530-29862348 |
| hs348 | chr14 | 36020024 | 36020998 | 974 | 36 | 348 | chr14:36020025-36020998 |
| hs388 | chr2 | 7774393 | 7775070 | 677 | 37 | 388 | chr2:7774394-7775070 |
| hs399 | chr2 | 60441495 | 60442515 | 1020 | 38 | 399 | chr2:60441496-60442515 |
| hs408 | chr1 | 10851570 | 10852173 | 603 | 39 | 408 | chr1:10851571-10852173 |
| hs411 | chr2 | 156726581 | 156727605 | 1024 | 40 | 411 | chr2:156726582-156727605 |
| hs416 | chr2 | 162094895 | 162095451 | 556 | 41 | 416 | chr2:162094896-162095451 |
| hs422 | chr2 | 172955879 | 172957052 | 1173 | 42 | 422 | chr2:172955880-172957052 |
| hs427 | chrX | 139169379 | 139171545 | 2166 | 43 | 427 | chrX:139169380-139171545 |
| hs433 | chr14 | 30741750 | 30743626 | 1876 | 44 | 433 | chr14:30741751-30743626 |
| hs480 | chr20 | 30191716 | 30192554 | 838 | 45 | 480 | chr20:30191717-30192554 |
| hs488 | chr13 | 95358263 | 95360017 | 1754 | 46 | 488 | chr13:95358264-95360017 |

TABLE 1-continued

| Element ID Element ID | Data retrieved from sequence database: human coordinates (hg19) chromosome | start | end | length | SEQ ID NO: | number | coordinates (hg19) |
|---|---|---|---|---|---|---|---|
| hs532 | chr13 | 28395961 | 28397536 | 1575 | 47 | 532 | chr13:28395962-28397536 |
| hs540 | chr13 | 71358093 | 71359507 | 1414 | 48 | 540 | chr13:71358094-71359507 |
| hs545 | chr1 | 243876467 | 243877893 | 1426 | 49 | 545 | chr1:243876468-243877893 |
| hs550 | chr7 | 13506207 | 13507276 | 1069 | 50 | 550 | chr7:13506208-13507276 |
| hs553 | chr2 | 172936519 | 172938249 | 1730 | 51 | 553 | chr2:172936520-172938249 |
| hs565 | chr11 | 31622822 | 31624118 | 1296 | 52 | 565 | chr11:31622823-31624118 |
| hs566 | chr14 | 29684896 | 29686744 | 1848 | 53 | 566 | chr14:29684897-29686744 |
| hs582 | chrX | 81464240 | 81465016 | 776 | 54 | 582 | chrX:81464241-81465016 |
| hs590 | chr18 | 34719386 | 34720720 | 1334 | 55 | 590 | chr18:34719387-34720720 |
| hs595 | chr10 | 76177765 | 76179000 | 1235 | 56 | 595 | chr10:76177766-76179000 |
| hs599 | chr15 | 37652783 | 37654460 | 1677 | 57 | 599 | chr15:37652784-37654460 |
| hs609 | chr2 | 147172004 | 147173802 | 1798 | 58 | 609 | chr2:147172005-147173802 |
| hs611 | chr12 | 111495397 | 111496252 | 855 | 59 | 611 | chr12:111495398-111496252 |
| hs612 | chr1 | 91305562 | 91307215 | 1653 | 60 | 612 | chr1:91305563-91307215 |
| hs619 | chr13 | 72333516 | 72334988 | 1472 | 61 | 619 | chr13:72333517-72334988 |
| hs622 | chr14 | 99466200 | 99467144 | 944 | 62 | 622 | chr14:99466201-99467144 |
| hs631 | chr8 | 36957851 | 36958723 | 872 | 63 | 631 | chr8:36957852-36958723 |
| hs632 | chr20 | 2719208 | 2719789 | 581 | 64 | 632 | chr20:2719209-2719789 |
| hs634 | chr18 | 76006820 | 76008476 | 1656 | 65 | 634 | chr18:76006821-76008476 |
| hs636 | chr3 | 157882303 | 157883963 | 1660 | 66 | 636 | chr3:157882304-157883963 |
| hs643 | chr9 | 23004730 | 23005789 | 1059 | 67 | 643 | chr9:23004731-23005789 |
| hs649 | chr2 | 146689050 | 146690099 | 1049 | 68 | 649 | chr2:146689051-146690099 |
| hs653 | chr3 | 137185964 | 137186866 | 902 | 69 | 653 | chr3:137185965-137186866 |
| hs654 | chr3 | 147801015 | 147802169 | 1154 | 70 | 654 | chr3:147801016-147802169 |
| hs656 | chr10 | 131400948 | 131402279 | 1331 | 71 | 656 | chr10:131400949-131402279 |
| hs660 | chr15 | 67198974 | 67200134 | 1160 | 72 | 660 | chr15:67198975-67200134 |
| hs671 | chr1 | 97610491 | 97611741 | 1250 | 73 | 671 | chr1:97610492-97611741 |
| hs672 | chr10 | 120074039 | 120075696 | 1657 | 74 | 672 | chr10:120074040-120075696 |
| hs675 | chr2 | 144103882 | 144105644 | 1762 | 75 | 675 | chr2:144103883-144105644 |
| hs676 | chr6 | 97544611 | 97545759 | 1148 | 76 | 676 | chr6:97544612-97545759 |
| hs687 | chr4 | 54881222 | 54882455 | 1233 | 77 | 687 | chr4:54881223-54882455 |
| hs692 | chr11 | 15587041 | 15588314 | 1273 | 78 | 692 | chr11:15587042-15588314 |
| hs702 | chr2 | 105132815 | 105133830 | 1015 | 79 | 702 | chr2:105132816-105133830 |
| hs742 | chr8 | 78042571 | 78044201 | 1630 | 80 | 742 | chr8:78042572-78044201 |
| hs748 | chr10 | 78390590 | 78391875 | 1285 | 81 | 748 | chr10:78390591-78391875 |
| hs775 | chr18 | 77010009 | 77010795 | 786 | 82 | 775 | chr18:77010010-77010795 |
| hs781 | chr8 | 21907426 | 21908282 | 856 | 83 | 781 | chr8:21907427-21908282 |
| hs782 | chr8 | 21901089 | 21902326 | 1237 | 84 | 782 | chr8:21901090-21902326 |
| hs798 | chr12 | 16170590 | 16171824 | 1234 | 85 | 798 | chr12:16170591-16171824 |
| hs799 | chr7 | 9271308 | 9272358 | 1050 | 86 | 799 | chr7:9271309-9272358 |
| hs807 | chr7 | 22091362 | 22092557 | 1195 | 87 | 807 | chr7:22091363-22092557 |
| hs818 | chr9 | 128520992 | 128522653 | 1661 | 88 | 818 | chr9:128520993-128522653 |
| hs840 | chr4 | 66989480 | 66990366 | 886 | 89 | 840 | chr4:66989481-66990366 |
| hs841 | chr10 | 118854124 | 118855243 | 1119 | 90 | 841 | chr10:118854125-118855243 |
| hs844 | chr7 | 20832628 | 20833902 | 1274 | 91 | 844 | chr7:20832629-20833902 |
| hs848 | chr16 | 51491799 | 51493025 | 1226 | 92 | 848 | chr16:51491800-51493025 |
| hs852 | chr9 | 13750115 | 13751398 | 1283 | 93 | 852 | chr9:13750116-13751398 |
| hs853 | chr5 | 87083012 | 87084752 | 1740 | 94 | 853 | chr5:87083013-87084752 |
| hs876 | chr9 | 133540555 | 133541228 | 673 | 95 | 876 | chr9:133540556-133541228 |
| hs886 | chr4 | 181201559 | 181202529 | 970 | 96 | 886 | chr4:181201560-181202529 |
| hs914 | chr20 | 21214790 | 21217232 | 2442 | 97 | 914 | chr20:21214791-21217232 |
| hs921 | chr2 | 236962599 | 236964857 | 2258 | 98 | 921 | chr2:236962600-236964857 |
| hs952 | chr5 | 91442456 | 91444549 | 2093 | 99 | 952 | chr5:91442457-91444549 |
| hs953 | chr2 | 175203263 | 175204895 | 1632 | 100 | 953 | chr2:175203264-175204895 |
| hs956 | chr7 | 114299711 | 114302078 | 2367 | 101 | 956 | chr7:114299712-114302078 |
| hs957 | chr2 | 60761404 | 60763073 | 1669 | 102 | 957 | chr2:60761405-60763073 |
| hs969 | chr2 | 105317580 | 105319856 | 2276 | 103 | 969 | chr2:105317581-105319856 |
| hs971 | chr5 | 91970162 | 91972034 | 1872 | 104 | 971 | chr5:91970163-91972034 |
| hs978 | chr6 | 97754043 | 97755513 | 1470 | 105 | 978 | chr6:97754044-97755513 |
| hs981 | chr4 | 113442390 | 113443530 | 1140 | 106 | 981 | chr4:113442391-113443530 |
| hs987 | chr9 | 128869446 | 128870934 | 1488 | 107 | 987 | chr9:128869447-128870934 |
| hs998 | chr12 | 103406124 | 103408154 | 2030 | 108 | 998 | chr12:103406125-103408154 |
| hs1006 | chr10 | 102244842 | 102246334 | 1492 | 109 | 1006 | chr10:102244843-102246334 |
| hs1007 | chr7 | 20997668 | 20999102 | 1434 | 110 | 1007 | chr7:20997669-20999102 |
| hs1019 | chr7 | 20838843 | 20840395 | 1552 | 111 | 1019 | chr7:20838844-20840395 |
| hs1024 | chr5 | 92312840 | 92314645 | 1805 | 112 | 1024 | chr5:92312841-92314645 |
| hs1025 | chr2 | 73124730 | 73126091 | 1361 | 113 | 1025 | chr2:73124731-73126091 |
| hs1027 | chr18 | 22744668 | 22746270 | 1602 | 114 | 1027 | chr18:22744669-22746270 |
| hs1032 | chr10 | 119309200 | 119310544 | 1344 | 115 | 1032 | chr10:119309201-119310544 |
| hs1035 | chr6 | 98074091 | 98075722 | 1631 | 116 | 1035 | chr6:98074092-98075722 |
| hs1041 | chr9 | 82010246 | 82011547 | 1301 | 117 | 1041 | chr9:82010247-82011547 |
| hs1050 | chr4 | 109531908 | 109533465 | 1557 | 118 | 1050 | chr4:109531909-109533465 |
| hs1052 | chr6 | 18536628 | 18538267 | 1639 | 119 | 1052 | chr6:18536629-18538267 |

TABLE 1-continued

| Data retrieved from sequence database | | | | | | | |
|---|---|---|---|---|---|---|---|
| | human coordinates (hg19) | | | | | | |
| Element ID<br>Element ID | chromosome | start | end | length | SEQ ID NO: | number | coordinates (hg19) |
| hs1056 | chr18 | 76481722 | 76483257 | 1535 | 120 | 1056 | chr18:76481723-76483257 |
| hs1060 | chr5 | 92613862 | 92616844 | 2982 | 121 | 1060 | chr5:92613863-92616844 |
| hs1066 | chr2 | 63275695 | 63277103 | 1408 | 122 | 1066 | chr2:63275696-63277103 |
| hs1078 | chr9 | 82224085 | 82226757 | 2672 | 123 | 1078 | chr9:82224086-82226757 |
| hs1100 | chr6 | 41560717 | 41562075 | 1358 | 124 | 1100 | chr6:41560718-41562075 |
| hs1172 | chr5 | 92634702 | 92636476 | 1774 | 125 | 1172 | chr5:92634703-92636476 |
| hs1187 | chr5 | 50390899 | 50392257 | 1358 | 126 | 1187 | chr5:50390900-50392257 |
| hs1210 | chr2 | 66762515 | 66765088 | 2573 | 127 | 1210 | chr2:66762516-66765088 |
| hs1226 | chr7 | 21080801 | 21082086 | 1285 | 128 | 1226 | chr7:21080802-21082086 |
| hs1316 | chr3 | 62405817 | 62408099 | 2282 | 129 | 1316 | chr3:62405818-62408099 |
| hs1318 | chr8 | 77598007 | 77600645 | 2638 | 130 | 1318 | chr8:77598008-77600645 |
| hs1321 | chr5 | 50467950 | 50469989 | 2039 | 131 | 1321 | chr5:50467951-50469989 |
| hs1324 | chr1 | 213498112 | 213501134 | 3022 | 132 | 1324 | chr1:213498113-213501134 |
| hs1325 | chr7 | 25791903 | 25794282 | 2379 | 133 | 1325 | chr7:25791904-25794282 |
| hs1329 | chr8 | 28370867 | 28371860 | 993 | 134 | 1329 | chr8:28370868-28371860 |
| hs1334 | chr10 | 37054745 | 37057224 | 2479 | 135 | 1334 | chr10:37054746-37057224 |
| hs1336 | chr7 | 34097962 | 34100011 | 2049 | 136 | 1336 | chr7:34097963-34100011 |
| hs1339 | chr9 | 92292484 | 92293889 | 1405 | 137 | 1339 | chr9:92292485-92293889 |
| hs1340 | chr6 | 20867105 | 20870529 | 3424 | 138 | 1340 | chr6:20867106-20870529 |
| hs1341 | chr12 | 97468703 | 97471089 | 2386 | 139 | 1341 | chr12:97468704-97471089 |
| hs1345 | chr5 | 107299863 | 107302976 | 3113 | 140 | 1345 | chr5:107299864-107302976 |
| hs1358 | chr6 | 163276830 | 163279930 | 3100 | 141 | 1358 | chr6:163276831-163279930 |
| hs1359 | chr9 | 84264195 | 84266950 | 2755 | 142 | 1359 | chr9:84264196-84266950 |
| hs1361 | chr4 | 153287655 | 153290517 | 2862 | 143 | 1361 | chr4:153287656-153290517 |
| hs1538 | chr14 | 36911162 | 36914360 | 3198 | 144 | 1538 | chr14:36911163-36914360 |
| hs1578 | chr2 | 212254840 | 212257158 | 2318 | 145 | 1578 | chr2:212254841-212257158 |

| Element ID | hg19 coordinates | SEQ ID NO: | ID | EMT VZ | EMT SVZ | EMT MZ | CP VZ | MP VZ | MP SVZ | MP MZ | DP VZ | DP SVZ | DP MZ | LP VZ | LP SVZ | LP MZ | VP VZ |
|---|---|---|---|---|---|---|---|---|---|---|---|---|---|---|---|---|---|
| 12 | chr16 78510608 78511944 | 1 | hs12 | | | | x | x | | | | | | | | | |
| 22 | chr16 72254566 72255825 | 2 | hs22 | | | x | | | | | x | x | x | x | x | x | x |
| 37 | chr16 54650598 54651882 | 3 | hs37 | | | | | x | x | x | | | | | | | |
| 71 | chr16 51671181 51672039 | 4 | hs71 | | | | | | | | | | | | | | |
| 110 | chr7 21003280 21004750 | 5 | hs110 | | | | | | | | | | | | | | |
| 111 | chr7 42191728 42193638 | 6 | hs111 | x | x | x | | x | x | x | x | x | x | x | x | x | x |
| 112 | chr9 973435 975288 | 7 | hs112 | | | | | x | x | x | x | x | x | | | | |
| 119 | chrX 24915382 24918272 | 8 | hs119 | | | | | | | | | | | | | | |
| 121 | chrX 25007879 25009581 | 9 | hs121 | | | | | | | | | | | | | | |
| 122 | chrX 25017067 25018756 | 10 | hs122 | x | | | x | x | x | x | x | x | x | x | x | x | x |
| 123 | chrX 25400224 25402334 | 11 | hs123 | | | | | x | x | x | x | x | x | | | | |
| 145 | chrX 25018871 25020532 | 12 | hs145 | x | x | x | | | | | | | | | | | |
| 170 | chr2 164450144 164451758 | 13 | hs170 | | | | | | | | | | | | | | x |
| 174 | chr1 87821621 87823082 | 14 | hs174 | | | | | | | x | | | x | | | x | |
| 187 | chr3 71290418 71292584 | 15 | hs187 | | | | | | | | x | | | | | | |
| 192 | chr3 180773639 180775802 | 16 | hs192 | | | | | x | | | | | | | | | |
| 200 | chr1 51165195 51166786 | 17 | hs200 | | | | | | | | x | x | x | x | x | x | x |
| 204 | chr1 213597964 213599524 | 18 | hs204 | | | | | | | | | | | | | | |
| 218 | chr7 114056847 114058647 | 19 | hs218 | | | | | | | | x | x | x | x | x | x | |
| 240 | chr9 83727123 83728378 | 20 | hs240 | | | | | | | | | | | x | x | x | x |
| 242 | chr2 174114371 174115933 | 21 | hs242 | | | | | | | | | | | | | | |
| 244 | chr2 174988737 174990363 | 22 | hs244 | | | | | | | | | | | | | | |
| 262 | chr5 76940836 76941396 | 23 | hs262 | | | | | | | | | | | | | | |
| 266 | chr5 87168414 87169433 | 24 | hs266 | | | | | x | x | x | x | x | x | x | x | x | x |
| 267 | chr5 87239942 87241645 | 25 | hs267 | x | x | x | | | | | x | x | x | x | x | x | x |
| 268 | chr5 87692154 87693265 | 26 | hs268 | x | x | x | | x | x | x | x | x | x | x | x | x | x |
| 269 | chr5 90928612 90929226 | 27 | hs269 | | | | | | | | | | | | | | |
| 271 | chr5 93226985 93228322 | 28 | hs271 | | | | | | | | x | x | x | x | x | x | x |
| 281 | chr6 41523224 41523677 | 29 | hs281 | | | | | | | | x | x | x | | | | |
| 293 | chr7 1265154 1266318 | 30 | hs293 | x | x | x | | | | x | | | x | | | x | |
| 304 | chr9 8095553 8096166 | 31 | hs304 | | | | | | | | | | | | | | |
| 312 | chr9 81471747 81473114 | 32 | hs312 | | | | | | | | | | | | | | |
| 313 | chr9 81870622 81872224 | 33 | hs313 | x | x | x | | | | | | | | | | | |
| 322 | chr1 87821793 87822910 | 34 | hs322 | | | | | | | x | | | x | | | x | |
| 342 | chr14 29860529 29862348 | 35 | hs342 | | | | | | | | | | | | | | |
| 348 | chr14 36020024 36020998 | 36 | hs348 | x | x | x | x | x | x | x | | | | | | | |
| 388 | chr2 7774393 7775070 | 37 | hs388 | | | | | | | | | | | | | | |
| 399 | chr2 60441495 60442515 | 38 | hs399 | | | | | | | | | | x | | | x | |
| 408 | chr1 10851570 10852173 | 39 | hs408 | | | | | | | | | | | | | | |
| 411 | chr2 156726581 156727605 | 40 | hs411 | | | | x | | | | | | | | | | |
| 416 | chr2 162094895 162095451 | 41 | hs416 | x | x | x | | | | | | | | | | | |
| 422 | chr2 172955879 172957052 | 42 | hs422 | | | | | | | | | | | | | | |
| 427 | chrX 139169379 139171545 | 43 | hs427 | | | | | | | | x | x | x | x | x | x | x |
| 433 | chr14 30741750 30743626 | 44 | hs433 | | | | | | | | x | x | x | x | x | x | x |
| 480 | chr20 30191716 30192554 | 45 | hs480 | | | | x | x | x | x | | | | | | | |
| 488 | chr13 95358263 95360017 | 46 | hs488 | | | | | | | | x | x | x | x | x | x | x |
| 532 | chr13 28395961 28397536 | 47 | hs532 | | | | | | | | | | | | | | |
| 540 | chr13 71358093 71359507 | 48 | hs540 | | | | | | | | | | | | | | |
| 545 | chr1 243876467 243877893 | 49 | hs545 | | | | | | | | | | | | | | |

-continued

| | | | | | | | | | | | | | | | | | |
|---|---|---|---|---|---|---|---|---|---|---|---|---|---|---|---|---|---|
| 550 | chr7 13506207 13507276 | 50 | hs550 | | | | | | | | | | | | | | |
| 553 | chr2 172936519 172938249 | 51 | hs553 | | | | | | | | | | | | | | |
| 565 | chr11 31622822 31624118 | 52 | hs565 | | | | x | x | x | x | | | | | | | |
| 566 | chr14 29684896 29686744 | 53 | hs566 | | | | | | | | | | | | | | |
| 582 | chrX 81464240 81465016 | 54 | hs582 | | | | | | | | | | | | | | |
| 590 | chr18 34719386 34720720 | 55 | hs590 | | | | | | | | | | | | | | |
| 595 | chr10 76177765 76179000 | 56 | hs595 | | | | | | | | x | x | x | x | x | x | |
| 599 | chr15 37652783 37654460 | 57 | hs599 | | | | | | | | | | | | | | |
| 609 | chr2 147172004 147173802 | 58 | hs609 | | | | | | | | | | | | | | |
| 611 | chr12 111495397 111496252 | 59 | hs611 | | | | x | x | x | x | | | | | | | |
| 612 | chr1 91305562 91307215 | 60 | hs612 | x | x | x | x | x | x | x | | | | | | | |
| 619 | chr13 72333516 72334988 | 61 | hs619 | | | | | | | | | | | x | x | x | x |
| 622 | chr14 99466200 99467144 | 62 | hs622 | | | | | | | x | | | x | | | | |
| 631 | chr8 36957851 36958723 | 63 | hs631 | | | | x | x | x | x | | | | | | | |
| 632 | chr20 2719208 2719789 | 64 | hs632 | | | | | | | | | | | | | | |
| 634 | chr18 76006820 76008476 | 65 | hs634 | x | x | x | | | | | | | | | | | |
| 636 | chr3 157882303 157883963 | 66 | hs636 | | | | | | | | | | | x | x | x | x |
| 643 | chr9 23004730 23005789 | 67 | hs643 | | | | | x | x | x | | | | | | | |
| 649 | chr2 146689050 146690099 | 68 | hs649 | | | | | | | | | | | | | | |
| 653 | chr3 137185964 137186866 | 69 | hs653 | | | | | x | x | x | | | | | | | |
| 654 | chr3 147801015 147802169 | 70 | hs654 | | | | x | x | x | x | | | | | | | |
| 656 | chr10 131400948 131402279 | 71 | hs656 | | | | | | | | | | | | | | |
| 660 | chr15 67198974 67200134 | 72 | hs660 | | | | | | | | | | | | | | |
| 671 | chr1 97610491 97611741 | 73 | hs671 | | | | | | | | x | x | x | x | x | x | x |
| 672 | chr10 120074039 120075696 | 74 | hs672 | x | x | x | | x | x | x | x | x | x | x | x | x | x |
| 675 | chr2 144103882 144105644 | 75 | hs675 | | | | | | | | | | | | | | |
| 676 | chr6 97544611 97545759 | 76 | hs676 | | | | | | | | | | | | | | |
| 687 | chr4 54881222 54882455 | 77 | hs687 | | | | | | | | | | | | | | |
| 692 | chr11 15587041 15588314 | 78 | hs692 | | | | | | | | | | | | | | |
| 702 | chr2 105132815 105133830 | 79 | hs702 | | | x | | | | | | | | | | | |
| 742 | chr8 78042571 78044201 | 80 | hs742 | | | | | | | x | | | x | | | x | |
| 748 | chr10 78390590 78391875 | 81 | hs748 | | | | | | | | | | | | | | |
| 775 | chr18 77010009 77010795 | 82 | hs775 | | | | | | | | | | | | | | x |
| 781 | chr8 21907426 21908282 | 83 | hs781 | x | x | x | x | | | | | | | | | | |
| 782 | chr8 21901089 21902326 | 84 | hs782 | | | | | | | | | | | | | | |
| 798 | chr12 16170590 16171824 | 85 | hs798 | | | | | x | x | x | | | | | | | |
| 799 | chr7 9271308 9272358 | 86 | hs799 | | | | | | | | | | | | | | |
| 807 | chr7 22091362 22092557 | 87 | hs807 | | | | | | | | | | | | | | |
| 818 | chr9 128520992 128522653 | 88 | hs818 | | | | | | | | | | | | | (x) | |
| 840 | chr4 66989480 66990366 | 89 | hs840 | x | x | | | x | x | x | x | x | x | x | x | x | x |
| 841 | chr10 118854124 118855243 | 90 | hs841 | | | | | | | | | | | | | | |
| 844 | chr7 20832628 20833902 | 91 | hs844 | x | x | x | | | | | x | x | x | | | | |
| 848 | chr16 51491799 51493025 | 92 | hs848 | | | | | | | | | | | | | | x |
| 852 | chr9 13750115 13751398 | 93 | hs852 | | | | | | | | | | x | | | x | |
| 853 | chr5 87083012 87084752 | 94 | hs853 | | | | x | x | x | x | x | x | x | x | x | x | x |
| 876 | chr9 133540555 133541228 | 95 | hs876 | | | | | | | | | | | x | x | x | x |
| 886 | chr4 181201559 181202529 | 96 | hs886 | | | | | x | x | x | | | | | | | |
| 914 | chr20 21214790 21217232 | 97 | hs914 | | | | | | | | | | | | | | |
| 921 | chr2 236962599 236964857 | 98 | hs921 | | | x | | | | | | | | | | | |
| 952 | chr5 91442456 91444549 | 99 | hs952 | | x | x | | x | x | x | | | | | | | |
| 953 | chr2 175203263 175204895 | 100 | hs953 | | | | | | | | | | | | | | |
| 956 | chr7 114299711 114302078 | 101 | hs956 | | | | | | | | | | | | | | |

-continued

| | | | | | | | | | | | | | | | | | |
|---|---|---|---|---|---|---|---|---|---|---|---|---|---|---|---|---|---|
| 957 | chr2 60761404 60763073 | 102 | hs957 | | | | | | | | x | x | x | x | x | x | |
| 969 | chr2 105317580 105319856 | 103 | hs969 | | | | | | | | x | x | x | x | x | x | |
| 971 | chr5 91970162 91972034 | 104 | hs971 | | | | | | | | | | | | | | |
| 978 | chr6 97754043 97755513 | 105 | hs978 | | | | | | | | | | | | | | x |
| 981 | chr4 113442390 113443530 | 106 | hs981 | | | | | | | | | | | | | | |
| 987 | chr9 128869446 128870934 | 107 | hs987 | | | | | | | | x | x | x | | | | |
| 998 | chr12 103406124 103408154 | 108 | hs998 | | | | | | | | x | x | x | | | | |
| 1006 | chr10 102244842 102246334 | 109 | hs1006 | | | | x | x | x | x | x | x | x | | | | |
| 1007 | chr7 20997668 20999102 | 110 | hs1007 | | | | | | | | | | | | | | |
| 1019 | chr7 20838843 20840395 | 111 | hs1019 | | | | | | | | | | | | | | |
| 1024 | chr5 92312840 92314645 | 112 | hs1024 | | | | | | | | | | | | | | |
| 1025 | chr2 73124730 73126091 | 113 | hs1025 | | | | | x | x | x | x | x | x | x | x | x | |
| 1027 | chr18 22744668 22746270 | 114 | hs1027 | | | | | | | | | | | | | | |
| 1032 | chr10 119309200 119310544 | 115 | hs1032 | | | | | | | | | | | | | | x |
| 1035 | chr6 98074091 98075722 | 116 | hs1035 | | | | | | | | x | x | x | | | | |
| 1041 | chr9 82010246 82011547 | 117 | hs1041 | | | x | | | | | | | | | | | |
| 1050 | chr4 109531908 109533465 | 118 | hs1050 | | | | | x | x | x | x | x | x | | | | |
| 1052 | chr6 18536628 18538267 | 119 | hs1052 | | | | | | | | | | | | | | |
| 1056 | chr18 76481722 76483257 | 120 | hs1056 | | | | | | | | | | | | | | |
| 1060 | chr5 92613862 92616844 | 121 | hs1060 | | | | | | | | | | | | | | |
| 1066 | chr2 63275695 63277103 | 122 | hs1066 | x | x | x | x | x | x | x | x | x | x | | | | |
| 1078 | chr9 82224085 82226757 | 123 | hs1078 | x | x | x | x | x | x | x | | | | | | | |
| 1100 | chr6 41560717 41562075 | 124 | hs1100 | x | x | x | | | | | | | | | | | |
| 1172 | chr5 92634702 92636476 | 125 | hs1172 | x | x | x | x | x | x | x | x | x | x | x | x | x | x |
| 1187 | chr5 50390899 50392257 | 126 | hs1187 | | | | | | | | | | | | | | x |
| 1210 | chr2 66762515 66765088 | 127 | hs1210 | | | | | | | | | | | | | | |
| 1226 | chr7 21080801 21082086 | 128 | hs1226 | | | | | | | | | | | | | | x |
| 1316 | chr3 62405817 62408099 | 129 | hs1316 | | | x | | | | | | | x | | | x | |
| 1318 | chr8 77598007 77600645 | 130 | hs1318 | | | | | | | | (x) | | | (x) | | | (x) |
| 1321 | chr5 50467950 50469989 | 131 | hs1321 | | | | | | | | | | | | | | |
| 1324 | chr1 213498112 213501134 | 132 | hs1324 | | | | | | | | | | | | | | |
| 1325 | chr7 25791903 25794282 | 133 | hs1325 | | | | | | | | x | x | x | x | x | x | x |
| 1329 | chr8 28370867 28371860 | 134 | hs1329 | | | | | x | x | x | | | | | | | |
| 1334 | chr10 37054745 37057224 | 135 | hs1334 | | | | | | | | x | x | x | x | x | x | x |
| 1336 | chr7 34097962 34100011 | 136 | hs1336 | x | x | x | | | | | | | | | | | |
| 1339 | chr9 92292484 92293889 | 137 | hs1339 | x | x | x | | | | | x | x | x | x | x | x | x |
| 1340 | chr6 20867105 20870529 | 138 | hs1340 | | | | | | | | | | | | | | |
| 1341 | chr12 97468703 97471089 | 139 | hs1341 | | | | x | x | x | x | x | x | x | x | x | x | x |
| 1345 | chr5 107299863 107302976 | 140 | hs1345 | | | | | | | | x | x | x | | | | |
| 1358 | chr6 163276830 163279930 | 141 | hs1358 | | | | | | | | x | x | x | x | x | x | |
| 1359 | chr9 84264195 84266950 | 142 | hs1359 | | | | | | | | x | x | x | | | x | |
| 1361 | chr4 153287655 153290517 | 143 | hs1361 | | | x | | | | | | | | | | | |
| 1538 | chr14 36911162 36914360 | 144 | hs1538 | | | | | | | | | | | | | | |
| 1578 | chr2 212254840 212257158 | 145 | hs1578 | | x | x | | | | | | | | | | | |

| Element ID | hg19 coordinates | SEQ ID NO: | ID | VP SVZ | VP MZ | LGE VZ | LGE SVZ | LGE MZ | MGE VZ | MGE SVZ | MGE MZ | POA VZ | POA SVZ | POA MZ | Se VZ | Se SVZ | Se MZ |
|---|---|---|---|---|---|---|---|---|---|---|---|---|---|---|---|---|---|
| 12 | chr16 78510608 78511944 | 1 | hs12 | | | | | | | | | | | | | | |
| 22 | chr16 72254566 72255825 | 2 | hs22 | x | x | | | | | | | | | | | | |
| 37 | chr16 54650598 54651882 | 3 | hs37 | | | | | | | | | | | | | | |
| 71 | chr16 51671181 51672039 | 4 | hs71 | | x | | | | | | | | | | | | |
| 110 | chr7 21003280 21004750 | 5 | hs110 | | | | x | x | (x) | x | x | | | | | | |

-continued

| | | | | | | | | | | | | | | | | | |
|---|---|---|---|---|---|---|---|---|---|---|---|---|---|---|---|---|---|
| 111 | chr7 42191728 42193638 | 6 | hs111 | x | x | x | x | x | x | x | x | x | x | x | x | x | x |
| 112 | chr9 973435 975288 | 7 | hs112 | | | | | | | | | | | | | | |
| 119 | chrX 24915382 24918272 | 8 | hs119 | | | (x) | x | x | | x | x | | | x | | | |
| 121 | chrX 25007879 25009581 | 9 | hs121 | | | (x) | x | x | | x | x | | | | | | x |
| 122 | chrX 25017067 25018756 | 10 | hs122 | x | x | | | | | | | | | | | | |
| 123 | chrX 25400224 25402334 | 11 | hs123 | | | | | | | | | | | | | | |
| 145 | chrX 25018871 25020532 | 12 | hs145 | | | | | | | | | | | | | | |
| 170 | chr2 164450144 164451758 | 13 | hs170 | x | x | | x | x | | x | x | | | | | | |
| 174 | chr1 87821621 87823082 | 14 | hs174 | | x | | | | | | | | | | | | |
| 187 | chr3 71290418 71292584 | 15 | hs187 | | | | | | | | | | | | | | |
| 192 | chr3 180773639 180775802 | 16 | hs192 | | | | | | | | | | | | | | |
| 200 | chr1 51165195 51166786 | 17 | hs200 | x | x | | | | | | | | | | | | |
| 204 | chr1 213597964 213599524 | 18 | hs204 | | | | | x | | x | x | | | x | | | |
| 218 | chr7 114056847 114058647 | 19 | hs218 | | | | | | | | | | | | | | |
| 240 | chr9 83727123 83728378 | 20 | hs240 | x | x | x | x | x | (x) | x | x | | | x | | | |
| 242 | chr2 174114371 174115933 | 21 | hs242 | | | x | x | x | | x | x | | | | | | |
| 244 | chr2 174988737 174990363 | 22 | hs244 | | | | | x | | | x | | | | | | |
| 262 | chr5 76940836 76941396 | 23 | hs262 | | | | | | | | | | | | | | |
| 266 | chr5 87168414 87169433 | 24 | hs266 | x | x | | | | | | | | | | | | |
| 267 | chr5 87239942 87241645 | 25 | hs267 | x | x | x | x | x | x | x | x | | | | x | x | x |
| 268 | chr5 87692154 87693265 | 26 | hs268 | x | x | x | x | x | x | x | x | x | x | x | x | x | x |
| 269 | chr5 90928612 90929226 | 27 | hs269 | | | x | x | | x | x | | | | | | | |
| 271 | chr5 93226985 93228322 | 28 | hs271 | x | x | | | | x | | | | | | | | |
| 281 | chr6 41523224 41523677 | 29 | hs281 | | | | | | | | | | | | | | |
| 293 | chr7 1265154 1266318 | 30 | hs293 | | x | | | | | | | | | | | | |
| 304 | chr9 8095553 8096166 | 31 | hs304 | | | | | x | | | x | | | | | | |
| 312 | chr9 81471747 81473114 | 32 | hs312 | | | | | x | | | x | | | | | | |
| 313 | chr9 81870622 81872224 | 33 | hs313 | | | | | | | | | | | | | | |
| 322 | chr1 87821793 87822910 | 34 | hs322 | | x | | | | | | | | | | | | |
| 342 | chr14 29860529 29862348 | 35 | hs342 | | | x | x | x | x | x | x | | | | | | |
| 348 | chr14 36020024 36020998 | 36 | hs348 | | | | | | | | | | | | x | x | x |
| 388 | chr2 7774393 7775070 | 37 | hs388 | | | | x | x | | | | | | | | | |
| 399 | chr2 60441495 60442515 | 38 | hs399 | | x | | | | | | | | | | | | |
| 408 | chr1 10851570 10852173 | 39 | hs408 | | | | | | | | x | | | | | | |
| 411 | chr2 156726581 156727605 | 40 | hs411 | | | | | | | | | | | | | | |
| 416 | chr2 162094895 162095451 | 41 | hs416 | | | | | | | | | | | | | | |
| 422 | chr2 172955879 172957052 | 42 | hs422 | | | | x | x | | x | x | | | | | | |
| 427 | chrX 139169379 139171545 | 43 | hs427 | x | x | x | | | x | | | | | | x | x | x |
| 433 | chr14 30741750 30743626 | 44 | hs433 | x | x | | x | x | | x | | | | | | | |
| 480 | chr20 30191716 30192554 | 45 | hs480 | | | | | | | | | | | | | | |
| 488 | chr13 95358263 95360017 | 46 | hs488 | x | x | (x) | (x) | (x) | | | | | | | | | |
| 532 | chr13 28395961 28397536 | 47 | hs532 | | | | x | x | (x) | x | x | | | x | | | |
| 540 | chr13 71358093 71359507 | 48 | hs540 | | | | (x) | x | | | | | | | | | |
| 545 | chr1 243876467 243877893 | 49 | hs545 | | | | x | x | | | | | | | | | |
| 550 | chr7 13506207 13507276 | 50 | hs550 | | | | x | x | | x | x | | | | | | |
| 553 | chr2 172936519 172938249 | 51 | hs553 | | | | x | x | | | | | | | | | |
| 565 | chr11 31622822 31624118 | 52 | hs565 | | | | | | | | | | | | | | |
| 566 | chr14 29684896 29686744 | 53 | hs566 | | | | | x | | x | x | | | | | | |
| 582 | chrX 81464240 81465016 | 54 | hs582 | | | | x | x | | x | x | | | | | | |
| 590 | chr18 34719386 34720720 | 55 | hs590 | | | | x | x | | | | | | | | | |
| 595 | chr10 76177765 76179000 | 56 | hs595 | | | | | | | | | | | | | | |
| 599 | chr15 37652783 37654460 | 57 | hs599 | | | | | x | | | | | | | | | |
| 609 | chr2 147172004 147173802 | 58 | hs609 | | | | | | | | | | | | | | |

-continued

| | | | | | | | | | | | | | | | | | |
|---|---|---|---|---|---|---|---|---|---|---|---|---|---|---|---|---|---|
| 611 | chr12 111495397 111496252 | 59 | hs611 | | | | | | | | | | | | | | |
| 612 | chr1 91305562 91307215 | 60 | hs612 | | | | | | | | | | | | | | |
| 619 | chr13 72333516 72334988 | 61 | hs619 | x | x | x | x | x | x | x | x | x | x | x | | | |
| 622 | chr14 99466200 99467144 | 62 | hs622 | | | | | | | | | | | | | | |
| 631 | chr8 36957851 36958723 | 63 | hs631 | | | | | | | | | | | | | | |
| 632 | chr20 2719208 2719789 | 64 | hs632 | (x) | x | | | | | | | | | | | | |
| 634 | chr18 76006820 76008476 | 65 | hs634 | | | | | | | | | | | | | | |
| 636 | chr3 157882303 157883963 | 66 | hs636 | x | x | | | | | | | | | | | | |
| 643 | chr9 23004730 23005789 | 67 | hs643 | | | | | | | | | | | | | | |
| 649 | chr2 146689050 146690099 | 68 | hs649 | | | | | x | | | x | | | x | | | |
| 653 | chr3 137185964 137186866 | 69 | hs653 | | | | | | | | | | | | | | |
| 654 | chr3 147801015 147802169 | 70 | hs654 | | | | | | | | | | | | | | |
| 656 | chr10 131400948 131402279 | 71 | hs656 | | x | | | | | | | | | | | | |
| 660 | chr15 67198974 67200134 | 72 | hs660 | | | | | | | | | | | | | | |
| 671 | chr1 97610491 97611741 | 73 | hs671 | x | x | | | | | | | | | | | | |
| 672 | chr10 120074039 120075696 | 74 | hs672 | x | x | | | | | | | | | | | | |
| 675 | chr2 144103882 144105644 | 75 | hs675 | | | (x) | (x) | x | | x | | | | | | | |
| 676 | chr6 97544611 97545759 | 76 | hs676 | | | | | | | x | x | | | | | | |
| 687 | chr4 54881222 54882455 | 77 | hs687 | | | x | x | (x) | | | | | | | | | |
| 692 | chr11 15587041 15588314 | 78 | hs692 | | | | | x | x | x | x | x | x | x | | | |
| 702 | chr2 105132815 105133830 | 79 | hs702 | | | | | | | | | | | | | | |
| 742 | chr8 78042571 78044201 | 80 | hs742 | | x | | | | | | | | | | | | |
| 748 | chr10 78390590 78391875 | 81 | hs748 | | | | | (x) | | | (x) | | | | | | |
| 775 | chr18 77010009 77010795 | 82 | hs775 | | | x | | | | | | | | | | | |
| 781 | chr8 21907426 21908282 | 83 | hs781 | | | | | | | | | | | | x | x | x |
| 782 | chr8 21901089 21902326 | 84 | hs782 | | | | | | | | | | | | x | x | x |
| 798 | chr12 16170590 16171824 | 85 | hs798 | | | | | | | | | | | | | | |
| 799 | chr7 9271308 9272358 | 86 | hs799 | | | | | (x) | | x | (x) | | | | | | |
| 807 | chr7 22091362 22092557 | 87 | hs807 | | | | | x | | | | | | | | | |
| 818 | chr9 128520992 128522653 | 88 | hs818 | | x | | | | | | | | | | | | |
| 840 | chr4 66989480 66990366 | 89 | hs840 | x | x | | | | | | | | | | | | |
| 841 | chr10 118854124 118855243 | 90 | hs841 | | | x | x | x | | | | x | x | x | x | x | x |
| 844 | chr7 20832628 20833902 | 91 | hs844 | | | | | | | | | | | | | | |
| 848 | chr16 51491799 51493025 | 92 | hs848 | x | x | x | x | x | | | | | | | | | |
| 852 | chr9 13750115 13751398 | 93 | hs852 | | | | | | | | | | | | | | |
| 853 | chr5 87083012 87084752 | 94 | hs853 | x | x | | | x | | | x | | | | | | |
| 876 | chr9 133540555 133541228 | 95 | hs876 | x | x | | | | | | | | | | | | |
| 886 | chr4 181201559 181202529 | 96 | hs886 | | | | | | | | | | | | | | |
| 914 | chr20 21214790 21217232 | 97 | hs914 | | | | | | | | | | | | | | |
| 921 | chr2 236962599 236964857 | 98 | hs921 | | | | | | | | | | | | | | |
| 952 | chr5 91442456 91444549 | 99 | hs952 | | | | | | | | | | | | | | |
| 953 | chr2 175203263 175204895 | 100 | hs953 | | | | x | x | | | | | | | | | |
| 956 | chr7 114299711 114302078 | 101 | hs956 | | | | x | x | | x | x | | | | | | |
| 957 | chr2 60761404 60763073 | 102 | hs957 | | | | | x | | | x | | | | | | |
| 969 | chr2 105317580 105319856 | 103 | hs969 | | | | | | | | | | | | | | |
| 971 | chr5 91970162 91972034 | 104 | hs971 | | | | | | | | | | | | | | |
| 978 | chr6 97754043 97755513 | 105 | hs978 | x | x | | | | | | | | | | | | |
| 981 | chr4 113442390 113443530 | 106 | hs981 | | | | | | | | | | | | | | |
| 987 | chr9 128869446 128870934 | 107 | hs987 | | | | | | | | | | | | | | |
| 998 | chr12 103406124 103408154 | 108 | hs998 | | | | | | | | | x | x | x | x | x | x |
| 1006 | chr10 102244842 102246334 | 109 | hs1006 | | | | | | | | | | | | | | |
| 1007 | chr7 20997668 20999102 | 110 | hs1007 | | | (x) | x | x | | | | | | | | | |
| 1019 | chr7 20838843 20840395 | 111 | hs1019 | | | x | | | | | | | | | | | |

-continued

| | | | | | | | | | | | | | | | | | |
|---|---|---|---|---|---|---|---|---|---|---|---|---|---|---|---|---|---|
| 1024 | chr5 92312840 92314645 | 112 | hs1024 | | | | | | | | | | | | | | |
| 1025 | chr2 73124730 73126091 | 113 | hs1025 | | | | | | | | | | | | | | |
| 1027 | chr18 22744668 22746270 | 114 | hs1027 | | | | | | | | | | | | | | |
| 1032 | chr10 119309200 119310544 | 115 | hs1032 | | | x | x | | | | | | | | | | |
| 1035 | chr6 98074091 98075722 | 116 | hs1035 | | | | | | | | | | | | | | |
| 1041 | chr9 82010246 82011547 | 117 | hs1041 | | | | | x | | | x | | | | | | |
| 1050 | chr4 109531908 109533465 | 118 | hs1050 | | | | | | | | | | | | | | |
| 1052 | chr6 18536628 18538267 | 119 | hs1052 | | | | | x | | | | | | x | | | |
| 1056 | chr18 76481722 76483257 | 120 | hs1056 | | | | | | x | x | | x | x | | | | |
| 1060 | chr5 92613862 92616844 | 121 | hs1060 | | | | | | | | x | | | | | | |
| 1066 | chr2 63275695 63277103 | 122 | hs1066 | | | | | | | | | | | | | | |
| 1078 | chr9 82224085 82226757 | 123 | hs1078 | | | | | | | | | | | | | | |
| 1100 | chr6 41560717 41562075 | 124 | hs1100 | | | | | | | | | | | | | | |
| 1172 | chr5 92634702 92636476 | 125 | hs1172 | x | x | x | x | | | | | | | | | | |
| 1187 | chr5 50390899 50392257 | 126 | hs1187 | x | x | x | x | x | x | x | x | | | | | | |
| 1210 | chr2 66762515 66765088 | 127 | hs1210 | | | | | x | | | x | | | | | | |
| 1226 | chr7 21080801 21082086 | 128 | hs1226 | x | x | x | x | x | x | x | x | x | x | x | x | x | x |
| 1316 | chr3 62405817 62408099 | 129 | hs1316 | | x | | | | | | | | | | | | |
| 1318 | chr8 77598007 77600645 | 130 | hs1318 | | | | | | | | | | | | | | |
| 1321 | chr5 50467950 50469989 | 131 | hs1321 | | | | x | x | | x | x | | x | x | | | |
| 1324 | chr1 213498112 213501134 | 132 | hs1324 | | | | | x | | | x | | | | | | |
| 1325 | chr7 25791903 25794282 | 133 | hs1325 | x | x | x | x | x | x | x | x | | | | | | |
| 1329 | chr8 28370867 28371860 | 134 | hs1329 | | | | | | | | | | | | | | |
| 1334 | chr10 37054745 37057224 | 135 | hs1334 | x | x | x | | | x | | | | | | | | |
| 1336 | chr7 34097962 34100011 | 136 | hs1336 | | | x | x | x | | | | | | | | | |
| 1339 | chr9 92292484 92293889 | 137 | hs1339 | x | x | | x | x | | x | x | | | x | | | |
| 1340 | chr6 20867105 20870529 | 138 | hs1340 | | | | x | x | | | x | | | | | | |
| 1341 | chr12 97468703 97471089 | 139 | hs1341 | x | | x | | | x | | | x | | | | | |
| 1345 | chr5 107299863 107302976 | 140 | hs1345 | | | | | | | | | | | | | | |
| 1358 | chr6 163276830 163279930 | 141 | hs1358 | | | | | | | | | | | | | | |
| 1359 | chr9 84264195 84266950 | 142 | hs1359 | | x | | | | | | | | | | | | |
| 1361 | chr4 153287655 153290517 | 143 | hs1361 | | | x | x | x | | x | x | | x | x | | | |
| 1538 | chr14 36911162 36914360 | 144 | hs1538 | | | | | | | | | x | x | x | | | |
| 1578 | chr2 212254840 212257158 | 145 | hs1578 | | | | | | | | | | | | | | |

TABLE 2B

| Enhancer ID | human coordinates (hg19) | mouse orthologous (mm9) | Additional Comments |
|---|---|---|---|
| hs12 | chr16:78510608-78511944 | chr8:117268335-117269838 | dorsal midline |
| hs22 | chr16:72254566-72255825 | chr8:111960355-111961461 | only ventral parts of DP |
| hs37 | chr16:54650598-54651882 | chr8:94618458-94619728 | sulcus between EMT and CGE continuous with paraventricular area of 3rd ventricle |
| hs71 | chr16:51671181-51672039 | chr8:91988832-91989702 | only rostral |
| hs110 | chr7:21003280-21004750 | chr12:119958141-119959608 | |
| hs111 | chr7:42191728-42193638 | chr13:15634863-15636840 | ventral/rostral/dorsal midline of telencephalon is negative |
| hs112 | chr9:973435-975288 | chr19:25681768-25683668 | |
| hs119 | chrX:24915382-24918272 | chrX:90653081-90655923 | LGE manifold greater than MGE; weak in VZ of LGE |
| hs121 | chrX:25007879-25009581 | chrX:90555103-90556787 | weak in VZ of LGE |
| hs122 | chrX:25017067-25018756 | chrX:90546485-90548137 | |
| hs123 | chrX:25400224-25402334 | chrX:90035076-90037409 | MP: excluded from DG; absent from VZ and SVZ of entorhinal cortex |
| hs145 | chrX:25018871-25020532 | chrX:90544847-90546386 | and prethalamus |
| hs170 | chr2:164450144-164451758 | chr2:63800853-63802473 | |
| hs174 | chr1:87821621-87823082 | chr3:143836652-143838087 | element is an extended region including hs322 |
| hs187 | chr3:71290418-71292584 | chr6:99151224-99153431 | |
| hs192 | chr3:180773639-180775802 | chr3:34002549-34004729 | |
| hs200 | chr1:51165195-51166786 | chr4:109434849-109436376 | |
| hs204 | chr1:213597964-213599524 | chr1:192477619-192479001 | |
| hs218 | chr7:114056847-114058647 | chr6:15137323-15139118 | MP: scattered positive cells, more concentrated towards dentate gyrus. Ventral-dorsal gradient within DP. VZ-MZ gradient throughout cortex. |
| hs240 | chr9:83727123-83728378 | chr4:71144778-71146022 | LGE: negative in ventral |
| hs242 | chr2:174114371-174115933 | chr2:72264212-72265755 | LGE-VZ restricted to dorsal region, MGE-SVZ and MZ present but weak |
| hs244 | chr2:174988737-174990363 | chr2:72980728-72982329 | |
| hs262 | chr5:76940836-76941396 | chr13:95638850-95639388 | paraventricular area (diencephalon only) |
| hs266 | chr5:87168414-87169433 | chr13:84778588-84779575 | |
| hs267 | chr5:87239942-87241645 | chr13:84710013-84711772 | widely expressed throughout CNS; scattered radial clones; common in pallium/cortex; less common in LGE and even less common in MGE |
| hs268 | chr5:87692154-87693265 | chr13:84199108-84200220 | widely expressed throughout CNS; MGE: weak; absent from ventral/dorsal/rostral midline |
| hs269 | chr5:90928612-90929226 | chr13:80762168-80762775 | |
| hs271 | chr5:93226985-93228322 | chr13:78031473-78032794 | mostly (but not exclusively) caudal parts of LGE/MGE scattered radial clones |
| hs281 | chr6:41523224-41523677 | chr17:48051722-48052305 | stronger in MZ; only in the middle (both dorsoventral and rostrocaudal) of DP |
| hs293 | chr7:1265154-1266318 | chr5:140012199-140013382 | MP: only caudally |
| hs304 | chr9:8095553-8096166 | chr4:75346697-75347300 | LGE: ventral only, MGE: dorsal only |
| hs312 | chr9:81471747-81473114 | chr19:15414672-15416040 | |
| hs313 | chr9:81870622-81872224 | chr19:14965044-14966640 | |
| hs322 | chr1:87821793-87822910 | chr3:143836778-143837913 | subregion of hs322; scattered marginal zone cells; common rostrally, rare caudally except caudoventral cortex |
| hs342 | chr14:29860529-29862348 | chr12:51222566-51224516 | in LGE/MGE: rare/scattered radial clones, not homogenous |
| hs348 | chr14:36020024-36020998 | chr12:56715257-56716245 | MP extends into medial prefrontal cortex; apparent tangential migration from septum covering ventrorostral telencephalon |
| hs388 | chr2:7774393-7775070 | chr12:26576441-26577229 | expression possibly extending into dorsal MZ of MGE |
| hs399 | chr2:60441495-60442515 | chr11:24270835-24271855 | only in rostra! region of DP-MZ |
| hs408 | chr1:10851570-10852173 | chr4:148182890-148183525 | |
| hs411 | chr2:156726581-156727605 | chr2:56428876-56429891 | |
| hs416 | chr2:162094895-162095451 | chr2:61494199-61494773 | scattered MZ cells in most parts of cortex, but possibly migrated from EMT |
| hs422 | chr2:172955879-172957052 | chr2:71373435-71374614 | |
| hs427 | chrX: 139169379-139171545 | chrX:57796579-57798664 | subregion of MGE only; ventral Se only |
| hs433 | chr14:30741750-30743626 | chr12:52102388-52104278 | negative in part of DP, strong in MZ and SVZ of LGE and SVZ of MGE |
| hs480 | chr20:30191716-30192554 | chr2:152560612-152561308 | |
| hs488 | chr13:95358263-95360017 | chr14:118628839-118630633 | ventral-dorsal gradient in DP; in VP/LP more mosaic than in high activity region of DP; LP weakly positive and mosaic; MGE and POA very few scattered positive cells; rostral-most septal area positive, but definitive septal area negative |
| hs532 | chr13:28395961-28397536 | chr5:148034236-148035797 | MGE-VZ: scattered cells; MGE: rostral dorsal only |
| hs540 | chr13:71358093-71359507 | chr14:97500095-97501460 | dorsal LGE only |
| hs545 | chr1:243876467-243877893 | chr1:179080168-179081586 | |
| hs550 | chr7:13506207-13507276 | chr12:40027691-40028748 | possibly extending into POA |
| hs553 | chr2:172936519-172938249 | chr2:71354541-71356276 | within caudal part of LGE only dorsal |
| hs565 | chr11:31622822-31624118 | chr2:105673544-105674854 | |
| hs566 | chr14:29684896-29686744 | chr12:51045696-51047526 | |
| hs582 | chrX:81464240-81465016 | chrX:107040272-107041048 | |
| hs590 | chr18:34719386-34720720 | chr18:25535871-25537147 | |
| hs595 | chr10:76177765-76179000 | chr14:22071224-22072450 | PFC dorsal, not ventral |
| hs599 | chr15:37652783-37654460 | chr2:116149138-116150802 | |
| hs609 | chr2:147172004-147173802 | chr2:47039102-47040857 | active in diencephalon only |
| hs611 | chr12:111495397-111496252 | chr5:122482511-122483364 | CP mosaic |
| hs612 | chr1:91305562-91307215 | chr5:106993349-106995037 | mosaic in telencephalic areas |

TABLE 2B-continued

| Enhancer ID | human coordinates (hg19) | mouse orthologous (mm9) | Additional Comments |
|---|---|---|---|
| hs619 | chr13:72333516-72334988 | chr14:98471700-98473200 | LGE- and MGE-MZs show complex pattern |
| hs622 | chr14:99466200-99467144 | chr12:109016128-109017121 | scattered cells in DP-VZ |
| hs631 | chr8:36957851-36958723 | chr8:27495259-27496119 | possibly extending into DP |
| hs632 | chr20:2719208-2719789 | chr2:130177541-130178125 | small lateral zone of PFC |
| hs634 | chr18:76006820-76008476 | chr18:81705917-81707509 | |
| hs636 | chr3:157882303-157883963 | chr3:66839929-66841573 | |
| hs643 | chr9:23004730-23005789 | chr4:90103989-90105031 | small region of MP, probably missing dentate gyrus and subiculum |
| hs649 | chr2:146689050-146690099 | chr2:46521795-46522893 | possibly some SVZ cells are positive in these areas |
| hs653 | chr3:137185964-137186866 | chr9:100031290-100032189 | MP-expression locally restricted; likely subiculum |
| hs654 | chr3:147801015-147802169 | chr9:90587647-90588760 | |
| hs656 | chr10:131400948-131402279 | chr7:144193692-144194957 | VP rostrally and caudally separated by a gap; tangential migration emanating out from both rostral and caudal sources |
| hs660 | chr15:67198974-67200134 | chr9:63728005-63729314 | cannot be descibed with existing annotation scheme; likely entorhinal cortex precursor region |
| hs671 | chr1:97610491-97611741 | chr3:119064359-119065611 | DP predominantly in ventral half |
| hs672 | chr10:120074039-120075696 | chr19: 60278961-60280625 | |
| hs675 | chr2:144103882-144105644 | chr2:43833258-43835027 | LGE-VZ/SVZ only in scattered cells |
| hs676 | chr6:97544611-97545759 | chr4:24596353-24597477 | expression in LGE-MZ has appearance of tangential migration from MGE |
| hs687 | chr4:54881222-54882455 | chr5:75408486-75409693 | |
| hs692 | chr11:15587041-15588314 | chr7:122274934-122276253 | LGE-MZ possibly dorsal migration from the MGE |
| hs702 | chr2:105132815-105133830 | chr1:42422613-42423612 | cells in MZ of ventral and medial pallium likely tangential migration from EMT |
| hs742 | chr8:78042571-78044201 | chr3:5754492-5756119 | |
| hs748 | chr10:78390590-78391875 | chr14:23913849-23915139 | MZ cells straddle the ventral LGE and dorsal MGE |
| hs775 | chr18:77010009-77010795 | chr18:81008176-81008914 | mosaic in VP; LGE is scattered and mosaic; only dorsal LGE where expression is stronger in VP than dorsal LGE; absent from PFC and caudal telencephalon |
| hs781 | chr8:21907426-21908282 | chr14:71034305-71035125 | EMT: rostral only |
| hs782 | chr8:21901089-21902326 | chr14:71039797-71041000 | |
| hs798 | chr12:16170590-16171824 | chr6:137772070-137773298 | MP only caudally |
| hs799 | chr7:9271308-9272358 | chr6:9784714-9785886 | MZ cells straddle the ventral LGE and dorsal MGE, but also expression in the dorsal MGE-SVZ |
| hs807 | chr7:22091362-22092557 | chr12:119044146-119045319 | |
| hs818 | chr9:128520992-128522653 | chr2:34214751-34216394 | |
| hs840 | chr4:66989480-66990366 | chr5:85240355-85241286 | |
| hs841 | chr10:118854124-118855243 | chr19:59207451-59208587 | ventral LGE only; possibly also activity in most rostral MGE |
| hs844 | chr7:20832628-20833902 | chr12:120078517-120079917 | apparent tangential migration from EMT into MZ of entorhinal cortex and subiculum; dorsal pallial domain likely separate from EMT; mosaic in DP, dorsal-ventral gradient |
| hs848 | chr16:51491799-51493025 | chr8:91847783-91849077 | |
| hs852 | chr9:13750115-13751398 | chr4:81606321-81607769 | |
| hs853 | chr5:87083012-87084752 | chr13:84890969-84892679 | LGE-MZ and MGE-MZ may be tangentially migrating cells |
| hs876 | chr9:133540555-133541228 | chr2:31496164-31496831 | |
| hs886 | chr4:181201559-181202529 | chr8:51793522-51794489 | |
| hs914 | chr20:21214790-21217232 | chr2:146783502-146786549 | activity in diencephalon only |
| hs921 | chr2:236962599-236964857 | chr1:91744283-91746520 | MZ in caudal ventral cortex likely tangential migration from EMT |
| hs952 | chr5:91442456-91444549 | chr13:80138929-80141010 | caudal part of EMT likely migration to MZ of caudal ventral cortex; in MP dentate gyrus-like appearance |
| hs953 | chr2:175203263-175204895 | chr2:73113651-73115241 | dorsal LGE only |
| hs956 | chr7:114299711-114302078 | chr6:15361326-15363759 | both LGE and MGE dorsal only |
| hs957 | chr2:60761404-60763073 | chr11:23995054-23996665 | entorhinal cortex positive |
| hs969 | chr2:105317580-105319856 | chr1:42595564-42597875 | DP ventral-dorsal; LP mosaic |
| hs971 | chr5:91970162-91972034 | chr13:79484078-79485978 | activity in diencephalon only |
| hs978 | chr6:97754043-97755513 | chr4:24356000-24357444 | VP: rostral domain only, extends into PFC; moderate tangential migration |
| hs981 | chr4:113442390-113443530 | chr3:127329759-127330822 | activity in diencephalon only |
| hs987 | chr9:128869446-128870934 | chr2:33920352-33922048 | MZ positive in piriform cortex, accumbens and pallidum; origin of probable tangential migration unknown |
| hs998 | chr12:103406124-103408154 | chr10:86909379-86911404 | DP only positive in frontal cortex |
| hs1006 | chr10:102244842-102246334 | chr19:44588622-44590360 | expression mosaic, dorsal-ventral gradient in DP |
| hs1007 | chr7:20997668-20999102 | chr12:119963922-119965376 | |
| hs1019 | chr7:20838843-20840395 | chr12:120072953-120074549 | only dorsal-most portion of rostral LGE |
| hs1024 | chr5:92312840-92314645 | chr13:79076503-79078270 | frontal midline mesenchyme; probably meninges with no activity in actual brain |
| hs1025 | chr2:73124730-73126091 | chr6:85114949-85116468 | LP mosaic |
| hs1027 | chr18:22744668-22746270 | chr18:13945304-13946949 | mesenchyme under ventrolateral surface of telencephalon, no activity in actual brain |
| hs1032 | chr10:119309200-119310544 | chr19:59539995-59541288 | in VP, very mosaic and weak, maybe also in LP; in LGE only dorsal |
| hs1035 | chr6:98074091-98075722 | chr4:23945964-23947393 | rostral DP; dorsal-ventral gradient; mosaic |
| hs1041 | chr9:82010246-82011547 | chr19:14851206-14852476 | MZ of MP and VP likely tangentially migrating cells from EMT |
| hs1050 | chr4:109531908-109533465 | chr3:130439998-130441481 | MP dorsal only, dentate gyrus likely negative; DP dorsal only; clear intracortical boundary; dorsal-ventral gradient in DP |

TABLE 2B-continued

| Enhancer ID | human coordinates (hg19) | mouse orthologous (mm9) | Additional Comments |
|---|---|---|---|
| hs1052 | chr6:18536628-18538267 | chr13:47405953-47407586 | POA: small subregion; rostral-most sections unavailable, may extend into septum |
| hs1056 | chr18:76481722-76483257 | chr18:81349711-81351278 | within MGE only ventral with ventral-dorsal gradient; POA dorsal only; possibly few MZ cells in MGE and POA |
| hs1060 | chr5:92613862-92616844 | chr13:78740226-78743005 | |
| hs1066 | chr2:63275695-63277103 | chr11:21902483-21903827 | possibly extending into LP/VP; caudal-to-rostral and likely also dorsal-to-ventral gradient in pallium |
| hs1078 | chr9:82224085-82226757 | chr19:14639785-14642658 | EMT rostral only |
| hs1100 | chr6:41560717-41562075 | chr17:48008828-48010025 | EMT caudal only; cells in caudal MP-MZ and DP-MZ likely migrating from EMT |
| hs1172 | chr5:92634702-92636476 | chr13:78719845-78721773 | caudal-rostral and ventral-dorsal gradient |
| hs1187 | chr5:50390899-50392257 | chr13:117364725-117366094 | MGE dorsal only |
| hs1210 | chr2:66762515-66765088 | chr11:18816167-18818733 | MGE-MZ cells may have migrated from LGE to MGE |
| hs1226 | chr7:21080801-21082086 | chr12:119888961-119890205 | mosaic throughout; ventral PFC positive, probably from VP expression; expression in diencephalon (SPV) leading to migration of cells into amygdala |
| hs1316 | chr3:62405817-62408099 | chr14:13225035-13227325 | in EMT only caudal/ventral and possibly producing neurons migrating into caudal ventral pallium |
| hs1318 | chr8:77598007-77600645 | chr3:5223534-5226222 | rostral-most pole only |
| hs1321 | chr5:50467950-50469989 | chr13:117304210-117306202 | in LGE, MGE, POA possibly some VZ cells |
| hs1324 | chr1:213498112-213501134 | chr1:192551182-192554052 | |
| hs1325 | chr7:25791903-25794282 | chr6:51026185-51028597 | mosaic throughout; within DP, ventral-dorsal gradient |
| hs1329 | chr8:28370867-28371860 | chr14:65863910-65865029 | rostrally expression extends to VZ of DP/LP ("bulls-eye" pattern) |
| hs1334 | chr10:37054745-37057224 | chr18:8043681-8045850 | positive in rostral-most LGE only; MGE positive in intermediate dorsal-ventral position |
| hs1336 | chr7:34097962-34100011 | chr9:23182371-23184296 | EMT caudal-ventral only; may contribute cells to caudal/ventral pallium and/or CGE |
| hs1339 | chr9:92292484-92293889 | chr13:52015574-52016990 | MGE-MZ/-SVZ rostral/dorsal |
| hs1340 | chr6:20867105-20870529 | chr13:29701055-29703698 | MGE expression possibly originating from ventral migration from LGE |
| hs1341 | chr12:97468703-97471089 | chr10:92018471-92020553 | MP rostral only; absent in dorsal DP; MGE rostral only; POA very weak |
| hs1345 | chr5:107299863-107302976 | chr17:63520771-63522886 | novel domain in area of lateral entorhinal cortex; DP dorsal-vental gradient and rostral-caudal gradient; intraneocortical boundaries |
| hs1358 | chr6:163276830-163279930 | chr17:10936792-10939045 | |
| hs1359 | chr9:84264195-84266950 | chr4:71827361-71829994 | predominantly MZ expression |
| hs1361 | chr4:153287655-153290517 | chr3:84741019-84743495 | EMT caudal-ventral, contributing to MZ of ventral cortex and/or CGE |
| hs1538 | chr14:36911162-36914360 | chr12:57559065-57561475 | possibly also MGE |
| hs1578 | chr2:212254840-212257158 | chr1:68092503-68094701 | few cells in ventral caudal pallium; likely from EMT |

TABLE 3

Genomic intervals surrounding known telencephalon genes scanned for enhancers

| gene | sequence coordinates (hg19) | | | Elements tested in transgenics |
|---|---|---|---|---|
| | chr | start | end | |
| ASCL1 | chr12 | 103311381 | 103695720 | hs1122, hs1114, hs1540, hs998, hs967, hs1575 |
| BCL11A | chr2 | 58468514 | 60983381 | hs1076, hs1174, hs1012, hs1071, hs1018, hs1090, hs1063, hs1152, hs1232, hs1067, hs1199, hs1077, hs1154, hs1143, hs975, hs1119, hs1057, hs1209, hs1204, hs1021, hs1164, hs1072, hs1120, hs1535, hs1111, hs957, hs1176, hs1142, hs1113, hs1196, hs1181 |
| BMP4 | chr14 | 53620000 | 54863712 | hs1151 |
| CUTL2 | chr12 | 111375255 | 111798483 | |
| EBF1 | chr5 | 157286168 | 158526749 | hs1130, hs1208, hs1137, hs1022, hs1117, hs1123 |
| EMX1 | chr2 | 73119286 | 73169165 | hs1025 |
| EMX2 | chr10 | 119134937 | 119764428 | hs1032, hs1221, hs1087, hs1236, hs1551 |
| EOMES | chr3 | 27498245 | 28283123 | hs1557 |
| ERBB4 | chr2 | 211543829 | 213870762 | hs1578, hs1207, hs1541 |
| ETV1 | chr7 | 13935433 | 14187244 | |
| ETV5 | chr3 | 185655818 | 185867011 | |
| FEZF2 | chr3 | 62319321 | 62384021 | |
| FGF10 | chr5 | 43705589 | 44809026 | |
| FGF17 | chr8 | 21894407 | 21911155 | hs782, hs781 |
| FGF19 | chr11 | 69490165 | 69587796 | |

TABLE 3-continued

Genomic intervals surrounding known telencephalon genes scanned for enhancers

| gene | sequence coordinates (hg19) chr | start | end | Elements tested in transgenics |
|---|---|---|---|---|
| FGF8 | chr10 | 103454743 | 103541082 | |
| FGFR3 | chr4 | 1746895 | 1814759 | |
| FOXG1 | chr14 | 27066960 | 30045688 | hs1127, hs1075, hs1064, hs1539, hs1168, hs1523, hs1193, hs1201, hs1062 |
| FOXP1 | chr3 | 70666812 | 71731877 | hs1214, hs1231, hs965, hs1092, hs187, hs1116, hs973, hs1149, hs1010, hs1572, hs1160, hs997 |
| FOXP2 | chr7 | 113559064 | 114562208 | hs1069, hs1167, hs999, hs954, hs1215, hs956, hs1192, hs1080, hs966 |
| FOXP4 | chr6 | 41318615 | 41606252 | hs1225, hs1145, hs1100, hs1003 |
| FZD8 | chr10 | 35897863 | 37414784 | hs1588, hs1567, hs1589 |
| GAD1 | chr2 | 171574497 | 171785710 | |
| GBX1 | chr7 | 150841523 | 150872784 | |
| GBX2 | chr2 | 237033863 | 237102094 | |
| GLI1 | chr12 | 57851789 | 57866095 | |
| GLI3 | chr7 | 41742706 | 42949220 | hs1586, hs1132, hs1213 |
| GSH1 | chr13 | 28241547 | 28494176 | hs1568 |
| GSH2 | chr4 | 54934356 | 55092588 | |
| HES1 | chr3 | 193415315 | 194060494 | hs1563, hs1543 |
| HES5 | chr1 | 2458036 | 2485433 | |
| HMX3 | chr10 | 124817805 | 124913869 | hs1005 |
| ID2 | chr2 | 8468549 | 8869059 | hs1527 |
| ID4 | chr6 | 18468848 | 20100947 | hs1052, hs1580, hs1094, hs1542, hs1533, hs1175 |
| IKFZ1 | chr7 | 50136049 | 50509959 | hs961, hs972 |
| ISL1 | chr5 | 50138176 | 50690328 | hs1187 |
| LEF1 | chr4 | 108956323 | 109541811 | hs1545, hs1050 |
| LHX2 | chr9 | 126692417 | 127020242 | |
| LHX5 | chr12 | 113876080 | 114259862 | hs1571 |
| LHX6 | chr9 | 124962361 | 125003783 | |
| LHX8 | chr1 | 75232358 | 75669297 | |
| LMO3 | chr12 | 16517343 | 18233803 | hs1532, hs993, hs980 |
| LMO4 | chr1 | 87634884 | 89150255 | hs1134, hs174, hs1161, hs1217, hs1002, hs1058, hs1055, hs1198, hs1200, hs1135, hs1216, hs1068, hs988, hs1107 |
| MAFB | chr20 | 37668363 | 39657461 | hs1042, hs1237, hs1086, hs1234, hs1101, hs996, hs992 |
| MEIS1 | chr2 | 66311772 | 67624450 | hs1229, hs1110, hs1206, hs1197, hs1584, hs1565, hs1210 |
| MEIS2 | chr15 | 37102447 | 37392754 | hs1129, hs1178, hs1097 |
| NEUROG1 | chr5 | 134783038 | 134906374 | |
| NEUROG2 | chr4 | 113362829 | 113460499 | hs981 |
| NKX2-2 | chr20 | 21370463 | 22380988 | hs1205 |
| NR2E1 | chr6 | 108395941 | 108532717 | hs1033, hs1189 |
| NR2F1 | chr5 | 90679121 | 92936062 | hs989, hs982, hs1227, hs952, hs1084, hs1162, hs1109, hs971, hs1039, hs1155, hs1079, hs1153, hs1024, hs1049, hs1146, hs1560, hs1170, hs1060, hs1550, hs1034, hs1577, hs1172, hs1222 |
| OLIG2 | chr21 | 34185959 | 34442449 | hs1548, hs1188 |
| OTX1 | chr2 | 63273619 | 63344985 | hs1066 |
| OTX2 | chr14 | 57115002 | 57670114 | hs1579, hs1150, hs1218 |
| PAX6 | chr11 | 31805329 | 32112607 | hs1531, hs1082 |
| PBX1 | chr1 | 163325547 | 165172647 | hs1156, hs1185, hs1230, hs1202, hs1235, hs1144, hs970, hs1136, hs1191 |
| PBX2 | chr6 | 32152023 | 32158543 | |
| PBX3 | chr9 | 128508831 | 129089127 | hs1030, hs818, hs1102, hs983, hs1099, hs1095, hs1017, hs1000, hs1103, hs987, hs1015, hs1108 |
| POU3F1 | chr1 | 38489494 | 39305020 | hs1105, hs1124, hs1179, hs1001, hs1008, hs1098, hs1045, hs1546, hs1031, hs1139 |
| POU3F2 | chr6 | 97731052 | 99321600 | hs978, hs1564, hs1059, hs1220, hs1054, hs995, hs985, hs1233, hs1106, hs1128, hs1159, hs1081, hs1014, hs1035, hs1085 |
| POU3F3 | chr2 | 103433878 | 105654505 | hs1212, hs1125, hs1581, hs1112, hs1555, hs958, hs977, hs1147, hs1526, hs1126, hs1140, hs1554, hs1131, hs1534, hs960, hs1177, hs969, hs1121, hs1553, hs990, hs1093, hs1529 |
| POU3F4 | chrX | 82763251 | 83319284 | hs1029 |
| RARB | chr3 | 25469704 | 25639474 | |
| RARG | chr12 | 53601000 | 53645436 | |
| SALL3 | chr18 | 74982093 | 76829396 | hs1195, hs1186, hs1047, hs1083, hs1011, hs1056, hs1194, hs1141, hs1020 |
| SIX3 | chr2 | 45149606 | 45232343 | |
| SLC32A1 | chr20 | 37217104 | 37377096 | |

TABLE 3-continued

Genomic intervals surrounding known telencephalon genes scanned for enhancers

| gene | sequence coordinates (hg19) chr | start | end | Elements tested in transgenics |
|---|---|---|---|---|
| SP8 | chr7 | 20795247 | 21467688 | hs1019, hs1007, hs1226, hs1223, hs1148 |
| SP9 | chr2 | 175113365 | 175212879 | hs953 |
| SPRY1 | chr4 | 124235802 | 125585467 | hs1582, hs1525 |
| TBR1 | chr2 | 162267926 | 162290384 | |
| TCF4 | chr18 | 52626637 | 53255493 | hs1013, hs1561, hs1537 |
| TITF1 | chr14 | 36841574 | 36989414 | hs984, hs1166, hs1538 |
| TLE4 | chr9 | 82006948 | 84198598 | hs1041, hs1074, hs1078, hs1026, hs1183, hs1587, hs1004, hs1211, hs974, hs1228, hs1118, hs1163 |
| VAX1 | chr10 | 118764876 | 118934608 | hs841 |
| WNT7B | chr22 | 46239929 | 46436457 | hs1559 |
| WNT8B | chr10 | 102124587 | 102246402 | hs1006 |
| ZIC1 | chr3 | 147124407 | 148415664 | hs1043, hs1173, hs1184, hs1573, hs1038, hs1549, hs1203, hs1115, hs1224 |
| ZNF521 | chr18 | 22059920 | 23596218 | hs1053, hs1169, hs1180, hs1104, hs1027, hs962, hs1088, hs1544, hs1138, hs1566 |

TABLE 4

| tested element (hg19) | Near forebrain gene (see Table 3) | Neighboring Genes | Vertebrate PhastCons Score | extremely human-rodent conserved (Visel et al 2008) |
|---|---|---|---|---|
| chr12:103345263-103346680 | ASCL1 | PAH, ASCL1 | 797 | yes |
| chr12:103371347-103372610 | ASCL1 | ASCL1, C12orf42 | 801 | yes |
| chr12:103570982-103573398 | ASCL1 | ASCL1, C12orf42 | 639 | yes |
| chr12:103484342-103485519 | ASCL1 | ASCL1, C12orf42 | 812 | yes |
| chr2:58695819-58697323 | BCL11A | FANCL, BCL11A | 846 | yes |
| chr2:58748340-58750140 | BCL11A | FANCL, BCL11A | 771 | yes |
| chr2:58770304-58771290 | BCL11A | FANCL, BCL11A | 859 | yes |
| chr2:58799729-58800607 | BCL11A | FANCL, BCL11A | 701 | yes |
| chr2:58809796-58811611 | BCL11A | FANCL, BCL11A | 832 | yes |
| chr2:58811475-58812905 | BCL11A | FANCL, BCL11A | 771 | yes |
| chr2:58857680-58858956 | BCL11A | FANCL, BCL11A | 854 | yes |
| chr2:58859997-58861674 | BCL11A | FANCL, BCL11A | 850 | yes |
| chr2:58891096-58892548 | BCL11A | FANCL, BCL11A | 846 | yes |
| chr2:58948607-58950015 | BCL11A | FANCL, BCL11A | 852 | yes |
| chr2:58975738-58977115 | BCL11A | FANCL, BCL11A | 845 | yes |
| chr2:59102071-59103380 | BCL11A | FANCL, BCL11A | 750 | yes |
| chr2:59161996-59164461 | BCL11A | FANCL, BCL11A | 819 | yes |
| chr2:59178992-59180242 | BCL11A | FANCL, BCL11A | 772 | yes |
| chr2:59202276-59203399 | BCL11A | FANCL, BCL11A | 825 | yes |
| chr2:59203217-59204548 | BCL11A | FANCL, BCL11A | 827 | yes |
| chr2:59303870-59305029 | BCL11A | FANCL, BCL11A | 838 | yes |
| chr2:59304974-59306893 | BCL11A | FANCL, BCL11A | 873 | yes |
| chr2:59888700-59891476 | BCL11A | FANCL, BCL11A | 833 | yes |
| chr2:59894793-59896957 | BCL11A | FANCL, BCL11A | 785 | yes |
| chr2:59896819-59898978 | BCL11A | FANCL, BCL11A | 779 | yes |
| chr2:59998338-59999656 | BCL11A | FANCL, BCL11A | 805 | yes |
| chr2:60005531-60007545 | BCL11A | FANCL, BCL11A | 791 | yes |
| chr2:60055628-60056970 | BCL11A | FANCL, BCL11A | 842 | yes |
| chr2:60223849-60225179 | BCL11A | FANCL, BCL11A | 788 | yes |
| chr2:60516097-60518092 | BCL11A | FANCL, BCL11A | 839 | yes |
| chr2:60794812-60796264 | BCL11A | BCL11A, PAPOLG | 782 | yes |
| chr2:60855056-60856888 | BCL11A | BCL11A, PAPOLG | 844 | yes |
| chr14:53833457-53836210 | BMP4 | DDHD1, BMP4 | 782 | yes |
| chr5:157589029-157590477 | EBF1 | CLINT1, EBF1 | 832 | yes |
| chr5:158017768-158019067 | EBF1 | CLINT1, EBF1 | 808 | yes |
| chr5:158227696-158229500 | EBF1 | EBF1 | 814 | yes |
| chr5:158517785-158518914 | EBF1 | EBF1 | 788 | yes |
| chr5:158486120-158487498 | EBF1 | EBF1 | 830 | yes |
| chr5:158508842-158510137 | EBF1 | EBF1 | 809 | yes |
| chr10:119313709-119314860 | EMX2 | EMX2, RAB11FIP2 | 786 | yes |
| chr10:119491936-119493137 | EMX2 | EMX2, RAB11FIP2 | 793 | yes |
| chr10:119589659-119591176 | EMX2 | EMX2, RAB11FIP2 | 796 | yes |
| chr3:28033828-28035751 | EOMES | AK297461, CMC1 | 824 | yes |
| chr2:213141079-213142308 | ERBB4 | ERBB4 | 767 | yes |
| chr8:21907426-21908282 | FGF17 | FGF17, EPB49 | 590 | no |

TABLE 4-continued

| tested element (hg19) | Near forebrain gene (see Table 3) | Neighboring Genes | Vertebrate PhastCons Score | extremely human-rodent conserved (Visel et al 2008) |
|---|---|---|---|---|
| chr8:21901089-21902326 | FGF17 | FGF17 | 612 | yes |
| chr2:175203263-175204895 | FLJ46347 | SP9, CIR1 | 889 | yes |
| chr14 :27553786-27555661 | FOXG1 | NOVA1, FOXG1 | 728 | yes |
| chr14 :28398563-28400621 | FOXG1 | NOVA1, FOXG1 | 733 | yes |
| chr14:29743374-29745881 | FOXG1 | C14orf23, PRKD1 | 782 | yes |
| chr14:29894197-29895582 | FOXG1 | C14orf23, PRKD1 | 750 | yes |
| chr14:29911320-29912514 | FOXG1 | C14orf23, PRKD1 | 770 | yes |
| chr14:29960491-29962005 | FOXG1 | C14orf23, PRKD1 | 773 | yes |
| chr14:29226075-29227673 | FOXG1 | NOVA1, FOXG1 | 806 | yes |
| chr3:70701489-70702904 | FOXP1 | MITF, FOXP1 | 741 | yes |
| chr3:71026229-71026764 | FOXP1 | FOXP1 | 810 | yes |
| chr3:71099157-71100851 | FOXP1 | FOXP1 | 931 | yes |
| chr3:71253670-71255013 | FOXP1 | FOXP1 | 825 | yes |
| chr3:71446827-71448809 | FOXP1 | FOXP1 | 784 | yes |
| chr3:71499477-71500970 | FOXP1 | FOXP1 | 843 | yes |
| chr3:71507469-71508874 | FOXP1 | FOXP1 | 844 | yes |
| chr3:71573607-71574540 | FOXP1 | FOXP1 | 833 | yes |
| chr3:71590897-71592786 | FOXP1 | FOXP1 | 818 | yes |
| chr3:71153556-71155053 | FOXP1 | FOXP1 | 826 | yes |
| chr7:114052100-114053403 | FOXP2 | FOXP2 | 800 | yes |
| chr7:114055419-114056748 | FOXP2 | FOXP2 | 820 | yes |
| chr7:114142132-114143527 | FOXP2 | FOXP2 | 885 | yes |
| chr7:114261073-114263089 | FOXP2 | FOXP2 | 875 | yes |
| chr7:114287987-114290557 | FOXP2 | FOXP2 | 905 | yes |
| chr7:114292900-114293972 | FOXP2 | FOXP2 | 800 | yes |
| chr7:114326912-114329772 | FOXP2 | FOXP2 | 892 | yes |
| chr7:114463797-114464462 | FOXP2 | FOXP2, MDFIC | 820 | yes |
| chr7:114299711-114302078 | FOXP2 | FOXP2 | 905 | yes |
| chr6:41380559-41381515 | FOXP4 | NCR2, DQ141194 | 603 | yes |
| chr6:41434455-41435695 | FOXP4 | NCR2, DQ141194 | 815 | yes |
| chr6:41436815-41438024 | FOXP4 | NCR2, DQ141194 | 760 | yes |
| chr6:41560717-41562075 | FOXP4 | FOXP4 | 809 | yes |
| chr10:36072272-36074291 | FZD8 | FZD8, ANKRD30A | 428 | no |
| chr10:35925382-35927242 | FZD8 | FZD8 | 748 | yes |
| chr7:42432266-42433365 | GLI3 | GLI3, C7orf25 | 678 | yes |
| chr7:42252831-42254560 | GLI3 | GLI3 | 818 | yes |
| chr13:28318579-28320134 | GSH1 | POLR1D, GSX1 | 783 | no |
| chr10:124902927-124904638 | Hmx3 | HMX3, HMX2 | 831 | yes |
| chr6:18612650-18614840 | ID4 | RNF144B, ID4 | 688 | no |
| chr7:50333048-50334464 | IKFZ1 | C7orf72, IKZF1 | 726 | yes |
| chr7:50357638-50358644 | IKFZ1 | IKZF1 | 823 | yes |
| chr4:109531908-109533465 | LEF1 | LOC285456 | 753 | yes |
| chr12:17311784-17313759 | LMO3 | SKP1P2, RERGL | 808 | yes |
| chr12:17848111-17849347 | LMO3 | SKP1P2, RERGL | 823 | yes |
| chr1:88183654-88184961 | LMO4 | LMO4, PKN2 | 815 | yes |
| chr1:88402821-88404888 | LMO4 | LMO4, PKN2 | 842 | yes |
| chr1:88535719-88538390 | LMO4 | LMO4, PKN2 | 807 | yes |
| chr1:88577535-88578821 | LMO4 | LMO4, PKN2 | 728 | yes |
| chr1:88595049-88596320 | LMO4 | LMO4, PKN2 | 786 | yes |
| chr1:88646698-88648145 | LMO4 | LMO4, PKN2 | 846 | yes |
| chr1:88686076-88687740 | LMO4 | LMO4, PKN2 | 829 | yes |
| chr1:88841735-88843091 | LMO4 | LMO4, PKN2 | 832 | yes |
| chr1:88875731-88877192 | LMO4 | LMO4, PKN2 | 876 | yes |
| chr1:88025863-88027203 | LMO4 | LMO4, PKN2 | 767 | yes |
| chr20:37876814-37877600 | MAFB | DHX35, MAFB | 771 | yes |
| chr20:38580899-38582010 | MAFB | DHX35, MAFB | 681 | yes |
| chr20:38862746-38864025 | MAFB | DHX35, MAFB | 816 | yes |
| chr20:39334182-39335059 | MAFB | MAFB, TOP1 | 815 | yes |
| chr20:39347264-39348213 | MAFB | MAFB, TOP1 | 784 | yes |
| chr20:39472648-39473702 | MAFB | MAFB, TOP1 | 747 | yes |
| chr20:39483347-39484593 | MAFB | MAFB, TOP1 | 767 | yes |
| chr2:67414599-67416139 | MEIS1 | MEIS1, ETAA1 | 636 | no |
| chr2:66397542-66398943 | MEIS1 | SPRED2, MEIS1 | 830 | yes |
| chr2:66510556-66511795 | MEIS1 | SPRED2, MEIS1 | 802 | yes |
| chr2:66749539-66750931 | MEIS1 | MEIS1 | 864 | yes |
| chr15:37216993-37219601 | MEIS2 | MEIS2 | 869 | yes |
| chr15:37347604-37349955 | MEIS2 | MEIS2 | 876 | yes |
| chr15:37371729-37373137 | MEIS2 | MEIS2 | 849 | yes |
| chr4:113442390-113443530 | NEUROG2 | NEUROG2, C4orf21 | 819 | yes |
| chr20:21488551-21490021 | NKX2-2 | NKX2-4, NKX2-2 | 762 | yes |
| chr6:108435330-108436506 | NR2E1 | OSTM1, NR2E1 | 787 | yes |
| chr5:90768370-90769843 | NR2F1 | ARRDC3, NR2F1 | 775 | yes |
| chr5:90785763-90787167 | NR2F1 | ARRDC3, NR2F1 | 812 | yes |
| chr5:91271776-91272886 | NR2F1 | ARRDC3, NR2F1 | 765 | yes |

TABLE 4-continued

| tested element (hg19) | Near forebrain gene (see Table 3) | Neighboring Genes | Vertebrate PhastCons Score | extremely human-rodent conserved (Visel et al 2008) |
|---|---|---|---|---|
| chr5:91700124-91701467 | NR2F1 | ARRDC3, NR2F1 | 736 | yes |
| chr5:91765018-91766129 | NR2F1 | ARRDC3, NR2F1 | 734 | yes |
| chr5:91828131-91829295 | NR2F1 | ARRDC3, NR2F1 | 738 | yes |
| chr5:91940922-91942042 | NR2F1 | ARRDC3, NR2F1 | 760 | yes |
| chr5:92031088-92033197 | NR2F1 | ARRDC3, NR2F1 | 803 | yes |
| chr5:92035493-92036961 | NR2F1 | ARRDC3, NR2F1 | 813 | yes |
| chr5:92141511-92143537 | NR2F1 | ARRDC3, NR2F1 | 841 | yes |
| chr5:92219848-92221133 | NR2F1 | ARRDC3, NR2F1 | 764 | yes |
| chr5:92314781-92316083 | NR2F1 | ARRDC3, NR2F1 | 837 | yes |
| chr5:92426546-92428433 | NR2F1 | ARRDC3, NR2F1 | 803 | yes |
| chr5:92476842-92479105 | NR2F1 | ARRDC3, NR2F1 | 657 | yes |
| chr5:92526066-92527353 | NR2F1 | ARRDC3, NR2F1 | 806 | yes |
| chr5:92536353-92537380 | NR2F1 | ARRDC3, NR2F1 | 724 | yes |
| chr5:91442456-91444549 | NR2F1 | ARRDC3, NR2F1 | 854 | yes |
| chr5:91927845-91931024 | NR2F1 | ARRDC3, NR2F1 | 659 | yes |
| chr5:91970162-91972034 | NR2F1 | ARRDC3, NR2F1 | 862 | yes |
| chr5:92312840-92314645 | NR2F1 | ARRDC3, NR2F1 | 879 | yes |
| chr5:92613862-92616844 | NR2F1 | ARRDC3, NR2F1 | 853 | yes |
| chr2:63275695-63277103 | OTX1 | EHBP1, OTX1 | 736 | yes |
| chr14:57320664-57324319 | OTX2 | OTX2, EXOC5 | 696 | yes |
| chr11:31816452-31818421 | PAX6 | PAX6 | 752 | yes |
| chr1:163359231-163360494 | PBX1 | NUF2, PBX1 | 739 | yes |
| chr1:163507965-163509139 | PBX1 | NUF2, PBX1 | 670 | yes |
| chr1:164197827-164199172 | PBX1 | NUF2, PBX1 | 619 | yes |
| chr1:164620038-164621164 | PBX1 | PBX1 | 736 | yes |
| chr1:164668592-164669823 | PBX1 | PBX1 | 750 | yes |
| chr1:164672787-164674206 | PBX1 | PBX1 | 795 | yes |
| chr1:164700259-164701522 | PBX1 | PBX1 | 762 | yes |
| chr1:164604141-164605474 | PBX1 | PBX1 | 745 | yes |
| chr1:164805507-164806794 | PBX1 | PBX1 | 757 | yes |
| chr9:128516934-128518372 | PBX3 | PBX3 | 838 | yes |
| chr9:128525348-128527214 | PBX3 | PBX3 | 855 | yes |
| chr9:128606519-128608350 | PBX3 | PBX3 | 839 | yes |
| chr9:128640165-128641327 | PBX3 | PBX3 | 863 | yes |
| chr9:128666411-128667552 | PBX3 | PBX3 | 844 | yes |
| chr9:128735158-128736174 | PBX3 | PBX3, FAM125B | 823 | yes |
| chr9:128919674-128920432 | PBX3 | PBX3, FAM125B | 773 | yes |
| chr9:128645462-128647097 | PBX3 | PBX3 | 887 | yes |
| chr1:38627529-38629265 | POU3F1 | POU3F1, LOC339442 | 772 | yes |
| chr1:38656780-38657626 | POU3F1 | POU3F1, LOC339442 | 738 | yes |
| chr1:38735942-38737376 | POU3F1 | LOC339442, RRAGC | 795 | yes |
| chr1:38791998-38793333 | POU3F1 | LOC339442, RRAGC | 792 | yes |
| chr1:38819171-38820577 | POU3F1 | LOC339442, RRAGC | 761 | yes |
| chr1:39192609-39194134 | POU3F1 | LOC339442, RRAGC | 793 | yes |
| chr1:38712075-38713517 | POU3F1 | LOC339442, RRAGC | 807 | yes |
| chr6:97948958-97949898 | POU3F2 | MMS22L, POU3F2 | 776 | yes |
| chr6:98212329-98214701 | POU3F2 | MMS22L, POU3F2 | 756 | yes |
| chr6:98261649-98263117 | POU3F2 | MMS22L, POU3F2 | 792 | yes |
| chr6:98278782-98280694 | POU3F2 | MMS22L, POU3F2 | 810 | yes |
| chr6:98382462-98383929 | POU3F2 | MMS22L, POU3F2 | 821 | yes |
| chr6:98504034-98506058 | POU3F2 | MMS22L, POU3F2 | 798 | yes |
| chr6:98572398-98573780 | POU3F2 | MMS22L, POU3F2 | 764 | yes |
| chr6:98831075-98833042 | POU3F2 | MMS22L, POU3F2 | 778 | yes |
| chr6:98902034-98904516 | POU3F2 | MMS22L, POU3F2 | 853 | yes |
| chr6:99005894-99007499 | POU3F2 | MMS22L, POU3F2 | 842 | yes |
| chr6:98074091-98075722 | POU3F2 | MMS22L, POU3F2 | 825 | yes |
| chr6:98829860-98831049 | POU3F2 | MMS22L, POU3F2 | 774 | yes |
| chr2:103768696-103772482 | POU3F3 | TMEM182, LOC100287010 | 507 | no |
| chr2:103538361-103539868 | POU3F3 | TMEM182, LOC100287010 | 847 | yes |
| chr2:103548426-103549712 | POU3F3 | TMEM182, LOC100287010 | 808 | yes |
| chr2:104060734-104062561 | POU3F3 | TMEM182, LOC100287010 | 853 | yes |
| chr2:104063598-104065812 | POU3F3 | TMEM182, LOC100287010 | 758 | yes |
| chr2:104285458-104286792 | POU3F3 | TMEM182, LOC100287010 | 783 | yes |
| chr2:104576225-104577270 | POU3F3 | TMEM182, LOC100287010 | 822 | yes |
| chr2:104648312-104650249 | POU3F3 | TMEM182, LOC100287010 | 767 | yes |
| chr2:105300344-105301657 | POU3F3 | LOC100287010, POU3F3 | 716 | yes |
| chr2:105452973-105454169 | POU3F3 | LOC100287010, POU3F3 | 764 | yes |
| chr2:105516737-105518490 | POU3F3 | AK095498, MRPS9 | 719 | yes |
| chr2:103909358-103911221 | POU3F3 | TMEM182, LOC100287010 | 799 | yes |
| chr2:105464986-105467538 | POU3F3 | LOC100287010, POU3F3 | 780 | yes |
| chrX:82765974-82767821 | POU3F4 | POU3F4, CYLC1 | 727 | yes |
| chr18:75467090-75468311 | SALL3 | GALR1, SALL3 | 750 | yes |
| chr18:75496338-75498507 | SALL3 | GALR1, SALL3 | 822 | yes |
| chr18:75569573-75570862 | SALL3 | GALR1, SALL3 | 803 | yes |

TABLE 4-continued

| tested element (hg19) | Near forebrain gene (see Table 3) | Neighboring Genes | Vertebrate PhastCons Score | extremely human-rodent conserved (Visel et al 2008) |
|---|---|---|---|---|
| chr18:76009581-76010891 | SALL3 | GALR1, SALL3 | 737 | yes |
| chr18:76064036-76065306 | SALL3 | GALR1, SALL3 | 715 | yes |
| chr18:76070697-76071834 | SALL3 | GALR1, SALL3 | 787 | yes |
| chr18:76517730-76518836 | SALL3 | GALR1, SALL3 | 798 | yes |
| chr18:76461276-76462723 | SALL3 | GALR1, SALL3 | 813 | yes |
| chr18:76481722-76483257 | SALL3 | GALR1, SALL3 | 819 | yes |
| chr7:21019551-21021200 | SP8 | SP8, SP4 | 813 | yes |
| chr7:21239775-21240922 | SP8 | SP8, SP4 | 714 | yes |
| chr7:20838843-20840395 | SP8 | SP8, SP4 | 785 | yes |
| chr4:124383428-124386454 | SPRY1 | SPRY1, ANKRD50 | 613 | no |
| chr18:52699870-52701226 | TCF4 | CCDC68, TCF4 | 806 | yes |
| chr14:36907561-36909195 | TITF1 | DPPA3, SFTA3 | 877 | yes |
| chr14:36973775-36974585 | TITF1 | SFTA3 | 810 | yes |
| chr9:82274254-82276353 | TLE4 | TLE4 | 606 | no |
| chr9:82119097-82120855 | TLE4 | PSAT1, TLE4 | 802 | yes |
| chr9:82244801-82246758 | TLE4 | TLE4 | 826 | yes |
| chr9:82266057-82267053 | TLE4 | TLE4 | 808 | yes |
| chr9:82681268-82682692 | TLE4 | TLE4, TLE1 | 833 | yes |
| chr9:83122286-83123599 | TLE4 | TLE4, TLE1 | 810 | yes |
| chr9:83412700-83413972 | TLE4 | TLE4, TLE1 | 798 | yes |
| chr9:83711693-83712782 | TLE4 | TLE4, TLE1 | 762 | yes |
| chr9:82224085-82226757 | TLE4 | TLE4 | 800 | yes |
| chr9:84167351-84168176 | TLE4 | TLE4, TLE1 | 783 | yes |
| chr10:102244842-102246334 | WNT8B | WNT8B, SEC31B | 750 | yes |
| chr3:147125146-147126336 | ZIC1 | ZIC4, ZIC1 | 795 | yes |
| chr3:147378547-147380603 | ZIC1 | ZIC1, AGTR1 | 809 | yes |
| chr3:147393021-147394349 | ZIC1 | ZIC1, AGTR1 | 805 | yes |
| chr3:147748015-147749579 | ZIC1 | ZIC1, AGTR1 | 796 | yes |
| chr3:148006499-148007810 | ZIC1 | ZIC1, AGTR1 | 790 | yes |
| chr3:147563409-147566604 | ZIC1 | ZIC1, AGTR1 | 836 | yes |
| chr3:147651676-147653436 | ZIC1 | ZIC1, AGTR1 | 779 | yes |
| chr18:22139917-22141191 | ZNF521 | HRH4, ZNF521 | 817 | yes |
| chr18:22657391-22658788 | ZNF521 | ZNF521 | 826 | yes |
| chr18:22747310-22748975 | ZNF521 | ZNF521 | 874 | yes |
| chr18:22769112-22770579 | ZNF521 | ZNF521 | 853 | yes |
| chr18:22235986-22237388 | ZN F521 | HRH4, ZNF521 | 769 | yes |
| chr18:22744668-22746270 | ZNF521 | ZNF521 | 801 | yes |
| chr18:23432723-23434825 | ZNF521 | ZNF521, SS18 | 760 | yes |

TABLE 5

| ID | Tested Element (hg19) | Near Forebrain Gene (see Table3) | Directly Neighboring Genes | ChIP-seq support (if any) peak coordinates | peak height | Conservation Support (vertebrate phastCons score) |
|---|---|---|---|---|---|---|
| hs1156 | chr1:163359231-163360494 | PBX1 | NUF2, PBX1 | | | 739 |
| hs1185 | chr1:163507965-163509139 | PBX1 | NUF2, PBX1 | | | 670 |
| hs1230 | chr1:164197827-164199172 | PBX1 | NUF2, PBX1 | | | 619 |
| hs1202 | chr1:164604141-164605474 | PBX1 | PBX1 | | | 745 |
| hs1235 | chr1:164620038-164621164 | PBX1 | PBX1 | | | 736 |
| hs1144 | chr1:164668592-164669823 | PBX1 | PBX1 | | | 750 |
| hs970 | chr1:164672787-164674206 | PBX1 | PBX1 | | | 795 |
| hs1136 | chr1:164700259-164701522 | PBX1 | PBX1 | | | 762 |
| hs1191 | chr1:164805507-164806794 | PBX1 | PBX1 | | | 757 |
| hs1714 | chr1:232753930-232757436 | | SIPA1L2, KIAA1383 | chr1:232752534-232757345 | 8.834303 | 639 |
| hs1105 | chr1:38494689-38495688 | POU3F1 | UTP11L, POU3F1 | chr1:38492033-38495681 | 6.554722 | 783 |
| hs1124 | chr1:38627529-38629265 | POU3F1 | POU3F1, LOC339442 | | | 772 |
| hs1179 | chr1:38656780-38657626 | POU3F1 | POU3F1, LOC339442 | | | 738 |
| hs1001 | chr1:38712075-38713517 | POU3F1 | LOC339442, RRAGC | | | 807 |
| hs1008 | chr1:38735942-38737376 | POU3F1 | LOC339442, RRAGC | | | 795 |
| hs1098 | chr1:38791998-38793333 | POU3F1 | LOC339442, RRAGC | | | 792 |
| hs1045 | chr1:38819171-38820577 | POU3F1 | LOC339442, RRAGC | | | 761 |
| hs1546 | chr1:38835996-38838106 | POU3F1 | LOC339442, RRAGC | chr1:38835884-38837862 | 11.637023 | 783 |
| hs1031 | chr1:39192609-39194134 | POU3F1 | LOC339442, RRAGC | | | 793 |
| hs1139 | chr1:39248757-39250129 | POU3F1 | LOC339442, RRAGC | chr1:39247238-39250285 | 7.293627 | 770 |
| hs1134 | chr1:87803415-87805212 | LMO4 | LMO4 | chr1:87799160-87803500 | 7.293627 | 881 |
| hs174 | chr1:87821621-87823082 | LMO4 | LMO4, PKN2 | chr1:87820727-87823443 | 9.420391 | 928 |
| hs1161 | chr1:88025863-88027203 | LMO4 | LMO4, PKN2 | | | 767 |
| hs1217 | chr1:88065041-88066530 | LMO4 | LMO4, PKN2 | chr1:88063745-88067085 | 7.293627 | 826 |

TABLE 5-continued

| | | | | | | |
|---|---|---|---|---|---|---|
| hs1002 | chr1:88108084-88109396 | LMO4 | LMO4, PKN2 | chr1:88107117-88109064 | 6.752707 | 843 |
| hs1058 | chr1:88183654-88184961 | LMO4 | LMO4, PKN2 | | | 815 |
| hs1055 | chr1:88402821-88404888 | LMO4 | LMO4, PKN2 | | | 842 |
| hs1198 | chr1:88535719-88538390 | LMO4 | LMO4, PKN2 | | | 807 |
| hs1200 | chr1:88577535-88578821 | LMO4 | LMO4, PKN2 | | | 728 |
| hs1135 | chr1:88595049-88596320 | LMO4 | LMO4, PKN2 | | | 786 |
| hs1216 | chr1:88646698-88648145 | LMO4 | LMO4, PKN2 | | | 846 |
| hs1107 | chr1:88686076-88687740 | LMO4 | LMO4, PKN2 | | | 829 |
| hs1068 | chr1:88841735-88843091 | LMO4 | LMO4, PKN2 | | | 832 |
| hs988 | chr1:88875731-88877192 | LMO4 | LMO4, PKN2 | | | 876 |
| hs1006 | chr10:102244842-102246334 | WNT8B | WNT8B, SEC31B | | | 750 |
| hs841 | chr10:118854124-118855243 | VAX1 | KIAA1598 | chr10:118853518-118857229 | 10.93367 | 831 |
| hs1032 | chr10:119309200-119310544 | EMX2 | EMX2, RAB11FIP2 | chr10:119308625-119311760 | 7.384363 | 808 |
| hs1221 | chr10:119313709-119314860 | EMX2 | EMX2, RAB11FIP2 | | | 786 |
| hs1087 | chr10:119491936-119493137 | EMX2 | EMX2, RAB11FIP2 | | | 793 |
| hs1236 | chr10:119589659-119591176 | EMX2 | EMX2, RAB11FIP2 | | | 796 |
| hs1551 | chr10:119725799-119727161 | EMX2 | EMX2, RAB11FIP2 | chr10:119726124-119727860 | 8.293427 | 758 |
| hs672 | chr10:120074039-120075696 | | FAM204A | | | 884 |
| hs1005 | chr10:124902927-124904638 | Hmx3 | HMX3, HMX2 | | | 831 |
| hs1588 | chr10:35925382-35927242 | FZD8 | FZD8 | | | 748 |
| hs1567 | chr10:35972892-35975932 | FZD8 | FZD8, ANKRD30A | chr10:35973550-35974697 | 7.130961 | 609 |
| hs1589 | chr10:36072272-36074291 | FZD8 | FZD8, ANKRD30A | | | 428 |
| hs1082 | chr11:31816452-31818421 | PAX6 | PAX6 | | | 752 |
| hs1531 | chr11:31895594-31899062 | PAX6 | RCN1 | chr11:31895974-31898364 | 13.931647 | 732 |
| hs1122 | chr12:103345263-103346680 | ASCL1 | PAH, ASCL1 | | | 797 |
| hs1114 | chr12:103371347-103372610 | ASCL1 | ASCL1, C12orf42 | | | 801 |
| hs1540 | chr12:103405110-103408796 | ASCL1 | ASCL1, C12orf42 | chr12:103406141-103408491 | 13.128528 | 748 |
| hs998 | chr12:103406124-103408154 | ASCL1 | ASCL1, C12orf42 | chr12:103406141-103408491 | 13.128528 | 748 |
| hs967 | chr12:103484342-103485519 | ASCL1 | ASCL1, C12orf42 | | | 812 |
| hs1575 | chr12:103570982-103573398 | ASCL1 | ASCL1, C12orf42 | | | 639 |
| hs1571 | chr12:114101195-114103805 | LHX5 | LHX5, RBM19 | chr12:114096563-114102674 | 7.130961 | 620 |
| hs798 | chr12:16170590-16171824 | | DERA | | | 857 |
| hs1532 | chr12:17171711-17174776 | LMO3 | SKP1P2, RERGL | chr12:17172763-17174723 | 7.411117 | 689 |
| hs993 | chr12:17311784-17313759 | LMO3 | SKP1P2, RERGL | | | 808 |
| hs980 | chr12:17848111-17849347 | LMO3 | SKP1P2, RERGL | | | 823 |
| hs1574 | chr12:516066-518656 | | CCDC77 | | | 415 |
| hs1568 | chr13:28318579-28320134 | GSH1 | POLR1D, GSX1 | | | 783 |
| hs1127 | chr14:27553786-27555661 | FOXG1 | NOVA1, FOXG1 | | | 728 |
| hs1075 | chr14:28398563-28400621 | FOXG1 | NOVA1, FOXG1 | | | 733 |
| hs1064 | chr14:29226075-29227673 | FOXG1 | NOVA1, FOXG1 | | | 806 |
| hs1539 | chr14:29716885-29713340 | FOXG1 | C14orf23, PRKD1 | chr14:29711403-29713148 | 8.06735 | 806 |
| hs1168 | chr14:29743374-29745881 | FOXG1 | C14orf23, PRKD1 | | | 782 |
| hs1523 | chr14:29857930-29860548 | FOXG1 | C14orf23, PRKD1 | chr14:29858041-29863155 | 47.593761 | 915 |
| hs1193 | chr14:29894197-29895582 | FOXG1 | C14orf23, PRKD1 | | | 750 |
| hs1201 | chr14:29911320-29912514 | FOXG1 | C14orf23, PRKD1 | | | 770 |
| hs1062 | chr14:29960491-29962005 | FOXG1 | C14orf23, PRKD1 | | | 773 |
| hs984 | chr14:36907561-36909195 | TITF1 | DPPA3, SFTA3 | | | 877 |
| hs1538 | chr14:36911162-36914360 | TITF1 | DPPA3, SFTA3 | chr14:36911097-36914407 | 9.53908 | 832 |
| hs1166 | chr14:36973775-36974585 | TITF1 | SFTA3 | | | 810 |
| hs1151 | chr14:53833457-53836210 | BMP4 | DDHD1, BMP4 | | | 782 |
| hs1579 | chr14:57320664-57324319 | OTX2 | OTX2, EXOC5 | | | 696 |
| hs1150 | chr14:57419008-57421445 | OTX2 | OTX2, EXOC5 | chr14:57418860-57421589 | 7.130961 | 861 |
| hs1218 | chr14:57430887-57432346 | OTX2 | OTX2, EXOC5 | chr14:57430911-57432230 | 6.752707 | 865 |
| hs622 | chr14:99466200-99467144 | | C14orf177, BCL11B | | | 792 |
| hs1129 | chr15:37216993-37219601 | MEIS2 | MEIS2 | | | 869 |
| hs1178 | chr15:37347604-37349955 | MEIS2 | MEIS2 | | | 876 |
| hs1097 | chr15:37371729-37373137 | MEIS2 | MEIS2 | | | 849 |
| hs1053 | chr18:22139917-22141191 | ZNF521 | HRH4, ZNF521 | | | 817 |
| hs1169 | chr18:22235986-22237388 | ZNF521 | HRH4, ZNF521 | | | 769 |
| hs1180 | chr18:22616831-22618682 | ZNF521 | HRH4, ZNF521 | chr18:22617966-22620091 | 6.554722 | 814 |
| hs1104 | chr18:22657391-22658788 | ZNF521 | ZNF521 | | | 826 |
| hs1027 | chr18:22744668-22746270 | ZNF521 | ZNF521 | | | 801 |
| hs962 | chr18:22747316-22748975 | ZNF521 | ZNF521 | | | 874 |
| hs1088 | chr18:22769112-22770579 | ZNF521 | ZNF521 | | | 853 |
| hs1544 | chr18:23044107-23046853 | ZNF521 | ZNF521, SS18 | chr18:23043230-23046844 | 10.965025 | 662 |
| hs1138 | chr18:23283479-23284795 | ZNF521 | ZNF521, SS18 | chr18:23283556-23285743 | 8.293427 | 719 |
| hs1566 | chr18:23432723-23434825 | ZNF521 | ZNF521, SS18 | | | 760 |
| hs1013 | chr18:52699870-52701226 | TCF4 | CCDC68, TCF4 | | | 806 |
| hs1561 | chr18:52971887-52975873 | TCF4 | TCF4 | chr18:52972905-52974769 | 12.317114 | 778 |
| hs1537 | chr18:53018678-53020044 | TCF4 | TCF4 | chr18:53018171-53021014 | 12.317114 | 824 |
| hs1195 | chr18:75467090-75468311 | SALL3 | GALR1, SALL3 | | | 750 |
| hs1020 | chr18:75496338-75498507 | SALL3 | GALR1, SALL3 | | | 822 |
| hs1186 | chr18:75569573-75570862 | SALL3 | GALR1, SALL3 | | | 803 |
| hs1047 | chr18:76009581-76010891 | SALL3 | GALR1, SALL3 | | | 737 |
| hs1083 | chr18:76064036-76065306 | SALL3 | GALR1, SALL3 | | | 715 |
| hs1141 | chr18:76070697-76071834 | SALL3 | GALR1, SALL3 | | | 787 |
| hs1011 | chr18:76461276-76462723 | SALL3 | GALR1, SALL3 | | | 813 |
| hs1056 | chr18:76481722-76483257 | SALL3 | GALR1, SALL3 | | | 819 |
| hs1194 | chr18:76517730-76518836 | SALL3 | GALR1, SALL3 | | | 798 |
| hs1212 | chr2:103538361-103539868 | POU3F3 | TMEM182, LOC100287010 | | | 847 |

TABLE 5-continued

| | | | | | | |
|---|---|---|---|---|---|---|
| hs1125 | chr2:103548426-103549712 | POU3F3 | TMEM182, LOC100287010 | | | 808 |
| hs1581 | chr2:103768696-103772482 | POU3F3 | TMEM182, LOC100287010 | | | 507 |
| hs1093 | chr2:103792328-103793819 | POU3F3 | TMEM182, LOC100287010 | chr2:103790252-103794793 | 14.964228 | 807 |
| hs1112 | chr2:103909358-103911221 | POU3F3 | TMEM182, LOC100287010 | | | 799 |
| hs1555 | chr2:104016646-104019824 | POU3F3 | TMEM182, LOC100287010 | chr2:104017136-104019420 | 9.420391 | 758 |
| hs958 | chr2:104060734-104062561 | POU3F3 | TMEM182, LOC100287010 | | | 853 |
| hs977 | chr2:104063598-104065812 | POU3F3 | TMEM182, LOC100287016 | | | 758 |
| hs1147 | chr2:104285458-104286792 | POU3F3 | TMEM182, LOC100287010 | | | 783 |
| hs1526 | chr2:104353933-104357342 | POU3F3 | TMEM182, LOC100287010 | chr2:104354285-104357036 | 12.949564 | 635 |
| hs1126 | chr2:104576225-104577270 | POU3F3 | TMEM182, LOC100287010 | | | 822 |
| hs1529 | chr2:104578156-104580488 | POU3F3 | TMEM182, LOC100287010 | chr2:104578358-104581559 | 15.521493 | 656 |
| hs1140 | chr2:104648312-104650249 | POU3F3 | TMEM182, LOC100287010 | | | 767 |
| hs1554 | chr2:104686690-104688638 | POU3F3 | TMEM182, LOC100287010 | chr2:104687024-104688568 | 10.965025 | 670 |
| hs1131 | chr2:105032493-105034445 | POU3F3 | LOC100287010, POU3F3 | chr2:105031509-105034451 | 10.93367 | 806 |
| hs1534 | chr2:105044282-105047512 | POU3F3 | LOC100287010, POU3F3 | chr2:105045378-105048753 | 13.931647 | 747 |
| hs960 | chr2:105047627-105048798 | POU3F3 | LOC100287010, POU3F3 | chr2:105045378-105048753 | 13.931647 | 861 |
| hs1177 | chr2:105300344-105301657 | POU3F3 | LOC100287010, POU3F3 | | | 716 |
| hs969 | chr2:105317580-105319856 | POU3F3 | LOC100287010, POU3F3 | chr2:105317216-105320189 | 8.06735 | 831 |
| hs1121 | chr2:105452973-105454169 | POU3F3 | LOC100287010, POU3F3 | | | 764 |
| hs1553 | chr2:105464986-105467538 | POU3F3 | LOC100287010, POU3F3 | | | 780 |
| hs990 | chr2:105516737-105518490 | POU3F3 | AK095498, MRPS9 | | | 719 |
| hs953 | chr2:175203263-175204895 | FLJ46347 | SP9, CIR1 | | | 889 |
| hs1541 | chr2:211664571-211666475 | ERBB4 | CPS1, ERBB4 | chr2:211664330-211665926 | 8.600623 | 551 |
| hs1578 | chr2:212254840-212257158 | ERBB4 | ERBB4 | chr2:212254650-212259108 | 8.823664 | 665 |
| hs1207 | chr2:213141079-213142308 | ERBB4 | ERBB4 | | | 767 |
| hs921 | chr2:236962599-236964857 | | AGAP1 | | | 794 |
| hs1076 | chr2:58695819-58697323 | BCL11A | FANCL, BCL11A | | | 846 |
| hs1174 | chr2:58748340-58750140 | BCL11A | FANCL, BCL11A | | | 771 |
| hs1012 | chr2:58770304-58771290 | BCL11A | FANCL, BCL11A | | | 859 |
| hs1071 | chr2:58799729-58800607 | BCL11A | FANCL, BCL11A | | | 701 |
| hs1018 | chr2:58809796-58811611 | BCL11A | FANCL, BCL11A | | | 832 |
| hs1090 | chr2:58811475-58812905 | BCL11A | FANCL, BCL11A | | | 771 |
| hs1063 | chr2:58857680-58858956 | BCL11A | FANCL, BCL11A | | | 854 |
| hs1152 | chr2:58859997-58861674 | BCL11A | FANCL, BCL11A | | | 850 |
| hs1232 | chr2:58891096-58892548 | BCL11A | FANCL, BCL11A | | | 846 |
| hs1113 | chr2:58948607-58950015 | BCL11A | FANCL, BCL11A | | | 852 |
| hs1067 | chr2:58975738-58977115 | BCL11A | FANCL, BCL11A | | | 845 |
| hs1199 | chr2:59102071-59103380 | BCL11A | FANCL, BCL11A | | | 750 |
| hs1196 | chr2:59161996-59164461 | BCL11A | FANCL, BCL11A | | | 819 |
| hs1181 | chr2:59178992-59180242 | BCL11A | FANCL, BCL11A | | | 772 |
| hs1077 | chr2:59202276-59203399 | BCL11A | FANCL, BCL11A | | | 825 |
| hs1154 | chr2:59203217-59204548 | BCL11A | FANCL, BCL11A | | | 827 |
| hs1143 | chr2:59303870-59305029 | BCL11A | FANCL, BCL11A | | | 838 |
| hs975 | chr2:59304974-59306893 | BCL11A | FANCL, BCL11A | | | 873 |
| hs1119 | chr2:59476604-59477955 | BCL11A | FANCL, BCL11A | chr2:59476293-59477849 | 8.031059 | 778 |
| hs1057 | chr2:59888700-59891476 | BCL11A | FANCL, BCL11A | | | 833 |
| hs1209 | chr2:59894793-59896957 | BCL11A | FANCL, BCL11A | | | 785 |
| hs1204 | chr2:59896819-59898978 | BCL11A | FANCL, BCL11A | | | 779 |
| hs1021 | chr2:59998338-59999656 | BCL11A | FANCL, BCL11A | | | 805 |
| hs1164 | chr2:60005531-60007545 | BCL11A | FANCL, BCL11A | | | 791 |
| hs1072 | chr2:60055628-60056970 | BCL11A | FANCL, BCL11A | | | 842 |
| hs1120 | chr2:60223849-60225179 | BCL11A | FANCL, BCL11A | | | 788 |
| hs1535 | chr2:60498057-60502013 | BCL11A | FANCL, BCL11A | chr2:60500533-60503202 | 10.561487 | 768 |
| hs1111 | chr2:60516097-60518092 | BCL11A | FANCL, BCL11A | | | 839 |
| hs957 | chr2:60761404-60763073 | BCL11A | BCL11A | chr2:60760958-60762745 | 11.470763 | 904 |
| hs1176 | chr2:60794812-60796264 | BCL11A | BCL11A, PAPOLG | | | 782 |
| hs1142 | chr2:60855056-60856888 | BCL11A | BCL11A, PAPOLG | | | 844 |
| hs1066 | chr2:63275695-63277103 | OTX1 | EHBP1, OTX1 | | | 736 |
| hs1229 | chr2:66397542-66398943 | MEIS1 | SPRED2, MEIS1 | | | 830 |
| hs1110 | chr2:66510556-66511795 | MEIS1 | SPRED2, MEIS1 | | | 802 |
| hs1206 | chr2:66749539-66750931 | MEIS1 | MEIS1 | | | 864 |
| hs1210 | chr2:66762515-66765088 | MEIS1 | MEIS1 | chr2:66763070-66766365 | 13.091436 | 828 |
| hs1197 | chr2:66924703-66926115 | MEIS1 | MEIS1, ETAA1 | chr2:66921944-66924729 | 6.65441 | 841 |
| hs1584 | chr2:67414599-67416139 | MEIS1 | MEIS1, ETAA1 | | | 636 |
| hs1565 | chr2:67427102-67431497 | MEIS1 | MEIS1, ETAA1 | chr2:67427862-67429442 | 6.65441 | 714 |
| hs1025 | chr2:73124730-73126091 | EMX1 | SPR, EMX1 | chr2:73123532-73126312 | 9.504924 | 748 |
| hs1527 | chr2:8781394-8783591 | ID2 | RNF144A, ID2 | chr2:8781358-8783846 | 16.964485 | 644 |
| hs914 | chr20:21214790-21217232 | | PLK1S1 | chr20:21213336-21217052 | 10.93367 | 883 |
| hs1205 | chr20:21488551-21490021 | NKX2-2 | NKX2-4, NKX2-2 | | | 762 |
| hs632 | chr20:2719208-2719789 | | EBF4 | | | 750 |
| hs1042 | chr20:37876814-37877600 | MAFB | DHX35, MAFB | | | 771 |
| hs1237 | chr20:38580899-38582010 | MAFB | DHX35, MAFB | | | 681 |
| hs992 | chr20:38862746-38864025 | MAFB | DHX35, MAFB | | | 816 |
| hs1086 | chr20:39334182-39335059 | MAFB | MAFB, TOP1 | | | 815 |
| hs1234 | chr20:39347264-39348213 | MAFB | MAFB, TOP1 | | | 784 |
| hs1101 | chr20:39472648-39473702 | MAFB | MAFB, TOP1 | | | 747 |
| hs996 | chr20:39483347-39484593 | MAFB | MAFB, TOP1 | | | 767 |
| hs1548 | chr21:34221456-34223948 | OLIG2 | C21orf62, OLIG2 | chr21:34221397-34223878 | 10.40776 | 741 |
| hs1188 | chr21:34290782-34292115 | OLIG2 | C21orf62, OLIG2 | chr21:34289905-34293116 | 17.766947 | 802 |
| hs1559 | chr22:46240915-46242300 | WNT7B | ATXN10 | chr22:46237398-46242746 | 16.40776 | 486 |

TABLE 5-continued

| | | | | | | |
|---|---|---|---|---|---|---|
| hs1043 | chr3:147125146-147126336 | ZIC1 | ZIC4, ZIC1 | | | 795 |
| hs1173 | chr3:147378547-147380603 | ZIC1 | ZIC1, AGTR1 | | | 809 |
| hs1184 | chr3:147393021-147394349 | ZIC1 | ZIC1, AGTR1 | | | 805 |
| hs1573 | chr3:147563409-147566604 | ZIC1 | ZIC1, AGTR1 | | | 836 |
| hs1224 | chr3:147651676-147653436 | ZIC1 | ZIC1, AGTR1 | | | 779 |
| hs1038 | chr3:147748015-147749579 | ZIC1 | ZIC1, AGTR1 | | | 796 |
| hs1549 | chr3:147753310-147755618 | ZIC1 | ZIC1, AGTR1 | chr3:147753648-147754884 | 6.919402 | 784 |
| hs1203 | chr3:147802357-147803586 | ZIC1 | ZIC1, AGTR1 | chr3:147800794-147803205 | 17.766947 | 844 |
| hs1115 | chr3:148006499-148007810 | ZIC1 | ZIC1, AGTR1 | | | 790 |
| hs636 | chr3:157882303-157883963 | | RSRC1 | | | 920 |
| hs1712 | chr3:173448118-173452132 | | NLGN1 | | | 717 |
| hs192 | chr3:180773639-180775802 | | DNAJC19, SOX2 | chr3:180772860-180775028 | 7.293627 | 895 |
| hs1563 | chr3:193489359-193491333 | HES1 | OPA1, HES1 | chr3:193488976-193491260 | 6.65441 | 699 |
| hs1543 | chr3:193929360-193931457 | HES1 | HES1, CPN2 | chr3:193929132-193933564 | 10.965025 | 706 |
| hs1557 | chr3:28033828-28035751 | EOMES | AK297461, CMC1 | | | 824 |
| hs1214 | chr3:70701489-70702904 | FOXP1 | MITF, FOXP1 | | | 741 |
| hs1231 | chr3:71026229-71026764 | FOXP1 | FOXP1 | | | 810 |
| hs965 | chr3:71099157-71100851 | FOXP1 | FOXP1 | | | 931 |
| hs1092 | chr3:71153556-71155053 | FOXP1 | FOXP1 | | | 826 |
| hs1572 | chr3:71186391-71188583 | FOXP1 | FOXP1 | chr3:71185974-71188527 | 7.293627 | 759 |
| hs1160 | chr3:71253670-71255013 | FOXP1 | FOXP1 | | | 825 |
| hs187 | chr3:71290418-71292584 | FOXP1 | FOXP1 | chr3:71288860-71294549 | 9.53908 | 827 |
| hs1116 | chr3:71446827-71448809 | FOXP1 | FOXP1 | | | 784 |
| hs997 | chr3:71499477-71500970 | FOXP1 | FOXP1 | | | 843 |
| hs973 | chr3:71507469-71508874 | FOXP1 | FOXP1 | | | 844 |
| hs1149 | chr3:71573607-71574540 | FOXP1 | FOXP1 | | | 833 |
| hs1010 | chr3:71590897-71592786 | FOXP1 | FOXP1 | | | 818 |
| hs1545 | chr4:109254340-109257033 | LEF1 | LEF1, LOC285456 | chr4:109254524-109257107 | 11.768542 | 672 |
| hs1050 | chr4:109531908-109533465 | LEF1 | LOC285456 | | | 753 |
| hs981 | chr4:113442390-113443530 | NEUROG2 | NEUROG2, C4orf21 | | | 819 |
| hs1582 | chr4:124383428-124386454 | SPRY1 | SPRY1, ANKRD50 | | | 613 |
| hs1525 | chr4:124775814-124779530 | SPRY1 | SPRY1, ANKRD50 | chr4:124777645-124779158 | 17.215148 | 721 |
| hs840 | chr4:66989480-66990366 | | EPHA5, CENPC1 | chr4:66988731-66990409 | 8.293427 | 734 |
| hs1130 | chr5:157589029-157590477 | EBF1 | CLINT1, EBF1 | | | 832 |
| hs1208 | chr5:158017768-158019067 | EBF1 | CLINT1, EBF1 | | | 808 |
| hs1137 | chr5:158227696-158229500 | EBF1 | EBF1 | | | 814 |
| hs1022 | chr5:158486120-158487498 | EBF1 | EBF1 | | | 830 |
| hs1117 | chr5:158508842-158510137 | EBF1 | EBF1 | | | 809 |
| hs1123 | chr5:158517785-158518914 | EBF1 | EBF1 | | | 788 |
| hs1187 | chr5:50390899-50392257 | ISL1 | PARP8, ISL1 | chr5:50390582-50392463 | 8.06735 | 759 |
| hs853 | chr5:87083012-87084752 | | CCNH, TMEM161B | chr5:87082335-87085197 | 7.293627 | 825 |
| hs989 | chr5:90768370-90769843 | NR2F1 | ARRDC3, NR2F1 | | | 775 |
| hs982 | chr5:90785763-90787167 | NR2F1 | ARRDC3, NR2F1 | | | 812 |
| hs1227 | chr5:91271776-91272886 | NR2F1 | ARRDC3, NR2F1 | | | 765 |
| hs952 | chr5:91442456-91444549 | NR2F1 | ARRDC3, NR2F1 | | | 854 |
| hs1034 | chr5:91700124-91701467 | NR2F1 | ARRDC3, NR2F1 | | | 736 |
| hs1084 | chr5:91765018-91766129 | NR2F1 | ARRDC3, NR2F1 | | | 734 |
| hs1162 | chr5:91828131-91829295 | NR2F1 | ARRDC3, NR2F1 | | | 738 |
| hs1577 | chr5:91927845-91931024 | NR2F1 | ARRDC3, NR2F1 | | | 659 |
| hs1109 | chr5:91940922-91942042 | NR2F1 | ARRDC3, NR2F1 | | | 760 |
| hs971 | chr5:91970162-91972034 | NR2F1 | ARRDC3, NR2F1 | | | 862 |
| hs1039 | chr5:92031088-92033197 | NR2F1 | ARRDC3, NR2F1 | | | 803 |
| hs1155 | chr5:92035493-92036961 | NR2F1 | ARRDC3, NR2F1 | | | 813 |
| hs1079 | chr5:92141511-92143537 | NR2F1 | ARRDC3, NR2F1 | | | 841 |
| hs1153 | chr5:92219848-92221133 | NR2F1 | ARRDC3, NR2F1 | | | 764 |
| hs1024 | chr5:92312840-92314645 | NR2F1 | ARRDC3, NR2F1 | | | 879 |
| hs1049 | chr5:92314781-92316083 | NR2F1 | ARRDC3, NR2F1 | | | 837 |
| hs1146 | chr5:92426546-92428433 | NR2F1 | ARRDC3, NR2F1 | | | 803 |
| hs1560 | chr5:92476842-92479105 | NR2F1 | ARRDC3, NR2F1 | | | 657 |
| hs1170 | chr5:92526066-92527353 | NR2F1 | ARRDC3, NR2F1 | | | 806 |
| hs1222 | chr5:92536353-92537380 | NR2F1 | ARRDC3, NR2F1 | | | 724 |
| hs1060 | chr5:92613862-92616844 | NR2F1 | ARRDC3, NR2F1 | | | 853 |
| hs1172 | chr5:92634702-92636476 | NR2F1 | ARRDC3, NR2F1 | chr5:92634168-92637477 | 7.293627 | 787 |
| hs1550 | chr5:92741502-92744743 | NR2F1 | ARRDC3, NR2F1 | chr5:92742104-92745498 | 10.40776 | 813 |
| hs1033 | chr6:108435330-108436506 | NR2E1 | OSTM1, NR2E1 | | | 787 |
| hs1189 | chr6:108437243-108438452 | NR2E1 | OSTM1, NR2E1 | chr6:108437283-108443041 | 7.384363 | 778 |
| hs1052 | chr6:18536628-18538267 | ID4 | RNF144B, ID4 | chr6:18535962-18538169 | 8.834303 | 778 |
| hs1580 | chr6:18612650-18614840 | ID4 | RNF144B, ID4 | | | 688 |
| hs1094 | chr6:18662790-18664038 | ID4 | RNF144B, ID4 | chr6:18662926-18666129 | 12.949564 | 807 |
| hs1542 | chr6:19533421-19535679 | ID4 | RNF144B, ID4 | chr6:19532901-19535191 | 7.293627 | 541 |
| hs1533 | chr6:19719222-19722910 | ID4 | RNF144B, ID4 | chr6:19718442-19723115 | 11.470763 | 783 |
| hs1175 | chr6:19976157-19977513 | ID4 | ID4, MBOAT1 | chr6:19976077-19977874 | 13.550532 | 817 |
| hs1225 | chr6:41380559-41381515 | FOXP4 | NCR2, DQ141194 | | | 603 |
| hs1003 | chr6:41434455-41435695 | FOXP4 | NCR2, DQ141194 | | | 815 |
| hs1145 | chr6:41436815-41438024 | FOXP4 | NCR2, DQ141194 | | | 760 |
| hs1100 | chr6:41560717-41562075 | FOXP4 | FOXP4 | | | 809 |
| hs978 | chr6:97754043-97755513 | POU3F2 | MMS22L, POU3F2 | chr6:97754083-97755780 | 10.196738 | 811 |
| hs1564 | chr6:97912825-97915982 | POU3F2 | MMS22L, POU3F2 | chr6:97912601-97915206 | 10.965025 | 792 |
| hs1059 | chr6:97948958-97949898 | POU3F2 | MMS22L, POU3F2 | | | 776 |
| hs1035 | chr6:98074091-98075722 | POU3F2 | MMS22L, POU3F2 | | | 825 |

TABLE 5-continued

| | | | | | | |
|---|---|---|---|---|---|---|
| hs1220 | chr6:98212329-98214701 | POU3F2 | MMS22L, POU3F2 | | | 756 |
| hs1054 | chr6:98261649-98263117 | POU3F2 | MMS22L, POU3F2 | | | 792 |
| hs995 | chr6:98278782-98280694 | POU3F2 | MMS22L, POU3F2 | | | 810 |
| hs985 | chr6:98382462-98383929 | POU3F2 | MMS22L, POU3F2 | | | 821 |
| hs1233 | chr6:98504034-98506058 | POU3F2 | MMS22L, POU3F2 | | | 798 |
| hs1106 | chr6:98572398-98573780 | POU3F2 | MMS22L, POU3F2 | | | 764 |
| hs1128 | chr6:98829860-98831049 | POU3F2 | MMS22L, POU3F2 | | | 774 |
| hs1159 | chr6:98831075-98833042 | POU3F2 | MMS22L, POU3F2 | | | 778 |
| hs1081 | chr6:98902034-98904516 | POU3F2 | MMS22L, POU3F2 | | | 853 |
| hs1014 | chr6:99005894-99007499 | POU3F2 | MMS22L, POU3F2 | | | 842 |
| hs1085 | chr6:99089361-99091043 | POU3F2 | MMS22L, POU3F2 | chr6:99089365-99091231 | 10.196738 | 808 |
| hs1069 | chr7:114052100-114053403 | FOXP2 | FOXP2 | | | 800 |
| hs1167 | chr7:114055419-114056748 | FOXP2 | FOXP2 | | | 820 |
| hs999 | chr7:114142132-114143527 | FOXP2 | FOXP2 | | | 885 |
| hs1080 | chr7:114261073-114263089 | FOXP2 | FOXP2 | | | 875 |
| hs954 | chr7:114287987-114290557 | FOXP2 | FOXP2 | | | 905 |
| hs1215 | chr7:114292966-114293972 | FOXP2 | FOXP2 | | | 800 |
| hs956 | chr7:114299711-114302078 | FOXP2 | FOXP2 | | | 905 |
| hs966 | chr7:114326912-114329772 | FOXP2 | FOXP2 | | | 892 |
| hs1192 | chr7:114463797-114464462 | FOXP2 | FOXP2, MDFIC | | | 820 |
| hs1019 | chr7:20838843-20840395 | SP8 | SP8, SP4 | | | 785 |
| hs1007 | chr7:20997668-20999102 | SP8 | SP8, SP4 | chr7:20997062-20999329 | 6.752707 | 852 |
| hs1148 | chr7:21019551-21021200 | SP8 | SP8, SP4 | | | 813 |
| hs1226 | chr7:21080801-21082086 | SP8 | SP8, SP4 | chr7:21080455-21082857 | 8.06735 | 833 |
| hs1223 | chr7:21239775-21240922 | SP8 | SP8, SP4 | | | 714 |
| hs807 | chr7:22091362-22092557 | | CDCA7L, RAPGEF5 | | | 772 |
| hs1586 | chr7:42185602-42187508 | GLI3 | GLI3 | chr7:42185469-42187515 | 7.130961 | 689 |
| hs1213 | chr7:42252831-42254560 | GLI3 | GLI3 | | | 818 |
| hs1132 | chr7:42432266-42433365 | GLI3 | GLI3, C7orf25 | | | 678 |
| hs961 | chr7:50333048-50334464 | IKFZ1 | C7orf72, IKZF1 | | | 726 |
| hs972 | chr7:50357638-56358644 | IKFZ1 | IKZF1 | | | 823 |
| hs782 | chr8:21901089-21902326 | FGF17 | FGF17 | | | 612 |
| hs781 | chr8:21907426-21908282 | FGF17 | FGF17, EPB49 | | | 590 |
| hs1719 | chr8:32063683-32067187 | | WRN, NRG1 | | | 524 |
| hs1718 | chr8:33660674-33665591 | | DUSP26, UNC5D | chr8:33661561-33664104 | 24.108217 | 726 |
| hs1715 | chr8:33891203-33892738 | | DUSP26, UNC5D | | | 541 |
| hs631 | chr8:36957851-36958723 | | KCNU1, ZNF703 | | | 754 |
| hs1030 | chr9:128516934-128518372 | PBX3 | PBX3 | | | 838 |
| hs818 | chr9:128520992-128522653 | PBX3 | PBX3 | chr9:128519949-128522980 | 6.752707 | 881 |
| hs1102 | chr9:128522875-128525442 | PBX3 | PBX3 | chr9:128519949-128522980 | 6.752707 | 843 |
| hs983 | chr9:128525348-128527214 | PBX3 | PBX3 | | | 855 |
| hs1099 | chr9:128606519-128608350 | PBX3 | PBX3 | | | 839 |
| hs1095 | chr9:128640165-128641327 | PBX3 | PBX3 | | | 863 |
| hs1017 | chr9:128645462-128647097 | PBX3 | PBX3 | | | 887 |
| hs1000 | chr9:128666411-128667552 | PBX3 | PBX3 | | | 844 |
| hs1103 | chr9:128735158-128736174 | PBX3 | PBX3, FAM125B | | | 823 |
| hs987 | chr9:128869446-128870934 | PBX3 | PBX3, FAM125B | chr9:128869390-128871154 | 7.293627 | 876 |
| hs1015 | chr9:128919674-128920432 | PBX3 | PBX3, FAM125B | | | 773 |
| hs1108 | chr9:128945054-128946417 | PBX3 | PBX3, FAM125B | chr9:128944613-128946717 | 8.06735 | 827 |
| hs876 | chr9:133540555-133541228 | | PRDM12 | | | 763 |
| hs1530 | chr9:81010879-81014103 | | PSAT1, TLE4 | chr9:81011179-81014105 | 19.898262 | 771 |
| hs1585 | chr9:81052204-81055820 | | PSAT1, TLE4 | chr9:81051713-81055528 | 10.40776 | 800 |
| hs1041 | chr9:82010246-82011547 | TLE4 | PSAT1, TLE4 | chr9:82009683-82011502 | 12.708324 | 829 |
| hs1074 | chr9:82119097-82120855 | TLE4 | PSAT1, TLE4 | | | 802 |
| hs1078 | chr9:82224085-82226757 | TLE4 | TLE4 | | | 800 |
| hs1026 | chr9:82244801-82246758 | TLE4 | TLE4 | | | 826 |
| hs1183 | chr9:82266057-82267053 | TLE4 | TLE4 | | | 808 |
| hs1587 | chr9:82274254-82276353 | TLE4 | TLE4 | | | 606 |
| hs1163 | chr9:82590314-82593174 | TLE4 | TLE4, TLE1 | chr9:82589393-82592308 | 6.752707 | 807 |
| hs1004 | chr9:82681268-82682692 | TLE4 | TLE4, TLE1 | | | 833 |
| hs1211 | chr9:83122286-83123599 | TLE4 | TLE4, TLE1 | | | 810 |
| hs974 | chr9:83412700-83413972 | TLE4 | TLE4, TLE1 | | | 798 |
| hs1228 | chr9:83711693-83712782 | TLE4 | TLE4, TLE1 | | | 762 |
| hs1118 | chr9:84167351-84168176 | TLE4 | TLE4, TLE1 | | | 783 |
| hs1029 | chrX:82765974-82767821 | POU3F4 | POU3F4, CYLC1 | | | 727 |

| | | extremely conserved | Reproducible Enhancer Activity | | |
|---|---|---|---|---|---|
| ID | Tested Element (hg19) | (Visel et al 2008) | forebrain | other structures | Full annotation of activities |
| hs1156 | chr1:163359231-163360494 | yes | no | no | |
| hs1185 | chr1:163507965-163509139 | yes | no | yes | limb[4/6] |
| hs1230 | chr1:164197827-164199172 | yes | no | no | |
| hs1202 | chr1:164604141-164605474 | yes | yes | yes | hindbrain (rhombencephalon)[6/6] \| forebrain[4/6] |
| hs1235 | chr1:164620038-164621164 | yes | no | yes | hindbrain (rhombencephalon)[6/8] |
| hs1144 | chr1:164668592-164669823 | yes | no | yes | heart[5/12] |
| hs970 | chr1:164672787-164674206 | yes | no | no | |

TABLE 5-continued

| | | | | | |
|---|---|---|---|---|---|
| hs1136 | chr1:164700259-164701522 | yes | no | no | |
| hs1191 | chr1:164805507-164806794 | yes | yes | yes | forebrain[4/7] \| facial mesenchyme[3/7] |
| hs1714 | chr1:232753930-232757436 | yes | no | no | |
| hs1105 | chr1:38494689-38495688 | yes | no | no | |
| hs1124 | chr1:38627529-38629265 | yes | no | no | |
| hs1179 | chr1:38656780-38657626 | yes | no | no | |
| hs1001 | chr1:38712075-38713517 | yes | yes | yes | neural tube[9/11] \| hindbrain (rhombencephalon)[9/11] \| midbrain (mesencephalon)[10/11] \| forebrain [9/11] |
| hs1008 | chr1:38735942-38737376 | yes | no | no | |
| hs1098 | chr1:38791998-38793333 | yes | no | no | |
| hs1045 | chr1:38819171-38820577 | yes | no | no | |
| hs1546 | chr1:38835996-38838106 | yes | yes | yes | forebrain [4/5] |
| hs1031 | chr1:39192609-39194134 | yes | no | yes | nose[3/10] |
| hs1139 | chr1:39248757-39250129 | yes | no | yes | hindbrain (rhombencephalon)[5/5] |
| hs1134 | chr1:87803415-87805212 | yes | no | no | |
| hs174 | chr1:87821621-87823082 | yes | yes | yes | forebrain[9/12] \| limb[3/12] |
| hs1161 | chr1:88025863-88027203 | yes | yes | yes | forebrain[6/7] |
| hs1217 | chr1:88065041-88066530 | yes | no | yes | neural tube[5/8] |
| hs1002 | chr1:88108084-88109396 | yes | no | yes | heart[3/5] |
| hs1058 | chr1:88183654-88184961 | yes | no | no | |
| hs1055 | chr1:88402821-88404888 | yes | no | no | |
| hs1198 | chr1:88535719-88538390 | yes | no | yes | other[4/6] |
| hs1200 | chr1:88577535-88578821 | yes | no | no | |
| hs1135 | chr1:88595049-88596320 | yes | no | no | |
| hs1216 | chr1:88646698-88648145 | yes | no | no | |
| hs1107 | chr1:88686076-88687740 | yes | no | yes | dorsal root ganglion[5/6] |
| hs1068 | chr1:88841735-88843091 | yes | no | no | |
| hs988 | chr1:88875731-88877192 | yes | no | no | |
| hs1006 | chr10:102244842-102246334 | yes | yes | yes | hindbrain (rhombencephalon)[6/6] \| midbrain (mesencephalon)[6/6] \| forebrain[6/6] |
| hs841 | chr10:118854124-118855243 | yes | yes | yes | midbrain (mesencephalon)[3/8] \| forebrain[5/8] |
| hs1032 | chr10:119309200-119310544 | yes | yes | yes | midbrain (mesencephalon)[6/7] \| forebrain[6/7] |
| hs1221 | chr10:119313709-119314860 | yes | no | no | |
| hs1087 | chr10:119491936-119493137 | yes | no | no | |
| hs1236 | chr10:119589659-119591176 | yes | yes | yes | forebrain[3/3] \| limb[3/3] |
| hs1551 | chr10:119725799-119727161 | yes | no | yes | heart[3/7] |
| hs672 | chr10:120074039-120075696 | no | yes | yes | midbrain (mesencephalon)[4/5] \| forebrain[4/5] |
| hs1005 | chr10:124902927-124904638 | yes | no | no | |
| hs1588 | chr10:35925382-35927242 | yes | yes | yes | forebrain[5/6] |
| hs1567 | chr10:35972892-35975932 | no | no | yes | hindbrain (rhombencephalon)[6/8] \| limb[8/8] \| branchial arch[3/8] \| genital tubercle[4/8] |
| hs1589 | chr10:36072272-36074291 | no | no | yes | cranial nerve[4/8] |
| hs1082 | chr11:31816452-31818421 | yes | no | yes | neural tube[10/14] \| hindbrain (rhombencephalon)[14/14] |
| hs1531 | chr11:31895594-31899062 | yes | yes | yes | neural tube[8/8] \| midbrain (mesencephalon)[3/8] \| forebrain[4/8] |
| hs1122 | chr12:103345263-103346680 | yes | no | yes | eye[6/7] |
| hs1114 | chr12:103371347-103372610 | yes | no | yes | neural tube[4/6] \| hindbrain (rhombencephalon)[6/6] \| midbrain (mesencephalon)[6/6] |
| hs1540 | chr12:103405110-103408796 | yes | yes | yes | midbrain (mesencephalon)[5/4] \| forebrain[4/4] |
| hs998 | chr12:103406124-103408154 | yes | yes | yes | hindbrain (rhombencephalon)[7/8] \| midbrain (mesencephalon)[8/8] \| forebrain[7/8] \| nose[4/8] |
| hs967 | chr12:103484342-103485519 | yes | yes | yes | forebrain[4/4] |
| hs1575 | chr12:103570982-103573398 | yes | no | yes | midbrain (mesencephalon)[4/7] |
| hs1571 | chr12:114101195-114103805 | yes | yes | yes | midbrain (mesencephalon)[5/5] \| forebrain[4/5] |
| hs798 | chr12:16170590-16171824 | yes | yes | yes | neural tube[8/9] \| forebrain[9/9] |
| hs1532 | chr12:17171711-17174776 | yes | yes | yes | forebrain[11/11] \| eye[8/11] |
| hs993 | chr12:17311784-17313759 | yes | no | yes | hindbrain (rhombencephalon)[3/7] |
| hs980 | chr12:17848111-17849347 | yes | no | yes | hindbrain (rhombencephalon)[4/5] \| midbrain (mesencephalon)[4/5] |
| hs1574 | chr12:516066-518656 | no | yes | yes | neural tube[6/6] \| hindbrain (rhombencephalon)[4/6] \| midbrain (mesencephalon)[5/6] \| forebrain[5/6] |
| hs1568 | chr13:28318579-28320134 | no | yes | yes | hindbrain (rhombencephalon)[4/5] \| forebrain[3/5] |
| hs1127 | chr14:27553786-27555661 | yes | no | no | |
| hs1075 | chr14:28398563-28400621 | yes | no | no | |
| hs1064 | chr14:29226075-29227673 | yes | yes | yes | hindbrain (rhombencephalon)[3/5] \| forebrain[3/5] |
| hs1539 | chr14:29716885-29713340 | yes | no | yes | hindbrain (rhombencephalon)[4/5] |

TABLE 5-continued

| | | | | | |
|---|---|---|---|---|---|
| hs1168 | chr14:29743374-29745881 | yes | no | yes | hindbrain (rhombencephalon)[3/8] \| cranial nerve[8/8] \| facial mesenchyme[7/8] |
| hs1523 | chr14:29857930-29860548 | no | yes | yes | midbrain (mesencephalon)[11/13] \| forebrain[12/13] |
| hs1193 | chr14:29894197-29895582 | yes | no | no | |
| hs1201 | chr14:29911320-29912514 | yes | no | no | |
| hs1062 | chr14:29960491-29962005 | yes | no | no | |
| hs984 | chr14:36907561-36909195 | yes | no | no | |
| hs1538 | chr14:36911162-36914360 | yes | yes | yes | forebrain[4/4] |
| hs1166 | chr14:36973775-36974585 | yes | yes | yes | forebrain[6/6] |
| hs1151 | chr14:53833457-53836210 | yes | no | yes | limb[8/8] \| heart[3/8] |
| hs1579 | chr14:57320664-57324319 | yes | yes | yes | forebrain[4/6] |
| hs1150 | chr14:57419008-57421445 | yes | no | yes | eye[8/9] |
| hs1218 | chr14:57430887-57432346 | yes | no | yes | midbrain (mesencephalon)[7/7] |
| hs622 | chr14:99466200-99467144 | yes | yes | yes | forebrain[5/9] |
| hs1129 | chr15:37216993-37219601 | yes | no | no | |
| hs1178 | chr15:37347604-37349955 | yes | no | no | |
| hs1097 | chr15:37371729-37373137 | yes | no | no | |
| hs1053 | chr18:22139917-22141191 | yes | no | no | |
| hs1169 | chr18:22235986-22237388 | yes | yes | yes | midbrain (mesencephalon)[7/8] \| forebrain[5/8] \| trigeminal V (ganglion,cranial)[4/8] |
| hs1180 | chr18:22616831-22618682 | yes | no | yes | midbrain (mesencephalon)[5/6] |
| hs1104 | chr18:22657391-22658788 | yes | no | no | |
| hs1027 | chr18:22744668-22746270 | yes | yes | yes | hindbrain (rhombencephalon)[4/9] \| forebrain[5/9] |
| hs962 | chr18:21747316-22748975 | yes | no | no | |
| hs1088 | chr18:22769112-22770579 | yes | no | no | |
| hs1544 | chr18:23044107-23046853 | yes | yes | yes | hindbrain (rhombencephalon)[5/5] \| midbrain (mesencephalon)[5/5] \| forebrain[4/5] |
| hs1138 | chr18:23283479-23284795 | yes | no | no | |
| hs1566 | chr18:23432723-23434825 | yes | yes | yes | forebrain[4/5] |
| hs1013 | chr18:52699870-52701226 | yes | yes | yes | forebrain[4/6] |
| hs1561 | chr18:52971887-52975873 | yes | no | no | |
| hs1537 | chr18:53018678-53020044 | no | yes | yes | forebrain[5/6] |
| hs1195 | chr18:75467090-75468311 | yes | no | no | |
| hs1020 | chr18:75496338-75498507 | yes | no | yes | neural tube[4/9] \| hindbrain (rhombencephalon)[8/9] |
| hs1186 | chr18:75569573-75570862 | yes | no | yes | neural tube[5/7] \| hindbrain (rhombencephalon)[5/7] |
| hs1047 | chr18:76009581-76010891 | yes | no | no | |
| hs1083 | chr18:76064036-76065306 | yes | no | no | |
| hs1141 | chr18:76070697-76071834 | yes | no | no | |
| hs1011 | chr18:76461276-76462723 | yes | yes | yes | forebrain[5/7] |
| hs1056 | chr18:76481722-76483257 | yes | yes | yes | neural tube[5/8] \| midbrain (mesencephalon)[5/8] \| forebrain[7/8] |
| hs1194 | chr18:76517730-76518836 | yes | no | no | |
| hs1212 | chr2:103538361-103539868 | yes | no | yes | heart[4/6] |
| hs1125 | chr2:103548426-103549712 | yes | no | no | |
| hs1581 | chr2:103768696-103772482 | no | no | yes | eye [7/8] |
| hs1093 | chr2:103792328-103793819 | yes | no | yes | midbrain (mesencephalon)[9/9] |
| hs1112 | chr2:103909358-103911221 | yes | yes | yes | hindbrain (rhombencephalon)[10/12] \| midbrain (mesencephalon)[12/12] \| forebrain[12/12] \| limb[12/12] \| branchial arch[12/12] \| other[11/12] |
| hs1555 | chr2:104016646-104019824 | yes | no | yes | neural tube[4/5] \| hindbrain (rhombencephalon)[4/5] \| midbrain (mesencephalon)[4/5] \| liver[3/5] |
| hs958 | chr2:104060734-104062561 | yes | no | no | |
| hs977 | chr2:104063598-104065812 | yes | no | no | |
| hs1147 | chr2:104285458-104286792 | yes | no | yes | dorsal root ganglion[6/7] \| trigeminal V (ganglion, cranial)[4/7] \| cranial nerve[6/7] |
| hs1526 | chr2:104353933-104357342 | yes | yes | yes | forebrain[8/8] |
| hs1126 | chr2:104576225-104577270 | yes | no | no | |
| hs1529 | chr2:104578156-104580488 | yes | yes | yes | forebrain[4/4] |
| hs1140 | chr2:104648312-104650249 | yes | no | no | |
| hs1554 | chr2:104686690-104688638 | yes | no | yes | branchial arch[5/13] |
| hs1131 | chr2:105032493-105034445 | yes | yes | yes | midbrain (mesencephalon)[3/8] \| forebrain[5/8] |
| hs1534 | chr2:105044282-105047512 | yes | yes | yes | hindbrain (rhombencephalon)[7/7] \| midbrain (mesencephalon)[7/7] \| forebrain[7/7] |
| hs960 | chr2:105047627-105048798 | yes | no | no | |
| hs1177 | chr2:105300344-105301657 | yes | no | yes | heart[3/10] |
| hs969 | chr2:105317580-105319856 | yes | yes | yes | forebrain[9/9] |
| hs1121 | chr2:105452973-105454169 | yes | no | no | |
| hs1553 | chr2:105464986-105467538 | yes | yes | yes | neural tube[5/6] \| midbrain (mesencephalon)[5/6] \| forebrain[5/6] |

TABLE 5-continued

| | | | | | |
|---|---|---|---|---|---|
| hs990 | chr2:105516737-105518490 | yes | no | yes | hindbrain (rhombencephalon)[6/11] \| other[4/11] |
| hs953 | chr2:175203263-175204895 | yes | yes | yes | neural tube[13/13] \| hindbrain (rhombencephalon)[11/13] \| forebrain[10/13] |
| hs1541 | chr2:211664571-211666475 | no | no | no | |
| hs1578 | chr2:212254840-212257158 | yes | yes | yes | hindbrain (rhombencephalon)[4/5] \| midbrain (mesencephalon)[4/5] \| forebrain[4/5] |
| hs1207 | chr2:213141079-213142308 | yes | no | no | |
| hs921 | chr2:236962599-236964857 | yes | yes | yes | forebrain[6/7] \| limb[4/7] \| branchial arch[5/7] |
| hs1076 | chr2:58695819-58697323 | yes | no | no | |
| hs1174 | chr2:58748340-58750140 | yes | no | yes | dorsal root ganglion[6/6] |
| hs1012 | chr2:58770304-58771290 | yes | no | no | |
| hs1071 | chr2:58799729-58800607 | yes | no | yes | ear[4/10] |
| hs1018 | chr2:58809796-58811611 | yes | no | no | |
| hs1090 | chr2:58811475-58812905 | yes | no | no | |
| hs1063 | chr2:58857680-58858956 | yes | no | no | |
| hs1152 | chr2:58859997-58861674 | yes | no | yes | limb[4/5] |
| hs1232 | chr2:58891096-58892548 | yes | no | no | |
| hs1113 | chr2:58948607-58950015 | yes | no | no | |
| hs1067 | chr2:58975738-58977115 | yes | no | yes | dorsal root ganglion[3/7] \| limb[5/7] |
| hs1199 | chr2:59102071-59103380 | yes | no | yes | other[3/6] |
| hs1196 | chr2:59161996-59164461 | yes | no | no | |
| hs1181 | chr2:59178992-59180242 | yes | no | yes | heart[3/8] |
| hs1077 | chr2:59202276-59203399 | yes | no | no | |
| hs1154 | chr2:59203217-59204548 | yes | no | no | |
| hs1143 | chr2:59303870-59305029 | yes | no | no | |
| hs975 | chr2:59304974-59306893 | yes | no | yes | midbrain (mesencephalon)[4/7] |
| hs1119 | chr2:59476604-59477955 | yes | no | yes | neural tube[6/6] \| hindbrain (rhombencephalon)[5/6] |
| hs1057 | chr2:59888700-59891476 | yes | no | no | |
| hs1209 | chr2:59894793-59896957 | yes | no | no | |
| hs1204 | chr2:59896819-59898978 | yes | no | no | |
| hs1021 | chr2:59998338-59999656 | yes | no | no | |
| hs1164 | chr2:60005531-60007545 | yes | no | no | |
| hs1072 | chr2:60055628-60056970 | yes | no | no | |
| hs1120 | chr2:60223849-60225179 | yes | no | no | |
| hs1535 | chr2:60498057-60502013 | yes | no | yes | hindbrain (rhombencephalon)[4/5] |
| hs1111 | chr2:60516097-60518092 | yes | no | no | |
| hs957 | chr2:60761404-60763073 | yes | yes | yes | forebrain[4/4] |
| hs1176 | chr2:60794812-60796264 | yes | no | no | |
| hs1142 | chr2:60855056-60856888 | yes | no | yes | hindbrain (rhombencephalon)[3/3] |
| hs1066 | chr2:63275695-63277103 | yes | yes | yes | hindbrain (rhombencephalon)[5/5] \| midbrain (mesencephalon)[5/5] \| forebrain[5/5] |
| hs1229 | chr2:66397542-66398943 | yes | no | no | |
| hs1110 | chr2:66510556-66511795 | yes | no | no | |
| hs1206 | chr2:66749539-66750931 | yes | no | no | |
| hs1210 | chr2:66762515-66765088 | yes | yes | yes | forebrain[4/5] |
| hs1197 | chr2:66924703-66926115 | yes | no | no | |
| hs1584 | chr2:67414599-67416139 | no | no | no | |
| hs1565 | chr2:67427102-67431497 | yes | no | no | |
| hs1025 | chr2:73124730-73126091 | yes | yes | yes | forebrain[7/8] |
| hs1527 | chr2:8781394-8783591 | yes | yes | yes | neural tube[7/10] \| hindbrain (rhombencephalon)[7/10] \| midbrain (mesencephalon)[7/10] \| forebrain[7/10] |
| hs914 | chr20:21214790-21217232 | no | yes | yes | forebrain[9/10] |
| hs1205 | chr20:21488551-21490021 | yes | no | yes | hindbrain (rhombencephalon)[6/8] \| midbrain (mesencephalon)[4/8] |
| hs632 | chr20:2719208-2719789 | yes | yes | yes | neural tube[5/9] \| hindbrain (rhombencephalon)[5/9] \| midbrain (mesencephalon)[5/9] \| forebrain[5/9] |
| hs1042 | chr20:37876814-37877600 | yes | no | yes | neural tube[5/7] |
| hs1237 | chr20:38580899-38582010 | yes | no | no | |
| hs992 | chr20:38862746-38864025 | yes | no | no | |
| hs1086 | chr20:39334182-39335059 | yes | no | yes | hindbrain (rhombencephalon)[5/8] |
| hs1234 | chr20:39347264-39348213 | yes | no | no | |
| hs1101 | chr20:39472648-39473702 | yes | no | no | |
| hs996 | chr20:39483347-39484593 | yes | no | no | |
| hs1548 | chr21:34221456-34223948 | yes | yes | yes | forebrain[6/6] |
| hs1188 | chr21:34290782-34292115 | yes | yes | yes | neural tube[3/3] \| hindbrain (rhombencephalon)[3/3] \| midbrain (mesencephalon)[3/3] \| forebrain[3/3] |
| hs1559 | chr22:46240915-46242300 | no | yes | yes | neural tube[13/14] \| forebrain[13/14] |
| hs1043 | chr3:147125146-147126336 | yes | no | yes | neural tube[9/10] \| hindbrain (rhombencephalon)[9/10] |
| hs1173 | chr3:147378547-147380603 | yes | no | yes | neural tube[7/7] \| hindbrain (rhombencephalon)[7/7] |

TABLE 5-continued

| | | | | | |
|---|---|---|---|---|---|
| hs1184 | chr3:147393021-147394349 | yes | no | no | |
| hs1573 | chr3:147563409-147566604 | yes | yes | yes | hindbrain (rhombencephalon)[6/9] \| midbrain (mesencephalon)[6/9] \| forebrain[9/9] |
| hs1224 | chr3:147651676-147653436 | yes | yes | yes | forebrain[5/10] |
| hs1038 | chr3:147748015-147749579 | yes | no | no | |
| hs1549 | chr3:147753310-147755618 | no | no | no | |
| hs1203 | chr3:147802357-147803586 | yes | no | yes | neural tube[5/7] \| hindbrain (rhombencephalon)[5/7] |
| hs1115 | chr3:148006499-148007810 | yes | no | yes | midbrain (mesencephalon)[5/7] |
| hs636 | chr3:157882303-157883963 | yes | yes | yes | forebrain[7/11] \| limb[4/11] |
| hs1712 | chr3:173448118-173452132 | yes | no | no | |
| hs192 | chr3:180773639-180775802 | yes | yes | yes | forebrain[6/8] |
| hs1563 | chr3:193489359-193491333 | yes | yes | yes | midbrain (mesencephalon)[5/5] \| forebrain[5/5] |
| hs1543 | chr3:193929360-193931457 | no | yes | yes | neural tube[10/11] \| hindbrain (rhombencephalon)[11/11] \| midbrain (mesencephalon)[10/11] \| forebrain[10/11] |
| hs1557 | chr3:28033828-28035751 | yes | yes | yes | hindbrain (rhombencephalon)[8/8] \| midbrain (mesencephalon)[8/8] \| dorsal root ganglion[6/8] \| forebrain[8/8] \| trigeminal V (ganglion, cranial)[8/8] |
| hs1214 | chr3:70701489-70702904 | yes | no | no | |
| hs1231 | chr3:71026229-71026764 | yes | no | no | |
| hs965 | chr3:71099157-71100851 | yes | no | yes | limb[5/7] \| other[6/7] |
| hs1092 | chr3:71153556-71155053 | yes | yes | yes | forebrain[4/5] |
| hs1572 | chr3:71186391-71188583 | yes | no | no | |
| hs1160 | chr3:71253670-71255013 | yes | no | no | |
| hs187 | chr3:71290418-71292584 | yes | yes | yes | forebrain[8/9] |
| hs1116 | chr3:71446827-71448809 | yes | no | yes | facial mesenchyme[4/7] |
| hs997 | chr3:71499477-71500970 | yes | no | no | |
| hs973 | chr3:71507469-71508874 | yes | no | no | |
| hs1149 | chr3:71573607-71574540 | yes | no | yes | neural tube[5/10] |
| hs1010 | chr3:71590897-71592786 | yes | no | no | |
| hs1545 | chr4:109254340-109257033 | no | yes | yes | midbrain (mesencephalon)[8/8] \| forebrain[8/8] |
| hs1050 | chr4:109531908-109533465 | yes | yes | yes | forebrain[4/5] \| other[3/5] |
| hs981 | chr4:113442390-113443530 | yes | yes | yes | hindbrain (rhombencephalon)[5/6] \| midbrain (mesencephalon)[5/6] \| forebrain[5/6] |
| hs1582 | chr4:124383428-124386454 | no | no | yes | hindbrain (rhombencephalon)[6/8] \| midbrain (mesencephalon)[6/8] \| facial mesenchyme[4/8] |
| hs1525 | chr4:124775814-124779530 | no | no | yes | limb[5/10] \| heart[6/10] |
| hs840 | chr4:66989480-66990366 | yes | yes | yes | forebrain[10/10] |
| hs1130 | chr5:157589029-157590477 | yes | no | yes | limb[6/10] |
| hs1208 | chr5:158017768-158019067 | yes | no | yes | limb[9/10] \| branchial arch[9/10] |
| hs1137 | chr5:158227696-158229500 | yes | no | no | |
| hs1022 | chr5:158486120-158487498 | yes | yes | yes | neural tube[10/11] \| hindbrain (rhombencephalon)[10/11] \| midbrain (mesencephalon)[9/11] \| dorsal root ganglion[8/11] \| forebrain[6/11] \| trigeminal V (ganglion, cranial)[10/11] \| cranial nerve[9/11] |
| hs1117 | chr5:158508842-158510137 | yes | yes | yes | neural tube[7/8] \| hindbrain (rhombencephalon)[7/8] \| forebrain[7/8] |
| hs1123 | chr5:158517785-158518914 | yes | no | yes | cranial nerve[5/9] |
| hs1187 | chr5:50390899-50392257 | yes | yes | yes | hindbrain (rhombencephalon)[5/7] \| forebrain[7/7] \| eye[5/7] |
| hs853 | chr5:87083012-87084752 | yes | yes | yes | forebrain[7/7] |
| hs989 | chr5:90768370-90769843 | yes | no | no | |
| hs982 | chr5:90785763-90787167 | yes | no | no | |
| hs1227 | chr5:91271776-91272886 | yes | no | yes | midbrain (mesencephalon)[4/] |
| hs952 | chr5:91442456-91444549 | yes | yes | yes | neural tube[11/12] \| hindbrain (rhombencephalon)[9/12] \| midbrain (mesencephalon)[12/12] \| dorsal root ganglion[12/12] \| forebrain[9/12] \| eye[12/12] \| trigeminal V (ganglion, cranial)[11/12] \| facial mesenchyme[2/12] |
| hs1034 | chr5:91700124-91701467 | yes | no | no | |
| hs1084 | chr5:91765018-91766129 | yes | no | no | |
| hs1162 | chr5:91828131-91829295 | yes | no | no | |
| hs1577 | chr5:91927845-91931024 | yes | yes | yes | midbrain (mesencephalon)[6/11] \| forebrain[10/11] |
| hs1109 | chr5:91940922-91942042 | yes | no | yes | limb[10/11] |
| hs971 | chr5:91970162-91972034 | yes | yes | yes | neural tube[6/8] \| forebrain[6/8] \| cranial nerve[6/8] |
| hs1039 | chr5:92031088-92033197 | yes | no | yes | limb[3/7] \| cranial nerve[7/7] |

TABLE 5-continued

| | | | | | |
|---|---|---|---|---|---|
| hs1155 | chr5:92035493-92036961 | yes | no | no | |
| hs1079 | chr5:92141511-92143537 | yes | no | yes | neural tube[6/9] | hindbrain (rhombencephalon)[7/9] | midbrain (mesencephalon)[7/9] |
| hs1153 | chr5:92219848-92221133 | yes | no | yes | branchial arch[3/10] | eye[7/10] |
| hs1024 | chr5:92312840-92314645 | yes | yes | yes | forebrain[8/9] |
| hs1049 | chr5:92314781-92316083 | yes | no | yes | other[7/8] |
| hs1146 | chr5:92426546-92428433 | yes | no | no | |
| hs1560 | chr5:92476842-92479105 | yes | no | no | |
| hs1170 | chr5:92526066-92527353 | yes | no | yes | eye[8/8] |
| hs1222 | chr5:92536353-92537380 | yes | no | no | |
| hs1060 | chr5:92613862-92616844 | yes | yes | yes | hindbrain (rhombencephalon)[6/14] | forebrain[10/14] |
| hs1172 | chr5:92634702-92636476 | yes | yes | yes | forebrain[9/11] | eye[9/11] |
| hs1550 | chr5:92741502-92744743 | yes | no | no | |
| hs1033 | chr6:108435330-108436506 | yes | no | no | |
| hs1189 | chr6:108437243-108438452 | yes | no | no | |
| hs1052 | chr6:18536628-18538267 | yes | yes | yes | forebrain[7/13] | branchial arch[7/13] | cranial nerve[9/13] | other[8/13] |
| hs1580 | chr6:18612650-18614840 | no | no | no | |
| hs1094 | chr6:18662790-18664038 | yes | no | no | |
| hs1542 | chr6:19533421-19535679 | no | no | no | |
| hs1533 | chr6:19719222-19722910 | yes | yes | yes | midbrain (mesencephalon)[5/7] | forebrain[6/7] | eye[5/7] |
| hs1175 | chr6:19976157-19977513 | yes | yes | yes | forebrain[4/8] | nose[7/8] |
| hs1225 | chr6:41380559-41381515 | yes | no | no | |
| hs1003 | chr6:41434455-41435695 | yes | no | no | |
| hs1145 | chr6:41436815-41438024 | yes | no | no | |
| hs1100 | chr6:41560717-41562075 | yes | yes | yes | hindbrain (rhombencephalon)[7/8] | midbrain (mesencephalon)[8/8] | forebrain[7/8] | other[6/8] |
| hs978 | chr6:97754043-97755513 | yes | yes | yes | forebrain[3/4] |
| hs1564 | chr6:97912825-97915982 | no | yes | yes | forebrain[6/7] | other[3/7] |
| hs1059 | chr6:97948958-97949898 | yes | no | no | |
| hs1035 | chr6:98074091-98075722 | yes | yes | yes | forebrain[8/8] | limb[3/8] |
| hs1220 | chr6:98212329-98214701 | yes | no | yes | branchial arch[4/5] |
| hs1054 | chr6:98261649-98263117 | yes | no | no | |
| hs995 | chr6:98278782-98280694 | yes | no | no | |
| hs985 | chr6:98382462-98383929 | yes | no | no | |
| hs1233 | chr6:98504034-98506058 | yes | no | yes | neural tube[3/4] | other[4/4] |
| hs1106 | chr6:98572398-98573780 | yes | no | no | |
| hs128 | chr6:98829860-98831049 | yes | yes | yes | forebrain[4/6] |
| hs1159 | chr6:98831075-98833042 | yes | no | no | |
| hs1081 | chr6:98902034-98904516 | yes | no | yes | hindbrain (rhombencephalon)[6/9] |
| hs1014 | chr6:99005894-99007499 | yes | no | no | |
| hs1085 | chr6:99089361-99091043 | yes | yes | yes | neural tube[7/9] | midbrain (mesencephalon)[5/9] | forebrain[7/9] |
| hs1069 | chr7:114052100-114053403 | yes | no | no | |
| hs1167 | chr7:114055419-114056748 | yes | no | no | |
| hs999 | chr7:114142132-114143527 | yes | no | yes | midbrain (mesencephalon)[4/6] | facial mesenchyme[4/6] |
| hs1080 | chr7:114261073-114263089 | yes | no | yes | ear[3/5] |
| hs954 | chr7:114287987-114290557 | yes | no | no | |
| hs1215 | chr7:114292966-114293972 | yes | no | no | |
| hs956 | chr7:114299711-114302078 | yes | yes | yes | midbrain (mesencephalon)[3/7] | forebrain[6/7] |
| hs966 | chr7:114326912-114329772 | yes | no | yes | hindbrain (rhombencephalon)[6/11] |
| hs1192 | chr7:114463797-114464462 | yes | no | yes | hindbrain (rhombencephalon)[5/5] | midbrain (mesencephalon)[3/5] |
| hs1019 | chr7:20838843-20840395 | yes | yes | yes | forebrain[4/6] |
| hs1007 | chr7:20997668-20999102 | yes | yes | yes | forebrain[3/3] | facial mesenchyme[3/3] |
| hs1148 | chr7:21019551-21021200 | yes | no | yes | limb[4/4] |
| hs1226 | chr7:21080801-21082086 | yes | yes | yes | neural tube[12/16] | hindbrain (rhombencephalon)[12/16] | midbrain (mesencephalon)[13/16] | forebrain[14/16] | eye[12/16] | cranial nerve[10/16] |
| hs1223 | chr7:21239775-21240922 | yes | no | no | |
| hs807 | chr7:22091362-22092557 | no | yes | yes | forebrain[8/9] |
| hs1586 | chr7:42185602-42187508 | yes | no | yes | limb[3/3] |
| hs1213 | chr7:42252831-42254560 | yes | yes | yes | hindbrain (rhombencephalon)[5/6] | midbrain (mesencephalon)[5/6] | forebrain[3/6] |
| hs1132 | chr7:42432266-42433365 | yes | no | no | |
| hs961 | chr7:50333048-50334464 | yes | no | no | |
| hs972 | chr7:50357638-56358644 | yes | no | no | |
| hs782 | chr8:21901089-21902326 | yes | yes | yes | hindbrain (rhombencephalon)[10/13] | midbrain (mesencephalon)[10/13] | forebrain[9/13] | tail[6/13] |
| hs781 | chr8:21907426-21908282 | no | yes | yes | forebrain[10/12] |

TABLE 5-continued

| | | | | | |
|---|---|---|---|---|---|
| hs1719 | chr8:32063683-32067187 | no | no | no | |
| hs1718 | chr8:33660674-33665591 | yes | no | no | |
| hs1715 | chr8:33891203-33892738 | no | no | yes | neural tube[4/6] \| dorsal root ganglion[6/6] \| trigeminal V (ganglion, cranial)[6/6] \| cranial nerve[6/6] |
| hs631 | chr8:36957851-36958723 | yes | yes | yes | forebrain[6/7] \| cranial nerve[7/7] |
| hs1030 | chr9:128516934-128518372 | yes | no | yes | hindbrain (rhombencephalon)[6/7] \| midbrain (mesencephalon)[6/7] |
| hs818 | chr9:128520992-128522653 | yes | yes | yes | forebrain[6/6] |
| hs1102 | chr9:128522875-128525442 | yes | no | yes | branchial arch[3/7] |
| hs983 | chr9:128525348-128527214 | yes | no | no | |
| hs1099 | chr9:128606519-128608350 | yes | no | no | |
| hs1095 | chr9:128640165-128641327 | yes | no | no | |
| hs1017 | chr9:128645462-128647097 | yes | yes | yes | forebrain[7/9] |
| hs1000 | chr9:128666411-128667552 | yes | no | no | |
| hs1103 | chr9:128735158-128736174 | yes | no | no | |
| hs987 | chr9:128869446-128870934 | yes | yes | yes | forebrain[4/5] |
| hs1015 | chr9:128919674-128920432 | yes | no | yes | midbrain (mesencephalon)[4/7] |
| hs1108 | chr9:128945054-128946417 | yes | no | no | |
| hs876 | chr9:133540555-133541228 | yes | yes | yes | neural tube[7/11] \| hindbrain (rhombencephalon)[7/11] \| midbrain (mesencephalon)[7/11] \| forebrain[7/11] |
| hs1530 | chr9:81010879-81014103 | yes | yes | yes | forebrain[3/3] \| limb[3/3] |
| hs1585 | chr9:81052204-81055820 | yes | yes | yes | neural tube[3/4] \| hindbrain (rhombencephalon)[3/4] \| midbrain (mesencephalon)[3/4] \| dorsal root ganglion[3/4] \| forebrain[3/4] \| eye[3/4] \| cranial nerve[3/4] \| nose[3/41 |
| hs1041 | chr9:82010246-82011547 | yes | yes | yes | neural tube[7/7] \| hindbrain (rhombencephalon)[7/7] \| midbrain (mesencephalon)[6/7] \| forebrain[7/7] |
| hs1074 | chr9:82119097-82120855 | yes | no | no | |
| hs1078 | chr9:82224085-82226757 | yes | yes | yes | neural tube[7/8] \| hindbrain (rhombencephalon)[7/8] \| midbrain (mesencephalon)[7/8] \| forebrain[7/8] \| cranial nerve[7/8] |
| hs1026 | chr9:82244801-82246758 | yes | no | no | |
| hs1183 | chr9:82266057-82267053 | yes | no | no | |
| hs1587 | chr9:82274254-82276353 | no | no | no | |
| hs1163 | chr9:82590314-82593174 | yes | no | yes | branchial arch[6/11] \| trigeminal V (ganglion, cranial)[8/11] \| cranial nerve[8/11] |
| hs1004 | chr9:82681268-82682692 | yes | no | yes | hindbrain (rhombencephalon)[7/10] \| midbrain (mesencephalon)[8/10] \| limb[4/10] \| branchial arch[3/10] \| nose[5/10] |
| hs1211 | chr9:83122286-83123599 | yes | no | no | |
| hs974 | chr9:83412700-83413972 | yes | no | yes | other[4/7] |
| hs1228 | chr9:83711693-83712782 | yes | no | no | |
| hs1118 | chr9:84167351-84168176 | yes | yes | yes | forebrain[6/7] \| branchial arch[4/7] |
| hs1029 | chrX:82765974-82767821 | yes | no | no | |

TABLE 6

| Genes | | | Anatomical Domains and Subdomains | | | | | | | | | |
|---|---|---|---|---|---|---|---|---|---|---|---|---|
| | | | EMT | | | CP | MP | | | DP | | |
| Gene Nam | ISH data source | stage* | VZ | SVZ | MZ | VZ | VZ | SVZ | MZ | VZ | SVZ | MZ |
| Arx | Allen Brain Atlas | e11.5 | x | x | x | | x | | | x | | |
| Ascl1 | Allen Brain Atlas | e11.5 | | | | | | | | x | | |
| Bcl11a | Allen Brain Atlas | e13.5 | x | x | x | | x | x | x | x | x | x |
| Bcl11b | Allen Brain Atlas | e13.5 | | | | | | | x | | x | x |
| Cux1 | Allen Brain Atlas | e11.5 | | | | | x | | | x | | |
| Cux2 | Allen Brain Atlas | e13.5 | | | | x | | | | | | |
| Dbx1 | Allen Brain Atlas | e11.5 | x | | | | | | | | | |
| Dlx1 | J. Rubenstein** | e12.5 | | | | | | | | | | |
| Dlx2 | J. Rubenstein** | e12.5 | | | | | | | | | | |
| Dlx5 | Allen Brain Atlas | e11.5 | | | | | | | | | | |
| Dlx6 | Allen Brain Atlas | e11.5 | | | | | | | | | | |
| Ebf1 | Allen Brain Atlas | e11.5 | | | | | | | | | | |
| Ebf3 | Allen Brain Atlas | e11.5 | | | | | | | | | | x |
| Egr3 | J. Rubenstein** | e15.5 | | | | | | | | | | |
| Emx1 | J. Rubenstein** | e11.5 | | | | | x | x | x | x | x | x |
| Emx2 | Allen Brain Atlas | e11.5 | x | x | x | | x | x | | x | x | |

TABLE 6-continued

| | | | | | | | | | | | | |
|---|---|---|---|---|---|---|---|---|---|---|---|---|
| Eomes | Allen Brain Atlas | e11.5 | | x | x | | | x | x | | x | x |
| Esrrg | Allen Brain Atlas | e11.5 | | | | | | | | | | |
| Etv1 | J. Rubenstein** | e12.5 | | | | | | | | x | | |
| Etv5 | Allen Brain Atlas | e11.5 | | | | | | | | x | | |
| Fezf1 | J. Rubenstein** | e15.5 | | | | | | | | | | |
| Fezf2 | Allen Brain Atlas | e11.5 | x | x | x | | x | x | x | x | x | x |
| Foxg1 | Allen Brain Atlas | e11.5 | | | | | | | | x | x | x |
| Foxp1 | Allen Brain Atlas | e11.5 | | | | | | | | x | | |
| Foxp2 | Allen Brain Atlas | e11.5 | | | | | | | | | | |
| Foxp4 | Allen Brain Atlas | e11.5 | x | x | x | x | x | x | x | x | x | x |
| Gbx1 | J. Rubenstein** | e12.5 | | | | | | | | | | |
| Gbx2 | Allen Brain Atlas | e11.5 | | | | | | | | | | |
| Gli1 | Allen Brain Atlas | e11.5 | | | | | | | | | | |
| Gli3 | Allen Brain Atlas | e11.5 | x | | | | x | x | | x | x | |
| Gsx1 | Allen Brain Atlas | e11.5 | | | | | | | | | | |
| Gsx2 | Allen Brain Atlas | e11.5 | | | | | | | | | | |
| Hes1 | Allen Brain Atlas | e11.5 | x | x | | | x | x | | x | x | |
| Hes5 | Allen Brain Atlas | e11.5 | x | x | | | x | x | | x | x | |
| Hey1 | Allen Brain Atlas | e13.5 | | | | | x | x | | x | x | |
| Hmx3 | Allen Brain Atlas | e11.5 | | | | | | | | | | |
| Id1 | Allen Brain Atlas | e11.5 | | | | x | x | x | | | | |
| Id2 | Allen Brain Atlas | e11.5 | x | x | | x | x | x | | x | x | |
| Id4 | Allen Brain Atlas | e11.5 | x | x | | | | | | x | x | x |
| Ikzf1 | Allen Brain Atlas | e13.5 | | | | | | | | | | |
| Isl1 | Allen Brain Atlas | e11.5 | | | | | | | | | | |
| Lef1 | Allen Brain Atlas | e13.5 | x | | | x | x | x | | x | x | x |
| Lhx1 | Allen Brain Atlas | e11.5 | | | x | | | | | | | |
| Lhx2 | Allen Brain Atlas | e11.5 | | | x | | | | | x | x | x |
| Lhx5 | Allen Brain Atlas | e11.5 | x | x | x | x | | | | | | |
| Lhx6 | J. Rubenstein** | e11.5 | | | | | | | | | | |
| Lhx8 | Allen Brain Atlas | e11.5 | | | | | | | | | | |
| Lhx9 | Allen Brain Atlas | e11.5 | x | x | x | x | x | x | x | x | x | x |
| Lmo1 | Allen Brain Atlas | e11.5 | | | | | | | | | | |
| Lmo3 | Allen Brain Atlas | e11.5 | | | | | | | | | | |
| Lmo4 | Allen Brain Atlas | e13.5 | x | x | x | x | x | x | x | x | x | x |
| Mafb | Allen Brain Atlas | e11.5 | | | | | x | | | x | | |
| Mef2c | Allen Brain Atlas | e13.5 | | | | | | | | | | x |
| Meis1 | J. Rubenstein** | e15.5 | | | | | | | | | | |
| Meis2 | Allen Brain Atlas | e13.5 | | | | | x | x | | x | x | |
| Neurod1 | Allen Brain Atlas | e13.5 | | x | | | | x | | | x | |
| Neurod4 | Allen Brain Atlas | e13.5 | | | | | | | | | x | |
| Neurod6 | Allen Brain Atlas | e11.5 | | | | | | | | | | x |
| Neurog1 | Allen Brain Atlas | e11.5 | x | x | | | | | | x | x | x |
| Neurog2 | Allen Brain Atlas | e11.5 | x | x | | | x | x | | x | x | x |
| Nhlh1 | Allen Brain Atlas | e11.5 | | | x | | | | x | | | x |
| Nhlh2 | Allen Brain Atlas | e11.5 | | | x | | | | x | | | x |
| Nkx2-1 | Allen Brain Atlas | e11.5 | | | | | | | | | | |
| Nkx6-2 | J. Rubenstein** | e11.5 | | | | | | | | | | |
| Npas1 | Allen Brain Atlas | e11.5 | | | | | | | | | | |
| Nr2e1 | Allen Brain Atlas | e11.5 | x | x | x | | x | x | | x | x | |
| Nr2f1 | Allen Brain Atlas | e11.5 | x | x | | | x | x | | x | x | x |
| Nr2f2 | Allen Brain Atlas | e11.5 | x | x | | | x | x | | | | |
| Olig1 | J. Rubenstein** | e12.5 | | | | | | | | | | |
| Olig2 | Allen Brain Atlas | e11.5 | | | | | | | | | | |
| Otx1 | Allen Brain Atlas | e11.5 | | x | | | | | | x | x | |
| Otx2 | Allen Brain Atlas | e11.5 | x | x | | x | | | | | | |
| Pax6 | J. Rubenstein** | e12.5 | x | | | | x | | | x | | |
| Pbx1 | J. Rubenstein** | e12.5 | | | | | x | | | x | x | x |
| Pbx2 | Allen Brain Atlas | e11.5 | x | | | x | x | x | x | x | x | x |
| Pbx3 | Allen Brain Atlas | e11.5 | | | | | | | | | | |
| Pou3f1 | J. Rubenstein** | e12.5 | | | | | | | | | x | x |
| Pou3f2 | Allen Brain Atlas | e11.5 | x | x | | | x | x | x | x | x | x |
| Pou3f3 | J. Rubenstein** | e11.5 | | | | | | | | | | |
| Pou3f4 | Allen Brain Atlas | e11.5 | | | | | | | | | | |
| Prox1 | Allen Brain Atlas | e13.5 | | | | | x | x | x | | | |
| Rara | Allen Brain Atlas | e11.5 | | | | | x | x | | x | x | |
| Rarb | Allen Brain Atlas | e11.5 | | | | | | | | | | |
| Rorb | J. Rubenstein** | e15.5 | | | | | | | | | | x |
| Rxra | Allen Brain Atlas | e11.5 | | x | | | | | | x | x | |
| Rxrb | Allen Brain Atlas | e11.5 | x | x | | | x | x | | x | x | |
| Rxrg | Allen Brain Atlas | e11.5 | | | | | | | | | | |
| Sall3 | J. Rubenstein** | e15.5 | | | | | | | | x | | |
| Six3 | Allen Brain Atlas | e11.5 | | x | | | x | x | | x | x | |
| Sox1 | J. Rubenstein** | e15.5 | x | | | | x | x | | x | x | |
| Sox10 | J. Rubenstein** | e12.5 | | | | | | | | | | |
| Sox11 | Allen Brain Atlas | e11.5 | | | | | | | | | | |
| Sox4 | J. Rubenstein** | e15.5 | | | | | | x | x | | x | x |
| Sp8 | J. Rubenstein** | e12.5 | | | | | x | | | x | | |
| Sp9 | J. Rubenstein** | e12.5 | | | | | x | | | | | |

TABLE 6-continued

| Gene | | | Anatomical Domains and Subdomains | | | | | | | | | | |
|---|---|---|---|---|---|---|---|---|---|---|---|---|---|
| | | | LP | | | VP | | | LGE | | | MGE | |
| Gene Nam | ISH data source | stage* | VZ | SVZ | MZ | VZ | SVZ | MZ | VZ | SVZ | MZ | VZ | SVZ |
| Tbr1 | J. Rubenstein** | e12.5 | | | | | | | | x | | | x |
| Tcf3 | Allen Brain Atlas | e11.5 | | | | | | | | | x | x | |
| Tcf4 | Allen Brain Atlas | e11.5 | | x | | | x | x | | x | x | x | x |
| Tle1 | Allen Brain Atlas | e13.5 | | x | x | x | x | x | | x | x | x | x |
| Tle3 | Allen Brain Atlas | e11.5 | x | x | | x | x | x | | | x | x | |
| Tle4 | Allen Brain Atlas | e11.5 | x | x | | | | | | | x | x | |
| Tshz1 | Allen Brain Atlas | e11.5 | | | | | x | x | | x | x | x | x |
| Tshz2 | J. Rubenstein** | e15.5 | | | | | | | | | | | x |
| Vax1 | J. Rubenstein** | e12.5 | | | | | | | | | | | |
| Zfhx1a | Allen Brain Atlas | e11.5 | x | x | | | x | x | | | x | x | |
| Zfhx1b | Allen Brain Atlas | e13.5 | x | x | | x | x | x | | x | x | x | x |
| Zfhx2 | Allen Brain Atlas | e11.5 | | | | | | | | x | | | x |
| Zfhx3 | J. Rubenstein** | e15.5 | | x | x | | | | | | | | |
| Zfhx4 | Allen Brain Atlas | e11.5 | | | x | | x | | | | x | | |
| Zfp503 | J. Rubenstein** | e11.5 | | | | | | | | | | | |
| Zfp521 | J. Rubenstein** | e15.5 | | | | | | | | x | | | x |
| Zic1 | Allen Brain Atlas | e11.5 | x | x | | | x | x | | | | | |
| Zic5 | Allen Brain Atlas | e11.5 | x | x | | | x | x | | | x | x | |
| Arx | Allen Brain Atlas | e11.5 | x | | | x | | | | x | x | | x |
| Ascl1 | Allen Brain Atlas | e11.5 | x | | | x | | | x | x | | x | x |
| Bcl11a | Allen Brain Atlas | e13.5 | x | x | x | | x | x | x | x | x | | x |
| Bcl11b | Allen Brain Atlas | e13.5 | | x | x | | x | x | | x | x | | x |
| Cux1 | Allen Brain Atlas | e11.5 | x | | | x | | | x | | | x | x |
| Cux2 | Allen Brain Atlas | e13.5 | | | x | | | x | | x | x | | x |
| Dbx1 | Allen Brain Atlas | e11.5 | | | | x | | | | | | | |
| Dlx1 | J. Rubenstein** | e12.5 | | | | | | | x | x | x | x | x |
| Dlx2 | J. Rubenstein** | e12.5 | | | | | | | x | x | | x | x |
| Dlx5 | Allen Brain Atlas | e11.5 | | | | | | | | x | x | | x |
| Dlx6 | Allen Brain Atlas | e11.5 | | | | | | | | | x | | |
| Ebf1 | Allen Brain Atlas | e11.5 | | | | | | | | | x | | |
| Ebf3 | Allen Brain Atlas | e11.5 | | | x | | | x | | | | | |
| Egr3 | J. Rubenstein** | e15.5 | | | | | | | | | x | | |
| Emx1 | J. Rubenstein** | e11.5 | x | x | x | | | | | | | | |
| Emx2 | Allen Brain Atlas | e11.5 | x | x | | x | x | | x | x | x | | |
| Eomes | Allen Brain Atlas | e11.5 | | x | x | | x | x | | | | | |
| Esrrg | Allen Brain Atlas | e11.5 | | | | | | | | | | | |
| Etv1 | J. Rubenstein** | e12.5 | x | | | x | | | x | x | x | x | x |
| Etv5 | Allen Brain Atlas | e11.5 | x | | | x | x | x | x | | | | |
| Fezf1 | J. Rubenstein** | e15.5 | | | | | | | | | | | |
| Fezf2 | Allen Brain Atlas | e11.5 | x | x | x | x | x | x | | | | | |
| Foxg1 | Allen Brain Atlas | e11.5 | x | x | x | x | x | x | x | x | x | x | x |
| Foxp1 | Allen Brain Atlas | e11.5 | x | | | x | | | | | | | |
| Foxp2 | Allen Brain Atlas | e11.5 | | | | | | | | | x | | |
| Foxp4 | Allen Brain Atlas | e11.5 | | | x | | | x | x | x | x | x | |
| Gbx1 | J. Rubenstein** | e12.5 | | | | | | | | | | | |
| Gbx2 | Allen Brain Atlas | e11.5 | | | | | | | | | | | |
| Gli1 | Allen Brain Atlas | e11.5 | | | | | | | x | | | | |
| Gli3 | Allen Brain Atlas | e11.5 | x | x | | x | x | | x | x | | x | x |
| Gsx1 | Allen Brain Atlas | e11.5 | | | | | | | | | | x | x |
| Gsx2 | Allen Brain Atlas | e11.5 | | | | | | | x | x | x | x | x |
| Hes1 | Allen Brain Atlas | e11.5 | x | x | | x | x | | x | x | | x | x |
| Hes5 | Allen Brain Atlas | e11.5 | x | x | | x | x | | x | x | | x | x |
| Hey1 | Allen Brain Atlas | e13.5 | x | x | | | | | x | | | | |
| Hmx3 | Allen Brain Atlas | e11.5 | | | | | | | | | | | |
| Id1 | Allen Brain Atlas | e11.5 | | | | | | | | | | | |
| Id2 | Allen Brain Atlas | e11.5 | x | x | | x | x | | | | | | |
| Id4 | Allen Brain Atlas | e11.5 | x | x | x | x | x | x | x | x | x | x | x |
| Ikzf1 | Allen Brain Atlas | e13.5 | | | | | | | | | | | |
| Isl1 | Allen Brain Atlas | e11.5 | | | | | | | | x | x | | x |
| Lef1 | Allen Brain Atlas | e13.5 | x | x | x | x | x | | x | | | x | |
| Lhx1 | Allen Brain Atlas | e11.5 | | | | | | | | | x | | |
| Lhx2 | Allen Brain Atlas | e11.5 | x | x | x | x | x | x | x | x | | x | x |
| Lhx5 | Allen Brain Atlas | e11.5 | | | | | | | | | | | |
| Lhx6 | J. Rubenstein** | e11.5 | | | | | | | | | | | x |
| Lhx8 | Allen Brain Atlas | e11.5 | | | | | | | | | | | x |
| Lhx9 | Allen Brain Atlas | e11.5 | x | x | x | x | x | x | x | x | x | x | x |
| Lmo1 | Allen Brain Atlas | e11.5 | | | | | | | x | x | | x | x |
| Lmo3 | Allen Brain Atlas | e11.5 | | | | | | | | | | x | x |
| Lmo4 | Allen Brain Atlas | e13.5 | x | x | x | x | x | x | x | x | x | x | x |
| Mafb | Allen Brain Atlas | e11.5 | x | | | x | | | | | | | x |
| Mef2c | Allen Brain Atlas | e13.5 | | | x | | | x | | | x | | |
| Meis1 | J. Rubenstein** | e15.5 | x | | | x | | | x | x | x | | |
| Meis2 | Allen Brain Atlas | e13.5 | x | x | | x | x | | x | x | x | x | x |

TABLE 6-continued

| | | | | | | | | | | | | | |
|---|---|---|---|---|---|---|---|---|---|---|---|---|---|
| Neurod1 | Allen Brain Atlas | e13.5 | | x | | | x | | | | | | |
| Neurod4 | Allen Brain Atlas | e13.5 | | x | | | x | | | | | | |
| Neurod6 | Allen Brain Atlas | e11.5 | | | x | | | x | | | | | |
| Neurog1 | Allen Brain Atlas | e11.5 | x | x | x | x | x | x | | | | | |
| Neurog2 | Allen Brain Atlas | e11.5 | x | x | x | x | x | x | | | | | |
| Nhlh1 | Allen Brain Atlas | e11.5 | | | x | | | x | | | | | |
| Nhlh2 | Allen Brain Atlas | e11.5 | | | x | | | x | | | x | | |
| Nkx2-1 | Allen Brain Atlas | e11.5 | | | | | | | | | | x | x |
| Nkx6-2 | J. Rubenstein** | e11.5 | | | | | | | | | | x | x |
| Npas1 | Allen Brain Atlas | e11.5 | | | | | | | | | | | |
| Nr2e1 | Allen Brain Atlas | e11.5 | x | x | | x | x | | x | x | | x | x |
| Nr2f1 | Allen Brain Atlas | e11.5 | x | x | x | x | | | | | | x | x |
| Nr2f2 | Allen Brain Atlas | e11.5 | | | | | | | | | | | |
| Olig1 | J. Rubenstein** | e12.5 | | | | | | | | | | x | |
| Olig2 | Allen Brain Atlas | e11.5 | | | | | | | x | | | x | |
| Otx1 | Allen Brain Atlas | e11.5 | x | x | x | x | x | x | | | | | |
| Otx2 | Allen Brain Atlas | e11.5 | | | | | | | x | x | | x | x |
| Pax6 | J. Rubenstein** | e12.5 | x | | | x | | | x | | x | | |
| Pbx1 | J. Rubenstein** | e12.5 | x | x | x | x | x | x | x | x | x | | x |
| Pbx2 | Allen Brain Atlas | e11.5 | x | x | x | x | x | x | x | x | x | x | x |
| Pbx3 | Allen Brain Atlas | e11.5 | | | | | | x | | | x | | x |
| Pou3f1 | J. Rubenstein** | e12.5 | | x | x | | x | x | | x | x | | x |
| Pou3f2 | Allen Brain Atlas | e11.5 | x | x | x | x | x | x | x | x | x | x | x |
| Pou3f3 | J. Rubenstein** | e11.5 | | | | | | | | | | | |
| Pou3f4 | Allen Brain Atlas | e11.5 | | | | | | | | | | x | x |
| Prox1 | Allen Brain Atlas | e13.5 | | | | | | | | | | | x |
| Rara | Allen Brain Atlas | e11.5 | x | x | | x | x | | x | x | | | x |
| Rarb | Allen Brain Atlas | e11.5 | | | | | | | | | | | |
| Rorb | J. Rubenstein** | e15.5 | | | x | | | | x | | | x | |
| Rxra | Allen Brain Atlas | e11.5 | x | x | | x | x | | x | x | | x | x |
| Rxrb | Allen Brain Atlas | e11.5 | x | x | | x | x | | x | x | | x | x |
| Rxrg | Allen Brain Atlas | e11.5 | | | | | | | | | | | |
| Sall3 | J. Rubenstein** | e15.5 | x | | | x | | | x | x | | x | |
| Six3 | Allen Brain Atlas | e11.5 | x | x | | x | x | | x | x | x | x | x |
| Sox1 | J. Rubenstein** | e15.5 | x | x | | x | x | | x | x | x | x | x |
| Sox10 | J. Rubenstein** | e12.5 | | | | | | | | | | x | x |
| Sox11 | Allen Brain Atlas | e11.5 | | | | | | | | | | | |
| Sox4 | J. Rubenstein** | e15.5 | | x | x | | x | x | | x | | | x |
| Sp8 | J. Rubenstein** | e12.5 | | | | | | | | x | x | | x |
| Sp9 | J. Rubenstein** | e12.5 | | | | | | | | x | | | x |
| Tbr1 | J. Rubenstein** | e12.5 | | | x | | | x | | | | | |
| Tcf3 | Allen Brain Atlas | e11.5 | x | x | | x | x | | x | x | | x | x |
| Tcf4 | Allen Brain Atlas | e11.5 | x | x | x | x | x | x | | | | x | x |
| Tle1 | Allen Brain Atlas | e13.5 | x | x | x | x | x | x | x | x | x | x | x |
| Tle3 | Allen Brain Atlas | e11.5 | x | x | | x | x | | x | x | | x | x |
| Tle4 | Allen Brain Atlas | e11.5 | x | x | | x | x | x | x | x | x | | |
| Tshz1 | Allen Brain Atlas | e11.5 | x | x | x | x | x | x | | x | | x | |
| Tshz2 | J. Rubenstein** | e15.5 | | | | | | | | x | x | | x |
| Vax1 | J. Rubenstein** | e12.5 | | | | | | | x | x | | x | x |
| Zfhx1a | Allen Brain Atlas | e11.5 | x | x | | x | x | | x | x | | x | x |
| Zfhx1b | Allen Brain Atlas | e13.5 | x | x | x | x | x | x | x | x | x | x | x |
| Zfhx2 | Allen Brain Atlas | e11.5 | | | x | | | x | | | x | | |
| Zfhx3 | J. Rubenstein** | e15.5 | | | | | | | | x | x | | |
| Zfhx4 | Allen Brain Atlas | e11.5 | x | | | x | | | x | x | x | | |
| Zfp503 | J. Rubenstein** | e11.5 | | | | | | | | x | x | | |
| Zfp521 | J. Rubenstein** | e15.5 | | | | | | | | | x | | |
| Zic1 | Allen Brain Atlas | e11.5 | | | | x | x | | x | x | | | |
| Zic5 | Allen Brain Atlas | e11.5 | x | x | | x | x | | x | x | x | | |

| Genes | | | Anatomical Domains and Subdomains | | | | | | | |
|---|---|---|---|---|---|---|---|---|---|---|
| | | | MGE | POA | | | Se | | | |
| Gene Nam | ISH data source | stage* | MZ | VZ | SVZ | MZ | VZ | SVZ | MZ | Comments |
| Arx | Allen Brain Atlas | e11.5 | x | | | x | | | | |
| Ascl1 | Allen Brain Atlas | e11.5 | | x | x | | x | x | | weak expression in pallial VZ/SVZ |
| Bcl11a | Allen Brain Atlas | e13.5 | x | | | x | | | x | |
| Bcl11b | Allen Brain Atlas | e13.5 | x | | | x | | | | |
| Cux1 | Allen Brain Atlas | e11.5 | | | | | x | | | |
| Cux2 | Allen Brain Atlas | e13.5 | x | | | x | | | x | |
| Dbx1 | Allen Brain Atlas | e11.5 | | | | | | | | |
| Dlx1 | J. Rubenstein** | e12.5 | x | x | x | x | | x | x | |
| Dlx2 | J. Rubenstein** | e12.5 | | x | x | | x | x | | |
| Dlx5 | Allen Brain Atlas | e11.5 | x | | x | x | | | x | |
| Dlx6 | Allen Brain Atlas | e11.5 | x | | | | | | | |
| Ebf1 | Allen Brain Atlas | e11.5 | | | | | | | | also expressed in the MP of the very rostral cortex |
| Ebf3 | Allen Brain Atlas | e11.5 | | | | | | | | |
| Egr3 | J. Rubenstein** | e15.5 | | | | | | | | |

TABLE 6-continued

| | | | | | | | | | | |
|---|---|---|---|---|---|---|---|---|---|---|
| Emx1 | J. Rubenstein** | e11.5 | | | | | | | | |
| Emx2 | Allen Brain Atlas | e11.5 | | | | | x | x | x | |
| Eomes | Allen Brain Atlas | e11.5 | | | | | | | | |
| Esrrg | Allen Brain Atlas | e11.5 | | | | | | | | not expressed in brain at e11.5 |
| Etv1 | J. Rubenstein** | e12.5 | x | x | | | x | x | | |
| Etv5 | Allen Brain Atlas | e11.5 | | x | x | x | x | x | x | |
| Fezf1 | J. Rubenstein** | e15.5 | | | | | | | x | also amygdala expression |
| Fezf2 | Allen Brain Atlas | e11.5 | | | | | x | x | x | |
| Foxg1 | Allen Brain Atlas | e11.5 | x | x | x | x | x | x | x | |
| Foxp1 | Allen Brain Atlas | e11.5 | | | | | | | | maybe weak cortex expression |
| Foxp2 | Allen Brain Atlas | e11.5 | x | | | | | | | |
| Foxp4 | Allen Brain Atlas | e11.5 | | x | | | x | | | |
| Gbx1 | J. Rubenstein** | e12.5 | x | | | | | | | |
| Gbx2 | Allen Brain Atlas | e11.5 | x | | | | | | | |
| Gli1 | Allen Brain Atlas | e11.5 | | x | | | | | | |
| Gli3 | Allen Brain Atlas | e11.5 | | x | x | | x | x | | |
| Gsx1 | Allen Brain Atlas | e11.5 | | x | x | x | | | | |
| Gsx2 | Allen Brain Atlas | e11.5 | | | | | x | x | x | |
| Hes1 | Allen Brain Atlas | e11.5 | | x | x | | x | x | | |
| Hes5 | Allen Brain Atlas | e11.5 | | | | | x | x | | |
| Hey1 | Allen Brain Atlas | e13.5 | | | | | | | | |
| Hmx3 | Allen Brain Atlas | e11.5 | | | | | | | | not expressed in brain at e11.5 |
| Id1 | Allen Brain Atlas | e11.5 | | | | | | | | |
| Id2 | Allen Brain Atlas | e11.5 | | | | | x | x | | |
| Id4 | Allen Brain Atlas | e11.5 | x | x | x | x | x | x | x | |
| Ikzf1 | Allen Brain Atlas | e13.5 | | | | | | | | negative at e13.5, may be positive later |
| Isl1 | Allen Brain Atlas | e11.5 | x | | x | x | | | | |
| Lef1 | Allen Brain Atlas | e13.5 | | x | x | x | x | x | x | |
| Lhx1 | Allen Brain Atlas | e11.5 | | | | | | | x | |
| Lhx2 | Allen Brain Atlas | e11.5 | | | | | x | x | x | |
| Lhx5 | Allen Brain Atlas | e11.5 | | | | x | x | x | x | |
| Lhx6 | J. Rubenstein** | e11.5 | x | | | | | | | |
| Lhx8 | Allen Brain Atlas | e11.5 | x | | | | | | | |
| Lhx9 | Allen Brain Atlas | e11.5 | x | x | x | x | x | x | x | |
| Lmo1 | Allen Brain Atlas | e11.5 | | | | | x | x | | early MGE marker |
| Lmo3 | Allen Brain Atlas | e11.5 | | | | | | | | |
| Lmo4 | Allen Brain Atlas | e13.5 | x | x | x | x | x | x | x | |
| Mafb | Allen Brain Atlas | e11.5 | | | | | x | x | | ISH data ambiguous |
| Mef2c | Allen Brain Atlas | e13.5 | x | | | | | | x | |
| Meis1 | J. Rubenstein** | e15.5 | | | | | x | | | |
| Meis2 | Allen Brain Atlas | e13.5 | | | | | x | x | x | |
| Neurod1 | Allen Brain Atlas | e13.5 | | | | | | | x | |
| Neurod4 | Allen Brain Atlas | e13.5 | | | | | | | | |
| Neurod6 | Allen Brain Atlas | e11.5 | | | | | | | | |
| Neurog1 | Allen Brain Atlas | e11.5 | | | | | | x | x | |
| Neurog2 | Allen Brain Atlas | e11.5 | | | | | x | x | | |
| Nhlh1 | Allen Brain Atlas | e11.5 | | | | | | | x | |
| Nhlh2 | Allen Brain Atlas | e11.5 | x | | | | | | x | |
| Nkx2-1 | Allen Brain Atlas | e11.5 | x | x | x | x | x | x | x | |
| Nkx6-2 | J. Rubenstein** | e11.5 | | x | x | x | | | | |
| Npas1 | Allen Brain Atlas | e11.5 | | | | | | | | |
| Nr2e1 | Allen Brain Atlas | e11.5 | | | | | x | x | | |
| Nr2f1 | Allen Brain Atlas | e11.5 | | x | x | | | | | expression is very strong in all layers of the CGE, and weaker in the LGE proper |
| Nr2f2 | Allen Brain Atlas | e11.5 | | | | | | | | strong caudal-rostral gradient; expression analysis based on whole-mount |
| Olig1 | J. Rubenstein** | e12.5 | | x | | | | | | |
| Olig2 | Allen Brain Atlas | e11.5 | | x | | | | | | |
| Otx1 | Allen Brain Atlas | e11.5 | | | | | | | | |
| Otx2 | Allen Brain Atlas | e11.5 | | x | x | | x | x | | |
| Pax6 | J. Rubenstein** | e12.5 | | | | | x | | | |
| Pbx1 | J. Rubenstein** | e12.5 | | | x | | | x | | |
| Pbx2 | Allen Brain Atlas | e11.5 | x | x | x | x | x | x | x | |
| Pbx3 | Allen Brain Atlas | e11.5 | x | | x | | | | | |
| Pou3f1 | J Rubenstein** | e12.5 | x | | x | | | x | | |
| Pou3f2 | Allen Brain Atlas | e11.5 | x | x | x | x | x | x | x | |
| Pou3f3 | J. Rubenstein** | e11.5 | | | | | | | | |
| Pou3f4 | Allen Brain Atlas | e11.5 | x | | | | | | | |
| Prox1 | Allen Brain Atlas | e13.5 | x | | | | | | x | expression in CGE (caudal LGE), and not clearly in the rostral LGE |
| Rara | Allen Brain Atlas | e11.5 | | | | | | | | |
| Rarb | Allen Brain Atlas | e11.5 | | | | | | | | |
| Rorb | J. Rubenstein** | e15.5 | x | x | x | x | x | | | |
| Rxra | Allen Brain Atlas | e11.5 | | x | x | | | x | | |
| Rxrb | Allen Brain Atlas | e11.5 | x | x | x | x | x | x | | |
| Rxrg | Allen Brain Atlas | e11.5 | | | | | | | | not expressed at e11.5 |
| Sall3 | J. Rubenstein** | e15.5 | | x | | | x | | | |
| Six3 | Allen Brain Atlas | e11.5 | x | x | x | x | x | x | x | |
| Sox1 | J. Rubenstein** | e15.5 | | x | x | | x | x | | |

TABLE 6-continued

| | | | | | | | | | | |
|---|---|---|---|---|---|---|---|---|---|---|
| Sox10 | J. Rubenstein** | e12.5 | | | | | | | | |
| Sox11 | Allen Brain Atlas | e11.5 | | | | | | | | not expressed at e11.5 |
| Sox4 | J. Rubenstein** | e15.5 | | | x | x | | x | | |
| Sp8 | J. Rubenstein** | e12.5 | | | x | | | x | x | |
| Sp9 | J. Rubenstein** | e12.5 | | x | | | | x | x | |
| Tbr1 | J. Rubenstein** | e12.5 | | | | | | | | |
| Tcf3 | Allen Brain Atlas | e11.5 | | x | x | | x | x | | |
| Tcf4 | Allen Brain Atlas | e11.5 | | | | | x | x | | |
| Tle1 | Allen Brain Atlas | e13.5 | x | x | x | x | x | x | x | |
| Tle3 | Allen Brain Atlas | e11.5 | | x | x | | x | x | | |
| Tle4 | Allen Brain Atlas | e11.5 | x | x | x | | x | x | | |
| Tshz1 | Allen Brain Atlas | e11.5 | | x | | | | | | |
| Tshz2 | J. Rubenstein** | e15.5 | x | | | x | | x | x | |
| Vax1 | J. Rubenstein** | e12.5 | | x | x | | x | x | | |
| Zfhx1a | Allen Brain Atlas | e11.5 | | x | x | | x | x | | |
| Zfhx1b | Allen Brain Atlas | e13.5 | x | x | x | | x | x | | |
| Zfhx2 | Allen Brain Atlas | e11.5 | x | | | | | | x | |
| Zfhx3 | J. Rubenstein** | e15.5 | | | x | x | | x | x | |
| Zfhx4 | Allen Brain Atlas | e11.5 | x | | | | x | x | | |
| Zfp503 | J Rubenstein** | e11.5 | | | | | | | | |
| Zfp521 | J. Rubenstein** | e15.5 | x | | | | | | x | |
| Zic1 | Allen Brain Atlas | e11.5 | x | | | | x | x | x | |
| Zic5 | Allen Brain Atlas | e11.5 | x | x | x | | x | x | x | |

*expression was annotated from e11.5 ISH data or inferred from the closest available stage
**data compiled from:
Long J E, Swan C, Liang W S, Cobos I, Potter G B, Rubenstein J L (2009), *J Comp Neurol* 512: 556-72
Long J E, Cobos I, Potter G B, Rubenstein J L (2009), *Cereb Cortex* 19 Suppl 1: i96-106
Flandin P, Zhao Y, Vogt D, Jeong J, Long J, Potter G, Westphal H, Rubenstein J L (2011), *Neuron* 70: 939-50
unpublished observations

TABLE 8

| Pallium Motif | Importance | Pallium and Subpallium Motif | mportance | Subpallium Motif | Importance |
|---|---|---|---|---|---|
| V$OTX2_Q3 | 0.0153 | V$MZF1_01 | 0.0306 | V$NEUROD_02 | 0.0064 |
| V$LMX1_01 | 0.0127 | V$CAP_01 | 0.0254 | V$HOXA7_03 | 0.0063 |
| V$AFP1_Q6 | 0.0064 | V$MZF1_02 | 0.0247 | V$DLX7_01 | 0.0063 |
| V$LIM1_01 | 0.0055 | V$LHX61_01 | 0.0124 | V$LBP1_Q6 | 0.0053 |
| V$S8_01 | 0.0051 | V$HMBOX1_01 | 0.0090 | V$NKX63_01 | 0.0053 |
| V$LHX5_01 | 0.0042 | V$MZF1_Q5 | 0.0081 | V$DLX3_01 | 0.0052 |
| V$HOXC4_01 | 0.0038 | V$PMX2A_01 | 0.0076 | V$Lhx3 | 0.0051 |
| V$PAX4_05 | 0.0037 | V$OCT_Q6 | 0.0071 | V$Pou5f1 | 0.0045 |
| V$OCT1_01 | 0.0034 | V$HNF4A | 0.0058 | V$HOXB7_01 | 0.0044 |
| V$PITX2_01 | 0.0031 | V$Lhx3 | 0.0051 | V$BARX2_01 | 0.0030 |
| V$ISL2_01 | 0.0029 | V$NKX63_01 | 0.0050 | V$OCT1_Q5_01 | 0.0025 |
| V$OTX3_01 | 0.0024 | V$OCT_C | 0.0049 | V$OCT_Q6 | −0.0025 |
| V$STAT5A_01 | 0.0024 | V$CREB_Q2_01 | 0.0048 | V$CAP_01 | −0.0022 |
| V$LMX1B_01 | 0.0023 | V$OCT1_Q5_01 | 0.0043 | V$AFP1_Q6 | 0.0022 |
| V$MZF1_Q5 | −0.0023 | V$PAX7_01 | 0.0041 | V$BARX1_01 | 0.0019 |
| V$HOXB4_01 | 0.0021 | V$LBP1_Q6 | −0.0037 | V$ESX1_01 | −0.0019 |
| V$NKX61_03 | 0.0021 | V$LH2_01 | 0.0037 | V$HMBOX1_01 | 0.0018 |
| V$DLX7_01 | −0.0021 | V$HOXB7_01 | −0.0035 | V$LIM1_01 | −0.0018 |
| V$LHX61_01 | −0.0020 | V$OCT1_08 | 0.0030 | V$HB24_01 | 0.0017 |
| V$OCT_Q6 | 0.0019 | V$NEUROD_02 | 0.0029 | V$Nobox | 0.0017 |
| V$PAX7_01 | 0.0018 | V$DLX2_01 | 0.0029 | V$LH2_01 | −0.0016 |
| V$OBOX5_01 | 0.0018 | V$PKNOX2_01 | 0.0028 | V$BRN4_01 | −0.0016 |
| V$OCT1_08 | 0.0017 | V$DLX3_01 | −0.0028 | V$IPF1_01 | 0.0016 |
| V$LHX8_01 | 0.0017 | V$OCT1_B | 0.0027 | V$RAX_01 | −0.0016 |
| V$1PF1_03 | 0.0017 | V$GCNF_01 | 0.0027 | V$OCT1_05 | 0.0015 |
| V$CHX10_01 | 0.0017 | V$OCT1_01 | −0.0027 | V$LMX1B_01 | −0.0015 |
| V$HOXA3_02 | −0.0017 | V$MTF1_01 | 0.0026 | V$PAX7_01 | −0.0015 |
| V$ALX4_02 | 0.0017 | V$S8_01 | −0.0026 | V$HOXC6_01 | 0.0014 |
| V$HOXA7_03 | −0.0015 | V$OCT2_01 | −0.0026 | V$LBX2_01 | −0.0013 |
| V$STAT5B_01 | 0.0015 | V$STAT1_01 | 0.0025 | V$IPF1_06 | −0.0013 |
| V$HOXC6_01 | −0.0015 | V$BARX1_01 | 0.0024 | V$DLX2_01 | 0.0012 |
| V$NKX63_01 | −0.0014 | V$DLX7_01 | −0.0023 | V$HOXD3_01 | −0.0012 |
| V$EMX2_01 | 0.0014 | V$OCTAMER_02 | 0.0023 | V$PAX4_05 | −0.0012 |
| V$HOXC8_01 | 0.0014 | V$BARX2_01 | 0.0022 | V$VAX1_01 | −0.0012 |
| V$Lhx3 | 0.0014 | V$IPF1_06 | −0.0021 | V$OCT2_01 | 0.0011 |
| V$MZF1_01 | −0.0013 | V$AREB6_01 | 0.0020 | V$AREB6_01 | 0.0011 |
| V$BARX1_01 | −0.0012 | V$ALX3_01 | −0.0020 | V$PIT1_01 | 0.0011 |
| V$LBX2_01 | 0.0011 | V$HOXD3_01 | 0.0019 | V$LHX61_01 | −0.0010 |
| V$PIT1_01 | −0.0011 | V$OTX2_Q3 | −0.0019 | V$HOXC8_01 | 0.0010 |
| V$VSX1_01 | 0.0011 | V$PAX4_05 | 0.0018 | V$S8_02 | −0.0010 |
| V$OCT1_Q5_01 | 0.0011 | V$CART1_02 | 0.0018 | V$CART1_02 | −0.0010 |
| V$ALX3_01 | 0.0011 | V$LMX1_01 | 0.0017 | V$STAT1_01 | 0.0009 |

TABLE 8-continued

| Pallium Motif | Importance | Pallium and Subpallium Motif | mportance | Subpallium Motif | Importance |
|---|---|---|---|---|---|
| V$VAX1_01 | 0.0010 | V$PITX2_01 | −0.0017 | V$HNF4A | −0.0009 |
| V$IPF1_06 | −0.0010 | V$HOXC6_01 | −0.0017 | V$HOXC4_01 | −0.0009 |
| V$OCT1_05 | −0.0010 | V$ISL2_01 | −0.0016 | V$OCT1_B | −0.0009 |
| V$PSX1_01 | 0.0010 | V$SIX2_01 | 0.0016 | V$CHX10_01 | −0.0009 |
| V$HOXD3_01 | 0.0009 | V$LHX3_01 | −0.0016 | V$OTX2_Q3 | 0.0008 |
| V$OCT1_B | 0.0009 | V$OCT1_05 | 0.0014 | V$GSH2_01 | −0.0008 |
| V$RAX_01 | 0.0008 | V$PIT1_01 | 0.0014 | V$ARX_01 | −0.0008 |
| V$LHX4_01 | 0.0008 | V$VAX1_01 | −0.0014 | V$MSX2_01 | 0.0008 |
| V$DLX2_01 | 0.0008 | V$HOXA1_01 | −0.0014 | V$STAT5A_01 | 0.0008 |
| V$STAT1_01 | 0.0007 | V$NKX61_03 | 0.0013 | V$STAT5B_01 | −0.0008 |
| V$NEUROD_02 | −0.0007 | V$HOXC4_01 | 0.0012 | V$LMX1_01 | −0.0008 |
| V$LBP1_Q6 | −0.0007 | V$IPF1_01 | 0.0012 | V$OCT1_01 | 0.0007 |
| V$Nobox | −0.0007 | V$SHOX2_01 | 0.0012 | V$LHX4_01 | 0.0007 |
| V$CART1_02 | 0.0007 | V$LHX4_01 | −0.0011 | V$HOXB3_01 | 0.0007 |
| V$Pou5f1 | −0.0007 | V$ESX1_01 | 0.0011 | V$OCTAMER_02 | 0.0007 |
| V$HNF4A | 0.0007 | V$ARX_01 | 0.0010 | V$HOX13_02 | 0.0007 |
| V$OCT1_Q6 | −0.0006 | V$OBOX5_01 | −0.0010 | V$PMX2A_01 | −0.0007 |
| V$OCT_C | 0.0006 | V$HOXA2_01 | −0.0010 | V$HOXA1_01 | 0.0007 |
| V$S8_02 | −0.0006 | V$AFP1_Q6 | 0.0010 | V$CREB_Q2_01 | −0.0007 |
| V$IPF1_01 | −0.0006 | V$MSX2_01 | −0.0009 | V$VAX2_01 | −0.0006 |
| V$DLX3_01 | −0.0006 | V$OCT1_Q6 | 0.0009 | V$HOXA3_02 | 0.0006 |
| V$HOX13_02 | −0.0006 | V$STAT5A_01 | −0.0008 | V$OCT1_08 | −0.0005 |
| V$ESX1_01 | 0.0006 | V$HOXA3_02 | −0.0007 | V$GCNF_01 | −0.0005 |
| V$LHX3_01 | −0.0006 | V$EVX1_01 | 0.0007 | V$HOXA2_01 | 0.0005 |
| V$AREB6_01 | 0.0005 | V$GSH2_01 | 0.0007 | V$NKX61_03 | −0.0005 |
| V$OCT2_01 | −0.0005 | V$HOXD1_01 | 0.0007 | V$HOXB4_01 | −0.0005 |
| V$OCTAMER_02 | −0.0005 | V$LIM1_01 | −0.0006 | V$PKNOX2_01 | −0.0005 |
| V$ARX_01 | 0.0005 | V$BRN4_01 | −0.0006 | V$VSX1_01 | −0.0005 |
| V$GBX2_01 | −0.0005 | V$PSX1_01 | 0.0005 | V$MTF1_01 | −0.0005 |
| V$MSX2_01 | −0.0005 | V$CHX10_01 | −0.0005 | V$EMX2_01 | −0.0005 |
| V$HOXB7_01 | −0.0005 | V$RAX_01 | 0.0005 | V$DLX5_01 | −0.0003 |
| V$HOXB3_01 | −0.0004 | V$VSX1_01 | 0.0005 | V$ISL2_01 | 0.0003 |
| V$DLX5_01 | −0.0004 | V$HOXB4_01 | −0.0004 | V$MSX1_02 | −0.0003 |
| V$HOXA1_01 | −0.0004 | V$S8_02 | −0.0004 | V$PITX2_01 | −0.0003 |
| V$PAX4_02 | −0.0004 | V$IPF1_03 | 0.0004 | V$LHX8_01 | −0.0003 |
| V$LH2_01 | 0.0004 | V$HOXA7_03 | 0.0004 | V$S8_01 | 0.0003 |
| V$PMX2A_01 | 0.0003 | V$DLX5_01 | −0.0004 | V$SIX2_01 | −0.0003 |
| V$MTF1_01 | 0.0003 | V$LMX1B_01 | −0.0004 | V$MZF1_01 | 0.0003 |
| V$GSH2_01 | 0.0003 | V$FREAC2_01 | 0.0004 | V$GBX2_01 | −0.0003 |
| V$CAP_01 | 0.0003 | V$HB24_01 | −0.0004 | V$PSX1_01 | 0.0003 |
| V$MSX1_02 | −0.0002 | V$AHRARNT_01 | 0.0003 | V$MZF1_02 | 0.0002 |
| V$CART1_03 | −0.0002 | V$EMX2_01 | −0.0003 | V$OCT1_Q6 | 0.0002 |
| V$BARX2_01 | −0.0002 | V$Nobox | −0.0003 | V$OCT_C | 0.0002 |
| V$CREB_Q2_01 | 0.0002 | V$HOX13_02 | −0.0003 | V$HOXD1_01 | −0.0002 |
| V$HOXA2_01 | −0.0002 | V$ALX4_02 | 0.0003 | V$CART1_03 | 0.0002 |
| V$HOXD1_01 | 0.0001 | V$PAX4_02 | −0.0003 | V$ALX4_02 | −0.0002 |
| V$SIX2_01 | −0.0001 | V$CART1_03 | 0.0002 | V$FREAC2_01 | −0.0002 |
| V$BRN4_01 | 0.0001 | V$VAX2_01 | 0.0001 | V$AHRARNT_01 | −0.0001 |
| V$HMBOX1_01 | 0.0001 | V$HOXB3_01 | −0.0001 | V$IPF1_03 | 0.0001 |
| V$MZF1_02 | −0.0001 | V$LHX8_01 | 0.0001 | V$SHOX2_01 | 0.0001 |
| V$GCNF_01 | −0.0001 | V$HOXC8_01 | 0.0001 | V$OTX3_01 | −0.0001 |
| V$VAX2_01 | 0.0001 | V$GBX2_01 | −0.0001 | V$LHX5_01 | 0.0001 |
| V$PKNOX2_01 | −0.0001 | V$STAT5B_01 | 0.0001 | V$PAX4_02 | −0.0001 |
| V$FREAC2_01 | −0.0001 | V$MSX1_02 | −0.0001 | V$LHX3_01 | −0.0001 |
| V$EVX1_01 | 0.0001 | V$LHX5_01 | 0.0000 | V$MZF1_Q5 | 0.0000 |
| V$SHOX2_01 | 0.0000 | V$LBX2_01 | 0.0000 | V$ALX3_01 | 0.0000 |
| V$HB24_01 | 0.0000 | V$Pou5f1 | 0.0000 | V$OBOX5_01 | 0.0000 |
| V$AHRARNT_01 | 0.0000 | V$OTX3_01 | 0.0000 | V$EVX1_01 | 0.0000 |

TABLE 10

Microarray Data

| 1 Areas or cells of interest Genes of interest | 2 Expression levels ES Lhx6-GFP$^+$ | 3 ES Lhx6-GFP$^+$ | 4 MGE Lhx6-GFP$^+$ | 5 Comparison between groups (fold changes) ES-GFP$^+$ vs ES-GFP$^-$ | 6 MGE-GFP$^+$ vs ES-GFP$^-$ | 7 MGE-GFP$^+$ vs ES-GFP$^+$ |
|---|---|---|---|---|---|---|
| Ventricular Zone | | | | | | |
| Hes5 | 11.62 | 13.39 | 11.72 | 0.29 | 0.31 | 1.07 |
| Oligodendrocytes | | | | | | |
| Olig2 | 8.80 | 11.63 | 9.59 | 0.14 | 0.24 | 1.73 |
| Pallial | | | | | | |
| Emx1 | 7.57 | 6.83 | 6.11 | 1.67 | 0.61 | 0.36 |
| Pax6 | 6.38 | 7.65 | 5.97 | 0.43 | 0.33 | 0.75 |
| Subpallial | | | | | | |
| Dlx1 | 14.14 | 12.14 | 14.36 | 4.00 | 4.67 | 1.17 |
| GAD1 | 13.89 | 11.59 | 13.28 | 4.92 | 3.22 | 0.65 |
| Zeb2 (Zfhx1b) | 7.92 | 8.30 | 9.50 | 0.77 | 2.31 | 3.00 |
| LGE/striatum | | | | | | |
| Ebf1 | 8.67 | 10.35 | 8.25 | 0.31 | 0.23 | 0.75 |
| MGE & CGE progenitors | | | | | | |
| Nkx2-1 | 11.67 | 10.09 | 12.94 | 2.98 | 7.20 | 2.41 |
| NR2F1 (dorsal MGE & CGE) | 13.23 | 12.62 | 12.71 | 1.52 | 1.07 | 0.70 |
| MGE subpallial neurons & globus pallidus | | | | | | |
| Lhx6 | 13.16 | 9.20 | 14.02 | 15.50 | 28.20 | 1.83 |
| Lhx8 | 11.49 | 7.55 | 13.13 | 15.31 | 47.56 | 3.11 |
| Sox6 | 11.86 | 9.69 | 13.21 | 3.92 | 10.00 | 2.55 |
| Globus pallidus | | | | | | |
| Etv1 (ER81) | 7.04 | 8.51 | 11.12 | 0.43 | 6.75 | 17.20 |
| MGE interneurons | | | | | | |
| ErbB4 | 10.16 | 8.39 | 10.13 | 3.46 | 3.33 | 1.01 |
| MafB | 11.63 | 9.68 | 11.78 | 3.86 | 4.28 | 1.11 |
| Maf (cMaf, vMaf) | 9.94 | 8.22 | 10.29 | 3.30 | 4.19 | 1.27 |
| Npas1 | 10.69 | 7.86 | 8.31 | 7.13 | 1.57 | 0.22 |
| Sst | 14.22 | 11.79 | 13.21 | 5.39 | 2.69 | 0.50 |
| Hypothalamus | | | | | | |
| Nkx2-2 | 9.24 | 10.61 | 6.68 | 0.44 | 0.07 | 0.19 |
| Otp | 6.92 | 7.16 | 6.84 | 0.85 | 0.80 | 0.95 |
| Rax | 9.10 | 7.21 | 7.05 | 3.70 | 0.89 | 0.24 |

TABLE 11

| | DlxI12b | | | 692 | | | 1056 | | | 1538 | | |
|---|---|---|---|---|---|---|---|---|---|---|---|---|
| | mCh | GFP | mCh/GFP | mCh | GFP | mCh/GFP | mCh | GFP | mCh/GFP | mCh | GFP | mCh/GFP |
| Day 9 | 0.0% | 0.5% | 0.1% | 0.0% | 0.6% | 0.0% | 0.2% | 1.1% | 0.0% | 0.0% | 0.7% | 0.0% |
| Day 11 | 0.1% | 0.8% | 0.3% | 0.0% | 9.5% | 0.1% | 3.0% | 2.2% | 0.0% | 0.0% | 2.4% | 0.0% |
| Day 13 | 1.2% | 1.4% | 0.6% | 0.0% | 7.7% | 0.0% | 3.2% | 3.6% | 0.0% | 0.0% | 3.3% | 0.0% |
| Day 16 | 1.6% | 3.1% | 0.5% | 0.0% | 6.9% | 0.2% | 2.0% | 2.6% | 0.0% | 0.0% | 5.6% | 0.0% |

What is claimed is:

1. An isolated polynucleotide comprising an enhancer comprising the sequence of SEQ ID NO: 120, and further comprising a heterologous inducible promoter and a reporter gene, wherein the enhancer and the heterologous inducible promoter are operably linked to the reporter gene.

2. The isolated polynucleotide of claim 1 further comprising a gene that is capable of inducing pluripotency.

3. A vector comprising an isolated polynucleotide of claim 1.

4. An expression cassette incorporating the isolated polynucleotide of claim 1.

5. A non-human cell comprising the expression cassette of claim 4.

6. A vector comprising an isolated polynucleotide of claim 2.

7. A set of vectors for labeling subregions of a mouse forebrain, comprising the vector of claim 3, and a second vector comprising an enhancer selected from the group consisting of SEQ ID NOS: 83, 84, 99-104, 106-108, 110-118, 121-128, and 144-145.

8. A method for detecting oligodendrocyte progenitors comprising: (1) providing the vector of claim 3; (2) transfecting an embryonic stem cell with the vector; (3) directing neuronal differentiation of the transfected embryonic stem cell; and (4) detecting oligodendrocyte progenitors by detecting reporter gene expression.

9. A method for detecting and isolating oligodendrocyte progenitors comprising (1) providing the vector of claim 3; (2) transfecting an embryonic stem cell with the vector; (3) directing neuronal differentiation of the transfected embryonic stem cell; (4) detecting oligodendrocyte progenitors by detecting reporter gene expression; and (5) isolating the oligodendrocyte progenitors expressing the reporter gene.

10. A method for driving reporter gene expression in medial ganglionic eminence (MGE) ventricular zone (VZ) or subventricular zone (SVZ), or preoptic area (POA) ventricular zone (VZ) or subventricular zone (SVZ) of a mouse, comprising (1) providing the vector of claim 3; (2) using the vector to generate a transgenic mouse; and (3) detecting expression of the reporter gene in the MGE or POA of the transgenic mouse.

* * * * *

SEQUENCE LISTING

<160> NUMBER OF SEQ ID NOS: 159

<210> SEQ ID NO 1
<211> LENGTH: 1336

<212> TYPE: DNA
<213> ORGANISM: Homo sapiens

<400> SEQUENCE: 1
agctagctaa ttgcttcttc agttgaagac ctaaatgagt tttaaagtga aatgcatatc 60
tctaagggct aagtagccaa cacaataggc aattgagata ggaaagacta atttagaaaa 120
ggttgttttg ttcgtttttc tttttccttc cctcccttcc tgatttccca tcttcttcct 180
ccctcttctc tcccctctcc cccttctcct ttccgtcctt cctccttcag ttccctcttt 240
cctctttttc accctttttat ttaacattat aaatacgatg ggattgtgtc tgcgcttttg 300
ttggtaatta aataaattat ttatacattt aacacaatct tgaattacca ggtgatcatc 360
ttaggcactc aaaagcataa gagcccttga aagcaatatc taagcataga tattccatag 420
cacgtcttac aatctaaata ttgcttttag tgtaatcgaa gcagcaagag tagtcacagc 480
agttgatgga ctatttttca aattgatttc aaaaatgtat ttaaggggat gatcttctag 540
tctagattac ctattgattt ttaatatgaa aagctcatta tgtaagcagt aaccgcatat 600
aaaaacctag caaacctttg cataaatcct ttaattgaat ttccagagcc tgtggttcta 660
cttttttttt aattaaatct atttcttttt ttaagtgtta ctgtgtaatt tgcatgctgt 720
gaagaggccc tgtcccagat aaagtgccat tgatccttat taaacctcac ctctgggctt 780
gcttaaaact aactggaaaa attaaagtgt tcatgccgca atgcacttat agcttgtgtg 840
ataggattat ggaaaaaata ataaaactaa tttccagggg agaatttcta atgtgagatt 900
ttattttttt tcaatttgat aattaatagt gaaatcatat catatatata aatcatattt 960
tagcctataa actgaaatgg caattaggaa agataatata tacttgatgt aaaaccatgt 1020
tacgtgcgga taatctttta gcactttaat tttttaattg tagaaggaga gaattatgaa 1080
ttcaagtcaa acacattaaa tggtgggttt catccaaaaa atctgattct tttactatgt 1140
actgtattag tggatttata atattagtgg gaggaagtat aaaagatatg gaaaaagata 1200
ttctggttat gttcgtgcta aaatgtgtgt attagaatta ccaggggaaa gaaaaatata 1260
aaagctgcaa taggttttc tattttttaa tacctaacat ttgttatttt aaaagcaata 1320
aaatccccta aagaaa 1336

<210> SEQ ID NO 2
<211> LENGTH: 1259
<212> TYPE: DNA
<213> ORGANISM: Homo sapiens

<400> SEQUENCE: 2
gagagagggc tcagagacag tactcggcct tgcatttttc tccaggcctt gcaggatgca 60
aggtggacag tgctgcagtc ctgtggatct ggtgccctag gctctgcaga cacattgagg 120
ggacccaggg ctctgaacaa atggccagat ggtaagaaca catccctcga gttgtttctt 180
ccagttgcat ttttccctaa tcactgtctg ctttgggaaa ggtcgatcaa cctagcaaaa 240 gtacccccctg gacatcttca ctaggtccac tgactgctcc ccagaactct cagtttcctg 300
aggattgtgc cctttccctt cctttcctgc tgcagcttct cagcctaagc gaacctagag 360
agagcaaggg tggggaagga gagcaggggt atgtgattgc gctgagaaca ccaaaagccc 420
ataaagtctg aaaggttaag caaagactga ggcatgaaga gtgaaaattc tccattcaac 480
aataatcctc gccccctgcc acccctgaca tctcttctta aaatggaaag aaagggtgca 540
tgatgacatt aggcacttta aaatatgcaa aattaggagc tggtgcagac ctcattaaca 600

-continued

```
cccgcctcca acatcattaa gatgtttcca agaaaattaa ttgagagact cattaaaaat     660

aaattaagaa aaatgtgttg cagagcgcct gcactcagct cataaatcac agctcagtgc     720

tctggcccgc tgctccggca attaactcca acctatttgt tttatcctga ctgtgaaaat     780

tagaaagcag acgtggagat tagattagga atgtctgtca agcggaactt ggagtgaata     840

ttttaggata caaaatggaa accaggaaaa caaagacagc agagatttca ttctgaggag     900

cttgtctttg aaaagtgaca ggcagatgaa gggtgctgga gggagagtat ggggaaggag     960

tacctactct cgggaaggat gaagggggag agaaaagaac agatgtttaa actcttctga    1020

ccaggaatcg tgcaatacat ttgcattata aatataaaca gttacacatc ttagtaaagc    1080

tggcattgag acataaaatt gatgttcctg atgatacttc atatgtcata ctttaatgtt    1140

tagacataga gtcatttggt tgaatcactc gaaagagtta ctggtctctt gcaatatttt    1200

atgtatcagt gatgaccaca tgttcctcta tatgaggtga aatatgccag cctcttccc     1259
```

<210> SEQ ID NO 3
<211> LENGTH: 1284
<212> TYPE: DNA
<213> ORGANISM: Homo sapiens

<400> SEQUENCE: 3

```
cccttccacc tttatccaca atatcctcga gtggacatca ctggggttcc tctgaatgac      60

tgagttgcct cttcattatt ccgcccaaga tgtcagctaa ggctgtttac aaatccaagg     120

attctcttgc caaatataca gtctgttctc caagctttca tgttataacg aaatgagtaa     180

caagcaagac atcttaatat cctattctgc tagaaagtga gatatttccc ctccctcgtt     240

cttaacagat aaattaatat catcaaacat tctgaaaaga tcttttatga aaacatctca     300

cttgccaaaa aagaaaagtt gtattataaa actggagaaa tttgtttcaa cttgttaaaa     360

gccctattct cagccatgaa ttcggttccc gttttttttc ccccttcaat taatttcaca     420

ctaatccatt tctttatcag gcgttggagt gaatgcatgt ggatcgagtg atgaggatga     480

gggggcaatg gaggtgtttg gctctgtaat ttcatccttg aattttgtga ttactaacag     540

gacaactttt ttaatttgct cttttgtctg gattccctgg ctgacaatct gctcggtgag     600

ctcggctttt taatcaatca cctacataat caaatgtcac tggctatctg ctccgtgtaa     660

ttacttttgc aattaaaaat caacctcaag ttgcctcatc taattagagg gatgggcaga     720

ttttcatcta gattgatttt ttaataaata ttgacttaaa atgccataat ctcatcatat     780

tctttcattt tctttgtacc aaaaatcaaa caaatggaag aattagcaag cagaaggaat     840

cgagggactt caaaagcttc tgctggttca gacacacaaa actatgctgt acagaagccc     900

agcttagctt gcctaataac aacactcaat agcttccacc ttttattgga aaaaagaaca     960

aagcaattca atgattatat ttcacaccaa cattgttgca agcccaccat tctaagagct    1020

cctaatttca tttattgtac tgccaaagac aatcatttct atgaatgata ttatttcctt    1080

taaaacaatc ccacacatgc tactagaatt ttttagcatt atgagaaaac atataatgct    1140

taatgctgga accgcaacca ctgagttttc ttaaacatat gaatgccact acagccagat    1200

aacttccttg tctttgctgc cgtgtgtctt ttatgtattg taattaaaac attgtcaata    1260

acacagttcg ttgcttttttg gttg                                          1284
```

<210> SEQ ID NO 4
<211> LENGTH: 858
<212> TYPE: DNA
<213> ORGANISM: Homo sapiens

<400> SEQUENCE: 4
ttgaggacag agacactggg aaaacactcc tggagaaact gcagagtagg ggcacatctc 60
ataaaaatct accttgtgtc caggatgaga ctgtatttcc tccacgcgcc tcaacctaat 120
ttcctgtgga tttcagatca tcttttattt ccaattatgc tgctgttcac attatcgatt 180
tggaggatac aaatgttgaa tgacaagaga gggagaagaa ggagggggga ggagaattcc 240
attttgcctg aaggataaga tactcgaaat gccacccgca cagcctctct gaagcgttca 300
tcaacgtggc agaggctggc tcaattatct ttgtgtcaga tgattatctg agagcttaat 360
ttaatctcca ttatcctccc ccgtcatatt tcaattaaat ctgctatcag agtgttaaca 420
catctttgaa cctgctattt cttcagttaa ttttccacta agaggtgctg gagagtaaca 480
gatgtcataa ttatgcaatt attaagtgta tttgacactc gttctctcag gattttgtgg 540
ttagggtagg agggttggaa aattaatctg atgacaatat gcttccgttg tgatccgtaa 600
caccactgca ggctggggga ctgtcctccc gctgtttccg aggctgccgc caaggaagat 660
aaaggattaa ctgattgtgc gtcagattcg tttcactttt gtatgtctgg taaattggat 720
gagttcatta ggctgagcag aacaccagag gcattttttt aaaaaataaa aaaaaacctt 780
cttcaagacc tcaagaagta caacaagtac atctcaggga atatggtaaa gttatcaact 840
atagagttaa gggcagtt 858

<210> SEQ ID NO 5
<211> LENGTH: 1470
<212> TYPE: DNA
<213> ORGANISM: Homo sapiens

<400> SEQUENCE: 5
atatagacat gtgatggcat ctgtaattcc aaccagtcct caggagaata tccacagatg 60
cctttttgga gccttctcta agataatgaa ataggctctg gtcagagaca ctgtacctca 120
cactgtataa cagctttcga cataaatctg gagcatgatt tgcatttgaa agcaccagat 180
caatatttga ggagggatta ttttttatca acttggctct aattctctga aatatacagt 240
tattttttaa atgtcaagac caactacacc cacactggca tgaaatagct ttgtcaaaaa 300
agttgaaaaa aattaaacgt aaattttgtg ttgacataat ccaggttaag tctaaaaaag 360
aaaaatactt acttttgtaa aatgagaggc tattttatca ctcagagaat gtcacatcaa 420
ttgtaaagcc atcaggccca aggtttggtg gtgattgctt catatttact gttagtccag 480
caacggggat ggtactttta cagtctttgg acagactagt gagtgtgaca tttaaagtgt 540
tgatttttgc agcacttatg ttaattgttg taattttcct gatgaaccac cattctggtt 600
tcctgatgca gccaagatag ttttacattt tctatgcagg gcctctttgc catttggtct 660
gtgtagtgtc agcttcgagt gctactgaaa gcagacaaaa ttgcaagcaa attgcatcag 720
attgccaaca ttgtgaaaag gtaaattgct tgcaaatcta tttaaaccac tgccctattt 780
tcatcagctt cagtacttgg tattcatgat tgcttaattg gcgacctttc ctattgtgta 840
gtgctttatg gtgtaatgga aagcgatctt taccaaacca attacccttt ttttctcagc 900
actacattat tgctgtgatt gcaactgcca gtcctttgta aatgaacttt ctgatttcaa 960
tgatgttttt aaaatgtaag atagaaaaaa gtggcattca tattgtgcga tgttctattt 1020
tgaagcctct ttgtagtcac cattgtctgg gaaaatggac tgaagggtta cacagtacct 1080
acaaatatcc atgtaactat tattaatatt attataatgt cctcctttgt actgcagctc 1140
aattaggaaa ggataggaga aatattttgt caccctgtca agtgcacagg aagtgcattt 1200
gaggcttctt ttttgacaca tacattatct ctagtaataa gattcgtttt aaggagtggt 1260
gatgaagata caaaatcaat ttaaataaaa ttcacattgc tagttttatg gtcactcaac 1320
atttaaaggg gagctttaaa tgactcaaat attcagactt agaataaaag cttaatttta 1380
aaagagatag ttgtgagcat actaagaaat agtgaatttt taagatctta ggttctgaat 1440
atacatgcca agacacagca aaacatgact 1470

<210> SEQ ID NO 6
<211> LENGTH: 1910
<212> TYPE: DNA
<213> ORGANISM: Homo sapiens

<400> SEQUENCE: 6
gtgattcctt caagataaaa acaaaactct gccaggcatc actaactaag gacacctcct 60
gtcacctaac aaaattagct gattaggagc tcacagtaca cgtgttcacc ccttttccc 120 acttaacatt gattttccct taaaacccat tttaataccc actactcctc tcttgtccca 180
agacctagaa gatgcggagt ataagagaac agacaatact tacaacacag tccccaggct 240
ctggctagct actttgcgcc aacttctctt ggtgagctct ctctagctgc gcagaccctc 300
taggaacatt ctcggtatct ctctgcctcc ctctccctct ccctctccca ggcaatgctg 360
ctcccattag aggaattaaa agtggttgga gccatgctaa atttaacaag ctcattagta 420
ttctttctga gtgcttccga gtgaactctc cctattcaag cctctctctc cagcagaagg 480
gtcaggcggc taatcattaa atcaaactaa tgtcacccta tcacaatcag cctgagagaa 540
ggagggttta ttatttcagt ttatgctaaa taaacggttt tacaaatggt ccccaagcaa 600
ggtcaacagc agcttcaatt acaagacaaa cttaacaaga gttgctataa accaagtact 660
ctgtattgac ttaagaacag gctccactcc acatattgcc actagcagga ttgtacagga 720
atgcatattg taaaataaag gaaggggtga gctttttttct ttgccagaat ttgcgagtgc 780
acagcgactc ctcattcacc tctctccaac cagctagccg ctcagctcaa ttcaccccac 840
acaaaggctg gagcctagac ctcaatggac cgagtgaaac atgttcaaaa ctaggctctc 900
tattgtgact gaatttctta acatcttttc aaaaagcgga gaatgccttg aggctaaagg 960
aagaaacagg ctaatggtga attgggaatt ctgagcaaat ttcagagccc tttcctccta 1020
gcttttgagg ttgaaagcaa gctctttcct ttcaagtttc aaagtccttt ttcctcccgc 1080
agtgtcacag aaggatttga aaagaaggta attgtgctcg cagtctccct gatcagagct 1140
tacgtcctat ttctggtatt tcggaatact tcttgcaata atagtgcata tagctcaatc 1200
ccttaaccgg cctgcactct gcaattgctc attaaatgaa caattgcggg tataaaatgc 1260
cttttatgtt caaggtctgg atataagata agcattctag gactctaaat ttggtttact 1320
aaggaaactc tccatcatta aattacaaaa ctgaagtcag aatatcaggc tttcccagaa 1380
aagtggcact caggttgcag ccagccaaaa tgaagggagg atggggcggg cagggaggag 1440
gcaacaaaat gttaaggggg ggtgggggga aagaccggag gatactcaga tttctagcca 1500
aatgagattc taacaagaaa atactatttc catatttaag gtctgagttt gtgaaacctt 1560
gtaacttcta tattgaatga tataataaag tcacgttcaa atgaattaaa atacaggact 1620
gaggctccat aaatatgttg ttgactaatc tggacccctc acaagcaaac atcttcccca 1680
tccttaagaa aagaaataac cctttcccat cattatttac atcatctcat gtgatcctca 1740
cagcaaccca atgatggcgg taggacaagg tattaggccc agctcagaaa ctagccgtca 1800
tgtcccaggt gagtaagtga tgcaaagaaa cttcccagta tgctttactg aatccacacc 1860
tccctgtccc ctgttaacag gacaagagct ctgttcctgg gtaggctttt 1910

<210> SEQ ID NO 7
<211> LENGTH: 1853
<212> TYPE: DNA
<213> ORGANISM: Homo sapiens

<400> SEQUENCE: 7
agaagctgac caggtgagag ctgagtagtt cacgcacagg aagaggggac aagtttttct 60
gttttcacag gggttcctca cgctcaggct tccagcgtct gcctgcactg acatcatcgt 120
ggtcgcgatg aaaacagtga aataggaacc ctgacctccc cttccatgag aatccagcag 180
agaatttgct gatgtgttat acatccggga caatcggaaa ctgccgtttt gattgagtat 240
tagttgggat gaggagcaca taccaggact cccagatctg gagtcctcac tttctcagca 300
agggcacctg catcctgagc ttttacatgt acacacaccc agcgattgtg tgtgccgaga 360
aagacccaca tacgcacatt gtttttttcct cttccacgat tatctgccag aattctactc 420
agttaattgc ggtttgagaa cacaccatcc acaggagagc accaatggat ctagtctagt 480
gaggttacat ttacttgtaa tcctccccct tccctttccc atttctttga tgatttttcc 540
cataagtgtg taagctactg ggacttagta gaagcaggcc gctcctccta aatgtgattt 600
ggaccatatg ctttctacat tcattcccgc ttcggctttt cttctctgca ctaactgcta 660
acacgttata gtcaccttga aatttcctct gctattttcc aattaaaagc ttaatagccc 720
tggaaacgga gttcatgtgg tgaagtttac cacagcccct tgttctgaaa ggctttctgc 780
tgggatccca ttatgtgctt gaataaaccc tttctgcaaa cagaaatggg actcggggtt 840
gtcaggtgtt gggttacaat agactttgag gcaggggaca ttttaccaac ataaatacaa 900
acctgtccct atagggagat gttgtcaaat actgggatat ggaaaacatt cccatcaaat 960
atgagaaaag gattactgca ctatatcaaa tgagtattta gatctcagcc cccgatgtgc 1020
accggagtga aacgggcccc cgggaccaaa tgccagactg tttgagtggc aacgagatag 1080
ggtggctagg tgaccgacgg gggaaaaggg gtcgccttgg tagtgaaagt gcccccacaa 1140
acctggtgca gagctcttct gctttccttt taaaaattta ttcatactca agttctttat 1200
acttcctcgt ttcactgttt gaagaaaatc ggaagaaatt tggttttgaa aaaagtcgtt 1260
ggtccccacg tttccaagag atccggaggt ttcagcgcaa tagttttcag ttaaggtgtc 1320
atttgaggcc ctctatatcg cagcacgtta aatgactcgc gtccagctcc ccatttccta 1380
gcctcgggcc tacagggctg gggcgacct ctgcctcccg tccccagagc ttacaaaatt 1440
ccttccagtt gtattttagg gcttgttttc ctagagaagg ttgagactag aggaaggatt 1500
aaagtggtgg gggaaggggc aagaccgagg ggtccctacc ccacgcggct ttggaggatg 1560
gcctcccagg gttagcactc gaatgctaga gcttcttgtc cacactctac caggtcagtg 1620
tcccgcgatc cccacctccc ggacgcgtat gaaacgggaa cagctaaggg cttcaaggga 1680
aacacacaac tggggttcgg ttttcaaccc tcctctccgc aaatcagcct tctgggcaga 1740
gggttggctg ctagaacgcc tggaggtgct tcccttgaat tcatggcaaa caccagagga 1800
aagttttcag gttgcttgct tacttccagg gcagtacaga gaaaagcggc ctc 1853

<210> SEQ ID NO 8
<211> LENGTH: 2890
<212> TYPE: DNA

<213> ORGANISM: Homo sapiens

<400> SEQUENCE: 8

```
tggactttgg gaggaaaaca ggcatagggc acagaagtgg ggggctgttc tggacaggaa     60
gatgaacaaa tgccttcctc ttctcttcac tgcccccccc cccaccaacc cccacctcag    120
cagagggaag ggatgcatct gctatcccca ctcatcactg gactccccaa gggccaggtg    180
tgcagttcgt tcacctcagg gagatccagt gcctggaact cagtgcatac ccaagtgatg    240
tttgttgaat gaatgaatct tagttagagc ccacgtctac aaacgaaaaa agagcaaaaa    300
gcttgtttcc atttccagtt cttgtttctg aagaaaatga agggcttttc tttctcccca    360
gagaccacat cttcttggcc cctctaccta gaccaatgca gagatgttcc agggatgttc    420
agtctagccc cctttcagtt ccttactctt tcccacctat tcctctccct tcttagatcc    480
ttcttgtgtt tatgcacagt atttgtttgg caagtgcctt gggaactagc aaaaccatga    540
ggacattttc ctgtcaccga taccctctaa tgtgtccctt ttgagttggc agcttaaact    600
gcttgctgaa taaaacatta acttcttcac cccaaccttg tccttactca attctggctt    660
cacagcttta ttgacagcaa tgcttatcaa cccactttta tggtgggctg aaagagattg    720
actattattg tgcccagatt aaatggggga gtaatgccac ccctgtctga ttgtgttgta    780
attggtcaga gttatataca ggtgcaattt gtaatatttt cagtaaatta aatttttttc    840
tctttggctt ttattgatgt atgttcagat gcccattagg gcttcctttt ttccagtgga    900
aattgcagca tgttaatttt cacacaaatt acagcaatag caggtatctc tatttgatac    960
attataacag gagcaatcaa ggataattga gtgcctttca gatggaaacg ggtgcattca   1020
cttcaattca aagcgagtcc atttatcgcc taatcggtct ttaaacacta aatttctgga   1080
acaaaaattc ttgtcataat tttgcttaag tgtatttgga aatcacagtc ctttgagcaa   1140
ggataattga aatcaaatcc ctttcaatgg aggtgacatt tctacatttt cccaattgaa   1200
attaatttca aaaattgagc atgaatatct tcaaatggca ggcaattata gctttcaatg   1260
ggaagaaatt atgcgcacaa aaaagtggag acatcaaata ccgcttcagc taaatgtctt   1320
tgtttccaac tgtgtttgcc ttgtaaagat ttacatatat tgacttatta tgcaaccttg   1380
agatgcagat cgccttcctt tttcatctga gcccattaaa attaactaaa attggaacgt   1440
tcttgttaag cttcatcaaa actgtttgga atttactgca gctgcagaaa tgtgttcata   1500
atagaactta acccttcaaa gacttgaatt ctaccccccat tttttttaaa tctggaattc   1560
taacttcagc gcatttcatt gtttcacttt taatgattca aaagaggagt ggtgaagaac   1620
tgatatgcta attgtcttct ctttttgtca tctggtaccc atgggatctc aggtaaatct   1680
ctggagcctg tccccctttga aaactgccct gaaggacaat actgagttcc cagagggcac   1740
caatatgcca acctttaata tttaaatgta atcatatcaa gccgatttcc cactcctcac   1800
aataggaatt gctcttattg ttggactgtg acaaactctg tgggtttcct gctgcggacc   1860
ttttcctact aagaaccttt tctcccaatt gttttattgc cacattaatg ctgctattaa   1920
gatccgtgtg ctataaatta gataagcttt atatattttt ttattcatcg tgactttctt   1980
ctgttttcca agggtaaaag tatattgaga actgactctt gcaagcactt acttttcgaa   2040
agtagtttag aagcaatcta gccatgtttt acagttatag cggcaattgt ttcaacaacc   2100
ccaaaaaaat tgcattactg aaatatattt catgggtgca attggccagg gacagggagg   2160
gcagcaggcc atttctttta ttaaggtctt gcgcaaatgt tatgaagagg gcagtatctc   2220
aagaaacaat ttcacagctg gtttgctcct aagccactca agcctaaaaa tgcaccgaat   2280
```

tcctggtgga aaaaaaagaa atagatgtca ctcccaaaca aagacaggtg ctaagctgcg 2340
ggagatgaga gaaggggtga aaacagtatc cagctttaat agcaaaagca aatgctagct 2400
aatggcccat tctcaggaac tcgttaagtc atctctaagc aaccacagga taatacactc 2460
gttatttctg ctggtatgtt tcctaaaagt gaggcgtatt gctttgagcc cagaatctta 2520
gtggatagtg cgcctcacct ctgtattaac ctgttggcac gagacctttc ctgccgtctt 2580
atgccttctt aatggaattt ttattagtca tttgggtgtt cttttttact ttattttctt 2640
tgctcttaat ttttagcttt ttaactaaaa atgtttttaa gttacctaat gtttttttgtg 2700 tcctataaga gaatttcccc ccttggttca cctgctgatt ggtttttgtg tatgataaat 2760
tattcagagc ttatgcaaag tgtttaatgt attttccaag ttattgtttt agtggaagat 2820
ggacatttgt ctttgggtag gaatatgtgg gttttttacg ttcaaagcag gagttgtttt 2880
ctgctcaaat 2890

<210> SEQ ID NO 9
<211> LENGTH: 1702
<212> TYPE: DNA
<213> ORGANISM: Homo sapiens

<400> SEQUENCE: 9
tgggtgatga acatgttttc tgctggggta gtaactcaga actctaggcc tttggtacag 60
ttgatcctta ataagactta gtttcaggtt ggaaactgtt tgttgaaggt caacattttg 120
ttgctgcttt ttctgctcaa atgtagtata gaatcatgtg gaggataaaa ttttgctagt 180
tgttcagcgt atccagaaca gagttctggc agttaaggcg tacaatactc ttgtatacct 240
caatgatggc gctttttaaa cattagggta gttttaaaaa attgcaataa agtcattgta 300
attcatagac catgctgtaa tacagagata cgtgtaaaat acaatctgtg tacctgattg 360
caggtaacag agttaaatgt accagcaatt tcaaacacag tttgatattt cctataataa 420
aatataatgt aaaaaattaa atatccaata tcaatggatt ctaaatggtt ttgatatttc 480
tttttgtcct ttcccatgaa gagtaattta tttccctttt taaagtgtgg gcagaatgat 540
tactagcgca ctgtaatgta attgtgttgc attgataaaa taaaaattgt cctttatctg 600
tgtcctgata atgttcaatt tacaggctgg cttctctgcc acctcttcag tgctttgagt 660
attccagttc tcctcccttc ctgctctgag agcgcacaga actgtttgaa atccactggt 720
acaattgtca aatcaattat tcattctctg caattatgct cgcacaaaga acattttgct 780
ggtctgaatg atgattaaat taacagctat tccagctgcc tgataacatc taatagaata 840
ttcataagcc caaaatggaa tgaattatct ccattaactt catcatgctc acttaattac 900
atgcttgtta ttgtatttac accttgttag ataccgctga agctgatcca gtggctggcc 960
gggaattgga agcgtctgtc atggggcagt tggagcgcgt tttgtaggaa atgctattta 1020
ttttaaatgc tccacctgct gggagccgag gttagtcagc agcactgaga tgaattggga 1080
aacggggtgt aaaaagaaat aatgtgcttc tgacaggctc cgtggctttt aagttgctct 1140
cattcagcca cttcacaaaa aattatttta ttccatctct cagtgatgat gacatgattg 1200
ctttttggta atcatttacc attctgattt tattttttga agtaaattgt ctgaagtaat 1260
aggttcttgg aattacagcg tgccttgctt ttttcttaga actttattta agcttgtctt 1320
ccagcattta acccgagtcc cctctttcgt ttgatcttct aactttattt atacaacagt 1380
gcttaatgat cctgcacaat gtgtttcttt tttttttttc cttctctaca acctcccccc 1440
ccacacccac ccaaaaaaaa attctgtcca gtatggttga cagtactttt tataacctca 1500
gcaagggggc tgcatgggca attttcttcc gacatgacaa atgcaaacac ccaaaaccca 1560
accctgagag aatcacttca tccagttgaa aggaaatttt ttatctcttt caaggtgact 1620
cttttgccac tgaaacatgg taaggggcac gactcttacc ttctattctt gtctatagaa 1680
gtggcattct ttacattgct tt 1702

<210> SEQ ID NO 10
<211> LENGTH: 1689
<212> TYPE: DNA
<213> ORGANISM: Homo sapiens

<400> SEQUENCE: 10
ggagttaatc ttgtgactgt tgcccaggat gtgggggtta atcaaagttc caagactgga 60
atttgggaga agttgaaagg gaatgaattc actgcccctc accatcaccc ctttctccag 120
cccttactac ctcttacctc caacacacac accatgctcc tcaatatact tcttcaaaca 180
tcatttaaaa ttagtttggc ggaagatgca acagtaagga aactccaaaa acagattttc 240
ctgtttgttt tagggtttta agaaaaacac caagccccag accctcttgt caggatgccc 300
gaccctttaa ttcgatgctc ccatcccaaa tttaaagctg ccattccctg ctcctcactg 360
tctctctccc gccccctctt tcttctctct ctctgtctct ctctctcttt ctcacccccct 420 ctcacctaaa tatttcttaa ttgaacagtt tgtggtggag cttccttata gcagtttaat 480
agattaactc atctcagcca gcctcaaatt tcagattaaa attccttcat cccgaaggca 540
gcattatcag gttgttggag gctgttttca aaccttggtt ttgaatagca gcggctctgc 600
attaatttaa ccactaagct aataagtagg tttcgttttg ttatgctaag ctttattgct 660
tttcttttga tcagaatggt gttgttgagc aaagcagcag acaaggcatt ctttgatgag 720
ggaattagcg ctccattctt cctctattat tcatagcgca gtggaatatg taagtacctg 780
agggtgtcaa aggagcgcag gttctattgc aaagtgctcg ccttgtttct ctcaatagct 840
gactatgaga tgataaaccg cttaatacac tgtgctaatt ggatgagagc aaaaagagat 900
gggaattaag gcgaggcaaa aggagaaagt gcaaccagcc ttcaattcac tctttcacca 960
ctttaacagc accaaaggag gcacaagctt tctataagca gactagaggt tttgtgcaga 1020
gataaaatga acgtgttagt ggattcaagt aatacactaa ttattgcaca gtataaatac 1080
cactactggt tttataacag ggaggtaaac ttcttttgag agggttatag gattgcttgg 1140
cagtggtgta gaacctaata agggcccaga gtaataaccc cctggattaa caaaattgct 1200
gcttgtagaa gtatgattca ggcttttacg aagatttccg gagaatgaat aaaaatgact 1260
gaatgacatt tcttaatgta taaccggtaa tcactcccat atctttaaag gaaaaaaatg 1320
tatacttcaa actggaccct taataatgtc cagggaggga taacaagact tcttcctttg 1380
aaaaatgctt ccccccaccc cacgcccccg cccgctctcc ccaccgtcag gtagtgggtt 1440
ttcttcttcc tgtcccccag ccaggctgtc actctcagtg aaatatgcag ttgttctggg 1500
gacttctgtg ttccaaaata ttattttagg ccccatttaa gaccccccttc attcagacac 1560 actcactttt gggtatacac ataaacacat gctcatggac ttttttttct cctaaagcaa 1620
gttgggctaa cctattataa tttgtttttc tctcacatca gccccttttg tcactctagt 1680
aagatcaca 1689

<210> SEQ ID NO 11
<211> LENGTH: 2110

<212> TYPE: DNA
<213> ORGANISM: Homo sapiens

<400> SEQUENCE: 11
ggaaacatta aacaattcaa gatagtcaat atcttattgt atcaaaagga ttggcctagc 60
aaagaagtat tatagggtg aagtgaatgt gggctatagt aatctaggac tgagtttgac 120
taggggagtg gaataagagc aaaagggagg cttgcttgac tggaggaaaa gcatcaggaa 180
atatgttgag ttgtggctaa gcatgtgatc tggggacaaa taagaaatct tcctaatgta 240
aatcattgga attatctcat agataagttt ttcaatgctt ttagcattgc cttgaatact 300
ttctggacta agatggcatg caaataacca aacaaagcct acaatgggaa tctgaagaca 360
ttttaagaat tgtgtgaatg tgcagaaaac caggatgttg ctacttgatt gacagttgac 420
tatgtacata taaaaacaca gagttatgga cttaatgcag gttaagcaag gtgtatttga 480
tggcatgtat acatcataca aatatgatct taccttgttt ttaattccat cttggtgaat 540
acaagcatat taaatattcc acttgcaatc gtttttctca gcagttcatc cattgacatg 600
cacacacacg catgtgagca gatgttttct agtacctttg gcagaagaat ttagtgcctt 660
gtacacatca cacctgccat gtcatgctta ttgattgagc aattcagctc gctgaaaggt 720
actgggttag atattaattt taaaatgaaa gccttcacat ctgctaatgc ctgccagtct 780
ctggagtgaa tgtgccattg aagccaacgg aagtgggcag aagcagcctt catgggtagg 840
actgacaagt tattttgagt ctactgaatt acctttattg ttgccccata cttataggca 900
gacctctcct tccgttaaac tccttcactc acagtacttc tgaaaatagc tctggtggtt 960
tggaactggt cttcctggat tttcacgcaa atggaatatt tgtggtagtt gagtgataaa 1020
tggtgagata atggtgtttt acaggcagtg aaatgacaag gtcagtttta attaagctga 1080
gatcaacctc agtctgtatt gcacacttct gattaggtta tttcaaatta acataagttt 1140
ttggagactt cgctgaagtc agtggtgtta aacaccagct gtgctggcag agaagcgtgg 1200
gatatgagaa ggagatagca ttcacattga aattagcact tggcacaata taattctctg 1260
attgcaaact atgtggagtt gcctgtgcta attggttgat tttatttgaa gcagatgttg 1320
ttagctttcc caataatgat ctggagagaa attcttttga aagacatgcc atgttaggat 1380
ctctgcagta taataagcta attacaactt taagtacttg cagtaattag cacaatgtgt 1440
ataaagtgtt cctgatcttt tcaccctgcc gcattattgt cagggcagct tgaaaaacaa 1500
aaaggaatgc tagatggatt gagtctccct ggtctagcct cttcgtttcc cagacttctg 1560
cactaaagag ataatgaact cgacttaaat ccttctcttt caagcatgcc aaaaaaggtt 1620
taggaaccaa cccccaccat acaacgccca aaaaatggag agtgaaattt gccaaactaa 1680
atgttgcttc aaacacatat gcctttaaga ggcagtgaag tcttcaaaca ttagcaaacc 1740
gagaccgtta acatatttat ttcatgttca cttattttat tgtttaccaa tttggtccat 1800
ggatcaaacc cgtattttat ttgggaacat tataccatca cacctccaag ttaaacctct 1860
aactttcctg tatagatacc ttcaaatgtt tctgtaagcc taaaatccag tctctccata 1920
cttttaaaca ccaagttgtt acagacacat attttgctta tgttaataat gagagtgaag 1980
acataggagt agatgtggct ccccacatct tcgtatgtga gaaaaatgga gaaaaaaatg 2040
aatggggaag aaaataattg atagagacaa attcttaata acatagtaag caaagtccac 2100
aaatggtaag 2110

<210> SEQ ID NO 12

<211> LENGTH: 1661
<212> TYPE: DNA
<213> ORGANISM: Homo sapiens

<400> SEQUENCE: 12

```
aactgttccg agccaatttc agcatggact ttagtttaag tctgagtttc aagtcccaag     60

gaggcccaaa gtttctcaac agtcactctc cctaattatt ccacttacct ccccacacac    120

ctaagatgcc cgccctgact actgtccaca gttcgggcca tgggtagttg gtgatggaag    180

gacacctctg ataatattat gccaaatgcg cccttttttgc cttccaggac ctcctccaga    240

tctggctaac ctgtctgaaa atgtagcaaa ttaacttact cctttccctc aaccctccca    300

cagaggcctg tcccaggctt caattacccc tcaccccaag atgctgtggg ggtggccctg    360

ggaaagcagg tgttgggcca ttctgccttg ggtgtgatag gacacagcca tgccctgaac    420

tgggccctcg caaactccct ggggctctgc atgtcctcca tggtggaaga ggtttgctta    480

aggttggggg gggggggtca gccgctccca gcattgtgac caagttccca gatattgggg    540

ccaaattggg ttgccattca ttaataatgc tcacaataag attaaatcat tctggaaaat    600

ctcataaaat ccccctaagt acgctccagt ggctctttcc aatccccatc attcagcact    660

tggggaggtt tggaaggaga agaaaattgg tttctttgct tttaatgctg ctttgaaaag    720

atactcagag tttttcatgc gtgacatgtc acatgtttaa tgtggacttg ctggaagtca    780

gggggtcttt agcgtgtgat atttatgggg aatattaagt gcagaatgag gtccctccag    840

ctggggaaag ttgaaagaat aggaggccca ggactgggct tgtttgcagc atcagaatga    900

cataggatta agagtttgta aaacaaggcg aggggttctc attggccagt aataaatgta    960

atccttggag gtaatttcac gcaatttgct tctgttccat ggaagggtca aatgagaaaa   1020

aatgacttaa aaaagagttc attaacagga agaatggtac tgtttctcgt ataccatcca   1080

actagcagcc tagagggggg aaaagaagcc ctactaaaca aaaaggcaaa atcgacgcaa   1140

aattgatatc gaccacaaca cacacacaca cacacagaca cacacacaca cacacacacc   1200

caactccttt ccctcagtct tctccagcag tcccgtctcc tccccaaact ctccagcggc   1260

cctgaccacc ccaggaaagc ggctttcact cagggagagc ctgtggatgt ggagtctgag   1320

ggttttagac tctcagacct ccagtaaggc cctagaaagt tcccaccggg cctactaaac   1380

ccgggaacgg agtgtgtggt aggaatggta gttggcggcc gctccccata ccccaggccg   1440

gggcccttct tgcgagtgcc gcccccgtga gtccagggct agcgttgggt ggcggtgatc   1500

cacccgacga cccaagtgcc agaagcggcc accagccggc gagccggttc cgtgagctct   1560

ccaacgtttc gggcgggcgg ggtctccggg cgtctggacc cggggttgga gaggagggga   1620

ttgaagttgg gggtgaaggg gggtgcagga taggaggcga g                       1661
```

<210> SEQ ID NO 13
<211> LENGTH: 1614
<212> TYPE: DNA
<213> ORGANISM: Homo sapiens

<400> SEQUENCE: 13

```
caacggaaac attagtgcat agtgactaaa atgattttat tcctttgcta ctggaattcc     60

ctaaagtaca gtggggccta tagagccagc ccacagctca tagggccttt cctccatcag    120

cttctggaat gaagaatgca ggaaaacatt gtctccatgt tgctgcaaga gaaacaataa    180

aagcttgatc agctgaatgc ttaaatatgg ctgaatgttt gatgagatga agatgtaatt    240

ttgtctatgt tccctaagga tctggattaa atatgactac agggcctaat caaatagcta    300
```

```
gtcactgaac aacggtccca actgcatttt tcattctagg catgcctttc tttccccccc    360
tcctccaagt acattactta ttcactggtt tgtcagcagt gtgcattatt agcgcttgag    420
agataaaact ttaagtgttg ctcccaatta gcacaacagt gaccacgcac catgctctgt    480
gcttaatgcc tgctctcaga gaggagctgg ttttgaaggt ctgaggtgga ggagaaaaaa    540
aatgaaacag cttaagcatt cattttgagt ggagagacag ctcctattaa catttaacag    600
catttgtgca acttggtgcg gaggttatga tgcaaatgag gaggaattaa aagtggccag    660
gggtttgtca ttgatggatt gcagtctggc ggtgttcaca cttctgccgt gtccatcaga    720
agcgattact gtgtaattaa accttatttc tctactcttc agtgcataat tactttgtga    780
atgtaaccat catctaaaaa agctaccaaa atgctttagc atttagtcta gcagtcattt    840
ccctagcttg tgtcagatat aaccatcaga cagtgcaaaa gaactgtcac ttttaataag    900
aggcaaaaaa ttaaatgaaa cagtatgctt attacaggaa aattaggcgt tcaagtggta    960
gagtcctttt ctgctatttg cataatttat tctttttttgt ccctcacacc agcagcttca   1020
ggcaattttc ttcacattta aatagatcgc acatttaagg ctacttaagg aaaattatca   1080
ctttgcatat tttaattgtt gtaaagaaag tgaatagaag aggtctgcag cttggactct   1140
tgagtcggtc agatgctcaa ctgtctgatt ctggagctcc ccactgctgc actagagata   1200
accctatagt tcacagctat ccacttgcat ttcatcagca tgcaaatgca gctccaagca   1260
ctacaataaa tggatctttg atatttacaa actagccatt aataactaaa acataatttg   1320
tttgacataa ctttagattc tcttatcact gtgccttctt tttttttctt tttcagagaa   1380
aaacctaagt ctttaacgtt tagaaaaact gagacagtcc actcaaactg agtcatgttc   1440
tacaggttcc agaaatatga tttgctacaa aattatgtca gttccattat gttggcaagg   1500
cagccaacat ttcaagttct tttgtttaat ttggactcac ttttattcaa ataaaaaatt   1560
caacaaaaaa ctctttcccc cataagaatt atagcaagcc aatggtgttt caaa          1614
```

<210> SEQ ID NO 14
<211> LENGTH: 1461
<212> TYPE: DNA
<213> ORGANISM: Homo sapiens

<400> SEQUENCE: 14

```
atttcctttg ttgggctgaa ttttcaaatc ctttatggag ctgcaacaga gataaaggct     60
caggacaaat gcagcgaact ccatcttcca agcagtgcca taaaaacagc ctgactcttg    120
ccttcctccc cgcaaagttc cacattctat aaataagcat tcctaacatg ggccctctta    180
ggccaactct cagcctggag ctaatgtttt acagcagagt tatgaacccc taaaaataca    240
ggtttgtgcc acaaacgatg gcaggcccat aagtatagca gcactactgg gcaccactat    300
aataagatgg agatttcacc atctaatacc tagatctcca ttagtaaatt ccacagctca    360
gtaagtttgc ttcattatct tattaggtaa aaagagcaag ccagcgcacc ctgaccaagt    420
cagcctgtcc agaatgctaa tagatgtagc actaaattat tctcctcttt taaagagttg    480
tgttagtgac attttgtttt tatcaagtaa tgcaattaga cttcagcctt aatatctctg    540
aggctgtcac atccctgaac tccgcagcac tgcttgccag ccgcaatcag aaataactct    600
gtcccttcaa cttaatgaaa aagaagtact tggccataaa cttgtagtca tcctctatcc    660
aatcatattg tcttgagtaa ttaaaatgat tagcttaatt agcttaatta actaaatttg    720
actacaggac atggccatat ggtgaagcaa aacaaagatg ggagctaatt aaagttaaaa    780
```

-continued

```
taatgcaggt tttaattaac tcaaccccta ggcatcaaca ttttcaaatt tatccaagct    840
gataattaaa aagtcctctt gcccaagcaa catttcttct ctgagctaat taaatctgga    900
aatgaattag caacacgaag ctccaaatat taattcctgc tagaagatga cttcacttcc    960
taatgaaatt aattagctgc gctggacctt caatcagacg ccaaacgctg tccatgaaca   1020
cagacctcat gtaatctagc gcaaggatac aagccctggg gcaagaattt acaatagtaa   1080
tgaacactct ttaactgggt gcctctccta atataccaaa ggaacatgaa gatccctttg   1140
tgccatgggc ttcctctcct gtttaaacaa gttggtctca cagatagtta aaaagtaggt   1200
tgcaaataat attacctgta aagcatactg ctaccggact gcagattaat cagttttagt   1260
tctctccact gaggtcgtgg tgtgagtgtg tgtgtgtgtg tgtgtgtgtg tgtgtataca   1320
ctctcttatg tgtgtagaga gaaagtatca tatcaaagat ttggtataat ggggaaagtg   1380
taacaccaag actcaggagt caacttgatc ttcctctaac cagctgtgtg actcagggca   1440
aatcatgtca cctctctggg c                                             1461
```

<210> SEQ ID NO 15
<211> LENGTH: 2166
<212> TYPE: DNA
<213> ORGANISM: Homo sapiens

<400> SEQUENCE: 15

```
cataagggag cacaggaaat tcactactgc tgaaagcaac acaatttgtg accataaact     60
acagaacggt gggggaaaag ccatcatttt aaataatagg tcccaagtct gacttagggg    120
cgagtggaga gcatttggcg tctcaaatta ctttaacagg gggccctgtc atatcccatg    180
gaaaggacac tccggtctcc cctccaccct ctaatccttc tttcttaaag gaacactcag    240
caagataatg aatcctttaa atgttacatc ttctgtcgtg cattattgtg gtgccgaaac    300
tcttcacatc aaacagtcat caggactatt acaaagtggg cttataagag aggggctgaa    360
aaggagctgt gtgaaaagaa gtggaaaatt aaagctgaag cagtcgaaga aagggcttaa    420
tttactggca tgtacagtat gcaaatgaga ttactctcag cttaactgca tcatttatgt    480
ccataataac ggcatcatca ttacagggct caaattaaat tacaccataa ttagcatatc    540
aaagtgattg gttaaagttt aaaacaaata cccaattttg ttaatgaaca gctgtaattg    600
tcatgtacac ttcagtgaaa actctctaaa caaatatatg ttttagaaga gaggaagatt    660
tttttttaag cagacaggtc tgtagcagag gtaaattgcc taaaaaaaga atgacatgga    720
ctattctatt aatgttaata tatgctgatc attttcaggt aataaaacat tctatcaaaa    780
caaggcttcg cttatattta gacaccttcc ctgctcttga aagtgacaaa ccaccagaaa    840
cctgcttcta cttgcagcaa tgataacaat gcaggggtga cctgtctcga acaagcaaag    900
gacatgttcg gtaacatgct attactaacc ccccatattc atttaaaaga cattcgtgtt    960
caaatcgtgc tgagtcaaag ctgatttttt tcctcattcc agcccaaaga gggaagagtg   1020
acagaaaact tgctgcacct atggcataga ccagaacgct cctaagctga tgccctgata   1080
acatattaga cagcctccaa ctcaatttct cctcatcgaa tcatagctac acagcagttt   1140
gaaacacaca gctgcactag ggaagtttgc tcttccatca ttaaaataca tcaggaggta   1200
cagctagcta ttgtcaattt tggctggaat cagcatgcac acaaatttcg tatatgtgaa   1260
accagacact aataataagc ttgtttccaa accttttgt tataaccatt taatgtcaga   1320
agagtttcta tacaaaaaga tttgtcaata atctggaggc tcacatgtga aaaagctttc   1380
cgcctaagat tgtcccattt cttaacaacg taccccatat gtcctctgag acaactgtga   1440
```

```
gggtacatcg ctgtgataca cagcatggca agccaaaata tattttgccc aaaaaggaaa   1500

aaaaaaaaaa aaagcacttt caaatatact taacaagcaa attgaatgtc ttattaaaat   1560

cgtattatct aaacagtgtt caaaaattta aagaaagtag cttttcattt tattcatcga   1620

agaatccatt aaagcttagg ctctgaagta gtatgtaaat tatgtgcctt tcaaggtaga   1680

gctagggcaa attcactcca tcaactaatg atgaacctca ttatgtgcag ggaggattca   1740

taatgaggaa agagccaccc gccattccat gttctaacat aaatccctgt aaaatttgaa   1800

tatctccccg tctaattaaa ggctactaat tccaatcacc ccctccatgg ccccaaagta   1860

aaaataaacc tctctaaaag cacagactac agttatattt ctaaagcagt actcgatcct   1920

gtttggactc agaaccttcc actcagatgt gtttttcgac aagcataatt agcagctttc   1980

taagatagaa acttaggggc tgctcaagct cattttggtt aaatacactg aatttctatt   2040

tttcaaagag cttcaccttg acagggctac agtgcatgca cagagatgat ccgcagccaa   2100

gaaaccaaca ggaatgtgcg agcacagtca taacgtaaaa taaaattctt agcactcgag   2160

tcccgt                                                              2166


<210> SEQ ID NO 16
<211> LENGTH: 2163
<212> TYPE: DNA
<213> ORGANISM: Homo sapiens

<400> SEQUENCE: 16

ttgccaaaaa tacattcctt attactagta agcctaggct gaaaataaga atttaacaaa     60

atgttgtttt ctgacttgat cttggggtgt ttttttaaac tactattttg catgttcaca    120

gcaaagttct tagcgcttgt tcattccctc agatcctttt ttttttcaat taaatagctg    180

ggaaaatgtg taaaactatt agctctaggc taaataaaat gaaaaaggta atatttagat    240

taatacactt ttaatgaaca ttttttgggg gggtaacaag cagaggaaca aaaataaaat    300

tgctgtatgg ctgctgcact tcagaaaaag agtcaagttt aatgataaat ctggccttag    360

agaaccagcc agaatggata gggtctgaat aggatttaaa aacccaactg tgtgcagaaa    420

ttagagtttt gcccctgaat catatggaat tacagtgctg ggtgcgtgtg ccatgcctac    480

acaataaagc ccagaggaag cagctatttc tgttggtttt attaaaccaa ccaagcaatt    540

taattctttt gttcaggaga gttctacttc attgattaac aaaagcaggg atataatttt    600

ttcagccttt ttgaaaagcc tgaaatgtca agccttttaa agcagattat tctgcctctg    660

tgcagtgaat acagccagag taaccttttg tctacaatta aatattctag cataaatata    720

aaagaaaatc agagatggga aagattgact cacgagagat tggagaggta gattcacaca    780

gtgatagtgc aagcagcttg cttctaatta aatatgcgac tgagtctcaa tgcatttgct    840

ttcagccgca gagagaagaa gctgcccaag aatggaaagg aagaaatata tcacatcatc    900

tgtctgtcca caggctttcc ttggggctta tgaaggtatt tttagaatttt tatattggca   960

tttttcaggg gagataaagg tgaaccctca agggcagtca gacaacagtc ttgaaagttt   1020

gggcttcctt gttggtacac taacctgact ttaatagctt tcttattagt caataaccaa   1080

ggttaatatc aatgactttg tttttagatt tgaagccatc atgtatgata ttgccagacg   1140

tattgctgtg ctttgggtga ccttttgtta ttttgaattg gggctactta ttgatttttc   1200

tctttttcgc ttactttatg ataaattctt taatgcatat tttggtattt gtaccttata   1260

agtatgaacc cagaaagcaa aattcaagta tccttagcta tttctaacaa aatgcatttt   1320
```

-continued

```
agaaaatgat aaggtttgca gttggagact tagctttatt tatattcata agcctttcat   1380
ctttatacat actcatggca ttttcaggga agtacttaaa tatggcactt ataaaatgct   1440
gatgacataa aatatggttg atcctcttag ggtttgctgc ttacacagaa aaatcggaaa   1500
ataataagaa tgaaatttct ctactctata actttacctt tccatttcag attttgacat   1560
tactgaaatt attggaatta ctttgaggaa ctttgcctgt tgagtgtctt atatgcacat   1620
aagaactttt cccatttgca ggtgaaattt gtatttgttt atgaaaataa ttgattggat   1680
tgaaacaaca tcggaattca gttggctttt agtttgtata tttactgtac ttaatgtgcc   1740
atgggttgtg attttgaata gaatcataga catcctgtgc attttggaag cttgccactg   1800
ggaaaggctt aatatttgta aattaatagt ttgcactcct caaaaagtgg ttagggcaat   1860
aattgaatgt tagcaataaa gcttaaaatt ttccatcttt tgagatttct ccctctttta   1920
ataagtaact ttgtcaagca acattctcta ttgaagggaa gaaaactttc aattgggtct   1980
taatatacta ttcacctttc cctttattaa tataaagatt atgtttagta ctgtgtttaa   2040
caagaaatgt acttacacaa gtatttaatc ttagctttct taaggaaata ggcaaatatc   2100
ttagttacta atattaaata tattaaagct tacacataaa gcactaaagg atgtcagaat   2160
tga                                                                2163
```

<210> SEQ ID NO 17
<211> LENGTH: 1591
<212> TYPE: DNA
<213> ORGANISM: Homo sapiens

<400> SEQUENCE: 17

```
aaatggttgg ctcaaataaa tggttctctt ttaagtgcat tttatccctt taggttcaca     60
caataacagc aatatatttt taaagtatat attttactca aaaaatacat aagtaagtca    120
gaaaccaaaa gctaacagat gtgtgacttc taattagtta taataatctc tgcttcaatg    180
ccattagaat gagccttcct tttcttttga aaactaaaaa agctttcctt tgaattttaa    240
actgtcaggg tgcttcaaag tcaatgtaca aaatctgctt tgattaaaat tttagacatc    300
tacagtgata actttatgaa aggaaaatat taaattataa ttatcctaaa cagacacagt    360
cttgtgaaac taaccctaca ttcatgttaa aacacaaaga gttgaatata atgaatttga    420
ttcatcctcg gacacaaagc ttcaccacag taaactcagt caactgttgc tcttgcgcct    480
atattcatgg tgcttaaata gcgcacttta aaacaaaaaa aactccaatt ggcttttcat    540
acatccaccc tccccaaaaa taacgcactt gaaaaactca aatgatatga aaggcttcaa    600
ggcctctttt ctccctttca taccccccct ttttttttta tttctgtttg cagtaatctg    660
cctttctctt tctcattgct acagagcaag cgaggaggct cagagctttg aaaagggggc    720
tgtgtgtaat gggtccacta gaattaattt acttgcacca aatccattga gcacagaggt    780
tcttttcccc cctctctctc tctcttctca aatcatttgg agtcgaacgc agcccccggc    840
ctttgtaatt ctagtaaagc acttaaagtg cacagtaggt gttcatgagg accatctggt    900
caaaagcaaa acaagctgct gattttgcct ttgaatagaa tgaagcaagt gtgaattagt    960
ctcttcaatt agcactatta caacctgtca agtgcatatt gtaaaacagg attattacag   1020
tattggtcac cagtgcaatt atttactctc tgccttttct tgcatataaa aaaatcttat   1080
gtttattagt ttctgataac tgaacggaat ttctcttaac ccaggcattt caaaactacc   1140
aacacataaa tcacagatga tgaaatgtgg tcagctatca tgtttgatac acatatctta   1200
agtaacaaaa ggctaaagac tgttcttaat tcttaaaatg tcattgcttc tatcgtcttg   1260
```

```
aaatgcaggt agacaaatac ttatatgggc caaaaaagat atccaatcca gattattcta   1320

aaatagttcc agagagggga aaagacttgt cagttccaaa gagctgcatt ataaatatta   1380

aatttattac ttcaggggat aatttgttaa gaatcacagg aaacctcaat atttataaaa   1440

tgatccctac tgatttatat tcatttgaag tggtatgatt tcaacagatc tcagttttca   1500

aatgcaactt gaaactaata atatatatgc atatttaaaa gatgcataat cgtcttttct   1560

gaaagctgaa taaaggcttg aattcactgc c                                  1591
```

<210> SEQ ID NO 18
<211> LENGTH: 1560
<212> TYPE: DNA
<213> ORGANISM: Homo sapiens

<400> SEQUENCE: 18

```
ccctgatgga cagtgctctc ctggctggaa taccagctac tgcgactttc attttgttgt     60

tgttttatgc aggatttcac accctatttc tcttgggcat tttgcaggca atggtctttt    120

accaaaataa accaagtcct tttgtaggcc caaacttcaa gaagcaggat gaggtgtagc    180

agccccttcc catccttctt ccctacctgt tatatttact aaagagaaaa agtatgttgt    240

gagaggcttc ctccgccagc accgctcttc ttccagcatc ctcaggcctg tccctcagct    300

tgcctctgtc ccagggcact gtgacaagga cagaggctga agcccaccct cacatagcca    360

gccactttgt cccttcctgc cccaagctca catcgctgtt ccagcaactc accagggcca    420

cggaggagcc gccatgtagc agggaagcaa gacccctcat ccacattctg aggatggccg    480

cccgctcacc cattacctac acaatctctc agttacatta aaaaaaaatc tttccccccc    540

ttaacaatag agaggaacaa atggttgaca aataacaaca gcagcagctc tccaacaaaa    600

gcacgcaatt attacaatta tactatcctt gattaggctg ccatgcattg catttcaatg    660

taattgatgt tgtaggttga cacatcggac accaaatatt ctcgcctgtc ccttctctct    720

tttgtttcag aagctgattt gcattttcta tgcttttagt aatgaagact tagcactttt    780

cctccattag aaaaaaaaag agagatacaa taatctgcaa ctcggcactt gtttaaggat    840

tctgaccctc gaaaatacca ctttgcttca cacattagct gcttacaaag aaggaagcta    900

atgtatcatc taattgggca aaccactgca tctgatttct ctcaatcaga ctattagctt    960

cgtaattacc catctgcctc gtgtggaaaa acggcaaggc gcacacccag ctaataacgt   1020

tctcaagagc tctccaccac aatgagagga ggcgacgtgg agggatatgg tctctaacca   1080

tttcggtgcc aaggtggcca cacaatgcag gagggctttg ccaaccttcc cccgcctgaa   1140

tgtgtttaat tatttgtctt taattagtca gagtttttga ggtctgttca ggattgctgt   1200

ccctgctgct gctgctgcgg tggcggtggt ggtggccggg gcggatgctg aaggatggtg   1260

accagcggga aggtggggag gcttcccgtg gcctctgcag gagacgcttg ggttgaggga   1320

ggaatgtccc cgagtttggc aggtgtcctc gagagagaat aaagattctc ccaagattgg   1380

agtagagtgt tttatacctc tttttgttcc ttttcttctt cttctgtggt tgagccccct   1440

ttttccccat gtgggtgaag ctgcaccctt tgcggcagag ccagagttaa cctgaggacg   1500

aggacatcag tggtggcctc cgcactgcca gggtgtgaac attctgactg ccaggtgacc   1560
```

<210> SEQ ID NO 19
<211> LENGTH: 1800
<212> TYPE: DNA
<213> ORGANISM: Homo sapiens

<400> SEQUENCE: 19

```
gttttcacgg aaagcagagt cctataccta acagagatta cggtattgaa gggttacagg     60
tatctgttta gaaatatggt gctctattag aaaacaactt gtttgacttt ttttttaaa    120
cccatgtaaa atttcacaga atatgctcac gttttatttt aaagatcact aaaattatat    180
gcattgaaat actaataatc tttgtaaaag gtggatagat aatttgttta ctttattatt    240
catgaaggca agtaaggcat ggtattctgc tattgtgggc atattattaa catttcatag    300
ggatttgtgc tggaatgtgg aatgctgctt cttcataatt taatactcct atgcataatg    360
aggtttgtga ttagttgata gagagaattg gcccaactcc attctgaaag cagataattt    420
acattgttct ctagagtcta gaatctaata ggttctttag tgcaataaaa ttaaatgcta    480
catgttttaa atttcagcat acaaatcccc ctggcaattt tctgttttta atttttgcct    540
tttgtttcct ctaaaacaat gaattttaaa aattgtttct agaacatata tttacctagc    600
tcttttattt agtatgtaca agtcaattag cactgttcat tagcagaatt gggtatttgt    660
tttaaagttt aaccaatcac tttgaaatgc taattatgat gtaatttaat tgcaagtcct    720
gtaatgatga tgctgatatt atcgacataa atgatgcagt taagcagtgg aatctcattt    780
gcatatgctt aaagcaagtt gaattgggct gtttcaatat cactttgctt taattttcca    840
cctctgttca caccagccct ttgggttttt aaagctgtgg tttcctattg atgatcagtg    900
ctttcatctt tattttaatg acaaaggggc aacaactgac actggaactg taaaaatgaa    960
aagcaaataa ttacttctat taaatatacg aactatgaaa cctttttttgg taatgatcat   1020
tctttagaaa ctgacaaatg catgcatttt tggtattttc ttatagcatt cttacacttg   1080
gaaatgatac tatgaaagaa atacacgaac tgatatacag taaagtgcta tgccccaaga   1140
tgtttctact ttgtgaaaag tactttattg catcttaaaa tgttgtagaa agtagacatt   1200
gcaatacatt tttcaaaaac tttctgtgca ttcagatttt tgtgagggta tattccttta   1260
aaaggaacaa caaggcgtta tactcatgat tgagctgata ttaaactcca gtggttatct   1320
gtttttgtag aggtttggac ttgggtaatt ttcttctgga aagattattt ttcttctgac   1380
caatttctcc tgttatgtcc taattggtta cataaatctt gtctggtatg aatgagaaat   1440
gtttctgtgt tgtcaagtgt aatcttcacc cttatttacc aattcattaa gatctattga   1500
tgcaggactg gtgagaggga atgacaacat aaatcagccc tccaacataa tgaccctaat   1560
cagctagaaa taactggaaa cgtcatgatg agctatgtct ctgtattact tcggcaagat   1620
tctgtggcta gcgaggtttg tgtctgcttc gatcattaac tttacatcca ctcaccttct   1680
tctaaagaag ttgtagtgac tcttgttagt attacaaagt tctttttctc agacatttga   1740
atctttagga accatagaag aaaaaaagaa agagaaaagg aaactcacag aacagacgtc   1800
```

<210> SEQ ID NO 20
<211> LENGTH: 1255
<212> TYPE: DNA
<213> ORGANISM: Homo sapiens

<400> SEQUENCE: 20

```
tccaagttaa tcctgccacc tacaaaagcg ttctcagttc atacagagtg tgagattagt     60
aatcactatt tgaccgcccc catgtaggca gggaaaaggg gaaaaaacga aacaacaaac    120
cctaagattc aaatgtgtta aacctatttc atctgtcaga tggcaaagga atgatcaagc    180
tgctgctggt tttcgttgat atgtttaagc tttcttattc tggtagggca cagtaagttt    240
tgcctttaat ttaagatgta gatttcatta caatgaacct cctgacatta acagagggct    300
```

```
tcctttttaa agcttcactt taattgctat tctcattatt ttgcaagctt ttgccctaac    360
atatcccagg ggtcttgaca acatgcttct tctcttttta aaaaacttca aggcctgatt    420
gtgataaatt gttaggggct gtgaataaac actagttaaa ttacagtatc taaaatagct    480
aataagggaa caatttatga tgtggaattt aaaaggaatc cctaattgca cttcagtttg    540
ctgcgaggat gcgccttcta taacattaac agctattttg ttttgtgagc tggctctgtg    600
ccagggtttg agagctaatt ggaattagaa taacatttct cacaggccat tcatttgctc    660
aggctgagta caaattacta tgcaagggag gctgagggtt cctaatgata caggataatg    720
atgttttatt cagattttaa cgaggtgtaa tcattctggt tgagagagaa aaagattaag    780
agggtgcaac aattaccaat ttttacaact gattaatcgc aagccattac ttgttcttgg    840
tcaaataggc attataatga ctattaccat tttcagctat ttttaatgca aattgcatta    900
gcttgtaaaa ccttgccaac tatgccacat aaatgatgtg cctgaatgag ccagagcaat    960
gaaagcatta aaaaaaaatt cactttgaca atgtacagag ggaggtttga gtgatgagca   1020
cgtatttcca aaatgttcag acagggcagg acgtttccag cagacaacac atttggcctc   1080
agctgttagt aaagagctga aagagacaca cactctgtca ccgagaaagt aaagggtagt   1140
acttctgtct taggtatgca tggtgaaaag tcctccccat tccatgtgca aagctctggt   1200
tcagagtaac taaacttgac agctgtacaa gaaaaggaag cttgtcaaat ggcat        1255
```

<210> SEQ ID NO 21
<211> LENGTH: 1562
<212> TYPE: DNA
<213> ORGANISM: Homo sapiens

<400> SEQUENCE: 21

```
cttaggcaag cgagatcaac ttctatattc gttaagaaac ccactctgac atagaataga     60
ttcttaatta ttcagaaatc aatagcaaga cttactatta tttttttcca tcatgaagac    120
ctagtacttt ccaatttcaa atacagttaa ggggaaaaaa gccctttcca aacatgtcaa    180
ctaacatctg aaccatttta gacagtcaag tgtgtaatgc atcatatgaa agtatgtctc    240
acttgatttg tttcacttta ttttaacatc atccttaaag ccccttttc atacataact    300
caaataacaa ccccccaaaa ggcaatataa caaccttatc tccaccggtg tctacttggc    360
accagtctgc cctgacctta gacacaagcc attgttaagg gtataacgca tttacatatt    420
ttgcaataaa acatcagtta tttgcattac tgtgtcaagt tttatttgat tctttcacct    480
aaaaatgact cattttcctt tcttgtattt taaaaaccaa ctactctaag cttgtttgag    540
aataatcaaa aattgcccat ttagctagaa gtcattttct tttcaaaagg caaatgttat    600
ttaatctttc agctgttcat tgtgccatca taaatacttt cttttcagca cagttgtggg    660
gactgaaatg agcccactaa ttgcctccca tttcgactga catgtggtgg tttagtggaa    720
agagaacaca gcagggagaa ggaaatagga ggctgagaaa atgagagcta attattttca    780
ctgcctcatg tcaggctctg tgtcagcctt gtttttacaa actggaaggt ttagcactaa    840
ataaaacaaa ctggcgtcat gtttttatat actggcagtg tcatggaagc agctgcacat    900
ctcaaagaca atataatgcc tgcgttcgca tggacaccat ctgacagaca ctgtgagcca    960
cggctaatga ggatatcaca gtggtgccaa gtgaaaggtg ctgaattatg tatgattctt   1020
catcagtaca gcaatagtcc tgtacatcat tatgagacat tgttttgctg aagagattaa   1080
aacattctta gttccagacc ctgcaaccta tacgcgctga aagaggttat taatggaatt   1140
```

-continued

```
tttagggaga gtttcttgtg gatttctttt tggttaaaaa aaaacaaatc tcatgggaca   1200

aagccatggt gggtcatgac actgtataga taaagaagag aagcaaatta accatacttg   1260

tattatcttt ttttaaaggc agcataataa aatatagtgt agcagggtta tacttaatga   1320

taaataaccc aggtgctatc acgggatgtt ccactctcct gcctttaaaa ctgcaggttt   1380

cagcagctga gctagataat agcaacgcat ataaaggagc cttcagaggc ctaaattgtc   1440

aacatcttac tacttttaat accagcatga acaaaatttt tatcgtattc ttatttcatc   1500

ttgcattact tcatagatgc cacaacagtc agttgtgact cttgtggctc ttccagtctt   1560

cc                                                                  1562


<210> SEQ ID NO 22
<211> LENGTH: 1626
<212> TYPE: DNA
<213> ORGANISM: Homo sapiens

<400> SEQUENCE: 22

attagaaaat ggagtgaggg gatatactga agaaagacta aattatattt ttcccctaag     60

aagaaaaaca aacaagacaa aattgagcct attatcgatg atccagcctc caaaatatta    120

aatcaactga ccagatccct ttttatttta gattaatttt ttgccaacac cttctccctg    180

cccacttctc ccgcagccgc acccccaata cccccaactc ccccaccccc cgaacctgcc    240

aaagcctcca ttacacaatg gcaagagccc tgcactggtg acctccaacc agctgcattc    300

actttcagaa catctctctc tgctggaaat ctaaaggcct tttagttagc aagctagtgt    360

gcattcagaa ggagtaactg caggaagagc ccaatgtgct ttgtttctct ggcctttctt    420

cacagaaaga ttaatcatct gtgaaatgga aacggcaaac agcaagtgac acaaactgaa    480

cccttcaagc ctttcctcat cagttttgtg gttctgaatc taaaagctgc gtgtggcaag    540

gttctcctta caggcaggtg ttaataaaag gctctggggt ctgaaaggtc aaatttagct    600

cttccagaag aagtgcattt gagagtcatc tgggtgtctg ttgttgttgt tactaaagat    660

aatttatgga tatgttttaa atatgcattt ctcaaaattt attgtaacac aattattagt    720

aatcaatttc ctggattttt atcaatgtat tttactttac cataatcagt tattcttctt    780

taaatatcca tttgtataaa ttatctcaat atttagtata ccttccttcc aaattttgct    840

gttaccaaca ggaaaaataa ggaaaaagcc ttatatcctt agatcctgat ttgaaaccct    900

ccaggcaaag gacttcccac agattttaac aaggaagggg caagctgaaa acttttaatg    960

aaatctaaca tgttcggctt aagaataatc actttttactc ttctataact gaatttcact  1020

cataaatgtt taaaagtggc taatgtaaca ccatttccta caaggagaag atcaaagtgc   1080

tatattacaa atgcattatg attaaaaaag ccctgtgcag ccttgctatt aactgttctt   1140

taaaccctaa aaggcttccc atagatctca cttggcactg catatacaac ctttgacaag   1200

taatgtagac catttttatt cattgcctaa aattgtaggc aattatgtgc gtcacactgg   1260

ccacctgcaa attctgaatg cctgctctag ttgtcagtgc aaaaaactaa tgtcggaggg   1320

gattaatcta gggggagaga gtcctcttta atggctccag caggtgaaat ggcccagctg   1380

gttactatga tgagtggcca gaacagctta tgtagagaca cgcaacaaga ttatacaaaa   1440

gaaagaaaaa acagtcgtac catcttatat ttggttccat tagttttttc aattaaagaa   1500

agaaaacaga caaaagaaag ccaaacaaaa aataggggaa gaaattaaat tttaatcata   1560

taaaaagtat aaaatacttc tgtaactaca aacattttta caaaacctca gagcctcaat   1620

aagtgc                                                              1626
```

<210> SEQ ID NO 23
<211> LENGTH: 560
<212> TYPE: DNA
<213> ORGANISM: Homo sapiens

<400> SEQUENCE: 23
ttttctcccc cgcttcccag accctcgtcc cctccccgca acccgagtgc ggctaattcc 60
gggcgtctat attcactcaa ttagagaaat ctacagagaa gatcgatctt ccatctgcag 120
acatgccagc ttaacaaatt agattcttgt ttcgtgcagg tgatttggtg acagttgggg 180
aattagaagt aataagttgt tgtgtttgag cccgggcccc cgcccccgc ccgcgcccct 240 ccccgcccgg gggcccctcg gccgcgcccg ccgcccgggc accccctacc gcaccccca 300 gccggcccgc gccgccgccg ccgtcgccgc atcccccgcc gtaattagtg ctgctgccct 360
ccatgtgggc tcgattaaac cgtgatttag ccgaaagaaa tataattatg gctgcaaata 420
aaataatcag cattgaagag cgatttcctt aatgagatgg agcggttgca cgtcacggag 480
taaaggggtc tcattaagag gtggtaatga ggcttgggtg gatggtgcag ttacaaaata 540
gcccaactcc tctgcaggcc 560

<210> SEQ ID NO 24
<211> LENGTH: 1019
<212> TYPE: DNA
<213> ORGANISM: Homo sapiens

<400> SEQUENCE: 24
gggtttgtgg taatgcccag tgatgaatgt catagctggc atcttagata aaatgttctt 60
tctgaacaac acccaaatat gcttaaaatt gcagatgaca gttgtaagcc tttttgcctg 120
cttatctgtc tgccttcgat gtgaccctaa attaggcatc agaaggtgta gagtttaata 180
cagattccgg gcacaatata ccttctcaca attagttgaa agtgctgttt tgtaattaaa 240
gggtgaagtg gggcatgatg aacatatgga aaaggagacc cttaataagt gatggagcct 300
tcaaaagaaa ttgctaatta gtatgcattt gatgtgcact ataccaattt taagactttg 360
ccttgaataa attgctatgt tgggtgttcg aaggagtggt gagattagca tttacaaagg 420
gggcaatttt ctgtcttctt gactctgtta aatggaggaa ataacttcca agactggagc 480
agtagttagc ccatcaatca ttctcacagc tggaaactgg ggatcccaaa tgcagagatc 540
agttaatccg tcagctaata agttcatagt ggcaccatat ggcgcagggc cactccacac 600
tgggacaagg acagaactgt ttacacaggc atgctgcttt ctcaggtagc tccctgctga 660
cagaatcctt tgttctgaag gatcaattta ctttgcacag taaattgact gaattgatca 720
gttcagagca tataattgtt ggctaatcct gtggaatcat gtcccatcca tgtgagaggg 780
acaaaagggt gctgcccatg gcctggtctg gggctccatc ctggggctat tctcgtcgga 840
taggttggac actgattaaa ggaccagtgg acagtagatg tgttgtcagc attgacttca 900
aacgctaaag ggaagagaaa ccttgcaatg cccagaaggg ttttctgggt gtctttactc 960
aactggtatc atgacttaac ttggaataga aacagtcagt caaggcaatt taggtgcaa 1019

<210> SEQ ID NO 25
<211> LENGTH: 1703
<212> TYPE: DNA
<213> ORGANISM: Homo sapiens

<400> SEQUENCE: 25

```
ctttaaattg ccagcatggt gaagatgtaa tgtgtcacct aggcccttgt ctttatttca     60
gtctgtagtg gtggaagcca caaaacttat acaccatatt atccactgca atgagaatac    120
agctagcccc aaatcaaatg cttttctttc ctcaaagcct caacaatgtt gccctccccc    180
cctataaatt agcagtgttt agaaggagac ttgtgcacat tctatagatt attttaagga    240
aaagctctgt catccataat acatttgggc ttctttctag ttgaagattt ataatttttt    300
tattgatggg ttatgaatat tgacacagga gatattcatt gtttattgaa ggcttgttta    360
cataaaagat cttcacaggc taccccctaa gtctagaggt cctaaaccag tgtcagggag    420
ctgtctgggt atttttttccc acgtattgca ctgccattct accaacaata gaggcccatt    480
aacgtttggc ccttcaagtt actgcagccc aagcctcagt ggcaggacgt ctgcccaata    540
tgtaaaataa cggaatgaat ggattccttg gaaacaatga taacaagacc tggctgagct    600
aactgtgaca gcatgtggta attttccagc ccgctggccc tgtaaaggaa actggaacac    660
aaagcataga ctgcggggcg ggccagcctg aatagctgca aacaagtgca gaatatctga    720
tgatgtcata cgcacagttt gacagatggg gctggacaat ttttccccct ttaaacgtgt    780
tcttaactat ttgtattcca ctggcttctc acttgggaag ttcaatcctg taatcacctg    840
cttgaaagac taaacaaacc ttaactgtca tgtgcttgat tcaagtacca ccagttttat    900
gaagaaaaat gatatccatt attagtggct gaatgctgag gggagcagtg ggggagaggg    960
tgttgctgtg gattaatgca tcatctctgc tttcagctgt gggccaggtt ttgagtctag   1020
ctctgactga atcctgccat acactttgaa tagcataatg aagtattgtt attgcctcag   1080
tctagtcatt acatcaggga aacagacatc taaagttatc aaaactgatt actagctgag   1140
cttttgtgtc cataaaataa atgcattaaa aagaaggctt ttttttgtt gttcttatgg   1200
gtgttctatc aaggttggat gttttagtgt ttatagcact atgtgtcact gtgtgtaagt   1260
tggtgttagg gtatatctgt agtcagtact ctcccaaaac atgcccatat gtggatctgc   1320
atgcgtgtgt gtttaagctg gtgcatggga gacagagaaa atgaagattg acaacattta   1380
taaaaatgag acacaactca attaaaattc accgaaaata gtaaatgaac cagagtactc   1440
agtttaattg taatgacaca agactgtctt tttctaccct tcaaataagt agctgctttg   1500
gatctcacat gtcttcacca ttttattcat ttggttcttt ttatttactt ttcaaggaat   1560
ttatgtaaat atatgtaggc tacaaaatag gtctcagata cagcctgatt ctgtaatctt   1620
ttcatcaaat agctaaccaa agagagatag ccaaaggatt ctgtttatgg agaagtgaga   1680
tctgttccac agaaaagcat ggc                                           1703

<210> SEQ ID NO 26
<211> LENGTH: 1111
<212> TYPE: DNA
<213> ORGANISM: Homo sapiens

<400> SEQUENCE: 26

ttgaggttta gaatgggggt gcttttcctt attttaaaag ctttgcaatt tagactccga     60
gagccaggac tggttttcta tccatcggga cctgctcaaa ggtcacactc aagatcataa    120
gccatgttca catccttctt atgggaaaat gataaaataa tatccacagg catctgatac    180
taggggcatg gcctggacac acaccttgcc ctcttcccct tggccttgtc tgccttgaag    240
aatgaataga tccatcccca aagttgatgc ttcgaagtga ccagtcagat gctagcaggt    300
cagctggcta tcctcttgga tagagggtcc ataaattaaa gaaatgttgg tgtggttgaa    360
agaggaaggt agtccagccc aagggaagtc acgtaaatct ctccaggagc tttgttccca    420
```

```
gtagggagtg gggtgagag ttggggtagc tcggggctgt gggctgttat taatgccctg     480

gccctcctgc ggtgggtgct aacttgttgt gcatgagagc tgccaccatc cttcccaaac    540

atcgggcgct tggaaaagtc aagcacagtt gagccctgat tttcatttaa tagtcaaaac    600

caagatgcat ttgggctatg atgataggac agctcccttg aaaagattat ttgaactaca    660

aaggcattca tttagggcta gcaatgttgc aaaagggccc gctagaaatt agcagcctgt    720

cctggtattt ggagagcaag agtgacaact tattggaagt tctcaaggaa tcatttatat    780

ttcacactcc actaggcagc tgatttgaga ttgtctgtta gcataacaaa ggctctgagc    840

ctgtgaactt cagaaacctt tcgacctctt agctgctggc atgaatagcc cccagtcctg    900

cctatagaga tctcccaaag ctcccctgtt cgtggctaaa ttgttaatca gggtaattta    960

atatagtttt caatatgcct catctcttat tgggaaaggt attcacagct tccctacccc   1020

tgaaaaaaaa agttctttta ttcaagtgtg agaggggcag ctgcagacag acccccatcc   1080

cttgcttctc cccctactcc ttcacagcag c                                  1111
```

```
<210> SEQ ID NO 27
<211> LENGTH: 614
<212> TYPE: DNA
<213> ORGANISM: Homo sapiens

<400> SEQUENCE: 27

attggaattc agtatttatt ttggcattta acaaagtaat aaatatttct ctatattctg     60

cttaagtaat ggaacaaata ggactcaata tattacaagg tttaaattat aatattttta    120

aaaagcaaca gtgtgtgcct caagtgttgc aaacttgatt tgagcatttt atggtactcc    180

agtcagctgc ctattaaaag tgtgatcagg tagtttagac tgtgactagc tgtgtcaaca    240

gaaggaaagt ggaggattag tctctatggc aacgacaaag tatccctgtt tgtagacaga    300

caaattctgc tacatctgaa actgattgac aggtctattc ctttgcaact gacccataga    360

aattagcaag taaaagttat tatactgggt tgtattgaag ggttctcaat atcttaaagt    420

gctcttgtaa gtttttctgc agcatttgca tgagaaacct ggcaggaatt gttctgaggt    480

ttatatctat ggtttgatag attctttgtg ggggagtatt gctggtgaga ataacttaat    540

tttcagttct ctgtatgaca gaattgttgg agcatggatt gaggggaaaa cacacatcaa    600

agacccaaag ctga                                                      614
```

```
<210> SEQ ID NO 28
<211> LENGTH: 1337
<212> TYPE: DNA
<213> ORGANISM: Homo sapiens

<400> SEQUENCE: 28

tacctgggga acttcaaaat tggcacttat aattgccccc tcctccctca ataatacttc     60

acaaagcata ctgtcccttg taaaaatata ttatttcaat tatgtgcaca gtggtgtttt    120

aagaagaatt ccaaattttc attcacataa tcataaagac catcttccag gctccaaaat    180

ttaaaaaact agaacctcaa caataatata caactcataa cagcagcaac atcatcaaaa    240

aaactacaac acttttcttg attgaaataa gcaaaaagat atcaccagac aaatgtatac    300

tccaattctc attttgtctt tttgctggaa cattaaggag ttttatgtta tcacaaaacc    360

tcagaaacta ccaagcagaa aagaaacctt attatgagta actggcagta tctcattaaa    420

tctttcaatt gtccaatcgt ccacagcaga cctccaagag acttgtatat tatactcatt    480
```

-continued

```
gcaattaacc aaacaaaaga ttttaaccgc cagagcattc gggaaatgtt tggttgaggc    540

tgaagaagtg aaattatatt ccagggttgg ccagatgtca caaggggtga tatgcatgtg    600

ctcatttcat ctgcagcttt gtgctggacc tgtctattta cagcactaca gctaagcact    660

ctgaaggcct attcactcat gaatcctttc agaaagtgct gaagcacccc ttaagcccac    720

ttaactacca ttttcacaca ctctcccagc tctccttttt gtccttgctt acattacatc    780

aaacacagga acaaagcaag agaacagaaa ctcagaggca gagaatagac ccatcacaaa    840

tattaatttg aaaaggtgtt gaagtgcaga atctgctttt atgcacaagg acaacttgca    900

ttttttgtgt gagattctct tagctgcaat aagctaggtt ttcagccaaa gagaggcaaa    960

gactcaaagt gcaattatac acagggaact gcttcaaatc aaacaatgct ccgaactgct   1020

ttagatctat agtgataaag acttggcaag cactattaaa tagaagccct atatgagatg   1080

cagagttcac tctatggatg catacaaaag agaatacaaa aagaatactt ttcacacaaa   1140

agtaaaacta caatttcact tttaattcac ttgcaaacaa cactttaata caatttcttt   1200

ttataagatt cttcttagca taaactatga ctccttaaaa gtagtttcaa ctaattttta   1260

ctatatctgt tcttaacatg ccaattagaa gttctatact acctctgggg gggggaaaac   1320

cacacaccac tgtgtca                                                  1337


<210> SEQ ID NO 29
<211> LENGTH: 453
<212> TYPE: DNA
<213> ORGANISM: Homo sapiens

<400> SEQUENCE: 29

cccagaaatg gccatactca gtggtttgtc ccaggccctc tagagcccct cctgtgccca     60

aaggaaaccc tggtgccaaa ggcaccacca gaaccaggct ccagatggcc attcaggccc    120

tgggcgaatt gcccctaccc cttaaccagc aggcccccca cataagacgt cactatttaa    180

ttagccgtct ctgattaacc aaacttggca ttcggctcct cttgccctca tctttcccag    240

ctccgaatca atggctttga tatgctaatt agggagtaat ttaatttcaa aaggccgcaa    300

ttaacaaggg tgttgtggac atgctgtagt taagcggagt aatctaattt gcattagtaa    360

caagcaggga ctaattagaa gcttaattag acacttagat ggctcttatg tttactttct    420

taatgagatg gagtgggatc tttggttctc ttt                                 453


<210> SEQ ID NO 30
<211> LENGTH: 1164
<212> TYPE: DNA
<213> ORGANISM: Homo sapiens

<400> SEQUENCE: 30

atgacctgag agcgtttcct ggaagccgcg cagcccctct cccggcctcc accatcgggg     60

ccgctcaccc tctggggact ctggccccgg gaccccggga tccaggcccg gtgcgcgcgg    120

ctccggcccc gagcgcgctg tccaggctgg atccccacca ggcggcgctg cgcccctccg    180

agcccgcccg gccgcgctct gcaaaccgat gctgtttaat taacgtgcaa attgagtaga    240

ttaaatgact ctaaataatt agccacagat cctacaaaca ggataacaga tttaattaag    300

cagcgatata gattttggaa actgttaatg tatttttaga atggcagctc agatccttca    360

cttttccccc ctaacttcaa acatgtaact acggccctcc gaacgtggat aaatatctgg    420

aaacaagatt acgcctgtta acttcaacta atagaaatgt gggtttaaca ggaacttgca    480

cggctccggc gccggcgccg ctgcagcccg cgtggcccgg gccgggccgg ttctgtttgg    540
```

-continued

```
ctttgttgtt cttggtgcgc gcggtctggc gcctgggccc tgggcagaga gggtcagaac    600

atacaggagg aaggggaagg gagaaggtga gtgaaaaata caatccaatt tcattatatc    660

aatcacattt aattggcaat ttgtacgagc aatgaccggg ctggctttag gtaaaactat    720

tagacgacag gcggatgtgc tactaaaact cttggttagt taattagtgt ctgaactgcg    780

gagggaaagg atcctagatt tactctctac aaagagagag cagcccagac aattcattag    840

gcaggcggct tgtaaattag agctaagtta acctgatttc ccttaattaa aacatctttt    900

ctcgtttacg atgtggatat aagtagatct ccagggtttt gaattttctg caacagcaga    960

tggtcagcta gaagcagata atagttaacg ctttctctct accagatctg aacaacgtga   1020

gccgccggcc catctgagga ttaaaaggag ccataacaaa gagtgttaac ccttcgcagt   1080

cttccagctc cccagactcc aagggcggag ctgcccctgg cctgggggca ccaatagggc   1140

accggtgacc aggactgcag atcc                                          1164
```

<210> SEQ ID NO 31
<211> LENGTH: 613
<212> TYPE: DNA
<213> ORGANISM: Homo sapiens

<400> SEQUENCE: 31

```
agctaatcct gcctcctgcc taagggtact ctgggagatg attgaaattt taaagatata     60

aaaacacact aaaatggtaa caaatgactc agcaatgtgc cttctaaggt ggacagattc    120

ttggtaggca gccctaattg ctgcaatcgt ttttaggtat tctaatgcac tcagctgaat    180

tatgcaccac actgcttctg aatgacacag ccatttctga ctccattaat atggaagatt    240

tcagccaaat gctcttaaac gatagcttct ctttatttgt aatttcagac tctattgatt    300

tccttctgtt cccttcatta tgatttcaat tgattacctt ggcaactgca ataacaatga    360

ttgcacttga cactgtctga gactcttgag atggtatttg aataggaatg gtataatttg    420

ggggaaagtg cctgcaagaa cctgtcatta gcagtacact tacactttac ttttattgac    480

cttcctctct ttcgagtggg cccttgtcac agagttggct gttaacaggg ctacagtagt    540

agttcagatt tctgtgcctc ttcaaagagt aaaagattat tattattaaa gagaatggag    600

tgggcttgca tat                                                       613
```

<210> SEQ ID NO 32
<211> LENGTH: 1367
<212> TYPE: DNA
<213> ORGANISM: Homo sapiens

<400> SEQUENCE: 32

```
caatgtggga aggcaaaagg agaagcaaag tagtgaagtg gggcagccca gagggagggc     60

taaaagcaat tcccagctgc cgatagattt cagttcatca ttgttgattt tggactaaaa    120

ccttctttcc agccaagcag gcaagcagaa gtgaatttat cagatgtgat ttttatcaga    180

acccaccgta tgtggcggcc ggcagtcacc acgggacccc ggagcctgtg attggctctg    240

acacatccga ccgaaagggc tcttattcca agaatgatct tctttttttag atggtattga    300

gttgggactg attttgatag ccagtttcag tcaagaatca taaagttatt gcacatttaa    360

aactgtcggt atgagaatca ttctctccct cttttctctc tcatcatttc gctgggctgc    420

aaggttacag aaaggtctaa tcaattgtca aactctcttt tatcaccgag aaggtggtaa    480

gaaaaaaaaa aaaaaaaaac acctctaact gccctactgt agggggttct ttcactacac    540
```

```
agcacccttt tccacataca atgctgccgt gattaatgtc ctcccacctc agaccttgtt    600
aaaacctgtt ctctcaagca gccagtggag cacagtgaga ggagggccga ggttgcataa    660
atcaacgtgt tctcacagcc cccaggatat ccattataga tgccagctgg atggctggaa    720
gatagagaaa aatgaatatt gtatcctgtg gccttttgcc tctaatgacc acttttcaac    780
atttttgaag gcatgattaa attttgataa ctggggaagt cactctgagc aggctgaaat    840
agagataaat tgacggaggg tctgacatct cagtggagag caggcaacta attagtgtgt    900
gaagcgcact ctgaaagaga tgtaaaaggg aggcaggttt aatcagagga gctgctgagg    960
tacaggaata gtcagagata attgcggcct aggtagaaat cacaggctca atgagcggct   1020
ttttctgtct gcttgattgg cagccgctga cctagtggcc ggcacccttg aacccttaca   1080
acagcaacgg ccttgtcaaa gcaatttgct tgccgctctc cgtgaccagt tatttcagcg   1140
gcagagctgg gacaccccgc tggagagggc actccgctcg cctggctggc agggagctgg   1200
gcggaacagc ctcgttattt ctgatgactt tacttttgaa cccagtcgcc ctttcttgct   1260
ccccaactct ccatagccca ctcacacaga ggcgtgctcc cgggagggac agcttctaca   1320
aagacacagt gtcagggcaa tttggttgtt catttgagga gtgggga                 1367
```

<210> SEQ ID NO 33
<211> LENGTH: 1602
<212> TYPE: DNA
<213> ORGANISM: Homo sapiens

<400> SEQUENCE: 33

```
aggtcatttc ccttgaaatc ttcaggtcgg tttcccactt gctttgaatg tgtgtgctca     60
cacaattgtt ttcatatcct tctctctgtc tctttttctc tctctctctc atcaggagcc    120
tttcagggtc ttgcctgtaa tctgtaattc ctgttcacac gactgtgggc gttttaggac    180
gtccctgggc agttatgaaa ctactgaccg gtggagcctt tcttgcagat ggatttcatt    240
caggacttgt gctattatat taatgggttt aatttaaaca ggactagcct cgctggccaa    300
attactgcca tttaaatcaa ttggtttagg gggaaaggca gcctgaccag agctattaga    360
cttcaattta ttactgtatc ggcttttaaa ctgggcaaag caagtttgct aatgtctgtc    420
ctctatcctt tgagcttgag tacaaaacac agtaatgaga gtctttcgag ttttttttt     480
tttaaaaagg ggaggcggga gaaaaagaag aaaaagaaaa aaaaaacata ttcatttaag    540
tcaatgtttt atgagccaag accaggtagc cctccaaaga atgcaaacca taggatcctg    600
tgggtgccgt tcatgtccct tcattaaatt gagattcaaa taatctaaca gatgtattag    660
tttaaaaaga ctttatactt ggattttccc ccttataaaa aataagcgct gcttttttt     720
ttcacacatt tcaacctgat tcaaatagaa aagcaaaagg gaagaaaatg ctttagatgt    780
gctcttttga ttttttccaa tctcgcctga ataaaatgga atgagagatc aagaacactc    840
aattaattgc aacattgggt gtcactagga gagggaggga gagatgaagg gagcattagg    900
gatgcacaac ccttaacaaa tgcatagatt caaagaagga agaagaaggg gaataaaaaa    960
gcgtgtctgt attttattgc actcggtaag cttttcgctt gtatttatag ctgcaattat   1020
atctcaatga ggtttgtcta cagtgttggc ttcacgctaa ttttccccct cactgcattc   1080
ttggaatagg ctcggactgt ttatgaacca gacatattga cctcatttac agctagcagt   1140
ttaaatccat aatttttcca cccacaatcc ctctttgaca ttccggcggt gcggccggct   1200
cagcgagact gaactaaaag tctcacactt cattgaacac cattatgcgg ctttatgctt   1260
ataagcctgt ttccctcggc tgcctttcag ctttgctgga gatcggtttg gccacaggcc   1320
```

```
ggcagtgatt aactggaaga atccaataaa tcaccctgtc agccagcagg ctctcctcac   1380

tatgtctaca catcgacatt tggatttgca cctctctctc tctttctttc tctctctctt   1440

ttgattttct atccctcttt ctctctccgc cccactttct acagagccat taaaacacct   1500

ctttaccttc acacaaggtg aacttgaatc gctattgtga gtatggctca ctcccaccag   1560

ccctctggga gataaacccc tttgatttgt ggagttttcc cc                       1602


<210> SEQ ID NO 34
<211> LENGTH: 1117
<212> TYPE: DNA
<213> ORGANISM: Homo sapiens

<400> SEQUENCE: 34

ccctcttagg ccaactctca gcctggagct aatgttttac agcagagtta tgaaccccta     60

aaaatacagg tttgtgccac aaacgatggc aggcccataa gtatagcagc actactgggc    120

accactataa taagatggag atttcaccat ctaataccta gatctccatt agtaaattcc    180

acagctcagt aagtttgctt cattatctta ttaggtaaaa agagcaagcc agcgcaccct    240

gaccaagtca gcctgtccag aatgctaata gatgtagcac taaattattc tcctctttta    300

aagagttgtg ttagtgacat tttgttttta tcaagtaatg caattagact tcagccttaa    360

tatctctgag gctgtcacat ccctgaactc cgcagcactg cttgccagcc gcaatcagaa    420

ataactctgt cccttcaact taatgaaaaa gaagtacttg gccataaact tgtagtcatc    480

ctctatccaa tcatattgtc ttgagtaatt aaaatgatta gcttaattag cttaattaac    540

taaatttgac tacaggacat ggccatatgg tgaagcaaaa caaagatggg agctaattaa    600

agttaaaata atgcaggttt taattaactc aacccctagg catcaacatt ttcaaattta    660

tccaagctga taattaaaaa gtcctcttgc ccaagcaaca tttcttctct gagctaatta    720

aatctggaaa tgaattagca acacgaagct ccaaatatta attcctgcta gaagatgact    780

tcacttccta atgaaattaa ttagctgcgc tggaccttca atcagacgcc aaacgctgtc    840

catgaacaca gacctcatgt aatctagcgc aaggatacaa gccctggggc aagaatttac    900

aatagtaatg aacactcttt aactgggtgc ctctcctaat ataccaaagg aacatgaaga    960

tccctttgtg ccatgggctt cctctcctgt ttaaacaagt tggtctcaca gatagttaaa   1020

aagtaggttg caaataatat tacctgtaaa gcatactgct accggactgc agattaatca   1080

gttttagttc tctccactga ggtcgtggtg tgagtgt                             1117


<210> SEQ ID NO 35
<211> LENGTH: 1819
<212> TYPE: DNA
<213> ORGANISM: Homo sapiens

<400> SEQUENCE: 35

aacaccgttg atccaggtta taaaactcaa atgcttaaat attttacatt cctagataaa     60

ctgattgaag agccaagact tgtcttaaaa aaaaattctc agcttacaca ctcattcatt    120

cgcgcgtgca gacacacaca cacaatgcat ttaacatacc cacccccccc ccaccatcct    180

gcaaagttat agttctcagg cttttcaatt tttatgtttt acattcctat atttaacaga    240

ttgatatttt cctgtttgtt ctctttaaga tttcttttct acatacagag tgtattcatg    300

tgctatccta atgaggaaat gacgagtttt tatcaacctt attaaacata cacccagaag    360

atatccattt gaataagggg ccaattacta agtgtgtctt cagttagaaa gaacttagct    420
```

```
tttaccttgt actttggctc tccatgtctc taattaattg aatcttgaaa tcgttggact    480

ttcagcttaa gagaagactg aagaagggaa cttaacaaca ctgcctattc ctttatgtct    540

agaacgggct aaaaaaaaaa aaaaacacct gtaatgctaa aagactcagg cttttgtctg    600

tttctaatat tacttttctg cctaattgcc atcactgcca cgtacattag gcccttttc     660

agcagggtta aaacagggcc agtgatgaat ggaaaactga ttgtactgct gtcaaacttg    720

aatgtgaggc ttattctaga gatagaagta tgaggaaaag gacagagaat tgcacttcat    780

taaagctcta ccaagctgat tggagtggag gaggtaattg agatttaaag tggcattccc    840

atcacactgt cccttttca acttaacaac tgtcattcaa gccacatagg gcaacaattg    900

gccagatttc ccagctcttc tgagtaataa aacagacact caccttctgg ctattcgttt    960

tacttacttt gttctaattt ccaattcatg tgtcattagt gaacgaagat tgacaagaaa   1020

tagctttgac ctcacagatt tgaccttcaa ccccaaagac ccaactctag tctgaacata   1080

ggttggaata tgctaagaaa cacctttcct ttgcacaaga atgaatggca gtttttcat    1140

cattgtacca cccctgctt gccactacat ttagactatg agacatgtca actgcctgtc    1200

acaattacaa tagacacagc aaaccagaat ttccccaaa tccaagggga acttcgcgaa    1260

caaagagtaa attttattgc acagattttg gagacctcca atttgtagag ccataatgaa   1320

tgcatcccac agacaaatag gtagttgtta attatcccag caatttcttt ttttaatgtg   1380

ctaacaacac agcacgctaa gccttcatat cctactctgt tacctgatga tctcatcaca   1440

tttgcaacga tggtagtctg ggaagaaggc attattttag caagtatgca tgacaataag   1500

ttacatgatt ataatccctt attttcatga tttaataaaa agaaagtgtg atattttgga   1560

aacaaatggg tttagctaca cctttactaa atcagttgaa gtagtttacc tatagaatca   1620

ctttatgata aacgtaatct ttgtattttc cttgactgag tatcctaaag cttagatata   1680

ccaattttgt gtcatcaaaa catgctgtgg ataaaaaatg ttgaagggca agacctatga   1740

cctgaataag aaccctcaat gaatttaaaa gtattttatg cctttcacac agttttgaat   1800

agcaattggg tcctggaaa                                                1819
```

<210> SEQ ID NO 36
<211> LENGTH: 974
<212> TYPE: DNA
<213> ORGANISM: Homo sapiens

<400> SEQUENCE: 36

```
tgaggtggga agcaatagga caagatgcat attaaaatga tcagcatcaa ggattttaca     60

tgaggataat acggacattt ttgagtctta acataaacaa gtaatatggc acacttttaa    120

agggggtata tggttataaa tagaagagga tgaaactgat ggtacaatct aaataatacc    180

acatatctca caacttgttg gaaagtactt ttttcattgg gggagattca cagctgccga    240

attttctgca gttaatagag tcctttgatt cacagcagtg ccccttgtac aaaaaaatact   300

ggcctttgtg tattaccaga aactaatttt ctatttggct gaaaagggaa aaatggggtt    360

attgcttctc cctcctacag agcttttcat tatgcctgat gcactcaact tctaagctct    420

tctgagaaaa aaaataactg aagaggcaag aggtagaaaa atgagcttgt tagcacatta    480

gaagtgaagt atcttggtgg gccctagaaa ttcccagtgg tgtgttaact tatcactcta    540

tgcatgctgg cactgatagt cttccaattg atcactctct tttcgcacca aaggtgctgc    600

caggaagcaa aggctgaagg cccacaggag aacagtctgc tatcaaaaca agctgttttt    660

aaaagtctgc ttgaatgggt aaaatgcttc atgaaaagta gggtggagac acctacctgc    720
```

ttttaaaaat gttctacttt cagagggcct ataaatgaaa tattttacat tatatttaga 780
atttatataa aaattaggca gaaagaaagc aaatgttaat atttctaaag caggggagga 840
tatttccaat gtagtaaatt catcaaagca agaaaatgat tatctagcta aaatacattt 900
tgcagactaa ttctacttcc ttatacaaag aggcttataa aatggaaaaa atcctaatac 960
acagctgcac aaaa 974

<210> SEQ ID NO 37
<211> LENGTH: 677
<212> TYPE: DNA
<213> ORGANISM: Homo sapiens

<400> SEQUENCE: 37
ccacaccaac tctgtgatcc acaaaaatct tgcatttaat acagcaacga cacctataat 60
ggggaagggg tgggggtggg gaggccgcac atttcaccat ttccatctag atgaggagca 120
aacaaagaga taattataaa ctgtttctct tattgttgca ctcgcattag acatgtgcat 180
ctctctctcc ctctccctcg ctcgctgtcc tttttttttt tttctccaca gaaaagtaat 240
tctgttgtgg agatggcacc aggtgcacgg ggtgacctca cacacaccaa atcgggagct 300
gacatccatc acactttgaa attttggatt tcatcatttc ctgatctttc taaagggatc 360
acagcacctg gccctcacag ctgtagttca tttagaaagc aatttaaaaa ccgagaaaaa 420
agcaaatgac atcttgctgc ctcagccttg tcattaagta tagcagaatg gccttcattt 480
atgaggcaca tggctaagaa ttaatatctt tcagggcttt ctcgagtaga gattacaaaa 540
ggtttgaaag accactaaat aattagtggt atgactgagg caagcaaaaa aaagggggggg 600 aagaatccct ctttttcgtt ctacagaaga aaatcagaaa ttacactgac tttagtgtgt 660
cctaaatgtt gggaggc 677

<210> SEQ ID NO 38
<211> LENGTH: 1020
<212> TYPE: DNA
<213> ORGANISM: Homo sapiens

<400> SEQUENCE: 38
ggtgggaact gaaacatcag atgtttatta aatgccatag cggtggcgac tactttgcac 60
agtgagccca gaagtgtatg ctgtcacttt aaaaaaaatt gagccgatgc caggctagtc 120
atggtaatgc tcccatggca tgattagatt catgcccagg gttgtatttg catatgatat 180
tcagggcatg attttttat tgttcttaat cagagccgaa tgtcaacaaa ataaatgaag 240
ttgcgagttg aagtgaaatt tttatcacat cagggatgtg ctttttctcc catttatcac 300
agcccatatt gagagagtga aatttttga aaatgtggta atcaatggaa gagctccata 360
tggcagggat caaaggtgtt acatagtgtg tggttctgct ttattgccag ccagtactgt 420
taattggaca acaagatcag aggcaatatt aaaatccaat taaattgata tgaacagatt 480
gccaagtgat gtacactaat gtataattga gtatcaagcg aatgcaagtc cccgtcttct 540
gcttctacct cctgaataaa tgatggcgcc atagaggaca gaaacaagtt tgcacattag 600
ctgcacagct ctgggctctc atttgttact ttcagagttg atgactttg gttttcctcc 660 tagtctgtct taaagagaca ggcccattcc ctgtccccca agcccccacc ctttaccccc 720
cacctggggt gggttttctt ccccgaaatc attttcccct ttcggggcct ggaaatgaaa 780
cccatgtttc atatgcttca ttacatgtct attatatagc aggtcttaaa gagcagtgca 840
ttgataatat attgtgctag ttgtaaatga tctgtccatc tggagcggca cgctaacaca 900
tttctaatgc cgtttcccag atataaatta tagcagaatg tttctcaagc tgaaaggaaa 960
gagaaagcaa gcaagcaaag ccctgaatga acactgtcag aatacctcgg cacacaaagg 1020

<210> SEQ ID NO 39
<211> LENGTH: 603
<212> TYPE: DNA
<213> ORGANISM: Homo sapiens

<400> SEQUENCE: 39
cacctccctt gtctccaaac tacacaacct ttcagtgggt ttccagccca ggcgtggact 60
gcactgctga gggctgcgag aatgacagcc tcatatgtct gaaagctgac acttcagcct 120
tgaaaagaaa tgggggaaaa taagctgttg acttcttggt taaagtattt tcttgttcta 180
ctcatgttct tatgtcactg ggctaaaaaa agagagagag aaaaagaggg ggagagagag 240
agagagaaga gagagatgac tttccttgaa tgatctgttt aacctaagcc agaggaaaaa 300
aaagaaagtc attaattact tatgtgagct attgcttcag aaagacaata aacctgcccg 360
gtcgccatgg atatgacata tttgctctga aaacaacaca ataattagca aaggggaaag 420
atacaaggag aatatgcaaa ctcctgagtt taaagccaca gtgctctttt ctactcgtaa 480
gcctctgttc tgtttgcaat ccaaatcaaa caaattttaa aaatatagca aagagggaaa 540
taataggaat ggttcctctc gcctctgagc tgagcagcaa caaccactct acctccctcc 600
ctc 603

<210> SEQ ID NO 40
<211> LENGTH: 1024
<212> TYPE: DNA
<213> ORGANISM: Homo sapiens

<400> SEQUENCE: 40
cgtaacatga attttatgat ggaatcatat gattatatag atactgctag cttgagacaa 60
taggaactgg aatgctgtgg cctggaatct tgttctttat gtattaataa cagacttctg 120
agcacacata ttcactttca gatttttaag caattagttt gcagatgtca ctaaataaat 180
ggcattcatt ccttaagcag gaaccatacc tgttaaccat ctcagcctat tctagcttta 240
aagctgggct tgatgtgcac agcatgctca aaaactgtac tcacagttca aatgagctgg 300
attacagacc atgaccactg agaccctcac atgacaaagc ctttgtgtaa ttaatatgca 360
gggtaaaatg ctccctggac tgctgctaaa gcgatttaaa tcatgcacat aaaaaatgta 420
atcacaaatt tagcatggtg gacagagtag tcacactggg cttgattgca tagaaggttc 480
caagtgtgtt ttaaatgtcc tttaagattg agattaagac ttgtacttac aagatgcata 540
ttaatctaaa actcaacatt tttcagtgtg ggatcacagt aggagaacat tatgggcaat 600
agaggttcat tctaatccca gtaggtaatt acactttgaa ataatattct ttaattaaat 660
cttgtttgca gttgattgat ttaaacacta aatctaaaac cctaaatttg agtttttatc 720
aatttttgat gcttattgca cacaacttgg gctttaattg atgtttctga agttttaaag 780
cccttgtccc ccatatcctg gtttagaatt tagtataatt atcaacatca ttctttaata 840
ctcttgatgg cttcttctgg aaactcggta agtttgagca ctttcacaat tttaatatat 900
acctgaaagg tttttaatat atcacaattc cagtatttac atacatgatt cttctatcac 960
acctttaata gacacataat ctaatccctt ctctgaaata ctgacagagg ttctatttc 1020 caaa 1024

<210> SEQ ID NO 41
<211> LENGTH: 556
<212> TYPE: DNA
<213> ORGANISM: Homo sapiens

<400> SEQUENCE: 41
cgcacagaca cccaatttcc catatacaga taaatgcaca catgtatacg cgaaaggtta 60
actcggcgga ggactcgccc aaataagcac cgggattgca tttaaaataa taataataaa 120
taaataaata aactaggaag gaaagcgggg ggagggaagc agaagtcggg aagaaaagag 180
aaaagcagca ggctgattac gaggtgtcaa aactgccagg agcaagaagg tgatagcaat 240
caggggtgag aagagtgcgg cattcgtgcg gggcaactaa ttatccgtct catttgagaa 300
gagcagcatt tgaggcagca gcgttcgcct gctgaacggt gacagattgg cgcggaggag 360
aggggaggtg ttaaaacaat ggagccgggc gcgcgagcgc tgctgcatgc taatcagccc 420
tccctccgcc tgcctgccgc gctccctcct tcctcccggc ctccctcctc cgcgctccct 480
cctcccgcct gcggcgctcc ctcctttcca gcgggccccg cgccgccgcc gccacccgct 540
tcctgctccc tcgctt 556

<210> SEQ ID NO 42
<211> LENGTH: 1173
<212> TYPE: DNA
<213> ORGANISM: Homo sapiens

<400> SEQUENCE: 42
gggggtcttc ctaggttcaa tttcccctag gagatgtgac tttgctagtg cgaagatttc 60
tgtccggcat ctgactcagg tcccccagac ggcagctagg gcccaatgcc tcaagctaca 120
ggcaaaatct gtttggtcaa gcggattgta atactttgag atattagctt atactaattt 180
aataatctct tgctaacagt tcaaatagag aaattattag ttttagctca acgaaaacgg 240
tctttagtta ggctttatta taattataag cggttgtact ttttaaaaat gttaatctca 300
atataggcct aattaatgct gccttgttac tgacaagtag ttcatcaaat atctgattca 360
aagattttca taatgagtat attaattaaa ctatgaataa tctaaaggtg gttatattta 420
aacaatacct cattataatg attaaatact gatttcgaat attatgtctt aacaattgtc 480
acttagaaaa cacaaccttt ccttatgtat gagtctgtaa tggcaaaatg caattttggg 540
atttttttcc cttgttcaaa aaatgtgaaa ctcattttaa aacacttctg aaataggtta 600
cacacagctt aatgattatc aaaatgactc ttttctgcaa aaaaagaccc caaagtgcgc 660
gtacagctgc aaacccaaga gggtcagcat catttcactg tattctcttc ttgattacaa 720
gccgggccca tcaaacacaa cataattaca gtaatttcag gtttatttat tctaatgcag 780
tttccccatc tctctggtaa ttatgagcaa ttttttcgcc cagggaatct ttttgcatta 840
acaaaagaga taacgcactg aaagccaaat ttgctgtgca ttgagaaaag gaaaaaaaaa 900
aatcaaatag gtgcgagctg ccatctctgc aattctctgg taccggagcc ggcaaattgc 960
ttgcaggtgt atggagcaag cttgtcaatg gccaggcctc caaattagca aatgcacagc 1020
agcaaagtaa tgaagacaga cttagcaaaa ttgccaaaca acagatatcc ctttaatatc 1080
ttctctcacc cacactagct ctaaaaaggg gtaggggtag ggagagaagc aacagtcccc 1140
agccccctcc tcactggtct tggctttcag gag 1173

<210> SEQ ID NO 43

<211> LENGTH: 2166
<212> TYPE: DNA
<213> ORGANISM: Homo sapiens

<400> SEQUENCE: 43

```
attcttccac tcattgcttc ttaattagtc tagaactcca aagatgaaaa catcatagga     60
catttaataa gatgaaatgt taaaaatgta ctacttctga taatggtatt caatgtcaat    120
agtatttagt aatttttttt ttacaatttt cctcatttat tttggcatgt ttaggaatag    180
gaaaagaggc tgagtcagag accttcagta cttttattat taaatctacc tcatctccct    240
ttttgtatct ccctaccaga aaagaaatgg cctaagaatt tccacctgct tagtttgata    300
ttttaagaca tctcataaca ctttgatttc actaacatat tacccaaagc aactagtttc    360
catcaccttt accctcttac gaatccccaa actaagctta agaggaaatc acaagccgtg    420
taaaaaaaaa aaattagaac tatttcttcc ttcccctata tgctctactg gtgtcactta    480
actaaaactc ctcagtctgc gaccttgaga aacctagagg ctaaatagga ggagtagagt    540
attgaaggtc atcctctcga ccaccaccca aaaagaagag catatattca tcctaacagg    600
tatgtgtttt cataattatg gcagatggtg attgaagcaa aggcaattca aaaagggggg    660
cacgtgaaag caataatttt gaatgtttga catttgtttt gaaactacct tactaccccg    720
taccctttac catctgtctg ttatccctcc caacacccac ctctgtcttc ccacagggct    780
ccattgtgtg cagttcctgt ttctcagggg cggagctgtg ggaggcagcc atgggtgcca    840
taataggcac ctgcggccag cacaatgggc tgtgggtgct tgtgggagag acagattgat    900
gtattgtgca tgggggagga gggctgtcac ttgaatccat gtgaacccag gctttagggg    960
caagggagat tgacagcttt tgtaggttgc atttcttttt caaagcttgg ctttaataga   1020
cagtaagttt ggggccccag gctttcactc ccataattct aacagggcaa tcacgagcat   1080
tcagcatttc tttttacccc ccttgttacg cattaaatga tttcagtaaa ggaatgtgca   1140
gcattaatta gaatttgtta gcagatacca aggggaaaag tttcttcaca acaactatag   1200
gaggtgtcat ttgtacaaag actttttttgt tttctttccc cattacatta tcactgcaat   1260
atgtaaggta gtgattcttt tcatttaaat taagtggaaa gctactaaat cttgttttat   1320
tctccaaaaa gaataaggtc cttaacactt atcttttaac ttctttcatt tcctaaggtt   1380
ggtgtttact tttgctttca gtctgaccca tttactggtc tgtgtggttg tgtatccagt   1440
tttgtgtacc atttagctct tacaattaca agcaacccac tactgatata taaggattgt   1500
ttccaggtga aaatagctag caataatact ggaaatcatt gatactggag cccattttcg   1560
taatggtata ctgagaaacg ctaaaaatga gattgctata gatttgtgtc ctaacttatt   1620
ttctaacact atttttccct acttgatatt taaccttagc caagacacca aacttatgga   1680
agaatgaggc agtggcaaag aaatattttt tttcccgcag aaaacttact cctaaaccat   1740
gtcagttttt tttttaaaca tcaaaagttc tccctcacac acatacacag atagcatcat   1800
ttccttagag caagtaagaa aatggtcttt ttgtttagta tctgtttcct attattttaa   1860
aaataatccg gacattttag aattatatag gaagaaaact aatgtcagat aggatatctt   1920
ataaacacac tctctggcat cctgagaact gataaaacat tactaaaatt tctggtgtga   1980
tttttttcta acatctctca tataaaatca ttttctcagt agaaggagtt ggaggctaat   2040
tgaattagaa tttcccctac tcaattgttt tatttaaatg tgttaaggac aacagtgaaa   2100
aatattgtct accattattt ctcagaaaga acatattctc acacagttgt ccggctctgt   2160
ctataa                                                              2166
```

<210> SEQ ID NO 44
<211> LENGTH: 1876
<212> TYPE: DNA
<213> ORGANISM: Homo sapiens

<400> SEQUENCE: 44
gtgacagaaa aaaaagaaac agttttataa caataatgta aataccaggt ctaaatttat 60
tttgaggttt gttaaatggg gtggggggag cacaattccc aaaagcgaaa tttcagattg 120
taatgaataa tcacatgcca ctaaatattt gtgctggttt tgagacagcg tgccccataa 180
aactccaaga tgtggtcgaa tgtattaatg ttgctctaga caattcaggt ttctctatgt 240
atttaacctc cacccctgcc atggccttgt taattttgat ttctaagtga cttgggtacg 300
actacaaaaa ctaaacatat gtttaaatat gtacatacag gcattccttt tttgcccttt 360
ctaactgcag attatgacgt gagctatgat tatccatcaa agtaatttcc tctacccact 420
ccctctctca tcctcccacc ctccacattt gaacatgctt ctcttttcct tggggctcct 480
gttcagcttt ctgcagcaca gatccctgct gcctcggccg cctggaaaat agcctacagt 540
gcagctcagt atggcagcac atccccacgg cctgggtgtt tttccagacg gttttagaat 600
gattcggtat cgcatgagtt aaaaaaaatt ccccctggaa aagctaatta ttgcatgcag 660
atacttcttt gtgtgatcaa ggaggggaca atttaatagg ctctgtaata caaccaagaa 720
caaaattgct ttaaaggaag tctcttgttg agtgacaact ctgttgcctg agccaattag 780
gtcccaataa agagtgttga attggctcct gctttctcat taattatgtt ctgtcacaga 840
catggggctt gatttagcaa ttttgtatta cattaagata ctgaaaggcc gggaacaaat 900
ggctcactct gataataggc attctctaca cggtgtgaca tttactatcc agctgtccgt 960
aaggcagcct agcacttcag ttcaggggtt tatttgtcat tgcttcaaag ggacactcag 1020
cttttcacaa aaaaagaaac agagaggcta atagatagga caaaatgtac tgctgatatg 1080
ctttattaga gataggatgc tagggttttg ctaacaagct catccgttgg gactcagccg 1140
actttgctgc caatcatcct ctacacaaag gcgcactagt taacaaggag aaatgaatta 1200
cagacactta ttctgccggt gggatcacaa atacaccaat ctgtgaaaga ggcacaaact 1260
ccagagacaa actacatatt tgtcaataac ctcctagaaa gaaccctagt aattctttga 1320
agacctttga tttagcttcc ctctaaaata catgtatagg aaatgtttta gttaccatga 1380
cattctttct ttgttatttg tacaaatttt catcacatta aaaacagaaa actgaggagg 1440
tctgcaaatg ttttagtagg tatctataca ctacttttca tatcccacca cggggagctg 1500
ctgctttggt tatttcatta agaacaacag aaaattaaat ctttaaactt taggtttgag 1560
ctgtaatcca ccaatgccac aggaaataat ctataactct gaatttatcg tgtataccaa 1620
ttaagagagc aaggttaggg accgaatgaa aaccaagtct gtctgcttaa ataattagat 1680
gacttttaaa tcataaatat gtgtgtttgt gtatatgtat atgaatttac aatacagaaa 1740
catgaaccta aatcaatgtc tctatatatt aaatatggtg aaatatttta tacattgtat 1800
ttatgaaact aagccaaatc tctgacagta gcattgatca acatatttgc catttatatt 1860
atttaaacat tctcct 1876

<210> SEQ ID NO 45
<211> LENGTH: 838
<212> TYPE: DNA
<213> ORGANISM: Homo sapiens

<400> SEQUENCE: 45
acagtgcccg ctgtacaaag taagaaatta ataatggtca cgtttgtgat tattatttaa 60
acaccaagca gatattaaat attagggctc agagagggca tgcgacccgc ctgaattcac 120
tcagctgcag agctggaaag agaactcagg cctttttccc cacgctggaa ggggtagctg 180
gggcggagag gtggggggag cggtgaagaa accccaagcg gcccaagctg tgggtctggg 240
ttgggagact cgcaggtgtg ggcggggag gtaaggtgac ccttgctcag cgaccgcgcc 300
cgcaagaaac gcattcccag gcctcccgcc cggggtctgc aggtgacggg ctggggggag 360
cacgggaact agctagacca gtttgtcgtc tccatggcga ccgcccgcgc ggcgccagcc 420
tgacagtccg tccgggtttt atgaatgggt gacgtcacag gcctggcgtc taacggtctg 480
agccgctggt tcagacgctg acacagaccg gcccgggaag ggaggggga gactgtagct 540 ccgcagctgc cgcgccgtgg gagggagacc ctgctctgag gtctttgaga agaaaattta 600
aaaagcagcc aaaaatggga aaaaacatta aaaaatcacg aactgttgca ggttcaggaa 660
atttttgcaa ggagctgcaa attcaaggtg gaatcgaatg cagcctcact ccactgcgct 720
ctatctagtt cacttcccag ccacccagcc ccaaacttac tagactttcc cgaattaatt 780
gctcccaccc gggagggatc tgggtaggcc ctccgggtct caggaacacg aacagcaa 838

<210> SEQ ID NO 46
<211> LENGTH: 1754
<212> TYPE: DNA
<213> ORGANISM: Homo sapiens

<400> SEQUENCE: 46
taggtatccc ccagccccta cctttattag gaggcccggg tttcccccat taaacttata 60
ttcattcatt cattcattca ttcattcgtt cattcattca taccacgact attcagtgag 120
cacctaccat gtgccagaca cagtattaga ctctcaaaaa cgcggcataa atggaaacta 180
ggccctgaag ccagagcctc aggactggct cccgggaatg tttgaagatc atcgcgtatc 240
ttggaattgc caggcttcct gctccacaga ttccagcgct gggcaaatgg acacaaggaa 300
acataacttc tgcataactt ttactacttc tttccttttt tcttttttca agtagcaaag 360
gaccattaat tagaagaata attactgcta ccctatatta tcccaacctg ttcaatttct 420
atctgccgca gacaatgcta ataatggcaa ttattgcttc tataaacatc ccgaggcagc 480
actcttcccc ccgcagtgtg tgtgtgtgtg tttaaagaat atatataaaa agttccccgg 540
ctcatttgca tagcttcatc tttacctttt cccattcagc ccttgcaaaa gcatatctat 600
tcaaagccct tgcaaaaagc atatctattc aaagggcatt tagtccattt ctttcttggc 660
cggtaaacct attcatcaat tgttctgcct tgtagatcgc attctaatgc taatctagcg 720
tgttaaatat ctttttgttc ccctttcacc gttttgtcat tcagtttatc cagttttggt 780
cacccatttt atttatttat gcgcctgctc ctattcaggg gctcatgtat tttttattat 840
gttgtttcac tgtcacgcag tgtcaactta gtctattcaa tgggggctac ttgaaggccg 900
gagggacaaa gcgtgtacac attgcaccgc tattcattcc ggccagctgg atcggctgaa 960
aaaaaaacct tgtgaaaaga aacgcctcac aatggacaca gaagaagtgc acaatgctaa 1020
cagttttcca aataccactg attggtttct tcacaatgag gagaaagccg ccgctttttc 1080
ttagctccac ttcaacaaac aacactctca caaaacctcc caaccctgcg ttttgttctc 1140
ggacaaaacc tcctcgactg tctaaacgct cccactgaag gacaaaaaaa aaaaaaagga 1200
taaaaaaagc tcttttcacc atttcccttt ttttcccccc tgcaagagag aaaaaagaaa 1260

```
agggggggag gaattgtcag tgcattaata atatcagtct tttaaaagaa gagggctgac   1320
ctttgagatg cactgggctg agggagaaag aaaggaggag agattaataa agtttggacg   1380
gctccctcgg cctccgctgg gccgcgggcg caagaaagac gcggaccctc gaggcggacg   1440
agttgcggga acttcgcttg cctggaggac acggcggccc aggcggccgg gagcgccggc   1500
gccgagccgc gctctgattg gctggcgcga ccgtccctat ctgctccggg gagagtggaa   1560
tcttctctcc atcttctgcg ccccgagcct ggggtgagag ggagatccgc ggtgctttct   1620
cctatcttct tgggggaggg ggaggaggaa attgtcaagg gaagtaacaa tcgcggccag   1680
caaccctgct ctcccaaagc cacccccctcg cgcgacagcg tccccagcac cagttcttac   1740
tgcttacaca gcgc                                                     1754
```

<210> SEQ ID NO 47
<211> LENGTH: 1575
<212> TYPE: DNA
<213> ORGANISM: Homo sapiens

<400> SEQUENCE: 47

```
agctgttaaa acacccagca actctgagga gaaaaagccc aaagttcttg ttcggtttcg     60
cctggcactg gaaatgccgt caaaccagag cgcgaaacgg tctggtggag tatttctggt    120
atcagcatct tgcaattatt tgctcaaagg caagtgagtg tttctcccag gaccaaaaca    180
taaagtttgt tttggataaa tgcgcctaaa taccccatta aagctggcgc cctgaaaaga    240
gttctgctcc ccaaattgat ttaaagtatt aaagcaggat ttaaaggtta ttcacactcc    300
aggcagttta ttggcaccga agcacattca gagtttctat acagctcact atatttaaca    360
aattatttga gttattatgt aatcaggctg agaagtcgca cttgtaaact ctgctttaat    420
tgtgcagtta aacattttta caaaactcct atatttgcat ttgttaagat ttcagattag    480
accattttgt taattgcgcc atagtgctcc attttccccg gtgcgtcttt gcaaagcttt    540
ctttcccctt tcaatagcgc agcgtttacg ccctgggcta cctccaagcc cggagctcaa    600
aatgctcaat ttatttattc ttaattttgt ggcgatcatt catggaagca aaaaaggcta    660
cagtgtcctt tttaagaaaa gaaaagctaa ttcttgaagt gaccttggca gtctggtgcg    720
tgccccatcc gaacagagag ggcggcttgt gtcaacaagc cccatctac cagactcacc     780
cttgtcttta ttccaactaa tttttcgttt aagacttttc ttagacttgt ctcttatcta    840
tcagattaaa agagcagctt gtaacaaatc agtctgctcg atttacaaga gcattaaagg    900
gacacaaagg cagcaagctg cagttagtac ctgggtctgt tagacggtgc ggtgcctgca    960
gctgatttga tgggttggaa atgcgcacga aacaaaatac ttgaatcctg aaaaagaccc   1020
tttgtaagtt tctttagaaa tcaagcaatt ctgcatgaca aagaacaatt aataagccgt   1080
cttttcacaa accagcagct ggtttccccg tcaaggaaag ttggaaaaaa ttcaggctga   1140
atgcgcgcag aagctctttg cgcacagaca tctctccaag gtgacccatt tggcacagct   1200
gaaataaata accccgctca tgcccagaga gcgggggaac tgtcagaaac atttacgcta   1260
gaatatcttg aaattgcaaa tccttttatg ggggaggacg ctgccgatgt gggttaaatg   1320
gacaatgacg ctggttaagt tggagggtcc tttggagacg gacacgtggc ttctcaatga   1380
aagctgctcc gggctcgcgt ggccgccttc gccctgcaca cacttctcct cccaaatact   1440
tgaaaataga cagagaaaaa caagcaactc acaaactcag cccttggccc tggcggggaa   1500
acagaatttc tttgcacttt ttcagagata tagttttttt ttttttttct ttttaaagga   1560
```

```
cctgtttggc ctctc                                                  1575
```

<210> SEQ ID NO 48
<211> LENGTH: 1414
<212> TYPE: DNA
<213> ORGANISM: Homo sapiens

<400> SEQUENCE: 48

```
atgcaggtgt aagcactcaa gtttgatttc ctgaagtaga gcttttgtgt atgtgtggga    60
cttaaaaaaa tctgttggca tgcagtctcc caagtctcca tgtttatctg tttgtgatgt   120
catatgcaaa agcaacaaat cagtggatgc atctactaaa gcagatttta aaaaaaatca   180
cccaagcttc tcctgaacta taattcttgc ctagtaaaac atacatatat gaaaaatgta   240
taaaaatcaa atcaaaaatt aagacagtaa taaacacttt agacagattt cacataccta   300
agtcaaatgg tagttctaac acaggcattt atatgggcca attatataaa gccattttga   360
aaggctgctt ttcaccatgt ttcttcaatt cttcagagtc tgcggtgatg accaacatca   420
gatactatta aggagtcttc aagcgtgtaa ataatgatga tttcacaatg attacatatt   480
cactctacag ctggctgagt ttttacatct ccatttgtca ttgacgattg tgtccaatta   540
aatgattagc ttttaaaaac tgctgcacat tatgagtgtg aacttgtgtt ccattgcact   600
gagtgatgca gaaacaaact cattacagca tgtaattcac ccatattaaa taacaaacag   660
atggctgctg taaatgagag ctccttttt tcttcaaaag tgccaggaaa aaggtgtttt   720
tatttatctt tgtttccagc ttctttctgt tttcttgaca agtgggcagc tggttgctga   780
ggttttcaat tggtgcagaa gaatgaaaag cctgtttcca ttaatttccc cataaaataa   840
gtctttgaat catttctgtt ataaatgcaa gtgcagtagc aagctgctgc ttgattaatt   900
cacttattat gaagatttca tcttttataa gagggcctgc aggtaattta tcttgtttag   960
taagattaga aaaatgtaat tatcttgata cctttggacc cctctcattt taattgtgtt  1020
cccataaatt tcaaacataa agatgggaat tttttgtgca caaatgttcc aacatgtggt  1080
cgaaaaatgt gctttaagcc ctgcacaaaa atgtatcaag taaaatacat taggactgta  1140
ctaatgcagg aatgcataca aataaagcta gcacagaatt atagtcgtgt gtacaaacaa  1200
atatttgaat ttctggttcc ctagtcacca aacagctggg gtgaggtaaa ggaatttggg  1260
atttgttaga cttttttttat atgtccctgg ggaaatgaaa tctgtcttat gtatactaat  1320
aaaattaaaa ttgtgtttgt cttcaaatct tccaaactca agtcaatttc tactgggtat  1380
atatttcatg gactctcttc ccatcacttc catt                              1414
```

<210> SEQ ID NO 49
<211> LENGTH: 1426
<212> TYPE: DNA
<213> ORGANISM: Homo sapiens

<400> SEQUENCE: 49

```
cacaccaaat cacctgactg attccttcat caaaagctcc tcttggcagt tagcagtaca    60
cacctaacat tagccaaaca ggttatctac catcaacacg gagaaataag aaactttgta   120
ttgccattta aagaagttgc tttctaaaac tagacatgaa taagggagag aagaggaagt   180
attaaacccc taaactaatt aacgaaataa gggagggggg atgcaggaaa acaatgataa   240
ttagtatgta cccttggtta accaaatcca cacatacatt cattctgtat atgcacaaac   300
atcagcagca tcataaaccg tctcaagttc tagccattat tcagttcgac atctgcacat   360
gtttatgcgt ctctccaaac aacctcttga acaccctgct ggagctgtca tttttttctt   420
```

-continued ctccctatct ggcagatggc aagtcaacaa tcggcatcaa cagcagccga atatctcccc 480
ctccatccta ccccccctaaa cagacacaat aataacttct ttgtgcttcc ctacaatgca 540
gctgcttaaa ccatttcgct acaaggctgc tttgccttaa taaaaaaaaa aaaaaaaaaa 600
aaaaaaaaat cccttctgtc aagtctaaaa agcagcataa tgttaagcaa gctaaagcca 660
cagcacagct gcaaacgggc agacacattg acagctcctc ccttaacaaa gccctgtgaa 720
ttgaaggggg ttcatctgag gctcacacag taattagtat aaaaaagtcc gacagcctct 780
attatgctaa gggaaaaaaa aactggacag aactgggctg ctgttttgcg tcaagagttc 840
tgctgcagag tagataaatc atgttgggtt ttttcctctc tttttaaaga cagtaataag 900
gaggatgaga gaagctaatt tgaaaacttg gacacagtaa ttgtaccata tggtgagcat 960
ttatcctttc tgaaatgcac gctaacagtc acttacatgc acactgcttt gttttacagt 1020
tgttattctc tctaccatat tcataaaatg gatttgaata tctgatactc aagataagtt 1080
gtgtgtaatt agcaagagaa ctgcctaggt ttaatttatt ggccttgcac tgcaatctag 1140
taaaatgcaa aacaaaatta aacaatgtgt ccactttgta cagatatttt ttctttaact 1200
caacaaaaca ctaatgaata caagttcatt ggagtgtttc taagttaagg cacagtgtat 1260
tttgaaaatt ccaacagaat aaactatagc tgttgataag atttctgata tgtcaccata 1320
agaataattt ttcagaaaga tcacctggtt taattttgta tttcactgaa gcagatgtaa 1380
ctcttcctca tatacatcag taaacctaga tgcaagagaa atttcc 1426

<210> SEQ ID NO 50
<211> LENGTH: 1069
<212> TYPE: DNA
<213> ORGANISM: Homo sapiens

<400> SEQUENCE: 50
agttttggct gtgactttag ccattgcttt gttttattgt aatcagatac attggcatga 60
aactacttgt aacagattcc aaaagtatat gctgggcttt ttattggcat atcaaacagg 120
gaagcattca ggccatacat tagcaagcag ccaagtaatt aataataaca cacgtgaaag 180
aaaatgaata ttttggttga gaatcagaat gagaagtaag acaaaggcct gggattcgtg 240
tccttgccct cagcagcagc aaaaataatg ttatgaatag catttaactt gaatttgcag 300
caaactgctg cttttatcat aaacaattgc cagatggtat acattatctt tcttttttct 360
cctttcacaa aagcagcatt aattgcagag cagcccaggg ctccactcag ctcatcagtg 420
tgataacact tcatgaccct gattagccgt cagtctactc aattaaaaag atcatttaga 480
cattcaccca atcatttgcc tatcgagcca cctgggcctc aaccaggggc tccattttta 540
acattctcct gccctctctc atcttgccta gctttttttac atatctccaa aagacgtaat 600
tgaattaaat aaagcgtctc aggggcagct gcaacatctg ctgtttgtgg tatgtcaagc 660
cttcagcatt aaaaacagtt acatatgctc taaattagca ggtcgcagag atgaaacagt 720
cgatgatagt gtttttgtgc cagcgtgaga agcagctcac agctgtgtgc aatttacaat 780
taaaggcttt atcagagctc aattgtacta gtgaatcaag tggtgagagg tcagttagtg 840
aattagacca attagagctt gtacagttaa attatctgtc ttattaccta ctgataaaca 900
gccttgtcat atctttgctg gaatgatgaa gctgaatgag ttttatgaag tgataataca 960
agttcactgt agtggaactt agtgatatgt gaattcaaaa tctatagcaa caaaatggtt 1020
ttatataacc ttttaaaata gctatataac agggaacttt gaattggtt 1069

<210> SEQ ID NO 51
<211> LENGTH: 1730
<212> TYPE: DNA
<213> ORGANISM: Homo sapiens

<400> SEQUENCE: 51
atgatcacat cagtgccctt taaagtactg ttctcattaa tatgaaccat tgaatacttc 60
ccatttgtct aaaggatgga aggcttagtc accttgaaaa gatgctgcct ttttttcttc 120
gtaagccttc aaatacttta agaaaaaagc cagtaaaata tcagttaaat gtatttatgg 180
ctttaaaaat attgtaacag tgtctgaatc aaactttagt aaaatctctt tgggttatat 240
ctgagaagct tttattgaag actttgaaca aaattgtgtt tttgacagtt ttaaattata 300
ggctaactag cctgggaaaa aaggatagtg tctctctgtt ctttcatagg aaatgttgaa 360
tcagacccct actgggaaaa gaaatttaat gcatatctca ctatcttact gtccatgaat 420
ataatagaaa tgaattcaaa atgcagtttt atttttgcaa atgggatgag tcgatagatg 480
cacctcatat ttttgaacac ctagggttca acaaatttac tggtggtgct cttgcatttt 540
aacaaaattt attcttcagt agaagggggc agagaacact agattcttat tcaagcattc 600
tatcgagctc tgcattcatg gctgtgtcta aagggcatgt cagcctttga ttctctctga 660
gaggtaatta tccttttcct gtcacggaac aacaaatgat agctaactac agaggcacat 720
ttgcagtagt cacattcatc aactgcagaa aaaaaaattc aatttaattg tgcaacacag 780
ctgcacatgg gcttttgagc atttctgttg ttctccctgt ctcgctattc ctccctccag 840
atctattttt taaacttttt ttctggttat tttttcccct ttttgtctct tcttccattt 900
ttactctctg tactttcttg ttaaagtaat tttcctttgt ggctctcatt ctttttcccc 960
cattgaaggc tatgaatgta gaaaattatc acaattactc atataattga gcctctttgt 1020
agcaagtgca actccagtag cctttctcca tcatgaaaat ggtttcatta tagggttttt 1080
catattctct gacaccatct acacagagga acaggcgtgc agatgagatg tgctaggaac 1140
aggctagatc agtaaggtca cagtaggaat aattagctct gctatggaaa gagcatctag 1200
gccttttact gctacataaa tgtactgtcc atggctttta gtcacaaaaa aaacttacta 1260
acaaatggag ctcccgccta ctactttgaa aaaaagattt gtatcaacac tacaattttc 1320
catcattaag actaataaca cagagcctag tatacatcaa ggggaataaa aagaaaaatc 1380
tcacattcaa gtggcggctg ggtgctgacc tttgttccct ttttttgtgt acgacttaac 1440
tctttacaaa aaagagccac acgccacacc aacatgcagg tgaactccag ctagtactag 1500
caaagcatag cattcagttg gaaaatttga taaatctcca tgcaggataa tgcatttcat 1560
tacatattca ctacattaat tctagctaca ttaaaaaaaa aagaagaaga agaagaagag 1620
tagaattgaa agtgacattg gattttagct atctggatac aaaggtcagt tttcacagag 1680
tatgaatttg catgtacaag ctttttttgaa aaccagatca gtcagtccca 1730

<210> SEQ ID NO 52
<211> LENGTH: 1296
<212> TYPE: DNA
<213> ORGANISM: Homo sapiens

<400> SEQUENCE: 52
ttgagcagaa aaatttggaa aattgttttt tcctgtaaga atatattttt attttcattg 60
ttaattgaaa agattaaagt ttttcatcag caataaaatt ttcatggcta ccttatgaat 120
attttagcta ccatatctaa ttttaatttc taaataaatt aataacaatt ataatgagaa 180

-continued

```
aagcttccaa ttttattttt acattttaat gaattatttg tgttctatat gtaaactgtc    240
tcagcatgaa atcaattttc tgccttgatt cattccaaat ctgagatttc tatcacatta    300
atattgtaat tagaaacatt aatagagacg gcaacttaaa aagcatactt tgcttcttgg    360
caatttagca tatttctctg agtgcatagg acttcaagaa ctttcagtcc actaataaat    420
ttattaactc aaacttaaaa gaagtgaaaa gtctctttct ttctctctcc ccatggccag    480
tctgctaaaa tagattattc atgcttattt gattcaggta ggcttttgca agcttcccta    540
ctaggcctgg gaatgtggta cattgaggcc ttttcagagg cttctgacat agaccaagct    600
tttattgcat ggtgttttat tatagccaaa tcctagtctc cacccagttt gtaggcactc    660
tgcttattct tttgaatcag gaaaggttat cacctacctt aatccatgct gctgcatgga    720
ttaaggacac cagtgtgccc caggattctc aaagaggatc ctggaaactt ctggtttttt    780
ctttttgct gtctttacta aattctattg ggcctgaggg ggatttgcat ctgaaatggg    840
caacctggtg tttttctcaa tgaagacatc agatcaaagt tcagttagtc aaggcctttc    900
taaaacatta agggggcttg gacttacaca ataaaaagat gagctctagc agagattgca    960
ataaaaacat tctgaactat aatccggata aagaatagat tataggccaa agaacagacc   1020
ttgtttaaat tgctttagac taataacttt acatttttta agtttgtacc ctatttttaa   1080
gaaacatttt aatattatat attttattta tcaatagttt catgataaat ggataaatta   1140
tgttttggga acaagaattc tgtacatatt ggattgaaaa gattagattg aagcaaactg   1200
atagcatatc ttattaatga aagtaagtag taccttatgg agggatgaac ggtcatttca   1260
ttttaaaaaa taaatgtcaa acccacagac tctgaa                              1296
```

<210> SEQ ID NO 53
<211> LENGTH: 1848
<212> TYPE: DNA
<213> ORGANISM: Homo sapiens

<400> SEQUENCE: 53

```
aatccactgt gaacaatctg ctaagttaaa gtcttattcc catatgtcag aaattaactt     60
gtctgcttca agcatttatc caataggaat ccacatccaa tgtattaaaa cttaatttaa    120
acttaattag tttgtgagca gtgttcaata aatcttctcc aagtctttct atagtgaaat    180
ctctgtagcc agatgttgat tgtgtacaca ttgttttgtg ttgcttgcat aaacattata    240
atcacatata gacaacagca gagctacaat atttagaaaa catttttcac acctccttat    300
taagcaagac tatgaaaatt atgactcatc actgcaccat tgtttttgcc tgtttctcg     360
tgctggttga acagtcatag gcagctggta ttaatacaat aggtagtgct tagggaatta    420
atgggtgatg tgtaatacac cacaaaggta tctgtcatgc ggaacaatag gcgcaatgat    480
ataagatgta tgtatttgaa aatttgctca aatgtgagtt ttccagcata aagacatacc    540
ttgactgtgc tgcaaaatta gtttttaaca attgtaagaa gtctgccaaa aaaaatctgc    600
ttttatttta tttgtgatcc tgagagcatt taagctacta ggagcaggga tatacgtgct    660
cctgttctct ctgctcctat caaaacaaca ctagagcgct tatgctccag ggagatttgt    720
atagaatctg acgcttgtat cagctctgaa aaaaacaaca aaattacagt ctgaggtgat    780
gcaaatgata tccttggtgc atcttcccca tgctcctgcg aggctcttga cagctgatgg    840
ttggattaaa caaaaagacc agtaacttat gactattagc tcaaagcaat catctctcat    900
tatttcaatt acatgggtaa atgcatgcaa tcatgtatca aatcactttt cccttttgaa    960
```

-continued

```
gaggttcttt tcagagtagg atttctgcca gaaaaaatgt gcaaatattt acactggttt   1020

ttcatccaac tgcacctttg tttggcaaaa ccaccctatg gctacaattc tgagtgatat   1080

tttgaaaaag ggggaaaaaa acaaaaaagg gaattggaaa tagtatgcgg ttttggtgac   1140

tcattagcag tctgtaaagg aggcatcttc cgttacttac tgctacctga cttgtcagta   1200

tgaatgtggc tcctattccc taaatcacac tacctgtgaa tagagctccg ctggccaatt   1260

caaggctctt taggcaacta tgattgatga ctcagtgact aggagaaaat tgccttcaat   1320

gaattattca tcaagctatc tctttgctgt taaagtagct gacaggaaag ttctgacact   1380

gcctaagcac aatccactta caaatcagtt acaaggaaat attaaaaata gctcggttac   1440

agcataccag cacagtatca agttggggct tttttctgtc tacattgagc atcacggaga   1500

acttgagcag ctcttcccat ttagccattg tgctaatggc agtaaaggca gtgattagat   1560

agaaagcaat gtgatttgta ttggctttga aacaatacac tgtttttaat aacacaaatc   1620

tctaaattta aggtagacag ttaatcaagc aaatggtaat atttaagcat cttccaagaa   1680

aataaataaa tacagtttgt ggaggttaat ttatctttgc cttcctgtta ttgaattatt   1740

atgaacctag gaaaggatca agcccatatc tacttaggca tgttgtatat taatttttaa   1800

tatggaaatg atcaacatat agccgggaaa acatggcaaa aacatggt                1848
```

```
<210> SEQ ID NO 54
<211> LENGTH: 776
<212> TYPE: DNA
<213> ORGANISM: Homo sapiens

<400> SEQUENCE: 54

aacaaagcct ccataatttg acataattat gggttaccaa acttttgaaa aatcttagaa     60

atttgtcttg ccaatttggc tttactgcaa tcagtttctt ttatttgagg tacaatgtac    120

ttaaaactca cacattaaaa ggatgtaaaa caggcaaagg aagatagcat ttaactgcta    180

ttcatctaaa atatatattc ctatgtacag agagcctgga cagtgtcaaa tgaaacaagc    240

aattagtctc tttctaacag taagcagttc aaactgtaac atcatgccag ccgtgattaa    300

gaatgataca gcacatcatc attgtcaaca ctattcagcc aatgtaaacg ttagttagaa    360

atgcacttgt cagagaaaaa tgtgcctttg atttctatta cgctttccca gtaattgctg    420

tcatcagtgg caggttatta ttacagttga atagagtttc agtaattact tttgcacaga    480

ttctaacagc ttttagattg aaggatattc tgacaatttg aatactcttg acaacaatta    540

ccttttttcct ggttaacact gattcagtaa aattaaaaat taattctgtt cacaggaaac    600

atttatgtat gtcactggca agtggactga tattaaaaaa tgtgtaaatt gaacaatgac    660

ttagaatttt taaagtttct tttctcttaa gtatttttga aaatcggcat taaaagagat    720

gcagactatg ttgcttagat taatattaaa tgatgtggaa tgattgaaag aagtcc        776
```

```
<210> SEQ ID NO 55
<211> LENGTH: 1334
<212> TYPE: DNA
<213> ORGANISM: Homo sapiens

<400> SEQUENCE: 55

caagtatgcc cagaaatggt aactagaaag tagtacaacc taagaaatca tgaattcttc     60

ctttcaaata gcaggtggaa tttaaatgct agtttatggt tattattgga cctgcctttg    120

ctacttgagt cacttagcac atcagtagat ctgtaatatt tcatttacag accaagtaga    180

cgatttttgc tagattgatt tattgagatg agcgactaac taaaacaagt taaatctcat    240
```

```
tgtctcatcc ctgcattaat tttaacgtga atttagttgg gttaaatgga catttgtttt    300

tattatgtca aagatgagac ttttcctcca gtaaagcaga ataatgtatc tatatggtgt    360

tctaacttga acagtacata aagattagta aataaggccc cattaaaaat acttataatg    420

taagtaacat gagtcccagt agcatttcta atgtccatta atgcttattc ggaggatcag    480

agctcatttt actgagccat ttagtcaaac tgtgtgatta tttagaaagt taattcatgc    540

atactaaaac ctagcttaag taatgcagag ggtaggaggt aaaactctat ggagatgata    600

gtcctttttg ttatttaatg atcagccata attaacttgc aaatttgaaa taattagaac    660

aaattaaagg tatttaactt tgcctcccta aagaaaaatt caaattgcac caaatgcagc    720

tttaaattat tcaagtctca gaggtctagg ctagattttt tttttataat gccttttcta    780

tgatgagaat accaatctgc tctttgtcag aaggcatcct atcaagtaat tgttctttgt    840

gttaataaat gacagctatt cttctttgta aaagtatttc agtctcccaa gactacaaca    900

gcatttccat ggcattttaa ttcaataaaa caaaaggtta atgtttttct actttttaag    960

gaatgcaaat acatatggta ttcaattggt cctgaatgac atttaaaatt tgccattaaa   1020

gctcagacag actatcgcga tataagattt gggcaaaata gcaagaaaag ttcaaggtgc   1080

tctgaattac cagaatttca ttaaacttca agaactgaga atgtttttc tttccccacc    1140

ctaaatcagg gctactcaaa aattttcatt tagtatttta taatattaaa atatggaaat   1200

agagttcagt aaaatcttag gaacttaagg gtgacttaca gtgtagcaag cctaaatgct   1260

agggatttaa cctgtcttct gctatcttga tattgattat tttttcatca cttttaacag   1320

ctccatcaga tgct                                                     1334
```

```
<210> SEQ ID NO 56
<211> LENGTH: 1235
<212> TYPE: DNA
<213> ORGANISM: Homo sapiens

<400> SEQUENCE: 56

gccttaagta ggaaagaaac agctaaaaga tacataggtt attttgcttt ttaaaatttt     60

agcaaactat tctgtgaatc ttttgtgtgt ttggggctgt ttgtagagga aaatttcatc    120

aagcaacatt ttgggaacat tggccttttg tactctttcc taaataaaca gaaacttgta    180

ctccccaaaa taaaatgttt ctttgtatat tgttacctgc aagttattga taatggaagg    240

aacacctttt caatccttag tccccttcc cccaacacag cttttagatt gtcgataaac     300

ttcccagctc agtaattaac tgagctcagt cattgcaccc tgtatcatgt gattttttt     360

tccagtggaa tacattatta gagcacttac acagccagtc tagctgcagc agcccaggcg    420

gcaacagcag tgccattttt cacaaagaaa atgttgaaca ggagccaaat gtttggtggc    480

agtctgttgc taggaaatca aggtcctgag gcgattaatg acaaagcaag caataacaag    540

aaggcagaat tacagattta aaagagaaaa aagtggttgg tgttataatt acccaaagaa    600

atccgcactc attaaattgg ctgtttttat gattgacttt aattggaggt tagctcagat    660

atttagctcc tttcccaccc ctttaaacac acacaggcac ataatctgta gaactgcaga    720

cttgtttttc taagcattga gaggagcttg ccctgtaatt tgatccccac tgacagatgc    780

attttctatg ctgccatttt gaattaacct attgtagaac aattttcttc agccctgttg    840

aataaaacat ccagtctgat tacctccgat ggatttgata gagtaaaaga atgtacttct    900

cattgaagta gattgtttgc atggactcta ctgattgtga actctgccag taagcacaat    960
```

```
catttgtaat aaattttcaa agaaatttgt gaggaaaagg taatgagagt caccctttta   1020

tagtttaatg tttggcacct ccatcaaaat aatataattc ttataagaca gtgttatttt   1080

tccagtaagc ttttcacgtg gttttagaaa aaatttctga atcttcattt ggactattca   1140

tatatttagg aatagagtct tgtatttaca ctctaaaatg accattcttc ctccccaaca   1200

acagtatttt agtgcaagac tcaatatgca aagca                              1235
```

<210> SEQ ID NO 57
<211> LENGTH: 1677
<212> TYPE: DNA
<213> ORGANISM: Homo sapiens

<400> SEQUENCE: 57

```
tgggtttaag gtgagccttc tattgtagct accaattctc tttcctgtga tgagtccgga     60

ttctcaataa tcctagacaa ttactttagg tcctagtagg ttcttgtttt gaaaacaata    120

tagagatcaa gtactcacta caaataatta accaatagac acaggaaaca cttagaaaca    180

gtagtgttta tttcaagagg cataatctga ggtataaaaa tgcactttgc agtgggtact    240

cattttaata atttgcaata ttttttggat tatcaccaag attattttta ttttttttta    300

actgagggaa atatgtgtta tttcatcacg tgacatttct ttgaaaaatc tttcttgtct    360

agatgtggac cttaatgcat tatgcaaaac ccagggattt agatttttga cattgcatac    420

actcacaata tattctaagt ggagacatta tatgctaact tcttgtgaaa tcctgtagca    480

gctgcttggt tcatataata tgttgaaaaa tatttatgta gtttgttttc ttttctgtca    540

accctggtat cttatgaaaa ttttttttcaa atggccagta gctaaagtag tgactttagt    600

ttgacttaat attatgccac attgacagat gaaaactcct tctaaaaatg tcatttgagt    660

gctcgactaa tttgcattta gctcgaaagc ttttagtgct ttgcacattc acattataaa    720

catttgggtg aacattaata ccccagctaa acaaaaatgc tattcactcc aaccatttct    780

tccactacat aaaaactata aatgattctc ctaccaaaaa aaaaaaaaga atgcaacccg    840

aaaatcaatt atagtaacta tttagaaatg taaaggaaag gcagtaaaaa agtgacaaaa    900

aaatctttaa ttgtagggaa aatgtgcatc tttttttccc ccaacatgtg aataaaatgc    960

atttccttta acaatcacag ttacaataga tccatgcatc tcacaggaaa aaattgacaa   1020

tttgattatg acttgtactt tttgccgggg ccatgaaagt ggtttatgtt tgaaatgtat   1080

cagctggaaa gtacttatta ctcataaacg ctctgctatt tcactttctg caaagtgagc   1140

tgttaacaga tacaatttga gcagaatagc cagaggaggc cttttgatat gcagaagagc   1200

tgacccgcgt gctgagcctt taattgggtt tttaattttc caggccatct gacaatatca   1260

aacatgatcc cagtgcttga aatgttgatt ggaggctaag aaggatgtac tacaacatgg   1320

cattatggag agaaagagga aagaatgcag gtagagagga agacactgag aggcaaatca   1380

tctgcctggt gatttttgct ggttttagag aatatttcca aacagtttag catttcattt   1440

taaatgatga acatctgatt attttgtagt tatagtgaag atgtttgaaa atatttctaa   1500

attatacacc ttaagctact tagctaaacg gatctgctca agtgagaact ggaaaaaaag   1560

catcccgcaa tttaacatgt tttcttaggc aaacctacaa aagtaagaaa gtaaggttgt   1620

tgagaaaatg tttgattaat ttgcagttat ttaatgtttt ctttgaaaag ctcctga      1677
```

<210> SEQ ID NO 58
<211> LENGTH: 1798
<212> TYPE: DNA
<213> ORGANISM: Homo sapiens

<400> SEQUENCE: 58
ccttggaata attaggcttt cctaattatt tcacaaccac actaataatc tgaggtagat 60
gtttaatttc gtgtctttcc acacccccca actatttgga gatcacctgg ttttaacctg 120
catccagagc tgtcttgctg ggctaatgga gactcgtgtg gcacacgtca ggcggcagtt 180
aaatagggtt gctcctgctg cttccctcat tgcccaatta cctgactgac tcttgcaagt 240
catagctcat ggaatcctac aactgggcac accagggcac ctgatcaaac atgatttttc 300
aggcccacaa gtcacagttc tgctctatct caaagcaaag atctgccaag ctcttaagat 360
gatttagcct ggagtatttt aaataacttc agaaaatgca aagctttctg tcggtttgaa 420
cacttcctgt cactttttag aacacctggc actcaaatat ttaaattaca attccagctt 480
taatgtgaag gaactaacaa taaatccttt ctcttcccat aatacttcgg gtctgacttt 540
tctttaattt tctaaaaatg cagatttggg aaatgaaatt agcaatgcaa ggtgaaccta 600
gtgtgaattt tactgaagat tatgcaaatg caggaaatta taattctatc aggatgtcat 660
tacatgtgtc tacttagaca cacattttct gctatgttta agttaaacaa aacactaaat 720
gactatgtag tatgacatct cattaatatg tttccattca catctgtgcc tttagtataa 780
aaaaaaagac tgcttcaatg ataagagatt aggtccttta attagaaaca aatgacaaat 840
cactgttaac cccatgtgat gctttctaaa acttccatca catattcctc ttaaaacatt 900
attaaacata agttccccag atctacttcc tagaaagtgc catttaacaa aacccaggca 960
ggatgttaat actgaggcgg aattacaggt tgccaaagca tttcctgtga gaggattgac 1020
aggggatcat tttgttatgg ggccacctcc agtgtgttgt gacaaccact cattacacct 1080
ctaagcagag cactcagctg taggtttcta caagatgcaa atagctccaa atgggttcaa 1140
tttagagcga gtggataatg tatcactcat ttctctaagg tagaagcttt taatttccca 1200
agaacaggaa agagaggaac atttcagttt ctggaaaaaa aacattcagt taaccaacta 1260
tgcctgagaa atggagtcac aatagcaata tctgttacat tgtaaataaa aacacttcac 1320
ctgccttgtt tccccttggc ccaaaacgaa acaccaagtg gtcaagtgag catcacctct 1380
caataaatat aattacccac ttaagagctc aatgtcaaaa actagtaacc tctaagtgat 1440
ggtaggtttt tctcttacaa aaggaactgc ttacaaagct actatagtta attataataa 1500
tactcaaaaa gtgtttaaaa cacattttga tatagaaaaa atatcatgga aagctttcac 1560
agttggactt taatatttta gtgtgctagt ttttataccc ctctgtgatt ttactcccac 1620
tgttctatta ctgattttag taagtgttgc taacaatgga atacagcagc ctctactacc 1680
agctatttag aagagaggta cgctgatgtg gattggaaaa agtcaataag cccatttaag 1740
attcctgtgt ttaacaaagc cacaggagaa gccagcgagc tacaaaacat gcccatgt 1798

<210> SEQ ID NO 59
<211> LENGTH: 855
<212> TYPE: DNA
<213> ORGANISM: Homo sapiens

<400> SEQUENCE: 59
tcttcctgtc ttcctgtggg cccctcgctc cccacttctg ccagcagcct ccccttctgc 60
cagaaagagt gactcccacc tcaacagcct ggaagcactc caactaccgt actttcttc 120
aaataaaagc agctaattaa cattattctt taattattgc ctttatcaac aaggggtctg 180
atttctacca gcaggatagt tgctttccct taaactaccc aagtgaatgc ttcagttcct 240

```
ggtgcttttg aaatgaattt gatgtcatct gcccagagtc acttaatggg gacgcctggg    300
taatgactga acgcgctaac tccgttagca gccctggaag catgtaattt ggcccctcag    360
gcaacagcac ttttgaaatc tctggatagt tttgaactct ctgttcttaa ttaaatatgc    420
aatttttcac ggtaaccagg ttaattcttt tgtgttgtgt tgtaatactg ttaggaattt    480
tcatagttct tattaaacat tattcaggca ttgtgaattc cataattaaa aaaaatgaaa    540
agaacaaagc ttgattcact cctttctttt ccctggctaa tttatcaaat gaattttgca    600
aatttttctt tctgtcccca gacagtgtgg caagtgtttt aaaggggaag gatttaattg    660
ccctgtaggg attggctggt tatgaaggat ttggctgttt gattagtaaa cccagttggg    720
aatggtctaa tgctccatga tcttaaaaat tgtctgattg taccctctcc aaggaggcct    780
ctctcttcgt tatgtagagc atcaacttca cacaagtgtg attattaggt agtgaggaaa    840
gggaagagag aaaga                                                      855
```

<210> SEQ ID NO 60
<211> LENGTH: 1653
<212> TYPE: DNA
<213> ORGANISM: Homo sapiens

<400> SEQUENCE: 60

```
agcctctctc tccttcccta tcctgcccct ctccgactcc aagaataagt caccagagtc     60
ccctagaaga ttcttgagtt tctgctctta aacggctcct tttccaagga ggaacgaggt    120
ctgttttctg atgttggggc ctcagatact ctgtgattgc aacttaattt tgtcgttgct    180
tcttttcaag attatttgga atgaattgtt tcttttgttt actatccaac aaacgacctc    240
tgctaatctt gtattttatc tccctaacat atggaaaagc tatttattct agccaatcac    300
aataaagtga agaaaacccc attttatgga aaggtatata tcactagtct gttgatcatt    360
aaagatatga ttaccagtga aaaccctctg aaggtggcac atttatgctt ccaggaacag    420
atggggacac gcattttcct tgcaaatact tttgaaattg ctctactggt agcagtataa    480
aaatgatata cagatgccag ggccggcatg gccaggatga gtgcgccaga tttacacagt    540
aaagccttca cacgcgggct gtcagttttg attgatctct actatacctc aggaacttgt    600
tgactaggta gggaaacagt gcaaataatt cactgcagca agtcagataa ttcacacaac    660
caatcggtct gcttcacttt ctggctgtga catacgagcc ttccctacaa agatgcatca    720
ttttccagct tgagcaatat tcaatgtcag ggaagaaaag gtattaaagc cacacaaaag    780
gagttcgact atcgcagaac gagaagttat tttggtaatg ggggacagat cccgctctac    840
tccaagtccc accagagctt tcagacccaa ttgtcattat catattgatt aaaaaaaagt    900
tcgtcatagt gcaattttag gtttaacgcc aacagatcgg gaaagagcaa agaattatcc    960
cacaaaagca caacattctt accacaggga cgtttccctg ttccagttca ttgatggagt   1020
tgattaagtt taaatgaagc agacactgga taaaagtaag ggtattgacc actgggcacc   1080
gagatccgtg cttgaaagga cctgatacat gcagaaaagc aagatttgct aaatgctcta   1140
atcttcaatc aaatcttaca tcaatacaga caaagtttgg taatgagaga ttcaatgaag   1200
catgcgggag aaagaattaa tcctcttggt ctaaactggc ttcaactttg aagcttgctc   1260
cgaaggaaag acagttatct aaatgctaaa taagaaactt attgtacttt tcatggcatg   1320
ctaatctttt gtctatttca tctctattat gtgtatgctc atagattgca gttgtcatgg   1380
tgatgatatc tagccatgct cgggggatgg tggtgagaag ccggcgcgga ggtggaaaag   1440
acccccacgc aatccacagt acaaaaaaaa aagaaagaga gagagagaga gaggggagag   1500
```

gagtgggcgg ggaccggacc cctcctgagc tcttcccgcc aggcccaggc tccgctcacg 1560
tcagagtact aaggaggact gggcctcctg cccttggaac cgcgtggtga ggcgacctca 1620
gcgaggcgag cagcattcgg tagtggtagt gga 1653

<210> SEQ ID NO 61
<211> LENGTH: 1472
<212> TYPE: DNA
<213> ORGANISM: Homo sapiens

<400> SEQUENCE: 61
cacgctgccc tcactattat taagtgtcat tttcaaaaca aaacattagt gagaaattcc 60
agttaacttt ggaaagcaaa tatttttaaa tattaaagta aacaattttt aactctaata 120
tcttcatggt tcttgcataa tatgaaggac tgttctggga atttaaagtt tagcttcaat 180
aatgattact aaaccaagag aaatagatgt aaaaaagcag gacagctgga ggctcttgaa 240
ctatagttgt caaaagattt gtttgtgaaa catgcatttt attgccttgt atgcatgtta 300
taatgaggca tggacaactg caacattaca cttaatgact gcatttcttg tttcagccag 360
tttccttgtc ctcttgcaat taacgttttc ccagatcacc caaggctact ttgtcaggga 420
gaaaaaaaaa atctgaaatt cacataaatg agcaatgtca atagtttaga aagagtttac 480
ttagagaaca aagggccctt atgaggcact agtgagaaga aatggggaaa aaatgagtcc 540
tcacaatgta agcctttttct taaagcgact tgttatcaag cagttcagga tagtccctca 600
aatctgcatt aaaatgcatt tcattccatt gactcatttg cattaatttc tcccattata 660
tctgaaaatg gctgaatgtc tacccaacac aatgccacag cctatcacag gctaccacgg 720
cggccccagg tgccaattta ctcctcttag ttcttttcat tctgtttgct gattctgaca 780
actggagttc tcctctcagt ccaagggact tttcaattgg atttgctcgt ggtgacaaaa 840
ttgttgcttt gctgagagga gggggttctt tgattgagcg tctatcatgc tgccatggga 900
aagcgagagg cgaatgattc tcagtggctt ctgatttcca gtatttgttc agcattaggc 960
ccacttatct ccagaagaaa aagcaacatg tagaaagaaa gtgacaggca gaaacacact 1020
cacttgctcg ttcattctca ctgcgctctg tattcaaaca agggggacct attacactga 1080
aagctccaga tcagcctcac tcaattatca cagttaatcc ttatagctct ataaagtaaa 1140
tatttcatta caatttcaaa taaacagtca cccaatctaa tgaagcaaga actcaaagtg 1200
gcaatgtcat agaactcgtt accgtcatca aaggaaagga cacagccttg tctactaata 1260
atgaaaaaat agatactggc atatttatga actcaagggt gttgtagtgg tgaggatttc 1320
tttttcagtg ccattggcca atttatcttt ccaaatacaa ttcagttatc aaaattctat 1380
gtgtcttttt tctctctctc tttatttctc ttggtttttc accccaatct cttcatgggg 1440
atcatcatct tcactaccca tcatccacac ac 1472

<210> SEQ ID NO 62
<211> LENGTH: 944
<212> TYPE: DNA
<213> ORGANISM: Homo sapiens

<400> SEQUENCE: 62
tggtttagtg agctttccac actggtctag gggcccatga catttttgct ctgtcctgat 60
ggtgagattc cactctaaaa caaacccaac agggtcaggg ctgtttactc aaatatttcc 120
cccccaaaac cgagttgtga aaactgtcaa cctcaccaac gttggggaca cggatttgcc 180

-continued tccagcgtga gaagcgagtc ccctgccttt gcactgggga ccaatcagaa gacaagacaa 240
gccatggggt gcgggcgccc atggtatctg gccatctggg ggcccccgct tctctcggcc 300
ggctgtggag gcaagggaga ttttttttcc agagcttggt ggggctccat atggtcgaga 360
tcaaaggtgt tgctgggtgc atggttctgc tttatttcca agcactgctg ttaattagaa 420
aacaagatca gaggcagtat taaaatccaa ttaaattgat atgaacagat tgccaagtga 480
tgttcactaa tgtataattg agcaccatgc aaatttcggt ggctggcttt tgtttttttc 540
ccccacactc tggaatgaat gatgaggcta tgaagttttt cttcattgta aaaaacaaac 600
aagttaatgc attgatctag ggggtattgc cctggtgatt gatgaaaatg agagagaaat 660
agtaaagtgt gactttttga agggagggag taaagattct tctactcttc ctctttttc 720 tctccttggt tccacaccca tttcttatgc acagtggcag gcctcgcttt ctgttgacat 780
tccattgtta atgatccaga gaaagttcct ctggatttca aggatggatt gaaaacaaat 840
tttggaagtt tgaagacaaa catcacagat aaaaaaggat ctgtgtgcag gtaggttttg 900
ttttagtatt aatgttttgt atatgcctcc gtgtattaaa aaga 944

<210> SEQ ID NO 63
<211> LENGTH: 872
<212> TYPE: DNA
<213> ORGANISM: Homo sapiens

<400> SEQUENCE: 63
tccacccact cctttcagta gagtcctgac cttgcaggcc tgaatccccc ccatccatct 60
ccctacattg tgtctctccg gtgaactcat gctgggagat taattgctgc tatcacccct 120
aatccatcac acttcccaaa gattgttttg acatctagtt aatttttggc tgatgattta 180
tcaaattctt attactgtgc tctgaagggg ctcatttatt gtgttgattc atggtaatga 240
taaaagggaa gcattttgaa ttttaactac atttccctca tgcttcttct acccagtgta 300
gtaaaaaaag aaaaggggag ggggagggga ctgtagccag gaaactctta aacaattcag 360
aatgtggaag gaaagggaga ggggagaaaa ttcttccatt atgtgcgcaa aagccaaaat 420
gctgtaaaag gttacacaca catacataca cacacacaca cacacacaca cacacacaca 480
cacacgaagt atttttagca tctgggtctg aactacgttt ggaaagctta taccccctaag 540 gctcttaaac attgattgcc ctgtaatatt acctaaatgt ctactaccac tttattcaaa 600
tagaacttaa tggtaaatga cttcagtcat gtaccagtgg agatgtaaaa tgactgtctc 660
tgccaggcca gatggccatc ctacctttta aaagtgcaaa gagactttcc ttcactgctt 720
cggccactct ccagaccttc caaatttctc atttgccact cagcttttta aaataaacca 780
gatggtgagg agcccaaggc caacgttagt tactcttttt gcaaagactg aaggaagtta 840
atatctcaag gattgagctc agaagagact tg 872

<210> SEQ ID NO 64
<211> LENGTH: 581
<212> TYPE: DNA
<213> ORGANISM: Homo sapiens

<400> SEQUENCE: 64
cccagaggcc tcccattagt ggccactcca cccttcctcc tctcccctca ggcctggttt 60
ggggaaagtg gagccactgc cactcttggt gggcagctgg gggcccctta gcagtctctc 120 cacacccccct cccccttctcc tcaggcccca tgcccagccc tgaggtttgg agagcctagt 180
aagtgcccta tcaacatgtt aatcaaatta cttaggagct aaaattgacg ctgttcatta 240
attatacaag attatgctaa ttgtgcatgc aaatgcatgc aggggaacag aaggtgttca 300
ggcgcatggt gggccattag catagaggat ggggtgcggg tgcattggca tgctaatgta 360
tgcgccctgg ctatttatag tcctccagcc catctgcact gcagccacct ctacccgggt 420
ggggatcatg gtggggaggc caggtccagg cctggcaggt ggctgtggcc ctggggacag 480
tctatcttgg cttctaccgc aggctaagac caggaagcag cctgggccaa ccccacatgg 540
gcctgaacta ttacagtaag ctcctcattt cccttccctt c 581

<210> SEQ ID NO 65
<211> LENGTH: 1656
<212> TYPE: DNA
<213> ORGANISM: Homo sapiens

<400> SEQUENCE: 65
ctttcagagt tggtggggtc tttcgtcatc agtgggaaac aggacgtggt gcaggtcatg 60
ggtgccagcc caaaatgtga agagggcggt gttgctcaga tcaagagggt ctcacacgtg 120
ctgctgggga gggggtgagg ggggaggacc accacggaga gcttagagct gcacatagga 180
ctcgggtggg tgtcagggtg agatttctga gataatgagt ctcattacac ctccgaggtt 240
ggctacccag aaacccagct accttagggg ggtaaatata atgtaaagag gagaggagac 300
tagtgcgggg aaatgaaggc tgcagctgct tcccagcaca aacggtcctg cgagggcacc 360
cgcaccctcc ctccagaacg cagccgctct cccggggacg gaaggaaagt tcaagcaccg 420
gggccctcgc agtgggagac cagtcacatg ggcggcatca tgaaatttta ctgcaaaata 480
tcctcttttt cttatttgaa aagacaaatt attagcattt ttaaacaatt tcaatatgtt 540
taatggctga aagttaagct caaactgttc cgcttactga ataaagtgct aagtctgtaa 600
acaggaatct taagttaccc caagagtaca ctcattttaa attttacttg aaagcgggat 660
gtacgtttat tacaatttca aacaaaatgc taatgccatt aaacaaatga ggtttaggca 720
aattaactgc attttaatat tctgaaagcc tatgatatag gacattgtgt tacgaaacat 780
tggctagaag tatcagttgc aaggggattt tcatcgctgt gaatctcagg agaatatttg 840
taattagtat catttgccta atacttcagg ttaattagaa tatttaattg aatagctgta 900
atcttcagag atgactatat tatgatcaaa tcagcaccat ccccacgcac gctgatcaca 960
gggcggcagc ctgcctcact tctgctagct attcagccct ctggagcgtt cagcaacata 1020
agaaaaaatc tgtttcttac acttttgaat tttaatgatc catttgaact ctgccatcaa 1080
catttaatta ttctagaaaa aaaaaagtcc caaccatgac tcccatatgg catgttggca 1140
aatactcttg cccacagtgg cgtctgcacc tctccctggc agctccgaga agagatttaa 1200
cacagccttt tctccccctg aatgcgaggg cttctttttt aatagtgttt gcaaatacag 1260
accagatgaa gcctcacaga agaggttcct aggatactat tgaagcgcta ttaggaacag 1320
atgaattgag ttttagaatg cgacagtggg tttaatcctg tcacgtttcc gctggacctt 1380
ctgtacggtg tccagaaggt ctggggagtc aggtgcctgt ttggctaaac cccgttagca 1440
ggaaatgtca tattttttta agacatggag gggggcagca ctggggaggg gtttatacaa 1500
aaatcttcat cctgacttga gaggtagggt ctggaccctc ttaagtggta ggatttcacc 1560
atatacacat gtctttcata tacacacgtc tgtacatgtc ggcatcatgt accatccaaa 1620
cagtttgaaa attaaaggat catcgtggag tgattc 1656

<210> SEQ ID NO 66

<211> LENGTH: 1660
<212> TYPE: DNA
<213> ORGANISM: Homo sapiens

<400> SEQUENCE: 66
ttagctttta aattatagcc agtgtttttt ttctttgttt aagtgctgta tactttgtgg 60
cgcagaatta tatttctgtt tttaaaaagc atgtaggtag ctatgcttat aaaatgatgt 120
gaaatattgg tgatcccagg atatgtgtaa gttttctctt tgatggctga caatttacat 180
tgagaaattg ttttatagtg gcagtttagc taggtaactg aatataaatt taaatgcatt 240
tgttttaata gcatatttta tcttgtcttg ttttctaatt gaagagaagg ggccaaagct 300
aagtttgtat agaatttaaa ttcacttgga tatagtactt aagcatatta gtcaatattt 360
ataaaaaaag atagatgcac taaagttctc ctattaaggt tttaagatta ttgattggaa 420
aagagttgga aaatatcttt ttgtccctgt ttctccctat atagccttct tgaagtttct 480
ccaaattaga ttttaaatgc caattaggag gttgagtata ctaaaataaa agcaaatgca 540
accaaaatgg cctcacctta tggctagtta gggttttgag agaataagcg gaacctttgc 600
tctgagcatg gctttgagaa agatattcat cttaatgaac acattaatta gaaccataac 660
tatttataag ataattagaa atgaagcttg gtaaactgag cttttcctgc aattaatgga 720
ggattaatta ctggaggtaa tgaagtggat ttttaaatgc attaaggtga agtacagaga 780
tgagcaaggc tttgtgatag ttgcataatt atttcaggct gtttgagcat agctcatatg 840
agatcgttaa taagcatcat tgcatcgtta tgtatgcact taaaaagact taccaccaaa 900
atgactgcct aattatttct aattggcagg actctgtgta gtcattgagc tgtttgtagc 960
cattttaagg ttcatttaac tatccttggg gccatgtgat agatggaaaa agcttcaact 1020
acatgctggc cttggctggc gccgttaatc aattttggtg ggcttcagct taaatgcatt 1080
ttcttgtgca gaggtcaaaa cctgaagtag tccaagcgaa gttttgcttt ttgaagccac 1140
ttgactgtat tcattagcaa ttagtaaaat aattgtgtct gtcactatat ttggatttcc 1200
atatgacttg gtattctttt atcactgtct cttcttattc catatttgct ccactggaaa 1260
caaaatattc ttccaacaaa cccttttagc aacttcagtg tagtggcata tgtttccata 1320
tactaccttt cttcattcat ttattagctt aaacagtgta gtacatttca acacaatcat 1380
ctaatttgct cctgattgat tgctggtgaa agtttctact caaggacaac attttagggc 1440
ttttaaggac atctctaagg aattagtcat taagcattaa gagaggaagt aagaagtagt 1500
caaatccaat tctgacattt accagagttt tgtagttaga agcatctata tctaagatgt 1560
tgaaagctat acatattttt tgcacctatc cccacaagga cacatgataa caggcaaatt 1620
gtgtgacggg gataagctgg gtaatgtcta catttacttt 1660

<210> SEQ ID NO 67
<211> LENGTH: 1059
<212> TYPE: DNA
<213> ORGANISM: Homo sapiens

<400> SEQUENCE: 67
ggggatagaa tgaaccaaaa acacttggtt ctctctagtt aaatatttca tgcctgatct 60
gttgtagctt attctatgga aattaaaaaa aatatttatt tctatgttga gcttctttta 120
tttctggaga aagcatttca ggtacttgtt cctcgacttg tggtatttga aatatgaatt 180
ctgaattcgt ggcttatcaa taaaaacaca ttgactttca cggaggttga ctggtgtatt 240
ctagtacagg agtagaaaca tttacttaca ttgtgttcac agctgataaa ctgcagttgc 300

```
taacagtttg ttaattaaat cttagttaag ctttgtcctt cctgcttgaa aacaggaact    360
cttaacatct gaggctgcaa tttgcatgca tcagtcaaca caaatgctga acaaagtgct    420
tgtttaggta ataagataag gaggtgccct ctccacattt cagctctgac cgcctgagaa    480
gcaacatttc ccaagattcc cagctgctgc ttgttcaggc agctctgtgg tttgcgctgc    540
atattaattt ctgtccgaca cgggaattca atttgtactg tacatttcat ttcttcacag    600
atttagattt atttcatgtt ctctgctttt aattaactct ctggcacagc tgctggacag    660
gatagaaaaa ctcattgctc tccctgtgtt atgagtacac caccaatcat ttgccattta    720
gatggtggtg caggagctat cagtttctat ggcaaccaga gccgtggtga ttgattcctt    780
gccagtatgg catcaccaca gggagtgcag cttgtgattt ttgtatgctc gcaacatcca    840
tctaattaaa acaggattat ggaatcatcc cagtatatgt tcagcaacta cactgcattc    900
catttatgta aatgtcaaca ctattaaata cagtggtcag aagctgttta taaagaaata    960
cttgccttag tctttggttg tgcattggga agtgagggct taaccacctg gttttggcca   1020
tttattctct taaatggtag cctttaacca ggcacagtc                           1059
```

<210> SEQ ID NO 68
<211> LENGTH: 1049
<212> TYPE: DNA
<213> ORGANISM: Homo sapiens

<400> SEQUENCE: 68

```
tcaaatcttt actaccccca aaattccagc attgaatttc caggccaccc cacagcaact     60
tcattttaaa aatatgtttg attttatttt cctaatcttc ttgcagcctt tctttctttc    120
cctttcctct ctattccact gctgcatgct ttaattttgc tttcagtcgg tagtttaaaa    180
actttagctt ctaataactg gaaaaaatgg ttatttaaag ataactgcaa cttgcttaac    240
atgccaggct atcatatgct cagtgctttg aagctgcaaa ttaatgacga gcaggaacag    300
tgactatctt tcagaagaaa ctgacctctt tctaatggca catcgctaat gtcatctgtc    360
tactgcatct cattatgtga atttcacgga gttaaaaaaa aaagtatctt aaggctgtgc    420
acaaataaaa aggaccttct agtattaagc actttgaaaa tttttgatct ctcaaaacac    480
cttccttaga tactgcttcc cccttttgtg catggcatgc tgcttatgtc atctattctc    540
tgtgactaat tatgttaatt ttgtgccata aaagtaactg aaggctgtta aggaataaaa    600
gcttttgagt ggccttattt cataaacacc ccttttgaac aaggcacatt tagtcatatt    660
tgcagtaaca gaaagagtct tgtgctaaaa atacaacaaa ggctcttgaa tatggccatt    720
tattcccact ttattaggta atttatgaaa aagtatgaag ggaagccttt ttgttactat    780
aatttgcata aagctggtgc ccccattaatg agataacttc ctgccttttg tgtatcacca    840
gctggaaata gaaatggggg aacttttctg tagcccaatt acttaacctg ctgagttcag    900
agttggaaaa taaacaggat tcctatttgc cgaagaactt tattttggtt cctctaccct    960
gattttttaa aataaaaata attagaagaa agatgaaagc aaaattttaa aactaaaaat   1020
ttcagcaagg cttaatgtta gaatacgta                                     1049
```

<210> SEQ ID NO 69
<211> LENGTH: 902
<212> TYPE: DNA
<213> ORGANISM: Homo sapiens

<400> SEQUENCE: 69

-continued

```
gcagagtagg ctttcagagg taagtttgtg gttagtactt tagctctggt cagttgacca     60

taaatagatt tttatacttg cacataaact actctgattg cccacacata cctgtaagtg    120

gatttgcacg tgtgcgtgca cgcacacaca cacacatgca cacacacctc aaaaagcaat    180

ttcccccccca gaacatcaag aaagttcccc tttccactta aatgcttttc caaatagtct   240

tattttattt ttttttattt atttctctgc catatccttt tcaatctgga aagtgacttg    300

gcctcttttc ccccatctat tttctgcctt cctgctattc agtttaggca tgaaacacag    360

aactagattg aaagcattca atggctattc aatcggagaa gaaaagagcc ccttggagct    420

ttattagata tgaagatcca caataaaaat caatttctgc ctctttatgc agtttaaatg    480

acaaagcacc cacccattct gcggccattg tgctggggaa atgtaattca gtccccgagc    540

tgggcccaga gcaccgcgga ctccctgacc tgcactgaca gattccaata tgatacagac    600

cttcggagat aatgacagcc acttcatctc actgcaagaa aaaagttatc tgatatcttt    660

gagggttaaa aggctatgtg ggcagcattt tcaataaccc actaaatcag catcttaaaa    720

aatacctaag ctttgttcct ttaaaaaaaa tttgcccctt actcctaact cctttctga     780

gccccatctg atagtgtcac aagtgtctcc tgccaaatct attgagcctt cccttccttg    840

ccacagaagg ggaccctcct agataattag tccaagggga aacaaggtga gaaaaacgtc    900

tt                                                                   902
```

<210> SEQ ID NO 70
<211> LENGTH: 1154
<212> TYPE: DNA
<213> ORGANISM: Homo sapiens

<400> SEQUENCE: 70

```
aagtttgaac tgctcaagaa agattttttt gtgttgcaca gtgaaaataa atattaaata     60

tcaagatgaa actgaatatt tgaataccct cccaagcaca ttcccccata cacacacaca    120

cacacacaca cacacacaca cacacacaca cacaaataca catatacttt cctaccagca    180

gactaaatcc agctagttcc tgaaaggcgt ttattttgag aatcactatt gttttatttt    240

actacatttg tttggagact ttttaaaaat gactatatgc aaagaaatag caactgcatc    300

tgcaatctct agcagcagcc cttccttacg agactgtgta gggcatttgt gggtgttgtt    360

attgttgttg ttgcaatcta gctaataaag gctttctctt acacaagaga attttgacag    420

ggttgactcc agacagcttt ccagctgagg tctggggcct tgctgaactt tcaaaatttt    480

cccatttgag ctgcatcaaa gtgaaggaaa ttcaaggatc actaacgtct cagatggtag    540

cacttgccct aacaacgaag gttcaggaat tctttggagc aggctgaggt catttttctc    600

cccttttctc ctaatgcttt tctctattaa tcagagctca gagctcagat tggtcttcaa    660

cttcctccca atccttgcta agcctgtcat ttctagctat tatttacttt aatggacttt    720

ggctgatccc ttatgaagct ttggatctga gaataataag gctggagagc aacgggcata    780

gacatgggtg tgggtttgcc tgcagattaa ccgtggcaga tgggctttat tgcggtttcc    840

tgtgtactga gcgttgattg agagggtata atgagagagg tggtgtctac acaatggtca    900

cagccacttc attgcacttt gcgtctaaac aaccccattt ttctaaatct ttgggttgtg    960

aaattttagg aagtcagagc acaagaacaa gtacaaaaac aactgtaaat aaccatgaat   1020

gttaatccaa cactaattgg tcccttcttt cagtatgagt ccattttgct cagtttttaa   1080

aattctgggt aaattaatgg caaagatagt taaaatgttc ttgcattagg tggttttgga   1140

tgaaatagtg agca                                                     1154
```

<210> SEQ ID NO 71
<211> LENGTH: 1331
<212> TYPE: DNA
<213> ORGANISM: Homo sapiens

<400> SEQUENCE: 71
tgcctgggta atacctgagt gctcccggca ttacctgggg gctgccaccc tccctccccc 60
tccttccttt ccagctcaac attgaggtga actttttacc atgatcgatg tagctttctg 120
gtgtctacac agatttctgg atggcctcag aaatgtcaca tactgcttcg ggaatgtctg 180
caagtatatt tcatacattt tacctggcaa ttaaaaaaaa gtcatcttta agatattagc 240
atgtggatac cgaggttcca cacaaagcaa acaaagaggt cattcttagc agctaatttt 300
aaatcttcag gcaactatac gaacctatgt cacagtctct cccaaaattt attataatgc 360
ccttgttata aatttagaat atttttgcaa actcatataa acaagtaatt gatgcgacta 420
aaattcttgt cacatattta ttgcactatc agctaaaatt tttaagtgac aagaaccaaa 480
ataatcgtta atttttatag ggcaaggatc tggcttttttg tctgacacaa agctgtataa 540
aaaactgctt ctgattttat gcacattgtt tttagttaat gattttcagc tgtttgttgt 600
ttctctgata gcatgaaaat gtaccatatg ctcagcccaa agacagatga ttagcaagtg 660
agattccggg cagctgtctg actgagcgcg ttgggttgat agcattctgc tatcataatt 720
agcttaagct ttgggttaat taactttcta cctggatatg cataataata gcaaactgca 780
aaaagcaaga agctttcagt acatcaacaa cattgctgtc ttttttattt ggtatttcaa 840
gagcatatta gaatttcaag agtgattaat cctgggaata ttgtcatcta ctgtagattt 900
tatttgcaag ccagataata ctgaaacaat tggaatctat tatagagcag aaatagcatt 960
ttaaaattgt aattaaagtt tctaaaagca attgctaatt tcaaatgcct ttgttggcaa 1020
gaatattagg cacactgctt cttgtatggg cagcttgtcg ggcacaaaaa ataccagcac 1080
ttacactgtg aagaataaaa ctttctttta tttaagggct gtattgaaaa taatcagtta 1140
tttttatgta atttgaaagt aagattactc tgtagtttgc agaggtgctg ttcagactcc 1200
tagattgaag atattaaccc tgtgccctct tgcaggttct cacctttgtt acctcctgag 1260
cagtggaggg ctggaggcct gggtaggagt gcctggtgcc ctcttagaag atttgatgtg 1320
tgcgtgtgtc t 1331

<210> SEQ ID NO 72
<211> LENGTH: 1160
<212> TYPE: DNA
<213> ORGANISM: Homo sapiens

<400> SEQUENCE: 72
tcccagagcc aattccaagg ccaggcaagc caagtgctct ctactctact ctttcttctg 60
ggtgcagacc ctgtgagggg agttttggtt ttgccagcca cgaccaggcc agcccctccc 120
ttgtctggct tttgttagat tgtgttacaa ccttactgtt acttaactgt agaggacttg 180
gggatgtgcg tgctgtgtgt gtgagagaga gagtctgtgt gttaatagta acttgtgata 240
gatgcctttg gcgcccacac attcaataac acccacactc acaaaaaaag aagtggggag 300
gggagtcgtt ttatgggaga taacataact gcttgcaatt tggctattca ttgtatcttt 360
ggcattttat gtactgcatt agcggaggca atttcatgca tatggatata atgcattaag 420
tggaggcatt taaatatagt gaaactaatt ttatgatgat tagttgaagg aaaacattgc 480
attcgtatca tctatataga agccaatttg catgaaaatg cccaaagttg ctatgccaac 540
attttctgtg ctgctggtcg gggtcgcctc cgagtcaaga ctttgtatta aaaatcggtc 600
tccagtgccc atgtctttta attcattgca agctgtaggc catttgctca caaagcgctc 660
gcagtaaaac aaatgaatag ctaaaatact catttgcatg attcccattt gaaaacgatt 720
cccctgaaat taaaaaagcg tgttactcgg ttgtgaagat ggatgggcca gtgaggcggg 780
caattaatat tttcagcgtt ctctttaaag ccctcccaag actgagaaca gcacatgcta 840
gacaaattgg gccccacaac agtttcaggg cctcagcggc agcagcttgc ttccactgtc 900
tctcctttat tgtctcactt acattatgca gtaattaaaa ctatttacca ttcctactta 960
tctgccatct gccaccacgg aaggttcctc ttctttagaa agccttctta aagagcggca 1020
agaacaggag aagagttggc actgactctg gaaggggcct cgggggtctt ttcctgcccc 1080
tgccatgccc acccatccct ccatgaagcg aaggtgtcag gaggtcatgg tatgtgaagc 1140
tgagtttctg agtgagctgg 1160

<210> SEQ ID NO 73
<211> LENGTH: 1250
<212> TYPE: DNA
<213> ORGANISM: Homo sapiens

<400> SEQUENCE: 73
ctgagattgt gtgatgtgga gaaaaggaag atatgcagag atgttagcat ggccacaggg 60
tgatggtggt ggtggtgctg gggcaagtgt gcactactaa taggagaaga tgtcaaaaaa 120
aatgaagcat aataatagtg caatttatcc ttgctaaacg tactgcagtg tgctataatt 180
aaatatgaaa acctaaattt atctctatgt tcggttgtca ttaatttaac agggagtgca 240
catgttctaa tctaatggtt gatttttttt ctccatgtgc agcatattaa aatgtatatt 300
agcctcaagg tgcataaaca caaaataata gaccaaaggt tttggcctgt ggagaaaaaa 360
aatccatgct caaaggccgt caagtagctg tgatgcaggg gagacactca cttagcctca 420
ttaagccaaa gctctctttt gcttgtcttt tgttctgcat gacagcagcc tctttgttgt 480
ataataattc attccaagtt cgttccaagc taccgaaact ggtgaactgt ggccatttta 540
atgagaagta ttggtggtat gcataatctg gaagccacgt gggccagaca atcacagagc 600
actgcagcca gcaaaatgag atattgtcga aatcacaaat ttgtcaagtt gtttttggac 660
agggtattat aataagcact aaaatatgca tcctattact ctgcatctgc cagtcaaaga 720
tcactgtaat gaatgcgtgc tgcagggtat aaccaggccg ttttcctaag taaaacaaac 780
cacagagtac agaaaagaat tgtgtgggtt tttttttttt tttttggcat tgtttgactt 840
tttttttttt cctaatcctt ttgcaccagg agtcaggttc tcctggcatg gtgtccactg 900
ctagcagtga atacacaggc cctgctggtg ccagggagtt aacatgaata cattgctttt 960
ttaataggtg tgcttaccat ctgagaatac aaaacctcaa actcaaggct tcaattgagt 1020
ctactgaaga attcctggga gagaaaaggg aaaaaggagg agaaaaaaat atctctccca 1080
atgatcctaa gccttatgtt ttatcctttt ctacttcaaa tggcttagcc tttgggactt 1140
gttttgttgt ttgtttttct gtttgtttat ttttgctttt ttgtctgtct gttgatttat 1200
ttgcttttta gatgaaccta aagctttggg aagaaatggg tgagatgcta 1250

<210> SEQ ID NO 74
<211> LENGTH: 1657
<212> TYPE: DNA
<213> ORGANISM: Homo sapiens

<400> SEQUENCE: 74
ctgggttcca gaatataaaa gaatatcgtg ctgtgctgca gtattacaaa caaataaaat 60
aggccgaaaa gaatccccct tccacttcca taaaaagaaa aatgcatctt catgctcaat 120
gtaaacatca caaaagcttg gtcaatggtt taatatttaa aaaatggttt tgggtcatca 180
gataactata gcaacacaac gtggaaagaa attttttttaa atgaataaaa tatatacaaa 240
atttcttgta tgtgtagcca aagtatcagc attttccata tagaacatcc aatattttgc 300
tgcattttaa ttaaggtgtc taaacattat cacaaagaac tgcaaattgg tcagagcatg 360
cagtaaggaa aattaagctc taaaggcttt ttatcaccat atttcaggaa ccaagggtgt 420
aaaatgttct aatttgggat atattaaaag ccataaaagg tctttcaaaa agattaatgg 480
tactttgctt ggatttaaga taagggcttt agctggttgg aaaagcaggg ccctggctgg 540
acccttgagg cattcatctt tacagccact tggaagattt gtaaaagcgt ctgcataacc 600
tcaagcaaat gcacggcgac attttttttaa ttcctttcaa ttttacaggt ttagcgtgtg 660
taaatcatat tgggttgtaa aatagatata atggcacatc cttgcaacac agtacagatt 720
tttaaaagac aaacttcaaa ataaagttag tttttcttgc aaaatcttgt cattataaag 780
tttgctgata atcatttgaa gtatctgatt caaaccgctt aatctagcat aactgtaaat 840
ttcttatccg tttcagagta aattttactc atctcaaaat tactagcttg taacagattt 900
ataaagtttt cctccctttt gaacactttc aaggcactta tttaaaaata ccaattatca 960
tactttaact ttttatggaa taataggtct ctatgaaaaa tatttatgcc attctctttt 1020
gttctttaat taaatgaaaa cagatgtttt ctgaagtaaa gcggaaccat tactggagta 1080
cttaaagtgt taaggtcttt aatttttata tcagtttggt cgacaattct tgattgtctt 1140
tactcaagct caacattaat gtcaagcaag ttacctagga gacgaaagag atcaaagaga 1200
caaaaacccc tccaatgtct gattaatcaa gcctgcaaac agcttatttc ttttagcctg 1260
catgcaagta tgaaaatgag attctgggag ccgaacatgg tgcagatttg ttcattctta 1320
tcagaacaaa gccagcggca gcttatttca tggatcattg gcactgtcat cagtgctaca 1380
cagaacgggt gacagctcct cattttgagg cttgaacaaa attagcaaaa agtcggcaca 1440
aattagcctc tcatcttttt agtaatatga cattattcat ttacttttta tccaattttt 1500
aattttttcc ttgtcagcta tccctttcta gtgtctcttg catggcatca taaaatgcct 1560
tccaaaaaac aagcaaagaa atagccaaag ttgaaataac atacaaagtt caagaagcaa 1620
ataagaaaaa gtacttccaa tgactggtaa cactgtg 1657

<210> SEQ ID NO 75
<211> LENGTH: 1762
<212> TYPE: DNA
<213> ORGANISM: Homo sapiens

<400> SEQUENCE: 75
ggaagctcat tattcttcca aaataaagag ttaatttttt ccctactggt ctttccatct 60
ttgaaacacc atgagtcacg gtgtttccca tttcacaaac accacggatt ctttattgtc 120
tgtgaggctt ccatgtactg cagtaatttt gaattggata tgttatgtcc aaattgacag 180
tagtgattaa gccaaaaata agtgcatttt cctttaaatg ttagctgcag catcaagtaa 240
cattccctac attatgctat actgaaacaa gtcagtcggc accgaccaaa atgttgatgg 300
atatacagca gatcaaaaag aggagaatca ttttgaagtg ctcgctatct gtctgagacg 360

-continued

```
ataggcttct gaatttgtac ctctttgcaa aaagagactt cacattattt tgtcagtttg    420

tttcaatttg agaggtgttg aaaattggta ttcatttttt tgatataacc cttaaattgt    480

acaatttaag aaaactgact gaaagagata aattaaatgg gtagaaatat tttcaaatca    540

aagaccaact gacacatata aaaatgatgt atgtttctta catggtccac agggagaatt    600

ctgcaggctt gctatgatct ctacaatttg cttcagggca aactagattc tgggatattc    660

tattatccct ttggtctgtt tatcatggaa actgatgtac aaatcgagag gtctttttgg    720

tctctttctt tctatatggt tggaactggt aagaattcac ttatctcatg tcctcacctt    780

cggtaaagtg ctacagaaga gttcagtgac cagtaatcaa ttattattga gaagcaatca    840

attgctaatt tccataatta tgcacatcta aacactatga acaagaaaga gaaacaaagc    900

tgcactccca gcattgcctt gttagcagta ttttgttaac acaggctcta aaaaaagctg    960

ccgcagctgg taccacaaat gtgtttccag tattcaggcc atcaacgtga ttcgtcgcta   1020

aatgtataga atcagcttct tgctaaaaac tacaattaca ggtgatatac agattgaaat   1080

cacagggctg gtttgtcgaa gaaaattgtc ctaatgatgg gttttcggat ggggaatgca   1140

gctcttttct ttctctgtga tgggttgtga aggcagctgc acctgcctct atgctgtatt   1200

ctgccgcact taatgatatc tgatgatatc attaggcaaa gtgttcataa acagatgttg   1260

agcctgtgcc taaatgctgt cagatgagcg gttgctggcc tgaaacagta ttatttatat   1320

agaacattta cgtttgttat gttaataacc ccactattag ctctctggat gttgcgttag   1380

gaatgtaaat gtagttaata tgaataacaa cctctttact ctttgtgctg cagttgagta   1440

taacttttag gctttgggag agaaacaaag ataccccac caagtccttt tgacttcgtg   1500

attttttttt tttttttgg caccatttga aatttgatc agaagataaa tggtaagaat   1560

cctaagacag atgttaaata ttagaatttg atttcctca cggttcataa ttttgagaga   1620

ttttgatatc tgtaagttat tttgtgtgag cccagtttgt taccctaata aatcagagtg   1680

atgatcatgg acactcaatt gacaaagtat ccatttcaac tagaatgtcc taaacatact   1740

gtcagatatg gacccatttt tg                                             1762
```

<210> SEQ ID NO 76
<211> LENGTH: 1148
<212> TYPE: DNA
<213> ORGANISM: Homo sapiens

<400> SEQUENCE: 76

```
ctgatggatg agctcttttg agctcttaat gttcttactg cttttagaga actgtaagga     60

ttttggggca aaggaactaa tactgaagta agcagagcag tgagacgggg ggaaaacatt    120

tacaggatat tcctgccctt ggttttatct tctcatcatt taacagcagc agaataaatg    180

ggtctgctaa tgaaacagca ctgagaggtt aggtcattgg aagccttttt agtcattttg    240

tgcttttcaa gagcgaattt gttagaatta tgctgaatac ccacttaaag cctcagctga    300

taaccctacc tgtgttttat aactctgcac tgtcagaact cataataagt caaacattct    360

ttcagtggtg ctcataaggg agggaaaaaa accacgcaaa tttaagagta atttcagatt    420

gtaaatgaaa aggagaggca cgactgttca tttgcaccaa tcatgccttc ctttcatctg    480

ctctgattag gcctggtgcg gtttcatcag actcctccat caccgagctg tcactccagc    540

cgtctgttga ttgaaaacaa tcaaggctct gatggcacaa ttattctgac cctttaacta    600

gaggctgctg tgataatgaa aggttgatta tgatagtttg tgcctctttc agtttgccaa    660

gaaggttaat ttgggcatca gacggatgtt taatgggcgc ttgctggcta cactgaggta    720
```

aatgagaacg tgcagtcttg gatattgcac ggatatagtt tggctgtcaa tcattgtcat 780
ttggagtttg tgcctcacac tctggaaatc acattttatt ttttccttgg gatttaattt 840
attctgtgcc ctgaggaagt tctttcactc ggtgaccttc acagcagctt tctctgcctt 900 tttttttct tttttcaaat ggagctcaaa ggcacaacac atctagaaga gcattttgct 960
ttcattttca cttaaaaatg gaaactttaa aaatccgtcc ttatcactgc cttccaatag 1020
agcaaatgtt tccattccga ttgtgcagtg ggaaagtata aacgacaggg atactttagc 1080
cagtttgcta atgcagcagc tcacacagtt gttctgccct gtttcgcaca gtaaccagca 1140
aatgcagt 1148

<210> SEQ ID NO 77
<211> LENGTH: 1233
<212> TYPE: DNA
<213> ORGANISM: Homo sapiens

<400> SEQUENCE: 77
caagctgggt ttgaacagtt taatgttaca taataaaatt ttaatatgta tttaaagtat 60
ctactttaaa tagttacatt accttttagc atattaaaca tgctaaagac acaccaaagt 120
cacatagatg ccaattataa ttcataacta ccaatgaatt acgactactg ccttacattt 180
tccaagctta tgtcataaaa atcggaaaat caactacttc cctgggtaat aatatgccaa 240
tgactaattt attacattac tttttctgaa gagtcttttt ggcaagaatt ttaaagaaaa 300
aaaagtgccc ttgttaacaa tgatcagcag acctcacttg tttctttgta aagatagcct 360
tttagaggca gctctccttt taaatgaaaa tagggcagca gttatggtca cactttttgt 420
taatttagtt gccagtcagc cccaaatcaa aagaaaataa ggctgcagag tgtaattaac 480
attcagttcg gtcgttttgt cccttgtcta gcccccaagc tttgttaaaa ttgccatctg 540
aatgctgaag gctgtaggga aatcgatttg attctaatcg caccatgaaa agaacatgat 600
ctaactgctt tcagccctcc gtaaatctgt actaggtctt tagcacaatg caacttccaa 660
tttaaaaagc actgaatgtc tcgtcaatga ctttgtgaag aaaaaagaac aaggagcaga 720
cataaaaatt ccaatagttg tttaagcatt aaagttcatt tgcatcacag cgaacctgaa 780
aagggctgac ctctcaaacc gcctctcagg tctatgaagt tgtagccttg acaagctcac 840
attgacagag ctcattgact ctgaaaggct actctatcaa tggtgaaaaa tggcaatagg 900
ttctactctg agcaggcatc tgcctgccca cccgctgcta aaccaatggc aaaaccgatt 960
caaaacctga atctaccttg taatctttct ttctagggcc ttttaataat agattaagat 1020
tactatacaa tttgaggttt tacttttact gatgattttg ggggtgggtg gatgatgaaa 1080
gaactagagc agaacaagtt ttccaagccc actgttttat attaatgtat aaaatagtac 1140
ccaaaagctt aatactacat tctgcaaata cttattactt aaagaaaaaa atgtagttac 1200
caccatcatt tcatcagaag tttaaaccca tgc 1233

<210> SEQ ID NO 78
<211> LENGTH: 1273
<212> TYPE: DNA
<213> ORGANISM: Homo sapiens

<400> SEQUENCE: 78
acatctcagt ggctcataag attctactga ccagagctct gcagagccca gggtgcaggc 60
tgggaaggag aaagcaaagg ggacctcaca agtcagagtc attggtttca tttcccaata 120

```
tccaaatgcc tctgtccaat aagacctata accaatttcc cagagaaggc ccccgaagag    180
gctgagcttg atggagttgg gtagtgggct ttttttttt ttttttttt tggcttttt      240
ttggactaaa agcaatttcc attttatgcc ttttgtctct tcatccaagc aaatgccggt    300
gggatctggc aacctgagtt caatagccag tccttttggt ctttcaaagg ctatgaatgt    360
aataagagca ctcaaccctt ctgaagatat gcaaatccgt gcatttaaaa gatttacatt    420
catccttcac aggccctgaa atataaatat gaaataccca gaaccttgtc acttcagtaa    480
taattaagct gatggcctat tatgttcgat tgcaaatcaa tatagtatct tttggtgcca    540
cttgagttct tgagggttgg cgcggggcca gctccagtta tacaattgaa ttgctgcagc    600
tgcctgggaa acttcgctgc cgttcccatt caggaagaat aggcgggtaa caatggtgac    660
cagcctccct acagtaattg tgtacgagga cacatttcca atggggtttt tgttcagcag    720
gtgctgttat tttagtttaa tttgaattct gaaatatgga ggagagaagg agaccaatct    780
taacagcatc taacctacag ctgttcgaaa gaggccagca aacagcatat gttgcttaga    840
tggaaatcat aattgctcat tctccctggg atgttggccc accaacgtgg agcctctgaa    900
attagctggc atttttctgg cattttcctc agtggtgagg cctctgcaga gctcaggagg    960
aactattcta gagtggctcg ctccctggga ggctttggtg gtggcggctg ctgcgtctcc   1020
tttttcttct ccttccctct ttctccttca tggtaggctg aggtgaattc caaacactac   1080
acaaaacaca tccagggttg gcctcctcat tggaggctgc catggggcgc acaaggaaac   1140
aggcagtggc gaggtctggt ggagccccag ggccagactc tctctgagag cagcgaccaa   1200
cacccctggg tcagggtcag ggcaagagga aaactcagat agtaaggaga atagcatcaa   1260
cacagacacc ctg                                                      1273
```

<210> SEQ ID NO 79
<211> LENGTH: 1015
<212> TYPE: DNA
<213> ORGANISM: Homo sapiens

<400> SEQUENCE: 79

```
agcctagagc acaacaaccc cagggacaga tgtgacagga aagtggaagg tcattaacgg     60
tttcatcccc attattatag gcccaaagcc cacccttatg atgcactctg ctctaagagg    120
gctagaaaac cagtatcttt catagtaatg acttccagtt tacagccttc atttgttata    180
tttcctcaat agctgttgtg ttgagattaa ctgcataaat ggtctgcagc tgtctgttat    240
gaattaaggg agtttaatca aagtatttct aatgtacagc ataatgataa tacatggggg    300
aagtactatt taagagataa tgatggcttc agaagatcac tgttgtaatg tttagtgcat    360
atgccttcag cattgaattt gttgttgttc tgaatatgct taatggatca ctgaaaagct    420
gcctaatgcg ggattgtttg atggggctga cagagctgga attagcccat tgctgtttac    480
tgcatacagc cattaagatt aattgctgcc agataatttt gactgttttt atcttctgga    540
aaaagtgtca ctaatgggtt tataaattgg ttcactatta ctaatagtaa ggccagtgta    600
acacaataga atgtcagcta attctaaaga taaaggtaaa aaagtataaa gtactatatg    660
gcttgctagt tttaagggat actgttatct aataacagac agactgatat atgatgctca    720
ttaatgctat ttcctgagct ttgggttgaa cctaatagat gctaataaag tcttatttga    780
tgtcccatta aaaagctcaa tctgttttct gcattaatgc ccagtgttgt ttatcacatc    840
tttgatgact aaaacccaag ttccaatctg tttcataacc aagctttttc tgagtgtctt    900
tatccctatt ttggtttttc tacacatgaa atgtgtacaa ccaaatcaga agaattaata    960
```

acgcacataa atttataatc atgatatatg gtgtatgtta cctgtgaagt ttaca 1015

<210> SEQ ID NO 80
<211> LENGTH: 1630
<212> TYPE: DNA
<213> ORGANISM: Homo sapiens

<400> SEQUENCE: 80
aatgggcaat attttgtggc tttttaaatt acctgatttg ggaatgttaa aatattcttt 60
tctgttgaaa aacatatgtg aaaatatgcc tctcaactta tgtgaactta gtgaaaacgt 120
tcagtgattt tgtttgttgc caatgctgtt tttctacttg tattgaatta tagccatatt 180
gtgtttattt atgttatgat gattagtatc attattttaa atttgtgtct ctctgcttgc 240
agacttcctc ttgattggta cagtatgaca acaggtaata gatacaatag cactaaaaca 300
gtcatcatcg ctgctgggat gagaaacccc tcctctttgc ttttttttaac cttcctcagc 360 tggaaagttt tgacatctgc tggtttggga catggctgag cagctgtcag cagtagggta 420
gctgctttca gcagcagttg gcgggatggc agggtgccag cttgtaccat ctgtgcgcct 480
gacatttcat tctaattaac agtagggtta attgttctgg caggctcaaa tgtagtgtct 540
aacattaccc aagggaaaca tgtacaagtg caggagtggc agggagctgg ggacaagcat 600
cgctaacaaa accatcgagg gagagtggtt aacaactagc ggtgatttta ctagctggcc 660
acttgcaata aggctaaggt attttttatt ctgatgaatt atgccaagcc tgtaatgata 720
tagaaggaat caagcttaga aaggctgaga ctgctgcctt agggcaattg tgagggaaca 780
atttgcatgt tattactgca tattcatacc taattgtgtt aggctttgct aatagagcag 840
aatgacagta tgaaaaatcg agcaactgct ttagaggcaa caaagccaat atttttttct 900
tcctacacta tgagtgctga atgatcattt agacatttag ttgctcaata tgacaagtcc 960
accatttgtt agcttgacat attataattt ataaaggagt attctaattt tacttttagt 1020
ttattcttct cattttatac aatattcatg atagcaattt gaatggggat attcatagct 1080
attgtgagta gctgtgattt aaataaaact atatttggta tgaaatatta ccattgtttt 1140
atgatgtatt aattttaatg tttaaatagc tttttcatat gttaatataa cataaaccaa 1200
gagttgatga gaaatcctta ttatagtggt gctcactcac attgctatag ttaatgtctc 1260
aacatttcca ttatatgaag acctattttt agtgtggctt ggacaaagaa attgtcatgg 1320
ggtgcaaagc caaaatctgc tgttttagaa aagtgactac agattcattg aactgagtat 1380
ccgattccat ctcctaagca gataatattc ttaagaaatt ttaagcccag tagtacattt 1440
tttatgttag cccacaatgc cttttaaaat ctttttatgg aagctcagag aagacaagga 1500
attagaaaat ttaactttag aagactacat tttaaaactg gtaacatata tcttccatct 1560
aattttcttt cttttctgat ttataaggcc atagttatat ctttgatttg ttccaatttg 1620
gcatttgaat 1630

<210> SEQ ID NO 81
<211> LENGTH: 1285
<212> TYPE: DNA
<213> ORGANISM: Homo sapiens

<400> SEQUENCE: 81
tgcaaagcac agaaggcatt tccccagcct tcttatcatc acctgagtca ggtccgtgga 60
cagttaagaa gagcttggct aattccatca gcttggctct ctctgccctg ttctgactga 120

-continued

```
caggccgggc ccctgctcat ccctgaaaac tagcatcggg gaatgacata cagtttgata    180

acataagatg cttaggtttt ttggctcaag tgagatgttc agagctaata gccctgcgag    240

ctgagtttta gctgtgatct gcaccttgag atatccgtta tgtctggatc aggaaaaagg    300

gaaaagaatg agagcttatt tctagaaagg tttccgatga gcagcatttg tcattgaagg    360

ggaagatggg tataattagc ttgtcagtct agtttgggct gagcaggctg tctctgctaa    420

gaaagatgga ctaactgcca gggccactga caggcagtcg atagcgcagc aattaatgtc    480

ataaataatt ccagaaccaa ttacatcaaa atggactcag agctttaaaa aggtacagaa    540

ttctcttatt cttcctgcta acagcaagaa acagctttca tttttctctg taattacttt    600

tcattgtata tagcaataca gctgagcttt tctgtccata tttaagcctt gtctttctcc    660

aagcctcttc ccccaccacc agcctccctc cttcacccca caggataagg ctgttaaagt    720

tgttcttccc tgccagagca gtggggtgaa tgtataatct tttaacttgg ctgttgcagg    780

agaactccag ctacacctaa atgattaaga gccaagtttt tgaaaatgtc atggacaatg    840

acagcacagt gccccaaaca atggcatttg gaaatgaaga catttgtgaa ataaatggat    900

ttgtcttatt attttaaagg ttgctgtgac tttgcttaca ctgaatttat tgatttttcc    960

cccttctcct tctccttcct cttcttgttc tcctcctcct tctgtacagt tgcaggcata   1020

gaagctgggc caactattcc ctctacactg caaccacaat tcagtactgc ccatgtgtgc   1080

taatgggcat tttttttttt tccaaaggag gatcagtctc ttaaacatag cgttttacta   1140

aaaagctatt ctcttcagct gtctcaactc ttcagctagt tctctgtgca ttacagtaca   1200

tatgtagata acacaaaggc tattataccc ataatagcaa tgacatacca gataccactg   1260

gtgctaatag tctctctctc ttttc                                         1285
```

```
<210> SEQ ID NO 82
<211> LENGTH: 786
<212> TYPE: DNA
<213> ORGANISM: Homo sapiens

<400> SEQUENCE: 82

gtttaaaggg gttgggagaa gacaacatat acttggcttc aaagtgatta cattcactag     60

tcaagcatct gaccacatct gtcttcatca atgagaaagg taataatgct ttgatgatct    120

gcatatcggt gtgcagtggg cggctttgaa tgtttccatc caatacgtgg catttttga    180

aaggaaactt tgtattcatt tctgaatgtt tttgtcctgg cttttacagt tcctcactgc    240

tatgttgcag gggaaagtgt gaggtggtgg ttatgcattt tgcaagacag tgattcttta    300

ttttattaca aaaaaagacc aactctggaa ggccagatta aatcattcct ttcacttttt    360

aatgggattt ggatgaatag agtaaaatat gcactttgca ttcattgata gcatctttag    420

gttgaggtaa ttgagtcttt tttccctgag tgaatgaata atgacttcat ctgatcctca    480

gtgaggcctg aaacttagac cgcctttgtc acagcaaaag gatctgggct ttgaaacatg    540

ctctacttcc ctggcttaat ttttcttcat tttaatccaa aaacctattt ttctcaataa    600

ttcaagcata aactatgtag tagttgaagt agcggaaatt gcacgatatt tgtcctggtt    660

gtgctgcttt ttaaatagag ctgataaatc agccgctgtg gtcttcagct gccccattct    720

caagggaagg cacagcccat acccgcagca gcgttgggaa cttcagaact ggttgagtac    780

cgctcc                                                              786
```

```
<210> SEQ ID NO 83
<211> LENGTH: 856
```

<212> TYPE: DNA
<213> ORGANISM: Homo sapiens

<400> SEQUENCE: 83
tgggaggtgg gtgcagctac agtctcagtt gatggcgagc gccggcgcag agtctgacac 60
ccccaccacg gggcaattta gaaggtgggg acagcggcag ccaagaggga ggtccccggc 120
cctgggacag acattctccc tactgctcgt cataattgct tttcaccagg ttactttttt 180
ctctccccca tcacaaagag ccttaatccc agtgaagacc gcgccgtgtt gggggtagtt 240
ttctgggatg tgtgtcggga gggtggtctg gagccacagc tgataactgg cgagttcaat 300
gggacttaac gggggcaaca cccagcaatt acttgaggac aaagggttgg gggcccccca 360
ggtgtagaag actggacttt ggggggtggc tggggaggag gctgggaagg aggtgtgttg 420
gggagggggc tcttaaaatc cctctgattt ccgcaggaat ttgagacatt ctttaaaact 480
ctagactgcc tccccgctag cccggctctc cggcccaccc ctgcccctcc ctcgctcggg 540
ttagagacgg cttcaaaggt ggacggggcc ctttgtcttg cctccgcttt cttctcggcc 600
tttctccggc ccctccctcc ctccctctct ttgacctccc cggtaccgac aggcctctgg 660
gggctggctc cagaaagccc tcactgtttt ctttcttgct ttttgaggtg agacctggca 720
gggagggaca gagaagggag agggagaggg agggccgctc cagaggcctg tgctgtccca 780
gggagtgccc tcatcccacc ccatccccga ggtatccagc gcctgctccc gccctgggtc 840
tctgggtctc tgggtc 856

<210> SEQ ID NO 84
<211> LENGTH: 1237
<212> TYPE: DNA
<213> ORGANISM: Homo sapiens

<400> SEQUENCE: 84
accccactcc catcaatatg gatgcctggg gtgggggtct cgtgagcatg tccagaatgc 60
ctggccaggg tgaggtgact cctcacctag agggcacaga ggtcaagccc aaagaggttt 120
gtttgggacg ggatgcaggg ttcgcttctc cacactcccc ccaccccaag tcggcccccc 180
acctccctcc atgcacacct cccaccccca agtctcagcc cccagtgcga ggcttgctcc 240 ctttttttgtg atcctccata aaagtgcagc tattaaaatg cactggtcca gaaccgctct 300
ggggagagat cgcttggctt tcccaggcca gaggcccgct tctcttcata tccagtgggg 360
actttttttg aaggtaaatg ccttttctct gggagaggga aaggggcagc ctttgaagca 420 gtggggggggt gggagaggga gagacaattc cccccccctt ccttccccct tttgctccag 480
ccccgttcca ggccttttgc ttcacacatc caggggggagc cagaagaaag cccccagcct 540
ggctgggagg gggctggggg tgggcccaac ctgttctgga ggggaactag cacaatggtg 600
cggctggccg ggcgtttatg gcctggctga ggccccattc aggactcagg gaaggtggca 660
aagcggtcct ttccccccttg aagtgccccc tcaccccccct gggagggggg gccagcaggc 720
cggaccacag ccatgcttga ggggctgtct gacaagcagc tgtctgcagt ggtggaaggg 780
gaggtcctcc cgcagcggga acatgaaagg gacaggctag gtcccgcggg gagagggact 840
tgtgggttgt gggctgtggg ggggcgtggg gctgcttttg tgaaaagctt gaagggggac 900
gaggaaagga gggggcttcg ggggggcgct ttctgctcct gacctggaac agactgccag 960
aggaggccgt cggccaagag gggcggaggg cctgaacctg ggccaggagg cggggctggg 1020
ataggcagga ccccaccccc tggaagggag gccagcgtgg ggcaggctgg gcaggtcccc 1080 cacccccaaat gctccagggt ggggcgaggg gcaggtcttg cagaggctag gcagaggctg 1140
ctctatgggg aggtgcaatt ggaaatgagc aacggtgcac agtaagtgtt aaccccgcgc 1200
aggttaaatg tccagctctg agagctgctc cctcact 1237

<210> SEQ ID NO 85
<211> LENGTH: 1234
<212> TYPE: DNA
<213> ORGANISM: Homo sapiens

<400> SEQUENCE: 85
tattgaagac ttttaatttg agggcttata tctttgcata ccctgcttaa ttttttttcca 60 agtgtcccat tgcagattgc aagtataagt tagtgtcgga attaccatac gaaactctct 120
ttctaacttt aatcggtaat ttctcagcaa tagaaaacat gatgctaatg aataatgtac 180
ccaaaagctc ttattatagg gttggtatga attccactta atgacaagct ttctcaagca 240
gcagttgatt tgaaatccta cttttcatta gtgaagtata aaatgttaat aataccttcc 300
actgtgctgt tcttttgtag catagcagca tatatcttcc ctgttcacca tggactcttt 360
ttaagatctt actagtaact tcctataaca taaataagat ttgttcaaga aataaaaatg 420
tgtgttttcc cattgttagc tatatgtttt tctaataatc acatccgaag cttattatac 480
agtagtagcc ttaagatatt atttttttaa atatactact ttggtcttaa tactagtttt 540
taatctcttc ttgtttctat gaagtctgaa tgagattttc aaaattgaat aataatttga 600
tccgttaatc ttttgaagct agtaatttta ttttcctctc tttgcagtct ctgaggttcg 660
caaatgaata gagcttcatt attgcagtct gcatttaata acaattatcc attatcttgt 720
aattaagact ccctgtaacg aatcatgagg acaatgcaaa aatacatagt acatttcttt 780
aatgaactgg aaaatgttca tcttgttcta tttagtaatg agttgctgaa tagtcattaa 840
atccactgga gaatagagct agatggattt tgaagactgt cttgagtttg tggttaatct 900
attagaatta aaatttcatc ttctattttt atcaacagct gattagaagt cattctgttt 960
gaccaaattg attagaagac catatacaag ggcagctgtt gtttaatgaa agtttttaat 1020
gaaactgtac catggagact tgtaattata gtccttagaa aagctttgag ttgccttaga 1080
ccacaaaaat agtattgtgc taaagatttc aaattaggaa aataaaaaat acaatttaat 1140
ataatactat aaatttatta ttaattttaa tttcaactaa tcacagttga atattagtct 1200
acttagtgtg ttccttttga ctttttcagc cctt 1234

<210> SEQ ID NO 86
<211> LENGTH: 1050
<212> TYPE: DNA
<213> ORGANISM: Homo sapiens

<400> SEQUENCE: 86
accgaggaca tgaactaaaa gaaagctaca gtgttccttc tcttctggct tagtcttagc 60
attttgtggg agctgcttac agaatcagga atcaaaagaa agacgatttg ggagcttatt 120
ttgtagagag ggatggttta gtagaagctt agaaagggat acactggcct tgtgttaagc 180
cctacagcac aggcatcact aattatttat atcctgctgt taagcgtaaa acaggcttga 240
ctgcccttac aacagctgca gtctcaccac gtgtgcagca ccatgaactt tatgtgtgag 300
ctctcctgaa gagctatcgg ggcacggggc actacaagca ggtagcatcg ttgtcagaaa 360
agccttctga agagtcctgg tgcattggca gcaattaatg caggtggtat tttagacaag 420
ggagctaatg agttttaata tgcatgcagg tgagggagtg ctgaatcagg agagccatta 480
atgaacctat gacagcctaa ttagctacaa tttaaaatct atggaatcta atcagaagag 540
ctgaacgctg ctgcaaatct gtgtatgaat gagtctttct aaatactcca atctgttgct 600
tagtcactga ttgatagtaa ttgctttttt tcctctattg tgcataggaa aatgcccaat 660
tttgctctga taagggagga cacaacactg aagttaaatg cctaagatgt ttagctcctt 720
aagtttaatc agtgagtgtt taaaaaaatc aaagtaaaat taatttgaac tctgaatata 780
gatgatttaa aatatactac caacttctta tatattgggt tggcaaagac aacatagcta 840
ttaacacccg acagcatatc tgaaaagcaa gcaaagatgc tgaaacatgc aaatgcataa 900
aatgcattta ttaatccgta atttgtttta aaaagcttta tttatgtcat cagagataac 960
agggctacat attttattga atacttgaga taatgaaaca gctttttgag gttaacacaa 1020
tctattaagc atcgaatttt tatgtggctg 1050

<210> SEQ ID NO 87
<211> LENGTH: 1195
<212> TYPE: DNA
<213> ORGANISM: Homo sapiens

<400> SEQUENCE: 87
accttccctc tgtggccagt ttcgaagact atgccaaaga acggggtaga aaaactagca 60
gaagggacga agagggaggg gggaagagag tgaaacacaa tagattatga atttgaaaat 120
tgccaattat cttgtatcat acagctcaga gccctggcac aatgatcagc cacaatccag 180
atttttcagc ttaaatggct ttacattcaa gcaagcaaat taaccataaa atagaggagg 240
ggggggaaca aaatattcca agaaagaata aaccgcagat aataagcacc aatctggtgt 300
tgaatgcagc ccaagatacc aattgtttta agtcacgaca aagacagctg aatgctcatc 360
ttgtggatgc agagcgagga tgattgcttg ccatgagtat cttctctcac aaataacagt 420
tttttcgctc ttaattttct gctaaattgg aagctaactg cttcccacat tgtcatcgga 480
acacctgcag ctgtgctgga tttctgcgca ccatttcttt taggtaaaac agcactccac 540
ttccttcagc tcctcattat gccgtgaggt cttcttttca ctgcactgca gcactaatga 600
ttcaggcagg ctggtcagtc attaagtgac aagcaaatga taccgtgtgc aacgtgtgag 660
taatcggtct gaacaaatga aatcacagac ttgcctttcc catcattcat ttcacaaaca 720
gtagcaatgt ggtgcacagc aggtagttca gttaaaacca gccttgtaaa acaaatttcc 780
tgcagccgtt taagtgaact gcgatgggct ggatgcttca gctagtggat tgtgcccgga 840
ggagttaaga aaggttgggg tggagggagg aagggagaga ggagctggga ggagagcctc 900
ggtacataca ttagagtaat taagggtttc gtgtcttatt ggtatgtttt tcatttgcat 960
ggatctcaga aatgactgtt ggattagcaa acccaaaaca tacagcatac atttcaatgt 1020
gccttgtcag gaggtagctg ttaagagact gaagcaaagt tcccaaataa atgctctaaa 1080
tttggagtca tgaagacgtc attgtaaatc agatggactg ctaggaagtt agtgatgcaa 1140
atcacagtga taaaaagctt catggctttt attttcacag tagatcccct tttgg 1195

<210> SEQ ID NO 88
<211> LENGTH: 1661
<212> TYPE: DNA
<213> ORGANISM: Homo sapiens

<400> SEQUENCE: 88
cccctccaga agattccatt catttaataa tgataataaa aattactgcc atttattgag 60

-continued

```
caatgtctgt gtgcagcaat gtctgcgtgc tgggtgcttt acatgcattt ctttaaaaaa    120

aattcatgct ttaaatctaa agtaatatat acttattggg aaaaataata taatgctgat    180

gacatattat ttcttaaact tgtagcaatg ctccaaggta ggtattttaa ttctcaattt    240

gcatatgagg aaggtgacac tgagaggtta agtaatttgt ccctgatccc atagtgagtg    300

acaccccagg ctgtctttgc ttcagaggtg gcagcagaac tactcaactt aggcagagaa    360

agtagtggaa atggttgatt caaagatggc aaaacctgag cttaaaaaaa tgtggtcagg    420

tccagagtga cactgagtgg cagcagagct gtggtcagca ctagtgtaaa tatttgtaga    480

caaccatgtt ttacagactt cagtttaatg gcaaaaatct gccctaaatg cctcagtaaa    540

tatatgctgg agaacagaag cctattcact gaagaaacaa ttgactttag cttttctgtt    600

gttaaagtgg cccctagtga tagtgctgca gtgactagat agagcagagg agaatggctt    660

cctcctggct ggtgggctgg cagtttcact ggcactgcca aatgtacttc ctatttgttg    720

tgcaagggaa ttggaacagt gaggcattta tcatatcatc ccctactcct catgcaagca    780

aaaaaggaga agttgtcaat gaaagaaaaa gaactgtaat cgcacattta catatgcttc    840

taattgttga tttggggatt ttctatgaat atagcttcac aaaacagatg ctgtttaaga    900

aaagggggaa cataattttg tggcaatga attaagtgtt tttgtggccc tctcatccgt    960

agctaggagc agtttgtgga ccgcgtctgt gaacgcggct cataattgtt tttcacacat   1020

aagttatgca aatgagcttt tatggcaact ggcataacaa ttagcatcct ccagcaatat   1080

tttagcaggt taattgcaaa atttctaaat tgtacatctg acttgttaat taggcatgac   1140

agaggtggta aaatagttat cttcaggcag tggcagccag gagctgcttg aaatgcaaag   1200

agcaacgatt gattggattt gagggttaca attgtgggag cactgctgtt gtcaagtgcc   1260

gctgagcagc tctgctccat cagttgcctc agagcaagaa ctcggtagtt gctgcgagga   1320

tcctgccatt tacaaatctg ctttatttaa ctctgcaact cttccattcc aacctatctg   1380

agcagtttat ttcacgcggt ttgttctgcg ttgggatcat taaaacgaga tggcaacaca   1440

aattattttg tgctcgaatt tcaggacgct gaaagtttac tttctatttt aaagttcatc   1500

tcaacatttt tctcttaaaa tagaaaaaaa gtcataaatt ccctatttta attaaattgt   1560

aaatttcagt tctcaagact tcatatgtga ttatttgctt tttaatgatt taactctttt   1620

aaacagtgca tctttttgtg cttcataggt tcattgcagg a                       1661
```

<210> SEQ ID NO 89
<211> LENGTH: 886
<212> TYPE: DNA
<213> ORGANISM: Homo sapiens

<400> SEQUENCE: 89

```
tagacttttc ccggtgtttt catctacata aggtggcatg cttgttttct gattactccc     60

atgatcccaa tgccttgtcc atccctgggg acaaatcaaa gaagaaaaat agaaggtcat    120

ctttgggtca ctgctattca gtttgctgtg ccaagctgaa aaccaaggcc attaaatatg    180

aaaatccact cattgtctca ggcttgattg tatcctgtct ttcagatcag actcaccata    240

gtcatagcaa ccctaatagg cggatgtgca ttggaccaca tcatttgcag ggtgtcttta    300

actgagaaaa gttttgttga aaatatgtgt gattaatgcc ttcaactatt atctctcatt    360

gaacagacat gaaagggggc tactttgtga gcccagataa gcctattgca tggccattaa    420

tggcatattc agcccttgct gaattaatct attattgcct cttgtctttg gtaaccataa    480

catgttgttg gaaggctgtg caaaatttga gtaactgaac cacagctcca gtaatccttt    540
```

agacctgggt gtaagagaag agtgaaaagc tgtttagtga ctaattgagt gtgctgtgct 600
gtttcattag tattaagcag tggttcttta ttttaatctg tttatatcag agtgatatat 660
caccttaaca tcatcagtta ctcagcaagc ttcacacagt tcctctatcc ataaatataa 720
ctaaaataaa agatcaatag aaaggcttaa atcttgtgta tgtgtgtgtg tttgcgtgtg 780
tgtgtttgtg tgtgtgtgtg tgacagagag agagagagag agagagagag agagagaacc 840
agagaaacag agagagacat agcactcaaa gcacaaacaa ccaaaa 886

<210> SEQ ID NO 90
<211> LENGTH: 1119
<212> TYPE: DNA
<213> ORGANISM: Homo sapiens

<400> SEQUENCE: 90
gaggcttccc agaagataag cgaagtttca taatcatttc cctggtttga acttagaaag 60
aaatgtaaat atatattatc attaagtgag ttgtgatttt aattactgga aaatgttatt 120
aattctgata agaattattc agaaggtaat aaagataaaa gctgtcaaaa ttaattaagc 180
acatattcat taaatccaag gtagcttcag tttccttatt gcataaatac aattaacact 240
taatctgaat ctcgataagt tacataatca tgtgcctcaa aatcaaggga ggatacaacc 300
ttggccttct ccgttttaca tgggaaaaca ttaatgacgc tgacatcgga gacaattaga 360
cagtgtcagc caattgtttt tagccagctt tctctcacat ctgtggtgtc tacaagcaag 420
aaggctcatt gtttccacag gcctccttcg ggccttggct ttttgtgtaa accgtcaatc 480
tcttggcgaa tatcaaagcc gtgaggaaat tagaacagac cagctctgct gccccacact 540
aaagcttagc agggtgcatc cactatgcta ctaattaggc agtgaccaac aaaataacct 600
gtcaatgtcc gctagccatt tcccacacac ctgcatttca taccctaata agcatacagc 660
aagagagaaa aagggataac tgctgaagtg tgaaaaatga acaaaatata acaatgtttc 720
catccccacc tatacttctg gcaattacca tttaacatta gggggactca acatgtctga 780
agactcacaa tacggtatct gaaactaaaa cccagggggg aaaccacaca ttgagactgt 840
attaaggttt gcttcgaaaa tatcacacta agaagaatct agagttatgt ataaaaccca 900
ggaaactgaa aatgaccata atttagatta gggaccagga gactgacttt ttaaaaacat 960
tttccattca agccattgaa agagaaatgc gtactattct cttcatcttt tccttccata 1020
aaacaaaaat atataacagg acagaaaata gaatatctga aaaaaagttt catttttttc 1080
cttacatttt ccactctgat ttagtgaatt tatgatcat 1119

<210> SEQ ID NO 91
<211> LENGTH: 1274
<212> TYPE: DNA
<213> ORGANISM: Homo sapiens

<400> SEQUENCE: 91
ctcaaagtct cttgcacaag tccatttgtg tagagaatat ttttgagtct acataagttt 60
tttttaattt tattttattt tgacagaagt tttgtggatg tcccctgaaa tagctcaatg 120
gttaattttt actgttcctc ttgtaactca gctgctacct ttgtgtgtgt gtgattcttt 180
gcttatatgg cagctcaatt agtgttgttt gtgtgtgtgt gctcggtttt ttctaatagt 240
cttattaaca agaaaaaagg tggcgaacag gttattctct taacctgacc tggctctaag 300
agtaagatga gcagcactga acagatgtcc ccatttaagc cgttcttttc ccacatgcct 360
gctggatatt gcaggcgcgc aggaagctcg cttcaaacct ggcccatttc aggccataat 420
ggccacgtta tttcggccca gtgaacacga acaaaatcgc gtgctttaga atcattcgac 480
tctgagtcca ggaaaagcag ggggtgtggt ggcagtgggg gtggctaggg aggggtgtat 540
atgagtgggg gagccgattt catctcggat cgcaggaaga gaacttgctc aaaagaattt 600
ttccccagca aaagtggtat aatttacagc gcaacttaat aatccgaggg gcaatgcaaa 660
agccctttgc gttgtaaacc gcttctaatt acctgccaga gcaattagct gactatcacg 720
aagaaattag atcgctcaat gtagcataaa taatgcgaat aattttgtaa gaagaatgga 780
aagcgagacc tggtgtttct ttataaggaa ataacacctc gtactgtaag agccctccat 840
gaacacatat taatgtctag gcatgcatgg caatgagtcc gagcaggagc cctctggctg 900
cggttcagca ctttttccgt ttacgtatgc ggggtgaaag tcggcttcca ggcgttcgat 960
ctccagcctt ccagctcaca gtaattaaca catagcgact tcaatgggaa aacctgtttt 1020
ccagatgatt tttacaatgc agctttatgt ctcatttggc agtttaaata gctggagttg 1080
ttttctggct tcatctctac tatcatctgt tgagcatatt ttgcttagaa tattgaatcc 1140
caaccaaaat ttgggtgcag gcttttgctg acttttattt tcttaagaag tggggatatc 1200
aggagccatt ttgaaggata ctagagcaaa gaattcttgt gaggacctgc tagtgccagc 1260
agatatttga gttc 1274

<210> SEQ ID NO 92
<211> LENGTH: 1226
<212> TYPE: DNA
<213> ORGANISM: Homo sapiens

<400> SEQUENCE: 92
ctaatgggct ctttcttttc ctcacacaga cagggctgct cttgccttgc tcatggggaa 60
agaccaaatc gctttctttg ttttctcccc cggggcaaac agcatcctgc cccgtccacc 120
tgttctctcc ctgtggcccc taaggtctcg gagtttggtg tcttgtatac tttgccttag 180
agaacaaaag acacactttg ttgaaatgtc atatgtcagc cgcgtccttc gattctatta 240
aaaccctttc tttctttcct ctttctttct tttttttctt tttgaaaaca ttatgggggga 300 aaaaggagag aaagagatcg aggagagcag cccacaaaaa aaaaaaaaaa aaaaaaaaaa 360
aaaaacgcag caaacccaag ccccactttg gggagttgaa acatctgcac tttctcagca 420
gtttgaaagg aaacaaaaaa ttgccaagtg gtataaaatt tgaagaaaaa ttacccaaag 480
gaggaatgga cgttaaccac gcttcaattc cccactatgg gttgacattt gaagtacttt 540
cttctctcct ctttctttct gattcacagt gtgtctaaag aggtgaattg ggcacacaaa 600
acccaacctc ctcttgccag ggtgggtatg aaatatgaaa gctagacgat tgtctgggct 660
cagtgcattg gaataacatt ggttaaatta tggatagttt ttgaatagtg tcactttttt 720
tttctctgca gatggttgtt cacacaagga gccgggtctg cataattgta tcactaatca 780
gcagtaaggc aattagttgt gtaagtgtgc tataatcatt ctaacagaag agatgacgaa 840
aagacaaaaa aaaggagggg ggggaccaaa atgtcttttc tgaatccatc aactgacagc 900
cataattaga tatatataat tgaaaattcc acagtagggg ggccagcttg tacaaatgaa 960
ttttctctgc tgcccttacg catttttgtc tgtggctgag catcccccctt aggaaaaggc 1020 agaaaactcg tcattccaaa agagtgcata ctgtactggg tattctttca ggccaatgat 1080
gtcagaataa caattttttt tttttttttt ggtgtggggg taggcatggg ctgggggggg 1140
acttggaggt tagtctgctg tgaagaccag ggcttcgcgt aagctgatat gaaatgcctt 1200
gctgtgtcgt cgttgctgtt attttg 1226

<210> SEQ ID NO 93
<211> LENGTH: 1283
<212> TYPE: DNA
<213> ORGANISM: Homo sapiens

<400> SEQUENCE: 93
tgcacgcgtg tatgtggtga gttaagctgt ttggcactta atggtttgga cctataccaa 60
aggcaaacca ctggagaaaa tacttgccat ttcaaggact gcataaggtg atggaatttc 120
ctctatgagg cataaatttc actcttgctg cccagctggc tgattgttca aattcagatt 180
caacgaacac atatttagag aaggagggaa gaggaggaga tgagtaatat caagctgtgc 240
agataagaag gccagggcta agtctttgaa tttgtgcaca atagaatgaa taccttttat 300
ccattcgccc cactaaacac caccaccagg aaaatcattt tccaattagt cagcaggttt 360
cagcgtcatt acctttgaga tcagatttgc taccattcaa aaacgcatca gaggcagtgg 420
aggaagagtt aagcatcatt cctggcatgc gaggtctggg aggaggtgaa attagattag 480
ctgcaggaaa acgggagggt ttacattacc agaggggctc tacctggctc caggcttaac 540
agtgaacaag gctttcagca tatggcatta caatggatta gtgatcaagt acgattaatc 600
ctaatagatc gtcttttgaa cctcagtggc ttgttaggtg agaaaaaatt gtctgtcccc 660
aaagtgtcag gtgaaactct catttgaggt aagactgcca tgtggagatg ggtctccatc 720
tggtggcttc cttttgtgaa actccaccag aaggtgtttt aatgaggctt ttatagcagg 780
caccacctgc cactaatctt cccctctaaa aaggtgtaat tgagggttgg ttttacagta 840
tggctcatat cctaaccttg ggaattcatc aagaaatgca aatctgggtg ggacggtgta 900
atcatgaaat gccattttgg cttttggttt agactgaagt agttatagaa atttgtggtg 960
ggctaattac aaccagctat atagtagctt ccccttttca gttagatcaa tacgtgtgtc 1020
atctcagaat taaataacca agttgatggt gaccatatgt gttcattcaa ttttttgcac 1080
atgtaaagag ttgcaaggct gctagtggtt cacacaattt aaaggtttca tttacactat 1140
taaggtttaa ctggtttgaa ttcactgcac attcgtcctc ttagtagatg cttcagttct 1200
acaatgcatt acttcaatga gacatgagca gattacaaaa tcaccggctc attttctatc 1260
tatgagacct ggggagtaga ggt 1283

<210> SEQ ID NO 94
<211> LENGTH: 1740
<212> TYPE: DNA
<213> ORGANISM: Homo sapiens

<400> SEQUENCE: 94
aaaggacaaa ccatgagaat cctgatagac tatacttgaa ataaaatagg aagtccacac 60
aactgaaggt gaacaaataa tgcaggctga aatgagtatc tcttcgaaag actacaagct 120
tccttttgac attcaagcaa ttcagtaagg agggaaagcg aaattgaatt tagccgatgc 180
aaatgaaatt aaaactaaat tggttgtcac atcaaactga tgttaactat gtaaatgttt 240
tctgtttatg aaactacagt ttagagtata taattctgca aaaataagaa tatttttgtg 300
ttcttttaaa atataaatta aaagggcaga ttatgaaatt gtttaaaatc cttgccactt 360
acccacgtaa tatcaaagga cctatgaatc atgaaaactg tggacataga gtattgaaat 420
aaacatacac atatagatat gcacatcaat acacatgcat gcttttctgg ccaagcagta 480
ccccattaca tcattgcttc aaatgcattc attctcttca atattgttgg ctgtttcagg 540
ttaactacca aaatcatttg cctgagaagc gagatttaat tgtcttacaa ctacctctgt 600
gaggtacaat agggattaca agtacccatt gattatacta ttgggtagaa taagggactc 660
ttattctagc atttctcatt cattttgtca ttgcattctc tttgaaagag accaaatggg 720
tcccagcagg tgaaagcaaa gaaacctgaa aggccccctt tgatgaatga caataccaca 780
accaccctcc cccccaccat ttttggagat tataaaacct tattaagtca tgccctgtta 840
gatattgatt gagagggagc taaactaaaa ccaacaatag cagcatggat cagagaacac 900
tgctttcatc aatgggcact aaacacagct aagctttcca atcttttctg ggggggcagg 960
gtggggggac ttttttttt actatttact tttgtttaaa ccattatcct agaaagtcat 1020
acaattatag ctactttgtc agttaagaat aaatcgtagt tgtctagcac ttcatctttt 1080
tgaatgtagc agtgtattgc acaaacaata ttatacttgg ttaagattca ggattattat 1140
tatgattatt ggggggtgca attctgggta attatcataa ttattcttga ctctgggact 1200
cctttgatga caacgttgct ttaaagtaaa ccacttggac ataaaaccca agatatttga 1260
aaagagactg ctgccagaat cagagttgaa aactcaccca tattttaaag ctatcttgat 1320
tatcaggctg tttgcgttcc tgggctgtct tttctgccat ctgtgagcgc cacagcaaac 1380
aaccccttta tgacaatcac ctcagtataa cttgaatatg tctgctttag aggagacttc 1440
tgtaataaga ctctgtgcta attaactgtc agccttttta aaaaaataaa taaataaatc 1500
agcagactgc attttagaaa gacactccac caaaaaattc ccaaacaaga tttaagttta 1560
tgtgccagac tgtaacttct actccatgtt ttttcaggcc ttcctctgag taaatctgtt 1620
tactttaaat acttctcatg tgataaaggt tttcattttt cttgccagtt gactacaggt 1680
agtaacattt gctcctcctt ctaaacagct acttgattca gtaacgttat cctccaaaaa 1740

<210> SEQ ID NO 95
<211> LENGTH: 673
<212> TYPE: DNA
<213> ORGANISM: Homo sapiens

<400> SEQUENCE: 95
cccggcattt acagccttac taggcgtgta atagcagttg actcaaaaag aaggggtttt 60
aaattcattt agttaacttg ggcttgaccc acgaaagttc ccacttaaac caagaacttt 120
aaaaggcagc cggggctggg gagggggtgg agggagggcg ggcggggaga aaaagccgcg 180
gggagagcga gggagagaaa gagagagcga gaaaagtttc ttttctttaa gatgtctcaa 240
gttcttattc ctcattcatc aacccgcaaa caatatcttt ccctggctct ggcatctctg 300
cgcgtcgccc tcttttcccc ctttacgatt tctgttcctc tcttaattta ccgtgaagac 360
taattccact tccattcacg ctatgtcaac catctaatcc ccctttttttg taaggggaat 420 tcctcggccc cttttaaaca agtcccctcc gcattgagct acaatttact gctacagcat 480
tcttccaggg ctaatgaatt tagaattagc aatttctttc gaatggagcc gaatgaatgc 540
gatcacttta acagcgtgac aaattgcccg ccgcgccgca atggacaccg tttaaccccc 600
ccctttcagc cggcccgctc gccgggtatt ttcccaggta gcttagaggg gaaccttgta 660
agacatggag gcc 673

<210> SEQ ID NO 96
<211> LENGTH: 970
<212> TYPE: DNA
<213> ORGANISM: Homo sapiens

<400> SEQUENCE: 96
ctcaattgat atttatatgt gtgcaggtct atcaacgtta ttgaaaagtt aatccaaagg 60
atttattgat tactctcaat ttctcagata ctgtcagttc acttttgaaa attattctct 120
tatgtaatat tgcactcttt tcagtaaaaa ggagagtttg tggctgttaa atatgcatga 180
ggcacaatag tttcacaaca aatcaaattt aattaaatga tgcatttcct ccacttacaa 240
aaggtttatt aaaggtttat ttgctcatgc aaattaaagt gttagagtaa aaatccacat 300
gaaacttggc actaacaatt aaaaaaatat tgaaagattt ctcgcctcgc tgcaatacct 360
tgctatgttt aaactgctca gcttgtcatt tagaatcttt aatgaaacca gggaggaggc 420
tatttatttg cataatagga cataatttgc tgtggtgagg ttttaattat ttataggctg 480
tctgaaatat ttaaaatggc atcactaagg agcatgaagt gttggataat gccttcattt 540
caggtttcct gccgtttctt ttatgggtca agcgatttat ttctaattag cataccaggc 600
tagtggcttt aaaaacataa ggaaaacaaa ttggtttcag tctgtttgca gcttgagtag 660
ttggagacgg ccaagggtca ctgacggaga ctgagcagag ttaagagatg aagccagaag 720
ccatcccagc acatggaaat cactgactca acagagccat actttcattt gtgcacactg 780
attactgtat gtagtagctt ctctttggta ggtagtgggt tagagttaat ggatttcatg 840
ttaattgtcc cttaaatatt ttctaccatt aacacatttc ttattggaaa tgatgtgtaa 900
gcaacagaaa atattccatt tccttggata aaagatacag taattactgt gtgcataggg 960
aaaaattcgg 970

<210> SEQ ID NO 97
<211> LENGTH: 2442
<212> TYPE: DNA
<213> ORGANISM: Homo sapiens

<400> SEQUENCE: 97
gacattgaga aagcaattgg attttgtaaa acatttctca gtctaataat ttcacatctt 60
gtctatattt tactaaacta aaatcaagca ttttcctcct tcaaattgag acagaggtat 120
tttgttatta gtatcgtttc cgtatgaaat taatttccta ataaattaca agtaatctca 180
tcatcccctt taagaaaaca aaaaaaaaaa ccacacaaaa aggccttgaa ggaactcttg 240
gttctaggca cttgataata atccagtgat gaaaaggtct gggtccagag tgcgtgggtt 300
tggcgtgctg tttgtcacgg tttggttctt gtgctgggct tggtgttgtt catatgccac 360
cctgggcttt ggagagctcc agttttgctg tttgtgctgg attcactgaa atttcttaga 420
ggcttacatt taaggatccc acttactgca gtcactcctt gtgctttatt gcttttacaa 480
gtggtctcga aacccggtac ttgagaataa acataacagt gcagtgctgc tgtagcactt 540
ttaaaattct tctttgctct attttgtcag tgagctgatg agcaacctca aaaaaagaaa 600
aaaaaaaaac ccactggacc taaaaaaaaa aaaaaaaaaa aatggcttcc tctgatgtcc 660
tagagacaat aattatgatg tgctagttaa gcccaaacta cagctgaggg attttacttt 720
aaagcagcgg cttgggcgca aaaatgcatt tatagctctt tgtctgcacc tcattatgtg 780
tgggcctgat tcattaagta attggtttgc agttgtttac atgagtatta aggccttctt 840
ttcagccgcc tttgagagat acattgtgca aatgttgcct gtgatgaatg cagaatgagg 900
gccagagggt ccgtcctatt ggctaaacag tgcactcctg ttgaaaagcc agagaaaggg 960
attgggtgct gctttgcata gcaatgactt tcttaataag cgttacagat taatacacac 1020

-continued

```
aagctataaa agatgcaaag agatactctt agcacattta tacatgctca tttcattgtg   1080

atggtggtgg ggttcgggtg ctttcatatt ccgtttttca gagcagcagc ttcagtgcat   1140

gagccgtaat agaatccgat gtttattgta ttataaatca cgggcaagta ggcagattgg   1200

caacagttta ttattaaaga ttctttcagt gtaaatcttt ttctaccatt gtatttgctt   1260

cagcaaaatc attttgtggt tgagtgggga tgaaaagcat aatgtacgaa ggagtgagtc   1320

ctaataggaa gccgttctcc aagtaaagac cacttgttcc cttttgttca ggggtgcatg   1380

ccagagcttc ctctcctctg caaacattgt ctcgctttac cttccccagc aagcggtttt   1440

cactctcccg gatccattg ttcaatggag agtatatttt aaaagcctgc ccttagctta   1500

ctggttcctg ccttgtaact tcagcttact ggttggacca gataatgttt taccaaaagg   1560

aaagggtgtg tgcttgcaac ataattgcct gggggaaagg tagcagaagt caccccgcca   1620

ctgtaccctg gcagggccac cgtgggtggc attctgtgcc agccttgcag ccaccagagc   1680

ggccagtgga gggcgccagc ctgcagctga tgctctgatg gcggtggcat tttctgtctt   1740

tgcctggtca ctgtgccatt ttccccagga taacataaag attataagga accaatagtc   1800

cagtgaaata aaaatgagtt tttcctgaaa gtcctttagg ttcttatata aaagcactct   1860

tctctgtctt gggtttggca catctccatt cttaaattcc actgaattag cagcttccta   1920

aatatgtcac gtttcttatc acaagcctac atacgttgtt ttttctgcac aaagcaaata   1980

agaacaatcg cttgattatt tgaagagaaa aagttaagtt gacctcaggc agctgaaagt   2040

ggcatcttct gtaggaaccc cgattaacca tcagggggcg ctcagacttt gttaaattac   2100

tggtaggcct ttaaaaccta aaattagtgt ttacagagat ttgttggcat agtcattggg   2160

atttttttct ttctggatta ttttttgcct tctgttttttc agaaacatat gtctgttttg   2220

aggaacgttc aagctgaaat tgctccttta gaaattgtaa tactgatttc cactagcagt   2280

caaaaattat tacaaatttt agaatttgga gtctaaagac tatgtcttat aataaattag   2340

ctattttcag ccttctaata agactccaga actggaagga tacttcctgc tgccgggagc   2400

cattcctcct tatcctggac atcatagaca gtgctcctgg ca                      2442
```

<210> SEQ ID NO 98
<211> LENGTH: 2258
<212> TYPE: DNA
<213> ORGANISM: Homo sapiens

<400> SEQUENCE: 98

```
cacctctgtg cctaaactcc cttcttgtct ttaacctata aaaagatgtc gccttcgata     60

ggaagatttg gggccagaca tcagaaatcc acgtgggaga gactggccgt acacttccag    120

atggaacaag tctgcccagt gatgtgagtt ccatctcttt ttgattctgg aactccactt    180

tcatcttatt tatgcacatg gagatattga taaaggggaa atgtatccaa actgaaaata    240

attggatccc tacagctaac tctgagatat taaaagcagt accacttggc tgtgtctttg    300

tcttgttagg tttgatcata agatcacaat gtagtaatct cgggctcaaa tttctggcat    360

aaagatgcac tgttccaaat gtggcctcag ggaacacgac tgcccacaca gccccaggat    420

tgtctcatct tattattttt caacagttct tggcctgctg aggtcaatgt tttgtctctt    480

ttgagtgttc ctctatgctt gacacctttt cctattttct ttcttaaaaa aaaaaaaaaa    540

aaaagggagg gggagaaagg agaaaaaaaa taaaaaaagg actttgccgc gatgaccaga    600

gtccatctgc agttgggtgg catctgctcc ccacatgtca ctttcctcat taacaagcaa    660

ttgaattaat taaatgctac tcagaacacg cataacaagc taccggcagt gtccaaatta    720
```

```
gcactgataa tcaaggatga tttcctttat tatcctgcta agtggtgtgc agactctgat    780
ctccctgtct gccctcatct atttacatac ccccagctcc tgcctttgga agcggaggtt    840
atcttaccta gttaatttgc cacgatcacc gagcatggcg gattgatgcc ctgcccctgc    900
cgccactgcc gggcccgggc cccctccccg gctgccctcc cccagcccca gcctttgtat    960
ctcaagctca ctgataaatt aaaggccacc cctgtggtct ctcaagtgag taatagaggc   1020
agaaatttca ttttgcaact ggctgattta atgatccaaa gggtaattaa tggcctgatt   1080
atcttaatgt taaatatgtc cggcagcaat tactgtgacc tcccgcttgt caaggtccgg   1140
gctgtgctct tctttcaatt aagttctctg ggcttaatg gtatgaataa actcctctga    1200
ttctatcatc ccggatgcag agggttcagg gagctggggg ctcgtttgga gttttaatca   1260
gcctgtcttc tactccggcg atcagagtta acaattatag caaggacagt ttaactttct   1320
tcttcgccgt gcagaccccc ctacatgtac acacatgcac acttttgtgt gtggctttat   1380
gtgccttgtt ttcatgtgtt tctttcagtg ctctcaggga gaattctgtt tgtggaggaa   1440
gctgctgtgc tctgtgagcc tcgtctcttc caatataaat tatcatgtga acgctgtggt   1500
ttttctattt gacaggctta attaattggc aggagccccc gaaaatgaca gtaccactaa   1560
ttgcaactca aagtgaattt ctgtcaccgc ggcgtgcttg tcagtgggcc tgccctggcc   1620
ccagccgcag agcgggtcca ccctcccagt ttccccgtcc aggcagggac tgtgccctgc   1680
tcaagccacg acagtggcag ccttctccga ggagccgtgg gtttgcaggc acaccgtctg   1740
ctggcaggag tgacatttac taccaataaa gtttatacat cctcggctat gcaaacgcaa   1800
cagctgctca gggacctcag cccttactta agatatttta gcaacttctc ttagcaagcc   1860
aacttggaat cagactgaga gaaccataac tcacttagcc acccttcatg actggatggt   1920
cctcattagc acactgctaa atatgcttca gtttactaga gctcagggcc cggatcagaa   1980
atattctgct ataaatatta agccaattag gaaaatgtac aaatgagaag tacgttaaca   2040
ctgcctttaa aataatacct acagattaca gttgacaaca gatagagcaa tgcatctagt   2100
gaacctccac cagggagctt ggtgggaatc caggcaagct ctccataaag actggctcta   2160
attataagaa aggtgattct aagaagattc tccatgaggt taagtataat gggatctgct   2220
ttttcaagga taactatact tgcatttgcc tttgaacc                           2258
```

<210> SEQ ID NO 99
<211> LENGTH: 2093
<212> TYPE: DNA
<213> ORGANISM: Homo sapiens

<400> SEQUENCE: 99

```
ggcatcagat aacagaagga agtgattgct attattgtaa aaggtagata aaatttgttt     60
tacttttgtg ctgttcatct aaagaattgc acaatatatt gaaaaaccag attcttgagg    120
aagtttaatc gatctcttgg ttgttaggct aaaaaacaat ttctaatcgt gaagagaagt    180
tactgtaatg tactttggac tcactatgta caattctccc tctaccgcca ggacttactt    240
gcattcaggc tttgctctag aagaaataag aagacatttt cttttagcat aatgaacaca    300
gctgtttagt tcttcaccag ttaacatttt caagtttagt ctagccaggt tttgaggggc    360
tgttctcttg tttacatgac tggctaatct agacaagagt ttaagggtaa ctatccctag    420
gaggtactga gagccagcag caggatggac agaggtgaaa ataagggaag aaaattcatc    480
tacataccca gcaggtatca gtcatttata tattcatctg ttttcagttc tcaacttgat    540
```

-continued

```
aagagtgtgt ccatttcatg gtgccatgca gagaaaatga agtgtgtaag gtcattcaat    600

aaagattaaa ttaaaaacat attcctattg caccctcagg gtccattagc cttgatgagt    660

gtacaaatac gttctttgtg ttatgtgctc catcctgaaa gagattgtgt gcttcgctca    720

ttataaatgt gcacctgaaa agactgaaca ttatcccctc ttttttaact gacctgtggc    780

caccgctggg ttcattagtg cagaacatct tttccactgg ctgagtctgc cctattgttt    840

gccttggcta gggtcaagtc aagggcaccc agcctagatt ggactcattt gtcacagggt    900

ctagcaacaa agctgatttc agcagagatg gggtgaattt catggggctg aaacacaacc    960

tttgacacca agtgcccagg gctgctcaga gttgcacaga tggcctgcca cccttaggca   1020

tccaggaaca aagaattggt gaattataac aaaaataaag tttccacagt cagcgtatat   1080

tttaagtgtt taaattattt gcagggattt ttgacagtct aaaattgcat cttgagcact   1140

tgtgataatc gctgtgcttt ttagactatg aaggaaaaaa acaattcagt tgggggctta   1200

ttgcttaact ggtgtaacgg tgtaaagtgt agcaatttag tgtggagtgc aggttttcca   1260

tggtcagcag gagctggcat gaacaatggg tcgtgctgag gtagcatgtg gaaaatgact   1320

ttaatacact atatagaatg gcttattgcc ttggtcaata ggctgcagtg aagatggtgt   1380

attcagccac ttgggaaggt taaacctgtc agggaacact gtgactgata tgcaggggct   1440

gcttatgagg tctctaatgg aaaaacctga caagcaaagt tataaaggtt acacttgaca   1500

catacttcag cattatgcct tatattaatc cattttttta aaggtagggt actttatatt   1560

tgttagaaat tgatgccaca atagtattaa cactccagag gaaacattta aactttgcag   1620

taaagtaagg aacattatag gatgagatca ctgcctgggt aaggacactt gtctaatatg   1680

ctagcatcat atttctcttt ctcacagtaa ataatctgct acattagtgc cttattatta   1740

tctttcagga ttcataattt ttaaaaacct cttcatgata ttttcctttt gtatttgagg   1800

gaatatatat tataattgca ttataatata tcctgagaga aggttaagag aacattgaat   1860

ttatgtttag gatgtttcat ccccttctca ttggaaaaga aaaactacag aataaaatcc   1920

tacttttgca ctgaaatttg gtgctgtggt ctagttcaat ataagtgggt gacctggagt   1980

tttccaaatg atttcccaag gatattattc ctgtgttagt atggtaattg gatattataa   2040

gtgttcttga tcaattaaat atatattggt aaaagtgaat ataattaggc acg          2093
```

<210> SEQ ID NO 100
<211> LENGTH: 1632
<212> TYPE: DNA
<213> ORGANISM: Homo sapiens

<400> SEQUENCE: 100

```
taaccttttc gtgggtcgat ttttttttcg gttgggaaaa aattccctta atgttagttg     60

taggtaatgt aaagtttatg tgggttataa aagccatact acatatacgt ttttgagaag    120

tcaaaattat ttatttgtat atcaacaaca taaattaaat tgggttgtaa ggacgtgtag    180

ttgtattact taatgtgaag gctctcaaaa ggtgacattt taaaactctg gagcgcctaa    240

aaaatgcaaa ggtccttggc agctttaatt ggggaggtgc ctaaacctct gggaggggtc    300

agagaaaact ctggtgggtt tgtttgtttt taaaaagtga tttaaaaaca actgtgaaag    360

gaaaacgctt aaaaaaaaag aagtctttta gctcccaagg ccctgtatgt tggaaggcaa    420

ctcaagggaa taaatcgcta gagtcaatac cccggaaaag acatttcatg cctaaatgaa    480

aatcttgtta aatgttatta attttgactt agagcacaca gcagcccccct gtgccttgta    540

ttcccttatt agggattcat gtcttatcaa atatctaatt aatctcctag acatcatttg    600
```

```
ttctggccaa ctttatctca gctggtccgc ggggaaaact ccaaatattc tctgtgacaa    660

agctcccttg aagatctttt taattgtcta aattaactgc accaaatttg catgtcaaac    720

ggtaaagggc aacctgagat aaaatgtaaa cgttttaaaa agcccccaaa ctaagcactt    780

gatttgataa ctaggctttt taatgttatg gaagacaact gctcctttcc ttttcaaaga    840

cggctgatct atgcaaatag tgaattggaa atgcctaggt ccccgcgccg tcaaatggcc    900

ctcgcaggtt atttgaatat cagtggcgct gcttctgaaa aggttcaagg atgctctctg    960

acttctttgt gattactcag tgcggcgtct tattctgaag aaaaaaactc aggaataatt   1020

aaaggctggg atcaggcctg ggaacacatt tgggacagga atctcattta gacagtctct   1080

ttcaaaataa ggcacagtta aattgaccag aaggcaatta ttgaaatgaa aattattttc   1140

actctctttg tcttctgacc accaacttaa cagccccagt ttaaaagagg gagaaaagag   1200

ggagagacaa aaagaaaatt ggtaaatgag ataatttcgc aattcgaaaa aaatgttaat   1260

ttagaaaata aagtacatat ttacagaata aaaatatttc taaaagattt cccacacaag   1320

aggaaataca agcgaagtca gcaccaacat attttttttt tccatttttg attactgtcc   1380

gccttgggaa tttgagcgaa gattttgatt tttaggaaag aaaaaataaa ttcttgttat   1440

taacaatcag caaaatgttt tctcggaaac tgttctgaaa caccaagtcg caaagtagcg   1500

ataaaacaga acgaaggtcc ccagcaggga gtttgcagcg tgacattcaa tggcttcttc   1560

cttctccttc ttgagctccc cgcggccagg ctgccccgct cttcttactc gagtttttct   1620

tcactttggc ca                                                       1632
```

<210> SEQ ID NO 101
<211> LENGTH: 2367
<212> TYPE: DNA
<213> ORGANISM: Homo sapiens

<400> SEQUENCE: 101

```
atgcagcaac ttggaaggta actacttttc cagcagtttt aagatgccta ccacagttcc     60

ttacagatag cacaaggaac atttatttac atgacataag cagattagta tctgcttccc    120

ctctttttaa cctgcctctt gaatggaatg aattccctct ctcaaaatga caagtgaaag    180

aataattttg cctctgatat agttttctaa tttggtgcaa ttaatagctg aggcttggca    240

gagaaacgag ggcctgacac actaattaca gtgtgagcac tcaatcatca acacctttgt    300

tagtcgcacg atattacttt ttctcttgca tattattggc taattagttt gaaaaatgtc    360

tgtttggctt gtgcaacaaa tggaggctgt aggttttgtc ttggtctgcg cctttttgtac   420

acatcatacc tcatcataca gactgaagct gccacgggag tgagggccat ggctactcag    480

ctggaactaa aagaaagtaa agtgaatatt atcctgtcag aacataaatg cagtttattt    540

acttagacaa aagggttcat ctatatccct gtccaaacaa cttcattgtc tgaatcttac    600

aaggagctaa aaaaaatgtt agttctatgc atctattttt ggaaaagagc aacgtctgga    660

aagataaggg cactcagcac agactaagtg aactgtttta ttttcatttc aaaaagcagt    720

cagaaacatc aattagccac aagccatttg gtacaaaagg ggaaaatgtt tgtagctgag    780

aagaatagaa gcagcaaagc actcatcagc atactgagaa ttttagactg tgagatatgc    840

taaagtgaat taatttggat ttaaaatgca aattaatctg gcaagcgatt acagatatat    900

gggtgtgaga ctcagaatgc ttttaattta caaaatgttt agatgttatt agttgctaca    960

gtatgtggta ctgtaaatga atgtaattgt tttatttatg cacagttact tggtatatat   1020
```

```
tttatatgat gaaaatgtca gcaataatct gtgcaatata tgttttggag ggttttcagt   1080

aagtaatatt tatgttgaag atttacattt tcttttgtta ctcattagat aatgtagtga   1140

atgttctgtc atttgattta ctgaaagaaa ttttaaaaga aatgaaagat gatttaatat   1200

cttagcttgg tctcatctcc acagctcggg gatccagcaa aactcattct gaacagctta   1260

ttagttctaa ctatatcgca tgcataataa aactgctcat ttgctcatta atattaaaat   1320

tatcatattc agagccatgg gcattaagat caatcaaatc cttggatttc aggtcagatg   1380

ctagatctgc ttatgctttt tttttttttt taagaattct tctcttaaag caagctagaa   1440

gcagcttgtc tttgtgcaaa tagaaagaaa tcttcatcaa aattactttg ttttatattc   1500

gtaatataag aattaggtca tttctgagta cttgatagct atatgccaat gtaccttgac   1560

aggaagaaat atttgcttag gtttataatt tgaattatgg aaaatactcg atgtaaatta   1620

tgtggtctac tgtatattta ttatagctaa aattttagga atgacttaat ttgatttaaa   1680

aatgttaatt ttgagtaatt actctaatac aaagctgcca acaacatctg tttgcataat   1740

cattatggga agaaaatgta ctctcgggtt ccagcaacga ctttcagttg agtttaacat   1800

ttacaaaaac tttattggga atttaaaaaa aatctaagtg tgtcttattg tgcaggcaga   1860

acgttacact gtaacttgca tatgtcatct aataatacag aataaacaaa ctctgtcatt   1920

tcattattat agggatgaaa agaatgcctt tgagcttatt tgcataaagc tttgtgcaaa   1980

attaacactt gtcactgtag ccttttttagc attttaatac ctcaagcagg actggttcct   2040

ttggacattt caaccatccc tgagtgcttg atcagggaca caacagagct gacctaattg   2100

ttctggcatt ttcaaagata ctgtaatttg tacagatatt gcaatttaga ccagttcaat   2160

gaaaggaagg ttttgacaca gctattatta aaatagcttg gaaggttctc ttatcacaaa   2220

gttcaaactg cagattccag taatttgtaa gtttgaggtt tgtaatatca tgccatattt   2280

tgattttaat acttaaacat gttaagattt ttcactctga ttaagtaaga tcaataatgt   2340

agtatgttgg gctgccttat tagacaa                                       2367
```

<210> SEQ ID NO 102
<211> LENGTH: 1669
<212> TYPE: DNA
<213> ORGANISM: Homo sapiens

<400> SEQUENCE: 102

```
cagcagctga atgagaaaac ttacttgatc taaaagataa aagagtcagc caaacccagg     60

cccaagtcct ttaggtgcca gccatctatc taaagaagaa acctaaagca ttgttagaaa    120

ggtttgtagt tctgtagcct tccctcctcc aaaggaggaa cctgatgtct taatacacta    180

taatagccaa ggcttcctgc catcaaactg ctaacaataa aactgccctg caatgttcgt    240

ggggaacaga aacaggcaat acatatttct ctatgtatct ggaagtgcct caatcatata    300

cttaaatttt acagtcttct ccccaaatga gaacgatttc cagccaacac gttcacaaac    360

tgtacttaac gttaaaagaa aacggataaa acatatgtaa ttactcaagg ttagacttct    420

aattcctcaa ttcactaaag gaaacttggc aagaagatgc atcattttgc tcctttctac    480

tggggcatct gaggaggaga gccactgagg cagctaatac acaaaacatg atcaaaagtg    540

attaacaaca gcttcatatg caaattacat taatgaagga gtgcaaagtc atcatgtaaa    600

ttaaatatgt caaatctctt ggtgaacttt taatcttgag aagaaaaaac actgctttaa    660

tttttttaca tcatcaattt tgcaagattg aaaatctaag aatcttggtg ctataaacaa    720

ttttcacctt ttttttctcc ttcagcaggc tgacaggcca gcctgatgtg caccgaatgt    780
```

acatgttaat aggccaatca aaaatgcaaa acaattcgca attactggaa ggacctaatg 840
gtcattagaa tttacaacta ggtaatgaac tgaagtctgc ccacaccatg catattcata 900
aagcaattta gcctttgaag attaaagaag tgcttaaaat tcaaatgagc tttagcaaat 960
tatcagtaag attcatccaa aaagcaaagg gtttttcttc ctatgatttc ctcatttttt 1020
taatgcaaaa ttgtaatatc ttccagactg agcttaaact aaacatagag cttctagtca 1080
agccaaaggg gctaagatac aaacagaggc tgcaaacatc gtcacggact ttgttcataa 1140
aactaagccc ttaagagcca aacctatctc taaacatggt aatttatcaa aaacagccca 1200
gagtcgctca taggcaatac tgcatagtcc tccaacagaa cagattaaca cgagtccctc 1260
cacccttcca aaaagccttt tccccctcaa gttgtctctc ctgtgtaaac atccactgtg 1320
gtataaaaac agctttttca ttggcttgga gtggcattaa ttttagaagt ttctgcttcc 1380
aaagggaaac cagcaagaaa ggagaagcac aggagggaga ggagcaaggt ctggtttact 1440
tctgaggagt gcaaatcctg ttgcttgaga tttgcctttc tgatttcctc cattcggcac 1500
cagccgcatt taatccatgg tgaacgggtc atgcagacat cagctgacat tcagaaagtt 1560
gtggtgtcca cccaccacca ccatcccacc ccagttatta gagagtatcg tgggaacctg 1620
gatttgcagg ctttccaatt actagtctgg agaagaatcc tttgcttga 1669

<210> SEQ ID NO 103
<211> LENGTH: 2276
<212> TYPE: DNA
<213> ORGANISM: Homo sapiens

<400> SEQUENCE: 103
tgattaaaat ggtccaacag cgggcgcccc tccccactac ctcggaagag caactattta 60
tcctttagaa tctaccttgt ccagggcttt tatatgcctg gcctttgaat cggtcatctc 120
ctgtttgtat cgtgactaag ggagaggctt tctggcaaaa tcttgtcagt gatggtgatt 180
tctcctccac attgctgctg aaactgggat gcagacttcc ttcacattgg ctttcttctt 240
caggaaatgc acaggagcct cttgccttgt aatacacagt ctgtctcatt cataaagtct 300
tgtcctggaa aatgcctcat tcatccctgc agaagacccg ccgttgggag ggcaggggcg 360
ttcgaaacct tgggagacag aagacaatag tggagtgctt ggcagcagtg cctgggctgc 420
tttagcaaca tgcacccacg ccagggagag gataaaacgc tgcagttgtt tacttgcctc 480
tctggagcaa aagagtctct tcgcctacaa tatagatgcc aaatcctcag gtcctgagtg 540
aggaaatgat gagcttcgcc ggggattggc atgaagtcct gtgctccaag atagcacggc 600
attttacttg aaagcattcg ttgtttaaag agaaaacgag aattgtggga ttttttgtca 660
atcgagagtc agccaacttc ctctcccact ggccgctcac acagaatgcc caccgtgccc 720
tgcggtgccc tgccacggag ccaggctggc ctgctctctg gccaccgaag gcacttgctt 780
ctctttcgga atctgatcac aggcaactta aatttgccaa cgttacccat attagtaatt 840
gcaaaataat aaacatggca aatttcctat taataaggca tccagtgtaa ctccttttgc 900
agaaagagct ctctggaatc ctaagcctaa taggtctgtg tttatttctc caccagcagc 960
ataatgtgac tgatttacaa gagtttaact caagtgttaa tctgacagtg acgaagagct 1020
cctcactggt gcagtcactt acactatcat attagttgcc tcctctatta aagcagtgtg 1080
gtcgataatt ggaatgcttt tatgtctagt ggttctgaca agcctcttct tcaggtcaca 1140
tatgggcggt ctagctctcc gctcagccca acagtggcaa ataatttaaa ctgagaaagt 1200

-continued attgttctcc tcgtattgtg gagcaagggc agttcaaggg aagtgagact gtgcactggc 1260
tacctgctgc tgtgcagtaa aataaggtgg acatgataca gggttgggag tacaattaaa 1320
tctattttgc accaatgtgt tgctggacag atgagtttcc acatggcaga gctttatgat 1380
ctttaaggta gactgaacta atagattggt gtggagcgca ctgaagttac caaggatgag 1440
aaagcaggca gtagtacatt tgaactacag gtttctcata tgctccacgt catgctgagt 1500
ttttatagct cctggctttc aaaaagcctg tttcaaagag gtttgcgcta gactgggcat 1560
gcagttttgc tctgcagata ttgtcgctac cgatttagtg gaatgcaatt aggaagccta 1620
aattaagtgg taatggagaa ccagctcttg aaactggggt ttccacggca accactgctt 1680
acaatacagc cttcagttag ttttcccact ttatctgcaa aatgcacaat tgagctttaa 1740
aacagctcgg tgctgaaaaa cgcactgtaa acaactgttt gcaatgagag ttttacactg 1800
tctttaaata caacaaacta tcacataaaa tttacttgcc ctccctaata aagcaaaatc 1860
tgggttggca atcagttagc gattttaaaa tttattattc ctttcccctg tttggattta 1920
tttttaaggg aagatgccac gagtcattag gtctcttaac tttggtcatt cttgctgcat 1980
tttcagctcc cctgacaatc tgcctatccc accagtccct tgctaaaatg tgtttcatct 2040
tagcaaataa ttgtttcaaa taaacataca atgtgctcct tttctaggtt cttttcgtat 2100
tttggtaaca ttttacagat tctgctcgtg ttttcccttt gtaacatgtc atagatttgc 2160
aagactttcc tatttactaa tttgttatta atcttctttc cagcttacta ctcttttaaa 2220
agtccacgtt tcatttctct gtacattcgg caattaacca tcgaggctgt cttttg 2276

<210> SEQ ID NO 104
<211> LENGTH: 1872
<212> TYPE: DNA
<213> ORGANISM: Homo sapiens

<400> SEQUENCE: 104
gtggcggaaa tcaatttaat aagtctaaaa gacagttcgg gttacgttat cagccagaca 60
ggaaatacac atgcaaagaa gaaaaagaag ctatgaaagg aagagtgtaa tgatgttaat 120
ttcttaattt gtttcctctg atgtaggatc tagacattag tatcattgtc agtacgtgtg 180
caagtcactt cagaaaaatc actcctgcag tagagctaat tgttatcaaa atgtaaaatg 240
tgttctgggt gttactgata ctacctattt gtacttggca aaacatatat ttttttccag 300
catcaaaatg gttaaaatga agaagccagg ttattacaca tttcaattcc agagtcaaat 360
ataaaaattt ctattatagg gacaattaat tacatctcaa aatggcaaat gtgcatcctt 420
gtcaggtaga gtgtactctg atggcctttc ctcaaacact gaatgtggag atttgatctc 480
ttctaatggt gctgagaaaa gggtaattac gctatggtca aagctaattt gctttctgcc 540
agatgaactg ttgtatttta ttgtacgctg acattttaaa gtaattacgg cactgttgac 600
cttagacaat tccagttgta tcgctgtcta cagctgcagc gcttggtcta cctttggctg 660
gcagacagtg gctgtaacga ggtaatgaca cggacaaaga gcaccatatg gggctccttt 720
gagatacaca aagcccagtg aaaggaaaca agaaaatttt aacatcatca ttacagtcac 780
acatctttac agctataaag ggtcctgtcc acgcgtgctt gtgcgcgtgc acatacacac 840
acaggcacac aaataatcta aacactttgc ctgcttgtac cttaggtgtg tgtgtgggtg 900
tgtttgcaca tgtttgagtg tgtgtgtgtg catgtgcgtg tgtgtgtgtg tttcttttgt 960
aaatggcagc atgcatcaag aagaaaaaga ggtcaggtag aactgaacgt gacggactgg 1020
tcttccactg acaggagttc aaaggctaaa gactattgat tgagataaaa gcccaggttc 1080
ttaactaatg ttaaagacac tccttgttgt ctgaaagctg tgcacataat taggcagaaa 1140
gaagagcact tcagccagca aatcactata aaccaagcct cattaaaata gatattagtt 1200
catttaaaga aagaagttat tattcattca tatattttaa tgagctatca ggctgtcttt 1260
tctatgataa gaaaaaaaaa aaacatgttc agagtttggc ctggttaatg tatccttgca 1320
aagatagcaa aatagattaa tatcactcaa aaagaataat gcttcatctt cttcaaggaa 1380
aaatgcacag gatattgaac tatagaatta ttgtcaagaa gaggtgggaa aaaactgagc 1440
tttaccatca tgttaaatat ttcaatctat ttgggtaggt ggaaatggac tatggaaatg 1500
tgagctcact tacaataagc catggaggtt gcctccatca tagcttattg cctacttatg 1560
tgacaattac atgaagcaaa ggaaagtcaa tgtatttcct tttgaattac atttctatca 1620
ttcagggttt ccccccttagt aattattgga agggtgcatg agttattatt tcattgagta 1680
aaaagataat aaaaattaca ttacagagat ggtagggttt cctgtagagt ccttaattta 1740
gtttaaactg tgaggactgt ttttctccta aatttgtttc ctagtttgtt tgtttgtttg 1800
tttttcatga atatttggag atctctatgc caatagtttt tggccttttt aaaggcaaag 1860
ttcatttgac aa 1872

<210> SEQ ID NO 105
<211> LENGTH: 1470
<212> TYPE: DNA
<213> ORGANISM: Homo sapiens

<400> SEQUENCE: 105
caaccacaaa cagcatagtg ggggcaaatc tgtgttaatg tgtatctaaa aagccaagaa 60
aaaccagagg cataatagat tcaagtcaat ttggggaggt tagttacttt gtcaattcta 120
tgtatgctgt ttgttttgta ggaaaaatat ttggtttaag aatagactag tgtcatccta 180
atccaccact ggtgataata ctgatgttca gactcttaaa aaaactttgt aaaaagacag 240
tgagctacag atgcatgtgc tgtattttta gctcacatac aaatattaga actcttatta 300
aaatgatagg gttttttttt tagcagagaa ggatgaatgc tgcataatta agtacagtat 360
ttaatttggc tgttgtgaag caaaagaata aggtaataat ttttattgta ctaatcagtc 420
tcaagatgtt ctctgtgtta attgggttaa aaaaattgca gtacttatta gaaattctaa 480
tttcacaatg cagcactgac aataagctca gccagtgaat tattcacatc tttaatttgc 540
tcacttaatg acagtgttct gtaatcagag tgcagagact gctgcctatg cattatgtat 600
gatgctcagg acttaaatgc aggacattat gaagctctca gtggttcagt aattagtttt 660
ccacaagaca ggatttagat attcagagat aaaagtccac agttggataa tattaaggtt 720
gcaacacaaa ataacaaagg aaaggaagct caaagtttgg actgaaactt tgtctctagg 780
gccttgtcca ccgtggaaac agaatcatgc cacctgaaat agttgcctag ctctgatcac 840
atgtttgaaa actgtttttg aacaaagttg tagcaggcaa ggcatttgaa caatttcagt 900
ggaccagagg ggaaagataa aacctttttta attagtgttc acagaagccc tgcaatatat 960
cctcctaaca agtctgtagt atgcatagca ggcatcctca atgtgctttg taacttagtt 1020
agtgcaaatg caaatcaggt tacaatagtg tttggctgta attgtgtttg taaaagggtt 1080
acatgcccaa atggagattg agcttgctca tggttttgtt ccaattgctt ctgagggaag 1140
gtttgaaaat caaatgagat attaagtaaa tctgggcatg aaaggaagta gatccgaatt 1200
gtcactgcaa ctttggaatt tcttacactt gtcagtttgg agttgtcagt ttttctttaa 1260
cgatgctacg gttgttctgt cataattatg taactttaat ggattaccca gcccattagc 1320
aatactttaa aaatgtatac taggtttcag aaaacatgtc acagtatcat ttctaaagtt 1380
taataagtaa cttgaaatct ttaagtgatt tttttaaaag aagaacatgc tgttatggta 1440
gactatatgg ggtatttttg agagcttaaa 1470

<210> SEQ ID NO 106
<211> LENGTH: 1140
<212> TYPE: DNA
<213> ORGANISM: Homo sapiens

<400> SEQUENCE: 106
tgacacacaa ggtcagtcag cttgctagcg cggaatcggc cccgcaggtg ctaggaggct 60
cacttccttc ttcgcagacg ctatacccta tccccacctg ctctggggaa ggcaaagctc 120
cgcagacttc ttatccctga ggcaacccgc tacccaaatg tccctcttct ttcccacgaa 180
ggaaagaaat taccgtagga gattttgcca atccatgcca gctttctgat tgttttcttc 240
aggtaagggg aaaagaacag ccagcgcgtg aatggagagc tgagggccca ctagggagag 300
aacctcttcc ccacccttcg gtgcctgcaa aaagggacat tggctatcca ggggaaagtg 360
caagaaagag agcactaatc gctgaaccag gagacaaaca cgattaccag ctccgagcct 420
tgagtcagaa agtctcatag actttaagat gttaatcccc agcataatcc ttcctttggc 480
gtgtaggaat agtgcagcca caagagttgt tttgttattt atattggcgt ttaataaaac 540
tcagccagtg gtgaatgggc tgcccactct ccaatggtaa ttaattccct atttcagtga 600
cccaattgtc ctgggacaga gcggtgggcc cgtcccagtg ccccgatccc cctttgtgcg 660
gatacactgc cctcgtgctt caacagctat ggaaactcat tcttttgatg tcattcaagg 720
agttttcctt gggcatcttc taaacttcaa ggaccctttt ctttctgcgt ttcatgaaaa 780
gcagtgcgag cttgaccacc tctgtagaat ttaatgattt ggtgaaaggg ccctttggga 840
tttgtgtaag gagttagaca gagagaaagg aaatttggca gcctgctccc tcgcagggac 900
cgtccctaac ctggaaaaca cagaactttg agaaatggat aaagatcttg aaagctgatt 960
ttccctctcc tttccccact aaggaaaaaa aaatacccaa aacaaacaaa acaaaactta 1020
attctcttct ggaaataaat gtatcgttta ttgttgctga tacaaattaa aagggtgatg 1080
ttgaggtaaa taagttcgaa tctttagcag agactcttcc ttaatctgta ccttttggga 1140

<210> SEQ ID NO 107
<211> LENGTH: 1488
<212> TYPE: DNA
<213> ORGANISM: Homo sapiens

<400> SEQUENCE: 107
agacttgcct tgtgttggag acagaacctt gtctgcagca tttcctctgc tgtttgaaag 60
aaatacataa ccagatattg gggaaaggc aattccagag gaatctacaa tagaaggtgg 120
cctgagggag aaggaatata acagggcaag tgtggagttg agggcagaca gcaaaccttt 180
cttcatcctg aacaggagtg gaatgagaga gggtgaagta aactcttgga ctcaagctcc 240
agccatggcc ctaggtgagg cgggtggcct agaacctcct ggaggggcat ggcatcgagt 300
cctttgctgc tcctggaagc aggcaggcat gccatgtgtc gaggcttcat cctgctgggg 360
agacagcctg gggcactcg gccccaaagt ttatttaagt gaaaaaaccc atccggagac 420
aagaaggagt gttacactac tgtcaagttt tagacgtcgc catcaagcaa aaaaaattac 480
atcccgtcct gacgagcgac taatcaaggc atggcaaacg gtcctgcaat aaattactcc 540

-continued

```
ggcgcgaaat aaaccacaca aacagaccga tgataataaa tgtaaattat ttctctgaag    600

aaattttctt ggtatatgag taatacgaac catcaggaag gcgtcttcct taacattaat    660

tacagaaaat gacaagtgag ctgatgactg ggaaggctca ttatctgaga acatattcac    720

aactttgcaa tttgcgcgag atgtactccg gctaaattaa tctcccttct ttgcatgagc    780

ctcttctaat tttcatgtta ttaacaggtt tgcagtatca gtcagtgctt gtcactctaa    840

tcaggtttca gcatgttcgc aaaagcgaag cgtcatttat aaggataagc cctcataatg    900

gtgcttgctt tcatgtggag aattctacaa ggctgctttt aataaggtac tttaatcatc    960

tcctttgctc aacttttggc cccactgttc ctttatgaag agtcattaaa agactttgaa   1020

gttcatcaag gaggaaaaat tcatgacatt gttcggatga ggttggggat ggttccaagg   1080

gggaagcctg gagggagtcc gggtgagagg gccctgttgg cttggggcct aaccatgggt   1140

gaggaggggc aacctgtacc catcgtctcc accatacaac accctgtagg ttaatatgcc   1200

ggggtcactg ctgaacaaag acctcactgg agagcagtcc aattggcaga gcatgttcta   1260

gggtcaatga tagacgatcc ttagagaagg ggccagccag gtcagcactc aggacagctc   1320

ccagcacgcc actatcactg tggagtctcg gaatcttttt gcgggttttg gatctattct   1380

gatgatctgc gcttgctttg gaaatctctc tgtctctccc ccaccccgcc ccgccgcccc   1440

tctctgtgtg tgtgttccct ctctctgttg catgtctcaa agggctag                1488
```

<210> SEQ ID NO 108
<211> LENGTH: 2030
<212> TYPE: DNA
<213> ORGANISM: Homo sapiens

<400> SEQUENCE: 108

```
ttttgaggtg cataggattt tttttcactt tgacaatctg cttctcatat tactttagct     60

ttctgtagtg agaaaaagca caggattagg ggtcaggtgc ctcaggctcc agaaccccat    120

ctgttagtaa atagctaacc tgatccagac cattccccgga tctgggcctc cagaccctca    180

tctggggacc atcattagga ttccttctgt gatttgatta ttttcctccc tgccagagcc    240

ggggaggagg ctaaaccctt gcatgcaagt ccaccaaagc tgtcctaaaa taataaagca    300

atttcctttg aaatggtcag aagaaaagtc aggaggccct tgcaaaatgt gatgaaaccc    360

agccccagct gaatattaag ttagcgaggg gtctgcaatg agggtggggg gctggggaga    420

gaagagagat gcagggttgg ggagagagaa attttaattg caattgtttg gcctgctgat    480

cctaggcaaa tgacaagaag cccccaagca gcctcaaaca cagatatttg aaaggcagag    540

acggctgggg gatggtttgg tttctccctc ccctctgagg ctgtttgagg aacggtctac    600

agtgctgaca agcacgggtt ttggaggcca ttgaaaagtt ttgggcctaa atagggtagg    660

cagcttggct taagtgttgc taaggaatac ctggcaacca gcaacaatag gccttttaga    720

gaatccaggg caaacagtga ccgtggtaat ggggtgggct taagggtctc cttgcccggc    780

tgggcccctc ctcttctcac acagaggcct gggcactggg ctatgttccg gaaattccct    840

gcacaaagcc ccattcagtg ggaggagggc caatgcgtgt gctttggggg cagtgggggt    900

ggagacaggg gatagggaga gggcggggga gggggtaccg gagaaggagc tttactgcca    960

aaaaaaaaaa aaaaaacctc tcaagtctct ttcttctcgc aaagactaaa agaggcacag   1020

aaagtgctaa gtttgtaaaa gagtctgaaa aggttcagaa aagtagcata aaaggaactg   1080

gggaacgccc cgtgaatttt gaacagagag cagaaaaggg accctaaaaa gcaattagtg   1140
```

-continued atgctgcttg taaatgaaga ggcacctagt ttggggtggg gagctgagtc tggaggtagg 1200
tgtgcagggg tgcagcaggt ggtgggggtt gaggggcagg tgaggagaat gaagtggggc 1260
gggaagcggg tgaggggaag gggaggccag tgaagaatgg atggatggaa actggggaac 1320
tgtggcctca gtccccactc taaccacatg ccttcaggct gctctctcct tgggctgtgc 1380
agatgcccca cccactcagt ttctgtcccc tggtaaggca gccccccgaa agtcatgggt 1440
gcctgggaca gtgaccagca cccagagtct gagcagtctc cccagtccct tcagtctctg 1500
ataaccatga aagaagccct gacgttctgt gtgagtgtag actgcacact cctcacaagt 1560
aggcaaatgg caggatgctc cagggagctg ggtgtctgcc tgcgttcctg gggggaggctc 1620 acatgacagt cagtgaagga aggccaggga gccaacaaat tagcgctcta caaattccac 1680
gtgcctgagc tgcataacat tcatgctgaa ataccctact caaaggctct aaagataata 1740
attttacatt tccagcagaa tgtgcacggt gacaattatc tgtattccta ctgtgtcgca 1800
gcatcaaccg ataatcaaga gaattatgtt ccagttgaaa gcagatttaa ataaacagac 1860
actaaatgga agccaataat agatgtacca aaatagtcca ggcaaggaag cagccattca 1920
gataaagagc tgtttagtcg aggagacatg aggcatccag agcgcagagt ttacagctct 1980
ctgtctgtgg ctcagcctgt ctgattcttt ctagctgtcc tctgcagacc 2030

<210> SEQ ID NO 109
<211> LENGTH: 1492
<212> TYPE: DNA
<213> ORGANISM: Homo sapiens

<400> SEQUENCE: 109
agtggtgaac aaccaccatt gctgcatcac ggagtttaag ttctcatctt acactcaatt 60
gccagggccg tggtcccttt acaaagtaga caactccaga actggtgctt gggaagacat 120
ctttgaggtc agccagtcaa acctttttgtg ttacagattt aaactgatgc tgagaaagat 180
gactggcttc ttcccccaac tagtaagtta ctgtggggag agtgcagagc acaggcccct 240
tccacctctt gtgtgctctt caggagccca tctgtctcag ccagaagaca gaaacagagg 300
gaggccctga gaagtgacaa ggacattggt tggggtgggc aaaacactgt ctccttcctg 360
tccctggcct gtgagcctaa acacaggcag agctttttct ttttgaaaag aatcgcagcc 420
tcaactggcc ttagcagcag gttagggcaa agacagagac ggggtcgtct tcggcgctgg 480
tggtgctggc ggtggtggga ggggagggca ggccagggca ctcgcctatt gtaggtctgg 540
attggatgct tccactcatt catttccttt taattaaccc gcattcctgg aggagaaata 600
tttatgttgg ctcccataga ggcaatcctc agactggaaa gaagggggaa gaaagcctgt 660
cttagcaaaa caatatctct aaagagctca agaagagaaa ataggagaac aaaatgccat 720
taaaatagcc ttctaccccc actggagtca atgaaaactt catttcacat gctaatccgc 780
cactccgccc ccttgtcttc tcacaacacc ttttccgaaa gtgtttggga aaagtcttcg 840
cagtcagtac acagctccct gcagctcaga cttctccttg tgttagttca gggccccaag 900
tggggctctc gctccagcag cggctttttt ctcccccact ttaatttaaa caaagacttc 960
ggagttcatc aacctcccac tgaaattcac agctgctgaa caaactaatc ccctctcccg 1020
gcctttcttc ccttcaatgg gctcttggct tcaaagacac tttgggaaag gactttgcta 1080
gggctcacac tgcttcatca atagaagtta gtgcaagtat tatctgaaga gcaagtggct 1140
ttacaaacaa atactgccta acaatccctc cctcccaaac acacacacat ctagcccgca 1200
gacatgatgg gatctacaac aggattaggg ctagcatccc ctggcttcac acccagtccc 1260
tttgtatagc tgagctcagc cctgaagtgg ggtagggaaa accctggaac tgaacaccag 1320
gcacggatga agggagacaa tccccccacc ctcaacacac ccagcagagt gaccacaaat 1380
gctgcaagga gagaacctaa ttcagtggga atggacacct tcctttaact ttcttgattt 1440
atctctccct aagcctctcc cctgccttac tagggtgcag gaagcaagaa ta 1492

<210> SEQ ID NO 110
<211> LENGTH: 1434
<212> TYPE: DNA
<213> ORGANISM: Homo sapiens

<400> SEQUENCE: 110
aagcaacaaa aatgcaagac taaactgtca aaaaatacca aagtttcaag ttcgtattta 60
gcaaaagtct tttcttataa tagagggtca ttttgtacat gaagtgcaag ggagaatgaa 120
aagacacaga aagagagaaa ggcagagaga gagagagaga gaaatccttt ttcatcctta 180
ccaaattagc ttgtgtttat aaagatgtca aaccttcatt ttacccaata aaacattttt 240
ggtgtggaaa tgatgttccc ctcgtgaatt tgcataaaag taaaatgatt tttaaaatcc 300
agctttgtaa accaatgtgg aactatgatt gttttaaacc tttaaaccaa aagcaaggca 360
tggtttttgt cttaaattta gaataaattg aaagcataca ttgatgttct ttgtttcaaa 420
tacattttgg aacccagcag accacattca acctagttaa attatctgaa tggatttggg 480
gaaaagagaa aggagcctgt tcattttaat ataccttcag aaatatttta cttcttgatg 540
atgacagcag ctcttgctga caactattaa tacattataa acaccccatc agagttatat 600
aaaaacatgt cagttttaaa gagaacatct ttgacagcaa attttctgat tgtgaaacag 660
ctgtgccttc agtacaatgc attaagtagt ttattccttt tagatagtta aattgtgcat 720
gaaatgttgc tggcgcaagg gctccaaatc tggcctgatt agcgaacatc tgttacattg 780
gaaaaattca tgtctaccct aattagctgt caggctgatg tacatcaggc ctgatggtga 840
gggatcctgc gctgtttaag tcaaacaggt tcctctcctc tcctgtcacc tgccctttca 900
aatctcttcc tttcatgggc tgctgtaatt agagatagtt ggacacacaa tggagcaggc 960
tacggtcagt tacagtccca tctgtgcaat atttttattc ccaccaaact tgggaaccga 1020
tatatgaagt agttcaacag cagcaaggct gttagatctg ttaggtctat gacatttgtt 1080
aatcttggct caagatcgtt ctctgaaagt cttaggatcc tggagtcatc atcttgtggt 1140
gactgaaggg taatctacag cttctgagga attgatcttt gtttcatttg ttttaaatag 1200
ggatagcgct caggtgattt tgaaatgtcg cagtgtgctg tagaatggca tgttactgta 1260
agatcaggta ttcaaaagaa aaagaagctc agtgttctgc agtgtccaga caactgacta 1320
tagacagcta caggaggcaa ctgacaccaa aagatctgat tttattgggt ttattagtcc 1380
agtgtacaca aggttttcca atgtaaataa aaactttcat tgacctgtgg atgg 1434

<210> SEQ ID NO 111
<211> LENGTH: 1552
<212> TYPE: DNA
<213> ORGANISM: Homo sapiens

<400> SEQUENCE: 111
agagaaagcc acagtccagt ttccatttcc cctgaagagc cagaaccagg gcgatgggtc 60
tttcccagca caaattcaaa aaagaaccaa acagtttcat ttcgacacaa tgacaacctc 120
ccaccttctc tttataaatt tttgatattt cgatcgaaat attctatcct acgttcagca 180

```
tgtttccatt gttttatatt ttactgaagg acctaaaata ttttaaagca gagaaaagaa    240
ctaaatgata ggcagagagg agatttaaat aaaattttta aaagccacaa atttacaatt    300
gtttttttaaa aagcatatct atgtatttaa aataatataa tgaattgaat catttaaaat    360
gcacccctgt cctttcaaat ctgttttttt tttttcaaaa aatttttgaa aatctaatga    420
gaaatatatt ttgacattcc aatccagtga attagttaag ggaaaactac ctaaaaagag    480
gcacactaaa cttttcttat ccccagtggg cggtgttaat catccagttt gagccttgta    540
gttttcattg tcgaatactt gggttctctc aaagggaaga acgttgggga cttgcattca    600
ctctttttca agaggagatt aaacacaaaa tcgatttaat ggagcatctg taatcttaaa    660
tacgagaagt caagagctaa agctataata gaaaggttag ctttcctcca ttgttcacac    720
aatctaactc atatttttgg aacttaatta tcaatgaaag ctaccacatc aatgcaatac    780
agtataggca aattacaaga accttttact tctcccaact gggtttaaat tgcaaatctt    840
aacactgaac agtgtgcttt tggcattgaa tattcaatac agggaaatgt gttttaagtg    900
aaccacccaa gggcccagga acatttgctt aataatgata ctttgcaatt ctatagggcc    960
tttcaggcaa ggatctcaag tggaatgctc tttaactata ccctgcatgg gaaaccttgg   1020
gaatatttta aagtgctcac ttaaggccta ttggaaagaa tcttttagta tagatttcac   1080
agtatgattt taagaaatga ggtactgcag aattttcagt ctcaggggta tcatattcat   1140
ggggatttgg tggttactga acatttatta gttactttat gtaaaggtta aaatgtacat   1200
tttctccaac tttttatttt caaaaaattt aaacctacag aaaataatgg tacaatgaaa   1260
catttaattt caaagaacac ccatattccc ttcacttagg ttcatcagct tttaacattt   1320
tgtgacaatt gcttagattt ttctaagtag atggatagct agacagacag acatatatgg   1380
atctactata tctgaataga taggtagatg tcagatatga ttatttgttt gttcatacac   1440
atacataaac ttacctcttt tatctatttc aagtaagtgg taaacatcac tgcactttat   1500
tcctaagtac taaagcgtgc ctatcctgat taaagggtat tctacataac ca           1552
```

<210> SEQ ID NO 112
<211> LENGTH: 1805
<212> TYPE: DNA
<213> ORGANISM: Homo sapiens

<400> SEQUENCE: 112

```
gtaaataaga aatttggccc tatttaaact ttatgaataa gtagattatt ttgctactag     60
ccataatttt aatttgaggt tcaccatatc ttgtatacct taagacatag taacaatact    120
tacatcaaat acttagacat ttttactgct attttactta gggaaagatg tgtttgttgg    180
ttgcttattt agatctttga caaattctcc acatcaaaca aggtcaagcc acaaataatg    240
cccaagatca actaaaaatc tagtaaagat caatgacttg aaatgtggat ttgaaaggat    300
gtgggtcaat gtaaaagctg caagaatttt tttcttcatt attttaaaac aaatgcacat    360
cttctgcggg taaaacagcc caaagcagtg tcttttaaac cacctatacc aaaagataaa    420
acaccttgga aacaacaagc ctttgacatc tgtgacacag gagacatgca gaagtcatta    480
agggtatccc gagggggttc caacagttgc ttcactttag ggtggatgtg agaaggctta    540
aaattaaatt actttaaaat aaagttagag cagtaagcaa tttcctgctt tctactcaga    600
agggtttccc gtgagaaaag aaagtgggca aaaagctcag acagacagac aaacatattt    660
acccctaggt ggaaggtaca aattaaatta gcctgctaca aaagggagat gttttctcct    720
tctgttcaga tgtcatggta gtgaggaaac atagtctggg gccaagaaaa atggcacaaa    780
```

tgcattcatc tgagctacca ttcatcctga tccaaggtct aaacagaaca cataaaagaa 840
cggcactgtt gaaggacttc ctctccctag ttaccaagtt gagacttgca aaggcacatg 900
ggagcagggg gtggggatct ttccagaatg tttcaatgtt gatggagtgt cagaggatgt 960
tatggagtta atgactgaat ctgaaatcac atcagtataa gttgattcca tatttcatag 1020
aaagagctgt attttatggt gcacagtatg gtgtgtttaa aggtacattg tgaactttct 1080
ttccctctgt agctggaaac caatataggc acttccaaag agtcaagtat ctattatagt 1140
gcctcattaa tatgcatgtt tttggcactc agtttggttc agctggtatg ctttccagta 1200
tctcattctt tatttatatg agactgggag gtgtgaccta tggagccagt tggctgtcat 1260
gaattggaat attcattaag cctcatgaat tatgcattag cctgcttata atactgagat 1320
ccacatttga tctagccaga actctctgct ttccattcaa cgaaacgatc cacattttgg 1380
tcaaactgta catgtgttcc atacactgca gaaggactgc ctgtatattt gccaccaaaa 1440
aggcttggag attttgcacc tcacatctga ctaagtgggt ttcatatttt tcgcttgttt 1500
gaagggcatt gcagacatgg ttctcctctg taaaacgagg ttagagtagc attcttccct 1560
agcctgatta ctatttccat ccattactgc ccttgcctat aaaagtcacc aatgactggt 1620
aagcagcctg gattacaaaa gatatgtagc tatctcctgg caatccacac acaaaagcaa 1680
agccaaatat aaaaaacatg gaaagtgctt ttaagaattt agtttctctt atctaaaaca 1740
aggaaaccct tttactgata accttatcat ttgtgatact tttttatgga taggtatatc 1800
ctggc 1805

<210> SEQ ID NO 113
<211> LENGTH: 1361
<212> TYPE: DNA
<213> ORGANISM: Homo sapiens

<400> SEQUENCE: 113
gcacatgagc atttgtattt gaataacagt gggtctgtgg gtttaaatca tgtatgcatc 60
aacaatgtac atatatgtga ttatgagtgc tggtatataa ccacatgttg tatttctggg 120
ttgctctcca ttcataattg ggtgtgcatg tgtgcgcacg tgacaggttg ttaccttgca 180
agcaggaact catgcaaagc tgtgcatgag atttatgtgt gtgtgatttt gacacggggc 240
tggtgtccct ggataaatga gtgtgttcag gcctgtgact ggggtacaac aattgtgtgt 300
tgagaaactg cagacagccc ttaggccatg tccagcgaga aggaaatgtg taaatgtttg 360
ttgaacacaa aacagaacag ccacaaaatg ccaggccctg tagtggcgcg gcaaatcgtg 420
gaagtttttt cctccctctt catctctccc tctccccagc atctcggccc ctctctggcg 480
tggttccctc acacctaagc ccaatggtgt tttgcaggct ttcagctgtt acctcagtcc 540
ctcctcgcct cattcccgat tcactccgtt gctataggta tgtttgaaac cccagcgtgg 600
tagattttaa ttagtcttcc tacagatggc caattaacat tcattacttt tgccttgagc 660
gattaattat gagtttggat agaaaaggag agaagaggag aggaagatgg gcaggtgaat 720
gaaaggagaa aagagaaggg ggtttgattg ggagtttgga atttttacac agagcaggct 780
ggtgggggag agggtgggaa agagccgttt caatcccctc actcccagcg gcctccctca 840
gcccacagct gctccgggcc cctaatcggc ttggctggcc cagccctcca ggaaaataga 900
gctcacaccc tcgtttggga ggccttaagc ctttggtgtt ccctgacccc aacccttca 960 taataccggc cctcttgttt cttgtgccag agctgggtgg gaactgtgtc aggaatcgcc 1020
caaaatattg cagataaccc agaaaggaag ctctgctgcc agtcactcct tgctagaatt 1080
gcagtggttc actatacaga tgagaaaact gaggcccgca taggaaatga cttcccccac 1140
ctcaggcccc ttggaaggtt ggggagagtc cagctttgtt gactccccag ctcagttctc 1200
tttctgctgc aaccagggtg gtttataaag attttgtgca acattccatg aacaggctga 1260
tttcaaacac agttcacatt cttctctgtg cacctaactg ccaaaagctc ctgtgattcc 1320
ccagcccatt gaaagactcc ttgagtgttg ttgctgggtt c 1361

<210> SEQ ID NO 114
<211> LENGTH: 1602
<212> TYPE: DNA
<213> ORGANISM: Homo sapiens

<400> SEQUENCE: 114
gtggttagag tgccaggaga tcacactgct gcccctccct gggcaccccc aggagggggg 60
cactcaattc actatttatg ctgaaagtga cagaagatga ccagctggca tttttttactc 120 ttatttgttt ttgtgtaatc agaataatag ttatacccac tggcgcagta taaatgcaat 180
acacctggat aggtctgccc ctccagaata cagaggaagg ggtattaatt cattttcaat 240
agagataata atgaacaccg atgtcgtgct ctttccgaaa gatatgactt tcgtgttcgt 300
gtgtggctaa gtatgtcaga gcatctgtac acaccagttt cactttcaaa catgcatttt 360
aaactgaagc actcttttaa ccccatatgg tttttcagtt gtactgtatt ctatgcttct 420
tttctttttc aaaatgcaat taatatggtt gtgtgttaaa tgattcagtg aaagtaaatc 480
ttttatattc aggtaagcaa ttcagccttg taaggtttta tgggaattag atttttctga 540
agtctgggtt gagcatgccc ataactctga cagagccctg caggctcttg tcttcacctt 600
caaatcataa gacagagaaa tcaagctccc tctgtgctct caattatacc aaaaaacacg 660
gagcagaagt cttcagtaat tcaatccctg tggaagcttc ttcacactgt ttgcgctgtt 720
ggaactgctg acagcagcaa tcccaccgtc ccccggtaga ctgtcaaagt tcctcataca 780
gtgtgagcag ctctgttctg tcccacagct ccttctccag agacctcaga gcacatgcat 840
gacttttgat gcttgcttga tacagtggcc aagaggccaa aaaacatcac aatgagagtt 900
ctcatactcc tacaaggtgc tttgtactca aagtaataag ttctgtggct acatgtgggc 960
ctgagttggt gtaatttaat cacaagtaca gctgcataaa cactgtacta aggaatgtct 1020
gcctgcaatt ggattctttc tttgaaaaca cactgtagaa aattcctgag tgccattttc 1080
catatggtta atgagcaaat gtatcatgac cagcttttaa aagtaatttg aatttatgag 1140
ttgcactgat tctagcacat gtgcataaga aatcacacat acgctgggct cttccttatc 1200
aggcaacacc atttcatcgt tttctgccaa acaacaccaa aaagaaccac tctgtgtgtt 1260
taattggctt aaatcatcag ttacagccta cagccattat ttccagaaac caccaaccgc 1320
ttctagtctc tcctgtcaaa aagtcttaaa ggtaggttag tccacatata acacaaaagt 1380
gctatccatt ttttaaagtt ttcctttata aatacagatt tgaaaaaaat ctttaaaact 1440
cactttctca acacaatctc tgctgttcca tcacattcaa gtttttctac tctttttaat 1500
gaaataaaag acacagggta cagatttttc tacaaatcaa acctgttgct atatacttca 1560
ttctctaccc tttgactgta gctcaagtgg gaagcataaa ca 1602

<210> SEQ ID NO 115
<211> LENGTH: 1344
<212> TYPE: DNA
<213> ORGANISM: Homo sapiens

<400> SEQUENCE: 115
gaaagatgag ggtggagaag ggagaagatt aggaaaactt aagtccttca gaaaagagat 60
gggagaaaag tttttcaacc agactttgcc cattgtatgc cctcctgagg gagtttagtt 120
tgaacttcag gttaaaatgc ttacttctct taacctctgg ttattaaaaa aaaactggac 180
atatagttac acattgagga ctactctccc aaaatattgg ggaaaacatg tagcagaatc 240
ttgcaacttc taaactttct gacttcaaac cccaaagtac aagtcttact tttccttcct 300
ttctttcctc ctctccctgg ccccaatctg ctgaaggtga tgggccaagc ccaagggcct 360
cagcagcctt ataaggcaag tgttctgaaa aaccttcaac tcttaatttt aacattaaag 420
aaaaagttgt aatcagactt ggaggaaact tagctttttt ccctccctcc ttccccccttc 480 tgggggtacg aggttgtttt tgcatgcttc atttgcttct tatcctgata ggctgcatta 540
atcagtttta tttccattga tagagaaacc tcgtctgttc tgttcgagct acaaagcgtc 600
ctgcgagctt ttgtgaaagt gcaaatcagt ttaagcaatt atcataccag gaatatgaag 660
gggaaagagg aggccttgcc cagtggtctc ctttaatctc ttaatccacg gatccagggg 720
ggctgcctgg acataattta ggacaatctc cccacccttt acactgtgat aaggccaagt 780
tacaatgcag ggcaaaaata caagctttgt taacatcttg ccttgaaaag ttaagattag 840
acattccgtg cacgtgtggg gactataggg cactatggaa atttttttctt tttttctcc 900 tcttctctaa agcagaattc attctccgtc tctttctcct ttcccccatc tctgcctgtc 960
ttccacctcc cctctttccc cccatttctg tccctctgta gaaacctggc tgctcatagt 1020
gcattttcac agactcttct tggaaggtgt gtgtgccgtg aggggataca ccgccgccgg 1080
gagttgccgg gggaggaggg agacggggtg gcctcaggag acccgggctt gcgtctcaca 1140
gggacaggtg cgcctcgggg tatcctggaa accctcgtgg ggcttccagg cgctttgaca 1200
gcacgaccct cagtgaccac cagctgtctc aagcgctttg cagtcagtgc tcccggaaag 1260
catccctttc tcttcaacaa gtacaaatta ccttttcctt ccactcacct tccaaaaccc 1320
ggaatacctc aaacaccgag ctca 1344

<210> SEQ ID NO 116
<211> LENGTH: 1631
<212> TYPE: DNA
<213> ORGANISM: Homo sapiens

<400> SEQUENCE: 116
tagtggaggc aaacagaatg cccatttgtt ttttggcctg acacctaggt catcattcat 60
gacagcttga tgcacattca ctgattccaa gtgtcaattg agaatggctg atgcaacagc 120
cccatagcac tcacatttgt tggaaaattc catgttgatc tttatatata tacatatata 180
tgtatataca catattacat atatacgtat atatgtatac acatatatgt atatatgtgt 240
gtatatatgt atatatgtat atctatgcat atatatgtat atataatgta tatacatata 300
tacacatata catatataca catatatatg cacacacaca tatatataca cacacacata 360
tatatataca cacacacata tatatataac agtagttgct taagcttcca atattggcct 420
cttcggtcat ggtacattat tttgagtgtt gggagtcagt atgcctgagg tgcaaagatg 480
atgatgtact tcctgtagac atgaaggcac tcagaaataa agcaaggcca ttgaactgtc 540
atttgttgtt cttcctactc aggcttttaa aaaagaaact aaggtcaatt aactgggaag 600
cttaacctct cttagcttgt ctttctttgc gtaggctttt agccttttaa ataaatcatt 660

```
tttttctctt ctctccctcc caacccccta tccattttga acacgttctt ggatttctca    720
tgctaggcct aaggagcaga ctgcttatat tcaagaatga tttggagggg ataaagtgtg    780
caagattttg aattcttgcc ataagtccct ggcagacagc caggcagcct cagaggaata    840
aggctaatga agggagggta aagaagatcc gggagtgtgg ctggtaatgc agtattcatt    900
taattgggag caggtaccgg tgcaaacttc tccattttaa ttggaaaaag ggaaggggat    960
tgttaaggac gaaggaaaaa agaatgcata aagtttccaa gccgaggagc caaaggcagc   1020
cctgtctatg ccagagaaag aactcaattt agggcaattt gctctgcaag ctgggctgca   1080
gcctcccctg ggaataggga tgaggaagaa aatgaaacca aaagagaact tgataaaatc   1140
acctagcaca gacaatctcg gtagaatagg ttttactgag ttaaatctgc cccaatcaat   1200
atgattcttt tcatataagt tacaaataaa aagccacaag attacaataa aaatcgagac   1260
tcgagcgctg ctgatgttgc acctgggagt cttaagaact tgttatggaa tatatgtttt   1320
tgcaactata atgtttgttt ttcctttcac cctggtcatg tgaatcaact gtttgctttc   1380
cttctctatc catttagttt tatatattgt ttttaaaacc caacagaggc aactctttct   1440
gcttaatttc tcttacacta gaggttgggg atcggtggtt tcattttgtt ttccaatgtg   1500
ttgaatctaa cgtagttctg atttctcata ctaataataa atgaagagat ttcttcttat   1560
tgtatatttt tgtgatgtaa ggaattataa atgttaatgt atgagtaaag gaataaaagg   1620
gaggcaagac t                                                        1631
```

<210> SEQ ID NO 117
<211> LENGTH: 1301
<212> TYPE: DNA
<213> ORGANISM: Homo sapiens

<400> SEQUENCE: 117

```
ccagaaccac caagagaagg tcattgtgaa ctcagcccag aagacagaac tgacgattcg     60
gtgaacagga acaatctttg actcctgtaa ggaatcccgc ccatcccaac actgcttagg    120
aggaagaggc ggttcccttt tttgagaaca tattttcaaa gctattctcc aaactgtgtg    180
cactaaaaag agcagtaaac actcatctca gtaaaactcc ttaaatacaa aaatatttag    240
tatgcccagt ttgactcctc tcagttattt tttttgttaa atactcaatg cagagtacaa    300
tttacttctc cattaaaaaa aaaaaatctt ttttccattc tgttttggtt tttgggtttt    360
tgttgtcatt tcttcctaaa gcactgtttc ctcacatttg catctcccag cctttttaat    420
gtgatattcc atttaaactg ccttttaatt gtatgtgctg ccttggcaga acatgactga    480
tgtactcgcg ttaattaggg ctccagtcag cagcccgtgc cagctggaaa ctgagaaaca    540
agcgtaaatt attctgtcat caatcagctc gaaaatgttt gaatcactaa ttagtttgca    600
atttgggtga cagtttatct gacgcaggcg gtgtcagaaa cttcagatct tagatgaata    660
atttgccagg aacaagcaca gattccctgc ttttaaatac atgaaggttt atctgcatgt    720
tgaaaggtgg ctcagcagtc ttcattaact tccaactggg actatgtaaa tcaggaatca    780
gtgtgagcct cttcaggtca tggtggctta gcagatgata tttagaaaaa gaaagccttt    840
tttcttttct cttttttat taataattca taaactgata gacaaggttg tttaggcttt    900
aactgcttta agaaatcaca atggttttca aaaaaaaagc aatcaccccc ttttacatga    960
aaattagttg tgctgcatct tgctgtttaa ctgatttatt ctccttcacc atcacgtgac   1020
tggaatgtta aatgggtagt gattattagc ccttgtcctt tcaagaagga tcgttattgg   1080
ggttttgtta aatggcagac ttatgtttct gcttcaaggg aaaggtatgt agactcgggt   1140
```

gagggcagga aggaagaaca agcagtaaaa tagaaaagag aaatttttgt ctaaaagcaa 1200
cgtaaaaatc tattatttat tcagttaggg gtggtggaac ggccccttgt tatttgaatc 1260
aaggagctgg cctaagtagt aactcccagc attaaccatg g 1301

<210> SEQ ID NO 118
<211> LENGTH: 1557
<212> TYPE: DNA
<213> ORGANISM: Homo sapiens

<400> SEQUENCE: 118
ttctgcctca ctcattttcc taataggtta atcctcttcc cttattcatt aaagtcattg 60
ttttctgtta atacattttt tctacttggt tcttctattc attagcaagc actgcttctt 120
tctgactgtg ctcataggtc ataaagcaaa tgagaaattt tcttgagcct cgttcttaag 180
ggatgcagat tgcaactact gctgtgctat acgctggagg aaagaaatca cataaagcga 240
ttagaaagga gaaaaaaaat aagtgaaact accttctcat gtacttcagg gttttcctcc 300
cttctgagtt taatatgaat caaacaggtg tgcattcaaa gcatgcaagt gtgtcttcat 360
tggcttttaa tcatcagctt gaagaaaatt cagatctctc agaaagagag aaaagtaaac 420
agctgagcac tgtgactcat ttacacttca aatatacttt gaattggtta ttcctcaatt 480
aatcaaatag ctggtgtatc cctaaagtag tataaagtga cgcactgtgt gaaatcaatt 540
tttctttcca aaatcattaa atccagtagc ctgtgactac atccctgcta attctggtac 600
cagtcctttc ctcctccatt aactttggca cgcctaacag cctgtcaaga ataatttccc 660
aggacgtaaa taattcagaa attaaaaatt aataaataat aacagagaac tactgggaaa 720
taggctgggt caattagtgc gctctgcatt ctgtttcttc acagcagggg gaggcagcca 780
cattcgttac ttgaatcttc ctttcgattc tgcagtctga tttacagctc ttcattactg 840
gatccagtca gacgcaatta cctccatcac tatctcagtt cctaacttca aagaaacgaa 900
cgttttcttg tctgcttttt ttctccttga agcaggctca gcttgacatc cctggaattt 960
ctaccacgca gactaattaa taagtcttcg acttatcata ttcacttctc ttctttgatg 1020
tgctacctta gtcaatcatc ccatttaatt agaatttcaa tgataacttt acttatcttg 1080
tggctagatg taaattaaaa taatgggatt ttaattctct ttcgtatggg gttatgacat 1140
tttggaagaa aaagtttcaa cacaaacatg atattatgta ctttttactt ttcatgtggg 1200
ggtgggggag cattttgcaa aattattttc ttcttgctac aaaagagtat tgctgttgag 1260
caagcaataa tgaaaatgca ctggattttt ctatagcatc ttttcaccaa gctttcatag 1320
gaaaacaatt gtcttcattt gcataaataa ttggaacaag acacaggacg tggaacaaga 1380
cacaaaggca gtggctacgt tttgggaaaa aaaaaaaaaa aaggatctcc agaaagtcaa 1440
ggagttgaca cactaaccct tttaactctt ttgccctttt ctgtcaatcc atgctatgtt 1500
tccattttga taaattctat agtggttttt ctagagttcc ccaaaataac acaagga 1557

<210> SEQ ID NO 119
<211> LENGTH: 1639
<212> TYPE: DNA
<213> ORGANISM: Homo sapiens

<400> SEQUENCE: 119
catagccacc cctctgagat attcttccct ctgctgatgt catgtggtgt ggaaaccctc 60
ttctcgtggc tgaaaacaat cctaaagaaa gtcagcctca tctggggagg gggtgcagcg 120
gggggagaat gggggaatgt ccctggccag gaggccggag gtgccccagg aagctgtttc 180
ctctgaatag ttaaatggct gcctctcaac ttgcacaatg tcacattgaa tttgaaacag 240
ggaacttttt atattttttc cctgattgtg ctggcacctg gcagatgcct atttaccaca 300
ggcatcaata cacatagtaa tcaaaggaaa tcagaggcac agattagcaa cagctgcaag 360
tcattagtga cagacacggg aaagcacaat tctgcaccca actttgaaat aaccaatatg 420
agtatttcag agcacgaggg ttaccgcagg gcactcgcta acatgagagc agccaaacaa 480
tagctgggct tgtctctcca gagagcactc ttctcaaagg cagcaccaca cactccgtat 540
tataaaccaa tcaatcacat gatattggtc cactgaacgt tagccctttg cagagtccat 600
gtgctgatct gatcttctga ccaaaggttg ttgaactgaa aaataacctc tggctggtgg 660
aaaactttgt tatcgcctgt cataatttta gtggtgggag tttgagtgta tttctgatga 720
cttaattata tgattgacct agttggaaag gggcatatag aggggaaaac aagacattcc 780
cctttcgcat ttaatctcat ttttccccaa atttctattt gaaaatcagc tatgattgat 840
agccgttctc ttggtagtta catattttca ttggcaacac taaccttagc ctactccaaa 900
aaatactatt caatttttag cttttcccta atcaattcat tcagtgcctc agtggaatac 960
aagttggtca tttaaaaatt tctagctgtt gcctgatatg tcccaaaaca aatttagcca 1020
gcatgggttt ctattttaga ccatctctgg aaatgcagat ttactgtaca actgggtaat 1080
ggcttagaga taaacagaca cagtgagccg ctgtctgatt agcaggactg ggcgaaattt 1140
agcattatat atatactgca ataattggac cattgcacca taggatgtaa agtaaattgt 1200
tctcagtgcc atacgtgggc tcttcttctt ttacttgata ctaaggttgg attatttcat 1260
tctgttttag aaatttctcc tttttccctg ctctccctac tcaaaaatta tcttctgaag 1320
gtttttctaa aaattcttct aagtaagttg ttttggagat taggataaga agggagaaaa 1380
tgctgccttt tatctggtgc agagccagcc attaaatatc agctctttaa caacaagcaa 1440
aaagctatta ttttagaaga aagctgccag agaacatgga tcccataggg catctgccac 1500
atcataggca ttcagatgca tgttgtaata gtcatatatg ttgtttcttt ccactgtcag 1560
agtcaacaga ttattttata cttaactaaa taccatgatc tcttagttta gggagatttg 1620
atttcttcag gtcattttg 1639

<210> SEQ ID NO 120
<211> LENGTH: 1535
<212> TYPE: DNA
<213> ORGANISM: Homo sapiens

<400> SEQUENCE: 120
tccctcacag aactcaggac taaaccgggg gctaggaggc ctcacatctc ggcccactcc 60
gcggcagccc cgcgccagcc aggaagacgt tatccgtcca tcgccggaga ctgttcgtgt 120
attagcaatt cactgtcaaa cgctcaagag tttgccaaag cataatagat gctttacatt 180
ttatgcataa ctagttctga gaccagggct ataaaagttt tctattaaca tgtaagcact 240
aagacaagtt ttttttcact tgataaatat acataactcc ttgacaatga ggcccttgtg 300
ttgctaatgg ggcccttaat ggagagttat atttccagga ttatatcttt attcagttgc 360
aaatgatttt tgggggggagt tttaatgctc tgctccgtct atgaataata gtatcgtttg 420
aatgcagcgg acacctggtg ccggaggaca gtggggctct gcagtgacct ggcgacgctg 480
ccaagttcgc attttcccag cctttcctac ccgctccatt cagcatctaa tttcattctc 540
cctcagcaga atgctagaca cttgtaactt tattctccct ccgcaaaaac ttgctctctt 600

```
gtaaggaaaa aatcctggaa gaaaaaaatt tctcttatca atctcttctt atatagagtc    660
tagtaatttg aaggctggct aaagtttcag gaaaaacctt ccaattaaat actgtaaaaa    720
gataaaataa cagtggcctt gctgctgccc aatagcttta ttgaagcgct cttttgttga    780
tttattgtac gttagccacc gagccgtgca aagaacatta cgtttcagaa agagctattc    840
gtatgcggcc tgcatccact ccaaaaacaa tcaggcctgt attgcgtttt gcaaatttat    900
accaggatgt tggtttagag tgtttccctg aaaagttttt caagtaagtg tctgctttca    960
tgggcgagag tgattgaggc acacaaacaa acctttgttt caaaactcac agatgtatgg   1020
ccgggctgag ctttgttttc ccctttaaga agtattctca gatttgtgtt tggagcacaa   1080
cacaggattg tacaaaaaaa aaaaaatcag cttgaggatg aatgtctcgt ataatctgag   1140
gcttttccag attttcccag ggttaatttt tctaccctga actttgcgtg ttgggtaggt   1200
tagggttttt ttttttttct ttaatttatt tatttgtttg ttcgtttgtt tttgttttta   1260
aattcaggca tgccatgaaa aagaatcctg cctacttcag ctttgaatgt ggcttcagga   1320
aacttcattt caaagctatt agggagtttg caagctccat aaatatactt ttgttcaagt   1380
tgcaatctgc ccttctctct cgcgggcgcc cgagcatcgt gctgggacat ccggcagccc   1440
caggctgcgc gacgtggagc caagaggaca gccacctggg tcggggctga aggaaatcct   1500
aagtgacaaa atatttagac ttcaaggcag gcatc                                1535
```

<210> SEQ ID NO 121
<211> LENGTH: 2982
<212> TYPE: DNA
<213> ORGANISM: Homo sapiens

<400> SEQUENCE: 121

```
ggactcattc tgcttccaaa tttttacttt ttctttggtc aatgtgggaa ccctctgacc     60
agtcatgaaa agtaggactt gatggcccgt catatgaaaa gctattaaca tagccacagt    120
tggccctgaa atatgctttc aagaatttag aagatttgcc aacccctatt tgaatttttc    180
ttcagaaaag tgcactttta ttaacaccct cttccctact gtggatgaaa atggtcacaa    240
tattctcatg gggaaaaaaa agaacattct caagagcctc tgtagatgga gaaatagagt    300
ttctggccaa gaataaaaat ggggaagtct aaaatgttta gagcctctga ttaaaccttc    360
agtggtatat ttctctcaga caaagcattt gtcacaagta gcttgtctgc ttgagtatga    420
tttatgtggc tggactgaaa ttggctgaat aatttatgct atttattgtt ctggaaagtt    480
tcttttctta ataaataaat aaataatgct gtgttaagag aagaggaaaa tagtggtaaa    540
tgtcagtcac atgaggaggg aaaaagttat ttttccatgt tggaagctaa taaagtgtat    600
ctaagaggaa tggtccccac atagaagggc aggactctaa taggtgaata ttctcagcat    660
tttgaatgaa accaattggc taagagaagc tgtcaaatag gtgtgaaatg agctaaaatt    720
acgagcgata cactttcttt taaggtactt tgctttgttc cttacagtgc cttgcagcaa    780
aaaaaaattt taatttaaat actgaaaatg gaatgcagct atattgattt aaattcacta    840
agcaagtatt ggaatctatt tcctgtttcc tgcataagtg tggagtgtgt gtgagtctat    900
gtatgtgctc gcgtttgaat gctgtcagct ttcctactat ttatgagtga gtcacagttt    960
attagaacct accacaatgt atattagcat aaaacacata acttgaattg tcagtttata   1020
aaattttcag aatgtatgat tatagttctg ttcttactgt agatttttac atagctccaa   1080
tgatttatcc cacctgctga aacactgggc taatatgaaa ccttgcttgt tttttgttag   1140
```

```
ggtttgtttt tgtgtgttgg gttgggtttt aggggttttt tttctctttg gttaccactt   1200

tatcatataa attttattcc tgaaacctat gccaaagaca gagttataga caaaagaatg   1260

gatggatgag tgtgcagaaa tacatgtggc tcaattcagc tgaaactgtt ttatagataa   1320

ctcactgtaa gctatgacta aaaatatttg aaatgtttac aggctgcata atatatatgt   1380

ttgacatatt aaaggagact tctatcagct gctcagtaac cattccagaa aaacgcctta   1440

aaagaactca agcaaaatca cagcccctca tctgcagtgc tgtttctaat ttgaaggcaa   1500

attcatctct gacatacagc agattctgtg caggtggaag caagcccctc tctgctcctc   1560

tccctgccag tcaaattatg tcatcagtga aggatcactg gtttttaatg atacggtggc   1620

ctccatactg agaagcagtc ctagcagagc agtatgcata gccaataaaa tggctgtcac   1680

caaattacaa ttgacactta acatcactaa atctgcagtg taattccttg tgacagttgt   1740

gtaggtatat tagaagaaaa taatttactt caaacccagc atgttagaca cattttcctg   1800

agcgtaattc atgtcacatt tacagtagcc aaagcaagca gtctcgaggc aaccttaatg   1860

caggaagaga tcatagatac taacatgttc attgaagtat gattatttat gcatgcaata   1920

aacaaagcta gagcagttgt tcattgtagg ttttaattgt tattgggggt tttaattgtt   1980

attgggtttt aaatgaatat tagcctcttt tgctgtaggg aataagaaaa actattaaaa   2040

aaaacaaagc cacattttat acggaaaaca ggcatcagct aaaaagtccg tttttcagta   2100

ttaaatggac attcatgtgg ccctcactcc taccacagct ccatattata tttggacttg   2160

aaattctgtg cccattacca catgacaaat gtatacacat ccatcttcca aaacgcaagt   2220

aaactaaaaa caagccagca actgtatttc tcttctctca gagtattaac attggggaac   2280

aaaggtttgt gaggcagact cagtttcttc tggaatgcta ttttgataca ttcatctgga   2340

gcaggtctgc agaaagaccc ttccctggcc ttataagcat atataaatat gtgacagagt   2400

taaaggtctc cactcttcag aatgaagtgg tttgaatgtc tggcgaaatg ggactgcaaa   2460

aaattcattc caactttgtc tctaggcaat tcacctttgg cccagtgatg atatgagtct   2520

ttctgctgat ggaggagata taataagtca gctcaggcag tctttagaag gcaggggcct   2580

atttgttagc agaatgaggc aggtgtactc ttctatggga gattagctca tcccagcacg   2640

ataattacct cacaggaagc cctcaaggtt acacatcaaa tgcaggagct gcagatccag   2700

tcctggaaat gggcatgcct gtatcgttaa gtagtcttac tttagaaact ccaaatttaa   2760

aaacacaaat cagtgagtga taatttccct gtcctttcat caagacatta acacgtctcc   2820

agcaagtgca agctcactga agaacaatag cctggattac agctcagctt cgaggtgagg   2880

gaattaacct ctgtctgtct gtcttagttg attttcttat caaagtgagg aactgcaaac   2940

aagaagtaag agaacccaca tttgactggc tgaggtcctt ta                      2982
```

<210> SEQ ID NO 122
<211> LENGTH: 1408
<212> TYPE: DNA
<213> ORGANISM: Homo sapiens

<400> SEQUENCE: 122

```
ggaggaatga gttaaggtgg aggaatgggg caaggtcacg cgccccggca ctggagggcc     60

aaccccggca cacagcggac tggccgggac tagggcagcg ccgggctatg gacgcggacg    120

ccggcgaagc gcaccccggg acgtccgcat attctttccc ccaaaactag tgcgctccag    180

ccggcgcctt tcctcggaac ctaaggaagg ggtatatttc gttgctttct ttaaacctca    240

gcacgatcac agtggctccg agccgcgggc ggctgaccgc gggcctcgcg ggctactcct    300
```

ggtaggggcc tgcgcgagcc taaggtgtgt ccccgcctgg gttagcgctg cgctctgcac 360
tgtttctttt cctcttaaag cttctttctc actcactctc tccctccttc tctctctcat 420
tttttcccca tttctctcgt tcttttattc agctttctct ctttctctcc cttttgtgaa 480
tgggccgcgg tgtctttgtt ctgtagagaa gcgcccgtgt cgctgacttt tgtgaaccag 540
agaaggatct tgtaaaacct ccttttctcc ttcgtacgcc cccactccca cccctcctcc 600
cctgcctctt tgattagatg ttccctcatc gtcaaaaaaa aaatgtaatt tcgttggtct 660
ggcggccact ttctttgaac attagctcgc tttcagctcc aacttcaatt agaaggagtt 720
gattttgaga gatcaacaaa agaaccgacc aaagccttat taaaggtcct aagaagatct 780
cccgggtcct ttgagaagca gttaaggaaa cagtgtgccc tccatcatat tctgttaccg 840
tattttattc ggactccaaa ggaaagtgtc gcttgggga gggggaagca ctttgatgag 900
cggcggccgc ggcccctttt cactcagcgg gctcccccctt cgttctcctc ctcctcaccc 960
agcgcccggt ccgctctcgg cgcccgaccc cgcagcccgg gcagcgcgag tgctccccac 1020
tgcgatgcgc ctggaggctc cttgacttgc cctcacactt aatcctgtgc aaactttta 1080 ccccgcctgt cggggtgggg gagtgggga gattagaaac aaggggtaga aattcctcga 1140
aagggaataa agtgcctaat tttcaggagg aggtgccatt taaaagattc gcctagctta 1200
gagttggaac gaaaactctt ttttgcactt ttaaaagtcc acccaggtag acgtgtttgg 1260
gaagtttttt cgggtgggaa atgggcttcg cccgtacgaa caatccgggg aaatcgcctc 1320
aaggaggatc cttacgcagc atgtggaaaa aagttgaggg caggggtctg tggccacatt 1380
ttccatcaaa aagtccctgt tagaggca 1408

<210> SEQ ID NO 123
<211> LENGTH: 2672
<212> TYPE: DNA
<213> ORGANISM: Homo sapiens

<400> SEQUENCE: 123
ttttggagta tgaagaaata aaggataaaa gattcttttc tgtgttttcc tgtttcgtta 60
ctacctggtc atgctcctag gccactgtcc atcagtactg tagagttagc ctgttgacag 120
tcacatgtca tgtgttgagt gcgtagccaa gggattttcg tagaatgcct tttttgtctt 180
tacatttttc tgagatattt tatccaaacc aaggttttct ttagcaggga tggtgatcat 240
ttttatttta tttattttt tgttggagaa tggtgtaaag gtgggtaatt ttgagagaga 300
ggaaatagaa tggtagtgag ttgagggtag gaaaatacat ctgcaacttt tattgttttt 360
taaatgagca tcttgatagg gaagatagaa tggaattgtc aaaaattgtt aatgtgtttg 420
acaaagtgtg gctgtcagta tgatcttttt gttacatttt gacatgaaca attgtccttt 480
tattggggct gttaatgcta ttttagaata tcatgagcat ctgaaggcaa tagtttagca 540
gtgtccataa agcatcaaat accattataa tatctagtaa ccctaacagc aatatttcag 600
aatccctgcc tgtttaaatg ggctatctgt gaatgtactt gctcagggat gcatgaccca 660
catcacctat aaatttgatt ggaagctaac agtactggcg tagcctgatg gatagcagat 720
tagagccctg attaaccatg tgattcaaag actgggaata tattgtctaa gcaagattca 780
tcagatgcaa tcagaatttc aagtggtcag atgaaattca aatgtgtgtt gtggcttttc 840
ctcccctatt gcttttcctc ctaggttgcc ttttttttcct tctttcccca aagctgaaaa 900
atacttcttt gatgaatctg ctccttaccc taaagctgtc tgtctgttat tcatcagaaa 960

-continued

```
gcaggtcgca gttcagtgag cagaagaaaa gattttaata gaagctgtgc caagggctgt   1020

aatgcatcat tttagggccc taattacatt acaatgacaa atatcaatgg tgacaacagc   1080

aataacctac atcctttaat ggctgtgctg gaaaaggagt ttgggcccca cgccattata   1140

ttagactcag tttcaaaaca taggccatta gaagtgtgtg tccacagtgt tattggctga   1200

tcgctaaagc ccagtggaaa ggcctgtaaa taaatgatgc ctccctaaag ctgggtcctg   1260

tgggacaaaa gaggcgaaat tagatgacca tgggagcagc agtgtttccg aggcaacttt   1320

agatttcaaa gtgaagaatg acctgcttaa ttttatgaaa tcacacacac accccacccc   1380

cccactgcca attagcctga ccatgaaaat ccattggcat gacaacttaa agaaattaag   1440

aagtctttta aacaaaagga gatctttaac ggaagtttgg aaggtttctg ccctcccgtt   1500

tctgttgtgt gtgtgttaac ctatgtgatt gaataaaaag gctcttctcc tttttacatt   1560

tatttttaag aaaatgtaga atttttttaa aaaatagttg ctcagactta atacagccta   1620

ggtccaaaat tttatttcac cagatgaata agtttcctta gagtcgtttt tattgcctag   1680

attatgtagg cgaactaaag aactcagttt tcttatgtgc ccacacattt ttcagccctc   1740

ctagcaaggg actattttat ttatgtaaac aacataatga cgaaaatatg cttggcagat   1800

ggttctaagc attagaatca tcagtttggt ctgccccaaa gtgtctcatt atcttttatt   1860

ctctccccct ccacctctcc ctgcaaaaag cttaacaacc aaatgcattt gagatgctgt   1920

actttcagcc tggtgaatgc tactctattt ttattgctca ccctggaatt tcaccccata   1980

accactgtgg tatgttcgtc caggtggaga gtggtttggt gattcccatt gcagctcttc   2040

atggtggctt aagcattctt aaaggatggc taaatgctcc atggggccag tgcagtaaat   2100

taaatcaggt cagcacagtt gggtccttat tcactgcagc ttattggtgc tgggtttttg   2160

tccatactgt taggaatgca ggctggaatg gaaagcttgg atttgaaact tcatggtgaa   2220

tttgtgtttt cttttggctg gtaaagtttt taaggtgctg gcatttaaaa gattgcatag   2280

ctacacagtt agaagggttg ctgatgaaag aaggaagcct agattgcaca agtagagtgt   2340

cactgtcatt ctggtaatga cttggcaaga aaaggcattt tggcctcac ataaaatgag    2400

gaactgaccc tggatggaat ttaagaatgt cttagggata gtaattgctt tacattttct   2460

gcctttcaat tcttcttagc tctctttcct ccattccatc attaaaatat aaactatttt   2520

gtatgtacgt gtattaaaaa aaactgtgta tttatacatc acaaaatata caaggcacca   2580

tctgaaaaat acaaattaag ataaacattg gtaaaactgt gagtaacttt ttaaagaaaa   2640

catgtagtgg tggtttttct tttaacttac tg                                 2672
```

<210> SEQ ID NO 124
<211> LENGTH: 1358
<212> TYPE: DNA
<213> ORGANISM: Homo sapiens

<400> SEQUENCE: 124

```
agtgggtgac tttgccagtt agcagtgttc tgctgctgcc tctgtgcctg aggccactgc     60

ctgagccttc ctcatggcac agcagaatcc atccagcttg aggtccactt tgaccttctg    120

gtttttttca gccaaatgca ttcatgttac ttgggaaata caccatctac acccaactct    180

gcttcccttc cacctctact ttccactcat ttctcagccc ctcaggtcat ctctgctcct    240

ctcccgaatt atttgtgctt tcttctttcc cttcttcacc tttgctggct cccaccctga    300

gatactttcc acctcagacc agggcagaag ggttgggagc gggcatggtg tgggcccagc    360

cagctgccgt tcatccaggg acagagctgc catctgccaa gctgatggtc cttgctggcc    420
```

```
ctccccgtgt ccatcccctc ccaaggcccg tgttgtgggc ccgtcctttt gtttacgaag    480
cccctgccag accccttaaa ttgccgttaa tgtttcagcg taacgaatta gtctctcatc    540
acgaatcagg cttcgaaatg agggaaaaaa gccccggtga ggccatcctc ggaaattggg    600
gtcattctca tttgcaaagc ggaggatcgg agccccgtaa tgcgggcaaa tttattccga    660
ggcaggagcc ccggcgtgat taggcccttt gtaattatcg ctccaagaga ttccactcca    720
gccgcccgcc tccctcgtgg attagcaagc gagtcggaaa aatacacagg atttaattag    780
aggcaaatta aaattggtaa tgaaatcggg ccagttgcaa gtggcaagag ttggaaggga    840
gagagggaga gggatctcca ggggcacggg ctgcctgccc tacccgcttt cttccccgtt    900
tagaaatgta aagaggagac aaggatgggg acgaggcggg ggaggctaag ggaggacagg    960
taacagggtc cagggatgca ggcagggatg gtgataactg ggagctggcc gtgggggcag   1020
cacagctgag agaggagggt gcagggacag gactgaggga cacgatgagg tggggcagac   1080
tagggcccta gtccgggctc ccatggtggt gaggggggaa ttgggccaag caccccgccc   1140
tcgcccaagc gtcctacaaa ccagatgacc tcaattcttg aagttatcct gccaggagga   1200
ggtgggacag acaaggtgac ttatcttctt tctctcctct ttctgcctct gggttgtcaa   1260
cccacactct cctctctccc tgtttatttc aacaagtatg tatgaggcct ttactgtata   1320
ccttgtgctc tcaaaatata agctgcctgt tctgagcc                           1358
```

<210> SEQ ID NO 125
<211> LENGTH: 1774
<212> TYPE: DNA
<213> ORGANISM: Homo sapiens

<400> SEQUENCE: 125

```
aggtgaccac atttcttcct aatattctga ataatagttc tataaacctg atatctatgc     60
ccagatctag tttcataaca ctggaattca aacttagagc tgaaatttcc atgaagttaa    120
ttctatcagc attcagcctc ccttagctgt ttcaggaatt catcttcgag aaactgtgct    180
tttttgtgtg tatttgtctt attaaatccg tgaaactaaa aatgcttgaa caaagtaaaa    240
cattaacacc aactttcaca gtaaattatt ttgtgtgaat gaaagctttt taagagtgta    300
agtcttggca taattaccca aaagtagttt agtaaatgcc atgaaacatt acatctgcat    360
atcaaaaatg cattctgtat gctacaggaa aattgtagta cggaggcaat tttctaatat    420
ttacatattt atagcaagtg cctgtcacag gaaagttaag ctcacctgta aaactttcat    480
gttacgtaac atgaagaacg tctcatgctt gggtgttcta ataaccatga tattatttta    540
acaattacac tatttaatac cttggattag ttcctctgat agtgctatta gctgtcacta    600
tactcaataa taggtgactt catctttgtt atgacatgat ctttcctact gtttgttgac    660
ctttcaatac aagggggagg ggacgctccc agccccccaa acctttaagc agctactgta    720
aagctgcggt ttaattctca gctggaatgt ttagaaaccc ttggtgctaa atacctcagt    780
ggactgctta aacaccaaca acagccttat ggggccttac ccgaccttaa acacatcttt    840
ttttgttgag aatattgcat tctgccacaa ttctgtgggc taaccctggg ctcacattaa    900
atataccagc ttcattgaag cttactgaat tgagttgagt tgttctttgt tttattctct    960
ctctgcttca ccccccactg ggactgggca gcctttcttc cagtggagcg tgctttaaag   1020
taacccaaag aagaggaggg ggaacggggg agaaaaacca aaaggtgcag ctaaggcccg   1080
taattagtct tgatcctcca agtctaaaat attttaacgc caggtttctg attgcagtat   1140
```

-continued gggcaaagtg gatttgggaa tgcagaaaag taattaggtc tgtgcattga agtgtggaga 1200
gcatttaaaa gtgaatgggt ggttactaca ttcttggcag gctgtttttt atcttttcat 1260
gctctgctgt tgttagaggt gatgggttta ttgcagtttt tgcactctgg aggtggctat 1320
gtttttctta acctagcctt ttgctctcca tctcaaaaat gaatcctcgt ggtgtaagga 1380
agaacaagcg aaatttttaa aaaataaaaa caaggcacat tgaccgaata ttatgcggtg 1440
aagcagaata agttgggaat aaacctcaat gccgcaacag gtcacttata aagattctgg 1500
gtttaattaa tgactcactg agcacaggac taacgggaga caatggtcac cccaaggaga 1560
aggaaaacaa aacatggtat tctctaacca tgttcacaga gccatccaaa ctatctgggg 1620
ggaaagctga catcattatg tcacttctgg gtcctggtat agaagataca aactataaat 1680
gtccgagttg tcaaaaatgc atgcttttga ttgcttcagt ctatagaatt gctgcaattt 1740
gctaagatca cgtctcttca gcccagacat tcat 1774

<210> SEQ ID NO 126
<211> LENGTH: 1358
<212> TYPE: DNA
<213> ORGANISM: Homo sapiens

<400> SEQUENCE: 126
ctatcaaaat tccaaagtct ctacctaggc atcaatattc ttacaaatct atgaattttc 60
tatcacacat tttttttcc actaaaggac actattttgc taatgcaaga aagccagtaa 120
atagaactga gcccaaactc tctaatacca agggctatgg tgaggctgat ccaggacttg 180
gtaagtagta tatcttattt tatttaaaaa aatcgatatt taatagtctg ttagctgagc 240
caaaaacaca caggctgcag aagaaacact tgtagattgc aaagtgatat ttaaagaaaa 300
atgcagactt gataagcatt tccatgtttc gtatatttgg ttttcaagaa aagatgttga 360
ataggccatt tgatatgtta gctgaatgca gctgtttaga tatttgtttg gtctactatt 420
gaatttttca ttaaaaatat gtggttaaca gcagccaacc tgatttgcat gtgtgtgttc 480
ctgatttgtt caccgcaatg cctcccgtct cctacatctt aatcacaccc aggcgcccgc 540
cccattacat taccagaagg gaagtgatgg acatcctttg actctcttca tgaccccctg 600
ataatcctgt ttcacacata ggctccctgc tgtaggaaac acaaaagctg ccactgtagt 660
tttttacttc cagtcgatat tctgacagac ttgatctagc aaattagtat gctgtggtag 720
gggcacgaca aaagaccctt ttgacacact ctgaatcaat accaaggccg acagagagcc 780
atttcaccgt agttctgtta tttttcccct tttgatgacc ctttgctttt tttccccagc 840
ttatatgacc ttgtcagatt taaaaatata atgttagaaa agtcatcctt gcacacacat 900
gtgcacacaa agaccatgta ggatatacta aaattcctaa taacaatgta aaagagaaag 960
gcagctggtg acgaaattca agtaccttta aaaaaatgtt tcttctttct accaaaaaga 1020
aagggaaaaa tagaaaataa tcagacatct tgaatagctg tgtatattag agaatatagt 1080
ctaattaggc caggttagtt ttcattttat gttatactta gttactggtt gccttcaaat 1140
tctaaaactt gttaaaatga aacataatgt aatctcatgg atgttttata ttttaagctg 1200
ttcattagtt atattaatca aggctcctga gtttaaaata gagagcattt tgttaaatat 1260
ttgaagttaa aatcattaga aagtaaactt caaataacta tggagaacaa aataaagtat 1320
taacaaaaat ataaggtctt tccttattaa cctttgcc 1358

<210> SEQ ID NO 127
<211> LENGTH: 2573

<212> TYPE: DNA
<213> ORGANISM: Homo sapiens

<400> SEQUENCE: 127
aaaagcccaa actattcttc aagttaactt tgatgaaata tatttttgcc aactttatct 60
cacagtcttg ttggtgacag gtcgagcctt ctcccactca tctaagatat tccatgaaca 120
tttgtgataa ccctgcagaa ataagtccac atctgtgccg gcatccgcac ctccctgccc 180
ccagcccagt tagatttaat gaggaaagtg tactttggga aacaaatacg gtggatctgc 240
ccaaattttg actaagactc ttccctcatc tataatccat tctggagaca gacagtgaat 300
tcacatcaat aaatgctttc gggagttgga aagggtttgc ttaagaaggt tcataaagat 360
aaaggtaatc tgatcactaa aaccatttaa agtttttaga ttttttttt cttcttaagg 420 gggaattccc tttagtttga ttgcaagata agagttttgt tgttaactaa gataaaatat 480
agtgctgaat aatctctgaa attaaaaact gaagtgcatg gtgcacagaa tagagaaaat 540
taaatagctt agacaacaat ggataaagag aaaagagttt tcatgaaaat tagcttagta 600
aaggtaaatt gcatttgaat cttaacttca gatctgggtg ctctgctatt tggcatatgt 660
tgaattgata atgcctgtgt gttaaagaat tctgattgtt tcttttgcct ctctcacagc 720
ttataaaaat gcaagcagac ccatctaatg aatattaata ggagtgatgt ctagataaca 780
cataaacccc gggatctgtg gactttggat ggagtagtca gagaggattt ctgtggcttt 840
atttaatacc aaatttacat acttttaaag aataaacatc atcttaatat tttaatatca 900
atattccaga gtggagattt tagtcaaata aaaagcttaa ttttgtcttc ccaaacatta 960
tgttcaccag ggtctgcatt ttaagagaca ggaaactgtt agctaaaaaa gaaattaact 1020
taatccccct tcattaagtt ccagtctttt tctgttactt agagacaagt aataattata 1080
cccgtagcaa tgcaaagcat gttttacact tttgttatac aaaagaactg cggttgttaa 1140
ggtgacagca aaagaaaatg agaacattga taaatactga tttttttttc ttaaatcttc 1200
tctgactctt gaaaataaat ttcactcagg tgtctgagag gccttttaat tcattaactg 1260
caaaaatcta cacatatgat tttagaaaat gtcaatcaac tagctaaaca atattttccc 1320
agctaaggtt ataaacagca gctaagtggg tggaaaatgt ctaaaacgac tatacatacc 1380
agttctttta taatgcataa aaagtgggca ttttgttttc aagctggtat ctttgggatg 1440
gaacttttag caagcacaca gtacatctca gcagtgtata ttatttaaag tgcattctct 1500
ctctctctct ctggcattgt gaagactttt taaattttag ctttacaaag gggggaaatc 1560
attaaaatgt ggtttgtacc attacattcc attatttgtc atctttatgg ctattctata 1620
gttttcattg acctttaatg gtaagcttgg tcaggagagg tgagcaggaa tgttcacata 1680
cttggctgag ggtgctgctt gagagtgtct gttagctggg cttcaatcca cgtccctgta 1740
gattttaatg tccctacaga ctgctggcag cctgcttcca gctgtggcag gcatgatgca 1800
gtgaattgct tttgaatgtt ctttactcaa ataggcagta attacaagct taaagaggtt 1860
tagtggtcca gtaaactaca taatcacccc tgaattagcc tgggctcatc agttgcagtc 1920
cagcaagctc cagtctgctg tttgtatgcc gtcttgatca catagcaacc tgatcagcag 1980
gtgtggagca gccagagtcc cccataaaca caactgtcta ctggggacaa tgatctctaa 2040
tgagatgagg ctacatcatc actgtaattt aagtgggaaa attagcacta gagaatgggt 2100
accagttcca ggggtcttta gtcatattgg gagcagcacg aattctccat ctcattctcc 2160
ctgtctctat ctttttctct ctcaaaaata tctcctcacc aaatgtacca ttttgcttct 2220

-continued

```
aacttacgga tactttattc tttagacaag gatttttcct gaataattaa tgctagacag   2280
ggcatctgta aaggcaataa tgattgctgt caacagactc attccaaaat ggcgttgtag   2340
tatttcatct tccttgtctt tctacttaat ggtttcaaaa tcctttctct ttgattttta   2400
aagtggaaaa gtgttcttca ggctggtgtt aggtctcctt ttagctgacg tgctctctga   2460
aattgtagag atgggctata catagtttga aaaagatcct tactttattg gagtttattg   2520
tataaatcag tcatgaactt tcttttcaga aaggtggtcc agtatagtgt gcc          2573
```

<210> SEQ ID NO 128
<211> LENGTH: 1285
<212> TYPE: DNA
<213> ORGANISM: Homo sapiens

<400> SEQUENCE: 128

```
cacctcaagt ctgctctgtc tgcgtgggtc ttctttaaaa gtaaagaaac aatcactttc     60
ctttattgaa gtgtgaagct tattgaagac aaagtttgtt ttttgaaata gtggctgtct    120
tttgattcat taaaagtggt tgataagtta aaccccttcc catttcagtc ccaaagattt    180
ttttaaactt tcgtaagcat taaatgtgag tggttttctg aaggaaatgt gacctgtata    240
accagttctc tttccctgat tttttaaggt ccattagaag tgagtaattc tgtgcatctg    300
taactttatg ccagtatttt taagaatttc aattcatttt ttcccctgcc ggcagtgaat    360
tttaaaagtc ttaaacatgc ccaaacatct caggggggtt aaagaaaatt ataatagtaa    420
ctagtttctc ccccctccct aaaaaaaaat agagcacact actgaaatta tttaaattga    480
ctgaggcttt taagcaagta aacacatttt aactaggttt tttcgcaatc cctccattca    540
tgccaactat agaaattagc cttcactctt ccttcactta cacatggata cacacacttg    600
catggacaca agaaaaattt cttttctcct gtcagcattc ctccccaaca atggttagat    660
tagtggcatg aaggcagccg cagagaaagg acattcaggc cagaaggctc cccacaggca    720
cagctggtag gggttaatgg cggctgaacc tcccagccag ggccttttct ctattgtgtg    780
ttccactcct gggaaggagg gacacttgtg acagcctctg ggtgcagcg gatcagaggt     840
agagcaactg ggtcacagag gactgttcca ggggaaggcg agtttaggaa aaacgcactc    900
tgaaatccaa atggtggtgt ttctaactgt gcacaactgc tgtgggaaaa tgcaaagcgt    960
ttagcaatat ggcttataag tttctaattc acatcttcat ataggagcct tacaggaaca   1020
attgggcagg gactttgaat cattcctatt ggaaagtgat tgaaatctga gtgaaaacta   1080
cacgtttggc taatgtatgt tattaaagtt tgtgtgctaa tgtctaggcg gtctattttc   1140
cacatggcat aaagactaga gtgcagacac aatggtcaga gggggagaag ctgggggcat   1200
cttgataaat aggaggttga aatttaagta gaaattgatt attatgcata catgtccaga   1260
taaagtaggt gtgctttaac acgca                                         1285
```

<210> SEQ ID NO 129
<211> LENGTH: 2282
<212> TYPE: DNA
<213> ORGANISM: Homo sapiens

<400> SEQUENCE: 129

```
aaccacacag ctggtttcca agcagatagt gaaaggacac aaatatacca tctaaaaggt     60
actgtctgga atcctagaat ttgaagacaa taagacccaa caactctaac tgggttaaga    120
acactttcca aagtcctcta gacagttttg aaactagatc tatttcaatt caatgaacat    180
gagctctttg gggaatgatt tctcataagg gaagaacatg atctttttag gagctggata    240
```

-continued

```
tggcattgag tggtttccaa aaagcagtca acatacaagg actgggtgca gggacaatat    300
tcagatggtg gtccaggagc tgggaggggt gttgggtttc agaagagaag gcagagtggc    360
atgaaggctg gaggagggaa gatggcagca gattggggag agcatggcag gcagcacagg    420
tggatggaga gggcatcttg atctcctagg agggaatatt tgggtgtcca tagcaactgc    480
ccaattaagg gagtctagaa aacaggttct gatgcctggg gcccaggaat gaggaaaata    540
aagacaaagt gctgcttttt aaaagttaac atgtgttttc accatgtaca gctgggttct    600
gcctccaatg gcgccctttc ctcttgcttt atttttactc tcaggaaacc gtattctcct    660
ctttctactt ctcactgcat atgactctat tttttttctc tttatgggag ggagaacgaa    720
cacacacaca cacacacaca cacacacaca cacacacaca ggcacacaca cacacacttg    780
ccagatcact tacccaaacc ttaccctggg gagccagcca tctcatttct gtaaaaggca    840
caaacctcag accattgtcc ttatacaaga tacacattca acatgctggg tgccctcgac    900
agctacagat ggtttgggat ccaccagcca ggaggtaaga agtctgcgtc aggtccccca    960
ttgaagtgtt cagatgggtc tagggcctga gcacagagag ttaaatcata aattagccat   1020
gagttaatac gtgaggcccg gatcactctg ccttgccgtc aatgcttctc gtccacaagg   1080
ctccctcccc cttcctcccc acaccccccca cccttttgag gtgacagaat aagaaattaa  1140
acacttgtgg gttcattcga aagagtgaat gaaattgaat aagctctcag tacttgaggc   1200
gcacagcgag cgcctgaatg gggcaaacct cctaagttga atggagtgtc ttttgggacc   1260
aatttgtctc ttttcactct ttattcttcc ctttttgctg acagatgtac aaaggcggaa   1320
ctgcgccgtg cagcttatcc gcatgcaccc acagcagctg tcacttttgt cgagcaagtt   1380
aatcaagcaa atgccaccat atcccacttt ctataaggaa caacatgtta tagacagtag   1440
tcttgctaga aagagacttt attttaactt tgattggctt cgttccccca cccctcctga   1500
cgcttccccc ttttcccccc aaaggagggg gaaggggggga ctttgcccaa gccaaggatt  1560
tggctatgac aatgtcagat ttcataataa tattgtgtgt gaggctggag acgcatttgg   1620
agttctttcc tagggatgga gggatgcccc gggtctgggt ttttttggag tgtgctattg   1680
tttgtgctgg actgttaggc tgcatgtctc aagttataaa aagaaaagcc gagggcagaa   1740
aatagtatta cgccacgaat gtcttggatt aattttattc ttttttcctt tgtaaagcag   1800
gttgtgttat ttacatattt cttttgataa gcctccttgc ctggctaagc ttacaaagac   1860
tgtgctaaat acataatagc atttctttgt gcatcttgtc gttagcgagt tctttaagtt   1920
gaatgcccaa atttatttct aatgtgcacc aacaaatgca agcaggcctc catttctcta   1980
attctgtgta agccaagtgg ggagccttta caagaattcc ctcacgtcca catccactta   2040
cccttctgcc tcagttacca ctatttgatg gtgttcagaa accacaggca agagtgagct   2100
tcattaaacg gtacgcagtg ctgacctcag ccactgcccc tgagccccca acctgaatgc   2160
caaaaccaga catattttga ataaacaaac tctttagaaa caatgcatat aggccacttt   2220
ccaatggcca agggatttgc cactttcaag agttggctaa cagctgacga tctatcggga   2280
aa                                                                  2282
```

<210> SEQ ID NO 130
<211> LENGTH: 2638
<212> TYPE: DNA
<213> ORGANISM: Homo sapiens

<400> SEQUENCE: 130

```
cagcaaccat tgtttaggag agtaataatc aagaggtgtc atttgcatac attgttgtta      60
tagctatcat tgcattttgt ggctgaatga cttagctgat ctatgttaaa tgaggccttc     120
ttcaattcct tttacatttt gtttctagca cttagtaggt gcaacgtttc tttttatcct     180
cttagagaaa gaaaattatg aaacaaaata tgtgacttga ctggaaagaa tacagagcag     240
aaatttggag agaggtcaaa ataaaagatt gtgactttat cacataatct tgggaaggcc     300
tactgtctat catttggtgg tgttttatgg tcttaaaccc tctggaccaa gttccgcaca     360
gctgcacgaa tttcatatgt gatagaacat tttttccatt cagtgtgaaa tgttccttcc     420
taaaaaacgt acaccagact cgcttaattt agtctgttaa aagaaatgca catgaaaaag     480
gacaaaaggc tctttaatct ctgcaagctg tttgtttttc ttcaagattc ctgtctattt     540
gggtttgaaa agtcatgttt attgaggaga tgattctgag gtgtgacatt aaaataatat     600
atgatttttg gactggtggc cacgcttctg cttaatttgc agaactactt tttatgcctg     660
tcaaaacaca gcgttaatct atccttattt acaattaatc tcaataaaat taatcttaac     720
tatgctttat tcagtggctt aaaatatcta attatattca attaactgct gtcatagtaa     780
ttaatattgc ttaattgact ctgcatatat ttatgtaaag ctcattaggt gctgctgact     840
ccttttccct ttcctacttg ctatttttgc tgttgtcaaa ccatgttcat ctcccaaggt     900
tcgacaatgt caatgagaac aaattctttc ttaacatttt cttgaaatga atgttcctgc     960
cttcctttga gaagatactc gttatgagtc tttaaagact aatccatctc cctctcttca    1020
ttttccttat ccctggtctc tagcactctc acaaaatatg ttctgtcatt gttgctagaa    1080
atatgagaag ccaggttaag ctttgtgttt ataaatgagg agcctttctg tgactgccta    1140
agggctgtac ccacagggag agggtttccc ccccttctaa gaccactcta agggttaaag    1200
acttggccaa ggttcaaact gagaagcgcc cagggaaagt gcatgtgaat atgtacaagt    1260
ttcatgtaat tagtgcttaa ttatattaac atatgcaaat tgtcaactta ggagcttgtt    1320
gagctggcaa agatcagcta ggcacaattg cagtattgtt ctgaaacaat aatggatttc    1380
aagttggatt gtggaaacac ataactagct atctaattta actcataccg tggtgaaatt    1440
tcattagtct ccatggagac tggtttaatt gtgctgacta atgttctggg ctgcagaatg    1500
tcctaaaaag aaagcgttgt ttgcctaatc caccttacaa tgacacttgt ttgtacatgt    1560
ttcccttgtg tgagaatttg catatgcaaa taaatagttt ctctgcccca tttgtcatgg    1620
ctgttcatta cccatgaaga ggacattgtt actaggctgt tactgagtct cccaagacgg    1680
gatagtgtca accagtccag ctacattctt tcataatttg tttctgatta atagaccaga    1740
gtgagtctca ttctttttgg gcatctgtaa aaggaaggtc acttctgtca cagaaaagag    1800
tttctgcagt aactgaagga ctttttcttc ttcttattct ccctttttcca cccattggtt   1860
aacataatca tatttaaaat aatggattct tgttctaaga atgcctctac taataatctc    1920
tggtttccta aagcaaaaag ataggaaaag aaaagagatt ctgttattgg aatattaatc    1980
ctgtttttga cagaaaggta aactgatata attgcttttc agttgaagga atgggggttt    2040
atacaagtgt gaaagcatcg gaaaaggatt agcatttttt tgcataatga aaagctctgt    2100
tgaatagggt cctgaatggc tgactgaatg actaagatga aaggaagatg aaaatgcagg    2160
cttctctttc tttatgtcta tgctccgctc tctctaaagt tatgtttgtc caagacttga    2220
gaaaacaagc aggggctcag atttcagcaa ctttataaga tgctgtgttt tcatcatcat    2280
tgggacgtaa tgtgtatgac aatagtgcag ctagaagatg atcaacagag gtttgtatat    2340
agaagagttt cagaaacatg ccaggctagc caaatattga ctattgggta tcaggaattc    2400
```

ccagcacttt gctggcaaaa acaattattt tagaagagcc aatagtatgg tgtggatatt 2460
taattcagtt aatgatggaa tataaggtgc ctgttttttt ccccataggc tataaataac 2520
tatctcgatt ggtgaaacac ttcacttggg aaagagttgt gtaatctgac ttttggcaat 2580
gttaagtgtt ttaagtggtc tatcagcttt tgtggctggg aagggagaga agagggta 2638

<210> SEQ ID NO 131
<211> LENGTH: 2039
<212> TYPE: DNA
<213> ORGANISM: Homo sapiens

<400> SEQUENCE: 131
aaattctgtt atgcaattct cacataagaa ttattagatg tattgcaaat gtcatacaat 60
aaactgaata taaacaaaac ataaaattat gatgtttatc tttattttca gattactgat 120
gcttctaaaa tgtattaata acattaaaat taaaagttaa atatcctgat agttaatata 180
agtgcaattt tgtaaaattc cacttttgtg caacacacag ctaactttta atattcattt 240
ctcattttct tatttttcta tattaatatc attgctaaag tacaacacaa atgctcaaat 300
ttgtttttaa aattagctga tgagctatat tttacagtaa ataatgtgtg attaaatttt 360
aagttatata agaatccact cactaatatc aaaatgtgtt tatggcctgg atactataat 420
ttactttact tcttgttaat tcgaataata aaatactcga aacatggtct tgaaagtttt 480
aggtagatac taatgtaaaa ctacctaacc gtcaggaata aaaacctgcc atcgatgcta 540
tttccattat ttaaaatatt gaattaaacc cagcacatac tgtaaattgt ttttgcttct 600
tccttttagg atagttgtga aaagtgaaat aaccaggcag ccttatctta ggtgagaccg 660
tttcggcttg gaaacaaaca aagctctctc tcgatgaact gggttcattt catatttgtg 720
taataccctg gaagaaatta ggtttcaata aagtccattt ttgtcactgc atgtagcaat 780
gaatatcaca cccagcaggg cacagtggca cctggctgtc cagaccccag tgtagcacaa 840
accatctggg ggtaattaca acaaggtatt ctttaaggac cagatgggag caaggaacag 900
aagcccctac ccctcccagt catttacaac ataattcctt tcaatgatat acttaatcct 960
cccaccagct atgcctttca gcttgctgtt gtcactgttc ctttatgtaa attcagacgc 1020
aagaccggga aaaagagggg gtgagacaga aagtacaaga aaaaaaggga aagggtgaga 1080
gagagcgcca ctggtgcctc tagggaccaa aagaaattat tcatccctaa attgttttca 1140
ccacagcgag tacagtaaca aattttttta aaaaaaagag gactgaaatt atcctaaaga 1200
aggtcaatgc gacagccctg tgtggcacca gctgaggttt actcagccac ctgttagcta 1260
gaaagctctc tgcacacgct tatgatgcat ttaaccagtt taaagggtct ttattgacag 1320
gccagccacc tccattcagc aggctggagc cataggcctg ctttgtggtc atatgtggca 1380
cacaagcctt aattcaatta cgctgtaagc ctatccaatc tgcatcactg ccctttcact 1440
tttgtgccat ttgtcttgca tattgtaaag aattttattt tgaagaggga aaggcaccct 1500
acaacccagt tgtctttatt tttcatgtaa ggttgtgccg caggtgcgcc gccacctttc 1560
aactcccgaa atgcattcat ctttaagcga tattttagag ggaagcagta tttattgttt 1620
ggtgacactg ctttgtgggt gttgctgatt tttatttttt ttttaattag gtatatgttc 1680
aaactctcca acacaccagc aaagagtctc caaacttgat tgttaaaaat tcaaaagaag 1740
aaacaaaaag aaaaacacac atgataaatg aaaatgacaa ttattagctt tgttctacaa 1800 ttttttttatt tagaaagaaa agtatttctt agagtgatca tatattaaat tttaaatttt 1860
ggattttcct caagtgtctg acacaaaata tgaatgtctg tatatatgag tgaggctcag 1920
tgctgctatg ttgcttgaaa atttctaata taagttccat agaaggtaat taaatatatc 1980
aagtctgctt atattgtttt gtattttggt actttcaatt ttccataaca ttggaccaa 2039

<210> SEQ ID NO 132
<211> LENGTH: 3022
<212> TYPE: DNA
<213> ORGANISM: Homo sapiens

<400> SEQUENCE: 132
gctttcacac aggaagctgt gagatggcgg cacccagcta gacattctgc ttaggtgaat 60
tatggatttg ccacactgag agttctcttg agactcaggt tcagaggaca tgtgtgtaca 120 catgggggc agatatatga ggggagggct gccgtggggt gggggctcta acagtaccgt 180
tttccctgct cccagcctca ttatcgctct ccaaggacct caatctcacc caggccagcc 240
ctgccccctt tctgcaccca gtaaacattg ctggcctgct ttctcatgaa tatggatttc 300
catcatccct cactgtaggg atagatgttg ggggcagagc tgttgattac atttccagcc 360
aatcattgcc cattagcagg gaagagcggt gggcattatc cctcttcagc gaggagccat 420
ttgcatttgg ttgggccccg ctttctttct gagcatctac ggaccctcag cgcactcaat 480
tactccggca tccggccctt cctctttcgc tttctaagtg tcttgattgg attggccaaa 540
tagcttggtg ctaactacag ctgtttagca tatccctggg tggagggtga taaggaccgc 600
agggtttgag ttggctgtaa cctgcagaaa caaatacctt tccctttctg cccatactgc 660
cttccaccct cctactaaaa gaatccgcag tggtttgcag ggaatagccc cagcaggcag 720
tagggtacgc gctccatgca ctttgcatct tttggggagg tccctccttc tagagttctc 780
tttctagtgc ccttgccccc ggagatgttg gtttcccaac tgccctgggg ggcctgaggg 840
gtctggcacg gatagatggt aagtttcccc accacttccg cttctgggaa agaggaagga 900
agtggatcta agcagagtcc gctgggaaag caggtcccct ccctattgga agttccggca 960
gcgctcctgg gccttatggg aaaattagag gcctgacctg ggagacaggc atgtttgtgt 1020
cctgctcaca aaccttggtc ataagtaacc tgtgaggaca actgagaatg acagagggtt 1080
tctttcgttc acaggatcat gttatcttca accccccttct gctgcccatg ttcccctgga 1140
aagcccttct ccagagtcag aaacatttgt ttgctcttgt taaggctgga gccatttccc 1200
ctccctcttc agggtttctc ccacccctca gctccctctt cttcagtgtt actagggatg 1260
ctgttttgtt ttcttttcct cttctgtttt gcccattcaa gaaaatgaaa gtgagcacct 1320
gagaaagaga gagcgggagg cagaggggga agagagactg tgagcaccaa atgatctgag 1380
tgtgatagag gaaggttacc tgtgtgtttg tcaacaagat gaaataaata agagaaaaaa 1440
aaagaaaaaa gaaaaaaaag acagcagtca aaggcaatca aatatgtatt taattaaagc 1500
aaacataaaa ataaaagtta catgttgaat caataaacag cacttttttc tacatgcatt 1560
ttgaacaaga cagatcagaa tcttgcatga tgaagacata atgtgtcata ataattagga 1620
acacagacaa aagaacagct aatcagcatg caaatgtatg cagttctggt gattcagatg 1680
aggcagattt ctacctcttt tttgcttgat tcatcttcat tgctaatcat ctgaaggctg 1740
ccaaatgttc actgacacta atgtattata ggtcaagaga ggcaggtctt cacctattac 1800
ccccccaaac aatatgcttc ccttccctgt ttcctcttca ggattttcag caatcactgc 1860
cagatgcaat cagactcctt gaataggagc aactgaggct tgtttgtggc tcggattcat 1920
tagaatcagg aggctgaaga aaggaataaa ttacttaatt gcacaaaaaa gttgcagcca 1980

-continued

```
aagtgatggt gagagaaact gattgtgtag atacgcatta ggccactctt ggaatggggt   2040

gtcttagaat agctggtagt ttggcctcac agattcagac agatttgggt gtcctccaaa   2100

acagatggct ccacatacca tctattcttc tctttgtcag gttttaccat ttatttgatc   2160

ttggtccctc tctgatgctg gttgtattag ttgtaacaca aatatgcatt cagatcatat   2220

ccatttagtc tggcctctcc caacttttgt tcttcctctt ttttcttttt cttttttttt   2280

tttttaatt ttctttttga gaagatggtc aagttgaatt aaacccttgt tgtccaactc   2340

ttgaatgctc cttcacatga aatgcaggaa atgggaagat tgcacaagcc tgcagtgcgg   2400

gggtgtgagc cctagactgg agggaggagg agggagaagc tgctcaaatg gggaaagaaa   2460

gaaaagaaaa gaaagaaaga aagaaagaaa gaaagaagct ctattttcca accacaggga   2520

taccttcctt gcctcaaact aactcttaat ccgttaaaaa aaagcacaat attatccagt   2580

gttgttcata cacaaccaag gaagaagaaa caaaaccatg cagagcagtc tcacaaatgc   2640

ttccttctct tttctctggc actttggcat gtgcctccag ccatggggcc tctgactcac   2700

acattccact caggtttttg gtcatgtgcc tgacttgcgg gtggtcttaa ggtcttgaag   2760

acagaacttc attttctctg tgaagttcct gcattgctac tagttgtgtg tgcgtgcgtg   2820

tgtgtgtgca tgtgtatgtg tgtgttttgg ggatggggtt gggaagaggg aggagaaggt   2880

tcagtatgag acaagaggca ctgacaggga agaaattggg aaataaatta tgattgattt   2940

ctatttggga agaaaaagta ttcagagagg taacttttct aatactgttg aaaagtaatt   3000

ggcaaagtgg attcacccag gt                                              3022
```

<210> SEQ ID NO 133
<211> LENGTH: 2379
<212> TYPE: DNA
<213> ORGANISM: Homo sapiens

<400> SEQUENCE: 133

```
aggcaagaaa acaggcaagt aataaataac atactcaagt ttatcctgag cccaaacaac     60

cctcagggct gaggctctgc agaccgcctt ccctgccaga cccactgcca ctcatctgcg    120

gcaaggggat gcctttcctg cctgaacacc caggccttca gccctgggta aaaatatctg    180

tattggtatt ttgtagcttt ttctcctgca cgctgataaa aacaaacccc gtttgtttaa    240

aaatcaactt ccccactccc tccgccctat ttccactcta ctctcatcct tttccaattt    300

tttttgaaa ccccttaaag gaaatgtcac ccaaacataa ggaattggtc attagtatgt    360

ctaatggtgg acatttttta tgtaacgctc tgaatctata gtgaacaaaa gcaactgttg    420

agaactctgc aaaaaaactg cccagcaatt ttaagttaat gggcaagatt aatggattgt    480

catataatgt gaagggaaag tattagaaag aaatgaaagt ggctagacaa aattggtttg    540

gaattggagt ctacctgaag gcccctcagc aagaacatta ctgtctgctg tattttcagc    600

taagcagtgt attaatttga aagccatgcc tcgtacggat acccagcact tagtggttgg    660

ttttatgttt aaaatgctta gtatgaaacc tgtgctgaaa atttgcccaa acatctcaca    720

gttgattgca aacccgagtg cctgggggct ctgagtccac acctcaagaa tgctggagtg    780

gggggacttt ctggctccac acctgggttt gtcaaggcct cttcgggctg ctgggaatgt    840

gccctgcctg ggcccgctg ctctcctcat cagccctctg acagattaaa acacaacagg    900

gtctgttgcc tgactgacac attcctctcc tgtctgcctc tgaaaggact ttatttaaca    960

gtcctggagt cgggctttga ctgacagatt gtgaagggta aaagtcattc agttccatta   1020
```

-continued

```
agctctgtaa ctgccctgga acaaaacacc ttccaaaaaa agtgtcggag ggaggggaaa   1080

atagagctgt ggagagtggg ggcatgagct ttcgggagaa aaaaaggggg tttcttttca   1140

ggttcaaaaa caatcctcct ctttgccttc tgtctatcaa ttagggcggc attcccagag   1200

ggaatacagg cccggcctca ttggtgtcat tcagctgcca atctcctgac agagacacca   1260

aagggcctca tgtagcgctg cggaaactgt ctgtcaggcc atcagcagct gctatgacga   1320

catcgcctct gtttttctag gactcttatg gaggggggag ttcaccccaa cagagtctca   1380

gagtctcgac tccaaacctc tgttcatatt ttccttttac aacccatccc cagtgtgaat   1440

ttcttcacaa aaacaacccc cggctccctt gcctggctcg gctacgaggt aaataatagc   1500

ttgccagcca aggacatggt cttgggtgtg agaaaggggt tctgcttctg ggaaaaaccg   1560

agtcgtgact gaacacattc aacgactctg gctcagatga gtccaaagaa acccgatttg   1620

cagtgaaagg tctccatcca ccgaaaggcc tgcacaggcc gcgtgtgaag agcagtgtgg   1680

ccccacagac ggcctcctgc tcagccttaa ccttgtttgg gttgctgtgg gtttcattcc   1740

cctggagttt tgcttggagc ctgaaggctc aagcacagct caacacttta agccaaactc   1800

agcaccaagc aaccacttcc cactgctctg tttttctgcc ttgctccccg ctttccccaa   1860

ggcctgactt acacggctgc cttgagtttg ccccaaagat tcctcagcct cagctgatca   1920

cacagaagac ccaagagtac aaaggaaggg cccgtttacc cgagctttct ggctggactg   1980

gggaaaatat ctttaccccc tccctgccct caactccctc ctgtccactc cagattctgc   2040

ctaagacttg gggaggcaga tccgggccac caatggccac ctgcaaagat agtggttgtc   2100

tctgcattct gtaaaggctg tgtttgtgat tcctggcatt tccctggaag tgttttcaca   2160

ttacagggag ctgcttccaa atggtaatga tagcactttg taccaaactg agagctggag   2220

caagttgctg ccaagccccc atggtcgggc catcgtgttg caacgcttct gcttctatta   2280

cagttcttca catgttccac ccgaaccgta caaaatgttt agccaaaccc tgtaagaaca   2340

tgtacataaa gctgtctcca tgctgccaag gtggtaaag                          2379
```

<210> SEQ ID NO 134
<211> LENGTH: 993
<212> TYPE: DNA
<213> ORGANISM: Homo sapiens

<400> SEQUENCE: 134

```
ctctctggga actctgcttt gacttgtgaa aacacatatt cttccgtgat aatgagaaat     60

ttctgtaaaa aactcactga aaaagtattg gaaggtattt aatatgctat cacagaacat    120

ttttaaaaat taaggtttga acaggaaaat aaacctatgg gattaaaggc gtttttacaa    180

acctaaagtt ttttgttttt ttatttaata caaaataatt cttaaagttt ggaccttttc    240

tcattaggca ttttattgtt acagaaaggg gatttttaaa aggtgtcatt tttagtcaca    300

gttattctga aaagttgttt ttgaataatt tctcattcta agggatctga aatagccatt    360

tttaaatttt caagaccatt ccacatttgg ttttatgttt aatgaattta gtcataatac    420

tcccaaaccc catagggtac agtttctatg gttaccagac cctttgtaga gtgacaaagg    480

ttggaattct gattctcgtg agtcaaattt tggcctttga ctgggtcccc tctgcacatc    540

cttgctaagc ttgggctgtt gctatgcttg aaggcttgtc agctagcagg ttcctatggt    600

aacaggaatg gaaatttgaa agaagaaaga gaatggtagc acaaaggctt ggttgatttg    660

aatttgaaca aagaatggaa ggttccctgt agtgcacctt tgttgtagaa accagaaatt    720

taattttaga aagttacttt ccagttgtaa acttcctata ccctggtctt gatttagtga    780
```

```
acaaaagtat tatggtttag ggaagtactc aataagaatc tttataattc agttagctaa    840

agttcctttt ctagacttca tagagctttc atagtatttc ttatgttata catttgttct    900

cagattttta gtgttcaggc tacctcattt aattttgatt ttgctgaggt caaaaattgt    960

taaggataaa aaaaaaatca gggcaatttg ctt                                 993
```

<210> SEQ ID NO 135
<211> LENGTH: 2479
<212> TYPE: DNA
<213> ORGANISM: Homo sapiens

<400> SEQUENCE: 135

```
cctttcttga atgtctttcc tggaatttta ttctaaatga cttttttta caatgaatat      60

tgccaaaaag aagaagagaa cagaatgctc tgagtgggtc aaagaatgct ggagaaaagt    120

aaaagacacg aaattcagca ttggttcagc ctttcttggt ttggtaaatt ttaagagtga    180

tttctggatg cttgcccagg atttcaggaa tgccaataaa caatctgtaa aataataagc    240

actacatttc attctggcag aaaacttttt aaaaatctat actaaagtcc gaacaagctc    300

aaggtcactt ctgggcttag gcctcatata gaatttttcc atagacttgg gaaagagaac    360

agagtttaaa tacaacatgc aaaagaaggc ttcatttgct cactcccaag tatctctttg    420

cacttaagag tgcttatctg caaagcacaa tgtttcattt caatggaata tttgacacag    480

aggctcaata gggctcccac tcatatttta ctttaattat taggcccaaa atgtacaatc    540

atttctttta tttataaata gcctttttaa aggaaatcaa agtctgacaa agtttggatt    600

tccatgcatt ttttgcatta atgatgacat caaacatgca ctcattatgc tctgttaacc    660

cttcagtcac caatcctagc actagtggct gtgcataact agtttttcct gatgatctaa    720

ctcacactaa ggccgagaat ctaaaaagag tccccttttg gtttaagctc ttggggccac    780

attgtgtttc tgtcacagga gtgatggtaa gagggactaa ttaaaagtcc agtgaatgtg    840

ccagggttaa aatcacaggc tctgctcatt aacagtcgtt tacctaaaga tatttccaaa    900

gaattccttc aatgtctgaa aagaacagaa cctgaagggg ggggagggag gaataagttg    960

agagagccat ttagaaatat tttatattag aagcagagtt ttgttttaat tcatggatgc   1020

tgtcaataga agaattcaat ttagtgagca gttcaaatat cgtttttttc ccatcggtgc   1080

aggcatgtat gtgtgcatgt atgagtgtgt gttttaaagg gggtggggga tagtctccct   1140

aagtctaacg agtagaaaaa gaaataggaa aaaaacatca gaaccatttt gttaattgtc   1200

tttttcctgc tgtttccatg gtaatactgg cagccagact tctctgcaga gtgacagtcc   1260

aacaattcac acactacacc ctttcaagca caatgaatgg ccgtgaaaga ggccgaacag   1320

gcaccattca ggaaacatgt gatatctact caatgcacta cctttcatcc acattttcca   1380

aattgcagtt aatttaattc taaacaaatg gctaaggggt acaaatgagg attagaagga   1440

aaagaacatc ttgagctcta atggggatgg tttgtgtgaa gaacaatata gcactttctt   1500

ctgttgccaa gaaggctgga tgtgaagatg tacttccctc ctcatctgaa gcctttgctt   1560

ggactctatg tcaacagtaa gaaccatggc agaaaatttc ttggcaaaac agagttcgtg   1620

taggttttgg cttcgcattt ggaaacatat tagatacagt gtgatattac tgcgttttac   1680

tatgaaataa aatataacat cagaattttt actgacatgt cggagctacc actttctata   1740

aagttacatt tttcttattc tttttttttt ttctttttga gatggagtct cactctgtcg   1800

cccaggctgg agtgcagtgg cgcaatctca gctcactgca acctctgcct gtcgggttca   1860
```

agcagttctc ctgcctcagc ctcctgagta cctgggacta caggcgtgcg ccaccacacc 1920
cagctaatat tttgtatttt tagtagagat gggttttcac catgctggtc aggctggtct 1980
tgaactcctg acctcatgat ccccctgcct cggcctccca aagtgttggg attacaggcg 2040
tgagccactg cgcctggtca catttttctt atttaacatc cttcaacttt tggtgaagaa 2100
aagcagtaaa gttccctgta acaattcaca ggacaagaca ttatctttat gcagtctaaa 2160
gttacaatat gatttgtatg tttaagtgtc agtaaagtag ggcatagtta cttgaaaaac 2220
aaaaacacaa caggaaaagg tggcataagg ccctgcaaac tatttcatgt tatttggttg 2280
gaagaatcaa gatgaccagc tgccatattc ttatgaattt ttagataaat gactcagaaa 2340
attcaggaaa atccatttga ggatacagca tatgtaaagc aacatttcta tttctatttt 2400
ttgaattaag gtagtgtttt ttattccagt ggtaggcttt acgtgttaca atattatgag 2460
caatttgttt agagatgcg 2479

<210> SEQ ID NO 136
<211> LENGTH: 2049
<212> TYPE: DNA
<213> ORGANISM: Homo sapiens

<400> SEQUENCE: 136
ctctgctttg ctcttgtccc aattctgatt tcttattgac atctcccatt cattctgtaa 60
aatttctcca actcctgcaa gatctctttc tttgttttct tttgccaggt tttgtttaac 120
atcgtaactg tcttttgcct tttcctcttt tctctccctt ctcaaatcag agctttcctc 180
ttatagccat tcaaagtaat atgtggttta tttattaata cttccccaag ggtttctcc 240 tgcctcacgg catccccgat ttctttgctg aagttttctc tctctaatcc tggcctccat 300
tgtagcccca aatggaaata gcatccttat ggaaatatct cttttcaaaa actcatagct 360
ccagcacact gaataaagca accattatct tctaaagcat gaggttcatt gaattcacct 420
cagcaacttg aaacctttta aagttttata cattttggga aggtgtcaaa cctattcaac 480
accttcccgt gaatgaaaaa atatatccat atattcagga catgtcctcc cttctctgtt 540
atagacagct tttaatttta ttcacatctg ttattattat aaacaaaagt tgctgttttt 600
acttgactgc caaatgaggc acaaaaaaca acagctgttg ctattgcaca actgaataaa 660
gaggagagga aaaaaagaaa aaaaaaaacc ctaattagtc ttgctttaaa aagcctcaga 720
cataaaactg aaagcctccc ataaaagaaa aaaaaagaag atacaataag tagacttgaa 780
catggtctgc ttataaatat tcattgggaa aaatgggatc acatcattat gccagtcctc 840
cgggaaccct cgctgctaat gaactcttgc agcacatgtt agtaataatg ggcttcctta 900
ttctacaaga caaaaacagg atgctgtgcc aacctggtgg ctcaagtaac tagcctcagc 960
aggccgccgt ggagtttcca gcttcacttg aattctgcca cttgtagctg gattgatagt 1020
tttcattgtg ctcttgctgg gggaggggat ggtgggggga ggtcaacgtt ctttatgtca 1080
ctggtgtctc attagccttt catcattgtg gaccacattt gggccagggg catccattcc 1140
tccaagcaga ggcctttccc tgccccaccc accccctcca cgccttgtca aagcttgttg 1200
gtgcccctgc caaggccccg gcctcagggg ccacctttct gtttctaggc ttccttccaa 1260
ccactcctcc agttcacact ttcccttctc gggggccagc aggaggtctt tggaagataa 1320
ctcagctcta tctaccatgg aaatcttgtt aaaaacttac ttcccctccc ctacattgcc 1380
tggggaaatt ttggaaaaaa aaaaaaaaaa gagatagaga ggaggagctt gtattccctg 1440
ctctgtcttt cctggctact gcatattctc tttttccaga tgtaaatgtt tcttgtggaa 1500
gaagggtttt atgattggat tccttgtcaa tcctgcctct cctcccccat cctgcaactc 1560
ccccagaggc aaaggagtgc catttgtgag aagggctatg agggctgaag tggggactgg 1620
gtcatcagga cactgtcatc tctccatctc taatacgtac tgagatttta tagtgacaac 1680
actaatctca tttaatgcta acatcacccc tctgaggtgg gtggtatttc tagaccctgc 1740
ttatggaaga gcctgcagca tgaccagagt cttacggcta attgcatatt acacaggtgc 1800
tctgacttta cagcttgtac ctgatttatt cccccatcta atttagtgat atcatcactg 1860
ccactttcat tttctgaaga cgagagatgg aagtttccac cgagatgtgg atgtagggaa 1920
tcgtagtcac atttgtttgg agtcttggct ttaaggtggc tctgctgcat tgggataaag 1980
caccttaatc ctcttggggc cgtcattccc tgggcctgag ctgacctcat ttggcttcat 2040
ctgcaactg 2049

<210> SEQ ID NO 137
<211> LENGTH: 1405
<212> TYPE: DNA
<213> ORGANISM: Homo sapiens

<400> SEQUENCE: 137
tcccaaaaag catggatgtt cctaaacagc cccctgagcc ctgccttcat gaatgtcagc 60
gtggggggct ccggcaggcc cacgtgggca tgtgccggtg agtgtgaagc ctctgtctgc 120
ctgtctgggt cccctgtaat tcatcagatg catgtttgta acaaaaggat catgccacac 180
gccagggatc tttgaaactg aaagtttggt tcttaaatga gcccaactgc aaaccaaatg 240
gtgtgtggag tgctgaacgg gtggggacaa aaatcgtggt ggaggaggtg gcttttctag 300
cagggcagca tttcacagca cgtgctgcca actgttgcaa aaagaaaaaa aaaatcctaa 360
gaagaagaaa gagagaggga aatgtacata ttcctgcagc cctgcaagtg ccctttcttc 420
ttcattgttc tctggagcag gcagcaggcc cggccaacag ctgtgcattg cgtgtatcac 480
taacagctgc tttttcctgg ggtgaaatta aaagattagg ggatatgggc acgtgctggc 540
ctcaggagcc caaacaatgc ttgatttagg gtgaaacttg tctggggaga ctgacaaagg 600
aggaggctcc gagttggcca ggggtcaaag aggggagctg gctttgacag agacaaaagg 660
agggaggggg tgggaggcag agggctaggg gagccaggcc aagtgaaaag aggcctcgca 720
gcagctgctc ctgccccaga aatttgagac gggtcttttc acaaacacaa atgcctgaga 780
agaatagggg gccacgctta gctgaaatgg ctcgtttgca aatgaaaagg agattgggag 840
cccttacatt ttccaagttt tcacctaaga ggatggaaaa tgattagtgt aggcaagaag 900
tgtgcagagg agcagatggg ccagccaccc tggagctgca ctctgtgttt acataacaat 960
catgcccact gccggggtgc agaagcccag gccccctaaa tgtccagcaa ggacactggc 1020
accccggaat tcgatcagtg cagttccagc tgggactcca caggacgtct ttgctacagc 1080
gtgtgtggat attaatttat gtgctggata aattaaatac acttataacc atgaagcggc 1140
aaggtgattg cagcaggagg caggctggca gacagcacgc cggtgtggtt gttgtccctt 1200
ggcaggatgc ctgacttccc agacttgctg tttcttcttg gcccctgctg agaacattgg 1260
aggagaaccc ctggcctgca cttcaccgtg tgtgacgaaa agggttttaa ccatgagcaa 1320
acacagggtt ggaagccagt cccccaaatc aggcagcaca gaaggaggat agcaatagcc 1380
atcttagtag gaaaagcacc tgcca 1405

<210> SEQ ID NO 138

<211> LENGTH: 3424
<212> TYPE: DNA
<213> ORGANISM: Homo sapiens

<400> SEQUENCE: 138
cctaaacatg cttggacatg tttctacaaa cccatccttg tctttttata taaaatattc 60
cttttgcact aagctaaaat taaagcaagc tgtatgtgac atttattggt gacttataca 120
gtagaccctt aacattcagg accaagcatt ctgtttttaa ctatttcttc ataccgtgaa 180
agtctgtgga gagaagcaat ttgaatttcc tgaggcttca atttgtgttt gaatagcttg 240
tactcttagg ctcaaatgga ggatcaagtc atttatttga tgagggagct tagccagcat 300
ctcggcattt gtatctcagt gtaatataga gtaaatctct tacaattttt tagttgtaaa 360
ttaccagatc tttgtttctg tatggaagat tgtcaccgaa aggaaagcta attattaatg 420
gcatgacctt tgtgaatttg gagatttata gacaataagg atctactgtg ttaatatttg 480
aacagttgtc aaataacggt tattttgatt tttggtcatt ttctaacatg taaaaagtgt 540
gattcacacc agcatgagtc attttgtgaa tgttcaaaaa acacgattta tgtttgaagt 600
gtatcgtgtt cagtttagat gactgaactg ctttatagtt gcagcccaga catcactaat 660
ctaacagatt tcagacgact gtcagattag gtgtgttgta ttattagaga cacagtatgt 720
tttcaggcca atttcagaac cagtggagga gtttggtcat tcttagcccc ttctgacagg 780
ataagtgttg tcacagagac catggtgaag gctgacacag aatcatggga cttcatggtc 840
tggtcctaac ctgtttctct gattttacat ttcattcctc tccaaggatg cacttatttc 900
agcagtatct ttgttgaata atttccccta tccctaaccc aaactagcac tatcaaaagc 960
ttcataatta cctgtcacct ggaatcgcct ttaatcacca ttaattcatt gttgctcact 1020
aatgtagagg ttaggaaatg ggaggtaaat ggccaaagta cgtattccat atatagtaca 1080
tctatatgga tgtatagagg gggcatgaat aggtattaag ggaatgagga agaaagctag 1140
gcaaatttgt cctttctttt gagctacgtg ttacttctgt ataataaaca aatcttatat 1200
tgcggtttaa ttagttcaga gacacacata ggcatacact catgcatgag gagaattata 1260
atttgtgcat ataaaaaggg aaatatcaac actgttgata tttttaatgg tgactttcct 1320
atttctgccg tgtagaaaag gtactaaata tcacccccat tctaaaagta gttttggtga 1380
aatctgaaag ggtctgctcc ttttttagtt gatccagact ccattgataa cactaaattt 1440
tcatgctgtt ctgcagttat agacccttaa acttagactc tctttgtact tcatcattgt 1500
aatttacaca ctaggttggt acattctctt caagacagtt tgccttgtgc ttccagctgc 1560
tccccaatag ccattgtgct gaataagcac ttatttcagt atgtccttga tacaattaat 1620
gcaggcatct gcagaagcgg ccgtggcagc agcagctgca gtgccttatg gaagccaact 1680
tctgcttagc attgtgataa aagaaatagt tttgagctgg aagctaatgt tggcttattt 1740
ttagcataaa aagagttgca cctgccaggg ctagcggagg accgaggttt gttgattaca 1800
cgttcttgtt agtgccattg ttattggtaa aatgggcatg atgtcatcct tatcaaactg 1860
aattggcacc ctgcagagtg acaaataatt taccctctgc ggttttatca gcatgggccg 1920
tgtgttagaa gtgactagag tgctgagttt tcacagttga atgctatgga actgcagagg 1980
tgtatgaaaa tgaaagggat tgatacttgt aatcagtgca catagtaatg gccaaggtgt 2040
aatgaaacat aagtgcacat ttagggtaat tatgctgcta ccaggtgggg ccctggggct 2100
ttgcatgtat agaagctgct tgaggtggcg gatgtgcagc gaggaatact gcagcaccat 2160
ctggtagatt ctcattttct cattaattct tctgtcccct aagtctgggc tacattgact 2220
ttgaacagca cttcatctgt tcagtatctc atctcatttt agttgggagt tgctctcaac 2280
agtggtattg atatgatgta attcacaatc tcggccatgt gagatatatt aaaacaaatc 2340
atctaattga ttttcttttt aagtaaagct aactgtccct agtaacattc acatgaccat 2400
ctgattctaa accatttacc actcttgtag ttatttaaat taaaatagag tatttgtttg 2460
atttaaatta gccaaatgaa ctttgttctt cagaataatt tataaataaa agtataattt 2520
aaagagtaaa tagtaaacca cattgcattt tccttggtca ttttttaacg tgtgtgtttt 2580
atttctacag gccgatgtag tttttgtctc aaatataaca aaaacttgtt tattagtgaa 2640
gcttcagaat aagaaagtac agtgatggtt gcccagcagt ataaacatac taaactccac 2700
tgaatgcaca gttaagaatg ggtaaaatgg ctaaaaacaa aaaaatagta tttgaggtta 2760
tatattgtgt aaggaagtaa aattcttaaa acttgccaaa ttaattttat acgaatgctt 2820
tcacataaca ttaaaaataa gatttctagc ataatattag taggtcatat atggttgatt 2880
tccttatcaa tatgaatatt aatatcatga aacattttta aagatccata gtatatattc 2940
atataacaca aatagtcaca atgaagtagc atctgatggc tgatttttta atgctgtata 3000
atttataacg gggtgcagtg tatcaaaata agacgatcta gcatctgtga ttgtaggtaa 3060
ctgacattag tgatttcacg atttctttaa taagtacaaa tataacattt atatggtctg 3120
agtgcttgaa cacctttcta taaataatag aaatgtcccc attaaaatgt tccacttaga 3180
gaatccccgt gcattttgtc attttatttc catgaatgtt ccaaaaatgg aaaacgagag 3240
aaaaacctat tcgcttcttc caaacactac atgaatgctc cctgtgatgc ccttgaggtc 3300
agtgtttgtc agtgtagtgc cacaaagatg tggagagctg ttctgtcagt gacgctgctg 3360
ccatctgaat ttcccatcac tcatttccaa cctattgtcc agatactgca ggcttcatga 3420
gagg 3424

<210> SEQ ID NO 139
<211> LENGTH: 2386
<212> TYPE: DNA
<213> ORGANISM: Homo sapiens

<400> SEQUENCE: 139
gggctcagtt gtgatcattg aagacatgga ttggtagcag ttcaggaagg gatagaagga 60
gtggtctctg cattgtgggt gaatggcgta ggcataggca ggctgccagc ctcccaggaa 120
ggctgccttc ccaggaaaaa gccttcagtc ccagttttcc ttatactcaa cagggctgag 180
gacagggaga actagaccca ccttcttagc tgctttttat tcactcatct accacttctt 240
gcttaagcag cccaggcatc cttatggggc ttagaatcca ctgtgttctg gggcccaagc 300
tctttccagc atctcaggag ttgtgatctt tgtgatgaga tcctctctga ggttgatctc 360
ctgtagtctc ttgctcatct agcccctatg gggaaaactt gaaccatttc ttcttttgga 420
gacttgctca gaggggaggc ctcacttcca ctcagcagtc atatgagcca ataaaagcag 480
atagactgga gttgagagtg cagctgttat aaactacagg agggtagcca tgttttcaga 540
atccccagag gcctatttta aaacggttac attataaatc agcaaaatct tagcaaaatc 600
cagagtttcc tagcctttta aacaagagaa ataatcagtc tagccttgtt ctttgcctta 660
atgcaccttg gcaataagag cttaaatgcc aaacaatgtt ttttctttca catgtgtgag 720
accgaggaac acttattgta aaagttaaac agagtgacag cttgctttgg ctgatgtgta 780
agagttcttg actgggctgc tttcctttct tccataataa gtagttaata gaaattcact 840
gacctgcagt gcagacttaa tttatcgcgt atatcaagtt gatttaacag gaatggaatg 900
tggtggaaca atagcttccc tctctcccca cctcttggtg atcctccgac attcgtttgg 960
aaagaaaatc agatttaaaa acatgtagaa cctttgtgat tttgaataat tggactatgt 1020
ttgaaaaaag tatttaatca atgacaatca tctgtttatt tgaaaaatgg ttgggttcag 1080
ggaggtggta tttatcttta aaattttcac ttgtaggaaa gactgaagtg gctgagtacg 1140
ctatgtgctt tgcactgtat aaagggaaaa ctgaaaatcc tgaattgctt cattctttca 1200
tggcatgttc tttatttaga aaatccttaa ttaattttgt gtgaaagcag acggtcaaag 1260
gatttaaaga agcagaaaaa catcttgaat ttcttactgc ttgcaaagtg ggaaagtga 1320 aaatggtaaa ctgattaaaa gaagtcatct tgaagcctac cattataatg agttgtaaat 1380
aacaacagtg acaaatctga atcatttaag aaagtttgcg caggattttt ccatttgaaa 1440
tgcatttttt ttccaatttt ggtctcttga gacatcagcc atttaaaagc atgatattgg 1500
aactaaccca gcatcacttt taattagcac agaaatgcta attatacttt ttctatgtga 1560
cgcttaatgc gagctgtcag gacactgcat tttttacatc agttgtggtg agatacacaa 1620
gatcaccaga cccactttaa aacgataaag accaatacat ctaaactgat gagtattttt 1680
aaactatagg gaagtgctac aagatgcata aaaataatgg catcaaagtg aaaaatttgg 1740
gctttttatt cacaccaagt acaagcataa tttcacaaat ttttcaatat ttgtggtctg 1800
tgaaaccaaa tttcttacca ttgaatcatt gaaaatacac ataaagcttg attttggaag 1860
aaaactactt tttcactaaa gaatcttttc gaaaatcaaa tagccaccct ctcttcattt 1920
tttagggctt cgcatttcag atttctttt agggctttgc attgcatttt agcttttagc 1980
ttttcgtaaa ggaaagtcta cttgtgttct tggcttttt tttttttt aacagctcta 2040 gggccgggca cagtagctca cacctcaatc ctagcatttt gggaggccga ggccgatgga 2100
tcacttgagg tcaagagttg gagaccagca gcctggccaa catgacgaaa ccctgtctgt 2160
actaaaaata caaaaattag ctgggcgtga tggctcatgc ttgtaatccc agctactcgg 2220
gtggctgaag caggagaatc acttgaaacc aggaagtgga ggctatgttt agccaagacg 2280
gtgccactgc gctccagcct gggtgacaga gcgagactcc acctcaaaaa aaaaaaaaaa 2340
aaaaaaaaaa aagaagatga cagctctagg aatgcaatgg ttgctg 2386

<210> SEQ ID NO 140
<211> LENGTH: 3113
<212> TYPE: DNA
<213> ORGANISM: Homo sapiens

<400> SEQUENCE: 140
gacctggcat caaccaaagg ttcccatttt cttcatccaa atggataatt ttgcccaaag 60
agatcacttt gtcatatgtg ctttcatgtg gtgagctggc agaattgctg ctgccttata 120
tgatcaaaca acaacaataa aaatcacagg ggatgcagtg tataggcaaa gtacaattag 180
agccatcaat tattctcagg gataaaactt attatttaga gaataaacat tacgaaatta 240
ctgattatct gttcctttaa aaaaattacc cagaatgaag agtaataaaa tgtaatacaa 300
atataaaatg taacacaaat atccaaactg gatcataact acacaagata aaaatcctga 360
gccaagaagc tgtacccaat tctcatactt taagaatctt aatagaactg atagtcccca 420
ttaaattttg tcccattatc attagtacac agttaagact ttatatacaa tggatagctt 480
taccttcaag gctatttata gcaagctaat aactgagacc ccaaagacct caatttacat 540
aaaaagaagg caaggctaca ttcacccagg tatacaaatc acaactatat agacaaaagc 600

-continued

```
tctaagaact cataatctct tctttttgga ttttgtcagg gatggctggc taattgggga    660
aactcatgaa agtaccttac aatccaatta gcacttcagt gcaattaagt ggtagaggct    720
tccctattct gcagagactg gctttgatct tgcagtgaaa agtgtccttc cttaaagctg    780
aggttttgat ttttttctca gtaattagtg ctaattgtaa acccaagcct gacctgctat    840
aaacagagtg ttttaccgca tttgacacca ggaccctaaa tcagtgttct cttttgtcta    900
tattgtactt gcttattaga aatctggcta ttttgctcaa catttgatgc acaatgggta    960
agtacatact aaagtcagct gaaacaaatg ccttgatctt aagagcttgt gtgggtattt   1020
tcattgatgt cttttaagcc cagttaccat aaaagtagtt gattgaattt cacttaagga   1080
atatactgta gtttttctac acaaagaatg actattcaaa agcagtttct aaagaggttt   1140
aacaacgctt gtatgtttgg aaaataaaaa caaaagatga aaatggtctt ttcatgggat   1200
caaatataaa gaactgcaga aatcaattgc agaattctcc tgaaaaatac ctattataac   1260
aatgcctgtt aaatcaattc attgtttcga tttataaaaa tgaattaaaa tagaggtcaa   1320
tgagtgagta ggctggtgag atatctctat atggaaataa gatgctgtaa aatagaaaat   1380
cccagacctt ctccaaggta tagataagat cctttgaaac tagcacacag tttccatgca   1440
aatgcaaagc agctggatgt tagatagaat gtttctccct caaatatgtt tttaaacata   1500
ccctgttcca ttatttagca aatgcttcct tcataggaaa aattatacat ggaggtatag   1560
ccagttgagg ttataatgtt agacactctg aattaggacc aatttagtga tcttgaaata   1620
gacatagtct agtgtacaga tacataatta ctggagggaa aaatatgttc ccaatacaaa   1680
tatgaattac acataaaata tgatgacacc aattagcact tcttacaaat agctattttg   1740
gtgatatttt tccccttagg gaaaaaaaat caagagtcta gtgacagttt tttttctata   1800
aaagacgata tgattgaatc tgactaaaac aaacaaaagg tagaatgggc tcttagaaat   1860
tttccctgat tttacacctt gtaaatttat tttaatcatt ttaaaaccag agtattacag   1920
gcataaaaat taaacaataa taaaaagcct gttgaaaact ttggggtatt tgccctatcc   1980
cttcccctcc tcctctccag acactacttt caactcttgc aagccattgc gttggctctt   2040
catctccata tttttaaatc agaaatggct caaagggata agccctgact atctgtattt   2100
tggagttact caggggaagg ggctgggata ttacatttag taccagactc tcacccctgt   2160
tttcagactg atctcaccct cttgagaccc tgcagtctcc aagccctgag gctctctaat   2220
tcaatcttcc aagagcatca tttcctgcca ggatggaagt ggtgaggtca tttgtccagt   2280
gacagagaat gtttcgagga aggagagatc aggagatcca gttgtaactt acacatactt   2340
ttcaagcaat ccctgtttcc actacccaca ccttcactac ctggctccca atttctcaga   2400
cctttctggg aggtaaactg ggtagctgct ctttggtact ttcaacctgg aagcattttt   2460
gttcgacctc acttctctca ctaaatcctt atcattcctt tacaaaattt gtgtggtaaa   2520
atgtatataa caaaattggc catgttaact gtttttaagt gcacaattca gtggcatcaa   2580
ttacacttac cttattgtac aactatcacc acatctagtt cccaaattcc ccatcattat   2640
gaacattttt ttattcttcc atctgctttc ctgttttgca ggttgtgttt taggagtacg   2700
gtgatctact ttaataataa ttgaaatgtg tgtttctttt ttccttgttt tgggtaattt   2760
ttcaagagaa gaatgcagaa gtatctttat tctgtcatca taaaaccaaa gtaccatctt   2820
ctcttttaaa gatgggacaa ctcttgcctg gaatgattaa gtaacttgat ctggctatca   2880
atgtgaatca gtggcatgac aagattaaaa cccaatttgc ttaattatct acccaaggta   2940
```

```
ccttccatca actacactat tcatatcatt attggagtcc ttgtgagtta ggatttcaat   3000

tttttttttct ttttttgtac atcgttttaa attgtgtata ccaaggagat tgagaatgat   3060

gtttctgtaa atattattat aacactaact gttggacagt tgctcagtag gaa          3113


<210> SEQ ID NO 141
<211> LENGTH: 3100
<212> TYPE: DNA
<213> ORGANISM: Homo sapiens

<400> SEQUENCE: 141

gcagttcctg gagcacagtg gacactgggt gggagacagg tgatttaact ggccttcctt     60

gggcaccagt gaacagatgt tgttgctagt cagttatggc cccttctcac ggagtccggg    120

ttcaggttct gcccctcatt tctcagacag cgtcccaggc cacctccacc catgccggac    180

tttatgcctt ccttgaccgg gagggccact tatccttgtt caggtccaaa gctgcgagtt    240

ttggttttgt tgttgttgtt gttattgttg tgtttagaga cttggtctgg ctctgtcacc    300

caggctggag tgcagtggtg tgattacagc tcaatgcggc ctcgaacttc taggatcaaa    360

agagatcctc ccacctcagc ctcccgagta gctgggacta cagtagtgtg ccaccatgcc    420

tggtaatttt ttaaattttt tgtagagata gggtctcact cttttgtcca gtctggtctt    480

gaactcctgg cctcaagcta tcttcccact tcggcctccc aaagtgctgg gattataggc    540

atgagccacc gcacctggcc taaaactgca ttgtgcatat agccgtggaa gtgctgaatt    600

gtattgttat cgggtacttt aatagtgata cattcaaccg gctgtgtggc cttgggagag    660

tcatttcaac atgatgaagg tccaagccca ggagatgatc agagaatcat cccgagtctc    720

ctgcagccct ggagcatctt ctggtagcaa ataatctaaa caggtatctt aataggtgag    780

cggcacgtct cgaagaaaaa aatctctcca cacaaatggt aaaggtcttg aaggagcacc    840

agatctgtag cgtgtgcagc accacacttt tcatatatga tgtgattagt gtaaataagt    900

agttgatttt gcttcataag tcaaatgatg attcttttac aaatagccgt ttgaataatt    960

ctttacacct gctacttagc catagttttg ctggaaggat tgagttttct tctgaagaca   1020

cagcactact ctgaagctta tttccccctg aattttgttt ttcccatttt tggctgagaa   1080

ggcatctgga gtgactccag cgggtttacc taggttttcc ctgaagaggt ttaggtgatt   1140

agacaataac agaaggaaaa gtagagttgc cagtaggtgg ctcactatga atgtgcttgg   1200

gacgggatca gacatgtcac ccctcctcca cttagccttt gttttcaatc cctgctgctt   1260

tgagcctttt tctataatgt ctgagtcatt tgcagcgggg tgggtaaaga ggggagaaag   1320

aagaaagcaa gcaagcaaca gcctttgagc tccggaatag caaaggcccc catcttgctc   1380

cgagagttca cagagtatag cccagtccga gttctctttt ccacgcacac ttgcttgttc   1440

ttttgttcct tgtgtccttg gcaaagactg aaagaactaa gcctggaata cttgggccct   1500

cccgtgtcac ttaagaaata ataagccatt gtcctcatta agccaccctt gttttagcaa   1560

atagaatcca gataccggag agggaacatt ttgaagggag gcagaattag agtagagatg   1620

ctttacaaaa ttccctagag aaactgcttt gtttctccta ttttattgct ccttactgag   1680

aagattcata ttcaaatggg ttggggttgt gaatagcggc ttgcacattc tcatgcaccc   1740

aggaaggcta tgattatggc taattacaat gaagaatgaa gctctaacaa gagtgttcca   1800

tcagattgtc attcatgcat gaagtaactt aggctggcca atggaggtgt gattttggta   1860

attacaaaca atgtggctat ttgaaaaatg cttagtaaat ctgttcaaga caaaataagg   1920

tctaattaat cactttagct ctgaattctc cagatgatcc atttgctctg ttttttttt    1980
```

tttaatttaa ggtctcttta ataaactaga tctaagatat aaaatatgtt ctcgttgccc 2040
acacttaaat gcaactgtgt tacctgtttc aaaggcttct taattctgcc aatcatgttg 2100
caacctgctt ttaatgcaac ttgacagaag gcttttaaaa ataaatgtgt gtatattctt 2160
gttgttacct gacaagaaaa tggtttatga aaagttactg taaaacatta actattaatt 2220
tagaagccat attggtatca tcattgtgct gacatatatt aactcttgaa tattcggtga 2280
atgttgtgtt tagcacttaa gtaatgtcta actatatgta ttagtttgtt ttcacactgc 2340
tataaagaac tacctgagac tgcataattt ctaaacaaaa gagttttaat ttactcacag 2400
ttccacatgg cgggggaggc ctcaggaaac ttaacaatca cggtggaagg caaaggggaa 2460
gcaaggcata tcttacatgg cagcaggaga gagatagaga aggcggaagt gccacacttt 2520
taaaccatca gatctcatga gaactcactc gctattatga gaacagcatg ggggagctgc 2580
ccccatgatc cagtcatctc ccaccaagtc cctcctttga cccatgggta taacaattca 2640
agatgagatt tgggtgggga cacagagcca aaccaatcac tatattatag gggagaaaaa 2700
gtaatatatt ttccttacct atcacaaggt tcgtggctga gaaccttaga gcaaaggaca 2760
gagtaacaag agaaaaacat cacatttatt taatagaggt tatgtgacat gggagccttc 2820
agaaatggag acccaaagaa acagagatgt gtgtactttt atggacaggc atgcagaagt 2880
aagactggag gatgaaatgg catgctccaa tcggtacaaa ctgggggcaa ctcagggaga 2940
cctgattgcc cagtttcttc tccgtgttcc tgagtgacat tccttccctc ctggtatagg 3000
gcagtactcc tgtcacatga ggtcttcagg gaagaagtga ggccgcaggt caaagagtgg 3060
ccttccctgc ggtcatggcc tgtttcaggg aagaaggggt 3100

<210> SEQ ID NO 142
<211> LENGTH: 2755
<212> TYPE: DNA
<213> ORGANISM: Homo sapiens

<400> SEQUENCE: 142
ggtgagaaat ggggactgtt aattcactca acaagcacag aaaaaataca acctctctct 60
gtctcctcga agagcaccca caggcccaag acacaccttg aactaaccta gaagctggat 120
gtccttgaga tgatttactt tttccaggtt tgataaagag aaatatcttt agccctgtca 180
agcaagcagt aaagctcctt gattgtacct taaagggaat gagaatgttt cggctcattt 240
gcattttaaa gggtactctt tcatgatctt tcacacttgt aatagatgtc taaaccgtta 300
aattactatt tcttttctta gcctgaaagt ggatgcagac taagagcgtg gcctctccca 360
ttgttcttta ccctaagtcg gcccctgaac aatactgaca gctgctatca aaccaggctg 420
catttactct gcgcgcagct gctgcttgta ggaacagaca gtttcccggt acctcctccc 480
ctctggggag acaggttgac acactgcatg ttcaatgaag gggtgcaaag gtccactgaa 540
ttgtcaaccc aattttatgc tacttcaatt ttccagaacg cacacaattc ctttcaggca 600
aaaatcaagc atatgccaca gcatgaaact taaggtgtgg gataattatt gatcaccaca 660
aacttgaaaa gagccttcgg acataaattc atatactaat ccaaaaatta caatgataaa 720
aaccgcacat gccagtatgc ccaagacaca caatgggcct aagtctcgct tgcattgcgc 780
ctgattcacc actttggttt actgttgcca aggcatccag agctaacctg cctttataat 840
aacctccaca acatttttcc tggactaaag ccattcgtaa aattagaaat tcatttgccc 900
ttctaaaaag atctgctatt tttattctct gattcagctc aaaatgggta ttacctatga 960

-continued

```
acatctggtt aatgcgattt cctccttcct aaagtgtagg tgcaaaggag attcacaaga   1020
gctgggcggt gcctttgaga atttaaacgt cagagttttg ccatcatgaa attatatgtc   1080
gtaatgtaga gtctatcaga aaacaaacat gttccacaaa gtttaaccgg gtacttgaga   1140
actgctttgc atatgttttc ttttaatcaa aacaggcttt tccatcctca ttcatttggg   1200
tgaaaaaatt ctgtgcttga gctacaagta caattcacta ttagtctttg ctaatcaaac   1260
acagtacatg caaaagtacc agtgaatatt tgatttgatc tctgaaataa agcaattcat   1320
tacacaagaa aagggtacag aaggcagcag acaaatgcag atgtaattgt gttttttgtt   1380
gaatgtgatt agagagccca ctaagtaaca gtcaaaaatg tgatactgaa ggagggggaa   1440
ggcagtgcct ggatctgggg ggaagaggag ggagaattgt ttatgcagag ctaagctgtc   1500
aagtgtaata aagcagcttg aataaaattt aagctgaaaa tccactgaag ctccccattt   1560
cagggaggaa aaagctatta aaaggaaatg aaggtcaccc tcctagttta tttcacctaa   1620
ttgactgcca atagcttacc acagacaact caactgcaga tctgcaattg agaaactgat   1680
gaaaggagag ttttcaagct gaggctcatt ctttaatcct ccttggctct tatgtttttt   1740
ctccatctcc agttgggatg taattttaag ccctgatgga ttaactggtt ccattgtctg   1800
tggccgtcat tggactatgg cactcttaat ccgtacagca gcatgtctaa ttatcattac   1860
aaagtgtctg agggaactat aaagaccagc agggcatcat ctcacaagca attaacataa   1920
attgataaat gagtgatttg aatctgctca aggcactcac atatgaataa aatcagaaag   1980
gacggtccct tgtttcagct ccttctttgg cttagtgtgg aaggggacga acacatgaga   2040
accatcccag gtcctgcagt ggggggcgga ggatgaactc atgcagggga tggaatgcac   2100
ggttcaccag attcattaat gcagagcaaa tgacttgtga ttgacaacca gtggctagca   2160
cggagcacta actgaactca agagaggaga gcagaacccc ggtgaaaagc cagggagcac   2220
tagggcagac aattaacaat tcttccatgg caagagagcg ctcttttcat tggtgtgtga   2280
cttaaaaatt catgaaagag gcacaagaaa gaacaagagc caacagttct ataggttcga   2340
ataccccaga aagcaaaagg caaaaagcaa ggataactaa atgaaatgat aattcagaga   2400
cccattttga cctcactgtg atctaacatt gtaagacaga agtgaggaaa gtatttaaaa   2460
ttctaaccta aagcttttac tagactaatg aagcaagggt ggtttaggtg tcacaggatg   2520
aactacattt attttcccac ttaaaagtag atttagggac gggcaagggg gtgcctgcct   2580
ttggacccag ctactcagga ggctaaggca ggaggatcac ttgagttcca ggccagagta   2640
ggcaaaatac caagaccccg gtctgtttaa aaagaatttt tttaattaat agatttttttg   2700
tcccctccta aaatgcttct cctgtcatct tccttatgct aagccctctt cctcc        2755
```

<210> SEQ ID NO 143
<211> LENGTH: 2862
<212> TYPE: DNA
<213> ORGANISM: Homo sapiens

<400> SEQUENCE: 143

```
atgagtttct gagttgccaa aagtgttgta acttatacta gctttaaaaa ctaaatgtaa     60
atcaaaacca caatgagata ccatctcaca ccagttagaa tggcgatcat taaaaagtca    120
ggaaacaaca ggtgctggag acgatgtgga gaagaaatag gaactctttt acactgttgg    180
tgggactata aactagttca accattgtgg aagacagtgt ggcgattctt caaggatcta    240
gatactattt gacccagcaa tcccattact gggtatatac ccaaaggatt ataaatcatg    300
ctacaataaa gacacatgca cacgtatgtt tattgtggca ctattcacaa tagcaaagac    360
```

-continued

```
ttgcaaccaa cccaaatgtc catcaatgat agactggatt aagaaaatgt ggcaaatata    420
catcatggaa tactatgcag ccataaaaaa ggatgagttc atgtcctttg tagggacatg    480
gatgaagatg gaaaccatca ctctgagcaa actatcacaa ggacagaaaa ccaaacaccg    540
catgttctca ctcataggtg ggaattgaac aatgagaaca tttggacaca gggctgggaa    600
catcacacac tggggcctgt cgtggggttg agggatgggg caaggatagc attaggagaa    660
atatctaatg taaatgacaa gttaatgggt acagcaaacc aacatggcac atgtatacat    720
atgtaacaaa cctgcacgtt gtgcacatgt accctagaac ttaaagtata aaaaaaaact    780
agctatactt gtatacattt catatatatt atatatattc acatatttta atctctatga    840
aaagaacaag ttctatttcc tttaaaatta aattgaatac tacatatgtt acacaaaatt    900
gcctagcttt attttgcttc agttgctttt catcagcatc tcccattgag agaggatata    960
tcaagaaata ctagttaata aaaaagggcc aaaaagacta agatcccact aaaatactct   1020
aataaaaatg atggttattt taattatact tcattcactt tggttttgtg aatatgcaaa   1080
atatgcaaga aatattttta acaatagata catttctggg cataccattc acttctaact   1140
ttgtatgcag ataaaacatt cctcgactta atcttcaacg tagtcaacac tatacacact   1200
gatatctaaa tctttagttt tcactttcta ataaatattc taatatacag aaactgaaga   1260
atgttattac cattttcaca aagcatctac atttttgtat atagatgtag acattttaag   1320
taaatatatt taagactacg acaacacaag ttgatgatac taggtgacag tattaatgct   1380
tttaaaatta tactaaagaa aaaacatact aatataaaga agaaaaaaac tggtaagttt   1440
tttttggagg aggtatggtt tgccatttat tacttttttt ttgtaagagt cgattaatat   1500
tctaaaaagg tctacgaaaa agctgaacaa cctctcaagc tctgaatcca tggcactgac   1560
cttaggactt tctcagaatg atttttaacg cactctgtta ttagtaaaac ctgttcaaac   1620
acatgcccca tctgccagca ccccatctgc aagagagctt cttattcttg tagacagtac   1680
aacttctgcc tgtttccttc tcttctctac ataccagctg tatggtaatg agcatgagca   1740
gctgaaaaat actgcattat aacaaagcta atatgaaaac agcagaatag gacttccctt   1800
caatgaagca gttgtagcat gaacatagct gataagctat taaatagagg taggggggtgg  1860
ttagaatttt acttctatgt gtgtgggatg cccgtgtgtg cggatgcatg catgtgtgtg   1920
tgttaaatat ggaatttctg tataacacag aaataacaag aaccaagaga agcacagggt   1980
actaaagaaa ggtctaattt tctaagtact tttgttaaaa tttgtgaatc agttctttaa   2040
atgttttaag tctcaattct tatgtagtaa tgatatatca ggtaccattt tgacaagaca   2100
gttttcaaat ttgttaaaaa gtatgttaca tttcttaatt accaaatttt gggggcttca   2160
gtaggaaaat ggtgtcagaa cttaaaatta taatggaaac tatatactag acattttagc   2220
agctaacata atatgtaaat caataacatg tatttttaat tcttatatag cgattttaaa   2280
aattccaatt taatgacatt tgaaaccaac acatttattc tgaacatctg agaatctcca   2340
aacaaactac caagatgtca catatgcttt tcttcatgta gggagacata atggggttaa   2400
tttttacata tatgatagtc gcactgaatg aatctacata atgtaagtag aaccaaatca   2460
cattaacttt ttatgcatgg tatctttcca ctcagagaag attaaaagtc actcaggaaa   2520
ctgtttaaga aaaattattc aaaatttatg ctgtgcatct tcttttacca cttgaagaaa   2580
ctaaaaatga aaaaaatact caaaatctct atcataagta ctattacatc aggagaatta   2640
attataaatt ttaccaacac atctaaaaat gtcttatgag ggcttcataa tagttacaga   2700
```

```
actcttgtac ataaccatgc tttccatggg ttatttcatt ttatccttac aacaaccctc   2760

tgtaaaaggt actactatta gctcttcaca gataaggctt agtaagtggt acagcaaaga   2820

acttaaaccc aggtccaact gaccctataa tccgcgctct ta                      2862
```

```
<210> SEQ ID NO 144
<211> LENGTH: 3198
<212> TYPE: DNA
<213> ORGANISM: Homo sapiens

<400> SEQUENCE: 144

gctgcctcaa acaagaatga aaccattttt ctcaaactgg tagaaaaacc ttatttcaat     60

tattttttct agtcctatac ttccagagga tgggaaactg ttcttaaaag tgcaatggac    120

tgacagaaag cagatccgcg gttgcctcca gggctggggg aggggattga ctgcaaaggg    180

gcgcacggga atttactggg gtgacagaaa gattccacat cacaattaag gtggtggtta    240

catgattgta tacatttgcc aaaatttact acatttacaa ttaaaatgag tggattgtat    300

tatacattgc tcaataaaac tatttttaaa tagctttagt aataagtgaa ctagtgcttt    360

ttttttggtg atcatttgca agaatactcc aaattcaata agaaccagga ttctcttttc    420

aaaagtccaa aaactagtaa caagtgctgt gttagatttg aagagctgga aggactttac    480

atacttaaat tccattttaa tctagttgaa actcccatag aaagaagaaa aaaatacatt    540

tttaaagtac agatttttat tcaataattc tttagttctt ttctctttta acttccctgg    600

ggggagcagg gaactctcat tctggtaccg atatttggat taaaacaaat atccacccat    660

tcattaaaag tttctctcat ataaaggaat tcattttttt tcttgattgg tgctagactc    720

acagacagac agaaataagc tgccattctt ccatttgata gccagacgct gccagttgta    780

gccagggtag tcatgctgtt aaattaggtc taatgaagga gtaattgctt tagatatagt    840

gaaccatttc aaagaaaaca aggattctaa ttgatttgca atttgtttgg cacattgcat    900

tgtctgcggc tattgattag tcttctggat ttcacactgc atgtgtttcc ctttattaag    960

ggaataacag gttactgatt actttctttc tgggtttaat gtagcggtta atgtctactt   1020

tgttcttgtg tcatgtcaca ggcgaggaag gaataatagg caagtgggtg gccctttgct   1080

aagcaacttc cctgctgctc tgagctgtgt gctctgagac aggctgaaaa gcagatcaag   1140

agaaagggtt agaatagcag gactcacaag ttaaggcctg agtcaggcta gacccagctc   1200

aaaacttggc tttcccctcc cagtcaaagc atagcatggg acaaagcagc tggtggtaga   1260

tttgttcttg tatcattcga ttatttgtag acaggatatg aatctatgcc cattgttttg   1320

cttaataggt atgcatgcta aatggatgca gaaaaagaat atttgagggt gaggtctttt   1380

ggttcattta accctttgga aagtgacatt ttgttggcac ctgggaagca cttgttgctg   1440

aggtgtcgat atgatcatca aaatggctct tatgtttata ccaactgcag gggagggaga   1500

aaaagttctc agggttgcag tcatttcatt gccctcaaag cacagcagga attattagct   1560

taccctggcg tgcccctttg ttttcctagg gctttgctcc tccagcagat actcatttaa   1620

ggcgaatcca ctgctttctg aaatgtgttt tgcaatggtg cacagaacag gcactcactt   1680

agcggatcta atcctttcat ggctcagctt gttaatgtag caaactgctg aaaatgggaa   1740

atggattctt taatgagaac agtcccttca tggctttatt ctcccagtcc aacccccagg   1800

cattcattca agtcccccca cgcccgacct cccacgccag gatcaggcac ccccacttcc   1860

cacccagcaa gcagcccatt ttccagcacg aagtccccca tctctaggcc ccttgcttcc   1920

ccacgacctt cccagagccc ttggaagctc acaaataaca aaggggtgta ggcagtaaaa   1980
```

```
gattcccttt ctctgcttca gttacctcct tcctaagcct gagcccgtct tttcctgtgc   2040

ttcaaatctg acatggttat agagtggagc cttttcctga taaattgcaa agtagctaac   2100

acccagggat tacatctaaa tttatcaaat aaacacactt ttgatataaa catactaccc   2160

aaggtattat agatttaata tctttcttta acatagcttt tgtactatac aggttgaata   2220

tccttgggac tagacatgtt ttggatattt ttggattttg gactatttgc atatacataa   2280

tgaggtctct tgggatgaga ctcaggtctc aacattaaat ttatttacgt ttcatataca   2340

ccttatagac atagcctgaa ggtaatttta gacaatacga tactaatttt gtgcatagaa   2400

caatgtttgt gttaagtgct attaagactt tttttaaagt gttaagactt ttccactgtg   2460

gcgtcatgtg agtactcaaa aagttttaaa ttttggagca ttttgggttt tggattttca   2520

gattaaggat gctcaacctg aattggattt tataatgatg ctgattgcca agggtttcaa   2580

aatggagcca atcagtgaaa gttaacttgg actctggtct ttattatttt tcttttacga   2640

tttttactcc tgtgggtctt cctgaagctt tggtacttct ctagaaatcc actccaaaga   2700

aaaaaaatca ggcctggcac agtggttcac atctgtaatt ccagcacttt gggaggccaa   2760

ggtgagagga tcacctgagg tcaggagttc aaaaccagcc tggccaacat ggcaaaatcc   2820

catctctact aaaaatacaa aaattagctg ggcgtagtgg tgcacacctg taatccgagc   2880

ttacccgaga ggctgaggca ggagaatcac ttgaacccgg gaggtgaagg ttgcattgag   2940

ccgaccgaga tcgccccact gcactccagc ctgggcgaca gagggagact gtctcaaaaa   3000

aaaaaaaaaa aaaaagtact cgaagcaggt aaagtttagg ttaagaagat attcaagatt   3060

acttggaagt catgacaggg cagcctggag tttgaagtgt acatttaaaa gagaaaatga   3120

ggatagttat gcccattttg ccttagagat aggaaagtaa attatgtgta catgagccca   3180

ggtctttccc tcatccaa                                                 3198
```

<210> SEQ ID NO 145
<211> LENGTH: 2318
<212> TYPE: DNA
<213> ORGANISM: Homo sapiens

<400> SEQUENCE: 145

```
cctggtggaa ctttaccaaa ttacaaacac tggccttacc ctcatcatta aacaccaatt     60

atttggcaag tatttaacaa atatttacta aatctctaca gtgaaagcac aggcactgtg    120

gtagatgcca gcaataccac catatattaa gaaagacatg gccactgtcc tttgagaatt    180

tgcactatca attataatct aagattgtta gaagaaaagg caagaatgaa acaaggcaat    240

ttatttcaag tctatggtta tatattagaa tgccaggtat tccaaaatat tcataattac    300

tagtgctcct ttgacctctt accttgcaaa agttgctgta ctgggtaatg tttgactaga    360

attacagctg agaaatgagt attgattgca cattttgcat tttacaaaac ctgagacgta    420

aacaatcaaa ggaacaactt acaagtcatt cttcatcagg gaacagttta ttatctatat    480

tcattatctg ggctagaatg gcttccattg taaaggcaac ggattaaaac aactgggact    540

cttgcggtta gtctgttcca agacataaag cgaggccatg ccctattaga atgcatccac    600

tgtccctgct ttgacaagtc tttcagtcag caacctgcca actctgtatc tggacaaact    660

gccaaatagc atcacagtaa taggagcatc ttcatgaatt ttcctgtttt cagcattaaa    720

atggaaaaaa tgctaagcaa aacccccttta gcattcattg tttttagggc tactggctgc    780

ttttttttatg tttctgtttc cattttttca gtttgctttt ttatctgttt tccatgataa    840
```

aaagcacctc attcacttcc ccgtggaagg gcaatgcagc tccaagggaa catctgtgag 900
gccaattagc tgggctggaa atgtgatata attgttgttt aaatatattt aaattacatg 960
ttaatcacga tgtcataatt tataagcttt gaaaataact ttttgtactt gagagccaag 1020
ccagatttta cttgtttttg ctgtttttag tttgaaacca gctcttctca tttctctctc 1080
cctcaattcc ccacacttga agagctgaac ttttaatatt ggaaagaatg acagctgcaa 1140
gtaaattggt tgagtaaaaa ttaagatcct cacagcagtc aaaatgagct ggagtgacct 1200
taaagttcga agcagaacaa agcaatgctc tcagttaaaa gcttttgttt ttccattgtg 1260
ctactttctg ctgtccatca aagtccagct ttgcagatct ttaggaagca gcactgggtg 1320
catctgttca attagctggt gaggcgattt actgtcagca gggcagagat agaaagaggc 1380
gggttaggaa ctggcaggtg atactgagtt tgttcctggt ggggggggttt gtaagggtga 1440 tggatggaat gagtttaatt ctgtggccat atcgctggga gattgtatga ttaacttgga 1500
cttaaatgcc agagattaaa gagaaggcaa gtatcagtaa atgaatcaaa tacggtatta 1560
aatgcacttt taaatacatc atgttctaaa atttactttt tagttgaatg ataaatatta 1620
gaacctttgt ctcatatgca cagtatttct tatatttgta ttatttaata ttgttcctga 1680
gaaattttat ttattaaata gatggactgt atcttgtgat atttttaaaa attattatac 1740
aaatctactt tcggaggaaa caaaaataca ggcctaatgc ctagcttcta tctaaattaa 1800
acaggtgatc aatgagagtc actttctaat ctttaaataa ttattacttt caatagtaat 1860
tataagatta caatttctag gttcaagaaa tactccaaat tcctttgact aaaataaaat 1920
gtctctgtaa gacgttgcta atccatcagc actaatttat tatccagaca cttccacata 1980
gtaactatta aaggttctca accttttatc ctccctgaca tatctgctta acactctgat 2040
gagcatctcc acactttcac aggtcacata gcaacataca gaaaatgttt attgcattat 2100
gttataatta ttgcattata aattataatt cctgatgcat ggttgtaact ctgcatcttt 2160
ctcacaactg agttcaacat accagtgttt tgagacgttt agatttagga ccttcatttt 2220
tcacagggca atcagaagga aacaaacaga atgtgtccat atgtgccaaa cccaataatg 2280
gctgggaaaa gcctactgag atttcagctg ctggctga 2318

<210> SEQ ID NO 146
<211> LENGTH: 20
<212> TYPE: DNA
<213> ORGANISM: Artificial Sequence
<220> FEATURE:
<223> OTHER INFORMATION: Synthetic Enhancer hs422 primer

<400> SEQUENCE: 146 aggggtctt cctaggttca 20

<210> SEQ ID NO 147
<211> LENGTH: 20
<212> TYPE: DNA
<213> ORGANISM: Artificial Sequence
<220> FEATURE:
<223> OTHER INFORMATION: Synthetic Enhancer hs422 primer

<400> SEQUENCE: 147
ctcctgaaag ccaagaccag 20

<210> SEQ ID NO 148
<211> LENGTH: 29
<212> TYPE: DNA
<213> ORGANISM: Artificial Sequence
<220> FEATURE:
<223> OTHER INFORMATION: Synthetic Forward primer to introduce DlxI12b-betaglobin-Cre vector

<400> SEQUENCE: 148
ctctggatcc acacagctta atgattatc 29

<210> SEQ ID NO 149
<211> LENGTH: 30
<212> TYPE: DNA
<213> ORGANISM: Artificial Sequence
<220> FEATURE:
<223> OTHER INFORMATION: Synthetic Reverse primer to introduce DlxI12b-betaglobin-Cre vector

<400> SEQUENCE: 149
gagaaccggt gcaggaattc atcgatgata 30

<210> SEQ ID NO 150
<211> LENGTH: 28
<212> TYPE: DNA
<213> ORGANISM: Artificial Sequence
<220> FEATURE:
<223> OTHER INFORMATION: Synthetic Enhancer hs692 forward primer

<400> SEQUENCE: 150
acaaggatcc cacatctcag tggctcat 28

<210> SEQ ID NO 151
<211> LENGTH: 29
<212> TYPE: DNA
<213> ORGANISM: Artificial Sequence
<220> FEATURE:
<223> OTHER INFORMATION: Synthetic Enhancer hs692 reverse primer

<400> SEQUENCE: 151
tctaaccggt cagggtgtct gtgttgatg 29

<210> SEQ ID NO 152
<211> LENGTH: 28
<212> TYPE: DNA
<213> ORGANISM: Artificial Sequence
<220> FEATURE:
<223> OTHER INFORMATION: Synthetic Enhancer hs1056 forward primer

<400> SEQUENCE: 152
gacaggatcc gtccctcaca gaactcag 28

<210> SEQ ID NO 153
<211> LENGTH: 28
<212> TYPE: DNA
<213> ORGANISM: Artificial Sequence
<220> FEATURE:
<223> OTHER INFORMATION: Synthetic Enhancer hs1056 reverse primer

<400> SEQUENCE: 153
gacaaccggt gatgcctgcc ttgaagtc 28

<210> SEQ ID NO 154
<211> LENGTH: 30
<212> TYPE: DNA
<213> ORGANISM: Artificial Sequence
<220> FEATURE:
<223> OTHER INFORMATION: Synthetic Enhancer hs1538 forward primer

<400> SEQUENCE: 154

-continued

```
tctaggatcc tgctgcctca aacaagaatg                                      30


<210> SEQ ID NO 155
<211> LENGTH: 30
<212> TYPE: DNA
<213> ORGANISM: Artificial Sequence
<220> FEATURE:
<223> OTHER INFORMATION: Synthetic Enhancer hs1538 reverse primer

<400> SEQUENCE: 155

agttaccggt ttggatgagg gaaagacctg                                      30


<210> SEQ ID NO 156
<211> LENGTH: 28
<212> TYPE: DNA
<213> ORGANISM: Artificial Sequence
<220> FEATURE:
<223> OTHER INFORMATION: Synthetic Beta-globin forward primer

<400> SEQUENCE: 156

ctataccggt agcccgggct gggcataa                                        28


<210> SEQ ID NO 157
<211> LENGTH: 29
<212> TYPE: DNA
<213> ORGANISM: Artificial Sequence
<220> FEATURE:
<223> OTHER INFORMATION: Synthetic Beta-globin reverse primer

<400> SEQUENCE: 157

gagaaccggt cgccgcgctc tgcttctgg                                       29


<210> SEQ ID NO 158
<211> LENGTH: 27
<212> TYPE: DNA
<213> ORGANISM: Artificial Sequence
<220> FEATURE:
<223> OTHER INFORMATION: Synthetic hsp68 forward primer

<400> SEQUENCE: 158

gagaaccggt gcatcggcgc gccgacc                                         27


<210> SEQ ID NO 159
<211> LENGTH: 28
<212> TYPE: DNA
<213> ORGANISM: Artificial Sequence
<220> FEATURE:
<223> OTHER INFORMATION: Synthetic hsp68 reverse primer

<400> SEQUENCE: 159

atattccgga ggcgccgcgc tctgcttc                                        28
```